United States Patent
Kahn

(10) Patent No.: US 8,293,743 B2
(45) Date of Patent: Oct. 23, 2012

(54) SUBSTITUTED IMIDAZO[1,2-A]PYRAZINE DERIVATIVES AS ALPHA-HELIX MIMETICS AND METHOD RELATING TO THE TREATMENT OF CANCER STEM CELLS

(75) Inventor: Michael Kahn, Los Angeles, CA (US)

(73) Assignee: Choongwae Pharma Corporation, Seoul (KR)

( * ) Notice: Subject to any disclaimer, the term of this patent is extended or adjusted under 35 U.S.C. 154(b) by 0 days.

(21) Appl. No.: 12/616,712

(22) Filed: Nov. 11, 2009

(65) Prior Publication Data
US 2010/0069333 A1    Mar. 18, 2010

Related U.S. Application Data

(63) Continuation of application No. 11/594,576, filed on Nov. 8, 2006, now abandoned.

(60) Provisional application No. 60/734,655, filed on Nov. 8, 2005.

(51) Int. Cl.
*A61K 31/495* (2006.01)
(52) U.S. Cl. .................................. 514/249; 544/349
(58) Field of Classification Search .......... 514/249; 544/349
See application file for complete search history.

(56) References Cited

U.S. PATENT DOCUMENTS

| | | | |
|---|---|---|---|
| 6,294,525 B1 | 9/2001 | Stasiak et al. | 514/183 |
| 7,232,822 B2 | 6/2007 | Moon et al. | 514/243 |
| 7,531,320 B2 | 5/2009 | Kahn et al. | 435/69.1 |
| 7,563,825 B1 | 7/2009 | Kahn | 514/789 |
| 7,566,711 B2 | 7/2009 | Moon et al. | 514/243 |
| 7,576,084 B2 | 8/2009 | Moon et al. | 514/243 |
| 7,585,862 B2 | 9/2009 | Moon et al. | 514/249 |
| 7,671,054 B1 | 3/2010 | Moon et al. | 514/243 |

FOREIGN PATENT DOCUMENTS

| | | |
|---|---|---|
| WO | WO 01/16135 | 3/2001 |
| WO | WO 02/092010 | 11/2002 |
| WO | WO 03/031448 | 4/2003 |
| WO | WO 2004/072076 | 8/2004 |
| WO | WO 2004/093828 | 11/2004 |
| WO | WO 2005/116032 | 12/2005 |
| WO | WO 2006/101858 | 9/2006 |

OTHER PUBLICATIONS

Barker, Nick et al., "The Yin-Yang of TCF/β-Catenin Signaling," *Advances in Cancer Research* 77:1-24, 2000.
Dean, Michael et al., "Tumour Stem Cells and Drug Resistance," *Nature Reviews: Cancer* 5:275-284, Apr. 2005.
Emami, Katayoon H. et al., "A small molecule inhibitor of β-catenin/CREB-binding protein transcription," *PNAS* 101(34):12682-12687 and 16707, Aug. 24, 2004.
Huntly, Brian J.P. et al., "Cancer Biology: Summing up cancer stem cells," *Nature* 435:1169-1170, Jun. 30, 2005.
Klein, C. et al., "Minireview: Targeting the p53-MDM2 interaction to treat cancer," *British Journal of Cancer* 91:1415-1419, 2004.
Ma, Hong et al., "Differential roles for the coactivators CBP and p300 on TCF/β-catenin-mediated survivin gene expression," *Oncogene* 24:3619-3631, 2005.
Pardal, Ricardo et al., "Reviews: Applying the Principles of Stem-Cell Biology to Cancer," *Nature Reviews: Cancer* 3:895-902, Dec. 2003.
Radich, Jerald P. et al., "Gene expression changes associated with progression and response in chronic myeloid leukemia," *PNAS* 103(8):2794-2799, Feb. 21, 2006.
Reya, Tannishtha et al., "Stem cells, cancer, and cancer stem cells," *Nature* 414:105-111, Nov. 2001.
Walensky, Loren D. et al., "Activation of Apoptosis in Vivo by a Hydrocarbon-Stapled BH3 Helix," *Science* 305:1466-1470, Sep. 3, 2004.
Vojkovsky et al., "Solid-Phase Synthesis of Heterocycles Containing an 1-Acyl-3-oxopiperazine Skeleton," *Journal of Organic Chemistry*, 63:3162-3163, 1998.

*Primary Examiner* — Douglas M Willis
(74) *Attorney, Agent, or Firm* — SEED IP Law Group PLLC

(57) ABSTRACT

The invention provides α-mimetic structures represented by Formula (VI) and a chemical library relating thereto. Additionally, the invention provides methods wherein α-mimetic compounds are used to treat cancer stem cells.

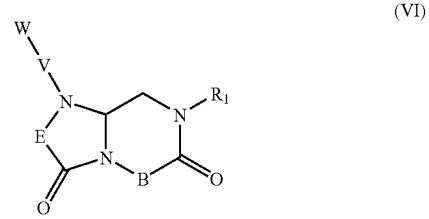

(VI)

2 Claims, 325 Drawing Sheets

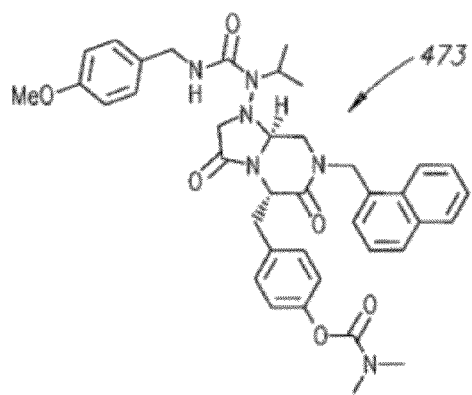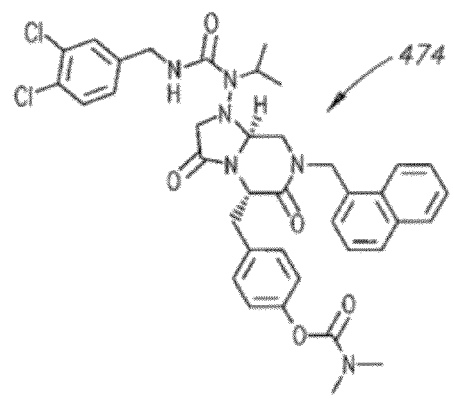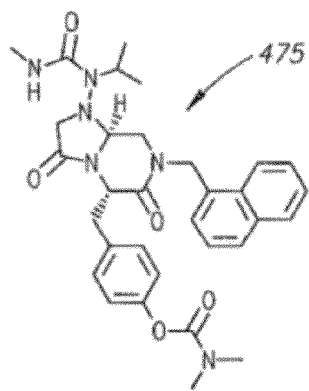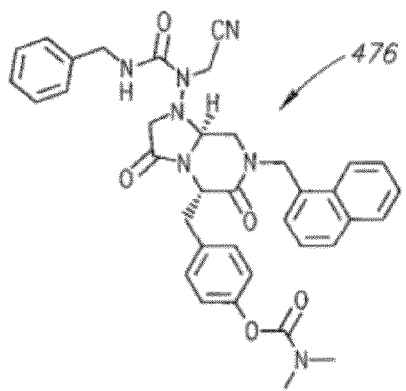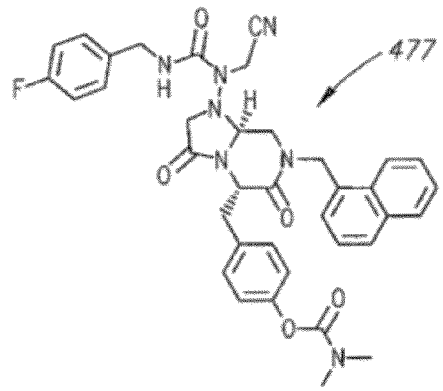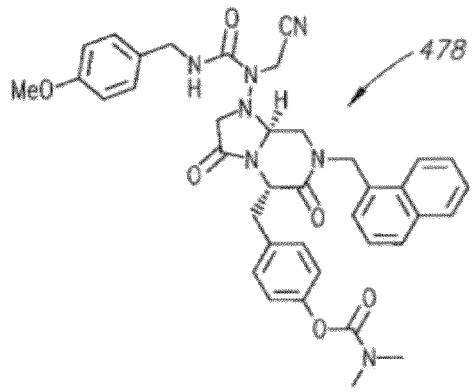
FIG.3K

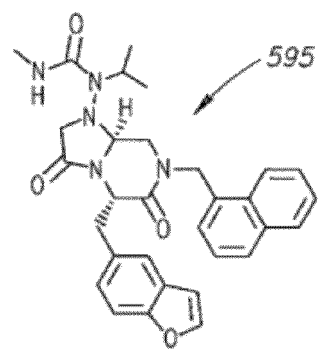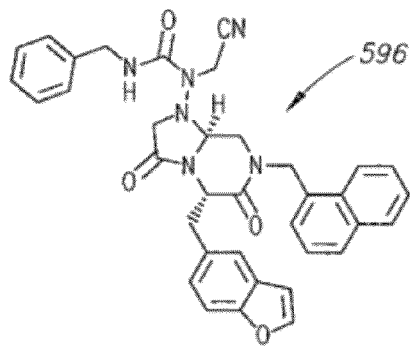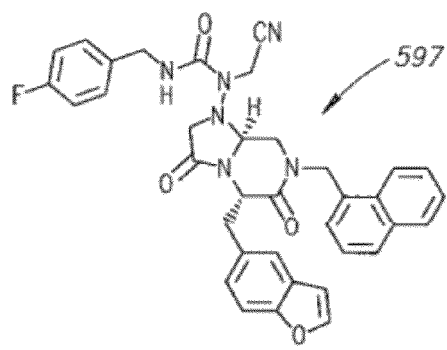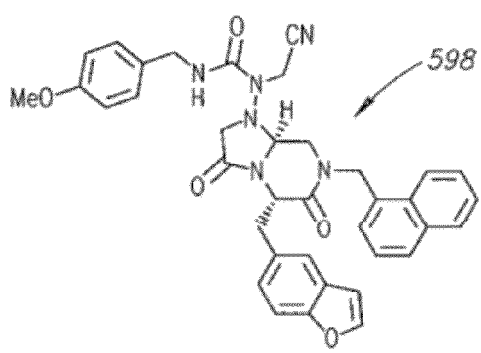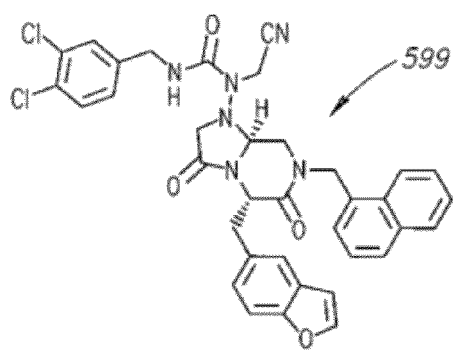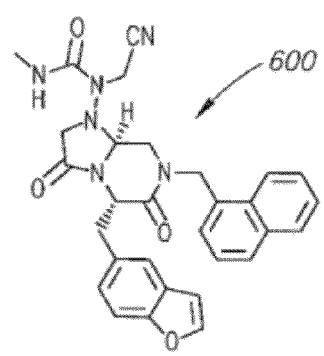
FIG.3AC

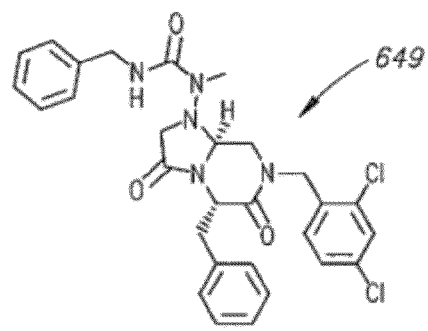
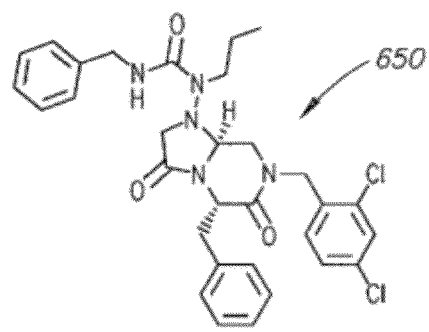
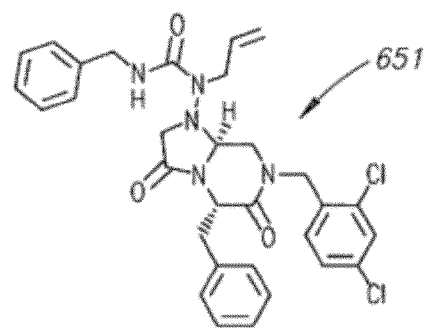
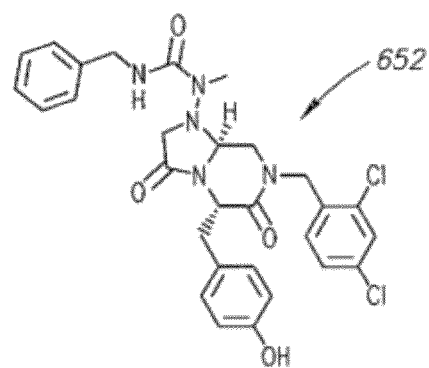
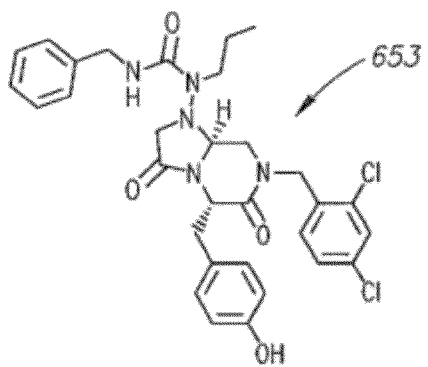
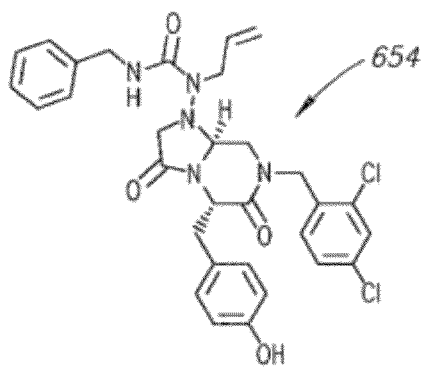
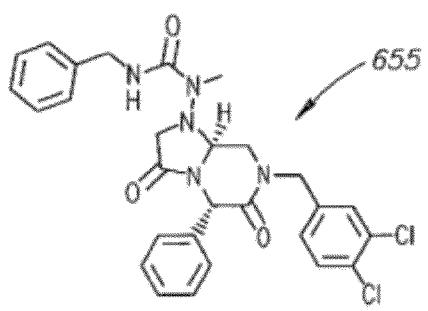
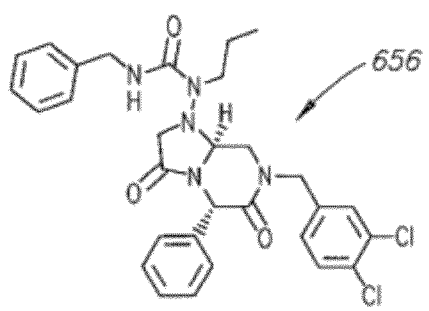
FIG. 4G

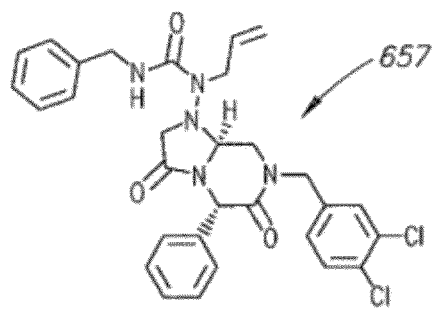
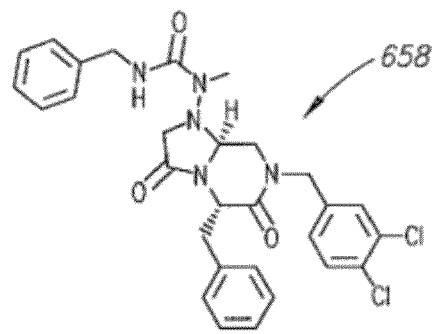
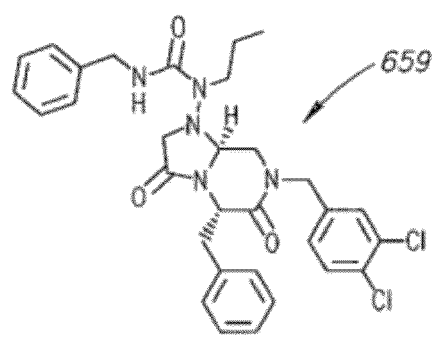
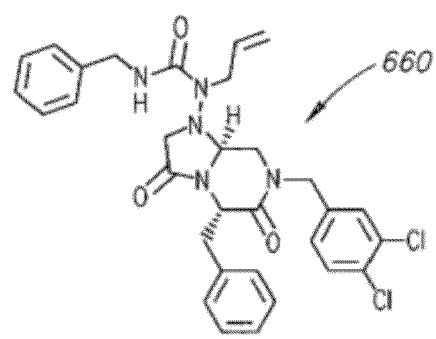
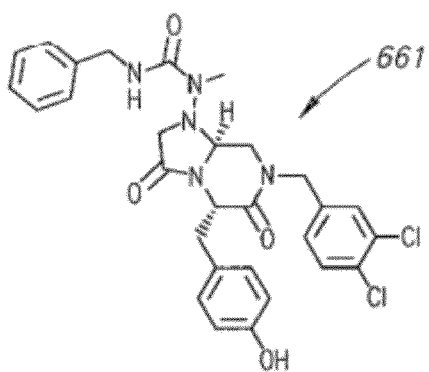
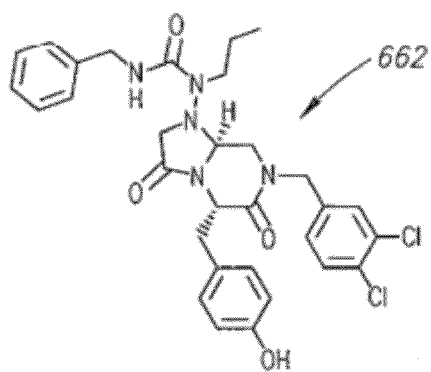
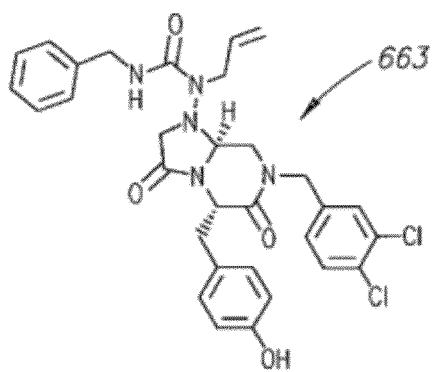
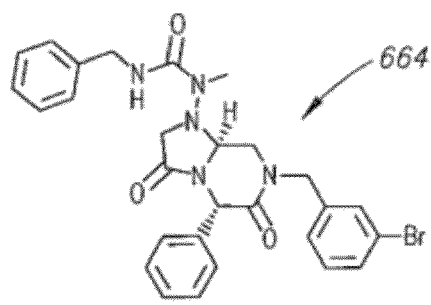
FIG. 4H

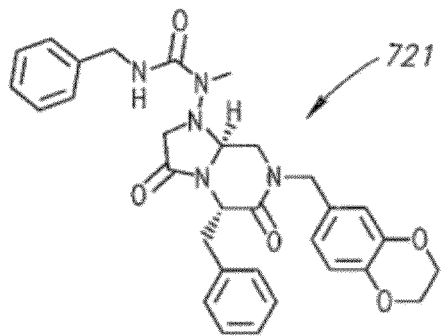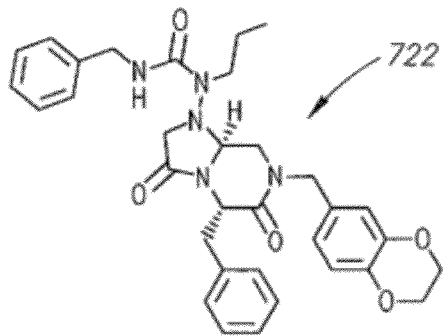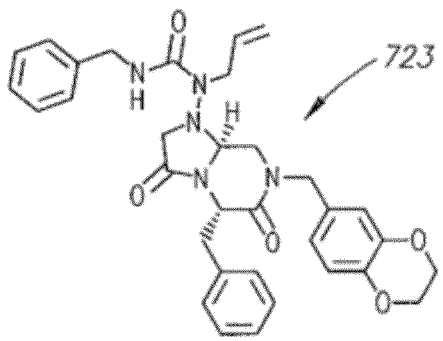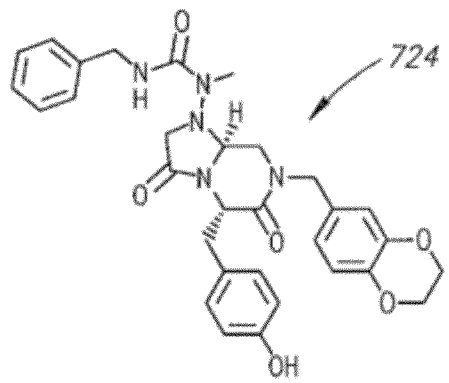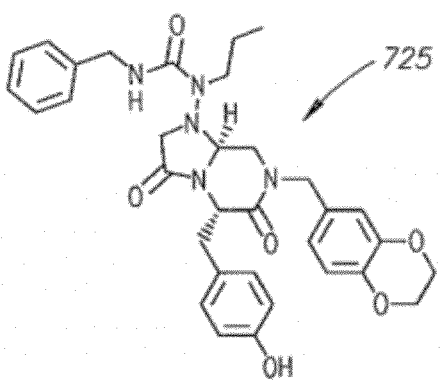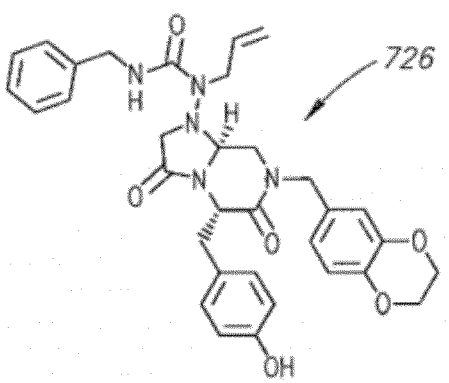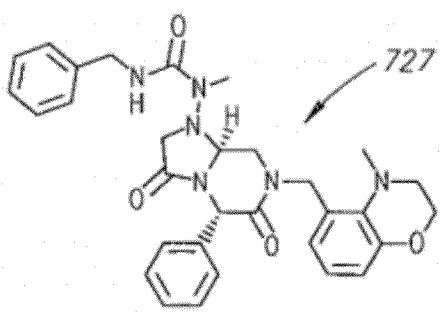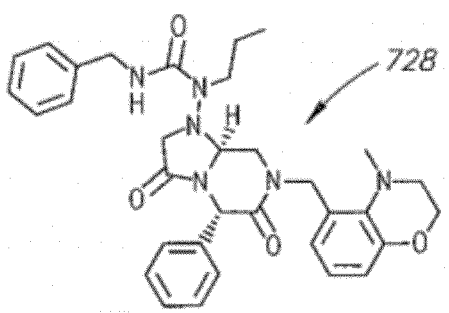
FIG.4P

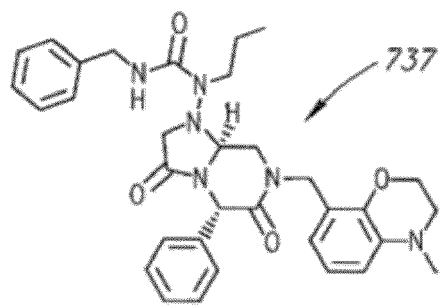
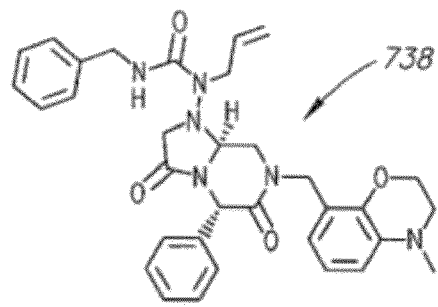
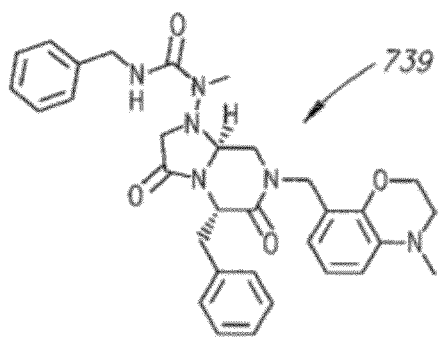
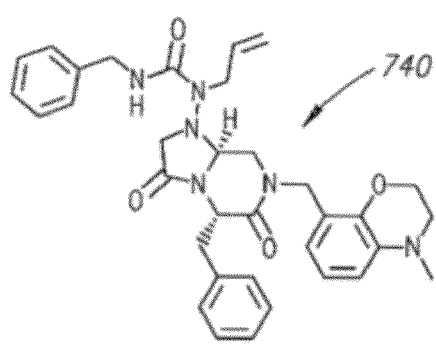
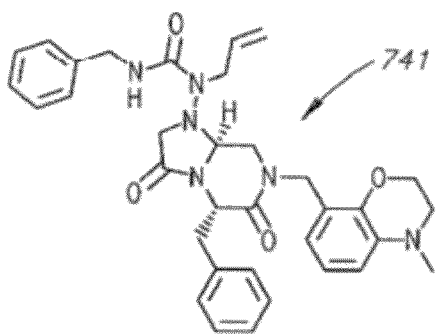
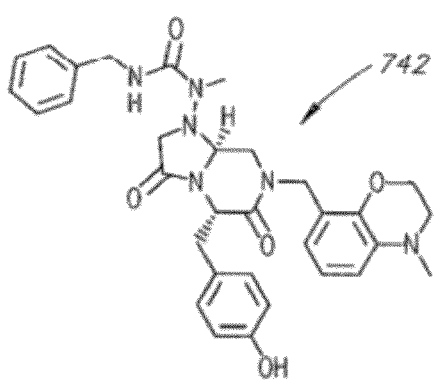
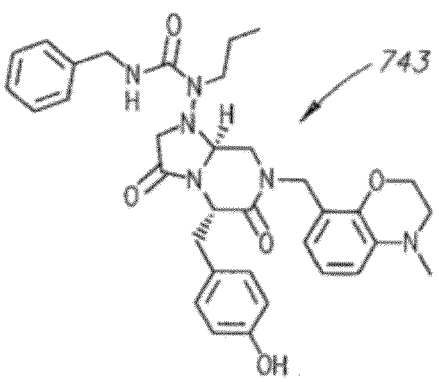
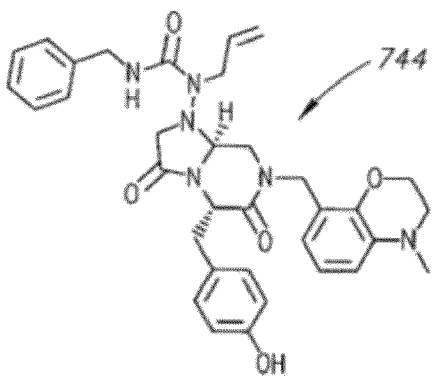
FIG.4R

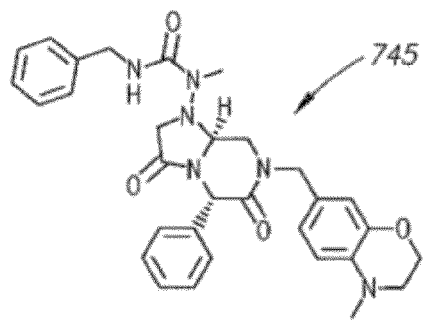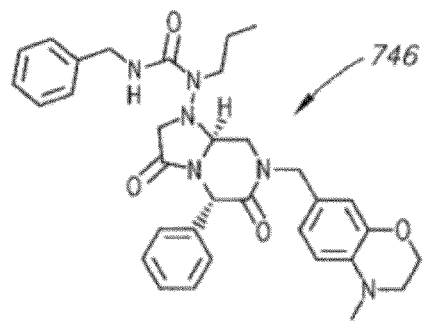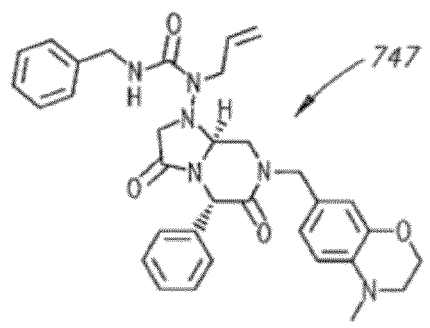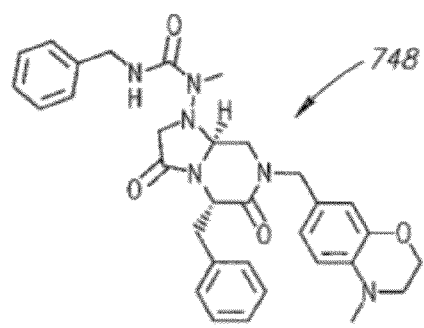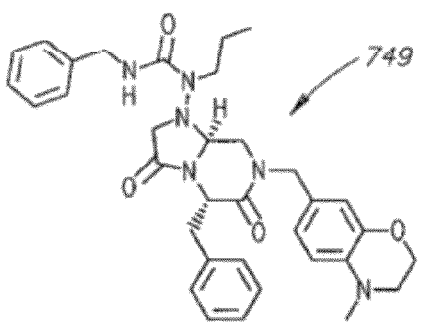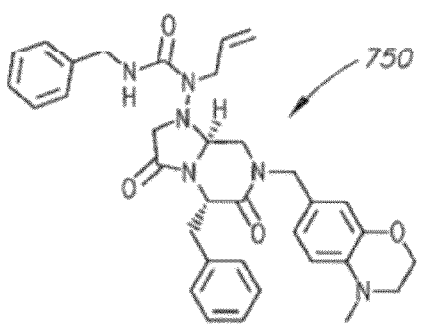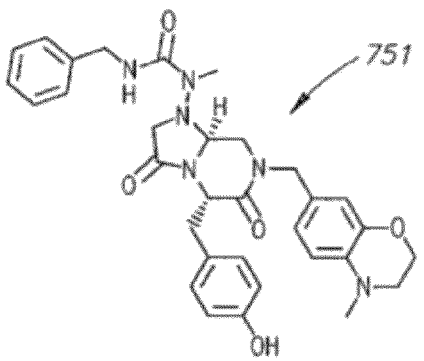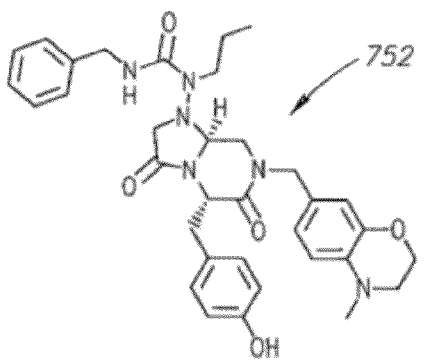
FIG.4S

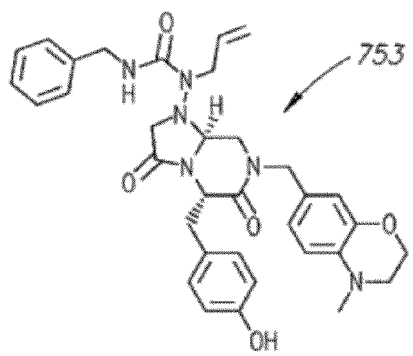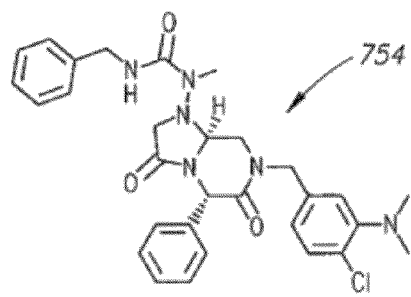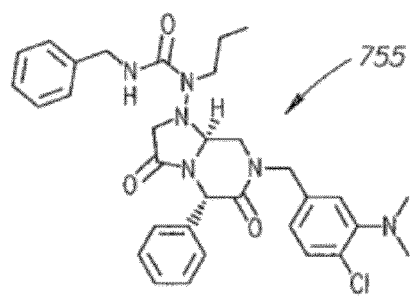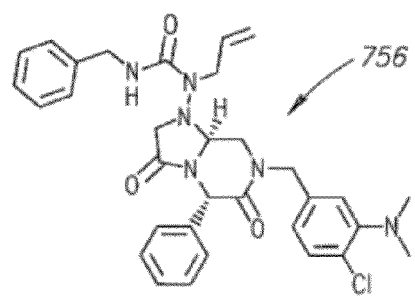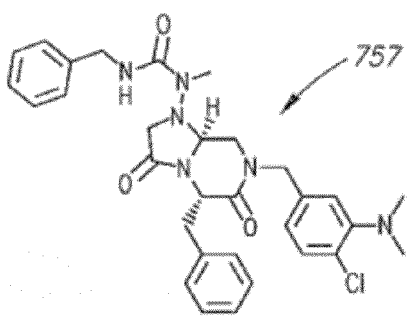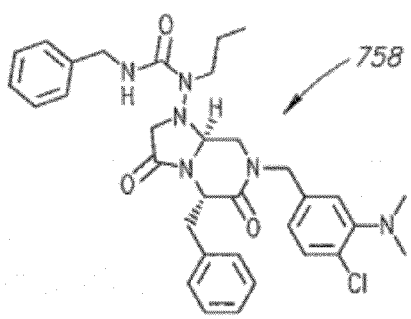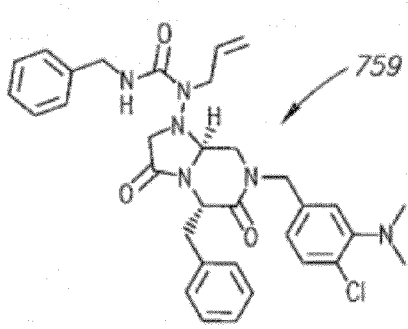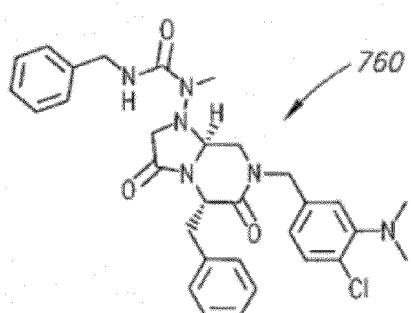
FIG.4T

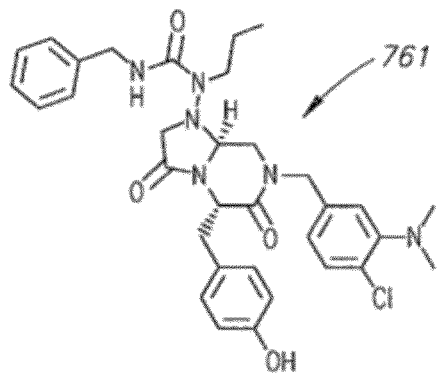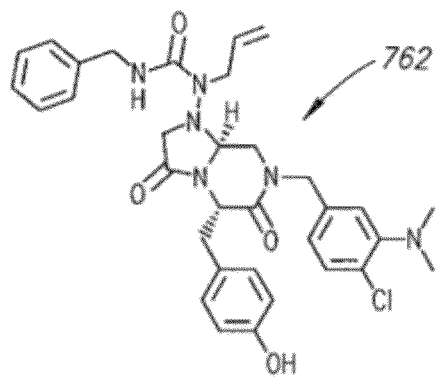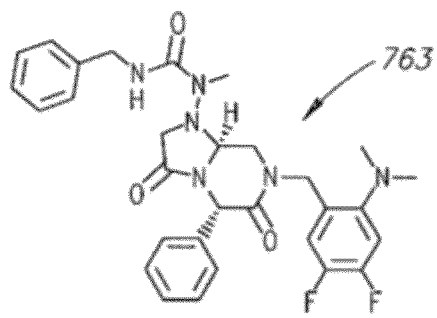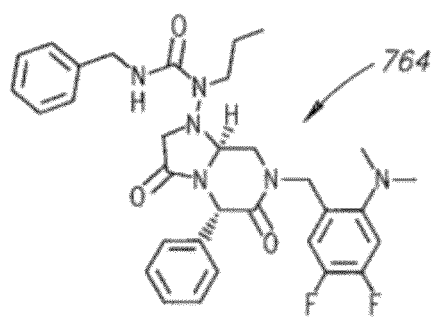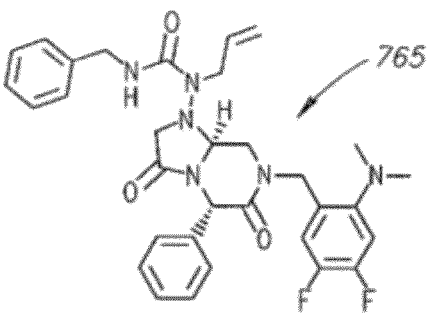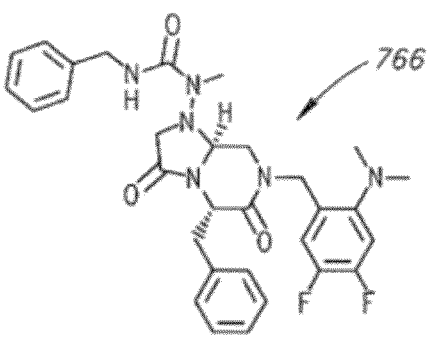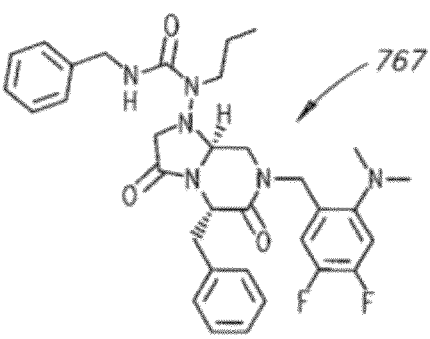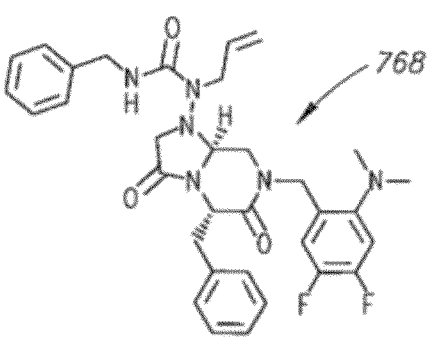
FIG.4U

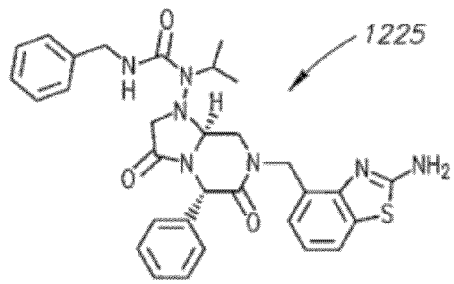
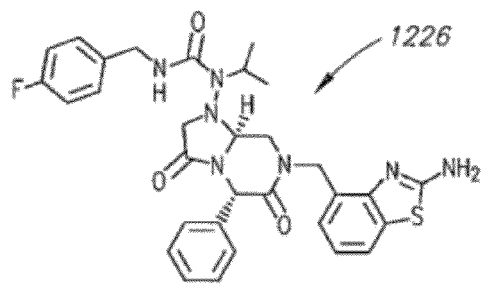
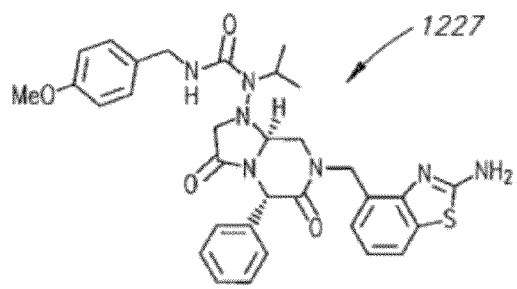
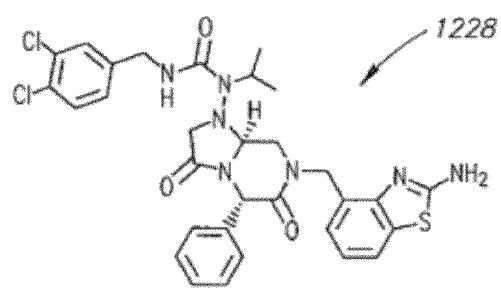
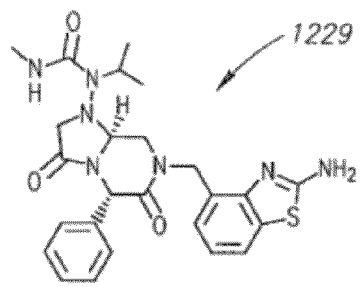
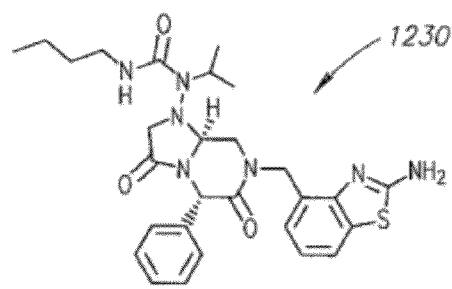
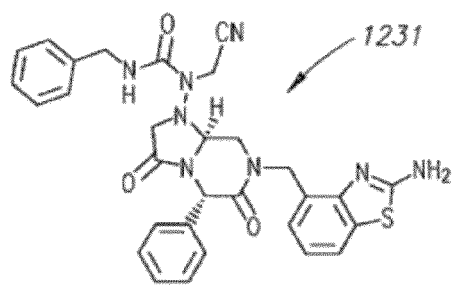
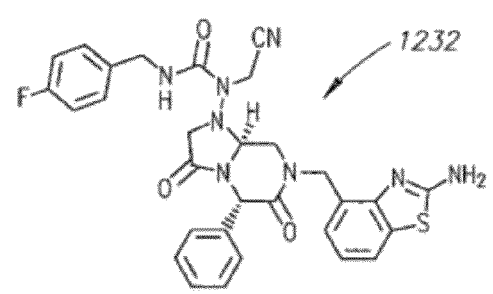
FIG.7D

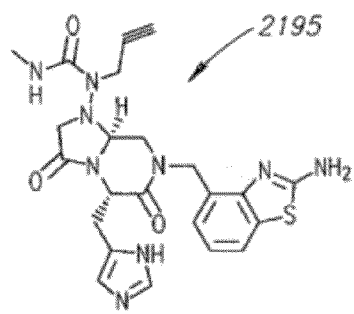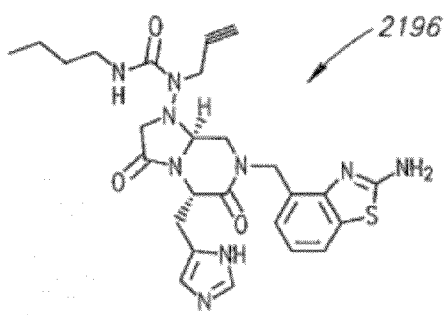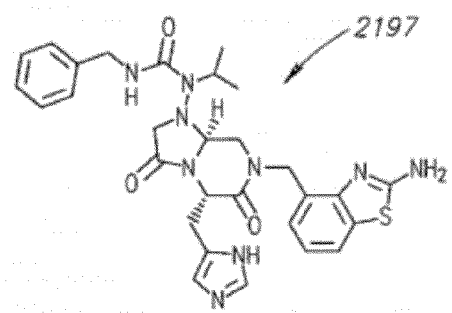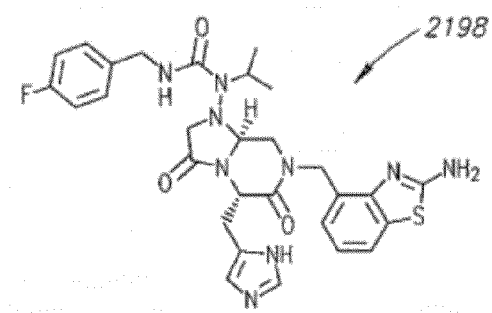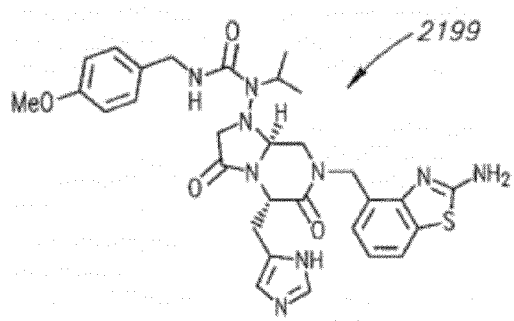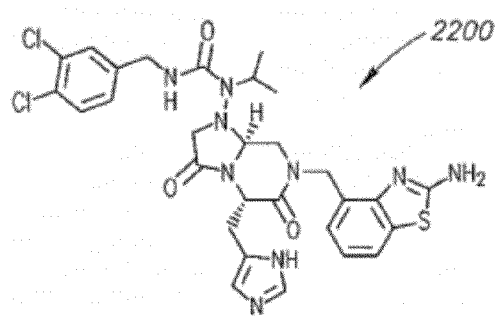
FIG.11AA

FIGURE 13
A.
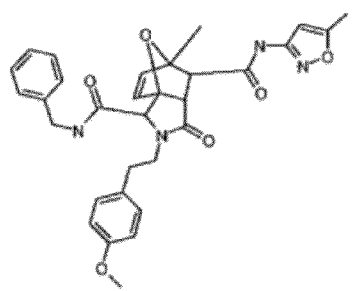
ASN 06387747
B.
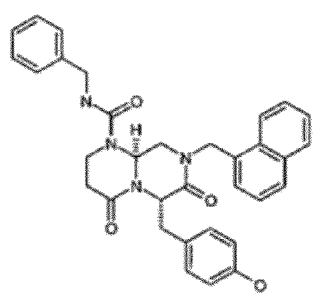
ICG001
C.

ICG-001 Does Not Affect Colony Formation Of Normal CD34+ Hematopoietic Cells

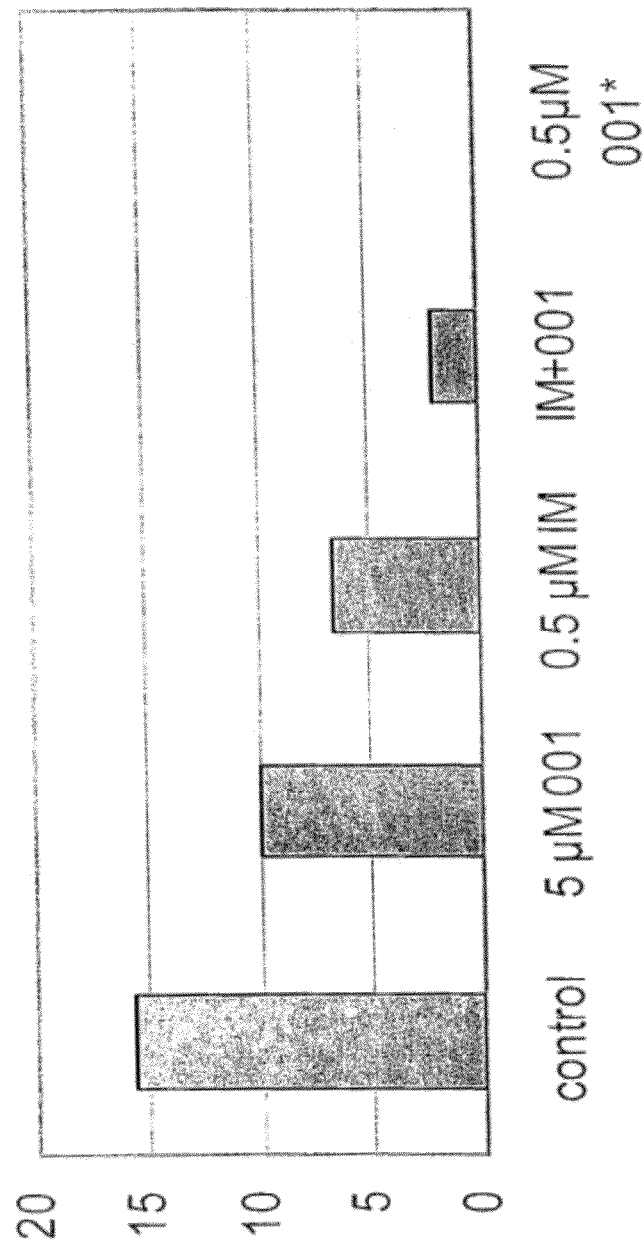

Colony Counts For 2 CML Patients

Patient 1 – Late Chronic Phase, off IM for 6 months
Patient 2 – Blast Crisis Patient on Imatinib Sensitivity of A2780 and its cisplatin-resistant variant, CP70, to cisplatin and ICG-001.

SUBSTITUTED IMIDAZO[1,2-A]PYRAZINE DERIVATIVES AS ALPHA-HELIX MIMETICS AND METHOD RELATING TO THE TREATMENT OF CANCER STEM CELLS

CROSS-REFERENCE TO RELATED APPLICATION

This application is a continuation application of U.S. application Ser. No. 11/594,576, filed Nov. 8, 2006, now pending, which claims the benefit under 35 U.S.C. §119(e) of U.S. Provisional Patent Application No. 60/734,655, filed on Nov. 8, 2005; where these two applications are incorporated herein by reference in their entireties.

TECHNICAL FIELD

The present invention relates generally to α-helix mimetic structures and to a chemical library relating thereto. The invention specifically relates to applications in the treatment of cancer and particularly cancer stem cells and pharmaceutical compositions comprising the α-helix mimetics.

BACKGROUND

Despite the clonal origin of many cancers, most primary tumors display a notable degree of cellular heterogeneity. Although modern chemotherapies kill a majority of the cells in a tumor, evidence clearly indicates that cancer stems cells often remain. The cancer stem cell hypothesis posits that a very rare population of cells within tumors are the only tumor cells with the capacity for limitless self-renewal. This concept has important therapeutic implications, and may explain why it is possible to treat many cancers until the tumor can no longer be detected and yet the cancer returns. There is a need in the art for compositions and methods that will inhibit, reduce, and/or eliminate cancer stem cells from a patient.

The present invention also fulfills these needs, and provides further related advantages by providing conformationally constrained compounds which mimic the secondary structure of α-helix regions of biologically active peptides and proteins and particularly selectively disrupt the β-catenin/CBP interaction.

SUMMARY

Provided is a compound having the following general formula (I):

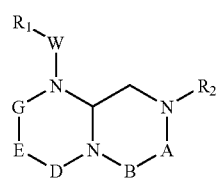

(I)

wherein A is —(C=O)—CHR$_3$—, or —(C=O), B is N—R$_5$— or —CHR$_6$—, D is —(C=O)—(CHR$_7$)— or —(C=O)—, E is —(ZR$_8$)— or (C=O), G is —(XR$_9$)$_n$—, —(CHR$_{10}$)—(NR$_6$)—, —(C=O)—(XR$_{12}$)—, —(C=N—W—R$_1$)—, —(C=O)—, X—(C=O)—R$_{13}$, X—(C=O)—NR$_{13}$R$_{14}$, X—(SO$_2$)—R$_{13}$, or X—(C=O)—OR$_{13}$, W is —Y(C=O)—, —(C=O)NH—, —(SO$_2$)—, —CHR$_{14}$, (C=O)—(NR$_{15}$)—, substituted or unsubstituted oxadiazole, substituted or unsubstituted triazole, substituted or unsubstituted thiadiazole, substituted or unsubstituted 4,5 dihydrooxazole, substituted or unsubstituted 4,5 dihydrothiazole, substituted or unsubstituted 4,5 dihydroimidazole, or nothing, Y is oxygen or sulfur, X and Z is independently nitrogen or CH, n=0 or 1; and R$_1$, R$_2$, R$_3$, R$_4$, R$_5$, R$_6$, R$_7$, R$_8$, R$_9$, R$_{10}$, R$_{11}$, R$_{12}$, R$_{13}$, R$_{14}$, and R$_{15}$ are the same or different and independently selected from an amino acid side chain moiety or derivative thereof, the remainder of the molecule, a linker and a solid support, and stereoisomers, salts, and prodrugs thereof, provided that where B is CHR$_6$ and W is —Y(C=O)—, —(C=O)NH—, —(SO$_2$)—, —CHR$_{14}$, or (C=O)—(NR$_{15}$)—, G cannot be CHR$_9$, NR$_9$, (C=O)—CHR$_{12}$, (C=O)—NR$_{12}$, or no atom at all.

Also provided is a compound, salts, and prodrugs thereof of formula (I), wherein R$_1$, R$_2$, R$_3$, R$_4$, R$_5$, R$_6$, R$_7$, R$_8$, R$_9$, R$_{10}$, R$_{11}$, R$_{12}$, R$_{13}$, R$_{14}$, are R$_{15}$ are independently selected from the group consisting of aminoC$_{2-5}$alkyl, guanidinoC$_{2-5}$alkyl, C$_{1-4}$alkylguanidinoC$_{2-5}$alkyl, diC$_{1-4}$alkylguanidinoC$_{2-5}$alkyl, amidinoC$_{2-5}$alkyl, C$_{1-4}$alkylamidinoC$_{2-5}$alkyl, diC$_{1-4}$alkylamidinoC$_{2-5}$alkyl, C$_{1-3}$alkoxy, phenyl, substituted phenyl (where the substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), benzyl, substituted benzyl (where the substituents on the benzyl are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), naphthyl, substituted naphthyl (where the substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), bis-phenyl methyl, substituted bis-phenyl methyl (where the substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), pyridyl, substituted pyridyl (where the substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), pyridylC$_{1-4}$alkyl, substituted pyridylC$_{1-4}$alkyl (where the pyridine substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), pyrimidylC$_{1-4}$alkyl, substituted pyrimidylC$_{1-4}$alkyl (where the pyrimidine substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy or nitro, carboxy, cyano, sulfuryl or hydroxyl), triazin-2-yl-C$_{1-4}$alkyl, substituted triazin-2-yl-C$_{1-4}$alkyl (where the triazine substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), imidazoC$_{1-4}$alkyl, substituted imidazol C$_{1-4}$alkyl (where the imidazole substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, $C_{1-3}$alkoxy, nitro, carboxy, cyano, sulfuryl, hydroxyl, or methyl), imidazolinyl$C_{1-4}$alkyl, N-amidinopiperazinyl-N—$C_{0-4}$alkyl, hydroxy$C_{2-5}$alkyl, $C_{1-5}$alkylamino$C_{2-5}$alkyl, hydroxy$C_{2-5}$alkyl, $C_{1-5}$alkylamino$C_{2-5}$alkyl, $C_{1-5}$dialkylamino$C_{2-5}$alkyl, N-amidinopiperidinyl$C_{1-4}$alkyl and 4-aminocyclohexyl$C_{0-2}$alkyl.

Further provided is the compound, salts, and prodrugs thereof of compound (I) wherein A is —(CHR$_3$)—(C=O)—, B is —(NR$_4$)—, D is (C=O)—, E is —(ZR$_6$)—, G is —(C=O)—(XR$_9$)—, and the compound has the following general formula (III):

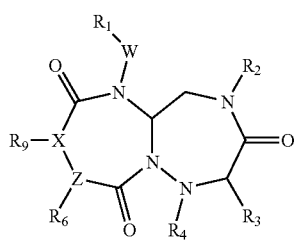

(III)

wherein $R_1$, $R_2$, $R_4$, $R_6$, $R_9$, W and X are as defined in claim 1, Z is nitrogen or CH (when Z is CH, the X is nitrogen).

Also provided is a compound, salts, and prodrugs thereof of formula (I) wherein A is —O—CHR$_3$—, B is —NR$_{4-5}$—, D is —(C=O)—, E is —(ZR$_6$)—, G is (XR$_7$)$_n$—, the α-helix mimetic compounds of this invention have the following formula (IV):

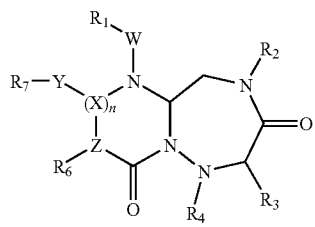

(IV)

wherein $R_1$, $R_2$, $R_4$, $R_6$, $R_7$, $R_8$ W, X and n are as defined above, Y is —C=O, —(C=O)—O—, —(C=O)—NR$_8$, —SO$_2$—, or nothing, and Z is nitrogen or CH (when Z is nitrogen, then n is zero, and when Z is CH, then X is nitrogen and n is not zero). In a preferred embodiment, $R_1$, $R_2$, $R_6$, $R_7$, and $R_8$ represent the remainder of the compound, and $R_4$ is selected from an amino acid side chain moiety. In this case, $R_6$ or $R_7$ may be selected from an amino acid side chain moiety when Z and X are CH, respectively.

Further provided is a compound, salts, and prodrugs thereof of formula (I) wherein A is —(C=O), B is —(CHR$_6$)—, D is —(C=O)—, E is —(ZR$_8$)—, and G is —(NH)— or —(CH$_2$)—, and W is a substituted or unsubstituted oxadiazole, substituted or unsubstituted triazole, substituted or unsubstituted thiadiazole, substituted or unsubstituted 4,5 dihydrooxazole, substituted or unsubstituted 4,5 dihydrothiazole, substituted or unsubstituted 4,5 dihydroimidazole, the α-helix mimetic compounds of this invention have the following formula (V):

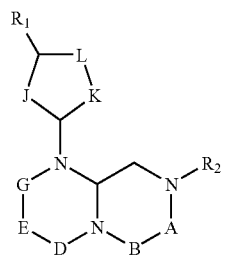

(V)

wherein K is nitrogen, oxygen, or sulfur, L is nitrogen, oxygen, —(CH)—, or —(CH$_2$)—, J is nitrogen, oxygen, or sulfur, Z is nitrogen or CH, and $R_1$, $R_2$, $R_6$, $R_8$, and $R_{13}$ are selected from an amino acid side chain moiety.

Also provided is a compound having the general formula (VI):

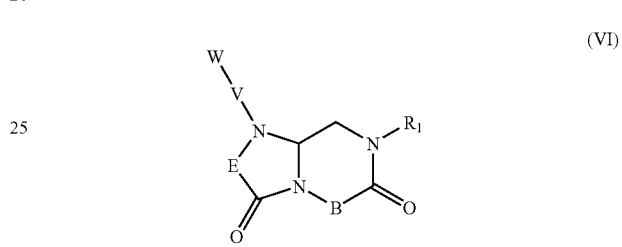

(VI)

wherein B is —(CHR$_2$)—, —(NR$_2$)—, E is —(CHR$_3$)—, V is —(XR$_4$)— or nothing, W is —(C=O)—(XR$_5$R$_6$), —(SO$_2$)—, substituted or unsubstituted oxadiazole, substituted or unsubstituted triazole, substituted or unsubstituted thiadiazole, substituted or unsubstituted 4,5 dihydrooxazole, substituted or unsubstituted 4,5 dihydrothiazole, substituted or unsubstituted 4,5 dihydroimidazole, X is independently nitrogen, oxygen, or CH, and $R_1$, $R_2$, $R_3$, $R_4$, $R_5$ and $R_6$ are selected from an amino acid side chain moiety or derivative thereof, the remainder of the molecule, a linker and solid support, and stereoisomers, salts, and prodrugs thereof.

Further provided is a compound, salts, and prodrugs thereof of formula (I), wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, are $R_{15}$ are independently selected from the group consisting of amino$C_{2-5}$alkyl, guanidino$C_{2-5}$alkyl, $C_{1-4}$alkylguanidino$C_{2-5}$alkyl, di$C_{1-4}$alkylguanidino-$C_{2-5}$alkyl, amidino$C_{2-5}$alkyl, $C_{1-4}$alkylamidino$C_{2-5}$alkyl, di$C_{1-4}$alkylamidino$C_{2-5}$alkyl, $C_{1-3}$alkoxy, phenyl, substituted phenyl (where the substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), benzyl, substituted benzyl (where the substituents on the benzyl are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), naphthyl, substituted naphthyl (where the substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), bisphenyl methyl, substituted bis-phenyl methyl (where the substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), pyridyl, substituted pyridyl (where the substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), pyridyl$C_{1-4}$alkyl, substituted pyridyl$C_{1-4}$alkyl (where the pyridine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), pyrimidyl$C_{1-4}$alkyl, substituted pyrimidyl$C_{1-4}$alkyl (where the pyrimidine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro, carboxy, cyano, sulfuryl or hydroxyl), triazin-2-yl-$C_{1-4}$alkyl, substituted triazin-2-yl-$C_{1-4}$alkyl (where the triazine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), imidazo$C_{1-4}$alkyl, substituted imidazol $C_{1-4}$alkyl (where the imidazole substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl, hydroxyl, or methyl), imidazolinyl$C_{1-4}$alkyl, N-amidinopiperazinyl-N—$C_{0-4}$alkyl, hydroxy$C_{2-5}$alkyl, $C_{1-5}$alkylamino$C_{2-5}$alkyl, hydroxy$C_{2-5}$alkyl, $C_{1-5}$alkylamino$C_{2-5}$alkyl, $C_{1-5}$dialkylamino$C_{2-5}$alkyl, N-amidinopiperidinyl$C_{1-4}$alkyl and 4-aminocyclohexyl$C_{0-2}$alkyl. Further provided is a compound, salts, and prodrugs thereof wherein B is —(CH)—(CH$_3$), E is —(CH)—(CH$_3$), V is —(XR$_4$)— or nothing, and W is substituted or unsubstituted oxadiazole, substituted or unsubstituted triazole, substituted or unsubstituted thiadiazole, substituted or unsubstituted 4,5 dihydrooxazole, substituted or unsubstituted 4,5 dihydrothiazole, substituted or unsubstituted 4,5 dihydroimidazole, and X is independently introgen or CH, the compounds have the following general formula (VII):

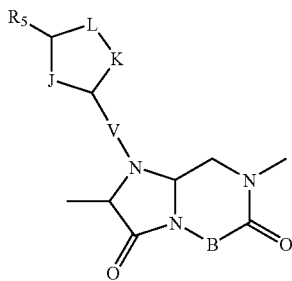

(VII)

wherein K is nitrogen, oxygen, or sulfur, L is nitrogen, oxygen, —(CH)—, or —(CH$_2$)—, J is nitrogen, oxygen, or sulfur, and R$_5$ is independently selected from the group consisting of amino$C_{2-5}$alkyl, guanidino$C_{2-5}$alkyl, $C_{1-4}$alkylguanidino$C_{2-5}$alkyl, di$C_{1-4}$alkylguanidino$C_{2-5}$alkyl, amidino$C_{2-5}$alkyl, $C_{1-4}$alkylamidino$C_{2-5}$alkyl, di$C_{1-4}$alkylamidino$C_{2-5}$alkyl, $C_{1-3}$alkoxy, Phenyl, substituted phenyl (where the substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), benzyl, substituted benzyl (where the substituents on the benzyl are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), naphthyl, substituted naphthyl (where the substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), bis-phenyl methyl, substituted bis-phenyl methyl (where the substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), pyridyl, substituted pyridyl, (where the substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), pyridyl$C_{1-4}$alkyl, substituted pyridyl$C_{1-4}$alkyl (where the pyridine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), pyrimidyl$C_{1-4}$alkyl, substituted pyrimidyl$C_{1-4}$alkyl (where the pyrimidine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro, carboxy, cyano, sulfuryl or hydroxyl), triazin-2-yl-$C_{1-4}$alkyl, substituted triazin-2-yl-$C_{1-4}$alkyl (where the triazine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), imidazo$C_{1-4}$alkyl, substituted imidazol $C_{1-4}$alkyl (where the imidazole substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl, hydroxyl, or methyl), imidazolinyl$C_{1-4}$alkyl, N-amidinopiperazinyl-N—$C_{0-4}$alkyl, hydroxy$C_{2-5}$alkyl, $C_{1-5}$alkylamino$C_{2-5}$alkyl, hydroxy$C_{2-5}$alkyl, $C_{1-5}$alkylamino$C_{2-5}$alkyl, $C_{1-5}$dialkylamino$C_{2-5}$alkyl, N-amidinopiperidinyl$C_{1-4}$alkyl and 4-aminocyclohexyl$C_{0-2}$alkyl.

Provided is a pharmaceutical composition comprising a compound of the following general formula (I):

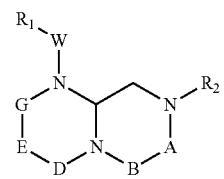

(I)

wherein A is —(C=O)—CHR$_3$—, or —(C=O), B is N—R$_5$— or —CHR$_6$—, D is —(C=O)—(CHR)— or —(C=O)—, E is —(ZR$_8$)— or (C=O), G is —(XR$_9$)$_n$—, —(CHR$_{10}$)—(NR$_6$)—, —(C=O)—(XR$_{12}$)—, -(or nothing)-, —(C=O)—, X—(C=O)—R$_{13}$, X—(C=O)—

$NR_{13}R_{14}$, $X—(SO_2)—R_{13}$, or $X—(C=O)—OR_{13}$, W is —Y(C=O)—, —(C=O)NH—, —(SO$_2$)—, —CHR$_{14}$, (C=O)—(NR$_{15}$)—, substituted or unsubstituted oxadiazole, substituted or unsubstituted triazole, substituted or unsubstituted thiadiazole, substituted or unsubstituted 4,5 dihydrooxazole, substituted or unsubstituted 4,5 dihydrothiazole, substituted or unsubstituted 4,5 dihydroimidazole, or nothing, Y is oxygen or sulfur, X and Z is independently nitrogen or CH, n=0 or 1; and $R_1, R_2, R_3, R_4, R_5, R_6, R_7, R_8, R_9, R_{10}, R_{11}, R_{12}, R_{13}, R_{14}$, and $R_{15}$ are the same or different and independently selected from an amino acid side chain moiety or derivative thereof, the remainder of the molecule, a linker and a solid support, and stereoisomers, salts, and prodrugs thereof, and a pharmaceutically acceptable carrier.

Also provided is a pharmaceutical composition comprising the compound of formula (I), wherein $R_1, R_2, R_3, R_4, R_5, R_6, R_7, R_8, R_9, R_{10}, R_{11}, R_{12}, R_{13}, R_{14}$, are $R_{15}$ are independently selected from the group consisting of aminoC$_{2-5}$alkyl, guanidinoC$_{2-5}$alkyl, C$_{1-4}$alkylguanidinoC$_{2-5}$alkyl, diC$_{1-4}$alkylguanidino-C$_{2-5}$alkyl, amidinoC$_{2-5}$alkyl, C$_{1-4}$alkylamidinoC$_{2-5}$alkyl, diC$_{1-4}$alkylamidinoC$_{2-5}$alkyl, C$_{1-3}$alkoxy, phenyl, substituted phenyl (where the substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), benzyl, substituted benzyl (where the substituents on the benzyl are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), naphthyl, substituted naphthyl (where the substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), bis-phenyl methyl, substituted bis-phenyl methyl (where the substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), pyridyl, substituted pyridyl (where the substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), pyridylC$_{1-4}$alkyl, substituted pyridylC$_{1-4}$alkyl (where the pyridine substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), pyrimidylC$_{1-4}$alkyl, substituted pyrimidylC$_{1-4}$alkyl (where the pyrimidine substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy or nitro, carboxy, cyano, sulfuryl or hydroxyl), triazin-2-yl-C$_{1-4}$alkyl, substituted triazin-2-yl-C$_{1-4}$alkyl (where the triazine substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), imidazoC$_{1-4}$alkyl, substituted imidazol C$_{1-4}$alkyl (where the imidazole substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl, hydroxyl, or methyl), imidazolinylC$_{1-4}$alkyl, N-amidinopiperazinyl-N—C$_{0-4}$alkyl, hydroxyC$_{2-5}$alkyl, C$_{1-5}$alkylaminoC$_{2-5}$alkyl, hydroxyC$_{2-5}$alkyl, C$_{1-5}$alkylaminoC$_{2-5}$ alkyl, C$_{1-5}$dialkylaminoC$_{2-5}$alkyl, N-amidinopiperidinylC$_{1-4}$alkyl and 4-aminocyclohexylC$_{0-2}$alkyl. Further provided is a pharmaceutical composition of formula (I) wherein A is —(CHR$_3$)—(C=O)—, B is —(NR$_4$)—, D is (C=O)—, E is —(ZR$_6$)—, G is —(C=O)—(XR$_9$)—, and the compound has the following general formula (III):

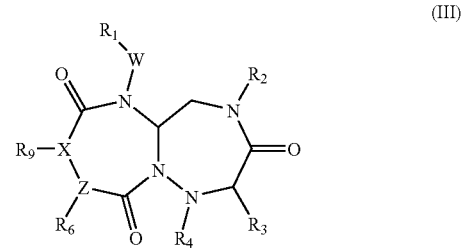

(III)

wherein Z is nitrogen or CH (when Z is CH, the X is nitrogen).

Also provided is a pharmaceutical composition of formula (I) wherein A is —O—CHR$_3$—, B is —NR$_4$—, D is —(C=O)—, E is —(ZR$_6$)—, Gi is (XR$_7$)$_n$—, the α-helix mimetic compounds have the following formula (IV):

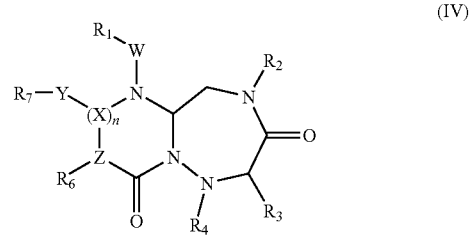

(IV)

wherein $R_1, R_2, R_4, R_6, R_7, R_8$ W, X and n are as defined above, Y is —C=O, —(C=O)—O—, —(C=O)—NR$_8$, —SO$_2$—, or nothing, and Z is nitrogen or CH (when Z is nitrogen, then n is zero, and when Z is CH, then X is nitrogen and n is not zero). In a preferred embodiment, $R_1, R_2, R_6, R_7$, and $R_8$ represent the remainder of the compound, and $R_4$ is selected from an amino acid side chain moiety. In this case, $R_6$ or $R_7$ may be selected from an amino acid side chain moiety when Z and X are CH, respectively. Also provided is a pharmaceutical composition wherein A is —(C=O), B is —(CHR$_6$)—, D is —(C=O)—, E is —(ZR$_8$)—, and G is —(NH)— or —(CH$_2$)—, and W is a substituted or unsubstituted oxadiazole, substituted or unsubstituted triazole, substituted or unsubstituted thiadiazole, substituted or unsubstituted 4,5 dihydrooxazole, substituted or unsubstituted 4,5 dihydrothiazole, substituted or unsubstituted 4,5 dihydroimidazole, the α-helix mimetic compounds of this invention have the following formula (V):

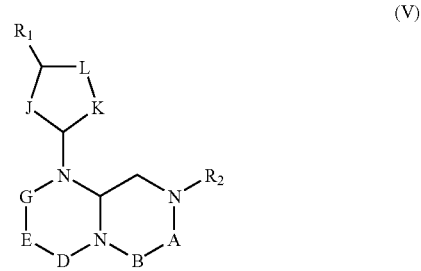

(V)

wherein K is nitrogen, oxygen, or sulfur, L is nitrogen, oxygen, —(CH)—, or —(CH$_2$)—, J is nitrogen, oxygen, or sulfur, Z is nitrogen or CH, and R$_1$, R$_2$, R$_6$, R$_8$, and R$_{13}$ are selected from an amino acid side chain moiety.

Further provided is a pharmaceutical composition comprising a compound having the general formula (VI):

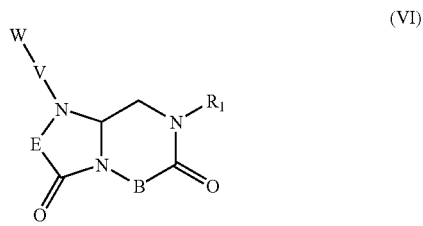

(VI)

wherein B is —(CHR$_2$)—, —(NR$_2$)—, E is —(CHR$_3$)—, V is —(XR$_4$)— or nothing, W is —(C=O)—(XR$_5$R$_6$), —(SO$_2$)—, substituted or unsubstituted oxadiazole, substituted or unsubstituted triazole, substituted or unsubstituted thiadiazole, substituted or unsubstituted 4,5 dihydrooxazole, substituted or unsubstituted 4,5 dihydrothiazole, substituted or unsubstituted 4,5 dihydroimidazole, X is independently nitrogen, oxygen, or CH, and R$_1$, R$_2$, R$_3$, R$_4$, R$_5$ and R$_6$ are selected from an amino acid side chain moiety or derivative thereof, the remainder of the molecule, a linker and solid support, and stereoisomers, salts and prodrugs thereof. In this pharmaceutical composition, wherein R$_1$, R$_2$, R$_3$, R$_4$, R$_5$, R$_6$, R$_7$, R$_8$, R$_9$, R$_{10}$, R$_{11}$, R$_{12}$, R$_{13}$, R$_{14}$, are R$_{15}$ are independently selected from the group consisting of aminoC$_{2-5}$alkyl, guanidinoC$_{2-5}$alkyl, C$_{1-4}$alkylguanidinoC$_{2-5}$alkyl, diC$_{1-4}$alkylguanidino-C$_{2-5}$alkyl, amidinoC$_{2-5}$alkyl, C$_{1-4}$alkylamidinoC$_{2-5}$alkyl, diC$_{1-4}$alkylamidinoC$_{2-5}$alkyl, C$_{1-3}$alkoxy, phenyl, substituted phenyl (where the substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), benzyl, substituted benzyl (where the substituents on the benzyl are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), naphthyl, substituted naphthyl (where the substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), bis-phenyl methyl, substituted bis-phenyl methyl (where the substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), pyridyl, substituted pyridyl (where the substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), pyridylC$_{1-4}$alkyl, substituted pyridylC$_{1-4}$alkyl (where the pyridine substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), pyrimidylC$_{1-4}$alkyl, substituted pyrimidylC$_{1-4}$alkyl (where the pyrimidine substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy or nitro, carboxy, cyano, sulfuryl or hydroxyl), triazin-2-yl-C$_{1-4}$alkyl, substituted triazin-2-yl-C$_{1-4}$alkyl (where the triazine substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), imidazoC$_{1-4}$alkyl, substituted imidazol C$_{1-4}$alkyl (where the imidazole substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl, hydroxyl, or methyl), imidazolinylC$_{1-4}$alkyl, N-amidinopiperazinyl-N—C$_{0-4}$alkyl, hydroxyC$_{2-5}$alkyl, C$_{1-5}$alkylaminoC$_{2-5}$alkyl, hydroxyC$_{2-5}$alkyl, C$_{1-5}$alkylaminoC$_{2-5}$alkyl, C$_{1-5}$dialkylaminoC$_{2-5}$alkyl, N-amidinopiperidinylC$_{1-4}$alkyl and 4-aminocyclohexylC$_{0-2}$alkyl. In certain embodiments, wherein B is —(CH)—(CH$_3$), E is —(CH)—(CH$_3$), V is —(XR$_4$)— or nothing, and W is substituted or unsubstituted oxadiazole, substituted or unsubstituted triazole, substituted or unsubstituted thiadiazole, substituted or unsubstituted 4,5 dihydrooxazole, substituted or unsubstituted 4,5 dihydrothiazole, substituted or unsubstituted 4,5 dihydroimidazole, and X is independently introgen or CH, the compounds have the following general formula (VII):

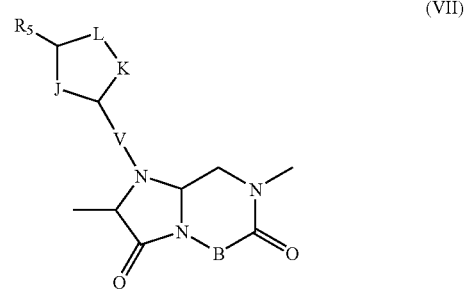

(VII)

wherein K is nitrogen, oxygen, or sulfur, L is nitrogen, oxygen, —(CH)—, or —(CH$_2$)—, J is nitrogen, oxygen, or sulfur, and R$_5$ is independently selected from the group consisting of aminoC$_{2-5}$alkyl, guanidinoC$_{2-5}$alkyl, C$_{1-4}$alkylguanidinoC$_{2-5}$alkyl, diC$_{1-4}$alkylguanidino-C$_{2-5}$alkyl, amidinoC$_{2-5}$alkyl, C$_{1-4}$alkylamidinoC$_{2-5}$alkyl, diC$_{1-4}$alkylamidinoC$_{2-5}$alkyl, C$_{1-3}$alkoxy, Phenyl, substituted phenyl (where the substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), benzyl, substituted benzyl (where the substituents on the benzyl are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), naphthyl, substituted naphthyl (where the substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), bis-phenyl methyl, substituted bis-phenyl methyl (where the substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), pyridyl, substituted pyridyl, (where the substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), pyridyl$C_{1-4}$alkyl, substituted pyridyl$C_{1-4}$alkyl (where the pyridine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), pyrimidyl$C_{1-4}$alkyl, substituted pyrimidyl$C_{1-4}$alkyl (where the pyrimidine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro, carboxy, cyano, sulfuryl or hydroxyl), triazin-2-yl-$C_{1-4}$alkyl, substituted triazin-2-yl-$C_{1-4}$alkyl (where the triazine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), imidazo$C_{1-4}$alkyl, substituted imidazol $C_{1-4}$alkyl (where the imidazole substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl, hydroxyl, or methyl), imidazolinyl$C_{1-4}$alkyl, N-amidinopiperazinyl-N—$C_{0-4}$alkyl, hydroxy$C_{2-5}$alkyl, $C_{1-5}$alkylamino$C_{2-5}$alkyl, hydroxy$C_{2-5}$alkyl, $C_{1-5}$alkylamino$C_{2-5}$alkyl, $C_{1-5}$dialkylamino$C_{2-5}$alkyl, N-amidinopiperidinyl$C_{1-4}$alkyl and 4-aminocyclohexyl$C_{0-2}$alkyl.

Provided is a compound selected from the group consisting of Compounds 1-2217, and pharmaceutical compositions comprising at least one compound of Compounds 1-2217. The pharmaceutical composition may comprise an effective amount of the compound and a pharmaceutically acceptable carrier.

Compounds of the invention may be used in the preparation of a medicament for eradicating pathologic stem cells in cancer therapy. The stem cells are leukaemic stem cells, the stem cells may be derived from solid tumors, and the solid tumor may be derived from breast, brain, lung, colon, liver, and intestine.

Therapeutically effective amount of the compounds are provided, wherein the amount is sufficient to cause cell death or inhibit proliferation and cause differentiation of stem cells in solid tumors or leukemias. The compound according to the invention may be used in the preparation of a medicament for achieving the differentiation of pathologic stem cells by causing a switch from CBP/catenin to p300/catenin transcription in cancer therapy. The catenin may be β-catenin or γ/p120-catenin.

The compounds of the invention may inhibit CBP/catenin signaling in cancer stem cells, such as by inhibiting CBP/catenin signaling in cancer stem cells thereby inducing differentiation of cancer stem cells and making them more susceptible to apoptosis induced by at least one specific pathway inhibitor. The specific pathway may be selected from the group consisting of EGFR pathway; Herceptin, Abl or Kit tyrosine kinase pathway (Imantinib).

Also provided are compounds of the invention delivered to the subject orally, transdermally, intravenously, topically, by inhalation or rectally; delivery may be by sustained release.

The pharmaceutical composition may be administered by a method selected from the group consisting of capsules, tablets, powders, granules, syrups, injectable fluids, creams, ointments, hydrophilic ointments, inhalable fluids, and suppositories.

Further provided are methods of treating a cancerous condition by administering at least one compound or pharmaceutical composition of the invention, wherein the cancerous condition is at least one selected from the group consisting of acute lymphocytic leukemia, acute nonlymphocytic leukemia, cancer of the adrenal cortex, bladder cancer, brain cancer, breast cancer, cervix cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head and neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovary cancer, ovary (germ cell) cancer, pancreatic cancer, penis cancer, prostate cancer, retinoblastoma, skin cancer, soft-tissue sarcoma, squamous cell carcinomas, stomach cancer, testicular cancer, thyroid cancer, trophoblastic neoplasms, cancer of the uterus, vaginal cancer, cancer of the vulva, and Wilm's tumor.

Further provided is a method for eliminating teratoma-forming stem cells prior to transplant into a mammalian subject, comprising incubating a stem cell culture with at least one compound of the invention, wherein the compound inhibits CBP-β-catenin interaction and thereby causes stem cell differentiation.

Also provided is a pharmaceutical composition used in the preparation of a medicament for eradicating pathologic stem cells in cancer therapy.

BRIEF DESCRIPTION OF THE DRAWINGS

FIGS. 13A-C. FIG. 13A shows the structure of the compound ASN 06387747. FIG. 13B shows the structure of the compound ICG001. FIG. 13C shows the structures of ASN 06387747 (green) and ICG001 (red) superimposed. In accordance with an certain embodiments of the present invention, each compound has three pharmacophore rings. Distances measured from the center of each pharmacophore ring may be based on a conformation generated by flexible alignment calculations. As shown in this figure, the distance between F1 and F4 is approximately 9.6 Å, the distance between F1 and F6 is approximately 9.2 Å, and the distance between F4 and F6 is approximately 10.3 Å.

FIGS. 21A-D. FIG. 21A shows that ICG-001 in combination with the respective chemotherapeutic agent was more effective that the chemotherapeutic agent alone or ICG-001 alone in decreasing cell proliferation/viability. FIG. 21B: ICG does not effect CD34+ normal hematopoeitic cells. FIG. 21C: ICG-001* aka PRI-004 completely blocks colony formation at 500 nM concentration. FIG. 21D shows that combination treatment with ICG-001 and imatinib reduced colony forming units more than did either drug treatment alone.

FIGS. 22C and D: RT-PCR analysis for Beta-Catenin, BMI-1, MDR-1, ABCG1, survivin and survivin splice variant delta Ex3in CD34+ cells isolated form bone marrow from an imatinib naïve CML blast crisis patient. Reference is CD34– cells from the same patient. FIG. 22D: colony formation assay with CD34+ cells from an imatinib naïve blast crisis CML patient. FIG. 22E: hematoxylin and eosin staining for CD34+ blasts treated with 0.5 µM imatinib alone (top) or in combination with ICG-001 5 µM.

DETAILED DESCRIPTION

Figure 1A:
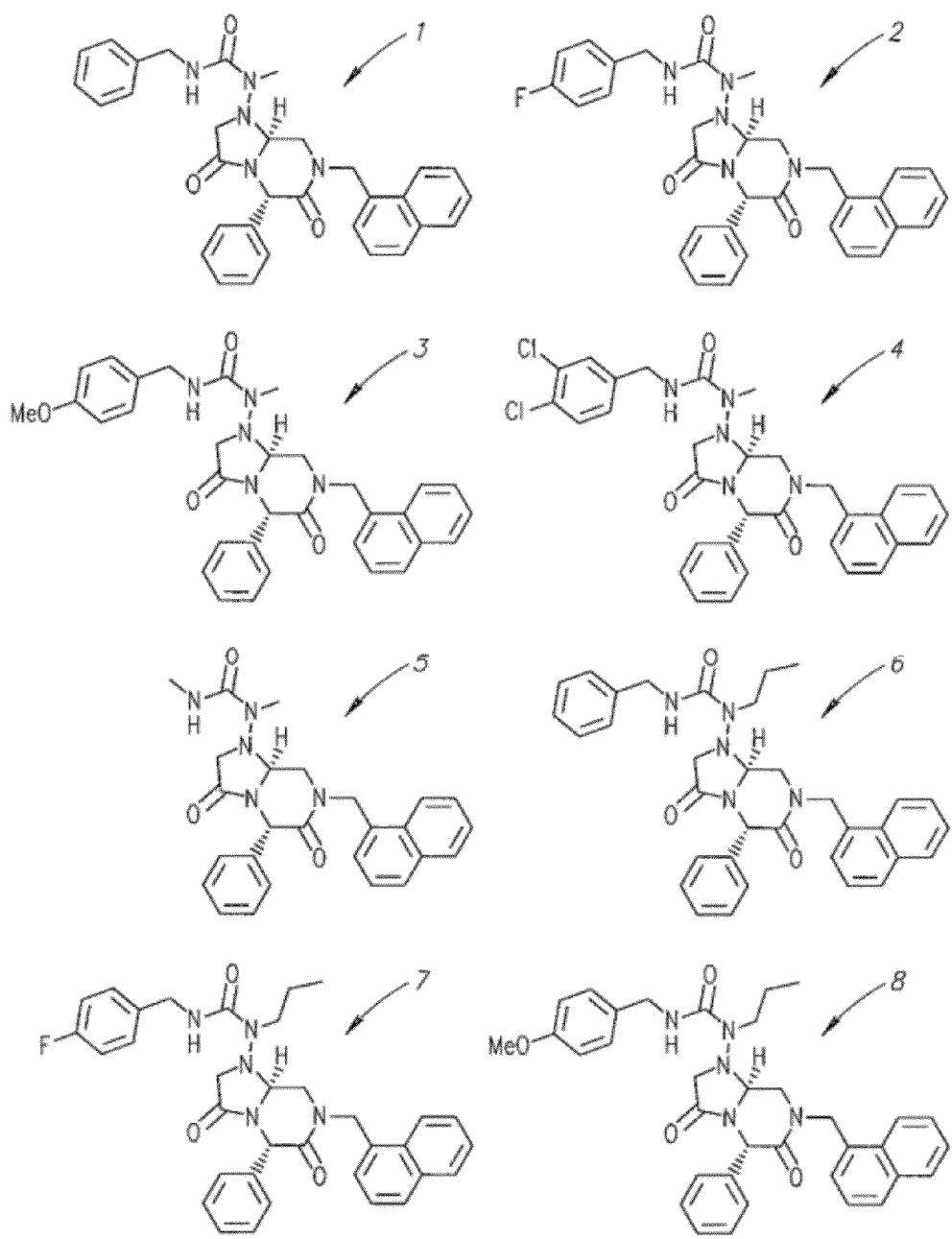
FIGS. 1A-Z shows the chemical structures of compounds 1-200.
Figure 1B:
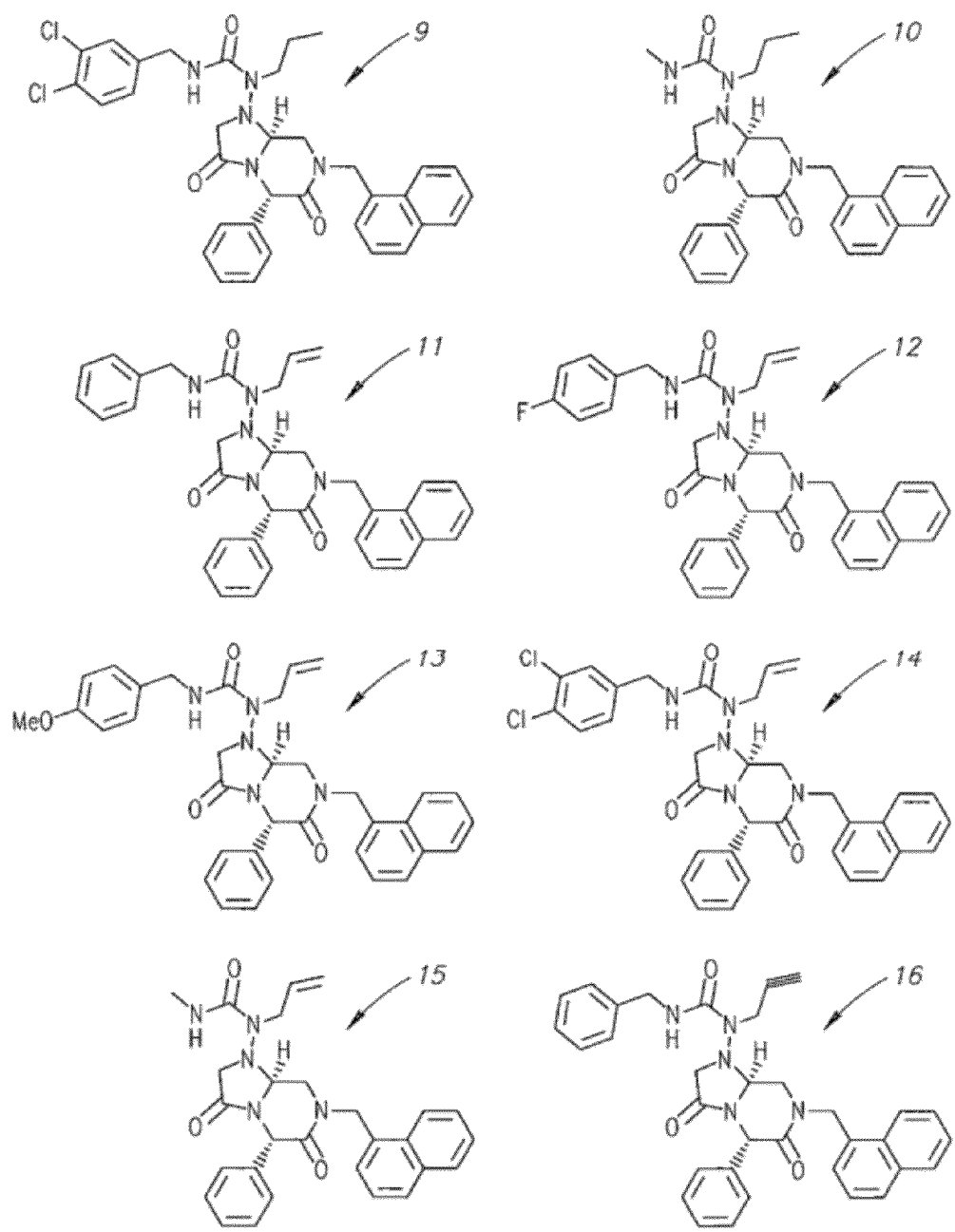
Figure 1C:
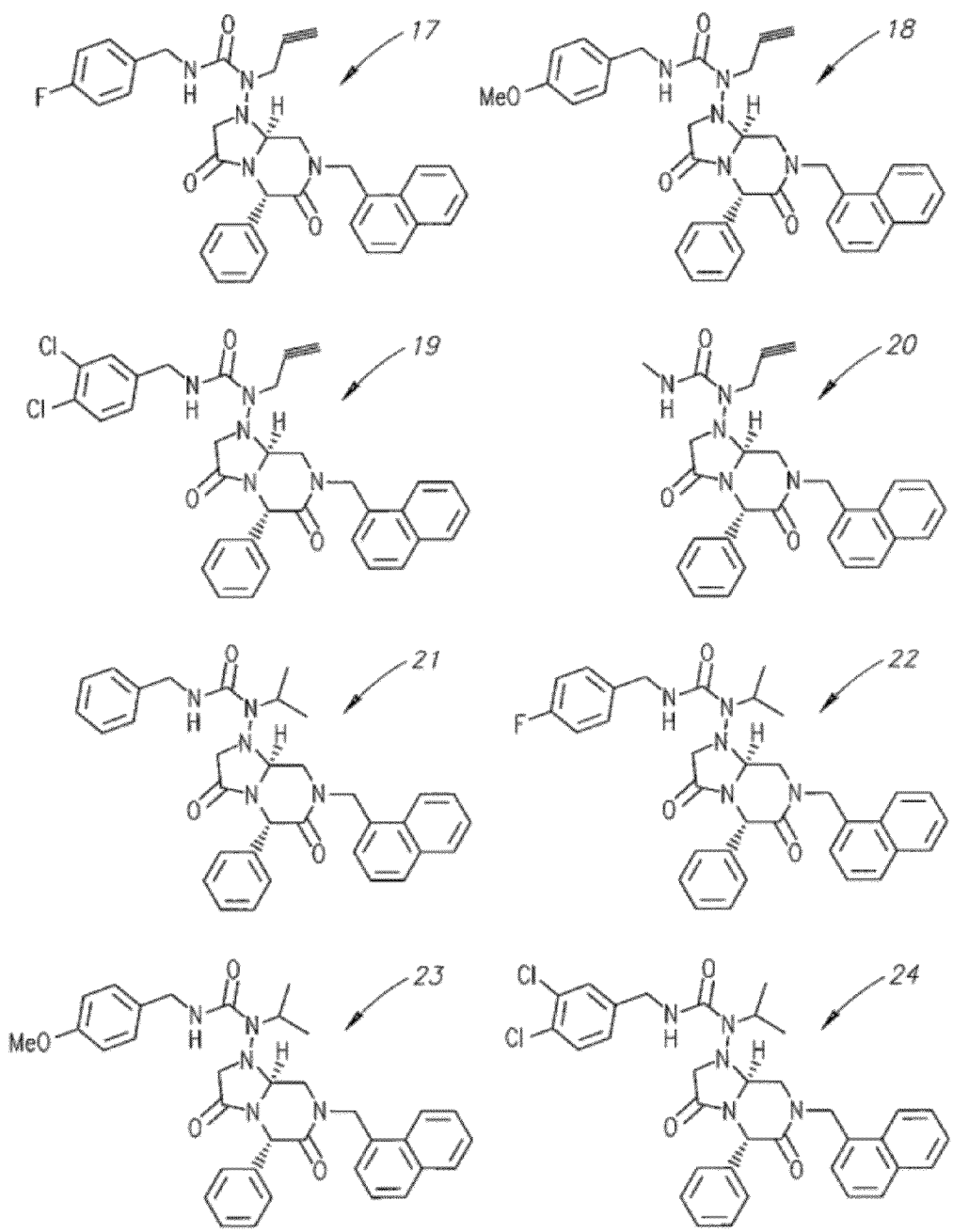
Figure 1D:
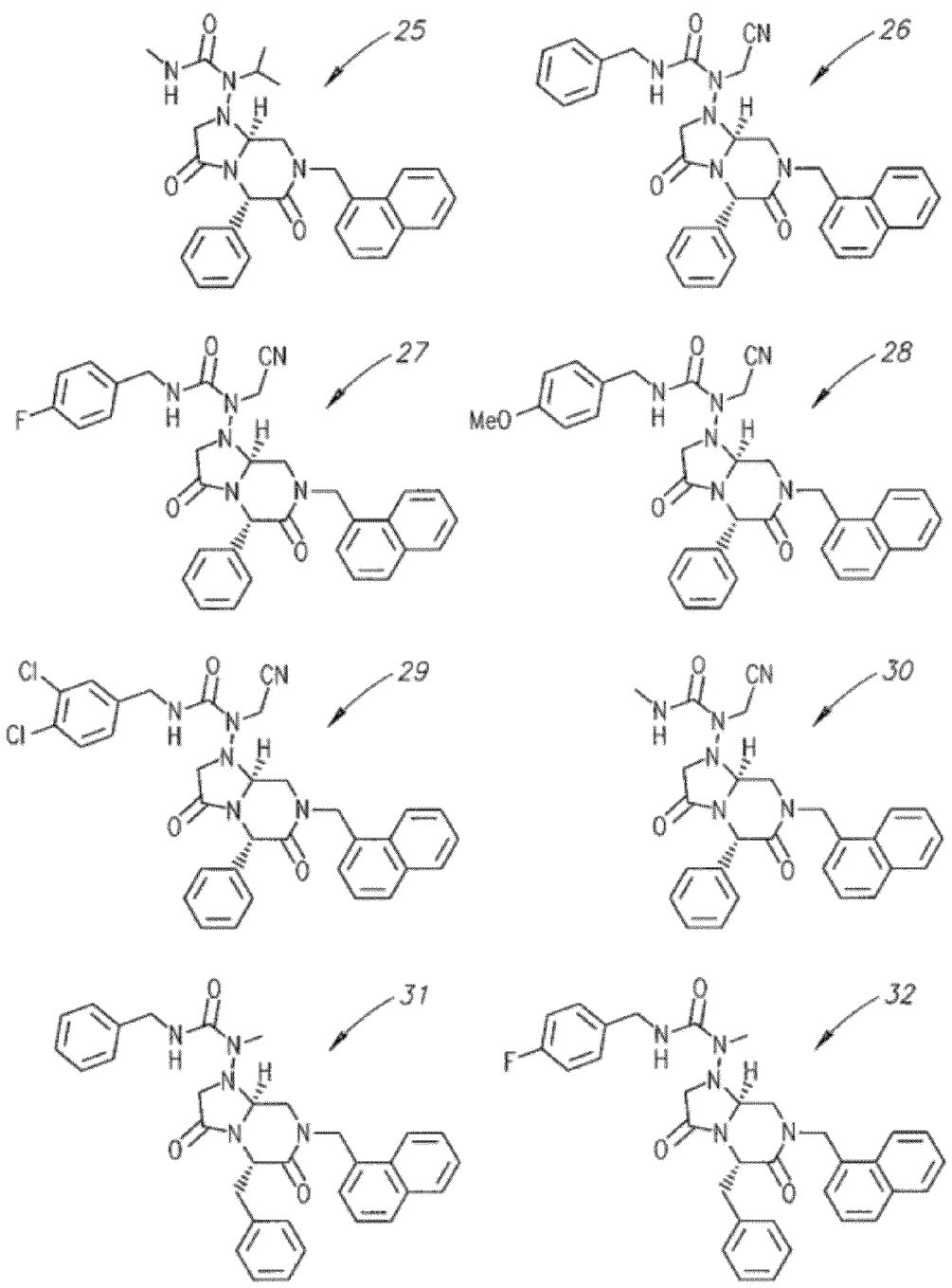
Figure 1E:
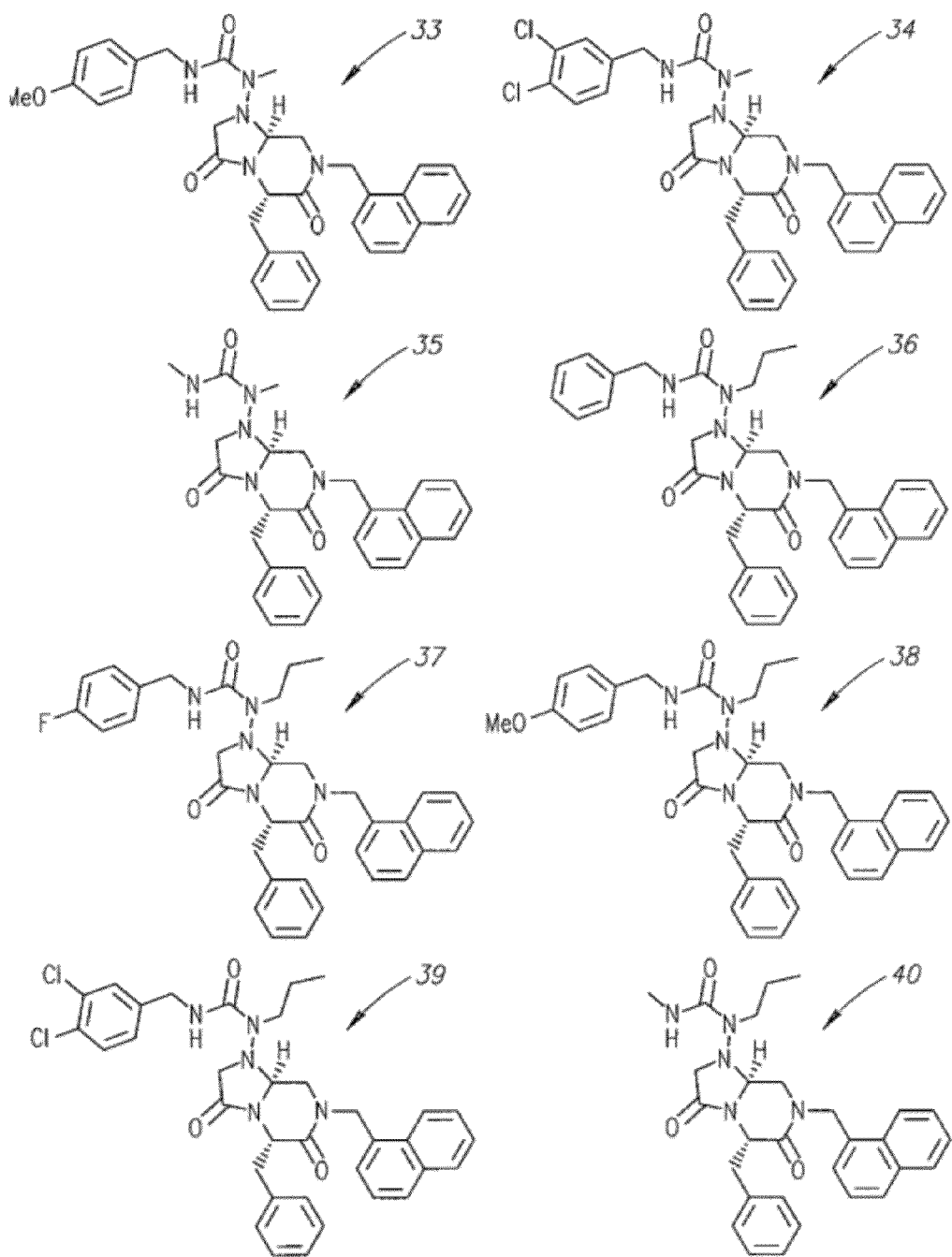
Figure 1F:
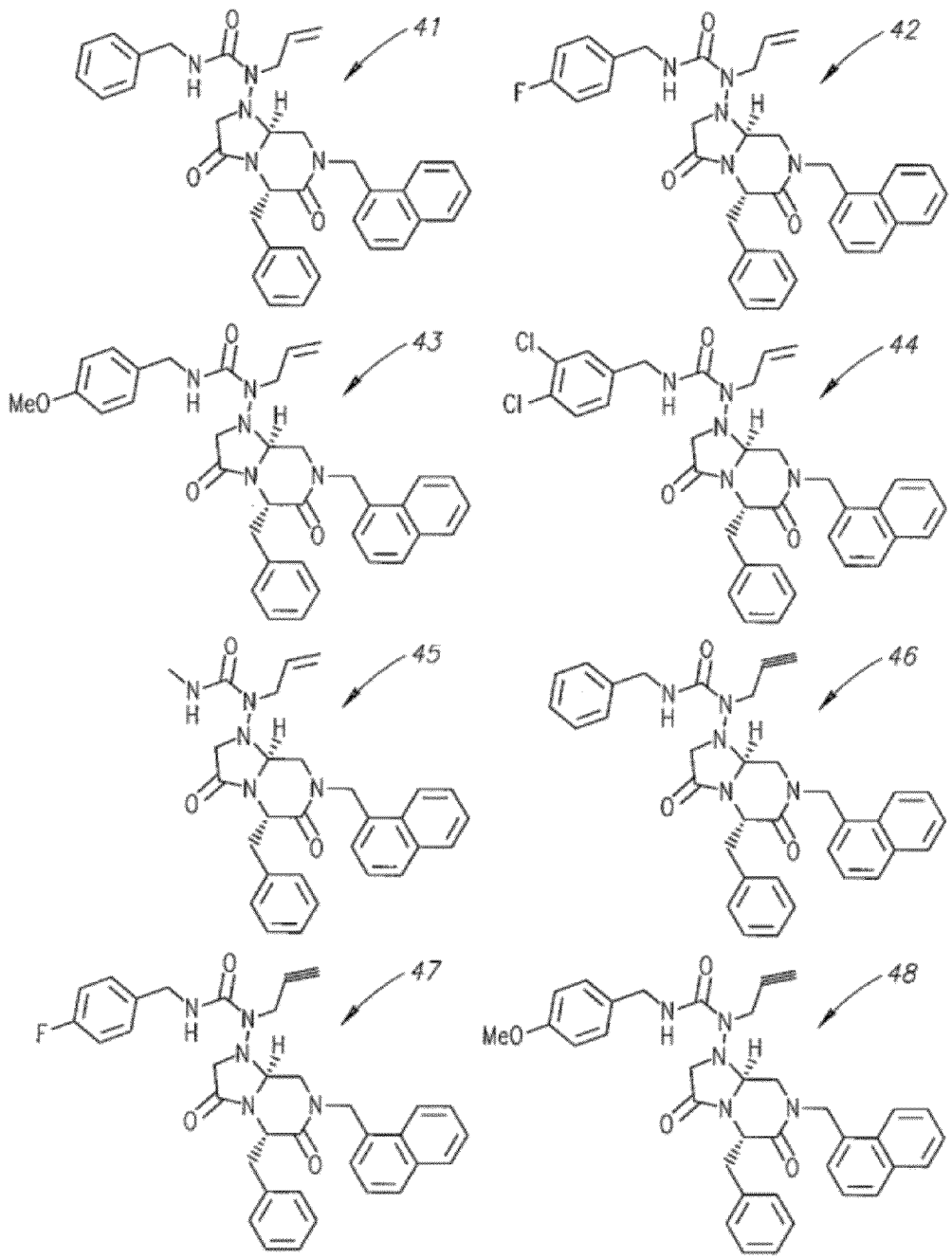
Figure 1G:
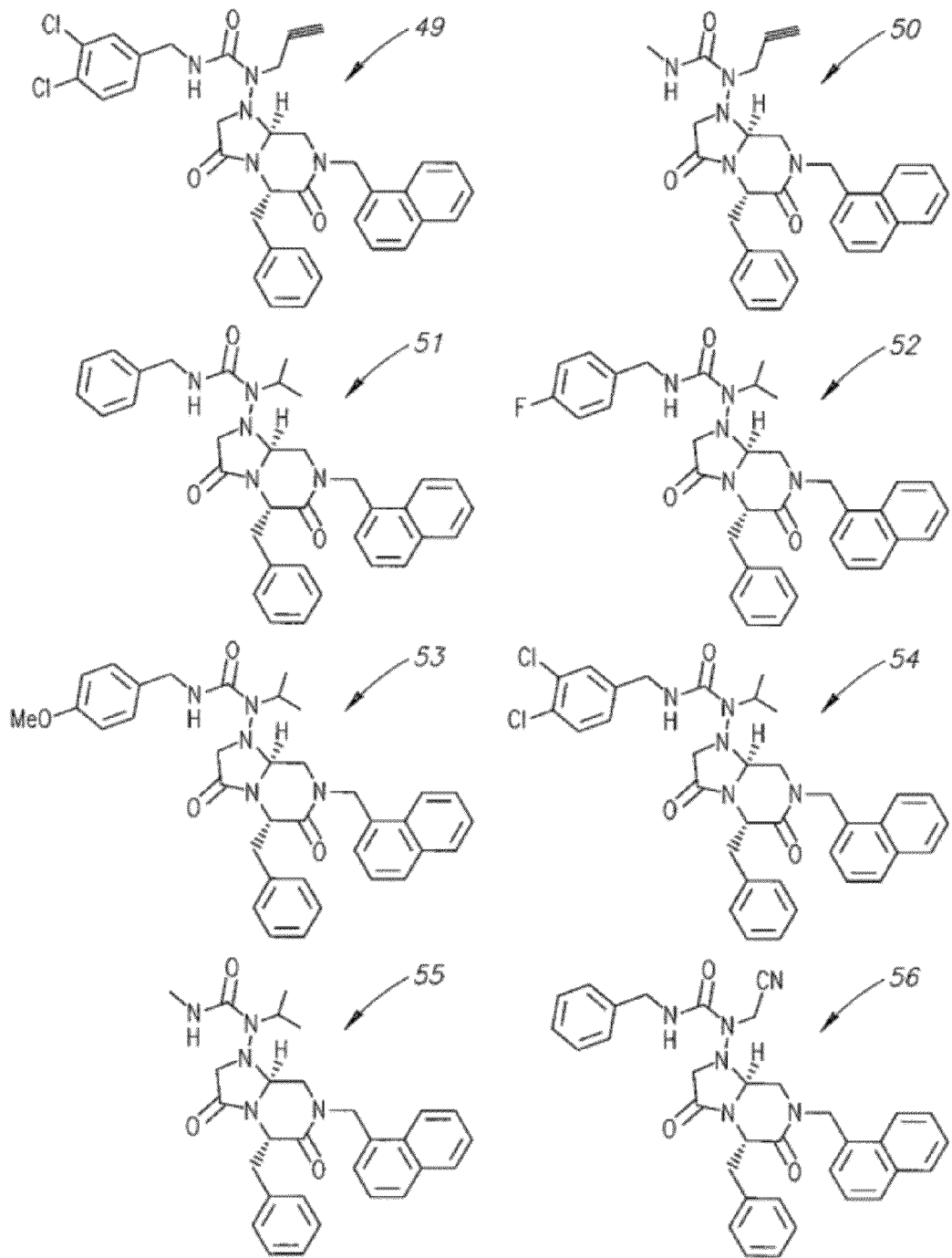
Figure 1H:
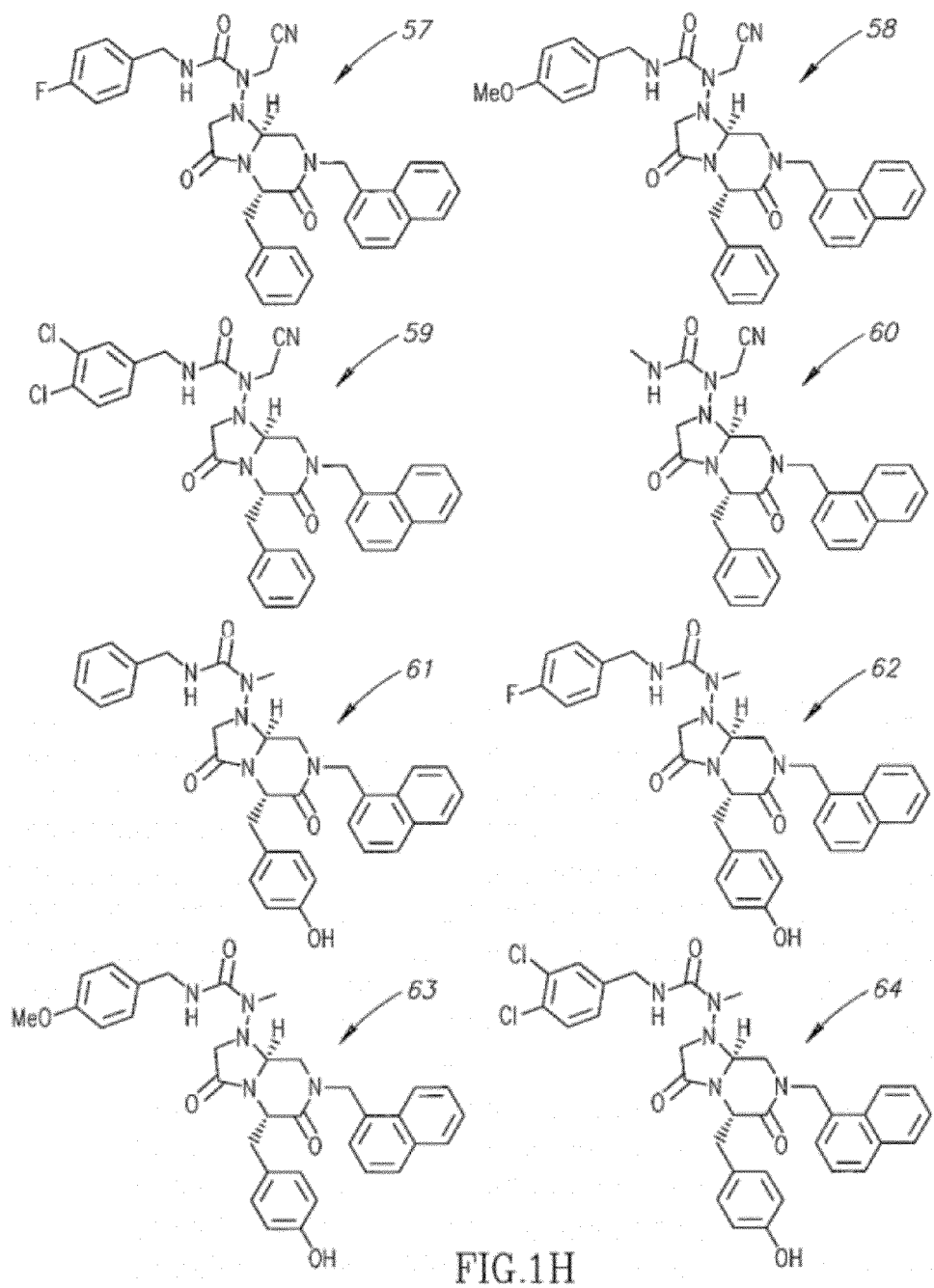
Figure 1I:
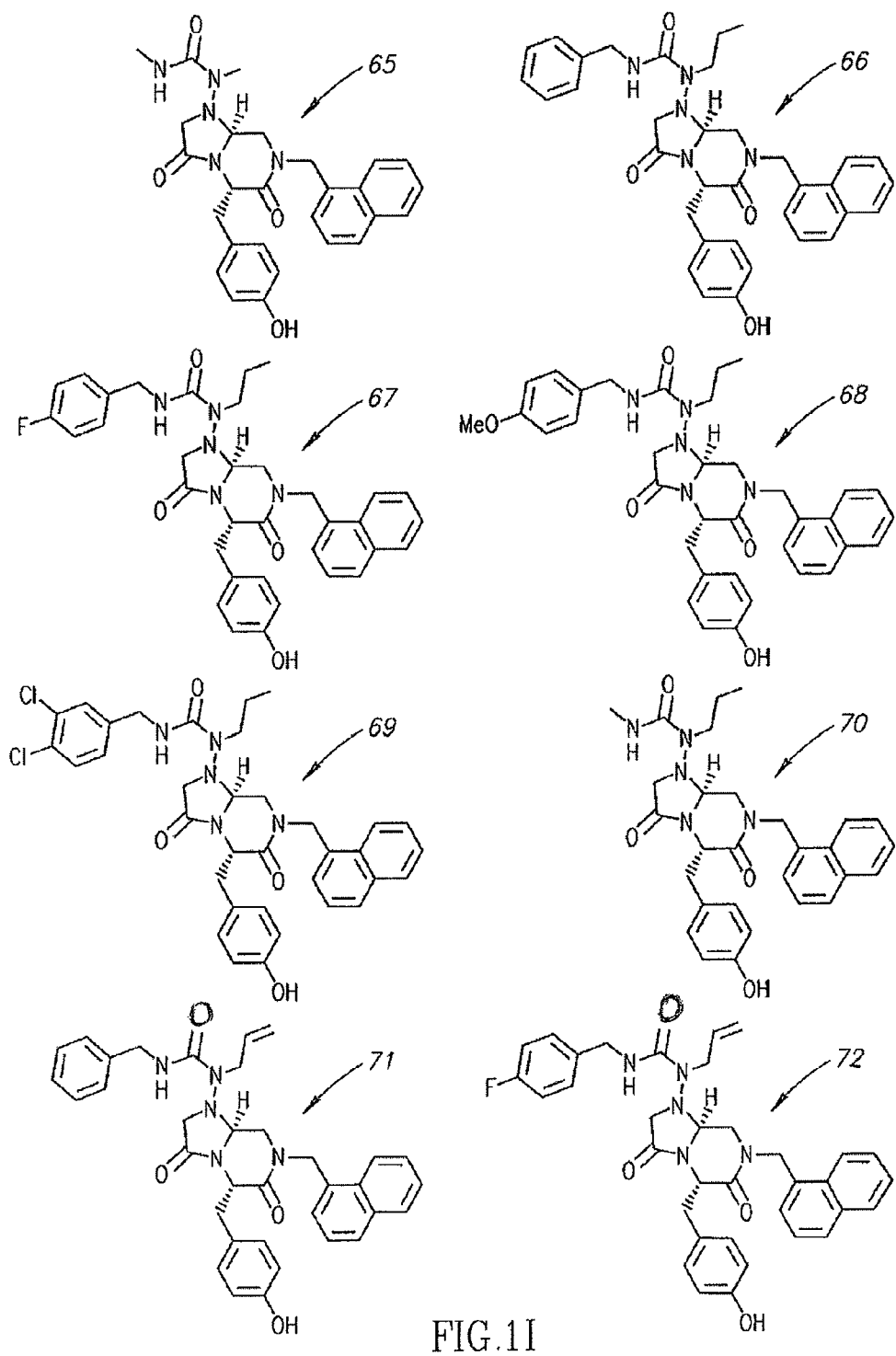
Figure 1J:
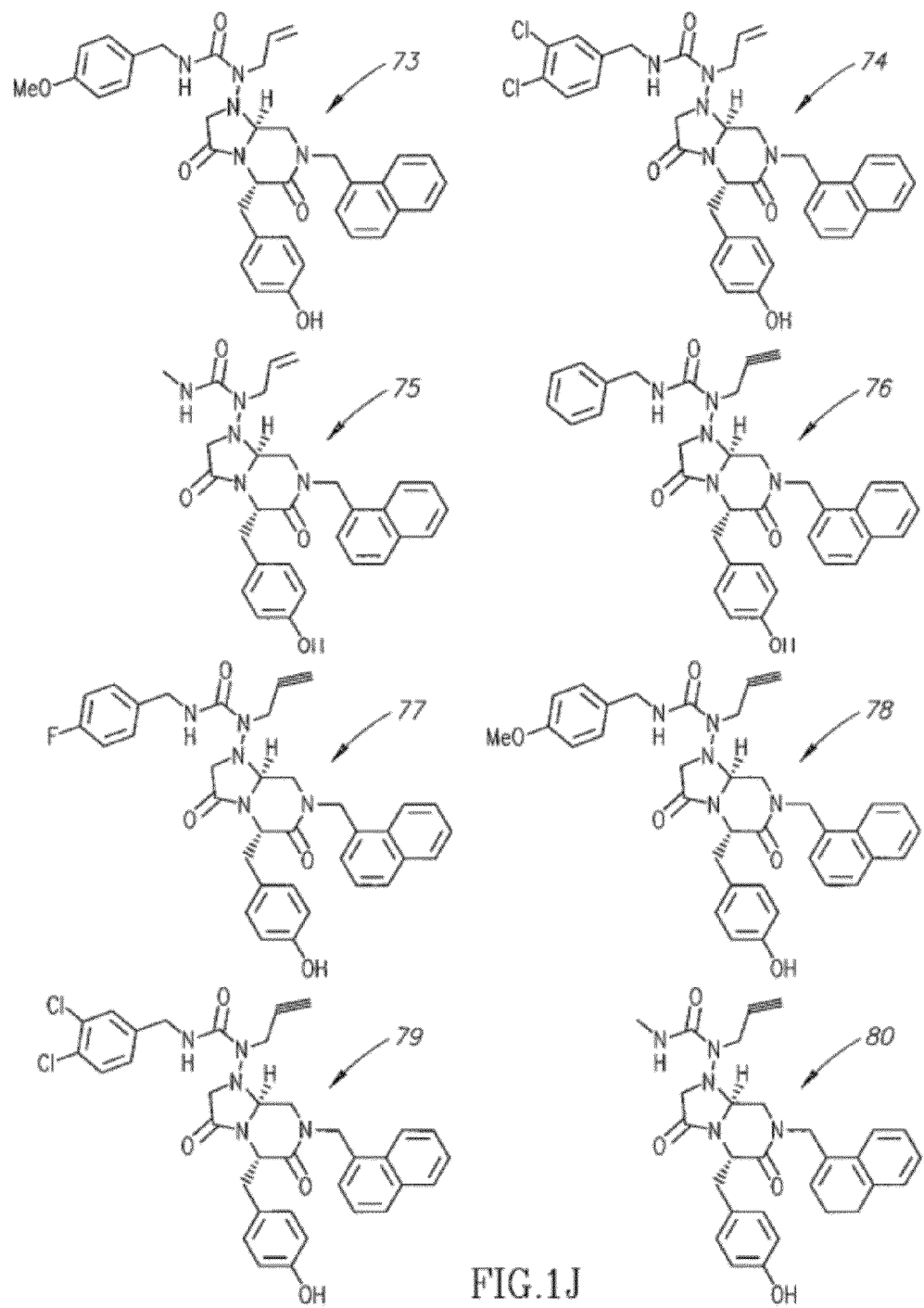
Figure 1K:
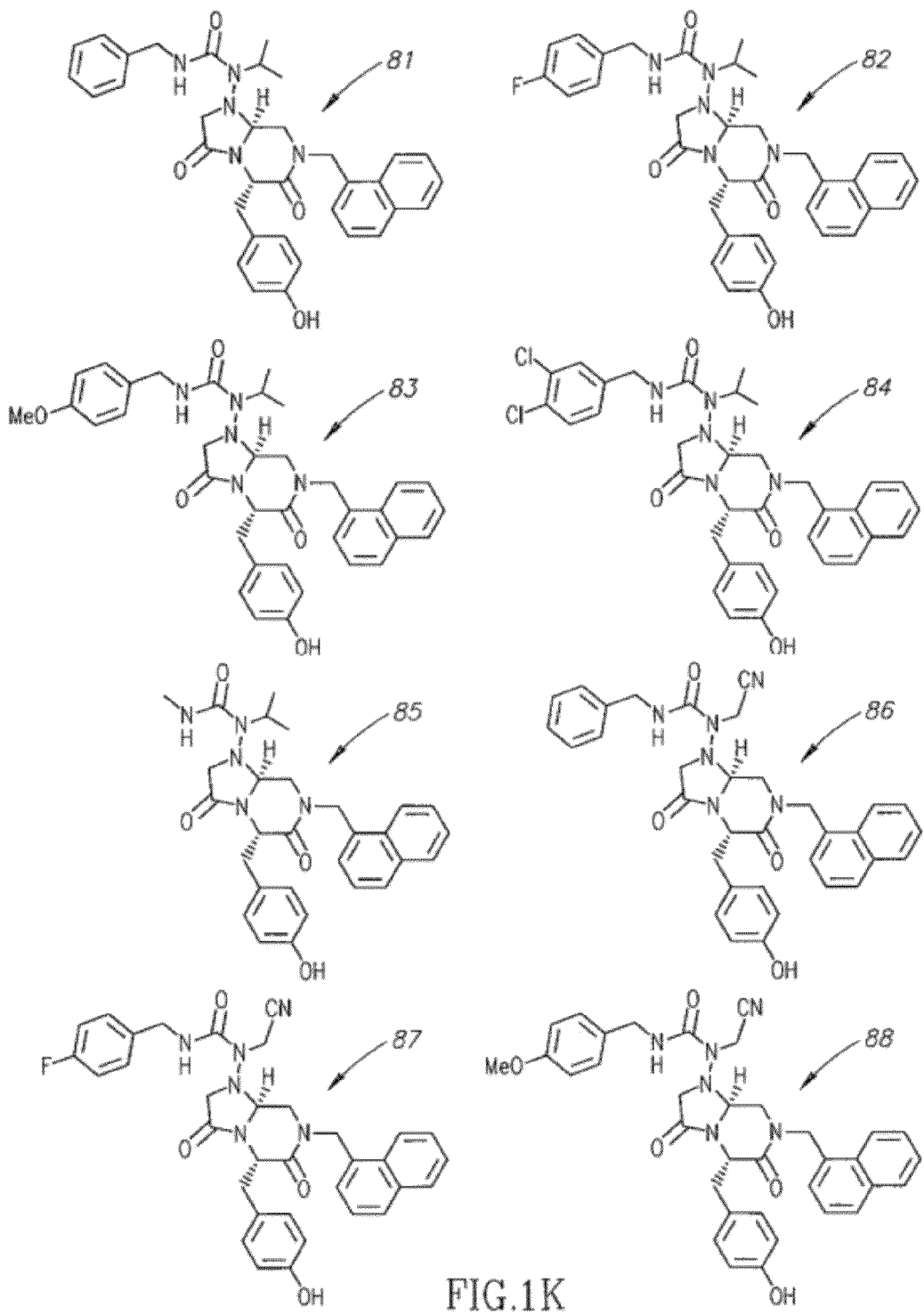
Figure 1L:
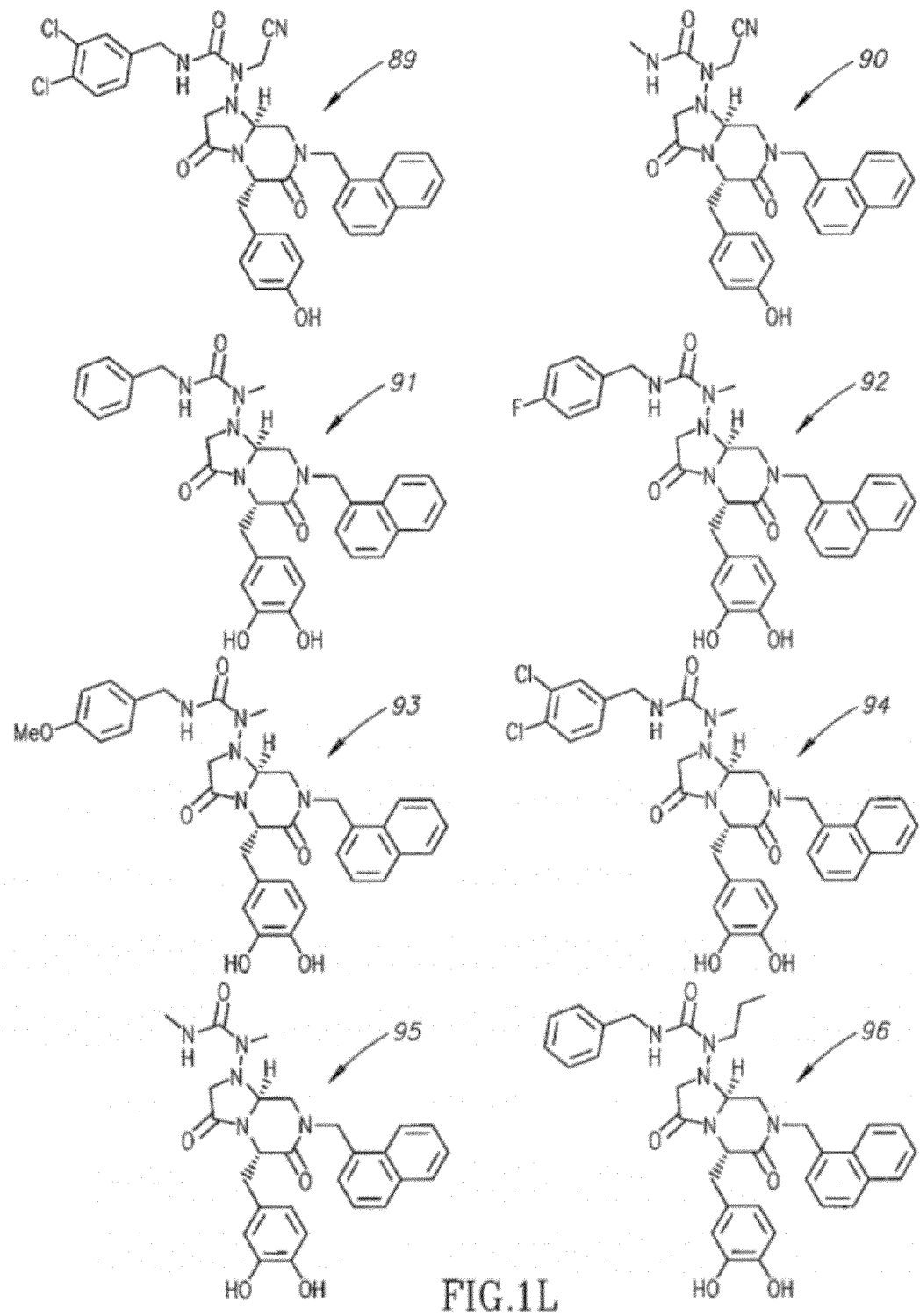
Figure 1M:
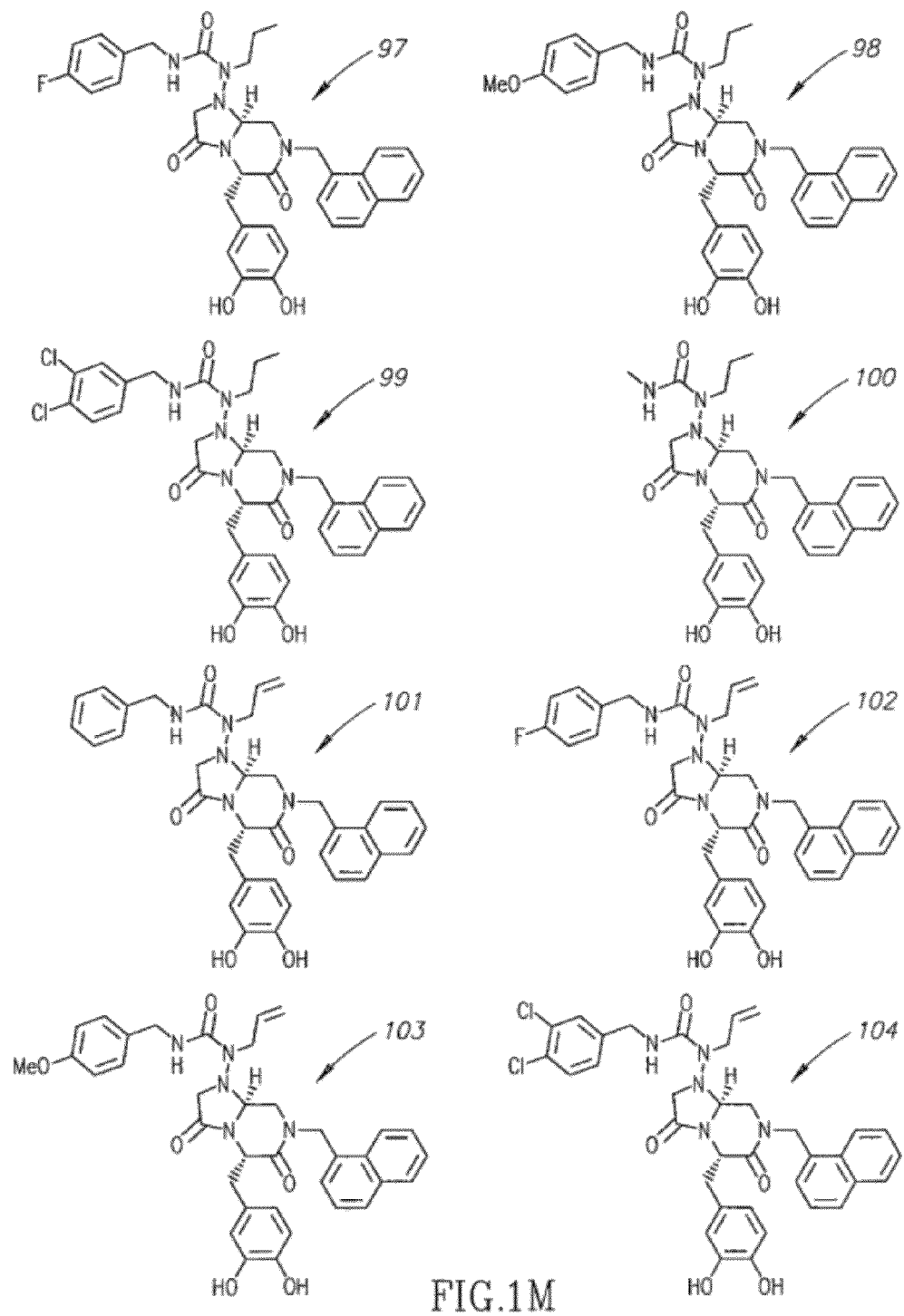
Figure 1N:
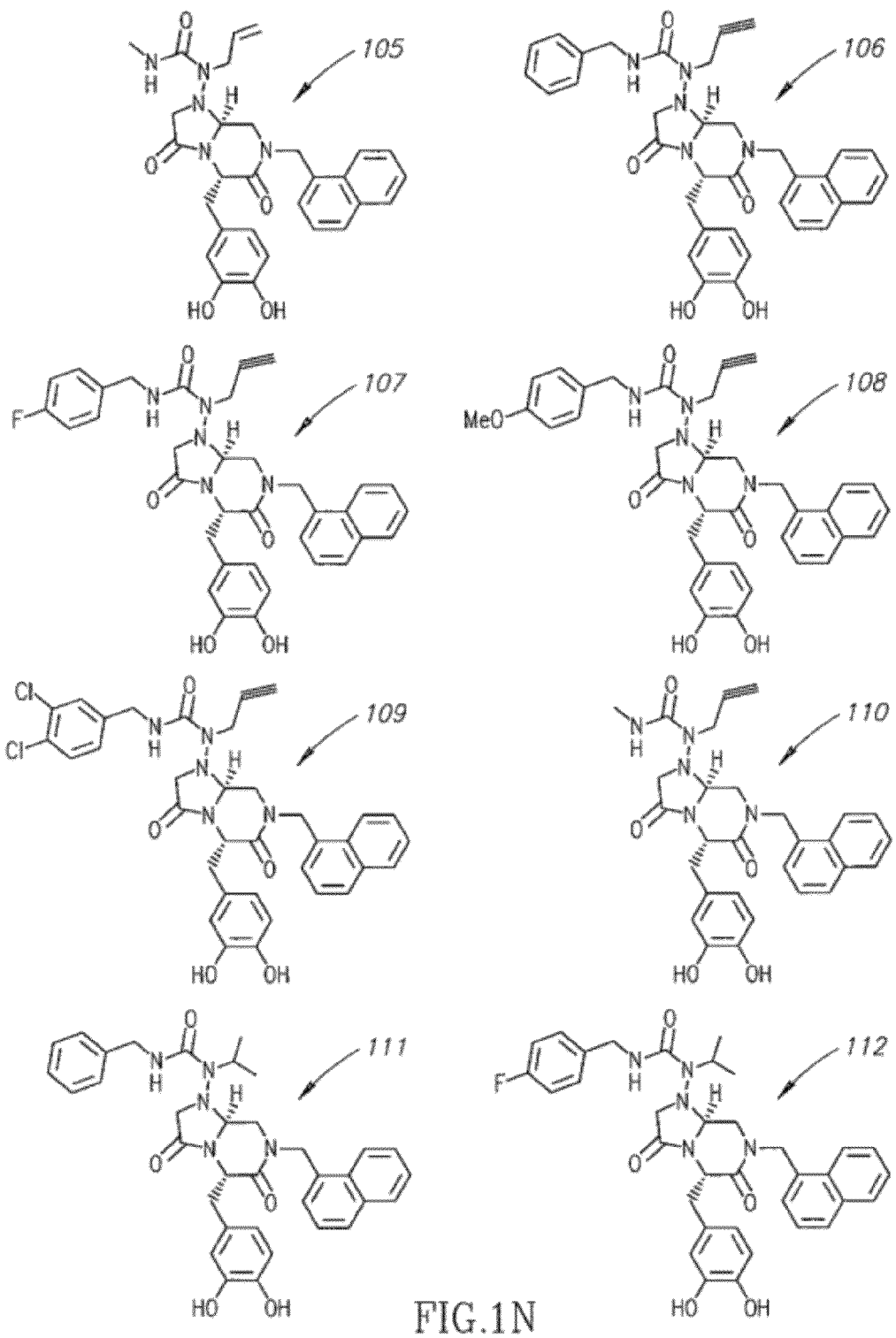
Figure 10:
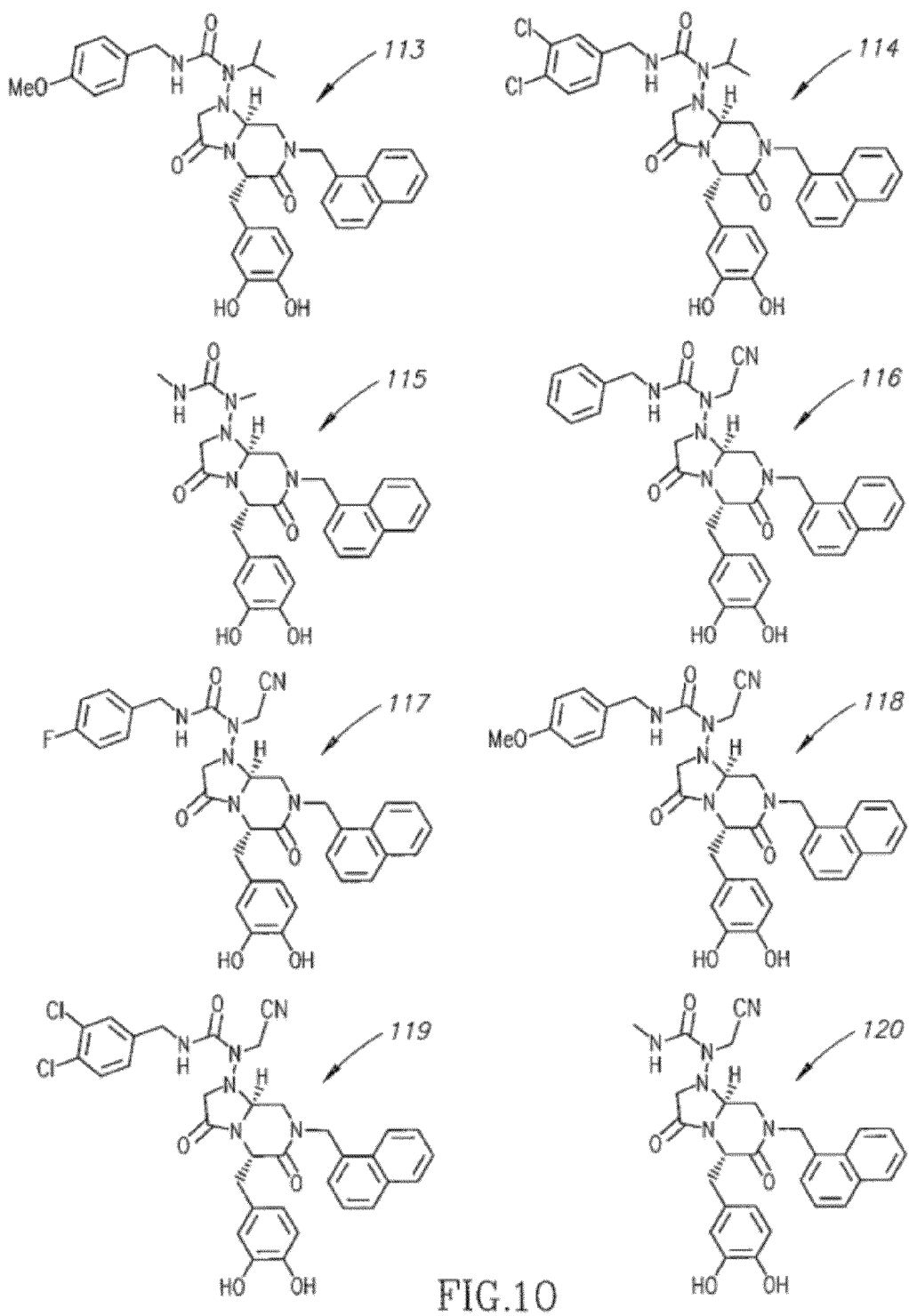
FIG. 10A-10AA shows the chemical structures of compounds 1801-2000.
Figure 1P:
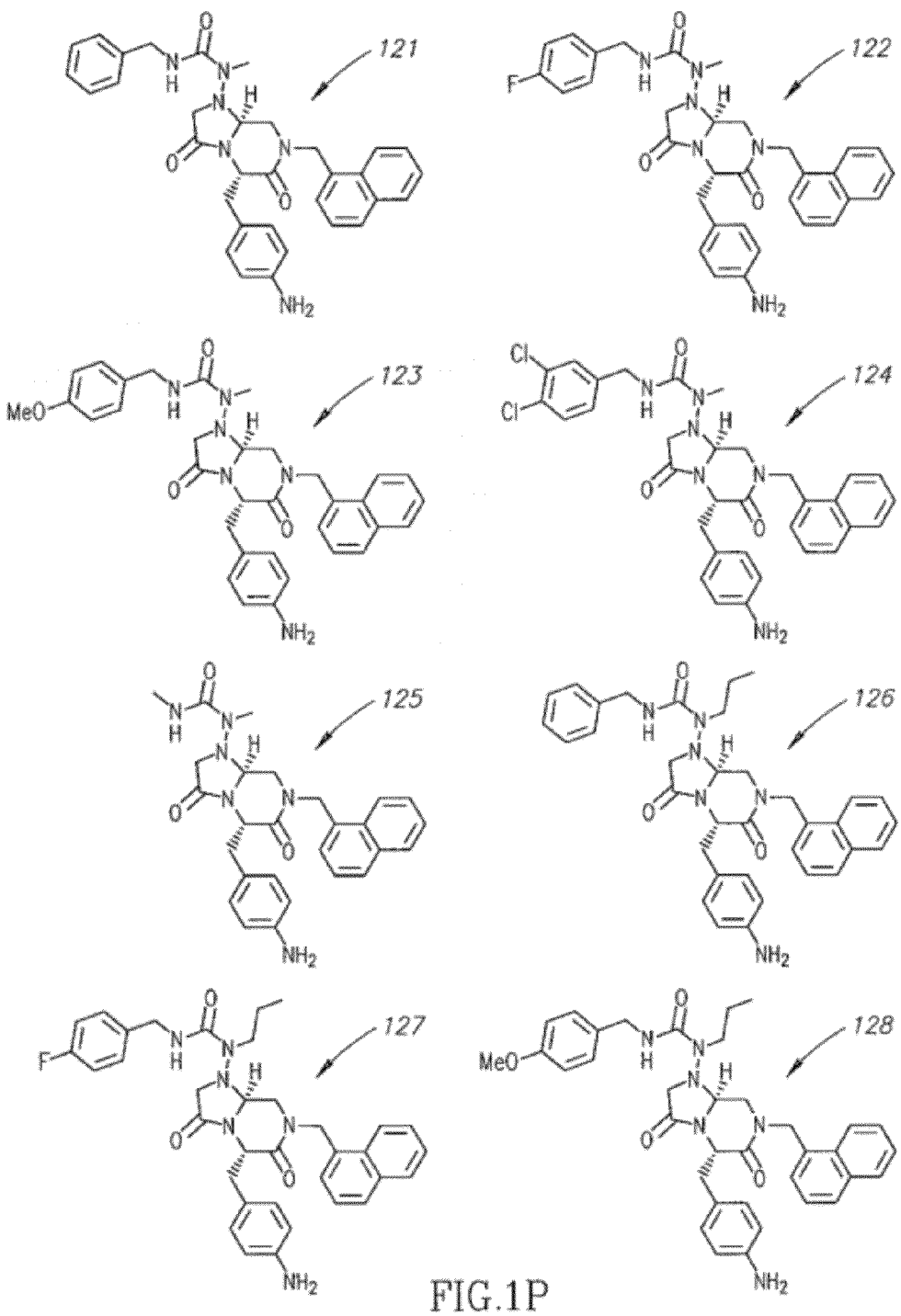
Figure 1Q:
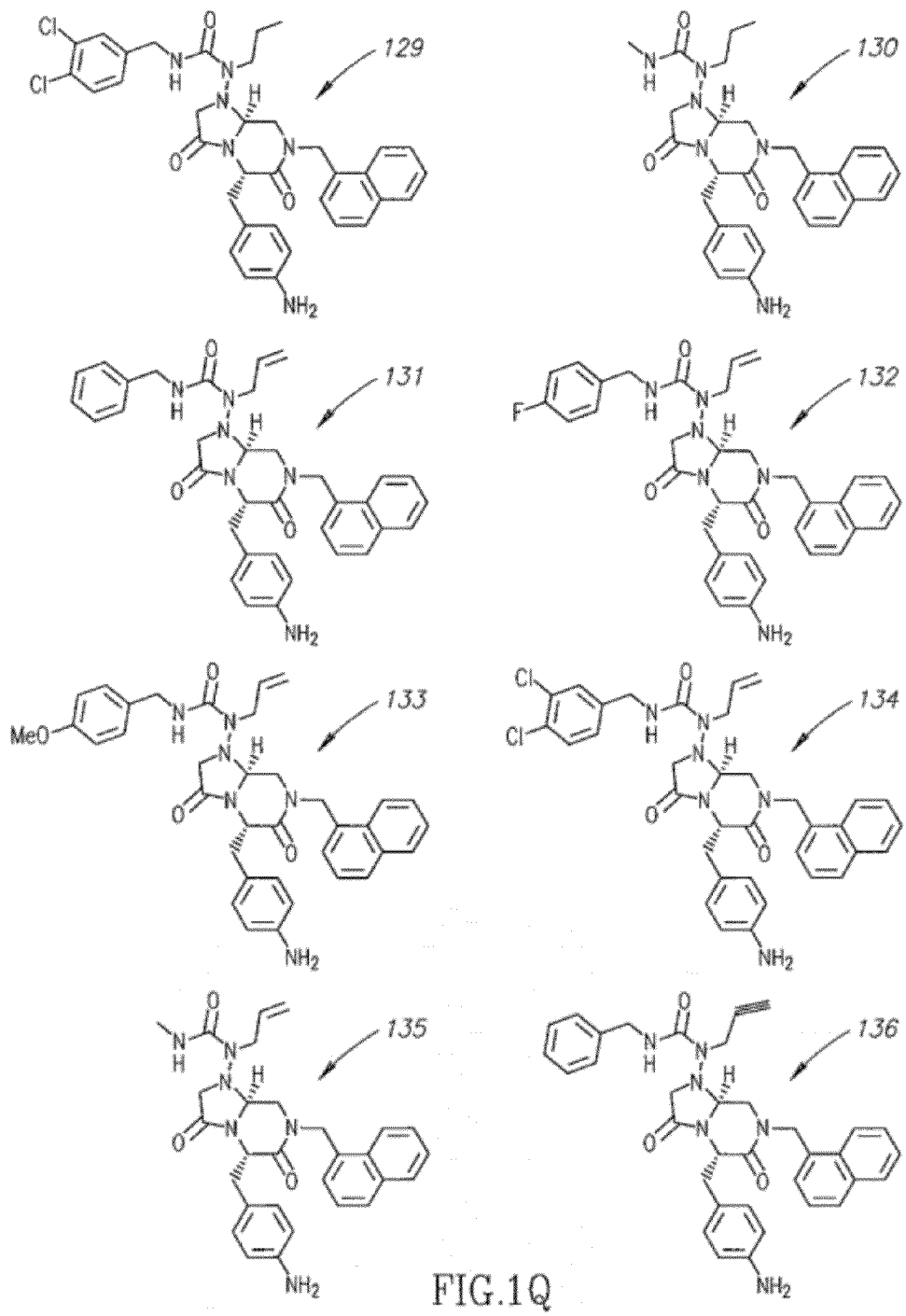
Figure 1R:
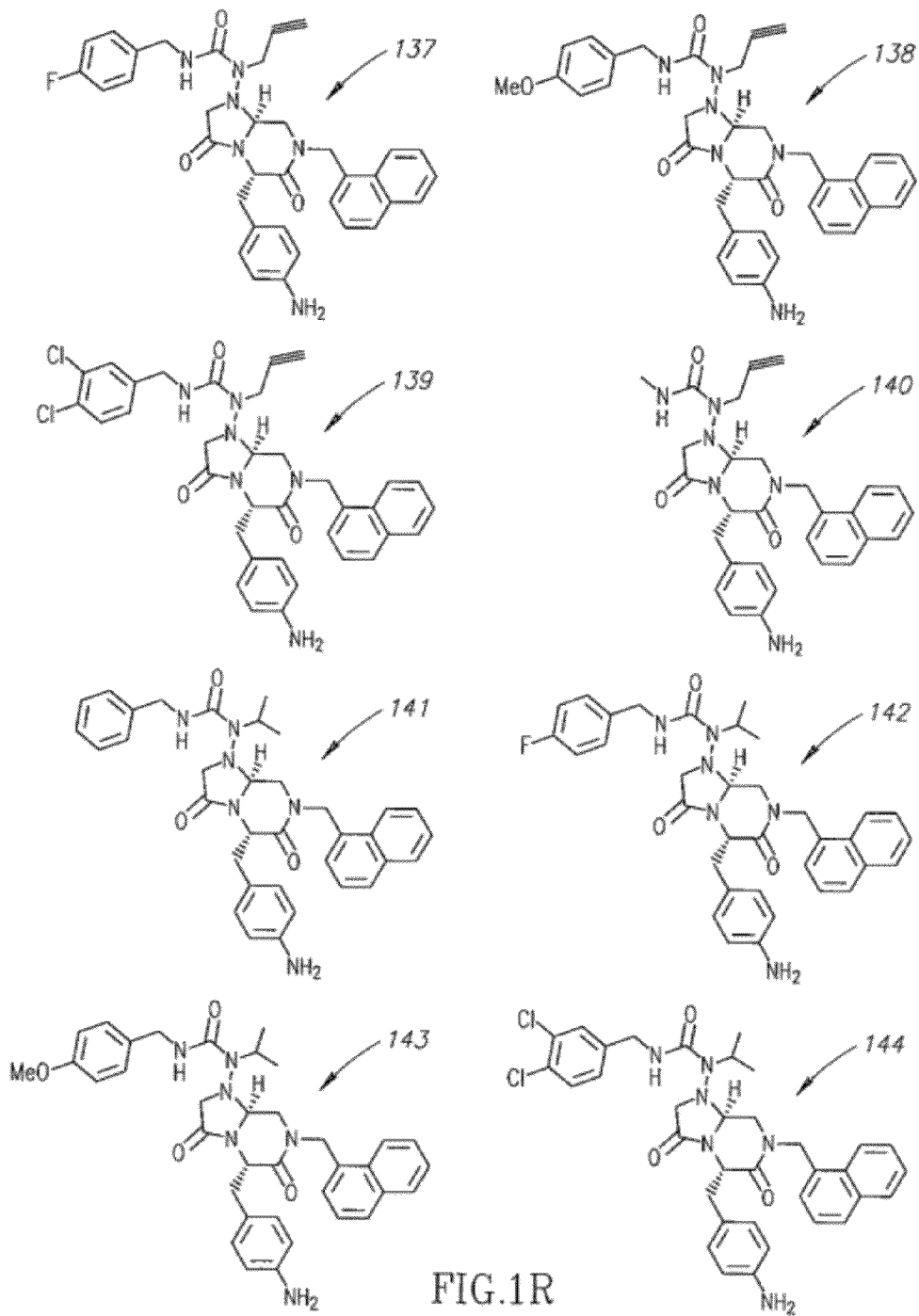
Figure 1S:
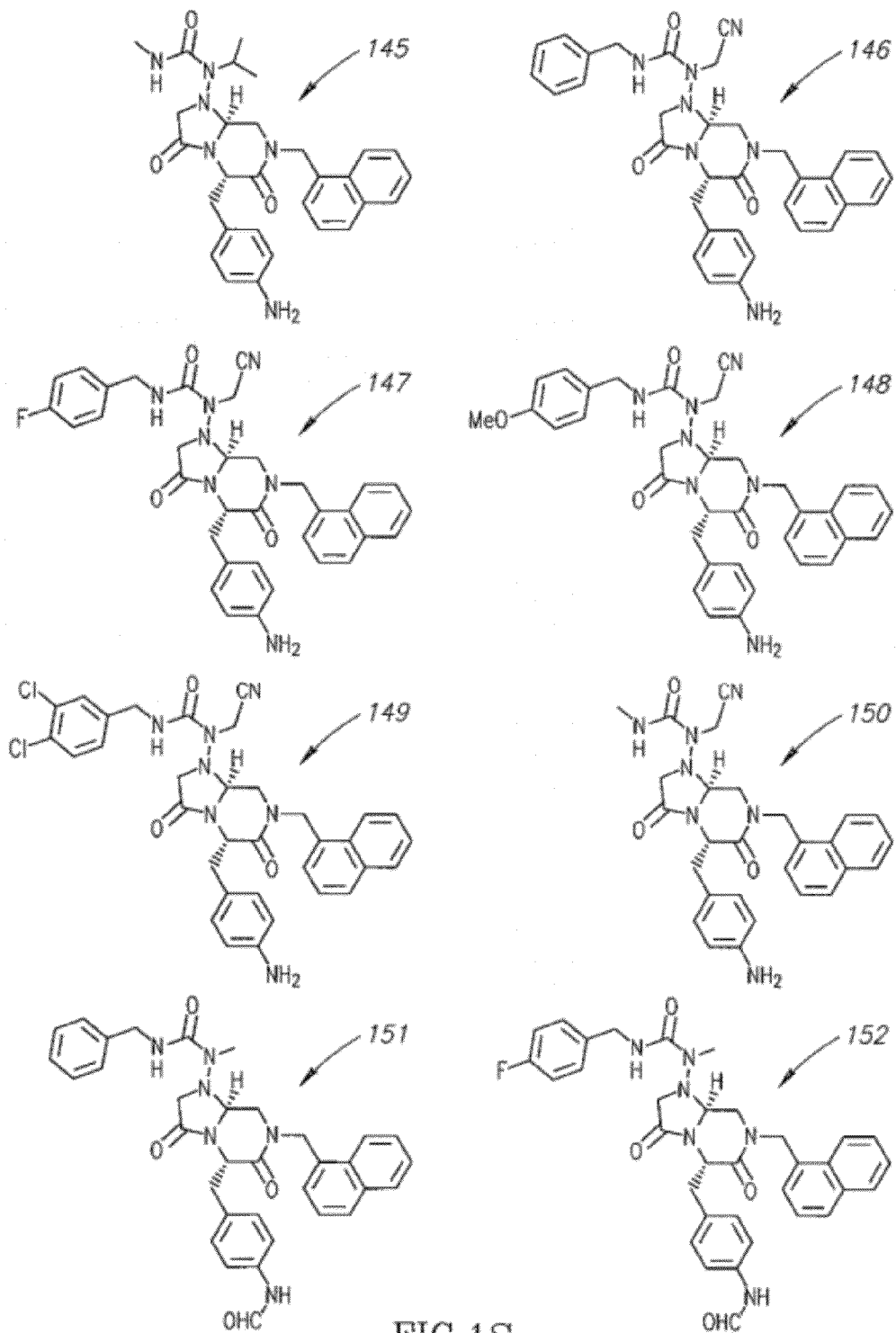
Figure 1T:
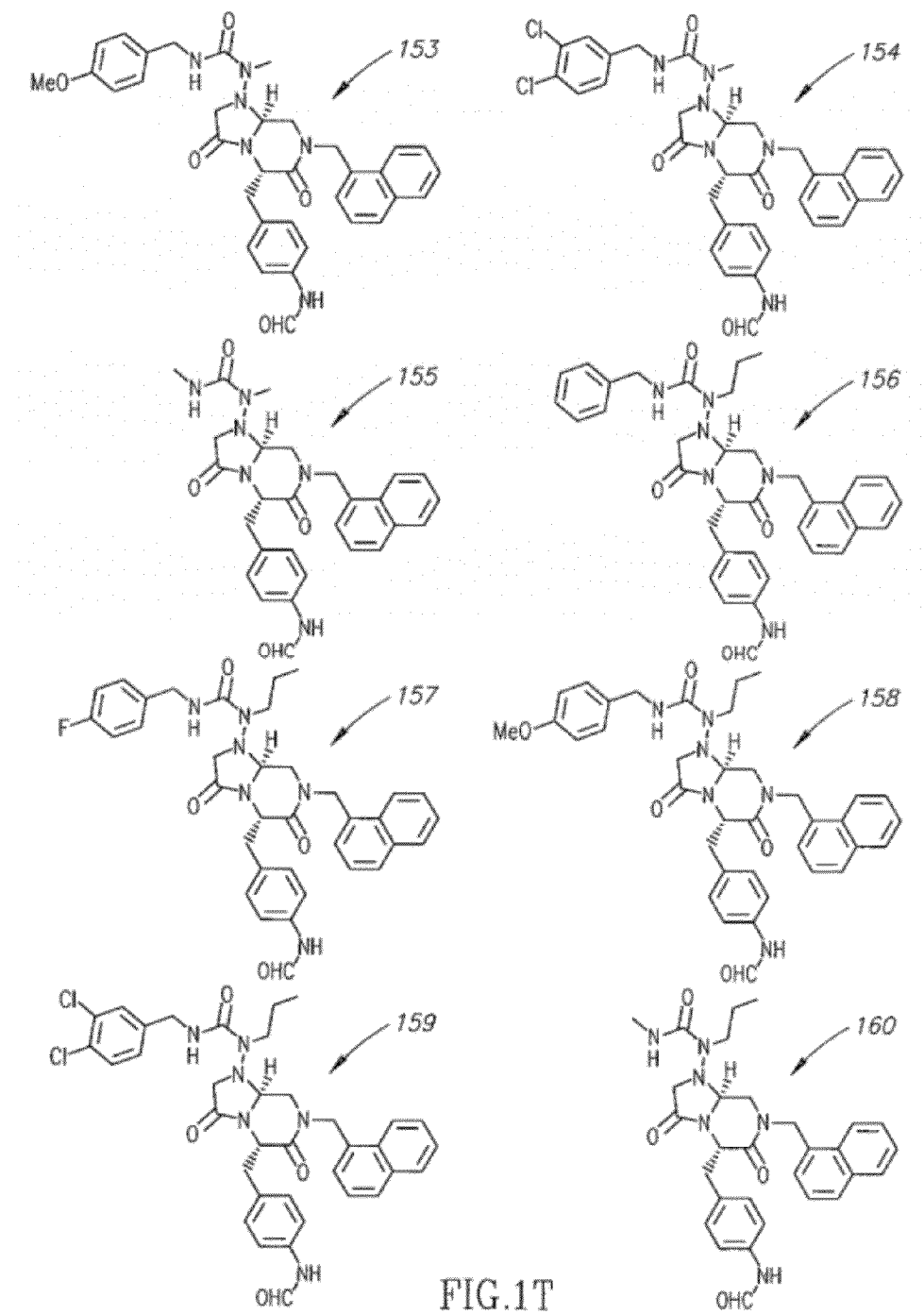
Figure 1U:
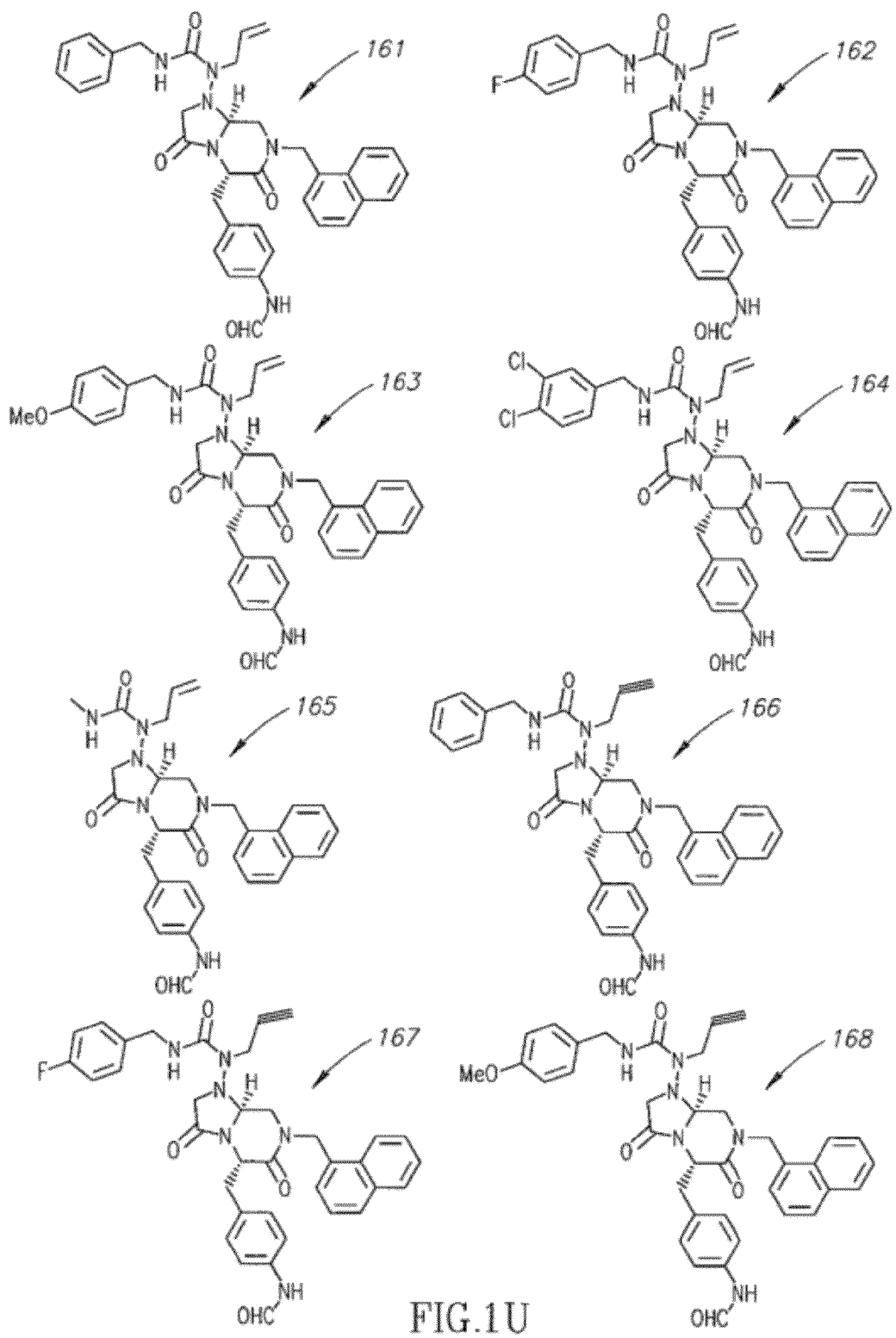
Figure 1V:
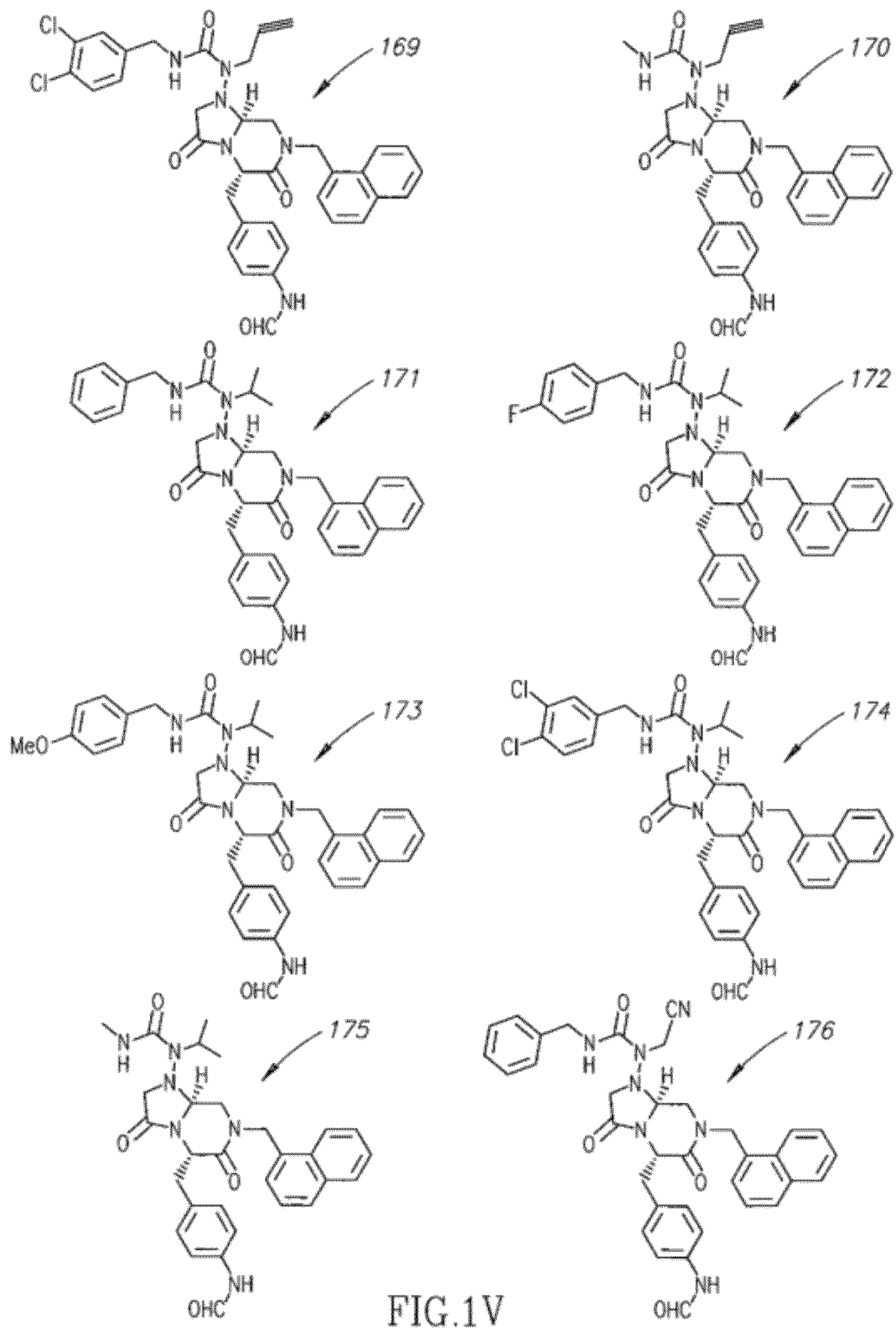
Figure 1W:
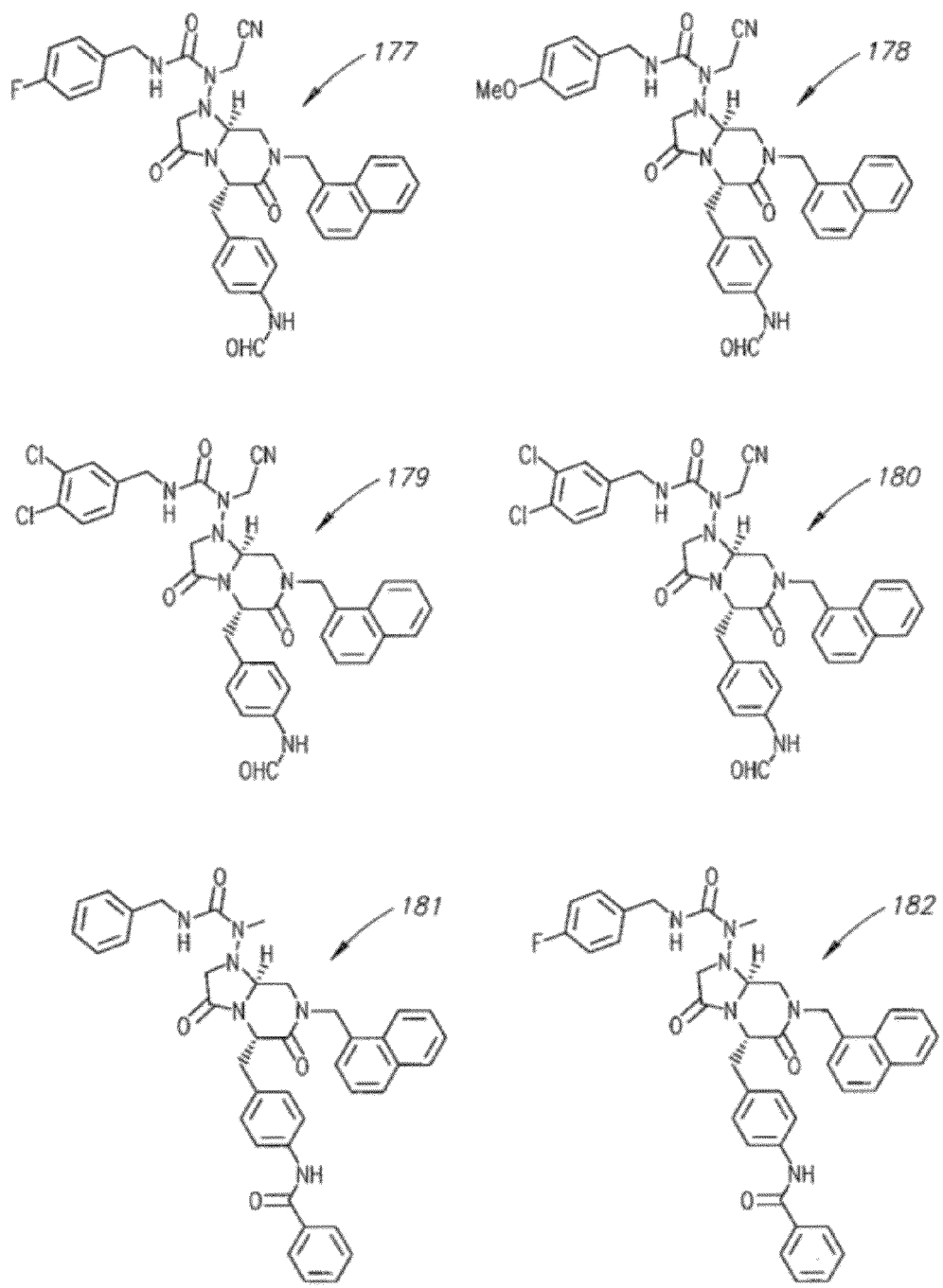
Figure 1X:
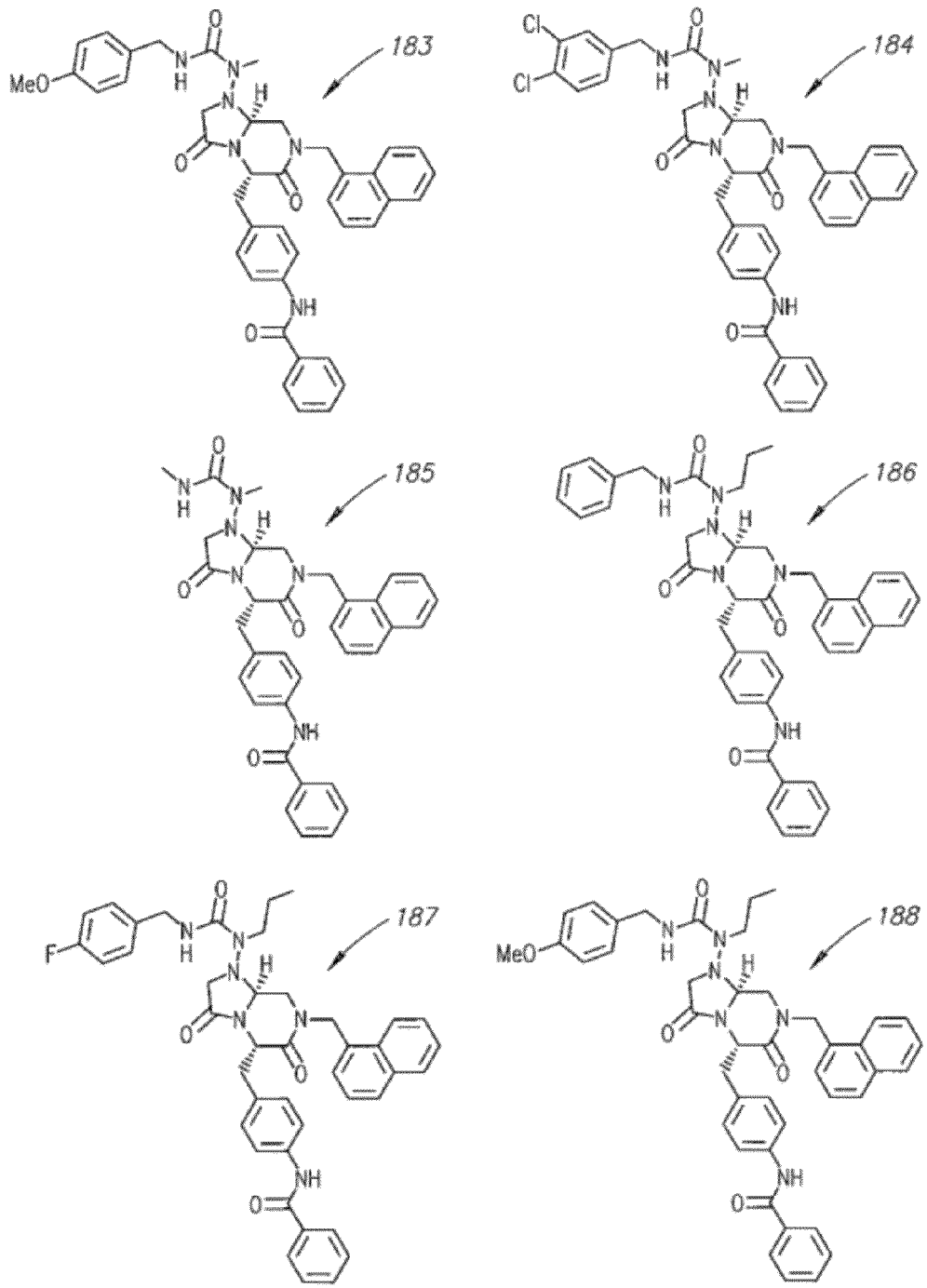
Figure 1Y:
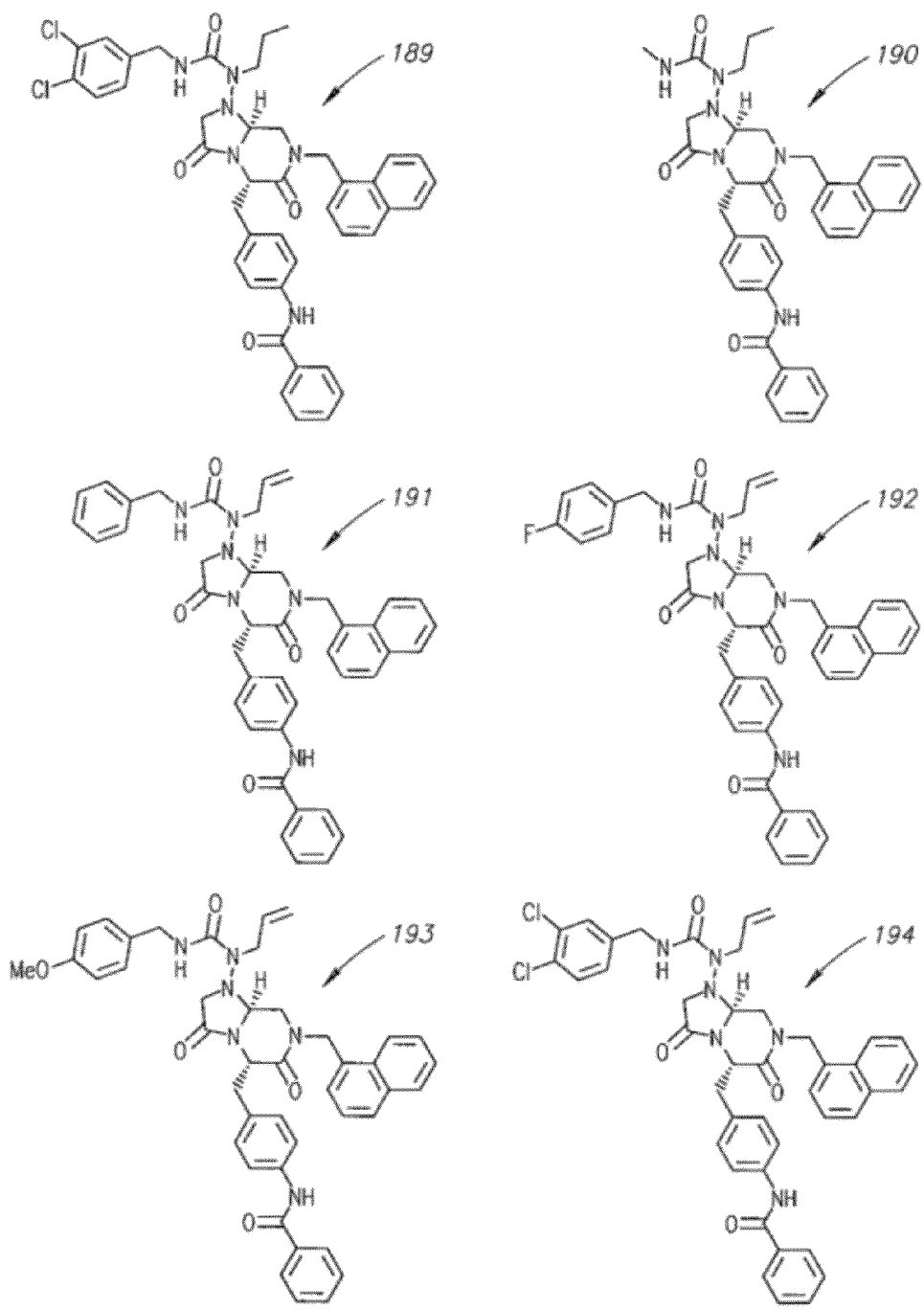
Figure 1Z:
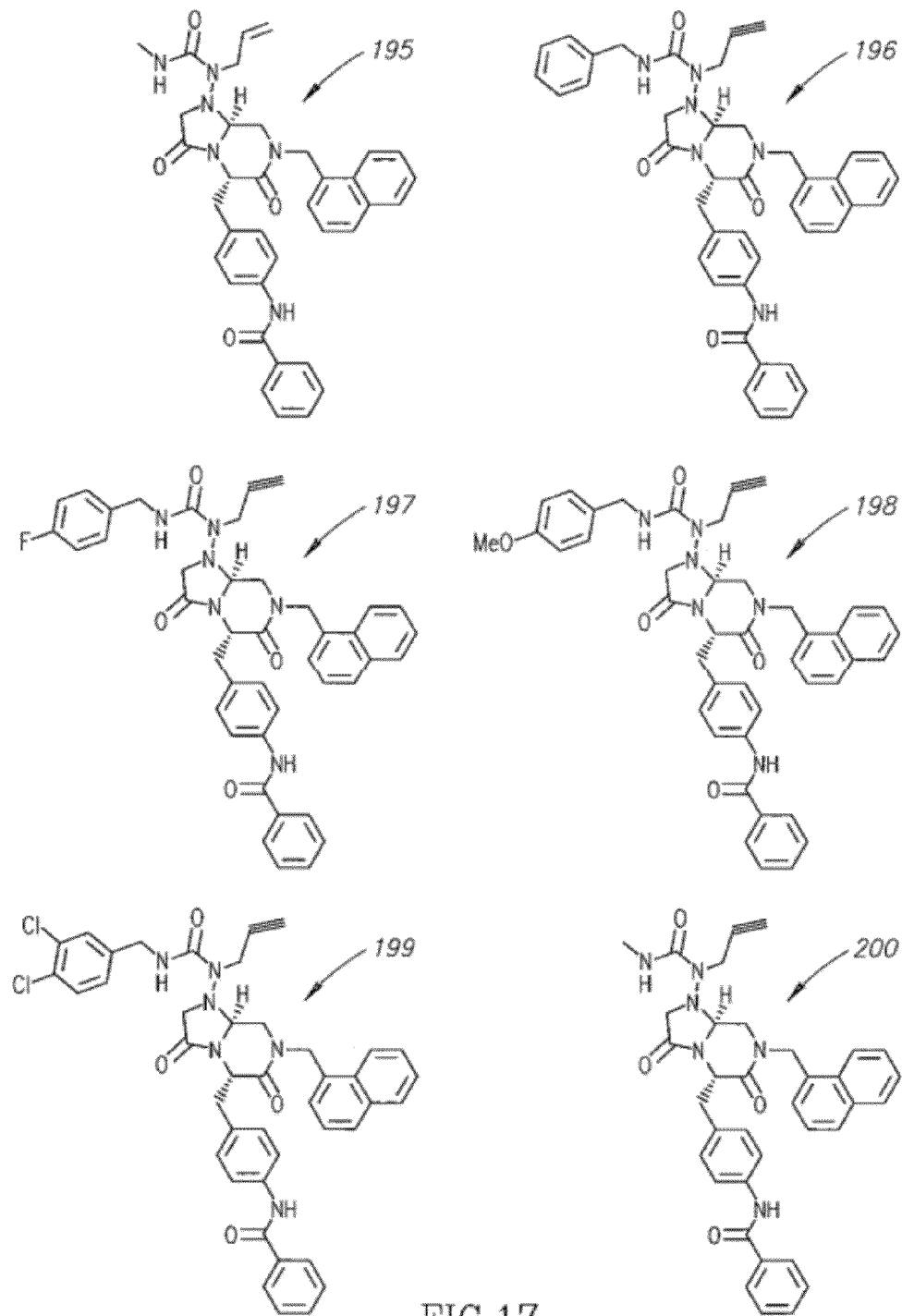
Figure 2A:
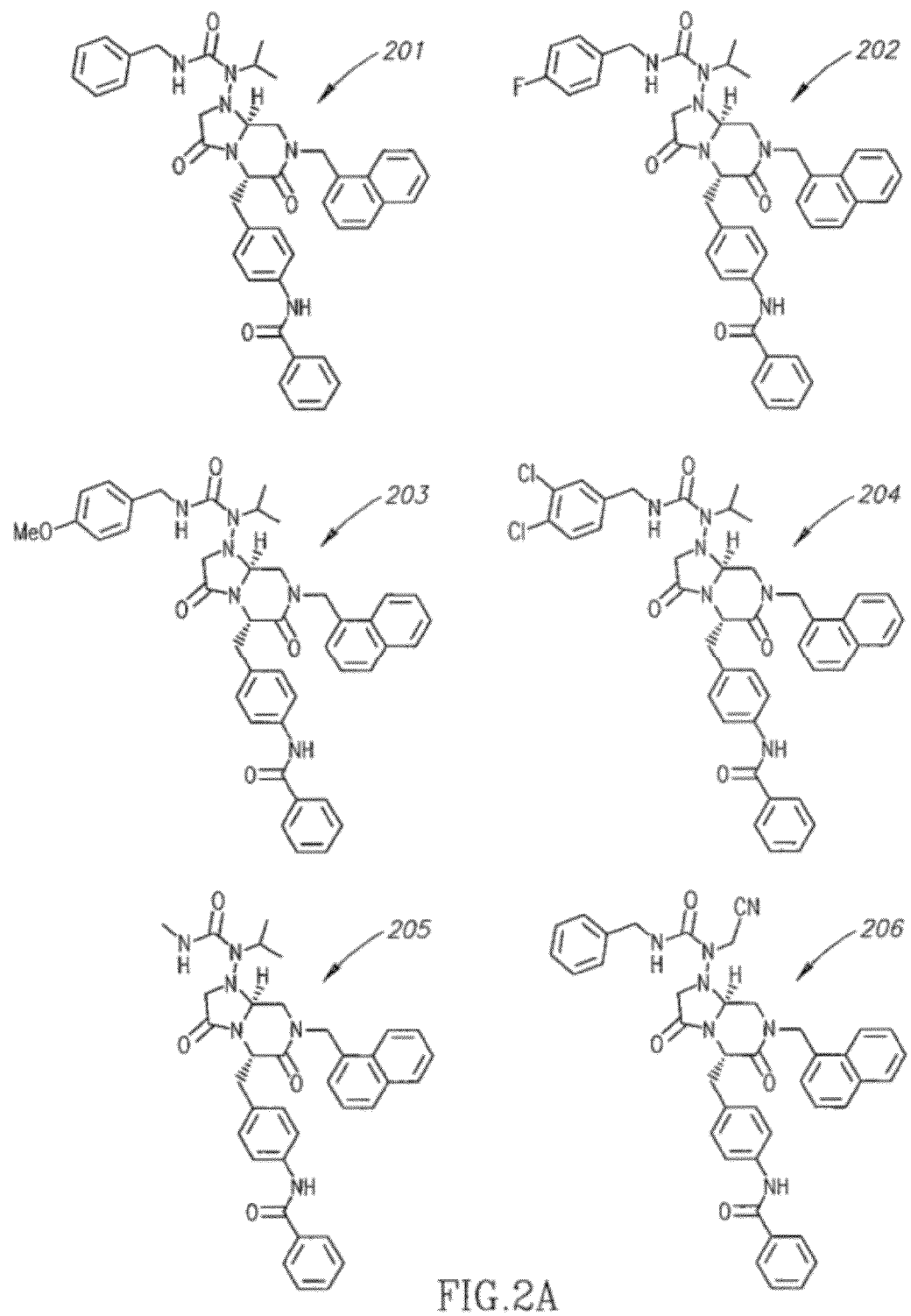
FIGS. 2A-2AD shows the chemical structures of compounds 201-400.
Figure 2B:
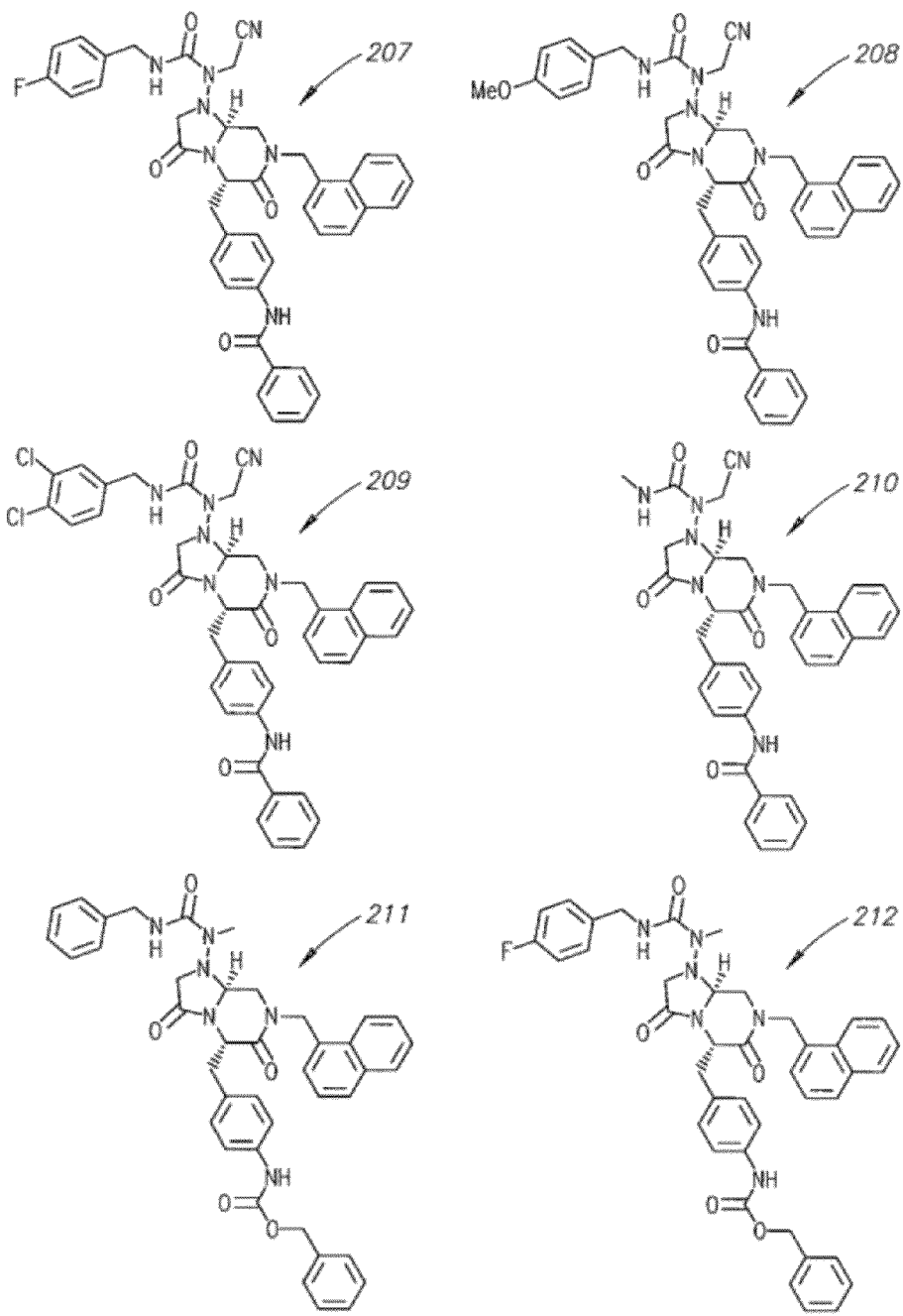
Figure 2C:
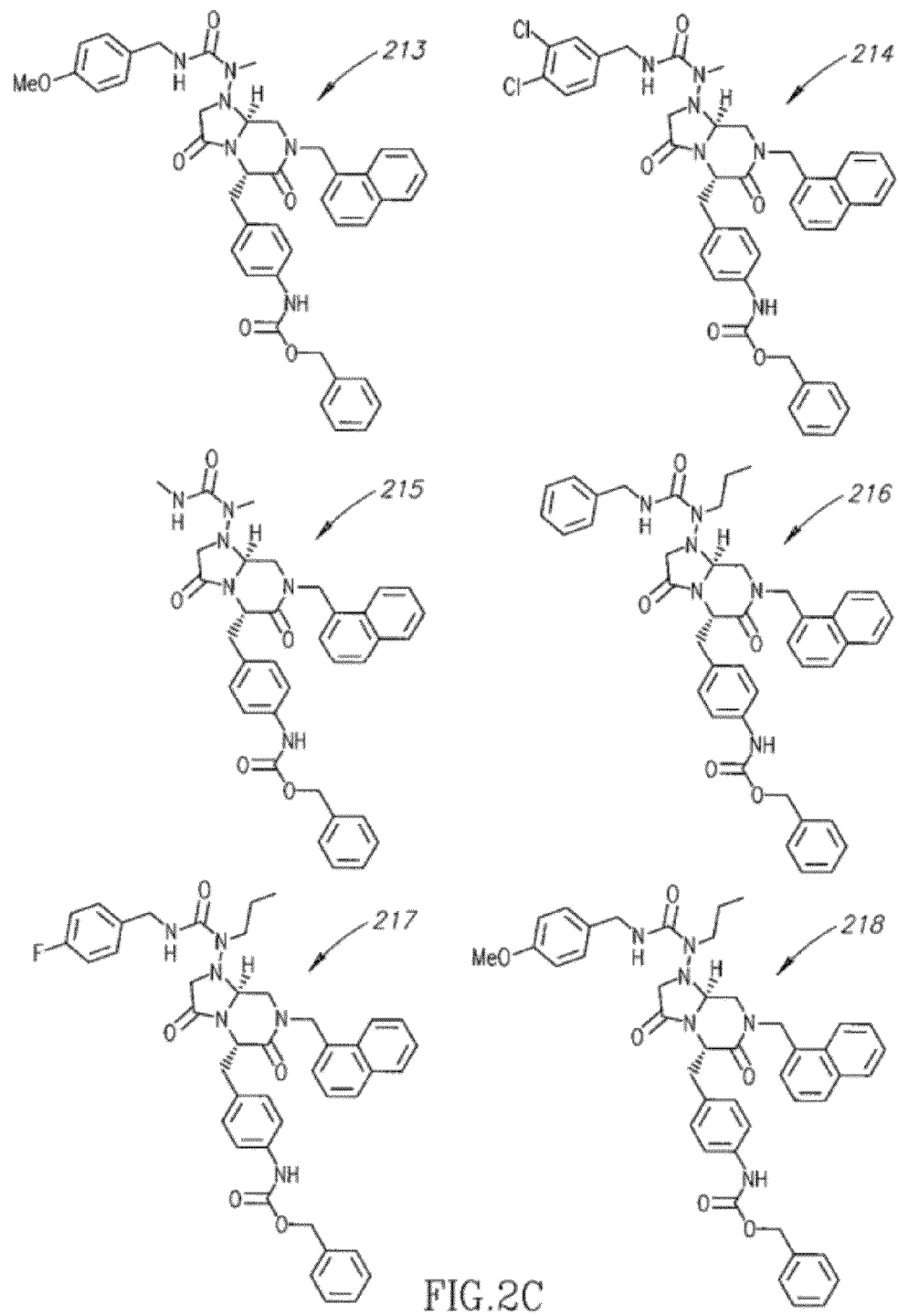
Figure 2D:
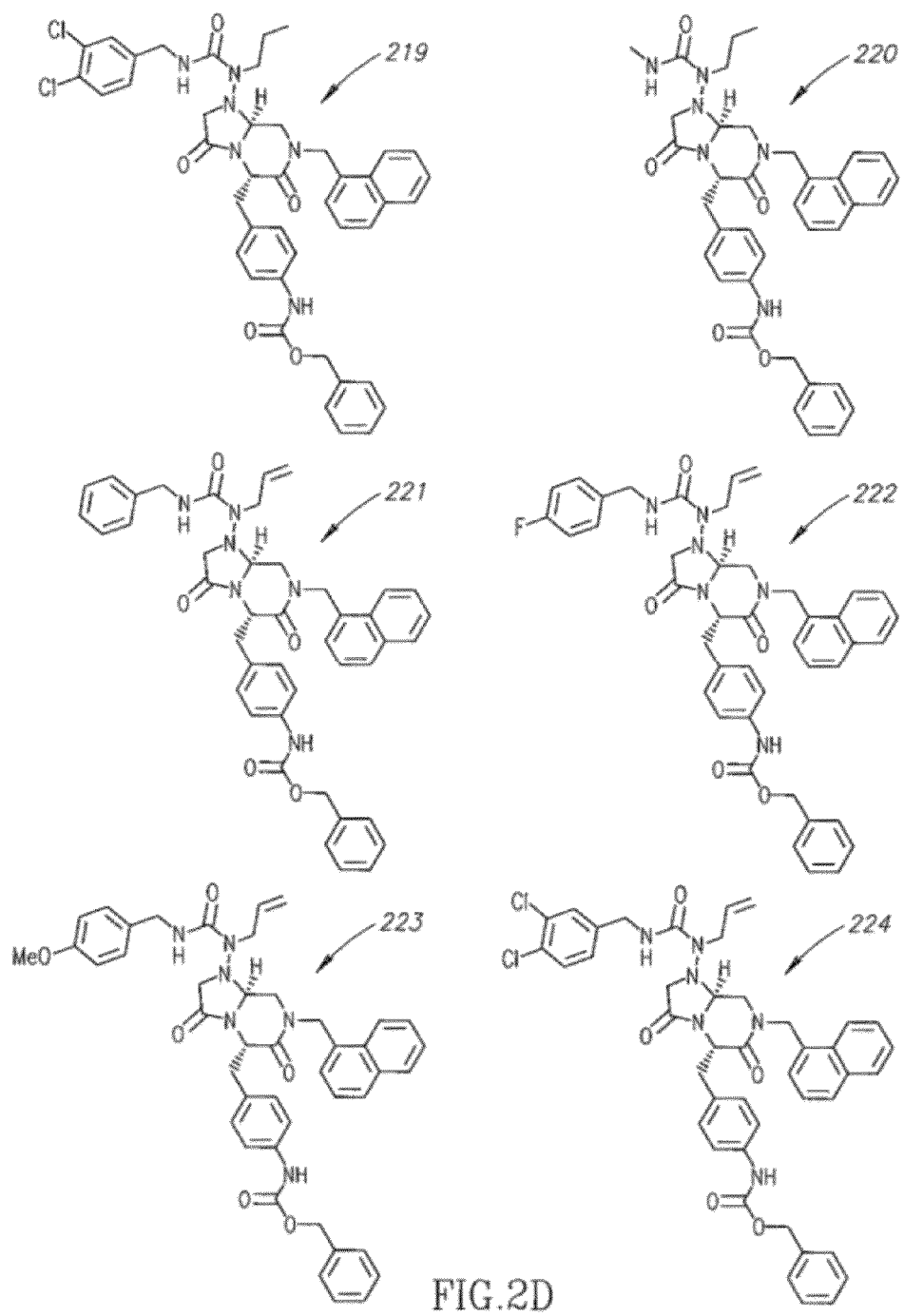
Figure 2E:
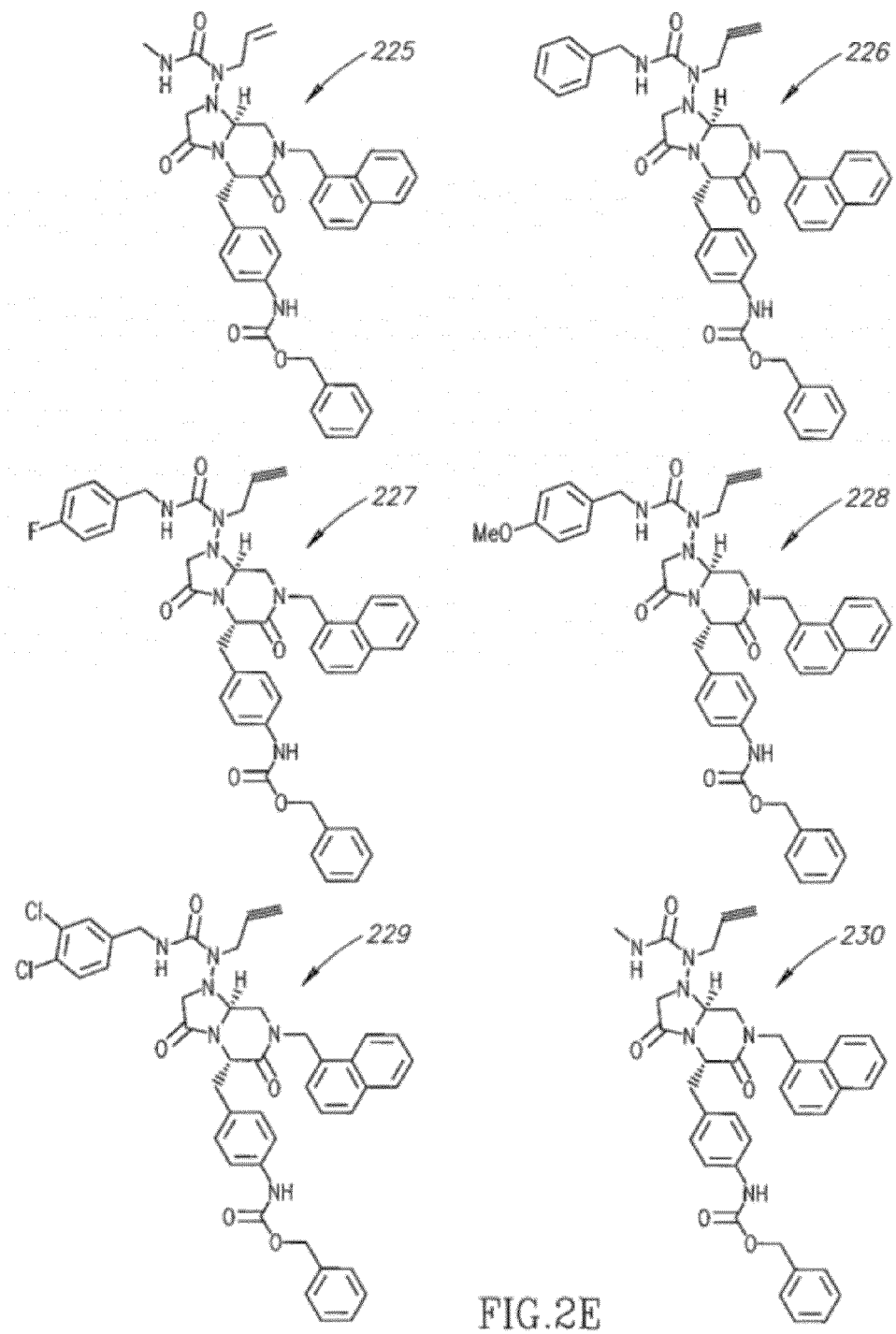
Figure 2F:
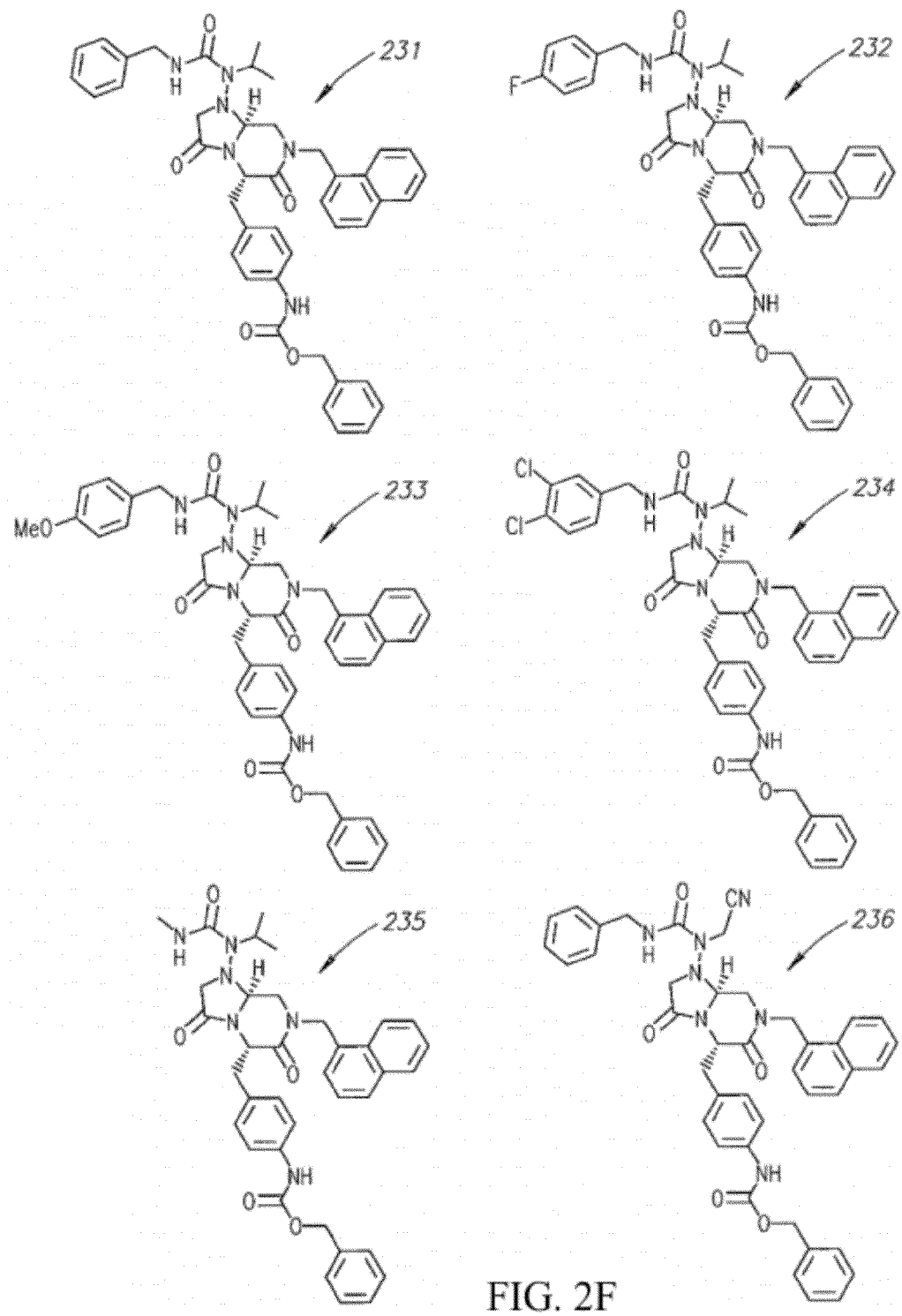
Figure 2G:
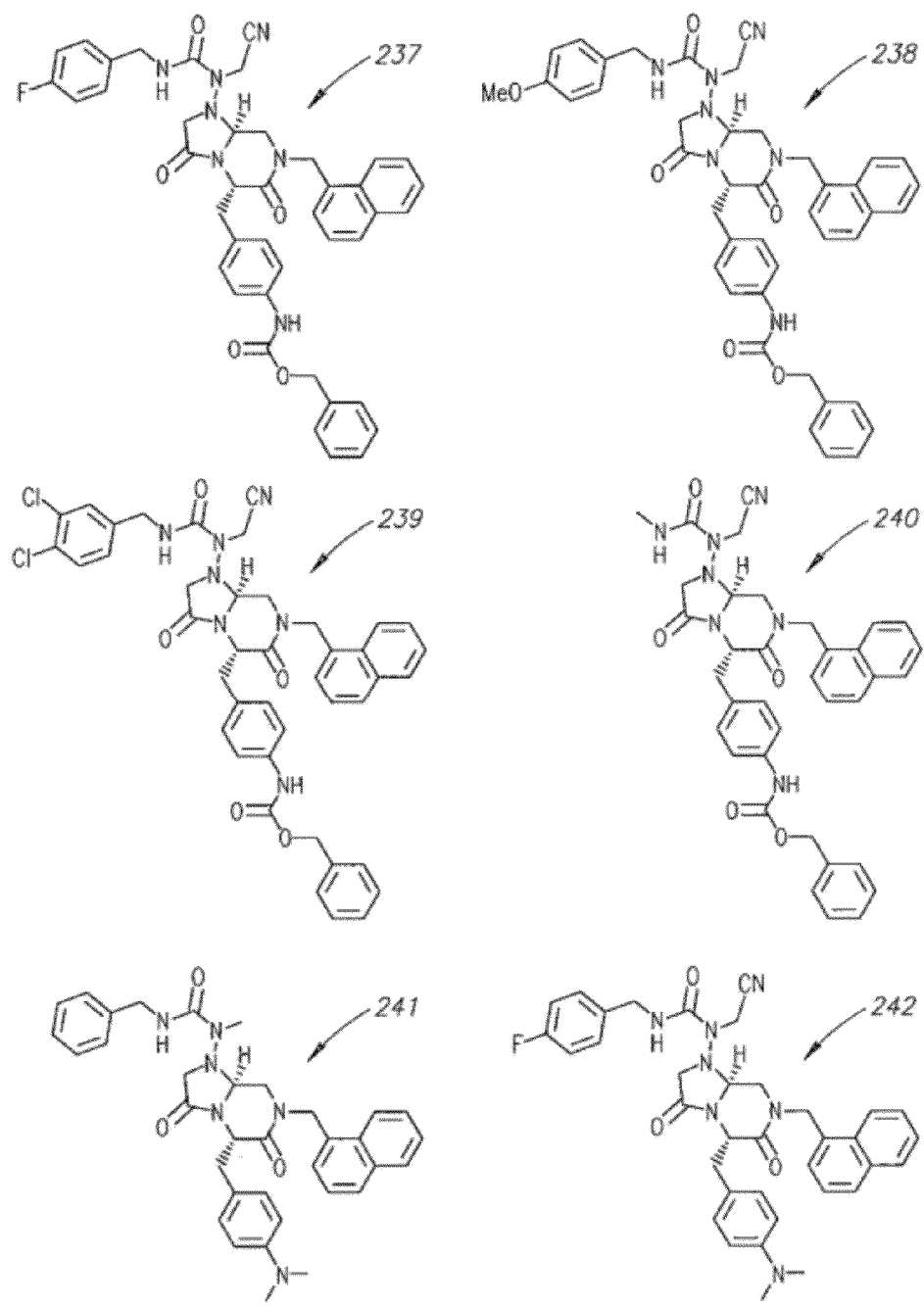
Figure 2H:
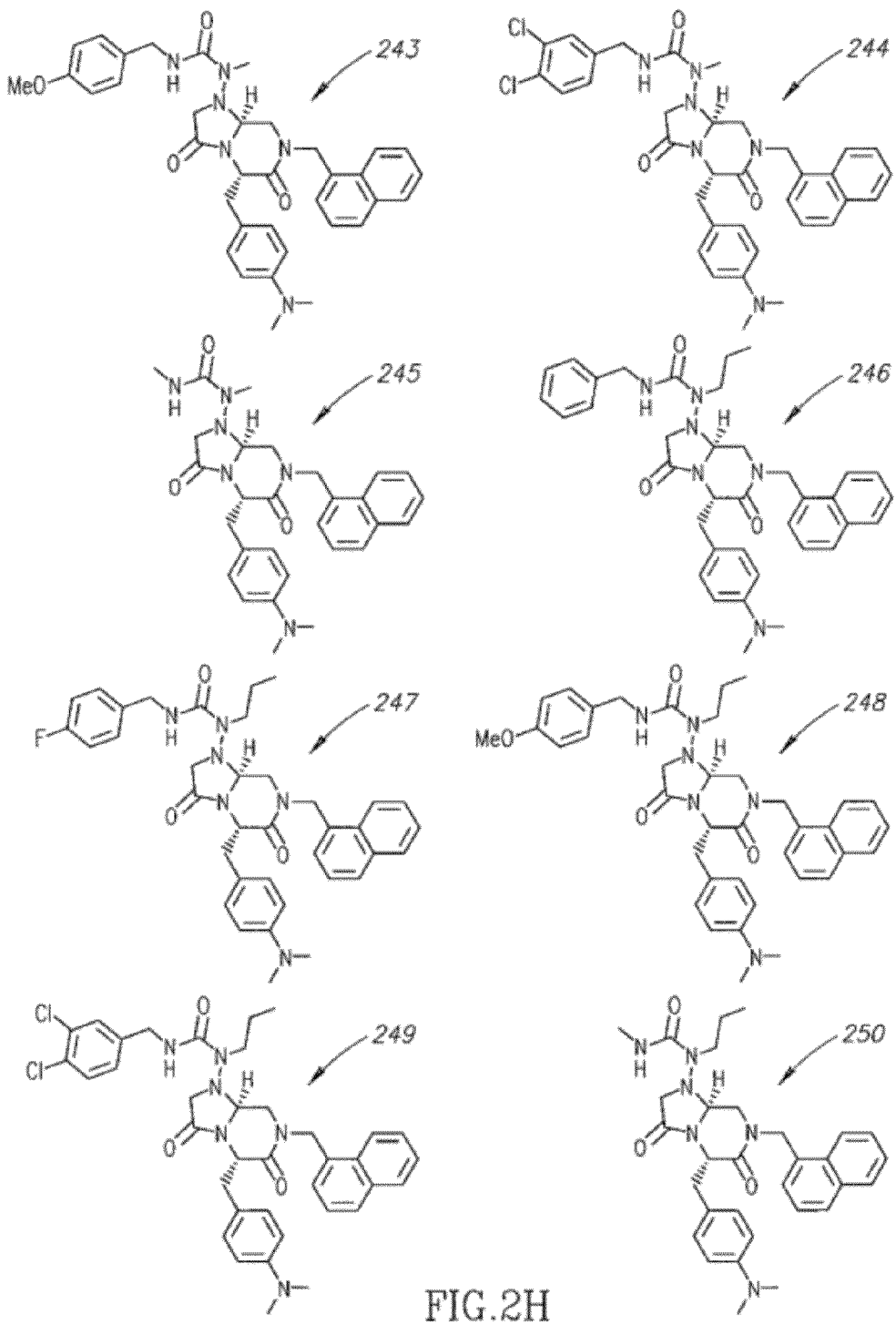
Figure 2I:
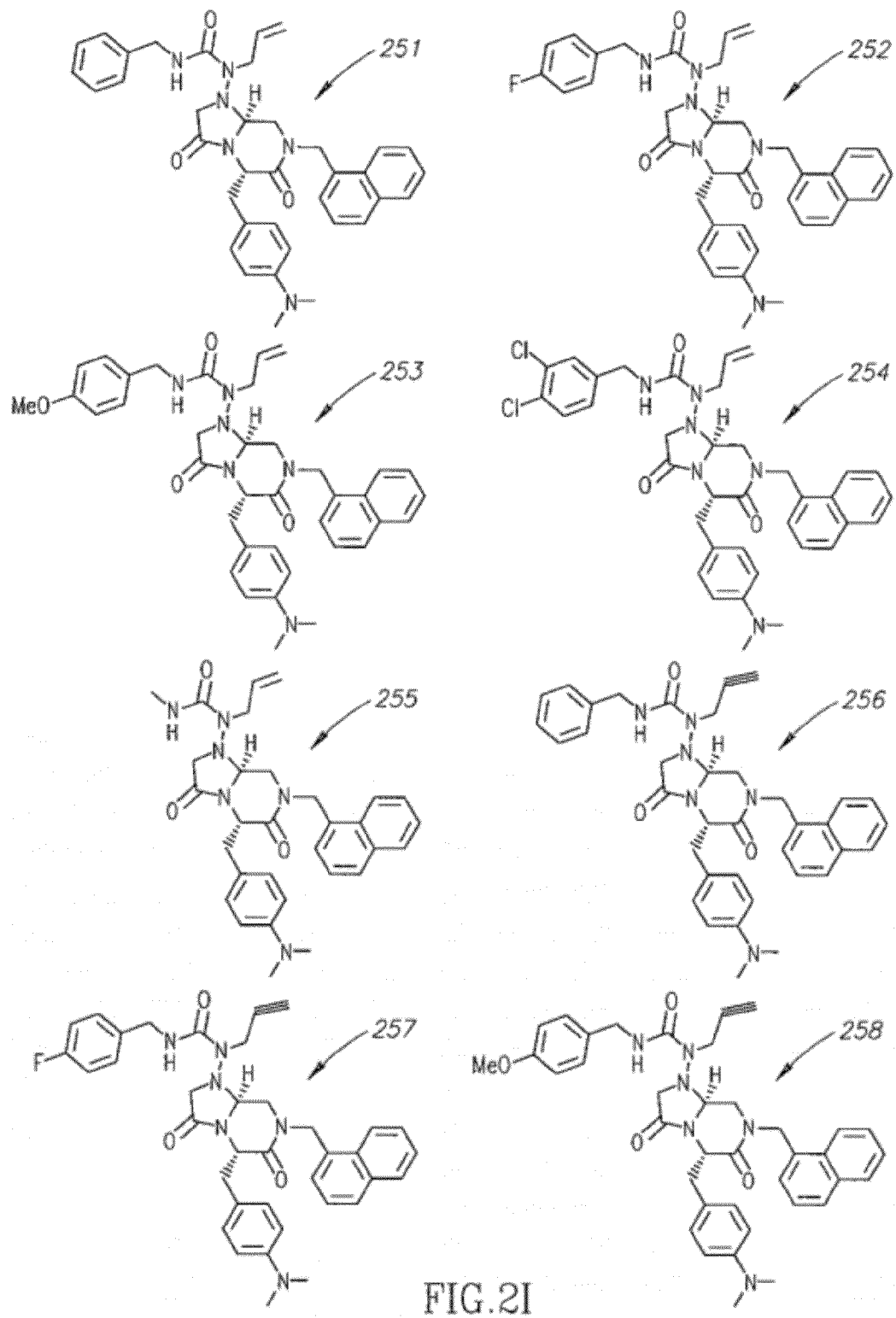
Figure 2J:
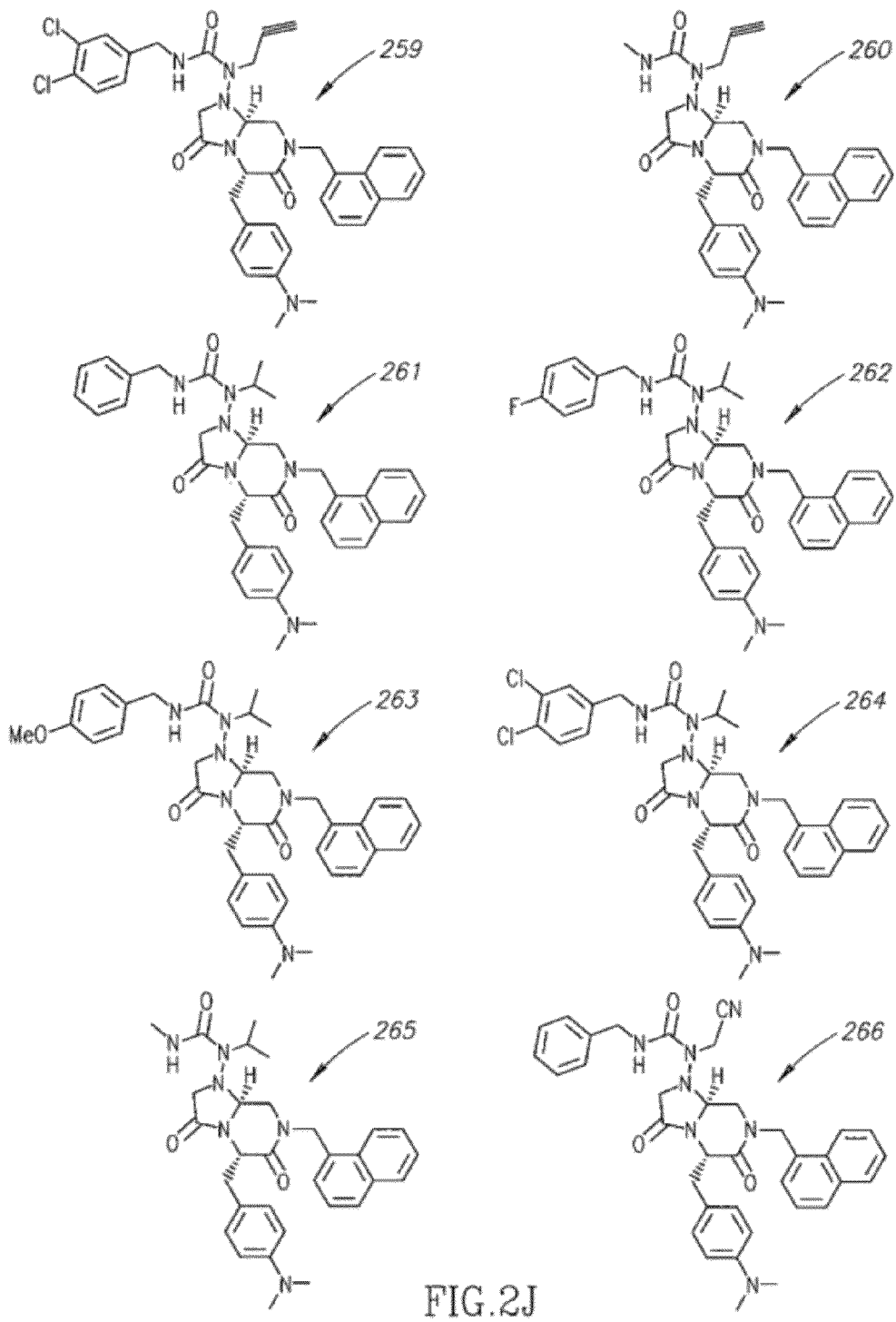
Figure 2K:
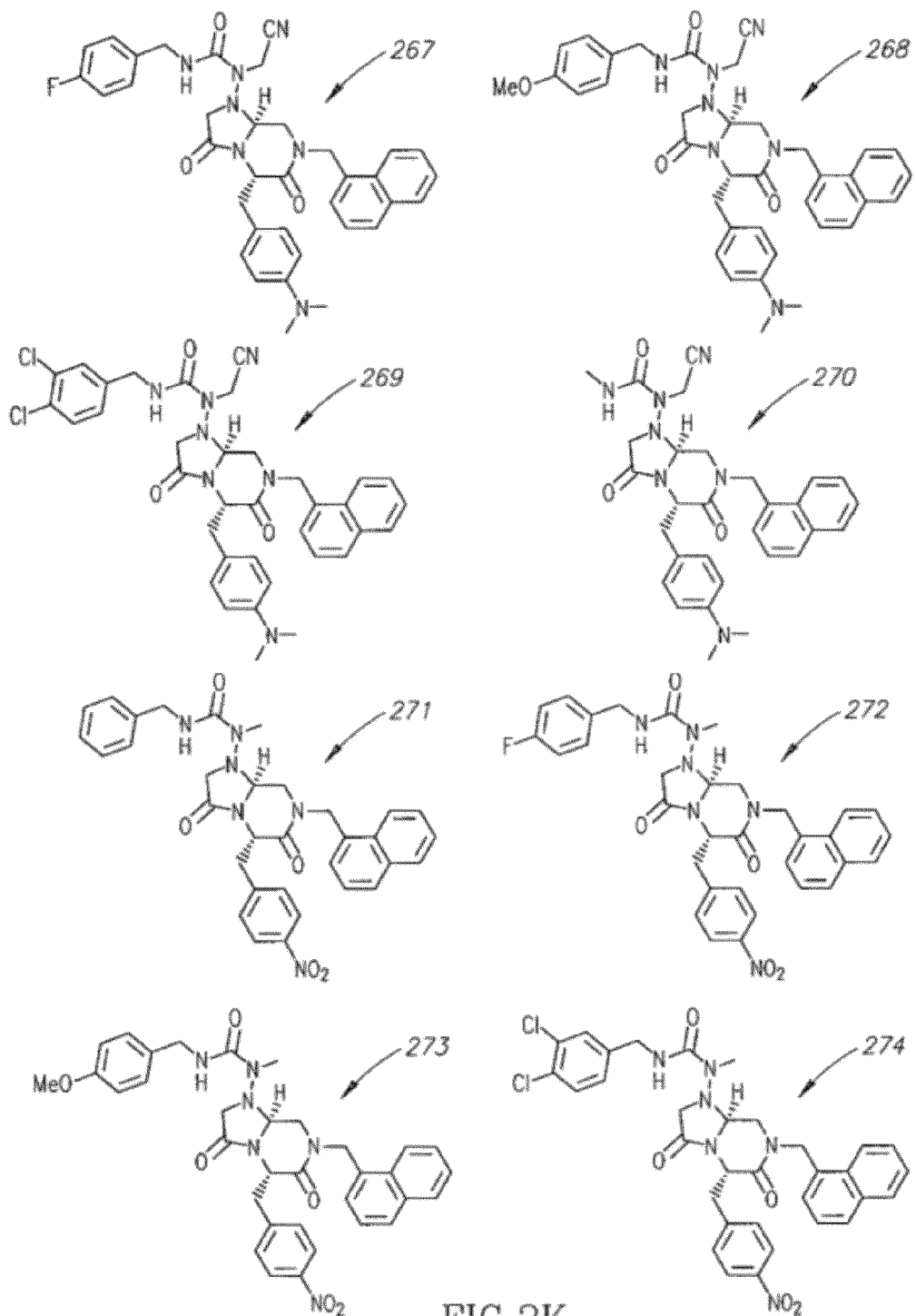
Figure 2L:
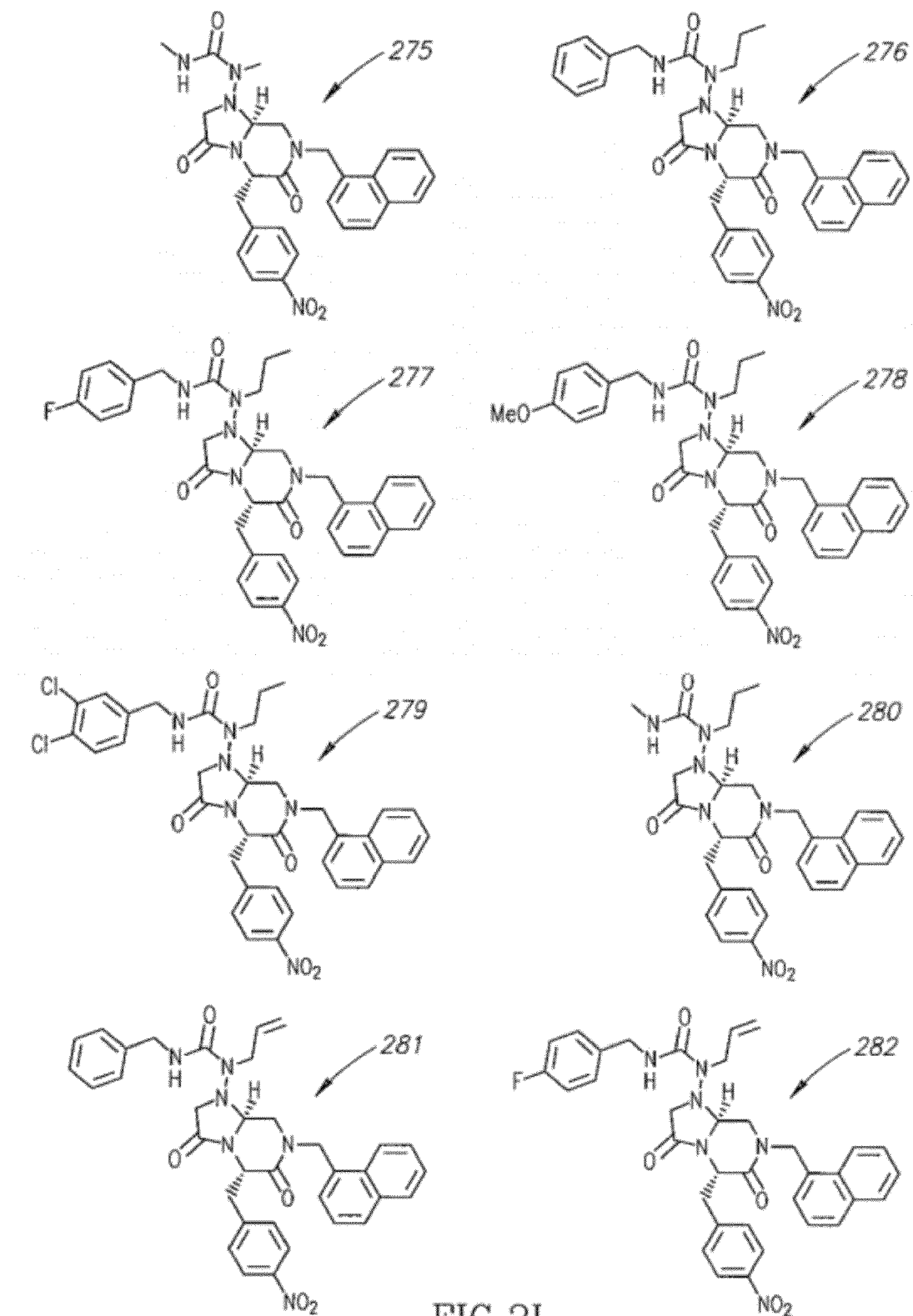
Figure 2M:
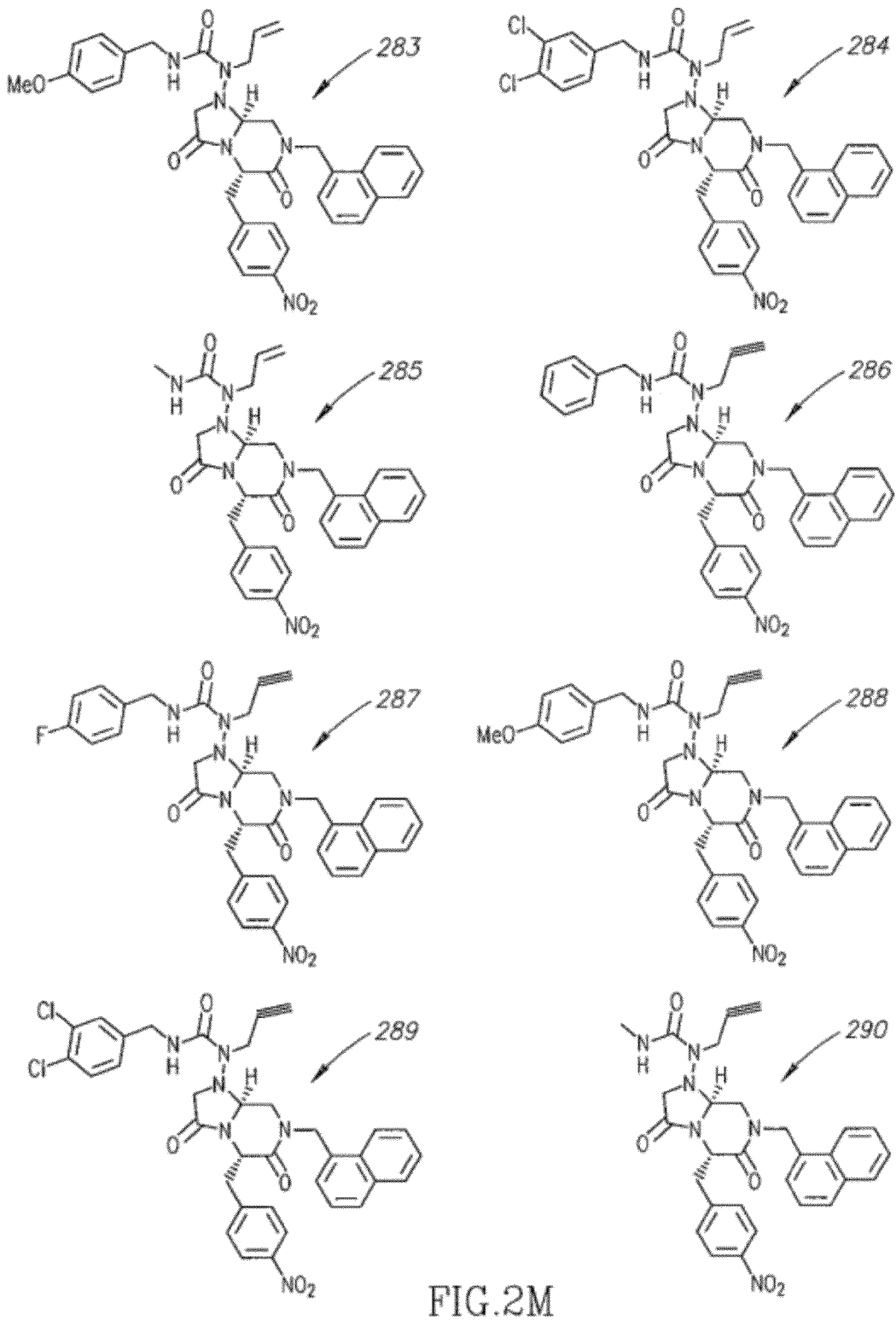
Figure 2N:
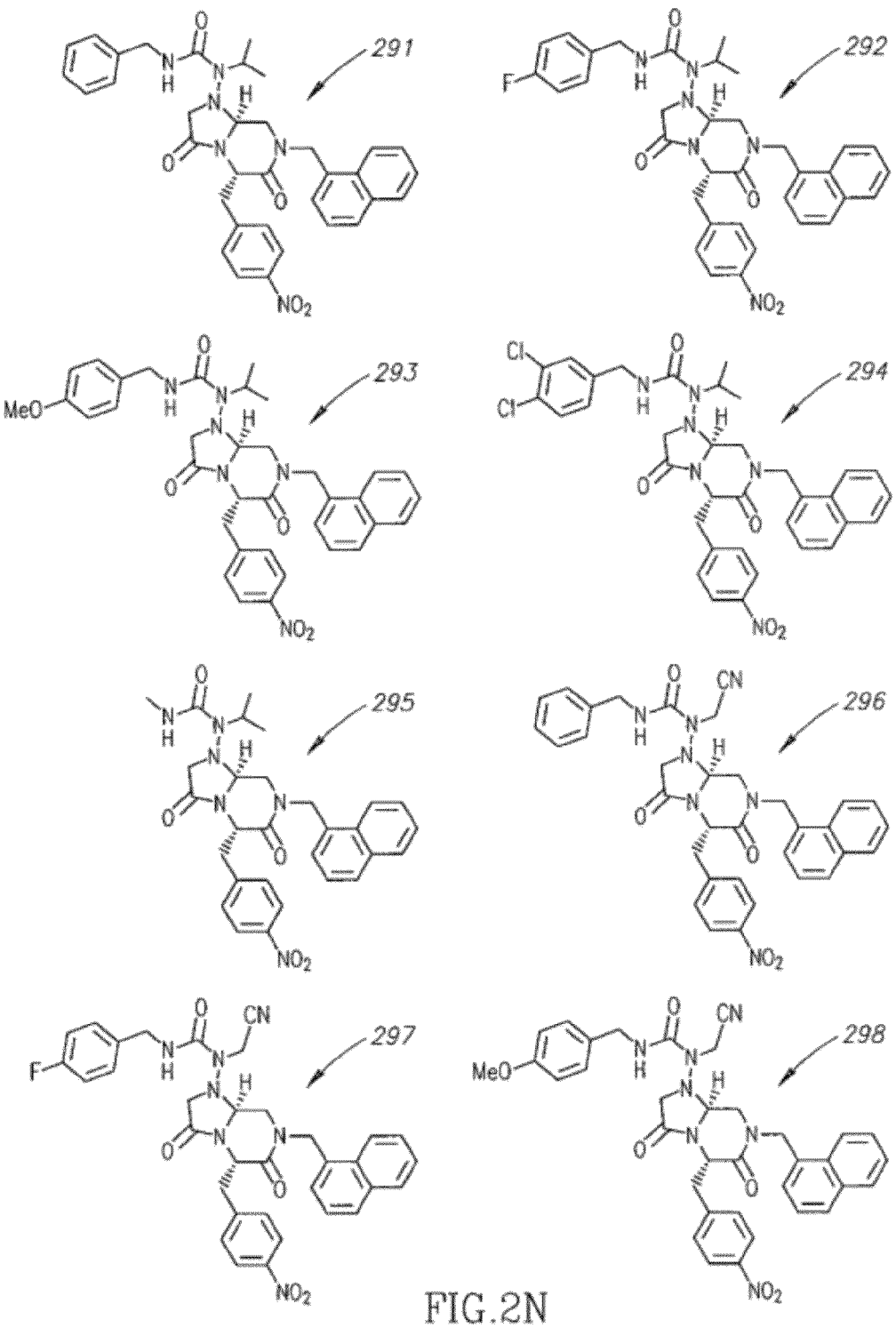

The present invention is directed to conformationally constrained compounds which mimic the secondary structure of α-helix regions of biological peptide and proteins (also referred to herein as "α-helix mimetics" and chemical libraries relating thereto, for the inhibition and/or eradication of cancer cells, particularly cancer cells having significant self-renewal potential, such as cancer stem cells.

Although there have been remarkable advances in the development of molecularly targeted drugs against cancer, for example imantinib (Gleevec) for the treatment of chronic phase CML, these agents in the end often fail. It is clear that new agents are needed to eradicate the cancer stem cells—literally the root of the problem.

Some parallels can be drawn between somatic stem cells and cancer stem cells (Pardal et al. Nat. Rev. Cancer. 3, 895, 2003). Both somatic stem cells and cancer stem cells are endowed with the ability to self renew and to differentiate. However, crucial differences exist. Whereas somatic stem cells differentiate to normal tissues, cancer stem cells differentiate aberrantly (Reya et al, Nature 2001, 414, 105-111). Despite the clonal origin of many cancers, most primary tumors display a notable degree of cellular heterogeneity. Thus, although modern chemotherapies kill a majority of the cells in a tumor, it is believed that the cancer stems cells often remain. ATP-binding cassette (ABC) multidrug resistance (MDR) transporters are believed to play important roles in protecting cancer stem cells from chemotherapy (Dean et al, Nat. Rev. Cancer 5, 275, 2005). The overexpression of P-glycoprotein (Pgp), energy-dependent efflux pumps of a variety of chemotherapeutic agents, resulting in multidrug resistant tumor cells was first demonstrated over two decades ago (Ling V. Cancer Chemother. Pharm. 40, S3-8, 1997; Sharom, F. J. J. Membr. Biol. 160, 161-175, 1997). MDR1 is a "TATA-less" gene, which belongs to a group of proteins whose genes lack a consensus TATA box within the proximal promoter region (Cornwell, M. M. Cell Growth Differ. 1, 607-615, 1990). Cells selected for their resistance to drugs often exhibit constitutive overexpression of MDR1. Additionally, efflux of Hoechst 33342 from normal murine hematopoietic cells identifies a "side population" (SP(+)) of negatively staining cells that are enriched for primitive progenitors (Feuring-Buske M., et al., Blood, 15:3882-9, 2001).

Mutations in the gene APC (adenomatous polyposis coli), which is a common early event in the majority of both hereditary and sporadic colorectal cancer, leads to the nuclear accumulation of β-catenin where it forms a complex with members of the T-cell factor (TCF)/lymphoid enhancer factor (LEF-1) family of transcription factors (8). To generate a transcriptionally active complex, β-catenin recruits the transcriptional coactivators Creb-Binding Protein (CBP) or its closely related homolog, p300 (9, 10) as well as other components of the basal transcription machinery. The MDR1 promoter contains several TCF/LEF binding sites between positions −275 and −1813. A link between APC mutations and enhanced MDR-1 expression via TCF/β-catenin driven transcription has been described (Yamada T., et al. Cancer Res. 60, 4761-4766, 2000).

It is becoming apparent that despite their high degree of homology and similar patterns of expression, CBP and p300 play unique and distinct roles in gene regulation. Data disclosed herein were generated using siRNA, ChIP assay and the chemogenomic tool ICG-001, which selectively disrupts the β-catenin/CBP interaction but not the corresponding β-catenin/p300 interaction (Emami et al PNAS, 2004) thereby interfering with a subset of Wnt/β-catenin regulated gene expression including survivin (Ma et al Oncogene 2005). The present disclosure demonstrates that TCF/β-catenin/CBP driven gene expression is essential for MDR-1 transcription. Furthermore, in the broader context, the disclosure shows that a CBP/β-catenin driven transcriptional cassette is critical for the expression of a "cancer stem cell-like" profile.

Embryonic stem cells can proliferate readily, in vitro and in vivo. In vivo, they can form teratocarcinoma-like tumors in adult mice if injected subcutaneously, intramuscularly, or into the testis. Thomson, J. A., et al., Science 282:1145-7:1998; Odorico, J. S., Stem Cells 19:193-204, 2001; Chung, Y., et al., Nature 439:216-9, 2006. Thus, hES cell-based therapy may lead to unwanted tumor formation.

To eliminate contamination of transplant material with residual undifferentiated ES cells, two different approaches have been reported. In one case, ES cell-specific expression in an engineered cell line of a compound that is toxic to undifferentiated ES cells is used and the culture conditions are modified to allow expression. This approach was used to eliminate mouse ES cells from a mixed cell population prior to transplant, Billon, N., et al., J Cell Sci, 115: 3657-65, 2002, and to express a suicide gene in the differentiated stem cells following transplantation, Schuldiner, M., J., Stem Cells 21:257-65, 2003. In another approach, the mixed cell population is treated with the ceramide analogue N-oleoyl serinol (S18) to selectively induce apoptosis of ES cells, Bieberich, E., et al., J Cell Biol. 167:723-34, 2004. In this case, subsequent teratocarcinoma formation following transplantation of mixed populations containing both ES stem and ES-derived neural stem cells was prevented, Bieberich, E., et al., J Cell Biol 167:723-34, 2004.

The compounds and methods disclosed herein provide another option for eliminating teratoma-forming stem cells prior to transplant. An advantage is that the treatment used a small molecule that has no toxicity in humans at the doses that would be used.

The synthesis and identification of conformationally constrained α-helix mimetics and their application to diseases are discussed in Walensky, L. D. et al Science 305, 1466, 2004; and Klein, C. Br. J. Cancer. 91, 1415, 2004. This disclosure further demonstrates that in conjunction with other chemotherapeutic agents, targeting cancer stem cells by antagonizing the CBP/β-catenin interaction not only eliminates the cancer stem cells which are resistant to normal chemotherapy, but also has an additive effect on the killing of other cancer cells that are normally sensitive to chemotherapy, by decreasing the transcription of anti-apoptotic genes such as survivin.

As shown in detail in the examples, compounds disclosed herein ICG-001 reduced MDR-1/luciferase activity in a doxorubin-resistant ovarian sarcoma line MES-SA/Dx5 and in the CML derived cell line K562. In these cell lines, there is an increased level of cytosolic and nuclear β-catenin. This activated Wnt/β-catenin pathway leads in twin to activation of the multiding resistance gene (MDR-1) in the cell lines.

By reducing MDR-A/luciferase activity, ICG-001 was a candidate for testing against patient CML cells. The examples further show that ICG-001 in combination with imatinib reduced total colony forming units in comparison with either drug alone. Morphological examination showed that the treated colonies had an increased state of differentiation.

In addition to being effective against ovarian sarcoma and CML cells, ICG-001 reduced stem cell markers in cells for other ovarian cell lines and melanoma B16 cells. ICG-100 and several other compounds, including PRI-001, PRI-002, PRI-003, PRI-004, PRI-005, and PRI-006 inhibited β-catenin interaction with CBP in SW480 cells, a cell line derived from intestinal carcinoma.

The wide range of cancers amenable to treatment with the compounds disclosed herein is consistent with β-catenin's role in several cancer-related events. These include expression of survivin, expression of MDR-1, and maintenance of a cancer stem cell population.

The compounds and methods herein are therefore suitable for treating cancers including but not limited to acute lymphocytic leukemia, acute nonlymphocytic leukemia, cancer of the adrenal cortex, bladder cancer, brain cancer, breast cancer, cervix cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head and neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovary cancer, ovary (germ cell) cancer, pancreatic cancer, penis cancer, prostate cancer, retinoblastoma, skin cancer, soft-tissue sarcoma, squamous cell carcinomas, stomach cancer, testicular cancer, thyroid cancer, trophoblastic neoplasms, cancer of the uterus, vaginal cancer, cancer of the vulva, and Wilm's tumor.

The α-helix mimetic structures of the present invention are useful as bioactive agents, including (but not limited to) use as diagnostic, prophylactic and/or therapeutic agents. The α-helix mimetic structure libraries of this invention are useful in the identification of such bioactive agents. In the practice of the present invention, the libraries may contain from tens to hundreds to thousands (or greater) of individual α-helix structures (also referred to herein as "members").

In one aspect of the present invention, a α-helix mimetic structure is disclosed having the following formula (I):

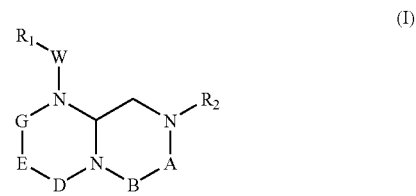

wherein A is —(C=O)—CHR$_3$—, or —(C=O), B is N—R$_5$— or —CHR$_6$—, D is —(C=O)—(CHR$_7$)— or —(C=O)—, E is —(ZR$_8$)— or (C=O), G is —(XR$_9$)$_n$—, —(CHR$_{10}$)—(NR$_6$)—, —(C=O)—(XR$_{12}$)—, —(C=N—W—R$_1$)—, —(C=O)—, X—(C=O)—R$_{13}$, X—(C=O)—NR$_{13}$R$_{14}$, X—(SO$_2$)—R$_{13}$, or X—(C=O)—OR$_{13}$, W is —Y(C=O)—, —(C=O)NH—, —(SO$_2$)—, —CHR$_{14}$, (C=O)—(NR$_{15}$)—, substituted or unsubstituted oxadiazole, substituted or unsubstituted triazole, substituted or unsubstituted thiadiazole, substituted or unsubstituted 4,5 dihydrooxazole, substituted or unsubstituted 4,5 dihydrothiazole, substituted or unsubstituted 4,5 dihydroimidazole, or nothing, Y is oxygen or sulfur, X and Z is independently nitrogen or CH, n=0 or 1; and R$_1$, R$_2$, R$_3$, R$_4$, R$_5$, R$_6$, R$_7$, R$_8$, R$_9$, R$_{10}$, R$_{11}$, R$_{12}$, R$_{13}$, R$_{14}$, and R$_{15}$ are the same or different and independently selected from an amino acid side chain moiety or derivative thereof, the remainder of the molecule, a linker and a solid support, and stereoisomers thereof.

More specifically, R$_1$, R$_2$, R$_3$, R$_4$, R$_5$, R$_6$, R$_7$, R$_8$, R$_9$, R$_{10}$, R$_{11}$, R$_{12}$, R$_{13}$, R$_{14}$, and R$_{15}$ are independently selected from the group consisting of aminoC$_{2-5}$alkyl, guanidineC$_{2-5}$alkyl, C$_{1-4}$alkylguanidinoC$_{2-5}$alkyl, diC$_{1-4}$alkylguanidino-C$_{2-5}$alkyl, amidinoC$_{2-5}$alkyl, C$_{1-4}$alkylamidino C$_{2-5}$alkyl, diC$_{1-4}$alkylamidinoC$_{2-5}$alkyl, C$_{1-3}$alkoxy, phenyl, substituted phenyl (where the substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), benzyl, substituted benzyl (where the substituents on the benzyl are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-3}$alkyl, nitro, carboxy, cyano, sulfuryl or hydroxyl), naphthyl, substituted naphthyl (where the substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), bisphenyl methyl, substituted bis-phenyl methyl (where the substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), pyridyl, substituted pyridyl (where the substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), pyridylC$_{1-4}$alkyl, substituted pyridylC$_{1-4}$alkyl (where the pyridine substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), pyrimidylC$_{1-4}$alkyl, substituted pyrimidylC$_{1-4}$alkyl (where the pyrimidine substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), triazin-2-yl-C$_{1-4}$alkyl, substituted triazin-2-yl-C$_{1-4}$alkyl (where the triazine substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), imidazoC$_{1-4}$alkyl, substituted imidazol C$_{1-4}$alkyl (where the imidazole substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl, hydroxyl or methyl), imidazolinylCalkyl, N-amidinopiperazinyl-N—C$_{0-4}$alkyl, hydroxyC$_{2-5}$alkyl, C$_{1-5}$alkylaminoC$_{2-5}$alkyl, hydroxyC$_{2-5}$alkyl, C$_{1-5}$alkylaminoC$_{2-5}$alkyl, C$_{1-5}$dialkylaminoC$_{2-5}$alkyl, N-amidinopiperidinylC$_{1-4}$alkyl and 4-aminocyclohexylC$_{0-2}$alkyl.

In one embodiment, R$_1$, R$_2$, R$_6$ of E, and R$_7$, R$_8$ and R$_9$ of G are the same or different and represent the remainder of the compound, and R$_3$ or A, R$_4$ of B or R$_5$ of D is selected from an amino acid side chain moiety or derivative thereof. As used herein, the term "remainder of the compound" means any moiety, agent, compound, support, molecule, linker, amino acid, peptide or protein covalently attached to the α-helix mimetic structure at R$_1$, R$_2$, R$_5$, R$_6$, R$_7$, R$_8$ and/or R$_9$ positions. This term also includes amino acid side chain moieties and derivatives thereof.

As used herein, the term "amino acid side chain moiety" represents any amino acid side chain moiety present in naturally occurring proteins including (but not limited to) the naturally occurring amino acid side chain moieties identified in Table 1. Other naturally occurring amino acid side chain moieties of this invention include (but are not limited to) the side chain moieties of 3,5-dibromotyrosine, 3,5-diiodotyrosine, hydroxylysine, γ-carboxyglutamate, phosphotyrosine and phosphoserine. In addition, glycosylated amino acid side chains may also be used in the practice of this invention, including (but not limited to) glycosylated threonine, serine and asparagine.

TABLE 1

Amino Acid Side Chain Moieties

| Amino Acid Side Chain Moiety | Amino Acid |
| --- | --- |
| —H | Glycine |
| —CH$_3$ | Alanine |
| —CH(CH$_3$)$_2$ | Valine |
| —CH$_2$CH(CH$_3$)$_2$ | Leucine |
| —CH(CH$_3$)CH$_2$CH$_3$ | Isoleucine |
| —(CH$_2$)$_4$NH$_3^+$ | Lysine |
| —(CH$_2$)$_3$NHC(NH$_2$)NH$_2^+$ | Arginine |
|  | Histidine |
| —CH$_2$COO$^-$ | Aspartic acid |
| —CH$_2$CH$_2$COO$^-$ | Glutamic acid |
| —CH$_2$CONH$_2$ | Asparagine |
| —CH$_2$CH$_2$CONH$_2$ | Glutamine |
|  | Phenylalanine |
|  | Tyrosine |
|  | Tryptophan |
| —CH$_2$SH | Cysteine |
| —CH$_2$CH$_2$SCH$_3$ | Methionine |
| —CH$_2$OH | Serine |
| —CH(OH)CH$_3$ | Threonine |
|  | Proline |
|  | Hydroxyproline |

In addition to naturally occurring amino acid side chain moieties, the amino acid side chain moieties of the present invention also include various derivatives thereof. As used herein, a "derivative" of an amino acid side chain moiety includes modifications and/or variations to naturally occurring amino acid side chain moieties. For example, the amino acid side chain moieties of alanine, valine, leucine, isoleucine and pheylalanine may generally be classified as lower chain alkyl, aryl, or arylalkyl moieties. Derivatives of amino acid side chain moieties include other straight chain or branched, cyclic or noncyclic, substitutes or unsubstituted, saturated or unsaturated lower chain alkyl, aryl or arylalkyl moieties.

As used herein, "lower chain alkyl moieties" contain from 1-12 carbon atoms, "lower chain aryl moieties" contain from 6-12 carbon atoms and "lower chain aralkyl moieties" contain from 7-12 carbon atoms. Thus, in one embodiment, the amino acid side chain derivative is selected from a C$_{1-12}$ alkyl, a $C_{6-12}$ aryl and a $C_{7-12}$ arylalkyl, and in a more preferred embodiment, from a $C_{1-7}$ alkyl, a $C_{6-10}$ aryl and a $C_{7-11}$ arylalkyl.

Amino side chain derivatives of this invention further include substituted derivatives of lower chain alkyl, aryl, and arylalkyl moieties, wherein the substituents is selected from (but are not limited to) one or more of the following chemical moieties: —OH, —OR, —COOH, —COOR, —CONH$_2$, —NH$_2$, —NHR, —NRR, —SH, —SR, —SO$_2$R, —SO$_2$H, —SOR and halogen (including F, Cl, Br and I), wherein each occurrence of R is independently selected from straight chain or branched, cyclic or noncyclic, substituted or unsubstituted, saturated or unsaturated lower chain alkyl, aryl, and aralkyl moieties. Moreover, cyclic lower chain alkyl, aryl and arylalkyl moieties of this invention include naphthalene, as well as heterocyclic compounds such as thiophene, pyrrole, furan, imidazole, oxazole, thiazole, pyrazole, 3-pyrroline, pyrrolidine, pyridine, pyrimidine, purine, quinoline, isoquinoline and carbazole. Amino acid side chain derivatives further include heteroalkyl derivatives of the alkyl portion of the lower chain alkyl and aralkyl moieties, including (but not limited to) alkyl and aralkyl phosphonates and silanes.

Representative $R_1$, $R_2$, $R_5$, $R_6$, $R_7$, $R_8$ and $R_9$ moieties specifically include (but are not limited to)-OH, —OR, —COR, —COOR, —CONH$_2$, —CONR, —CONRR, —NH$_2$, —NHR, —NRR, —SO$_2$R and —COSR, wherein each occurrence of R is as defined above.

In a further embodiment, and in addition to being an amino acid side chain moiety or derivative thereof (or the remainder of the compound in the case of $R_1$, $R_2$, $R_5$, $R_6$, $R_7$, $R_8$ and $R_9$), $R_1$, $R_2$, $R_5$, $R_6$, $R_7$, $R_8$ or $R_9$ may be a linker facilitating the linkage of the compound to another moiety or compound. For example, the compounds of this invention may be linked to one or more known compounds, such as biotin, for use in diagnostic or screening assay. Furthermore, $R_1$, $R_2$, $R_5$, $R_6$, $R_7$, $R_8$ or $R_9$ may be a linker joining the compound to a solid support (such as a support used in solid phase peptide synthesis) or alternatively, may be the support itself. In this embodiment, linkage to another moiety or compound, or to a solid support, is preferable at the $R_1$, $R_2$, $R_7$ or $R_8$ position, and more preferably at the $R_1$ or $R_2$ position.

In the embodiment wherein A is —(C=O)—CHR$_3$—, B is —N—R$_4$, D is —(C=O)—, E is —(ZR$_6$)—, G is —(C=O)—(XR$_9$)—, the α-helix mimetic compounds of this invention have the following general formula (III):

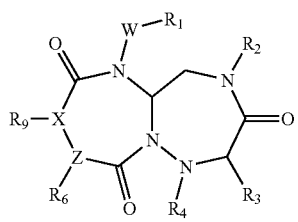

(III)

wherein $R_1$, $R_2$, $R_4$, $R_6$, $R_7$, $R_8$, W and X are as defined above, Y is —C=O, —(C=O)—O—, —(C=O)—NR$_8$, —SO$_2$—, or nothing, and Z is nitrogen or CH (when Z is CH, then X is nitrogen). In a preferred embodiment, $R_1$, $R_2$, $R_6$, $R_7$ and $R_8$ represent the remainder of the compound, and $R_4$ is selected from an amino acid side chain moiety. In a more specific embodiment wherein A is —O—CHR$_3$—, B is —NR$_4$—, D is —(C=O)—, E is —(ZR$_6$)—, Gi is (XR$_7$)$_n$—, the α-helix mimetic compounds of this invention have the following formula (IV):

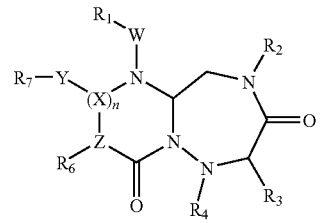

(IV)

wherein $R_1$, $R_2$, $R_4$, $R_6$, $R_7$, W, X and n are as defined above, and Z is nitrogen or CH (when Z is nitrogen, then n is zero, and when Z is CH, then X is nitrogen and n is not zero). In a preferred embodiment, $R_1$, $R_2$, $R_6$, and $R_7$ represent the remainder of the compound, and $R_4$ is selected from an amino acid side chain moiety. In this case, $R_6$ or $R_7$ may be selected from an amino acid side chain moiety when Z and X are CH, respectively.

In the embodiment of structure (I) wherein A is —(C=O), B is —(CHR$_6$)—, D is —(C=O)—, E is —(ZR$_8$)—, and G is —(NH)— or —(CH$_2$)—, and W is a substituted or unsubstituted oxadiazole, substituted or unsubstituted triazole, substituted or unsubstituted thiadiazole, substituted or unsubstituted 4,5 dihydrooxazole, substituted or unsubstituted 4,5 dihydrothiazole, substituted or unsubstituted 4,5 dihydroimidazole, the α-helix mimetic compounds of this invention have the following general formula (V):

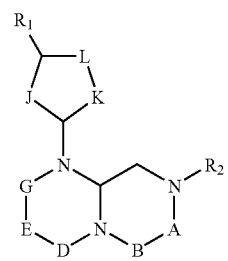

(V)

wherein K is nitrogen, oxygen, or sulfur, L is nitrogen, oxygen, —(CH)—, or —(CH$_2$)—, J is nitrogen, oxygen, or sulfur, Z is nitrogen or CH, and $R_1$, $R_2$, $R_6$, $R_8$, and $R_{13}$ are selected from an amino acid side chain moiety.

Alternative embodiments of the invention relate to compounds having the general formula (VI):

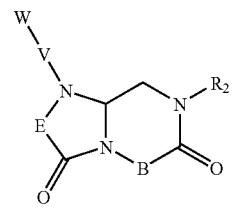

(VI)

wherein B is —(CHR$_3$)—, —(NR$_3$)—, E is —(CHR$_4$)—, V is —(XR$_5$)— or nothing, W is —(C=O)—(XR$_6$R$_7$), —(SO$_2$)—, substituted or unsubstituted oxadiazole, substituted or unsubstituted triazole, substituted or unsubstituted thiadiazole, substituted or unsubstituted 4,5 dihydrooxazole, substituted or unsubstituted 4,5 dihydrothiazole, substituted or unsubstituted 4,5 dihydroimidazole, X is independently nitrogen, oxygen, or CH, and $R_1$, $R_2$, $R_3$, $R_4$, $R_5$, $R_6$, and $R_7$ are selected from an amino acid side chain moiety or derivative thereof, the remainder of the molecule, a linker and solid support, and stereoisomers thereof.

In the embodiments of formula (VI) wherein V is —($XR_5$)— or nothing, and W is substituted or unsubstituted oxadiazole, substituted or unsubstituted triazole, substituted or unsubstituted thiadiazole, substituted or unsubstituted 4,5 dihydrooxazole, substituted or unsubstituted 4,5 dihydrothiazole, substituted or unsubstituted 4,5 dihydroimidazole, and X is independently introgen or CH, the compounds have the following general formula (VII):

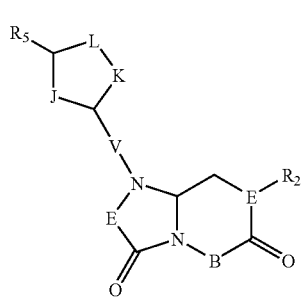

(VII)

wherein K is nitrogen, oxygen, or sulfur, L is nitrogen, oxygen, —(CH)—, or —($CH_2$)—, J is nitrogen, oxygen, or sulfur, and $R_2$ and $R_5$ are defined as described above.

In preferred embodiments of the invention, $R_2$ in structures I through VII comprises an aromatic ring substituent such as a phenyl or naphthyl group that is substituted with a basic moiety such a primary or secondary amine. The aromatic ring substituent may also be a heterocycle, such as a purine or indole. Some embodiments of the invention also provide for aromatic ring substituents that may be substituted with one or two halogen moieties.

A feature of many α-helix mimetic compounds is that they provide a scaffolding that places three hydrophobic functional groups, which may also be referred to as pharmacophore rings, in a specific, spatially-defined orientation referred to as an "optimized chemical space". The optimized chemical space may be triangular, with the centers of three functional groups forming the three points of the triangle. An example of an optimized chemical space is one in which the lengths of the three sides of the triangle are around 9.6±0.5 Angstroms (symbolized hereafter by "Å"), 9.2±0.5 Å, and 10.3±0.5 Å. FIG. 13C depicts two superimposed structures having three such pharmacophore rings forming a triangle in space. A number of different compounds exhibit such an optimized chemical space, and may be considered to be within the scope of the invention.

The compounds of general formula (I) of the present invention have one or more asymmetric carbons depending on it's substituents. For example, where the compounds of general formula (I) contains one or more asymmetric carbons, two kinds of optical isomers exist when the number of asymmetric carbon is 1, and when the number of asymmetric carbon is 2, four kinds of optical isomers and two kinds of diastereomers exist. Pure stereoisomers including opticalisomers and diastereoisomers, any mixture, racemates and the like of stereoisomers all fall within the scope of the present invention. Mixtures such as racemates may sometimes be preferred from viewpoint of easiness for manufacture.

When the compounds of general formula (I) of the present invention contains a basic functional group such as amino group, or when the compounds of general formula (I) of the present invention contains an aromatic ring which itself has properties of base (e.g., pyridine ring), the compound can be converted into a pharmaceutically acceptable salt (e.g., salt with inorganic acids such as hydrochloric acid and sulfuric acid, or salts with organic acids such as acetic acid and citric acid) by a known means. When the compounds of general formula (I) of the present invention contains an acidic functional group such as carboxyl group or phenolic hydroxyl group, the compound can be converted into pharmaceutically acceptable salt (e.g., inorganic salts with sodium, ammonia and the like, or organic salts with triethylamine and the like) by a known means. When the compounds of general formula (I) of the present invention contains a prodrugable functional group such as phenolic hydroxyl group, the compound can be converted into prodrug (e.g., acetylate or phosphonate) by a known means. Any pharmaceutically acceptable salt and prodrug all fall within the scope of the present invention.

The various compounds disclosed by the present invention can be purified by known methods such as recrystallization, and variety of chromatography techniques (column chromatography, flash column chromatography, thin layer chromatography, high performance liquid chromatography).

The α-helix mimetic structures of the present invention may be prepared by utilizing appropriate starting component molecules (hereinafter referred to as "component pieces"). Briefly, in the synthesis of α-helix mimetic structures having formula (II), first and second component pieces are coupled to form a combined first-second intermediate, if necessary, third and/or fourth component pieces are coupled to form a combined third-fourth intermediate (or, if commercially available, a single third intermediate may be used), the combined first-second intermediate and third-fourth intermediate (or third intermediate) are then coupled to provide a first-second-third-fourth intermediate (or first-second-third intermediate) which is cyclized to yield the α-helix mimetic structures of this invention. Alternatively, the α-helix mimetic structures of formula (II) may be prepared by sequential coupling of the individual component pieces either stepwise in solution or by solid phase synthesis as commonly practiced in solid phase peptide synthesis.

Within the context of the present invention, a "first component piece" has the following formula S1

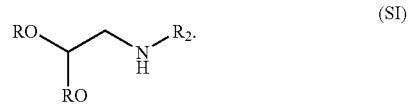

(S1)

Wherein $R_2$ as defined above, and R is a protective group suitable for use in peptide synthesis. Suitable R groups include alkyl groups and, in a preferred embodiment, R is a methyl group. Such first component pieces may be readily synthesized by reductive amination or substitution reaction by displacement of $H_2N$—$R_2$ from $CH(OR)_2$—CHO or $CH(OR)_2$—$CH_2$-Hal (wherein Hal means a halogen atom).

A "second component piece" of this invention has the following formula S2:

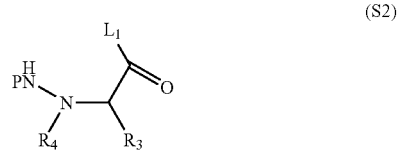

(S2)

Where $L_1$ is carboxyl-activation group such as halogen atom, $R_3$, $R_4$ is as defined above, and P is an amino protective group suitable for use in peptide synthesis. Preferred protective groups include t-butyl dimethylsilyl (TBDMS), t-Butyloxycarbonyl (BOC), Methylosycarbonyl (MOC), 9H-Fluorenylmethyloxycarbonyl (FMOC), and allyloxycarbonyl (Alloc). When L is —C(O)NHR, —NHR may be an carboxyl protective group. N-Protected amino acids are commercially available. For example, FMOC amino acids are available for a variety of sources. The conversion of these compounds to the second component pieces of this invention may be readily achieved by activation of the carboxylic acid group of the N-protected amino acid. Suitable activated carboxylic acid groups include acid halides where X is a halide such as chloride or bromide, acid anhydrides where X is an acyl group such as acetyl, reactive esters such as an N-hydroxysuccinimide esters and pentafluorophenyl esters, and other activated intermediates such as the active intermediate formed in a coupling reaction using a carbodiimide such as dicyclohexylcarbodiimide (DCC).

In the case of the azido derivative of an amino acid serving as the second component piece, such compounds may be prepared from the corresponding amino acid by the reaction disclosed by Zaloom et al. (*J. Org. Chem.* 46:5173-76, 1981).

A "third component piece" of this invention has the following formula S3:

(S3)

where G, E, and $L_1$ are as defined above. Suitable third component pieces are commercially available from a variety of sources or can be prepared by known methods in organic chemistry.

More specifically, the α-helix mimetic structures of this invention of formula (II) are synthesized by reacting a first component piece with a second component piece to yield a combined first-second intermediate, followed by either reacting the combined first-second intermediate with third component pieces sequentially to provide a combined first-second-third-fourth intermediate, and the cyclizing this intermediate to yield the α-helix mimetic structure.

The general synthesis of an α-helix having structure I' may be carried out by the following technique. A first component piece 1 is coupled with a second component piece 2 by using coupling reagent such as phosgene to yield, after N-deprotection, a combined first-second intermediate 1-2 as illustrated below:

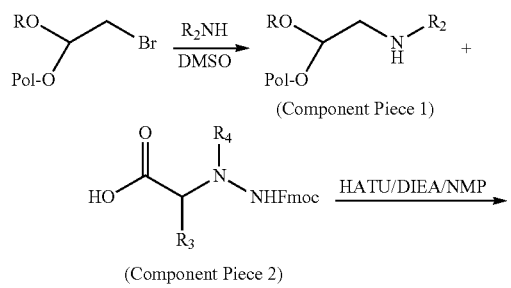

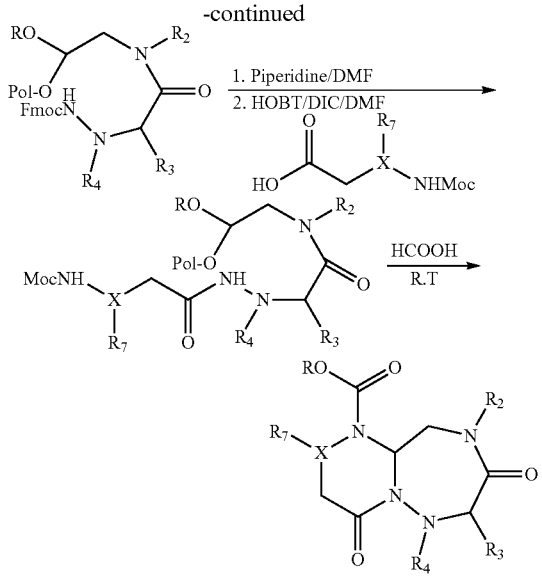

wherein $R_1$, $R_2$, $R_4$, $R_7$, Fmoc, Moc and X are as defined above, and Pol represents a polymeric support.

The synthesis of representative component pieces of this invention are described in the Examples.

The α-helix mimetic structures of formula (III) and (IV) may be made by techniques analogous to the modular component synthesis disclosed above, but with appropriate modifications to the component pieces.

As mentioned above, the reverse-turn mimetics of U.S. Pat. No. 6,013,458 to Kahn, et al. are useful as bioactive agents, such as diagnostic, prophylactic, and therapeutic agents. The opiate receptor binding activity of representative reverse-turn mimetics is presented in Example 9 of said U.S. Pat. No. 6,013,458, wherein the reverse-turn mimetics of this invention were found to effectively inhibit the binding of a radiolabeled enkephalin derivative to the δ and μ opiate receptors, of which data demonstrates the utility of these reverse-turn mimetics as receptor agonists and as potential analgesic agents.

The α-helix mimetic structures of the present invention will be useful as bioactive agents, such as diagnostic, prophylactic, and therapeutic agents.

Therefore, since the compounds according to the present invention are of α-helix mimetic structures, it may be useful for modulating a cell signaling transcription factor related peptides in a warm-blooded animal, comprising administering to the animal an effective amount of the compound of formula (I). Besides being useful for human treatment, the compounds of the present invention are also useful for veterinary treatment of mammals, including companion animals and farm animals, such as, but not limited to dogs, cats, horses, cows, sheep, and pigs.

Further, the α-helix mimetic structures of the present invention may also be effective for inhibiting transcription factor/coactivator and transcription factor corepressor interactions.

In another aspect of this invention, libraries containing α-helix mimetic structures of the present invention are disclosed. Once assembled, the libraries of the present invention may be screened to identify individual members having bioactivity. Such screening of the libraries for bioactive members may involve, for example, evaluating the binding activity of the members of the library or evaluating the effect the library members have on a functional assay. Screening is normally accomplished by contacting the library members (or a subset of library members) with a target of interest, such as, for example, an antibody, enzyme, receptor or cell line. Library members, which are capable of interacting with the target of interest, are referred to herein as "bioactive library members" or "bioactive mimetics". For example, a bioactive mimetic may be a library member which is capable of binding to an antibody or receptor, which is capable of inhibiting an enzyme, or which is capable of eliciting or antagonizing a functional response associated, for example, with a cell line. In other words, the screening of the libraries of the present invention determines which library members are capable of interacting with one or more biological targets of interest. Furthermore, when interaction does occur, the bioactive mimetic (or mimetics) may then be identified from the library members. The identification of a single (or limited number) of bioactive mimetic(s) from the library yields α-helix mimetic structures which are themselves biologically active, and thus useful as diagnostic, prophylactic or therapeutic agents, and may further be used to significantly advance identification of lead compounds in these fields.

In another aspect of this invention, methods for constructing the libraries are disclosed. Traditional combinatorial chemistry techniques (see, e.g., Gallop et al., *J. Med. Chem.* 37:1233-1251, 1994) permit a vast number of compounds to be rapidly prepared by the sequential combination of reagents to a basic molecular scaffold. Combinatorial techniques have been used to construct peptide libraries derived from the naturally occurring amino acids. For example, by taking 20 mixtures of 20 suitably protected and different amino acids and coupling each with one of the 20 amino acids, a library of 400 (i.e., $20^2$) dipeptides is created. Repeating the procedure seven times results in the preparation of a peptide library comprised of about 26 billion (i.e., $20^8$) octapeptides.

Specifically, synthesis of the peptide mimetics of the library of the present invention may be accomplished using known peptide synthesis techniques, for example, the General Scheme of [4,4,0] α-helix Mimetic Library as follows:

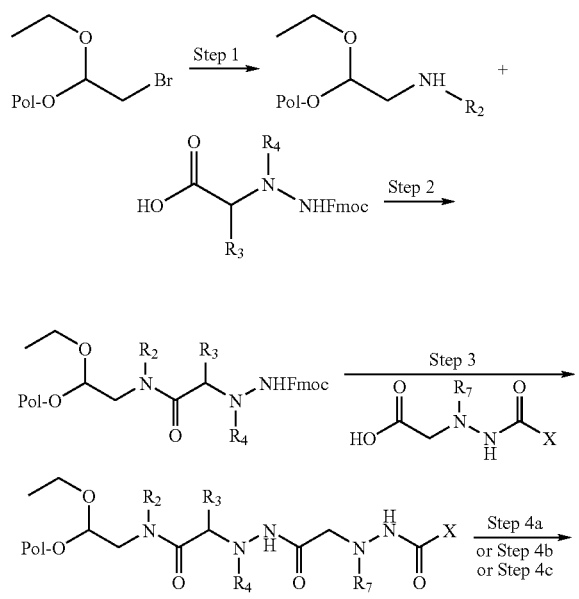

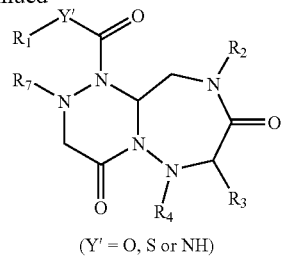

(Y' = O, S or NH)

Synthesis of the peptide mimetics of the libraries of the present invention was accomplished using a FlexChem Reactor Block which has 96 well plates by known techniques. In the above scheme 'Pol' represents a bromoacetal resin (Advanced ChemTech) and detailed procedure is illustrated below.

Step 1

A bromoacetal resin (37 mg, 0.98 mmol/g) and a solution of $R_2$-amine in DMSO (1.4 mL) were placed in a Robbins block (FlexChem) having 96 well plates. The reaction mixture was shaken at 60° C. using a rotating oven [Robbins Scientific] for 12 hours. The resin was washed with DMF, MeOH, and then DCM Step 2

A solution of available Fmoc hydrazine Amino Acids (4 equiv.), PyBop (4 equiv.), HOAt (4 equiv.), and DIEA (12 equiv.) in DMF was added to the resin. After the reaction mixture was shaken for 12 hours at room temperature, the resin was washed with DMF, MeOH, and then DCM.

Step 3

To the resin swollen by DMF before reaction was added 25% piperidine in DMF and the reaction mixture was shaken for 30 min at room temperature. This deprotection step was repeated again and the resin was washed with DMF, Methanol, and then DCM. A solution of hydrazine acid (4 equiv.), HOBt (4 equiv.), and DIC (4 equiv.) in DMF was added to the resin and the reaction mixture was shaken for 12 hours at room temperature. The resin was washed with DMF, MeOH, and then DCM.

Step 4a (where Hydrazine Acid is MOC Carbamate)

The resin obtained in Step 3 was treated with formic acid (1.2 mL each well) for 18 hours at room temperature. After the resin was removed by filtration, the filtrate was condensed under a reduced pressure using SpeedVac [SAVANT] to give the product as oil. The product was diluted with 50% water/acetonitrile and then lyophilized after freezing.

Step 4b (where Fmoc Hydrazine Acid is Used to Make Urea Through Isocynate)

To the resin swollen by DMF before reaction was added 25% piperidine in DMF and the reaction mixture was shaken for 30 min at room temperature. This deprotection step was repeated again and the resin was washed with DMF, Methanol, then DCM. To the resin swollen by DCM before reaction was added isocynate (5 equiv.) in DCM. After the reaction mixture was shaken for 12 hours at room temperature the resin was washed with DMF, MeOH, then DCM. The resin was treated with formic acid (1.2 mL each well) for 18 hours at room temperature. After the resin was removed by filtration, the filtrate was condensed under a reduced pressure using SpeedVac [SAVANT] to give the product as oil. The product was diluted with 50% water/acetonitrile and then lyophilized after freezing.

Step 4c (where Fmoc-Hydrazine Acid is Used to Make Urea Through Active Carbamate)

To the resin swollen by DMF before reaction was added 25% piperidine in DMF and the reaction mixture was shaken for 30 min at room temperature. This deprotection step was repeated again and the resin was washed with DMF, MeOH, and then DCM. To the resin swollen by DCM before reaction was added p-nitrophenyl chloroformate (5 equiv.) and diisopropyl ethylamine (5 equiv.) in DCM. After the reaction mixture was shaken for 12 hours at room temperature, the resin was washed with DMF, MeOH, and then DCM. To the resin was added primary amines in DCM for 12 hours at room temperature and the resin was washed with DMF, MeOH, and then DCM. After reaction the resin was treated with formic acid (1.2 mL each well) for 18 hours at room temperature. After the resin was removed by filtration, the filtrate was condensed under a reduced pressure using SpeedVac [SAVANT] to give the product as oil. The product was diluted with 50% water/acetonitrile and then lyophilized after freezing.

To generate these block libraries the key intermediate hydrazine acids were synthesized according to the procedure illustrated in the examples.

Administration and Dosage

The inventive compounds may be administered by any means known to one of ordinary skill in the art. For example, the inventive compounds may be administered orally, parenterally, by inhalation spray, topically, rectally, nasally, buccally, vaginally, or via an implanted reservoir. The term "parenteral" as used herein includes subcutaneous, intravenous, intramuscular, intraperitoneal, intrathecal, intraventricular, intrasternal, intracranial, and intraosseous injection and infusion techniques. The exact administration protocol will vary depending upon various factors including the age, body weight, general health, gender and diet of the patient; the determination of specific administration procedures would be routine to an one of ordinary skill in the art.

The inventive compounds may be administered by a single dose, multiple discrete doses or continuous infusion. Pump means, particularly subcutaneous pump means, are useful for continuous infusion.

Dose levels on the order of about 0.001 mg/kg/d to about 100 mg/kg/d of an inventive compound are useful for the inventive methods. In one embodiment, the dose level is about 0.1 mg/kg/d to about 100 mg/kg/d. In another embodiment, the dose level is about 1 mg/kg/d to about 10 mg/kg/d. The specific dose level for any particular patient will vary depending upon various factors, including the activity and the possible toxicity of the specific compound employed; the age, body weight, general health, sex and diet of the patient; the time of administration; the rate of excretion; the drug combination; the severity of the disease; and the form of administration. Typically, in vitro dosage-effect results provide useful guidance on the proper doses for patient administration. Studies in animal models are also helpful. The considerations for determining the proper dose levels are well known in the art and within the skills of an ordinary physician.

Any known administration regimen for regulating the timing and sequence of drug delivery may be used and repeated as necessary to effect treatment in the inventive methods. The regimen may include pretreatment and/or co-administration with additional therapeutic agent(s).

The inventive compounds can be administered alone or in combination with one or more additional therapeutic agent(s) for simultaneous, separate, or sequential use. Examples of an additional therapeutic agent include, without limitation, compounds of this invention; steroids (e.g., hydrocortisones such as methylprednisolone); anti-inflammatory or anti-immune drug, such as methotrexate, azathioprine, cyclophosphamide or cyclosporin A; interferon-$\beta$; antibodies, such as anti-CD4 antibodies; chemotherapeutic agents; immunotherapeutic compositions; electromagnetic radiosensitizers; and morphine. The inventive compounds may be co-administered with one or more additional therapeutic agent(s) either (i) together in a single formulation, or (ii) separately in individual formulations designed for optimal release rates of their respective active agent.

The pharmaceutical composition may comprise at least one compound disclosed herein, in combination with at least one cancer chemotherapeutic wherein said cancer chemotherapeutic works by a mechanism other than blocking CPB/catenin interaction. The cancer therapeutic can be selected from the group consisting of, but not limited to, cis-platinum, retinoic acid, histone deacetylase (HDAC) inhibitors such as Vorinostat (SAHA), and imatinib.

The pharmaceutical composition may comprise at least one pathway-specific inhibitor such as Her1/Her2 inhibitors; Notch inhibitors; Hedgehog inhibitors; EGF inhibitors; and PI3K pathway inhibitors. The Notch inhibitor can be a gamma secretase inhibitor, the Hedgehog inhibitor can be cyclopamine, the EGF inhibitor can be Iressa, and the PI3K pathway inhibitor can be rapamycin.

Pharmaceutical Compositions

This invention further provides a pharmaceutical composition comprising: (i) an effective amount of a compound of formula I, II or III; and (ii) a pharmaceutically acceptable carrier.

The inventive pharmaceutical composition may comprise one or more additional pharmaceutically acceptable ingredient(s), including without limitation one or more wetting agent(s), buffering agent(s), suspending agent(s), lubricating agent(s), emulsifier(s), disintegrant(s), absorbent(s), preservative(s), surfactant(s), colorant(s), flavorant(s), sweetener(s) and additional therapeutic agent(s).

The inventive pharmaceutical composition may be formulated into solid or liquid form for the following: (1) oral administration as, for example, a drench (aqueous or non-aqueous solution or suspension), tablet (for example, targeted for buccal, sublingual or systemic absorption), bolus, powder, granule, paste for application to the tongue, hard gelatin capsule, soft gelatin capsule, mouth spray, emulsion and microemulsion; (2) parenteral administration by, for example, subcutaneous, intramuscular, intravenous or epidural injection as, for example, a sterile solution, suspension or sustained-release formulation; (3) topical application as, for example, a cream, ointment, or controlled-release patch or spray applied to the skin; (4) intravaginal or intrarectal administration as, for example, a pessary, cream or foam; (5) sublingual administration; (6) ocular administration; (7) transdermal administration; or (8) nasal administration.

It should be understood that the examples and embodiments described herein are for illustrative purposes only and that various modifications or changes in light thereof will be suggested to persons skilled in the art and are to be included within the spirit and purview of this application.

EXAMPLE 1

Intermediate Synthesis

Synthesis of
2-Boc-amino-benzothiazoley1-4-methylamine

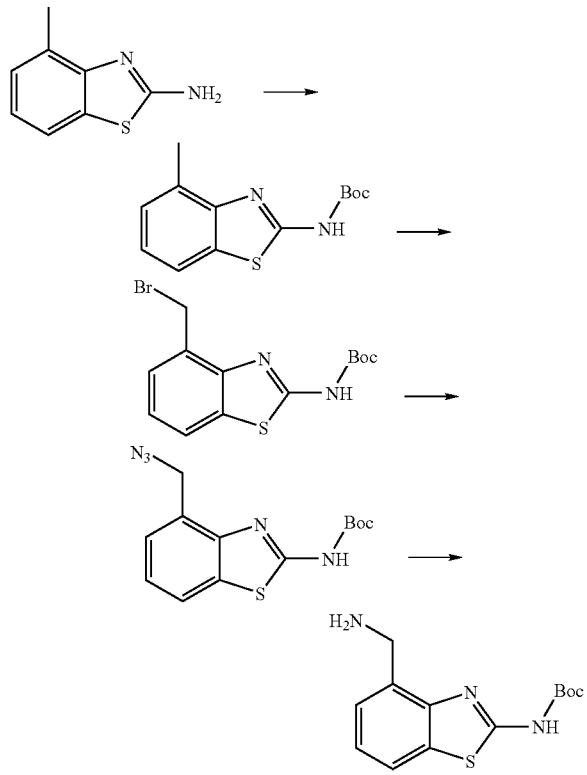

Step-1 (2-Boc-amino-4-methyl benzothiazole)

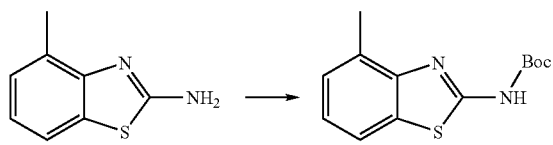

A solution of 2-Amino-4-methyl benzothiazole (25.0 g, 152 mmol) in 456 mL of dry THF was treated with Et$_3$N (42 mL, 300 mmol), (Boc)$_2$O (40.0 g, 183 mmol) and DMAP (3.7 g, 30 mmol) at 20° C. and stirred at 30° C. for 12 h. The resulting solution was concentrated in vacuo, diluted with EtOAc (200 mL) and filtered through a glass filter (Celite) washing with EtOAc (200 mL). The filtrate was washed with NaHCO$_3$ (saturated aqueous solution, 100 mL) and NaCl (saturated aqueous solution, 100 mL), dried over MgSO$_4$ and concentrated in vacuo. The residue was filtered through a silica gel plug (flash column chromatography) eluting with toluene:Et$_2$O=15:1 to 8:1 to afford 2-Boc-amino-4-methyl benzothiazole as a colorless oil (41.4 g, quant.) R$_f$=0.48 (toluene:Et$_2$O=10:1); $^1$H NMR (400 MHz, CDCl$_3$) δ 9.75 (1H, br s), 7.61 (1H, d, J=7.8 Hz), 7.19 (3H, m), 2.64 (3H, s), 1.47 (9H, s).

Step-2 (2-Boc-amino-4-bromomethyl benzothiazole)

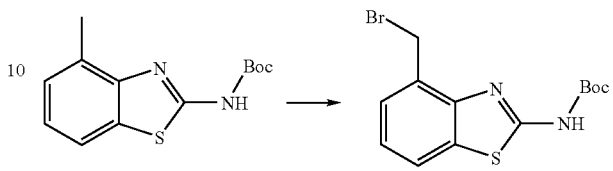

A solution of 2-Boc-amino-4-methyl benzothiazole (152 mmol) in 456 mL of dry CCl4 was treated with NBS (27.1 g, 152 mmol) and AIBN (3.2 g, 20 mmol) at 20° C. and stirred at 80° C. for 3.5 h. The mixture was retreated with NBS (7.2 g, 41 mmol) and AIBN (0.84 g, 5.1 mmol) at 20° C. and stirred at 80° C. for 11 hr. The resulting mixture was cooled to 20° C. and filtered through a glass filter (Celite) washing with Et$_2$O (200 mL). The filtrate was concentrated in vacuo. The residue was filtered through a silica gel column (flash column chromatography) eluting with toluene:Et$_2$O=20:1 to 10:1 to afford 2-BocNH-4-bromomethyl benzothiazole (46.7 g, 136 mmol, 90%) as a yellowish oil. R$_f$=0.51 (toluene:Et$_2$O=15:1); $^1$H NMR (400 MHz, CDCl$_3$) δ 8.27 (1H, br s), 7.72 (1H, d, J=8.2 Hz), 7.43 (1H, d, J=7.2 Hz), 7.24 (1H, dd, J=8.2, 7.2 Hz), 4.91 (2H, s), 1.56 (9H, s).

Step-3 (2-Boc-amino-4-azidemethyl benzothiazole)

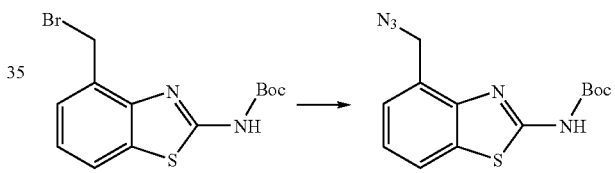

A solution of 2-Boc-amino-4-bromomethyl benzothiazole (46.7 g, 136 mmol) in 205 mL of dry DMF was treated with NaN$_3$ (8.80 g, 136 mmol) at 15° C. and stirred at 20° C. for 45 min. The resulting mixture was diluted with Et$_2$O (400 mL), quenched by addition of NaCl (1 g in 150 mL of H$_2$O) at 0° C. The solution was extracted with Et$_2$O (100 mL). The organic phase was washed with NaCl (2 g in 100 mL of H$_2$O) twice, dried over MgSO$_4$ and concentrated in vacuo. The residue was filtered through a silica gel plug (flash column chromatography) eluting with toluene:Et$_2$O=100:0 to 10:1 to afford 2-Boc-amino-4-azidemethyl benzothiazole (33.2 g, 109 mmol, 80%) as a colorless oil. R$_f$=0.48 (toluene:Et$_2$O=10:1); $^1$H NMR (400 MHz, CDCl$_3$) δ 7.75 (1H, d, J=8.2 Hz), 7.37 (1H, d, J=7.2 Hz), 7.27 (1H, m), 4.74 (2H, s), 1.52 (9H, s); $^{13}$C NMR (99.5 MHz, CDCl$_3$) δ 159.8, 151.9, 147.6, 132.5, 127.6, 125.8, 123.5, 121.3, 83.4, 51.4, 28.1.

Step-4
(2-Boc-amino-benzothiazoleyl-4-methylamine)

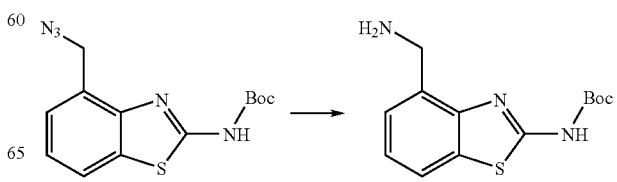

A solution of 2-Boc-amino-4-azidemethyl benzothiazole (11.6 g, 38.0 mmol) in 183 mL of MeOH was treated with Pd(OH)$_2$ (20% on carbon, 2.9 g), placed under an atmosphere of hydrogen and stirred at 20° C. for 1.5 hr. The resulting mixture was filtered through Celite washing with MeOH: NH$_4$OH (100:3, 100 mL) and concentrated in vacuo. The obtained yellowish solid was triturated with toluene (35 mL) and filtered to afford 2-Boc-amino-benzothiazoleyl-4-methylamine (6.90 g, 24.7 mmol, 65%) as a colorless powder. R$_f$=0.32 (CHCl$_3$:MeOH:NH$_4$OH=100:25:1); $^1$H NMR (400 MHz, CDCl$_3$) δ 7.67 (1H, d, J=7.7 Hz), 7.25-7.15 (2H, m), 4.85 (2H, br s), 1.58 (9H, s); $^{13}$C NMR (99.5 MHz, CDCl$_3$) δ 160.0, 152.8, 148.0, 134.5, 132.7, 124.4, 123.1, 120.0, 82.4, 44.3, 28.3; LC/MS [ESI+] (m/z) 280.2 (M+1)$^+$.

Synthesis of Benzothiazoleyl-4-methylamine

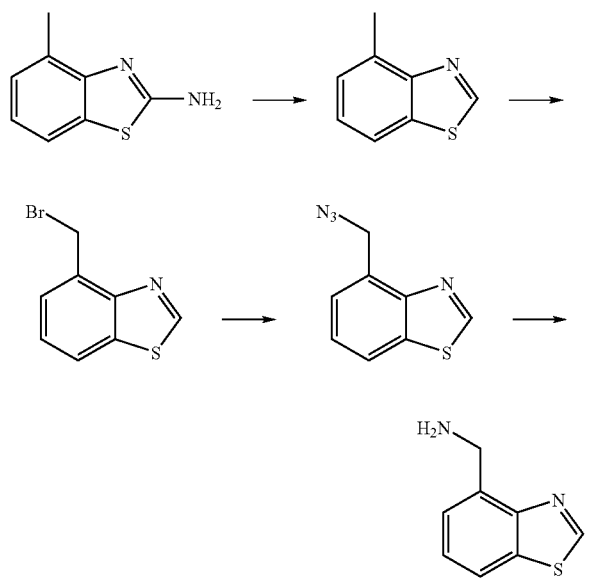

Step-1 (4-Methyl benzothiazole)

A solution of 2-amino-4-methylbenzothiazolee (24.5 g, 149 mmol) in 745 mL of 1,4-dioxane was treated with isoamylnitrile (40.0 mL, 300 mmol) at 20° C. and stirred at 70° C. for 0.5 hr. After the nitrogen evolution had subsided, the mixture was stirred at the same temperature for 1.5 h and concentrated in vacuo. The residue was submitted to silica gel column chromatography with hexane:Et$_2$O=3:1 to 2:1 as eluate to afford 4-methyl benzothiazole as a yellowish oil. (16.0 g, 107 mmol, 72%) R$_f$=0.45 (toluene:Et$_2$O=10:1); $^1$H NMR (400 MHz, CDCl$_3$) δ 8.98 (1H, s), 7.79 (1H, d, J=6.8 Hz), 7.33 (2H, m), 2.80 (3H, s).

Step-2 (4-Bromomethyl benzothiazole)

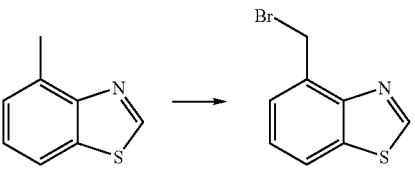

A solution of 4-Methyl benzothiazole (16.0 g, 107 mmol) in 535 mL of CCl$_4$ was treated with NBS (19.0 g, 107 mmol) and AIBN (2.28 g, 13.9 mmol) at 20° C. and stirred at 70° C. for 2.5 h. The resulting mixture was filtered through Celite washing with Et$_2$O (150 mL) and concentrated in vacuo. The residue was submitted to a silica gel column chromatography with toluene:Et$_2$O=50:3 to 50:5 as eluate to afford 4-bromomethyl benzothiazole as a yellowish solid. (20.4 g, 89.9 mmol, 84%) R$_f$=0.61 (toluene-Et$_2$O 10:1); $^1$H NMR (400 MHz, CDCl$_3$) δ 9.07 (1H, s), 7.90 (1H, d, J=7.5 Hz), 7.55 (1H, d, J=7.5 Hz), 7.41 (1H, t, J=7.5 Hz), 5.08 (2H, s); $^{13}$C NMR (99.5 MHz, CDCl$_3$) δ 154.1, 151.4, 134.3, 132.6, 127.0, 125.6, 122.3, 29.5.

Step-3 (4-Azidemethyl benzothiazole)

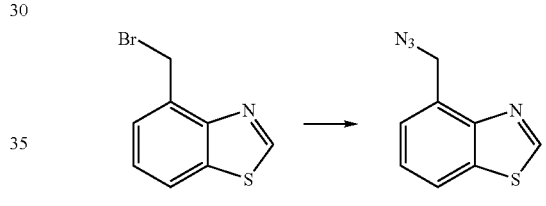

A solution of 4-Bromomethyl benzothiazole (20.4 g, 89.9 mmol) in 272 mL of dry DMF was treated with NaN$_3$ (7.00 g, 108 mmol) at 20° C. and stirred at the same temperature for 5 min. The resulting mixture was quenched by addition of NaCl (5 g in 150 mL of H$_2$O) at 0° C., diluted with Et$_2$O (200 mL) and extracted with Et$_2$O (200 mL×6). The organic phase was washed with NaCl (2 g in 100 mL of H$_2$O) twice and brine (100 mL). The resulting solution was dried over MgSO$_4$ and concentrated in vacuo. The residue was submitted to silica gel column chromatography with toluene:Et$_2$O=50:3 to 50:5 as eluate to afford 4-azidemethyl benzothiazole as a colorless oil (15.5 g, 81.5 mmol, 91%). R$_f$=0.48 (toluene:Et$_2$O=10:1); $^1$H NMR (400 MHz, CDCl$_3$) δ 9.03 (1H, s), 7.95 (1H, d, J=7.7 Hz), 7.49 (2H, m), 5.01 (2H, s); $^{13}$C NMR (99.5 MHz, CDCl$_3$) δ 154.2, 151.7, 134.3, 130.6, 126.0, 125.7, 122.1, 51.6.

Step-4 (Benzothiazole-4-methylamine)

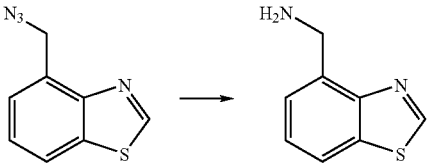

To a solution of 4-Azidemethyl benzothiazole (15.4 g, 81.0 mmol) in 243 mL of MeOH was added Pd(OH)$_2$ (20% on carbon, 3.1 g) and then hydrogenolysis at 20° C. After 1.5 hr, additional Pd(OH)$_2$ (20% on carbon, 0.87 g) was added and then hydrogenolysis. After further 1.5 hr, additional Pd(OH)$_2$ (20% on carbon, 1.27 g) was added and then hydrogenolysis for 1 hr. The resulting mixture was replaced with N$_2$ and then filtered through Celite washing with MeOH:NH$_4$OH (25:1, 260 mL) and concentrated in vacuo. The residue was submitted to silica gel column chromatography eluting with CHCl$_3$:MeOH:NH$_4$OH (100:0:0 to 20:5:1) followed by trituration with toluene to afford 4-aminomethyl benzothiazole as a white solid (10.5 g, 63.9 mmol, 79%). R$_f$=0.49 (CHCl$_3$:MeOH:NH$_4$OH=100:25:1); $^1$H NMR (400 MHz, CD$_3$OD) δ 9.23 (1H, s), 7.97 (1H, d, J=7.7 Hz), 7.46 (2H, m), 4.30 (2H, s); $^{13}$C NMR (99.5 MHz, CD$_3$OD) δ 184.2, 180.1, 165.3, 163.5, 154.9, 154.1, 150.1, 72.0; LC/MS [ESI+] (m/z) 165.4 (M+1)$^+$.

Synthesis of
4-Benzyl-3-Boc-2-methylsemicarbazidylacetatic acid

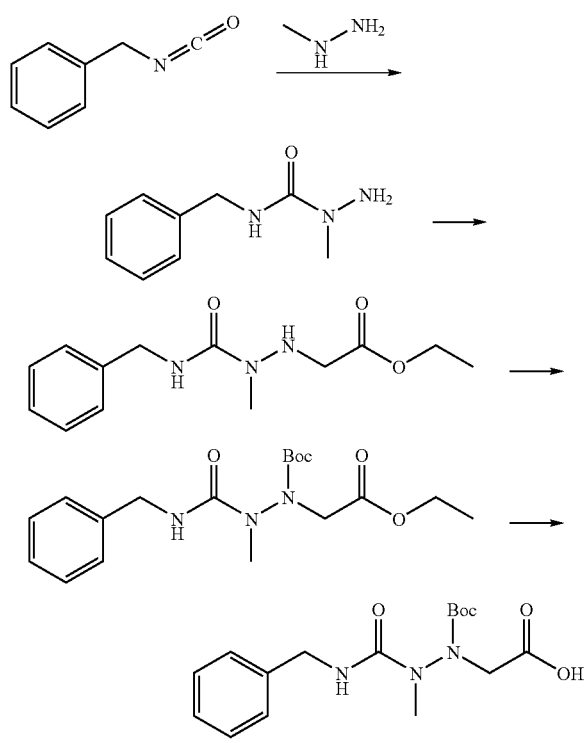

Step-1 (4-Benzyl-2-methylsemicarbazide)

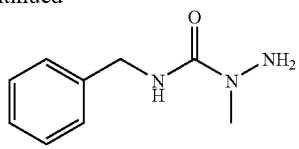

A solution of Benzyl isocyanate (1.85 mL, 15.0 mmol) in 7.5 mL of CHCl$_3$ was treated with methyl hydrazine (795 µL, 15.0 mmol) at 0° C. and stirred at the same temperature for 2 h. The resulting mixture was dissolved in 1N HCl (200 mL) and the solution was washed with CHCl$_3$ (50 mL×3). The aqueous phase was adjusted to pH 12 with 2 M NaOHaq and then extracted with CHCl$_3$ (100 mL×3). The organic phase was dried over Na$_2$SO$_4$ and concentrated in vacuo. The residue was recrystallized from hexane-CHCl$_3$ to afford (1.7 g, 9.5 mmol, 63%) as a colorless crystal. R$_f$=0.44 (CHCl$_3$:MeOH=9:1); $^1$H NMR (400 MHz, DMSO-d6) δ 7.28-7.19 (5H, m), 4.47 (2H, s), 4.20 (2H, d, J=6.3 Hz), 2.96 (3H, s); $^{13}$C NMR (99.5 MHz, DMSO-d6) δ 159.3, 141.1, 128.1, 127.1, 126.5, 43.1, 37.8; LC/MS [ESI+] (m/z) 180.3 (M+1)$^+$.

Step-2 (Ethyl 4-benzyl-2-methylsemicarbazidylacetate)

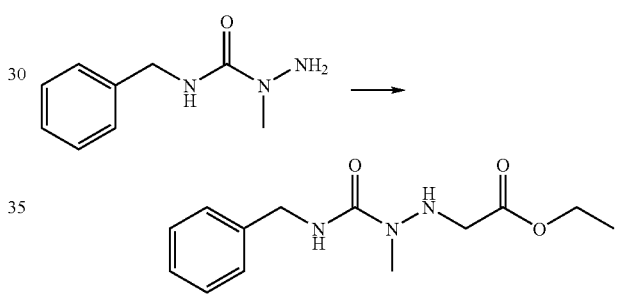

To the solution of 4-Benzyl-2-methylsemicarbazide (5.24 g, 29.2 mmol) in Toluene (58 mL) were added DIPEA (7.63 mL, 43.8 mmol) and Ethyl bromoacetate (4.86 mL, 43.8 mmol) and then stirred at 858 for 24 hr. The reaction mixture was allowed to cool to room temperature followed by dilution with EtOAc (100 mL). The mixture was washed with H$_2$O (50 mL) and brine (50 mL), dried over Na$_2$SO$_4$, filtered and concentrated. The crude was submitted to silica gel (250 g) column chromatography with Hex:EtOAc=1:1 to 1:9 as elute to afford a pale yellow oil (5.75 g, 21.7 mmol, 74%). R$_f$=0.36 (Hex:EtOAc=1:3); $^1$H NMR (400 MHz, CDCl$_3$) δ 7.34-7.21 (5H, m), 6.88 (1H, br s), 4.40 (2H, d, J=5.8 Hz), 4.18 (2H, q, J=7.2 Hz), 3.69 (1H, br t, J=4.8 Hz), 3.58 (2H, d, J=4.8 Hz), 3.08 (3H, s), 1.26 (3H, t, J=7.2 Hz); $^{13}$C NMR (99.5 MHz, CDCl$_3$) δ 170.8, 159.3, 139.9, 128.6, 127.6, 127.1, 61.4, 50.1, 44.4, 33.1, 14.2; LC/MS [ESI+] (m/z) 266.3 (M+1)$^+$.

Step-3 (Ethyl 4-benzyl-3-Boc-2-methylsemicarbazidylacetate)

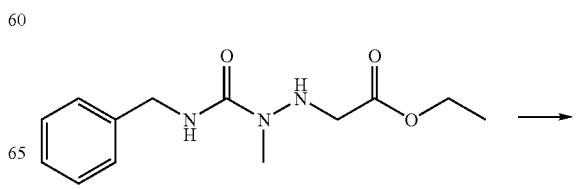

-continued

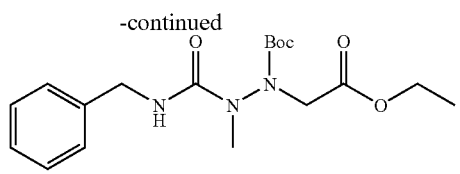

To the solution of Ethyl 4-benzyl-2-methylsemicarbazidylacetate (5.70 g, 21.5 mmol) in CH$_2$Cl$_2$ (43 mL) were added DIPEA (7.5 mL, 43 mmol), DMAP (1.1 g, 8.6 mmol) and (Boc)$_2$O (9.4 g, 43 mmol) and then stirred for 1 hr at room temperature. The reaction mixture was concentrated and then submitted to SiO$_2$ (250 g) column chromatography with Hex:EtOAc=7:1 to 1:2 as eluate to afford product (2.58 g, 7.06 mmol, 33%) as a pale yellow oil, and starting material (2.80 g, 10.6 mmol, 49%) was recovered. R$_f$=0.76 (Hex:EtOAc=1:3); $^1$H NMR (400 MHz, CDCl$_3$) δ 7.54 (1H, br s), 7.33-7.20 (5H, m), 4.59-4.46 (2H, m), 4.27-4.19 (4H, m), 3.72 (1H, br d, J=17 Hz), 3.03 (3H, br s), 1.39 (9H, s), 1.26 (3H, t, J=7.2 Hz); $^{13}$C NMR (99.5 MHz, CDCl$_3$) δ 170.7, 158.3, 139.8, 128.3, 127.6, 126.9, 82.7, 62.0, 51.6, 44.3, 34.4, 28.0, 14.1; LC/MS [ESI+] (m/z) 366.3 (M+1)$^+$.

Step-4
(4-Benzyl-3-Boc-2-methylsemicarbazidylacetatic acid)

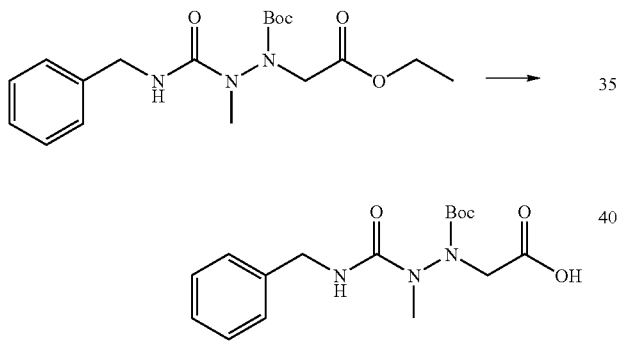

To the solution of Ethyl 4-benzyl-3-Boc-2-methylsemicarbazidylacetate (2.30 g, 6.29 mmol) in THF/MeOH/H$_2$O (2/3/1, 24 mL) was added LiOH H$_2$O (528 mg, 12.6 mmol) at 08. After stirred for 1 hr at room temperature, the reaction mixture was diluted with EtOAc (40 mL) at 08. The mixture was acidified with 1N HCl and then extracted with EtOAc. The combined extracts were washed with H$_2$O (30 mL) and brine (30 mL), dried over Na$_2$SO$_4$, added Et$_3$N (2 mL), filtered and concentrated. The crude was submitted to SiO$_2$ column chromatography with CHCl$_3$:MeOH=100:0 to 85:15 as eluante to afford a pale yellow sticky oil 4-Benzyl-3-Boc-2-methylsemicarbazidylacetatic acidδEt$_3$N salt (1.99 g, 4.56 mmol, 72%); $^1$H NMR (400 MHz, CDCl$_3$) δ 8.45 (1H, br s), 7.32-7.18 (5H, m), 4.58-4.22 (3H, m), 3.71-3.57 (1H, m), 3.08 and 3.01 (3H, br s), 2.82 (2.4H, q, J=7.3 Hz, Et$_3$N), 1.40 (9H, br s), 1.08 (3.6H, t, J=7.3 Hz, Et$_3$N); $^{13}$C NMR (99.5 MHz, CDCl$_3$) δ 174.2, 159.2, 154.1, 140.1, 128.2, 127.4, 12.7, 81.8, 52.2, 45.1 (Et$_3$N), 44.1, 34.5, 28.1, 8.3 (Et$_3$N); LC/MS [ESI+] (m/z) 338.3 (M+1)$^+$.

Synthesis of
4-Benzyl-3-Boc-2-allylsemicarbazidylacetatic acid

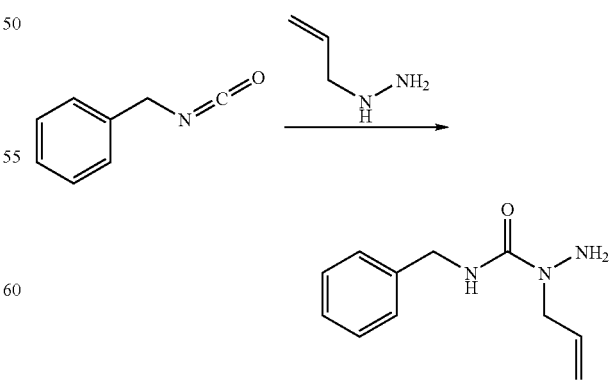

Step-1 (4-Benzyl-2-allylsemicarbazide)

To the solution of Allyl hydrazine (1.55 mL, 15.0 mmol) in 7.5 mL of CHCl$_3$ was added benzyl isocyanate (1.85 mL, 15.0 mmol) slowly at 0° C. and stirred at the same temperature for 2 h. The resulting mixture was dissolved in 1N HCl (200 mL) and the solution was washed with CHCl₃ (50 mL×3). The aqueous phase was adjusted to pH 12 with 2 M NaOH aq and then extracted with CHCl₃ (100 mL×3). The organic phase was dried over Na₂SO₄ and concentrated in vacuo. The residue was recrystallized from hexane-CHCl₃ to afford a colorless crystal (2.20 g, 10.7 mmol, 70%). R$_f$=0.50 (CHCl₃: MeOH=9:1); ¹H NMR (400 MHz, CDCl₃) δ 7.34-7.23 (5H, m), 6.77 (1H, br s), 5.77 (1H, ddt, J=16.9, 10.1, 6.3 Hz), 5.28 (1H, d, J=10.1 Hz), 5.22 (1H, dd, J=16.9, 1.5 Hz), 4.42 (2H, d, J=6.3 Hz), 4.14 (2H, d, J=6.3 Hz), 3.47 (2H, s); ¹³C NMR (99.5 MHz, CDCl₃) δ159.0, 139.9, 132.7, 128.6, 127.6, 127.2, 119.2, 52.8, 44.3; LC/MS [ESI+] (m/z) 206.3 (M+1)⁺.

Step-2 (Ethyl 4-benzyl-2-allylsemicarbazidylacetate)

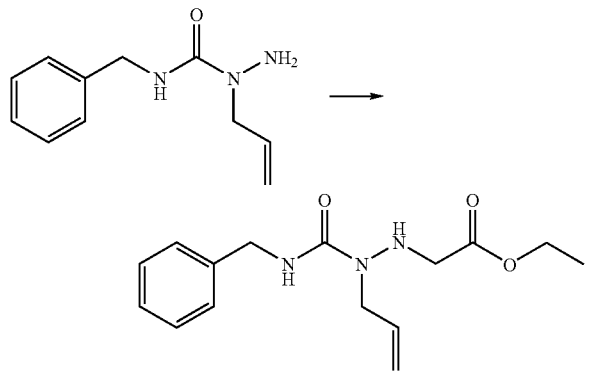

To the solution of 4-Benzyl-2-allylsemicarbazide (8.60 g, 41.9 mmol) in toluene (50 mL) were added DIPEA (14.6 mL, 83.8 mmol) and Ethyl bromoacetate (8.1 mL, 73 mmol) and then stirred at 958 for 39 hr. The reaction mixture was allowed to cool to room temperature followed by dilution with EtOAc (150 mL). The mixture was washed with H₂O (50 mL) and brine (50 mL), dried over Na₂SO₄, filtered and concentrated. The crude was submitted to silica gel (250 g) column chromatography with Hex:EtOAc=2:1 to 1:1 as eluate to afford a pale yellow oil (7.60 g, 26.1 mmol, 62%). R$_f$=0.30 (Hex: EtOAc=2:3); ¹H NMR (400 MHz, CDCl₃) δ 7.32-7.23 (5H, m), 7.02 (1H, br, s), 5.78 (1H, ddt, J=17.4, 10.1, 6.3 Hz), 5.25 (2H, m), 4.42 (2H, d, J=5.8 Hz), 4.16 (3H, q and br m, J=7.2 Hz), 3.98 (1H, t, J=4.8 Hz), 3.55 (2H, d, J=4.8 Hz), 1.25 (3H, t, J=7.2 Hz); ¹³C NMR (99.5 MHz, CDCl₃) δ 170.5, 158.9, 139.8, 132.5, 128.5, 127.6, 127.1, 119.2, 61.3, 50.0, 46.7, 44.3, 14.1; LC/MS [ESI+] (m/z) 292.3 (M+1)⁺.

Step-3 (Ethyl 4-benzyl-3-Boc-2-allylsemicarbazidylacetate)

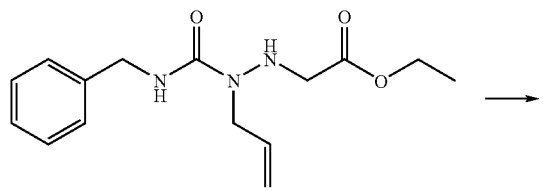

-continued

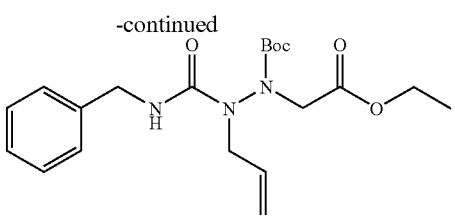

To the solution of Ethyl 4-benzyl-2-allylsemicarbazidylacetate (7.10 g, 24.4 mmol) in CH₂Cl₂ (50 mL) were added DIPEA (8.5 mL, 49 mmol), DMAP (1.19 g, 9.76 mmol) and (Boc)₂O (10.6 g, 48.8 mmol). After the mixture was stirred for 3.5 hr at room temperature, additional DIPEA (2.12 mL, 12.2 mmol) and (Boc)₂O (2.66 g, 12.2 mmol) were added. After the reaction mixture was stirred for additional 6 hr, the mixture was diluted with CH₂Cl₂ (100 mL) and then sat. NaHCO₃ (50 mL) was added at 08. The separated aqueous phase was extracted with CH₂Cl₂ (100 mL×2). The combined organic phases were washed with H₂O (100 mL) and brine (100 mL), dried over Na₂SO₄, filtered and concentrated. The crude was submitted to SiO₂ (300 g) column chromatography with Hex:EtOAc=7:1 to 1:1 as eluate to afford product as a pale yellow oil (6.61 g, 16.9 mmol, 69%). R$_f$=0.57 (Hex: EtOAc=1:1); ¹H NMR (400 MHz, CDCl₃) δ 7.77 (1H, br s), 7.34-7.21 (5H, br m), 5.88 (1H, br m), 5.20 (2H, br m), 4.62-4.46 (3H, m), 4.37-4.13 (3H, m), 3.92-3.65 (2H, m), 1.48 and 1.38 (9H, s), 1.26 (3H, t, J=7.2 Hz); ¹³C NMR (99.5 MHz, CDCl₃) δ 170.8, 157.8, 154.1, 139.8, 128.4, 127.6, 127.0, 119.6, 82.7, 62.0, 51.2, 44.3, 30.9, 28.0, 14.1; LC/MS [ESI+] (m/z) 392.4 (M+1)⁺.

Step-4 (4-Benzyl-3-Boc-2-allylsemicarbazidylacetic acid)

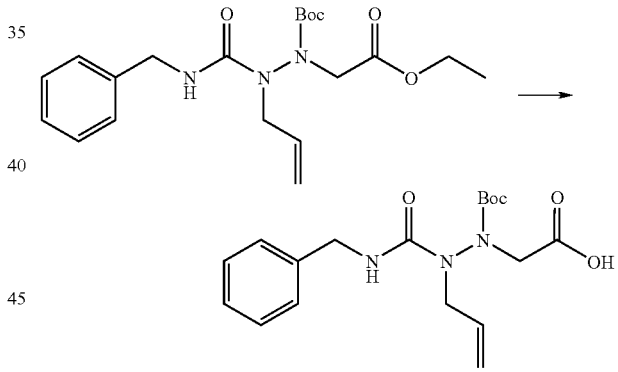

To the solution of Ethyl 4-benzyl-3-Boc-2-allylsemicarbazidylacetate (3.20 g, 8.17 mmol) in THF/MeOH/H₂O (2/3/1, 25 mL) was added LiOH H₂O (685 mg, 16.3 mmol) at 08. After stirred for 40 min at room temperature, the reaction mixture was diluted with CH₂Cl₂ (50 mL) at 08. The mixture was acidified with 1N HCl and then extracted with CH₂Cl₂. The combined extraction were washed with H₂O (30 mL) and Brine (30 mL), dried over Na₂SO₄, added Et₃N (3 mL), filtered and concentrated. The crude was submitted to SiO₂ column chromatography with CHCl₃:MeOH=100:0 to 85:15 as eluate to afford orange sticky oil 4-Benzyl-3-Boc-2-allylsemicarbazidylacetatic acidδEt₃N salt (3.66 g, 7.87 mmol, 96%); ¹H NMR (400 MHz, CDCl₃, rotamer) δ 9.44 and 9.34 (1H, br s), 7.35-7.18 (5H, m), 5.91 (1H, m), 5.17 (2H, m), 4.58 and 4.87 (2H, dd, J=15.5, 6.3 and 14.5, 5.8 Hz), 4.39-4.23 (2H, m), 3.89 and 3.80 (1H, dd, J=14.0, 8.2 and 14.5, 8.2 Hz), 3.58 and 3.52 (1H, d, J=17.4 and 16.9 Hz), 2.81 (5H, q, J=7.2 Hz, Et₃N), 1.44 and 1.42 (9H, s), 1.11 (7.5H, t, J=7.2 Hz, Et₃N); ¹³C NMR (99.5 MHz, CDCl₃) δ 158.9, 154.3, 153.6, 140.6, 134.2, 128.1, 127.4, 126.5, 118.8, 81.1, 55.6, 51.4, 44.9 (Et$_3$N), 44.2, 28.2, 8.3 (Et$_3$N); LC/MS [ESI+] (m/z) 364.3 (M+1)$^+$.

Synthesis of Compound No. 61

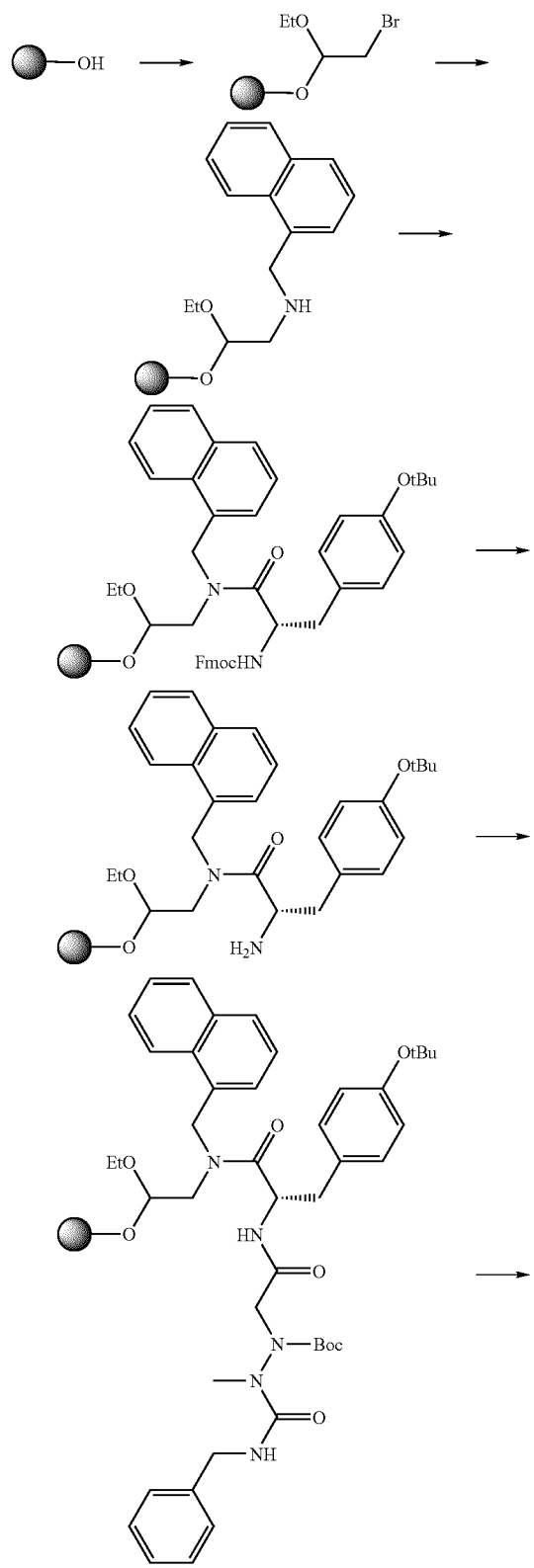

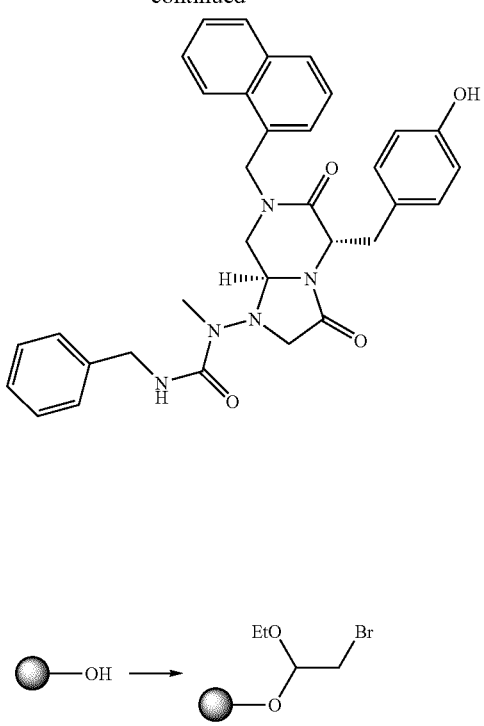

Step-1

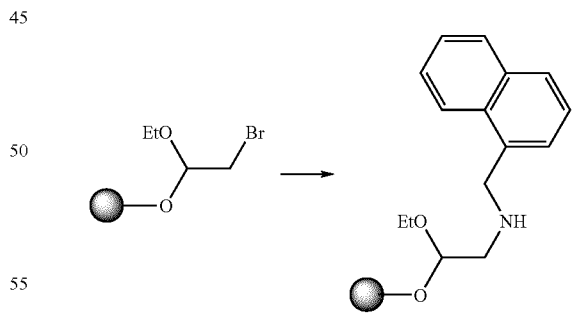

The hydroxy-functionalized resin (5.0 g, 0.68 mmol/g, Novabiochem) was placed in 200 mL round-bottom flask. To the mixture of the resin and PPTS (1.7 g, 6.8 mmol) in 1,2-dichloromethane (51 mL) was added bromoacetaldehyde diethylacetal (4.2 mL, 27 mmol) at room temperature. After being stirred under reflux for 4.0 hr, the mixture was filtered and the resin was washed with DMF 50 mL×3, DMSO 50 mL×3, 1,4-dioxane 50 mL×3, CH$_2$Cl$_2$ 50 mL×3, MeOH 50 mL×3, Et$_2$O 50 mL×3. The resin was dried under reduced pressure for over night to afford the desired bromoacetal resin (5.5 g).

Step-2

Bromoacetal resin (1.0 g, 0.9 mmol/g) was placed in 30 mL round-bottom flask. The resin was swollen with DMF (9.0 mL×5 min×1) and then treated with 1.0 M solution of 1-naphtylmethylamine (1.4 g, 9.0 mmol) in DMSO (9.0 mL) at 70° C. After being stirred for 12 hr, the resin was filtered and rinsed with DMSO (9.0 mL×5 min×3). The resin was washed with DMF (5.0 mL×5 min×3) and CH$_2$Cl$_2$ (5.0 mL×5 min×3). The resin was dried under reduced pressure to afford desired resin (1.18 g).

Step-3

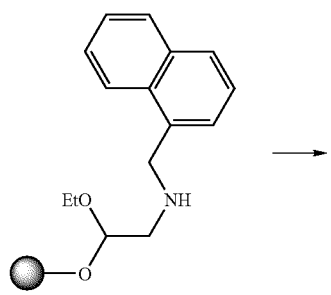

Naphthylmethylamino resin (1.18 g, 0.84 mmol/g) was placed in 20 mL plastic disposable syringe. The resin was swollen with DMF (9.0 mL×5 min×1) and then DMF (9.0 mL), Fmoc-Tyr(t-Bu)—OH (620 mg, 1.35 mmol), DIPEA (470 μL, 2.70 mmol) and HATU (513 mg, 1.35 mmol) were added at room temperature. After being shaken for 12 hr, in case of Kaiser test was positive, the same procedure was repeated. The mixture was filtered and the resin was washed with DMF (10.0 mL×5 min×3) and CH$_2$Cl$_2$ (10.0 mL×5 min× 3). The resin was dried under reduced pressure to afford desired resin (1.50 g).

Step-4

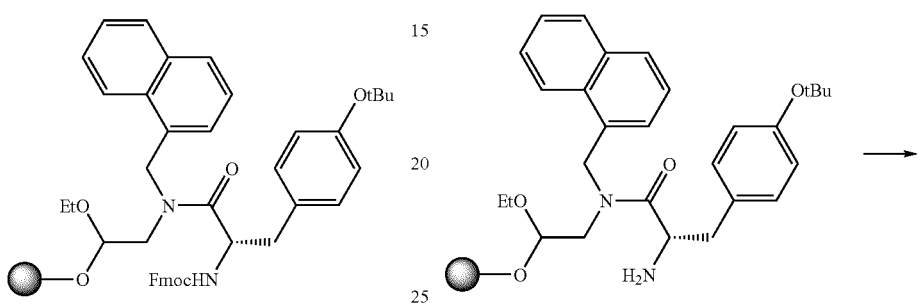

The 1-Naphthylmethylamino-Fmoc-Tyr(tBu) resin (1.50 g, 0.61 mmol/g) was placed in 20 mL plastic disposable syringe. The resin was swollen in DMF (10.0 mL) and DMF was sucked out. The resin was treated with 20 v/v % piperidine/DMF (10.0 mL) at room temperature. After being shaken for 1.0 hr, the mixture was filtered and the resin was washed with DMF (10 mL×5 min×3) and CH$_2$Cl$_2$ (10 mL×5 min×3). The resin was dried under reduced pressure to afford desired resin (1.48 g).

Step-5

The Amino resin (300 mg, 0.71 mmol/g) was placed in 20 mL plastic disposable syringe. The resin was swollen in DMF (3.0 mL) and DMF was sucked out. To the resin was added 0.3 M stocked CH$_2$Cl$_2$ solution of 4-Benzyl-3-Boc-2-methylsemicarbazidylacetatic acid (2.5 mL, 0.75 mmol), DIPEA (260 μL, 1.49 mmol) and HATU (284 mg, 0.75 mmol) at room temperature. After being shaken for 12 hr, the mixture was filtered and the resin was washed with DMF (5.0 mL×5 min× 3) and CH$_2$Cl$_2$ (5.0 mL×5 min×3). The resin was dried under reduced pressure to afford desired resin.

Step-6

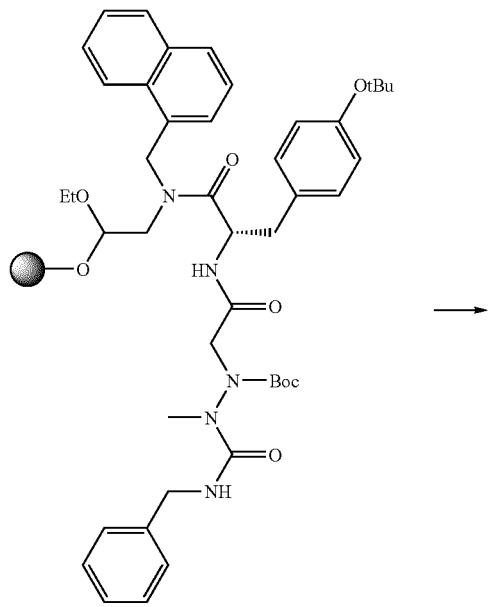

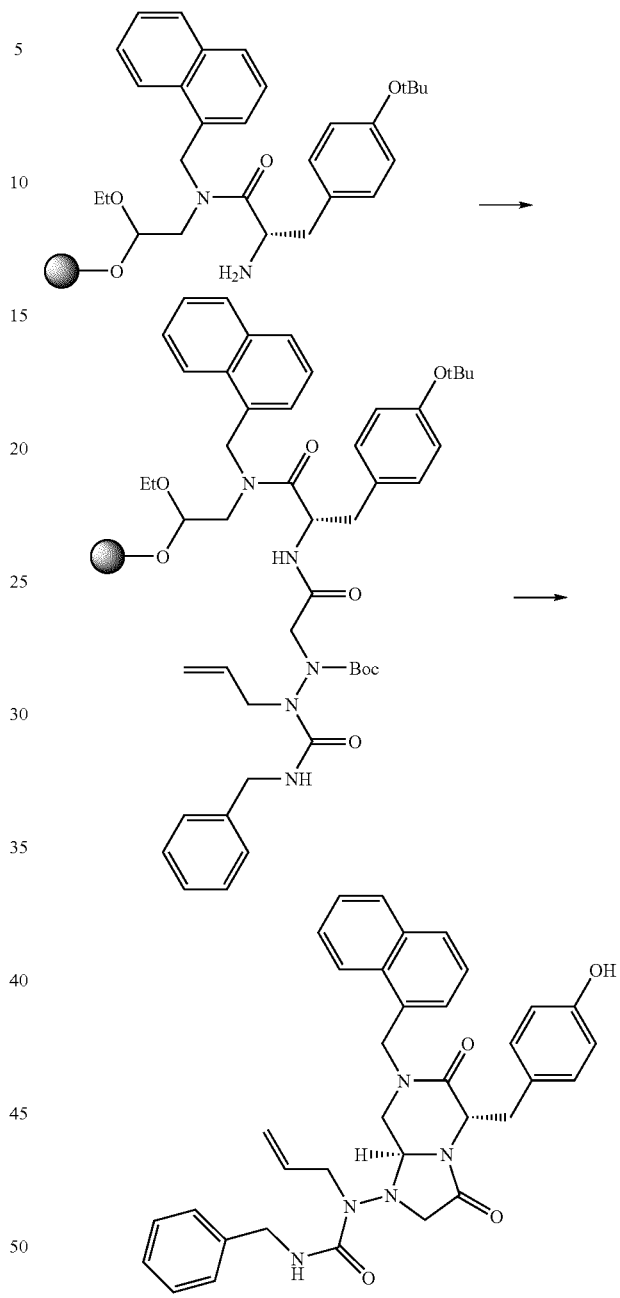

Synthesis of Compound No. 71

Step-1

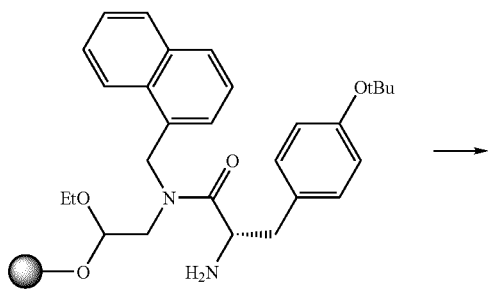

The resin (115 mg, 0.58 mmol/g) was placed in 5.0 mL plastic disposable syringe. After addition of 99% $HCO_2H$ (1.0 mL), the mixture was shaken for 12 hr at room temperature, the solution was collected by filteration. The resin was washed with 99% $HCO_2H$ (1.5 mL×5 min×2). The combined $HCO_2H$ solutions were concentrated and then submitted to silica gel column chromatography to afford Compound No. 61 (7.1 mg, 19% from bromoacetal resin). $R_f$=0.63 ($CHCl_3$:MeOH=9:1); $^1H$ NMR (400 MHz, $CDCl_3$) δ 8.06 (1H, d, J=8.2 Hz), 7.89 (1H, m), 7.84 (1H, d, J=8.2 Hz), 7.56 (2H, m), 7.38 (1H, dd, J=8.2, 7.2 Hz), 7.20 (3H, m), 7.12 (1H, d, J=6.8 Hz), 7.05 (2H, dd, J=7.7, 2.9 Hz), 7.02 (2H, d, J=8.2 Hz), 6.88 (0.5H, br s), 6.71 (2H, d, J=8.2 Hz), 6.05 (1H, t, J=5.8 Hz), 5.06 (2H, ABq, J=14.5 Hz), 4.80 (1H, dd, J=5.8, 2.5 Hz), 4.23 (2H, ABX, J=14.5, 5.8 Hz), 3.67-3.44 (4H, m), 3.21 (1H, dd, J=14.0, 5.8 Hz), 3.12 (1H, dd, J=11.0, 3.9 Hz), 2.86 (1H, dd. J=11.0, 9.1 Hz), 2.59 (3H, s); LC/MS [ESI+] (m/z) 564.4 $(M+1)^+$.

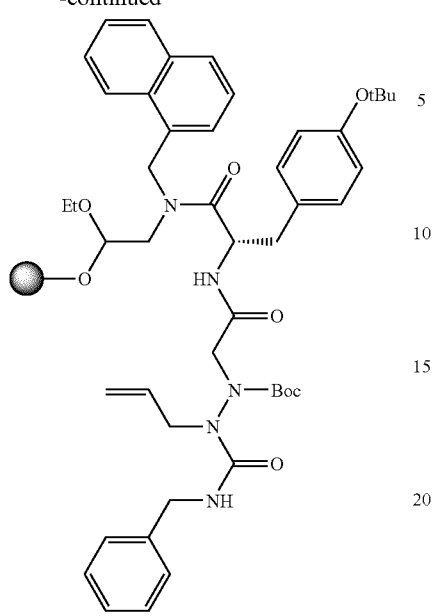

The Amino resin (100 mg, 0.71 mmol/g) was placed in 5 mL plastic disposable syringe. The resin was swollen in DMF (1.0 mL) and DMF was sucked out. To the resin was added 0.3 M stocked CH$_2$Cl$_2$ solution of 4-Benzyl-3-Boc-2-allylsemi-carbazidylacetatic acid (830 μL, 0.25 mmol), DIPEA (87 μL, 0.50 mmol) and HATU (95 mg, 0.25 mmol) at room temperature. After being shaken for 12 hr, the mixture was filtered and the resin was washed with DMF (1.0 mL×5 min×3) and CH$_2$Cl$_2$ (1.0 mL×5 min×3). The resin was dried under reduced pressure to afford desired resin.

Step-2

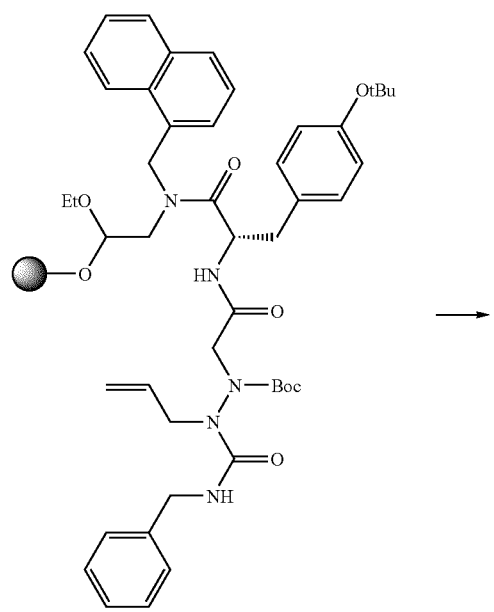

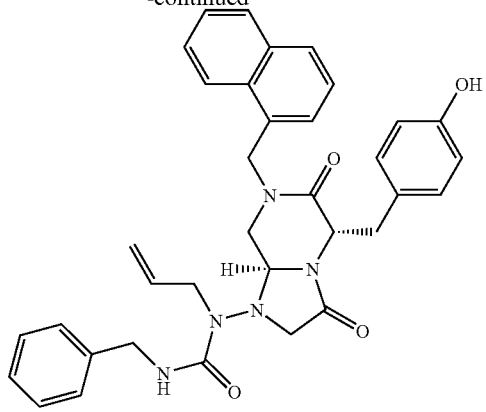

The resin (100 mg, 0.57 mmol/g) was placed in 5.0 mL plastic disposable syringe. After addition of 99% HCO$_2$H (1.0 mL), the mixture was shaken for 12 hr at room temperature, the solution was collected by filtration. The resin was washed with 99% HCO$_2$H (1.5 mL×5 min×2). The combined HCO$_2$H solutions were concentrated and then submitted to silica gel column chromatography to afford Compound No. 71 (11 mg, 26% from bromoacetal resin). R$_f$=0.63 (CHCl$_3$: MeOH=9:1).

Similar synthesis was carried out to obtain the compounds as shown as Compounds 1-1200 in FIGS. 1-6.

Synthesis of Compound No. 1273

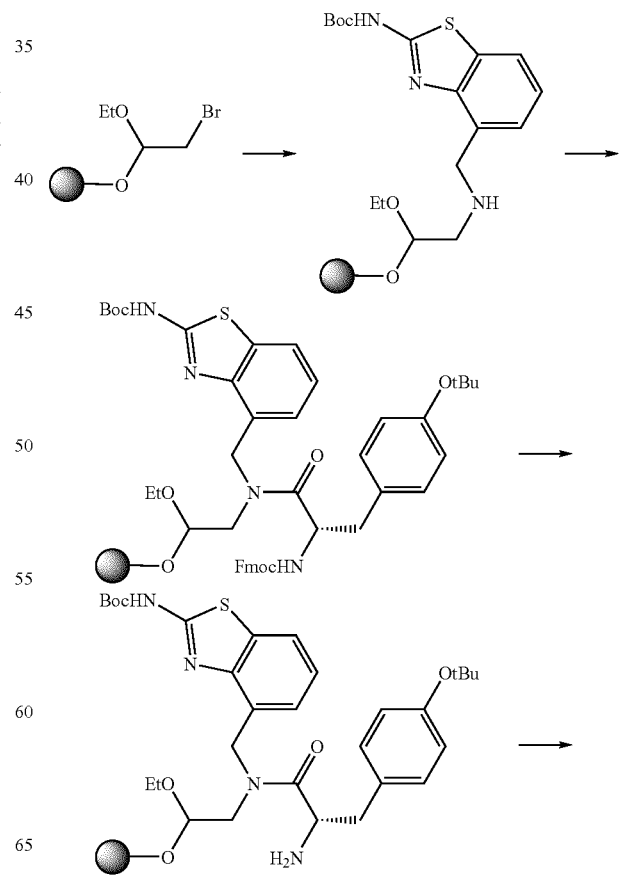

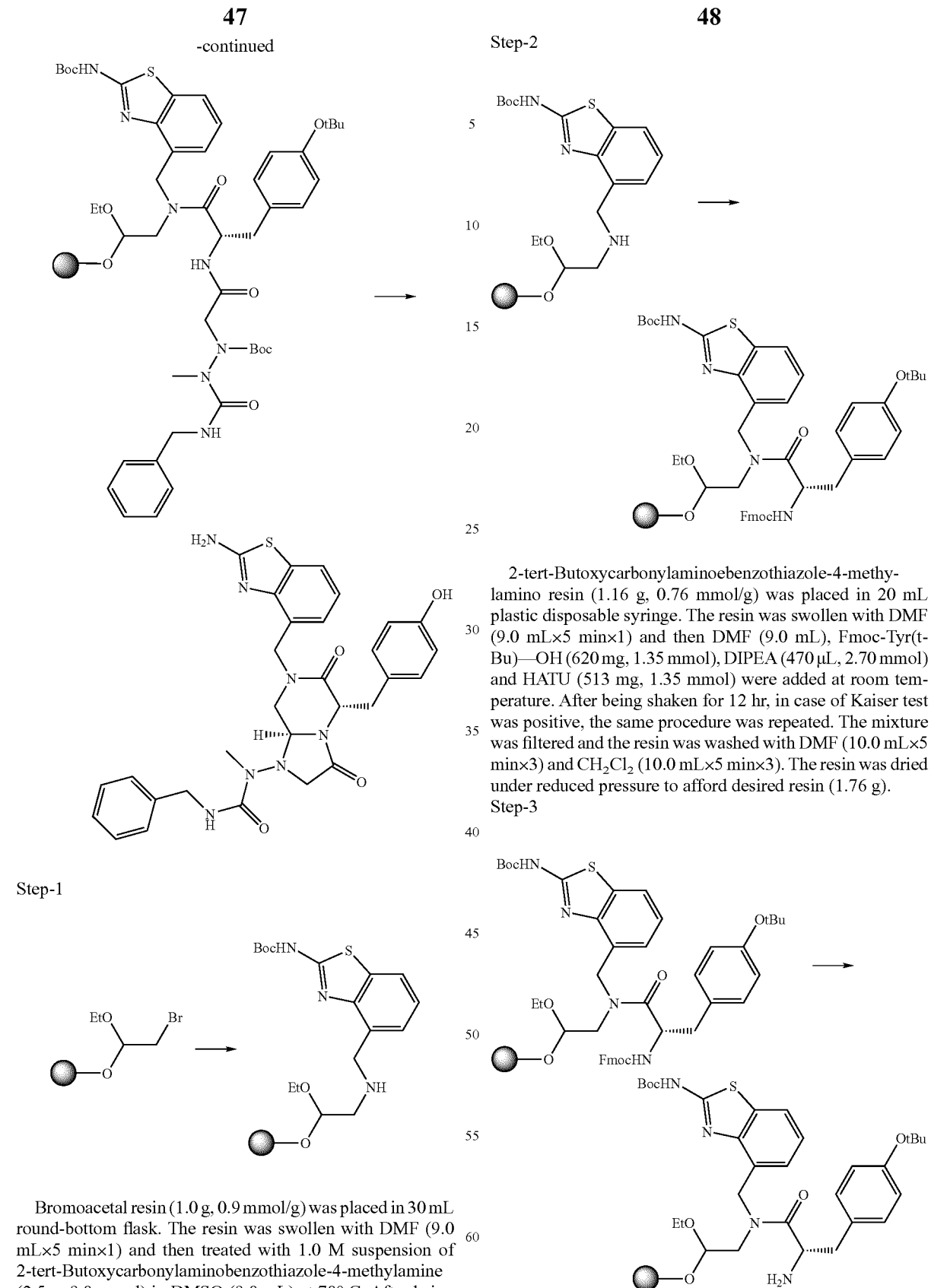

Step-2

2-tert-Butoxycarbonylaminoebenzothiazole-4-methylamino resin (1.16 g, 0.76 mmol/g) was placed in 20 mL plastic disposable syringe. The resin was swollen with DMF (9.0 mL×5 min×1) and then DMF (9.0 mL), Fmoc-Tyr(t-Bu)—OH (620 mg, 1.35 mmol), DIPEA (470 μL, 2.70 mmol) and HATU (513 mg, 1.35 mmol) were added at room temperature. After being shaken for 12 hr, in case of Kaiser test was positive, the same procedure was repeated. The mixture was filtered and the resin was washed with DMF (10.0 mL×5 min×3) and CH$_2$Cl$_2$ (10.0 mL×5 min×3). The resin was dried under reduced pressure to afford desired resin (1.76 g).

Step-3

Step-1

Bromoacetal resin (1.0 g, 0.9 mmol/g) was placed in 30 mL round-bottom flask. The resin was swollen with DMF (9.0 mL×5 min×1) and then treated with 1.0 M suspension of 2-tert-Butoxycarbonylaminobenzothiazole-4-methylamine (2.5 g, 9.0 mmol) in DMSO (9.0 mL) at 70° C. After being stirred for 12 hr, the resin was filtered and rinsed with DMSO (9.0 mL×5 min×3). The resin was washed with DMF (5.0 mL×5 min×3) and CH$_2$Cl$_2$ (5.0 mL×5 min×3). The resin was dried under reduced pressure to afford desired resin (1.16 g).

The 2-tert-Butoxycarbonylbenzothiazole-4-methylamino-Fmoc-Tyr(tBu) resin (1.76 g, 0.57 mmol/g) was placed in 20 mL plastic disposable syringe. The resin was swollen in DMF (10.0 mL) and DMF was sucked out. The resin was treated with 20 v/v % piperidine/DMF (10.0 mL) at room temperature. After being shaken for 1.0 hr, the mixture was filtered and the resin was washed with DMF (10 mL×5 min×3) and CH$_2$Cl$_2$ (10 mL×5 min×3). The resin was dried under reduced pressure to afford desired resin (1.42 g).

Step-4

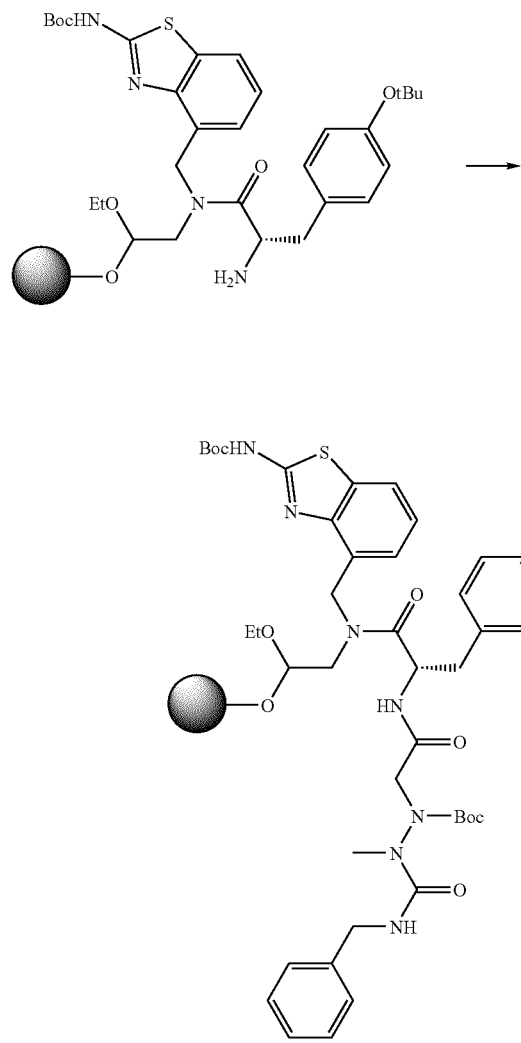

The Amino resin (350 mg, 0.65 mmol/g) was placed in 20 mL plastic disposable syringe. The resin was swollen in DMF (3.0 mL) and DMF was sucked out. To the resin was added 0.3 M stocked CH$_2$Cl$_2$ solution of 4-Benzyl-3-Boc-2-methylsemicarbazidylacetatic acid (2.7 mL, 0.80 mmol), DIPEA (277 μL, 1.59 mmol) and HATU (302 mg, 0.80 mmol) at room temperature. After being shaken for 12 hr, the mixture was filtered and the resin was washed with DMF (5.0 mL×5 min× 3) and CH$_2$Cl$_2$ (5.0 mL×5 min×3). The resin was dried under reduced pressure to afford desired resin.

Step-5

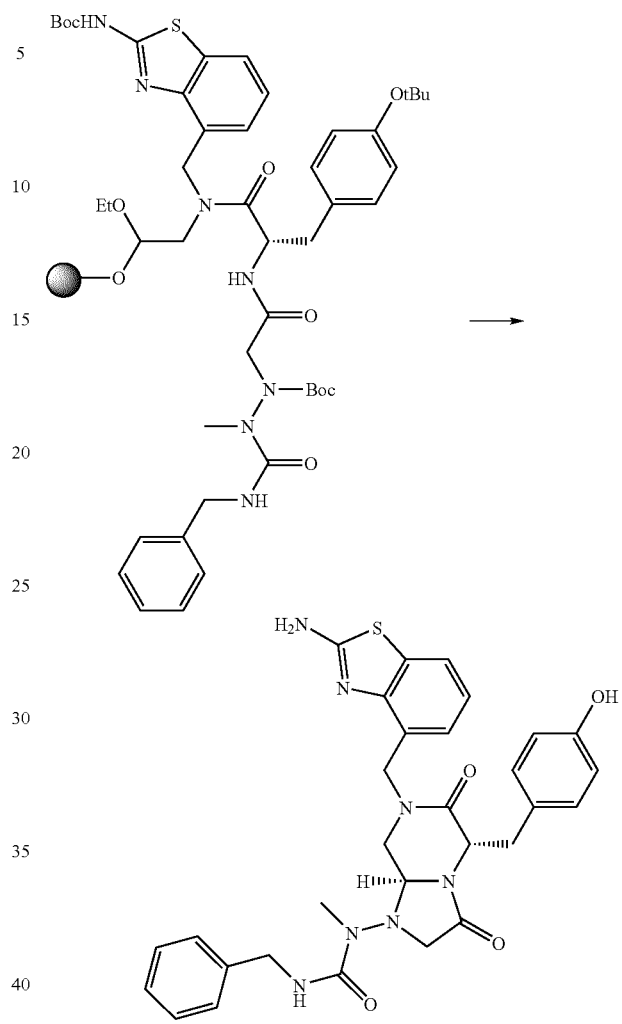

The resin (350 mg, 0.54 mmol/g) was placed in 20 mL plastic disposable syringe. After addition of 99% HCO$_2$H (4.0 mL), the mixture was shaken for 12 hr at room temperature, the solution was collected by filteration. The resin was washed with 99% HCO$_2$H (4.0 mL×5 min×2). The combined HCO$_2$H solutions were concentrated and then submitted to silica gel column chromatography to afford Compound No. 1273 (9.1 mg, 6.8% from bromoacetal resin). R$_f$=0.47 (CHCl$_3$:MeOH=9:1).

Synthesis of Compound No. 1285

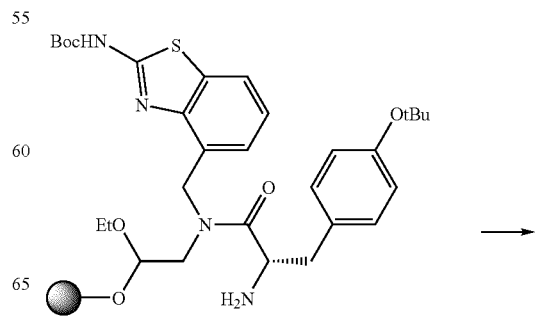

51

-continued

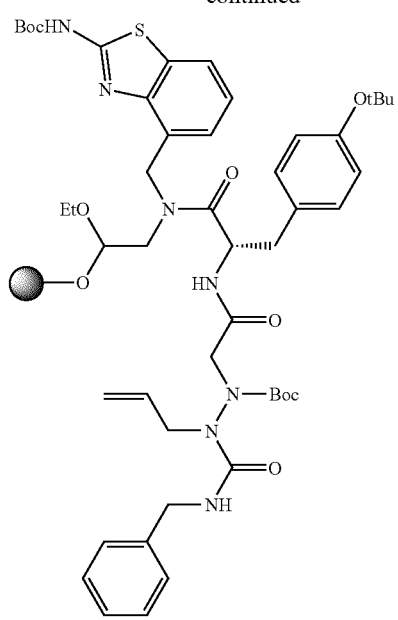

Step-1

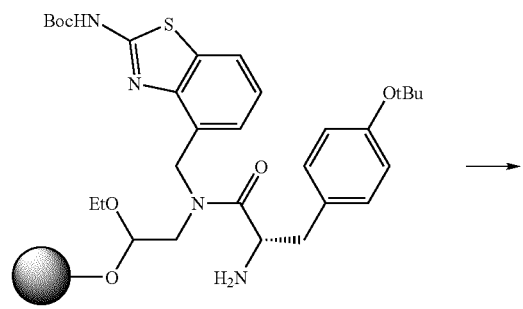

52

-continued

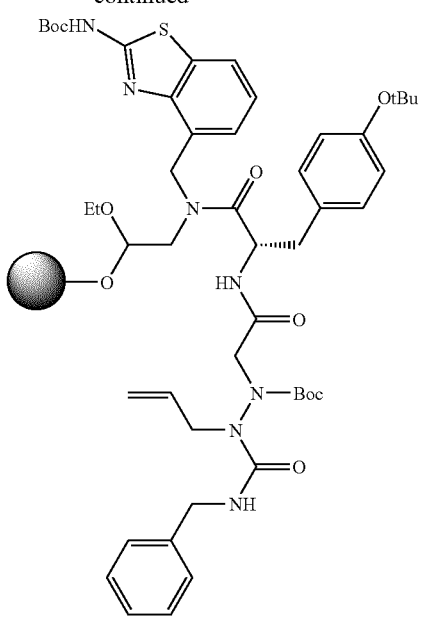

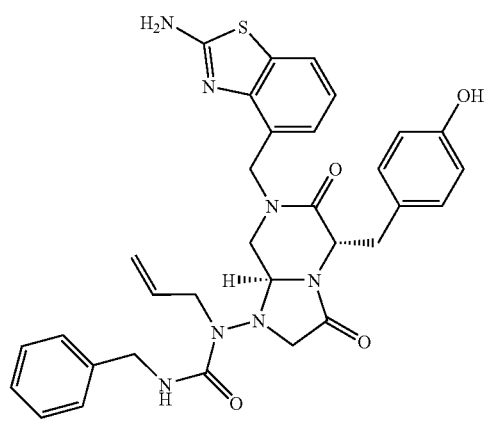

The Amino resin (350 mg, 0.65 mmol/g) was placed in 20 mL plastic disposable syringe. The resin was swollen in DMF (3.0 mL) and DMF was sucked out. To the resin was added 0.3 M stocked $CH_2Cl_2$ solution of 4-Benzyl-3-Boc-2-allylsemi-carbazidylacetatic acid (2.7 mL, 0.80 mmol), DIPEA (277 µL, 1.59 mmol) and HATU (302 mg, 0.80 mmol) at room temperature. After being shaken for 12 hr, the mixture was filtered and the resin was washed with DMF (5.0 mL×5 min× 3) and $CH_2Cl_2$ (5.0 mL×5 min×3). The resin was dried under reduced pressure to afford desired resin.

Step-2

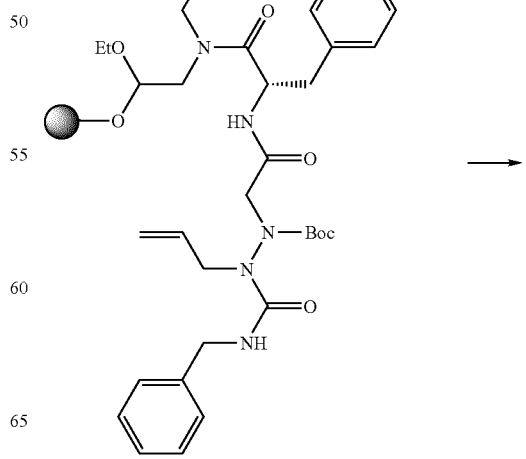

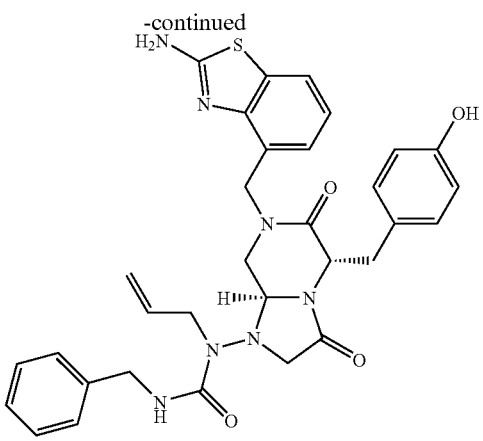

The resin (350 mg, 0.53 mmol/g) was placed in 20 mL plastic disposable syringe. After addition of 99% $HCO_2H$ (4.0 mL), the mixture was shaken for 12 hr at room temperature, the solution was collected by filteration. The resin was washed with 99% $HCO_2H$ (4.0 mL×5 min×2). The combined $HCO_2H$ solutions were concentrated and then submitted to silica gel column chromatography to afford Compound No. 1285 (18 mg, 13% from bromoacetal resin). $R_f$=0.52 ($CHCl_3$:MeOH=9:1).

Similar synthesis was carried out to obtain Compounds 1201-2200 as shown in FIGS. 7-11.

Synthesis of Compound No. 2201

To the cooled (0δ) solution of Compound No. 61 (18 mg, 0.032 mmol) in THF (500 δL) were added $Et_3N$ (13.4 μL, 0.096 mmol) and $POCl_3$ (14.9 μL, 0.160 mmol) and then the mixture was stirred till SM was disappeared on TLC (4 hr). The mixture was diluted with $H_2O$ (1 mL) and then $NaHCO_3$ was added at 08 to pH 8. After stirred overnight, the mixture was acidified to pH 3 with 1N HCl followed by extraction with $CHCl_3$ (5 mL×3). The combined extracts were dried over $Na_2SO_4$, filtered and concentrated to afford pale yellow powder Compound No. 2201 (17.1 mg, 83%). TLC: Rf=0.45δSilica gel F254, $CHCl_3$:MeOH:EtOH:$H_2O$:AcOH:nBuOH=100:40:10:10:8:58; $^1H$ NMR (400 MHz, $CDCl_3$) δ 7.98 (1H, d, J=7.7 Hz), 7.83 (1H, m), 7.77 (1H, d, J=8.2 Hz), 7.51 (2H, m), 7.35 (1H, t, J=7.3 Hz), 7.24-6.93 (10H, m), 6.07 (1H, br s), 5.86 (3H, br s), 5.34 (1H, br d, J=15.0 Hz), 4.76 (2H, m), 4.11 (2H, br ABX, J=15.5, 5.3 Hz), 3.62 (2H, m), 3.47 and 3.31 (2H, br ABq, J=15.0 Hz), 3.22 (2H, br m), 3.02 (1H, br m), 2.77 (1H, br t, J=10.6 Hz), 2.56 (3H, s); $^{31}P$ NMR (160.26 MHz, $CDCl_3$) δ −3.57.

Synthesis of Compound No. 2202

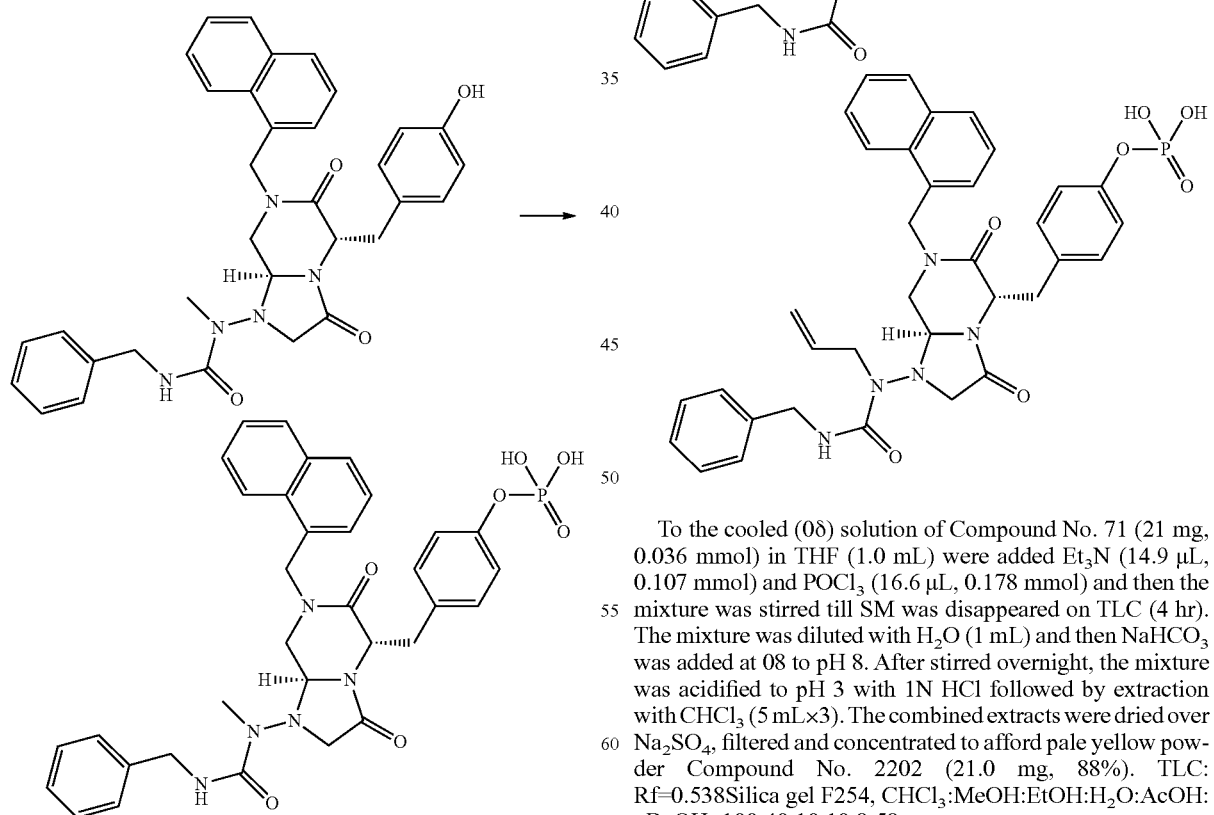

To the cooled (0δ) solution of Compound No. 71 (21 mg, 0.036 mmol) in THF (1.0 mL) were added $Et_3N$ (14.9 μL, 0.107 mmol) and $POCl_3$ (16.6 μL, 0.178 mmol) and then the mixture was stirred till SM was disappeared on TLC (4 hr). The mixture was diluted with $H_2O$ (1 mL) and then $NaHCO_3$ was added at 08 to pH 8. After stirred overnight, the mixture was acidified to pH 3 with 1N HCl followed by extraction with $CHCl_3$ (5 mL×3). The combined extracts were dried over $Na_2SO_4$, filtered and concentrated to afford pale yellow powder Compound No. 2202 (21.0 mg, 88%). TLC: Rf=0.538Silica gel F254, $CHCl_3$:MeOH:EtOH:$H_2O$:AcOH:nBuOH=100:40:10:10:8:58.

Similar synthesis was carried out to obtain Compounds 2203-2217 as shown in FIG. 27. Diastereomeric and Enantiomeric stereo isomers of Compounds 2203-2217 were obtained and are shown FIG. 12.

Table 2 below shows the molecular weight (M.W.) and mass for compounds 1-2217.

TABLE 2

| Compound No. | M.W. | Mass |
| --- | --- | --- |
| 1 | 533 | 534 |
| 2 | 551 | 552 |
| 3 | 563 | 564 |
| 4 | 602 | 603 |
| 5 | 457 | 458 |
| 6 | 561 | 562 |
| 7 | 579 | 580 |
| 8 | 591 | 592 |
| 9 | 630 | 631 |
| 10 | 485 | 486 |
| 11 | 559 | 560 |
| 12 | 577 | 578 |
| 13 | 589 | 590 |
| 14 | 628 | 629 |
| 15 | 483 | 484 |
| 16 | 557 | 558 |
| 17 | 575 | 576 |
| 18 | 587 | 588 |
| 19 | 626 | 627 |
| 20 | 481 | 482 |
| 21 | 561 | 562 |
| 22 | 579 | 580 |
| 23 | 591 | 592 |
| 24 | 630 | 631 |
| 25 | 485 | 486 |
| 26 | 558 | 559 |
| 27 | 576 | 577 |
| 28 | 588 | 589 |
| 29 | 627 | 628 |
| 30 | 482 | 483 |
| 31 | 547 | 548 |
| 32 | 565 | 566 |
| 33 | 577 | 578 |
| 34 | 616 | 617 |
| 35 | 471 | 472 |
| 36 | 575 | 576 |
| 37 | 593 | 594 |
| 38 | 605 | 606 |
| 39 | 644 | 645 |
| 40 | 499 | 500 |
| 41 | 573 | 574 |
| 42 | 591 | 592 |
| 43 | 603 | 604 |
| 44 | 642 | 643 |
| 45 | 497 | 498 |
| 46 | 571 | 572 |
| 47 | 589 | 590 |
| 48 | 601 | 602 |
| 49 | 640 | 641 |
| 50 | 495 | 496 |
| 51 | 575 | 576 |
| 52 | 593 | 594 |
| 53 | 605 | 606 |
| 54 | 644 | 645 |
| 55 | 499 | 500 |
| 56 | 572 | 573 |
| 57 | 590 | 591 |
| 58 | 602 | 603 |
| 59 | 641 | 642 |
| 60 | 496 | 497 |
| 61 | 563 | 564 |
| 62 | 581 | 582 |
| 63 | 593 | 594 |
| 64 | 632 | 633 |
| 65 | 487 | 488 |
| 66 | 591 | 592 |
| 67 | 609 | 610 |
| 68 | 621 | 622 |
| 69 | 660 | 661 |
| 70 | 515 | 516 |
| 71 | 589 | 590 |
| 72 | 607 | 608 |
| 73 | 619 | 620 |
| 74 | 658 | 659 |
| 75 | 513 | 514 |
| 76 | 587 | 588 |
| 77 | 605 | 606 |
| 78 | 617 | 618 |
| 79 | 656 | 657 |
| 80 | 511 | 512 |
| 81 | 591 | 592 |
| 82 | 609 | 610 |
| 83 | 621 | 622 |
| 84 | 660 | 661 |
| 85 | 515 | 516 |
| 86 | 588 | 589 |
| 87 | 606 | 607 |
| 88 | 618 | 619 |
| 89 | 657 | 658 |
| 90 | 512 | 513 |
| 91 | 563 | 564 |
| 92 | 581 | 582 |
| 93 | 609 | 610 |
| 94 | 648 | 649 |
| 95 | 503 | 504 |
| 96 | 607 | 608 |
| 97 | 625 | 626 |
| 98 | 637 | 638 |
| 99 | 676 | 677 |
| 100 | 531 | 532 |
| 101 | 605 | 606 |
| 102 | 623 | 624 |
| 103 | 635 | 636 |
| 104 | 674 | 675 |
| 105 | 529 | 530 |
| 106 | 603 | 604 |
| 107 | 621 | 622 |
| 108 | 633 | 634 |
| 109 | 672 | 673 |
| 110 | 527 | 528 |
| 111 | 607 | 608 |
| 112 | 625 | 626 |
| 113 | 637 | 638 |
| 114 | 676 | 677 |
| 115 | 531 | 532 |
| 116 | 604 | 605 |
| 117 | 622 | 623 |
| 118 | 634 | 635 |
| 119 | 673 | 674 |
| 120 | 528 | 529 |
| 121 | 562 | 563 |
| 122 | 580 | 581 |
| 123 | 592 | 593 |
| 124 | 631 | 632 |
| 125 | 486 | 487 |
| 126 | 590 | 591 |
| 127 | 608 | 609 |
| 128 | 620 | 621 |
| 129 | 659 | 660 |
| 130 | 514 | 515 |
| 131 | 588 | 589 |
| 132 | 606 | 607 |
| 133 | 618 | 619 |
| 134 | 657 | 658 |
| 135 | 512 | 513 |
| 136 | 586 | 587 |
| 137 | 604 | 605 |
| 138 | 616 | 617 |
| 139 | 655 | 656 |
| 140 | 510 | 511 |
| 141 | 590 | 591 |
| 142 | 608 | 609 |
| 143 | 620 | 621 |
| 144 | 659 | 660 |
| 145 | 514 | 515 |
| 146 | 587 | 588 |
| 147 | 605 | 606 |
| 148 | 617 | 618 |
| 149 | 656 | 657 |
| 150 | 511 | 512 |

TABLE 2-continued

| Compound No. | M.W. | Mass |
|---|---|---|
| 151 | 590 | 591 |
| 152 | 608 | 609 |
| 153 | 620 | 621 |
| 154 | 659 | 660 |
| 155 | 514 | 515 |
| 156 | 618 | 619 |
| 157 | 636 | 637 |
| 158 | 648 | 649 |
| 159 | 687 | 688 |
| 160 | 542 | 543 |
| 161 | 616 | 617 |
| 162 | 634 | 635 |
| 163 | 646 | 647 |
| 164 | 685 | 686 |
| 165 | 540 | 541 |
| 166 | 614 | 615 |
| 167 | 632 | 633 |
| 168 | 644 | 645 |
| 169 | 683 | 684 |
| 170 | 538 | 539 |
| 171 | 618 | 619 |
| 172 | 636 | 637 |
| 173 | 648 | 649 |
| 174 | 687 | 688 |
| 175 | 542 | 543 |
| 176 | 615 | 616 |
| 177 | 633 | 634 |
| 178 | 645 | 646 |
| 179 | 684 | 685 |
| 180 | 539 | 540 |
| 181 | 666 | 667 |
| 182 | 684 | 685 |
| 183 | 696 | 697 |
| 184 | 735 | 736 |
| 185 | 590 | 591 |
| 186 | 694 | 695 |
| 187 | 712 | 713 |
| 188 | 724 | 725 |
| 189 | 763 | 764 |
| 190 | 618 | 619 |
| 191 | 692 | 693 |
| 192 | 710 | 711 |
| 193 | 722 | 723 |
| 194 | 761 | 762 |
| 195 | 616 | 617 |
| 196 | 690 | 691 |
| 197 | 708 | 709 |
| 198 | 720 | 721 |
| 199 | 759 | 760 |
| 200 | 614 | 615 |
| 201 | 694 | 695 |
| 202 | 712 | 713 |
| 203 | 724 | 725 |
| 204 | 763 | 764 |
| 205 | 618 | 619 |
| 206 | 691 | 692 |
| 207 | 709 | 710 |
| 208 | 721 | 722 |
| 209 | 760 | 761 |
| 210 | 615 | 616 |
| 211 | 696 | 697 |
| 212 | 714 | 715 |
| 213 | 726 | 727 |
| 214 | 765 | 766 |
| 215 | 620 | 621 |
| 216 | 724 | 725 |
| 217 | 742 | 743 |
| 218 | 754 | 755 |
| 219 | 793 | 794 |
| 220 | 648 | 649 |
| 221 | 722 | 723 |
| 222 | 740 | 741 |
| 223 | 752 | 753 |
| 224 | 791 | 792 |
| 225 | 646 | 647 |
| 226 | 720 | 721 |
| 227 | 738 | 739 |
| 228 | 750 | 751 |
| 229 | 789 | 790 |
| 230 | 644 | 645 |
| 231 | 724 | 725 |
| 232 | 742 | 743 |
| 233 | 754 | 755 |
| 234 | 793 | 794 |
| 235 | 648 | 649 |
| 236 | 721 | 722 |
| 237 | 739 | 740 |
| 238 | 751 | 752 |
| 239 | 790 | 791 |
| 240 | 645 | 646 |
| 241 | 590 | 591 |
| 242 | 608 | 609 |
| 243 | 620 | 621 |
| 244 | 659 | 660 |
| 245 | 514 | 515 |
| 246 | 618 | 619 |
| 247 | 636 | 637 |
| 248 | 648 | 649 |
| 249 | 687 | 688 |
| 250 | 542 | 543 |
| 251 | 616 | 617 |
| 252 | 634 | 635 |
| 253 | 646 | 647 |
| 254 | 685 | 686 |
| 255 | 540 | 541 |
| 256 | 614 | 615 |
| 257 | 632 | 633 |
| 258 | 644 | 645 |
| 259 | 683 | 684 |
| 260 | 538 | 539 |
| 261 | 618 | 619 |
| 262 | 636 | 637 |
| 263 | 648 | 649 |
| 264 | 687 | 688 |
| 265 | 542 | 543 |
| 266 | 615 | 616 |
| 267 | 633 | 634 |
| 268 | 645 | 646 |
| 269 | 684 | 685 |
| 270 | 539 | 540 |
| 271 | 592 | 593 |
| 272 | 610 | 611 |
| 273 | 622 | 623 |
| 274 | 661 | 662 |
| 275 | 516 | 517 |
| 276 | 620 | 621 |
| 277 | 638 | 639 |
| 278 | 650 | 651 |
| 279 | 689 | 690 |
| 280 | 544 | 545 |
| 281 | 618 | 619 |
| 282 | 636 | 637 |
| 283 | 648 | 649 |
| 284 | 687 | 688 |
| 285 | 542 | 543 |
| 286 | 616 | 617 |
| 287 | 634 | 635 |
| 288 | 646 | 647 |
| 289 | 685 | 686 |
| 290 | 540 | 541 |
| 291 | 620 | 621 |
| 292 | 638 | 639 |
| 293 | 650 | 651 |
| 294 | 689 | 690 |
| 295 | 544 | 545 |
| 296 | 617 | 618 |
| 297 | 635 | 636 |
| 298 | 647 | 648 |
| 299 | 686 | 687 |
| 300 | 541 | 542 |
| 301 | 577 | 578 |
| 302 | 595 | 596 |
| 303 | 607 | 608 |
| 304 | 646 | 647 |

TABLE 2-continued

| Compound No. | M.W. | Mass |
|---|---|---|
| 305 | 501 | 502 |
| 306 | 605 | 606 |
| 307 | 623 | 624 |
| 308 | 635 | 636 |
| 309 | 674 | 675 |
| 310 | 529 | 530 |
| 311 | 603 | 604 |
| 312 | 621 | 622 |
| 313 | 633 | 634 |
| 314 | 672 | 673 |
| 315 | 527 | 528 |
| 316 | 601 | 602 |
| 317 | 619 | 620 |
| 318 | 631 | 632 |
| 319 | 670 | 671 |
| 320 | 525 | 526 |
| 321 | 605 | 606 |
| 322 | 623 | 624 |
| 323 | 635 | 636 |
| 324 | 674 | 675 |
| 325 | 529 | 530 |
| 326 | 602 | 603 |
| 327 | 620 | 621 |
| 328 | 632 | 633 |
| 329 | 671 | 672 |
| 330 | 526 | 527 |
| 331 | 635 | 636 |
| 332 | 653 | 654 |
| 333 | 665 | 666 |
| 334 | 704 | 705 |
| 335 | 559 | 560 |
| 336 | 663 | 664 |
| 337 | 681 | 682 |
| 338 | 693 | 694 |
| 339 | 732 | 733 |
| 340 | 587 | 588 |
| 341 | 661 | 662 |
| 342 | 679 | 680 |
| 343 | 691 | 692 |
| 344 | 730 | 731 |
| 345 | 585 | 586 |
| 346 | 659 | 660 |
| 347 | 677 | 678 |
| 348 | 689 | 690 |
| 349 | 728 | 729 |
| 350 | 583 | 584 |
| 351 | 663 | 664 |
| 352 | 681 | 682 |
| 353 | 693 | 694 |
| 354 | 732 | 733 |
| 355 | 587 | 588 |
| 356 | 660 | 661 |
| 357 | 678 | 679 |
| 358 | 690 | 691 |
| 359 | 729 | 730 |
| 360 | 584 | 585 |
| 361 | 716 | 717 |
| 362 | 734 | 735 |
| 363 | 746 | 747 |
| 364 | 785 | 786 |
| 365 | 640 | 641 |
| 366 | 744 | 745 |
| 367 | 762 | 763 |
| 368 | 774 | 775 |
| 369 | 813 | 814 |
| 370 | 668 | 669 |
| 371 | 742 | 743 |
| 372 | 760 | 761 |
| 373 | 772 | 773 |
| 374 | 811 | 812 |
| 375 | 666 | 667 |
| 376 | 740 | 741 |
| 377 | 758 | 759 |
| 378 | 770 | 771 |
| 379 | 809 | 810 |
| 380 | 664 | 665 |
| 381 | 744 | 745 |
| 382 | 762 | 763 |
| 383 | 774 | 775 |
| 384 | 813 | 814 |
| 385 | 668 | 669 |
| 386 | 741 | 742 |
| 387 | 759 | 760 |
| 388 | 771 | 772 |
| 389 | 810 | 811 |
| 390 | 665 | 666 |
| 391 | 565 | 566 |
| 392 | 583 | 584 |
| 393 | 595 | 596 |
| 394 | 634 | 635 |
| 395 | 489 | 490 |
| 396 | 593 | 594 |
| 397 | 611 | 612 |
| 398 | 623 | 624 |
| 399 | 662 | 663 |
| 400 | 517 | 518 |
| 401 | 591 | 592 |
| 402 | 609 | 610 |
| 403 | 621 | 622 |
| 404 | 660 | 661 |
| 405 | 515 | 516 |
| 406 | 589 | 590 |
| 407 | 607 | 608 |
| 408 | 619 | 620 |
| 409 | 658 | 659 |
| 410 | 513 | 514 |
| 411 | 593 | 594 |
| 412 | 611 | 612 |
| 413 | 623 | 624 |
| 414 | 662 | 663 |
| 415 | 517 | 518 |
| 416 | 590 | 591 |
| 417 | 608 | 609 |
| 418 | 620 | 621 |
| 419 | 659 | 660 |
| 420 | 514 | 515 |
| 421 | 578 | 579 |
| 422 | 596 | 597 |
| 423 | 608 | 609 |
| 424 | 647 | 648 |
| 425 | 502 | 503 |
| 426 | 606 | 607 |
| 427 | 624 | 625 |
| 428 | 636 | 637 |
| 429 | 675 | 676 |
| 430 | 530 | 531 |
| 431 | 604 | 605 |
| 432 | 622 | 623 |
| 433 | 634 | 635 |
| 434 | 673 | 674 |
| 435 | 528 | 529 |
| 436 | 602 | 603 |
| 437 | 620 | 621 |
| 438 | 632 | 633 |
| 439 | 671 | 672 |
| 440 | 526 | 527 |
| 441 | 606 | 607 |
| 442 | 624 | 625 |
| 443 | 636 | 637 |
| 444 | 675 | 676 |
| 445 | 530 | 531 |
| 446 | 603 | 604 |
| 447 | 621 | 622 |
| 448 | 633 | 634 |
| 449 | 672 | 673 |
| 450 | 527 | 528 |
| 451 | 634 | 635 |
| 452 | 652 | 653 |
| 453 | 664 | 665 |
| 454 | 703 | 704 |
| 455 | 558 | 559 |
| 456 | 662 | 663 |
| 457 | 680 | 681 |
| 458 | 692 | 693 |

TABLE 2-continued

| Compound No. | M.W. | Mass |
|---|---|---|
| 459 | 731 | 732 |
| 460 | 586 | 587 |
| 461 | 660 | 661 |
| 462 | 678 | 679 |
| 463 | 690 | 691 |
| 464 | 729 | 730 |
| 465 | 584 | 585 |
| 466 | 658 | 659 |
| 467 | 676 | 677 |
| 468 | 688 | 689 |
| 469 | 727 | 728 |
| 470 | 582 | 583 |
| 471 | 662 | 663 |
| 472 | 680 | 681 |
| 473 | 692 | 693 |
| 474 | 731 | 732 |
| 475 | 586 | 587 |
| 476 | 659 | 660 |
| 477 | 677 | 678 |
| 478 | 689 | 690 |
| 479 | 728 | 729 |
| 480 | 583 | 584 |
| 481 | 677 | 678 |
| 482 | 695 | 696 |
| 483 | 707 | 708 |
| 484 | 746 | 747 |
| 485 | 601 | 602 |
| 486 | 705 | 706 |
| 487 | 723 | 724 |
| 488 | 735 | 736 |
| 489 | 774 | 775 |
| 490 | 629 | 630 |
| 491 | 703 | 704 |
| 492 | 721 | 722 |
| 493 | 733 | 734 |
| 494 | 772 | 773 |
| 495 | 627 | 628 |
| 496 | 701 | 702 |
| 497 | 719 | 720 |
| 498 | 731 | 732 |
| 499 | 770 | 771 |
| 500 | 625 | 626 |
| 501 | 705 | 706 |
| 502 | 723 | 724 |
| 503 | 735 | 736 |
| 504 | 774 | 775 |
| 505 | 629 | 630 |
| 506 | 702 | 703 |
| 507 | 720 | 721 |
| 508 | 732 | 733 |
| 509 | 771 | 772 |
| 510 | 626 | 627 |
| 511 | 607 | 608 |
| 512 | 625 | 626 |
| 513 | 637 | 638 |
| 514 | 676 | 677 |
| 515 | 531 | 532 |
| 516 | 635 | 636 |
| 517 | 653 | 654 |
| 518 | 665 | 666 |
| 519 | 704 | 705 |
| 520 | 559 | 560 |
| 521 | 633 | 634 |
| 522 | 651 | 652 |
| 523 | 663 | 664 |
| 524 | 702 | 703 |
| 525 | 557 | 558 |
| 526 | 631 | 632 |
| 527 | 649 | 650 |
| 528 | 661 | 662 |
| 529 | 700 | 701 |
| 530 | 555 | 556 |
| 531 | 635 | 636 |
| 532 | 653 | 654 |
| 533 | 665 | 666 |
| 534 | 704 | 705 |
| 535 | 559 | 560 |

TABLE 2-continued

| Compound No. | M.W. | Mass |
|---|---|---|
| 536 | 632 | 633 |
| 537 | 650 | 651 |
| 538 | 662 | 663 |
| 539 | 701 | 702 |
| 540 | 556 | 557 |
| 541 | 640 | 641 |
| 542 | 658 | 659 |
| 543 | 670 | 671 |
| 544 | 709 | 710 |
| 545 | 564 | 565 |
| 546 | 668 | 669 |
| 547 | 686 | 687 |
| 548 | 698 | 699 |
| 549 | 737 | 738 |
| 550 | 592 | 593 |
| 551 | 666 | 667 |
| 552 | 684 | 685 |
| 553 | 696 | 697 |
| 554 | 735 | 736 |
| 555 | 590 | 591 |
| 556 | 664 | 665 |
| 557 | 682 | 683 |
| 558 | 694 | 695 |
| 559 | 733 | 734 |
| 560 | 588 | 589 |
| 561 | 668 | 669 |
| 562 | 686 | 687 |
| 563 | 698 | 699 |
| 564 | 737 | 738 |
| 565 | 592 | 593 |
| 566 | 665 | 666 |
| 567 | 683 | 684 |
| 568 | 695 | 696 |
| 569 | 734 | 735 |
| 570 | 589 | 590 |
| 571 | 587 | 588 |
| 572 | 605 | 606 |
| 573 | 617 | 618 |
| 574 | 656 | 657 |
| 575 | 511 | 512 |
| 576 | 615 | 616 |
| 577 | 633 | 634 |
| 578 | 645 | 646 |
| 579 | 684 | 685 |
| 580 | 539 | 540 |
| 581 | 613 | 614 |
| 582 | 631 | 632 |
| 583 | 643 | 644 |
| 584 | 682 | 683 |
| 585 | 537 | 538 |
| 591 | 615 | 616 |
| 592 | 633 | 634 |
| 593 | 645 | 646 |
| 594 | 684 | 685 |
| 595 | 539 | 540 |
| 586 | 611 | 612 |
| 587 | 629 | 630 |
| 588 | 641 | 642 |
| 589 | 680 | 681 |
| 590 | 535 | 536 |
| 596 | 612 | 613 |
| 597 | 630 | 631 |
| 598 | 642 | 643 |
| 599 | 681 | 682 |
| 600 | 536 | 537 |
| 601 | 551 | 552 |
| 602 | 579 | 580 |
| 603 | 577 | 578 |
| 604 | 565 | 566 |
| 605 | 593 | 594 |
| 606 | 591 | 592 |
| 607 | 581 | 582 |
| 608 | 609 | 610 |
| 609 | 607 | 608 |
| 610 | 497 | 498 |
| 611 | 525 | 526 |
| 612 | 523 | 524 |

TABLE 2-continued

| Compound No. | M.W. | Mass |
|---|---|---|
| 613 | 511 | 512 |
| 614 | 539 | 540 |
| 615 | 537 | 538 |
| 616 | 527 | 528 |
| 617 | 555 | 556 |
| 618 | 553 | 554 |
| 619 | 513 | 514 |
| 620 | 541 | 542 |
| 621 | 539 | 540 |
| 622 | 527 | 528 |
| 623 | 555 | 556 |
| 624 | 553 | 554 |
| 625 | 543 | 544 |
| 626 | 571 | 572 |
| 627 | 569 | 570 |
| 628 | 483 | 484 |
| 629 | 511 | 512 |
| 630 | 509 | 510 |
| 631 | 497 | 498 |
| 632 | 525 | 526 |
| 633 | 523 | 524 |
| 634 | 513 | 514 |
| 635 | 541 | 542 |
| 636 | 539 | 540 |
| 637 | 518 | 519 |
| 638 | 546 | 547 |
| 639 | 544 | 545 |
| 640 | 532 | 533 |
| 641 | 560 | 561 |
| 642 | 558 | 559 |
| 643 | 548 | 549 |
| 644 | 576 | 577 |
| 645 | 574 | 575 |
| 646 | 553 | 554 |
| 647 | 581 | 582 |
| 648 | 579 | 580 |
| 649 | 567 | 568 |
| 650 | 595 | 596 |
| 651 | 593 | 594 |
| 652 | 583 | 584 |
| 653 | 611 | 612 |
| 654 | 609 | 610 |
| 655 | 553 | 554 |
| 656 | 581 | 582 |
| 657 | 579 | 580 |
| 658 | 567 | 568 |
| 659 | 595 | 596 |
| 660 | 593 | 594 |
| 661 | 583 | 584 |
| 662 | 611 | 612 |
| 663 | 609 | 610 |
| 664 | 563 | 564 |
| 665 | 591 | 592 |
| 666 | 589 | 590 |
| 667 | 577 | 578 |
| 668 | 605 | 606 |
| 669 | 603 | 604 |
| 670 | 593 | 594 |
| 671 | 621 | 622 |
| 672 | 619 | 620 |
| 673 | 545 | 546 |
| 674 | 573 | 574 |
| 675 | 571 | 572 |
| 676 | 559 | 560 |
| 677 | 587 | 588 |
| 678 | 585 | 586 |
| 679 | 575 | 576 |
| 680 | 603 | 604 |
| 681 | 601 | 602 |
| 682 | 518 | 519 |
| 683 | 546 | 547 |
| 684 | 544 | 545 |
| 685 | 532 | 533 |
| 686 | 560 | 561 |
| 687 | 558 | 559 |
| 688 | 548 | 549 |
| 689 | 576 | 577 |

TABLE 2-continued

| Compound No. | M.W. | Mass |
|---|---|---|
| 690 | 574 | 575 |
| 691 | 497 | 498 |
| 692 | 525 | 526 |
| 693 | 523 | 524 |
| 694 | 511 | 512 |
| 695 | 539 | 540 |
| 696 | 537 | 538 |
| 697 | 527 | 528 |
| 698 | 555 | 556 |
| 699 | 553 | 554 |
| 700 | 497 | 498 |
| 701 | 525 | 526 |
| 702 | 523 | 524 |
| 703 | 511 | 512 |
| 704 | 539 | 540 |
| 705 | 537 | 538 |
| 706 | 527 | 528 |
| 707 | 555 | 556 |
| 708 | 553 | 554 |
| 709 | 497 | 498 |
| 710 | 525 | 526 |
| 711 | 523 | 524 |
| 712 | 511 | 512 |
| 713 | 539 | 540 |
| 714 | 537 | 538 |
| 715 | 527 | 528 |
| 716 | 555 | 556 |
| 717 | 553 | 554 |
| 718 | 541 | 542 |
| 719 | 569 | 570 |
| 720 | 567 | 568 |
| 721 | 555 | 556 |
| 722 | 583 | 584 |
| 723 | 581 | 582 |
| 724 | 571 | 572 |
| 725 | 599 | 600 |
| 726 | 597 | 598 |
| 727 | 554 | 555 |
| 728 | 582 | 583 |
| 729 | 580 | 581 |
| 730 | 568 | 569 |
| 731 | 596 | 597 |
| 732 | 594 | 595 |
| 733 | 584 | 585 |
| 734 | 612 | 613 |
| 735 | 610 | 611 |
| 736 | 554 | 555 |
| 737 | 582 | 583 |
| 738 | 580 | 581 |
| 739 | 568 | 569 |
| 740 | 596 | 597 |
| 741 | 594 | 595 |
| 742 | 584 | 585 |
| 743 | 612 | 613 |
| 744 | 610 | 611 |
| 745 | 554 | 555 |
| 746 | 582 | 583 |
| 747 | 580 | 581 |
| 748 | 568 | 569 |
| 749 | 596 | 597 |
| 750 | 594 | 595 |
| 751 | 584 | 585 |
| 752 | 612 | 613 |
| 753 | 610 | 611 |
| 754 | 561 | 562 |
| 755 | 589 | 590 |
| 756 | 587 | 588 |
| 757 | 575 | 576 |
| 758 | 603 | 604 |
| 759 | 601 | 602 |
| 760 | 591 | 592 |
| 761 | 619 | 620 |
| 762 | 617 | 618 |
| 763 | 562 | 563 |
| 764 | 590 | 591 |
| 765 | 588 | 589 |
| 766 | 576 | 577 |

TABLE 2-continued

| Compound No. | M.W. | Mass |
|---|---|---|
| 767 | 604 | 605 |
| 768 | 602 | 603 |
| 769 | 592 | 593 |
| 770 | 620 | 621 |
| 771 | 618 | 619 |
| 772 | 568 | 569 |
| 773 | 596 | 597 |
| 774 | 594 | 595 |
| 775 | 582 | 583 |
| 776 | 610 | 611 |
| 777 | 608 | 609 |
| 778 | 598 | 599 |
| 779 | 626 | 627 |
| 780 | 624 | 625 |
| 781 | 603 | 604 |
| 782 | 631 | 632 |
| 783 | 629 | 630 |
| 784 | 617 | 618 |
| 785 | 645 | 646 |
| 791 | 555 | 556 |
| 792 | 553 | 554 |
| 793 | 541 | 542 |
| 794 | 569 | 570 |
| 795 | 567 | 568 |
| 786 | 643 | 644 |
| 787 | 633 | 634 |
| 788 | 661 | 662 |
| 789 | 659 | 660 |
| 790 | 527 | 528 |
| 796 | 557 | 558 |
| 797 | 585 | 586 |
| 798 | 583 | 584 |
| 799 | 544 | 545 |
| 800 | 572 | 573 |
| 801 | 570 | 571 |
| 802 | 558 | 559 |
| 803 | 586 | 587 |
| 804 | 584 | 585 |
| 805 | 574 | 575 |
| 806 | 602 | 603 |
| 807 | 600 | 601 |
| 808 | 526 | 527 |
| 809 | 554 | 555 |
| 810 | 552 | 553 |
| 811 | 540 | 541 |
| 812 | 568 | 569 |
| 813 | 566 | 567 |
| 814 | 556 | 557 |
| 815 | 584 | 585 |
| 816 | 582 | 583 |
| 817 | 526 | 527 |
| 818 | 554 | 555 |
| 819 | 552 | 553 |
| 820 | 540 | 541 |
| 821 | 568 | 569 |
| 822 | 566 | 567 |
| 823 | 556 | 557 |
| 824 | 584 | 585 |
| 825 | 582 | 583 |
| 826 | 519 | 520 |
| 827 | 547 | 548 |
| 828 | 545 | 546 |
| 829 | 533 | 534 |
| 830 | 561 | 562 |
| 831 | 559 | 560 |
| 832 | 549 | 550 |
| 833 | 577 | 578 |
| 834 | 575 | 576 |
| 835 | 534 | 535 |
| 836 | 562 | 563 |
| 837 | 560 | 561 |
| 838 | 548 | 549 |
| 839 | 576 | 577 |
| 840 | 574 | 575 |
| 841 | 564 | 565 |
| 842 | 592 | 593 |
| 843 | 590 | 591 |
| 844 | 569 | 570 |
| 845 | 597 | 598 |
| 846 | 595 | 596 |
| 847 | 583 | 584 |
| 848 | 611 | 612 |
| 849 | 609 | 610 |
| 850 | 599 | 600 |
| 851 | 627 | 628 |
| 852 | 625 | 626 |
| 853 | 603 | 604 |
| 854 | 631 | 632 |
| 855 | 629 | 630 |
| 856 | 617 | 618 |
| 857 | 645 | 646 |
| 858 | 643 | 644 |
| 859 | 633 | 634 |
| 860 | 661 | 662 |
| 861 | 659 | 660 |
| 862 | 534 | 535 |
| 863 | 562 | 563 |
| 864 | 560 | 561 |
| 865 | 548 | 549 |
| 866 | 576 | 577 |
| 867 | 574 | 575 |
| 868 | 564 | 565 |
| 869 | 592 | 593 |
| 870 | 590 | 591 |
| 871 | 534 | 535 |
| 872 | 562 | 563 |
| 873 | 560 | 561 |
| 874 | 548 | 549 |
| 875 | 576 | 577 |
| 876 | 574 | 575 |
| 877 | 564 | 565 |
| 878 | 592 | 593 |
| 879 | 590 | 591 |
| 880 | 484 | 485 |
| 881 | 512 | 513 |
| 882 | 510 | 511 |
| 883 | 498 | 499 |
| 884 | 526 | 527 |
| 885 | 524 | 525 |
| 886 | 514 | 515 |
| 887 | 542 | 543 |
| 888 | 540 | 541 |
| 889 | 484 | 485 |
| 890 | 512 | 513 |
| 891 | 510 | 511 |
| 892 | 498 | 499 |
| 893 | 526 | 527 |
| 894 | 524 | 525 |
| 895 | 514 | 515 |
| 896 | 542 | 543 |
| 897 | 540 | 541 |
| 898 | 534 | 535 |
| 899 | 562 | 563 |
| 900 | 560 | 561 |
| 901 | 548 | 549 |
| 902 | 576 | 577 |
| 903 | 574 | 575 |
| 904 | 564 | 565 |
| 905 | 592 | 593 |
| 906 | 590 | 591 |
| 907 | 534 | 535 |
| 908 | 562 | 563 |
| 909 | 560 | 561 |
| 910 | 548 | 549 |
| 911 | 576 | 577 |
| 912 | 574 | 575 |
| 913 | 564 | 565 |
| 914 | 592 | 593 |
| 915 | 590 | 591 |
| 916 | 519 | 520 |
| 917 | 547 | 548 |
| 918 | 545 | 546 |
| 919 | 533 | 534 |
| 920 | 561 | 562 |

TABLE 2-continued

| Compound No. | M.W. | Mass |
|---|---|---|
| 921 | 559 | 560 |
| 922 | 549 | 550 |
| 923 | 577 | 578 |
| 924 | 575 | 576 |
| 925 | 519 | 520 |
| 926 | 547 | 548 |
| 927 | 545 | 546 |
| 928 | 533 | 534 |
| 929 | 561 | 562 |
| 930 | 559 | 560 |
| 931 | 549 | 550 |
| 932 | 577 | 578 |
| 933 | 575 | 576 |
| 934 | 537 | 538 |
| 935 | 565 | 566 |
| 936 | 563 | 564 |
| 937 | 551 | 552 |
| 938 | 579 | 580 |
| 939 | 577 | 578 |
| 940 | 567 | 568 |
| 941 | 595 | 596 |
| 942 | 593 | 594 |
| 943 | 573 | 574 |
| 944 | 601 | 602 |
| 945 | 599 | 600 |
| 946 | 587 | 588 |
| 947 | 615 | 616 |
| 948 | 613 | 614 |
| 949 | 603 | 604 |
| 950 | 631 | 632 |
| 951 | 629 | 630 |
| 952 | 501 | 502 |
| 953 | 529 | 530 |
| 954 | 527 | 528 |
| 955 | 515 | 516 |
| 956 | 543 | 544 |
| 957 | 541 | 542 |
| 958 | 531 | 532 |
| 959 | 559 | 560 |
| 960 | 557 | 558 |
| 961 | 501 | 502 |
| 962 | 529 | 530 |
| 963 | 527 | 528 |
| 964 | 515 | 516 |
| 965 | 543 | 544 |
| 966 | 541 | 542 |
| 967 | 531 | 532 |
| 968 | 559 | 560 |
| 969 | 557 | 558 |
| 970 | 501 | 502 |
| 971 | 529 | 530 |
| 972 | 527 | 528 |
| 973 | 515 | 516 |
| 974 | 543 | 544 |
| 975 | 541 | 542 |
| 976 | 531 | 532 |
| 977 | 559 | 560 |
| 978 | 557 | 558 |
| 979 | 552 | 553 |
| 980 | 580 | 581 |
| 981 | 578 | 579 |
| 982 | 566 | 567 |
| 983 | 594 | 595 |
| 984 | 592 | 593 |
| 985 | 582 | 583 |
| 986 | 610 | 611 |
| 987 | 608 | 609 |
| 988 | 566 | 567 |
| 989 | 594 | 595 |
| 990 | 592 | 593 |
| 991 | 580 | 581 |
| 992 | 608 | 609 |
| 993 | 606 | 607 |
| 994 | 596 | 597 |
| 995 | 624 | 625 |
| 996 | 622 | 623 |
| 997 | 523 | 524 |
| 998 | 551 | 552 |
| 999 | 549 | 550 |
| 1000 | 537 | 538 |
| 1001 | 565 | 566 |
| 1002 | 563 | 564 |
| 1003 | 553 | 554 |
| 1004 | 581 | 582 |
| 1005 | 579 | 580 |
| 1006 | 537 | 538 |
| 1007 | 565 | 566 |
| 1008 | 563 | 564 |
| 1009 | 551 | 552 |
| 1010 | 579 | 580 |
| 1011 | 577 | 578 |
| 1012 | 567 | 568 |
| 1013 | 595 | 596 |
| 1014 | 593 | 594 |
| 1015 | 523 | 524 |
| 1016 | 551 | 552 |
| 1017 | 549 | 550 |
| 1018 | 537 | 538 |
| 1019 | 565 | 566 |
| 1020 | 563 | 564 |
| 1021 | 553 | 554 |
| 1022 | 581 | 582 |
| 1023 | 579 | 580 |
| 1024 | 537 | 538 |
| 1025 | 565 | 566 |
| 1026 | 563 | 564 |
| 1027 | 551 | 552 |
| 1028 | 579 | 580 |
| 1029 | 577 | 578 |
| 1030 | 567 | 568 |
| 1031 | 595 | 596 |
| 1032 | 593 | 594 |
| 1033 | 561 | 562 |
| 1034 | 589 | 590 |
| 1035 | 587 | 588 |
| 1036 | 575 | 576 |
| 1037 | 603 | 604 |
| 1038 | 601 | 602 |
| 1039 | 591 | 592 |
| 1040 | 619 | 620 |
| 1041 | 617 | 618 |
| 1042 | 523 | 524 |
| 1043 | 551 | 552 |
| 1044 | 549 | 550 |
| 1045 | 537 | 538 |
| 1046 | 565 | 566 |
| 1047 | 563 | 564 |
| 1048 | 553 | 554 |
| 1049 | 581 | 582 |
| 1050 | 579 | 580 |
| 1051 | 537 | 538 |
| 1052 | 565 | 566 |
| 1053 | 563 | 564 |
| 1054 | 551 | 552 |
| 1055 | 579 | 580 |
| 1056 | 577 | 578 |
| 1057 | 567 | 568 |
| 1058 | 595 | 596 |
| 1059 | 593 | 594 |
| 1060 | 671 | 672 |
| 1061 | 699 | 700 |
| 1062 | 697 | 698 |
| 1063 | 685 | 686 |
| 1064 | 713 | 714 |
| 1065 | 711 | 712 |
| 1066 | 701 | 702 |
| 1067 | 729 | 730 |
| 1068 | 727 | 728 |
| 1069 | 561 | 562 |
| 1070 | 589 | 590 |
| 1071 | 587 | 588 |
| 1072 | 575 | 576 |
| 1073 | 603 | 604 |
| 1074 | 601 | 602 |

TABLE 2-continued

| Compound No. | M.W. | Mass |
|---|---|---|
| 1075 | 591 | 592 |
| 1076 | 619 | 620 |
| 1077 | 617 | 618 |
| 1078 | 561 | 562 |
| 1079 | 589 | 590 |
| 1080 | 587 | 588 |
| 1081 | 575 | 576 |
| 1082 | 603 | 604 |
| 1083 | 601 | 602 |
| 1084 | 591 | 592 |
| 1085 | 619 | 620 |
| 1086 | 617 | 618 |
| 1087 | 524 | 525 |
| 1088 | 552 | 553 |
| 1089 | 550 | 551 |
| 1090 | 538 | 539 |
| 1091 | 566 | 567 |
| 1092 | 564 | 565 |
| 1093 | 554 | 555 |
| 1094 | 582 | 583 |
| 1095 | 580 | 581 |
| 1096 | 538 | 539 |
| 1097 | 566 | 567 |
| 1098 | 564 | 565 |
| 1099 | 552 | 553 |
| 1100 | 580 | 581 |
| 1101 | 578 | 579 |
| 1102 | 568 | 569 |
| 1103 | 596 | 597 |
| 1104 | 594 | 595 |
| 1105 | 538 | 539 |
| 1106 | 566 | 567 |
| 1107 | 564 | 565 |
| 1108 | 552 | 553 |
| 1109 | 580 | 581 |
| 1110 | 578 | 579 |
| 1111 | 568 | 569 |
| 1112 | 596 | 597 |
| 1113 | 594 | 595 |
| 1114 | 540 | 541 |
| 1115 | 568 | 569 |
| 1116 | 566 | 567 |
| 1117 | 554 | 555 |
| 1118 | 582 | 583 |
| 1119 | 580 | 581 |
| 1120 | 570 | 571 |
| 1121 | 598 | 599 |
| 1122 | 596 | 597 |
| 1123 | 523 | 524 |
| 1124 | 551 | 552 |
| 1125 | 549 | 550 |
| 1126 | 537 | 538 |
| 1127 | 565 | 566 |
| 1128 | 563 | 564 |
| 1129 | 553 | 554 |
| 1130 | 581 | 582 |
| 1131 | 579 | 580 |
| 1132 | 539 | 540 |
| 1133 | 567 | 568 |
| 1134 | 565 | 566 |
| 1135 | 553 | 554 |
| 1136 | 581 | 582 |
| 1137 | 579 | 580 |
| 1138 | 569 | 570 |
| 1139 | 597 | 598 |
| 1140 | 595 | 596 |
| 1141 | 539 | 540 |
| 1142 | 567 | 568 |
| 1143 | 565 | 566 |
| 1144 | 553 | 554 |
| 1145 | 581 | 582 |
| 1146 | 579 | 580 |
| 1147 | 569 | 570 |
| 1148 | 597 | 598 |
| 1149 | 595 | 596 |
| 1150 | 540 | 541 |
| 1151 | 568 | 569 |
| 1152 | 566 | 567 |
| 1153 | 554 | 555 |
| 1154 | 582 | 583 |
| 1155 | 580 | 581 |
| 1156 | 570 | 571 |
| 1157 | 598 | 599 |
| 1158 | 596 | 597 |
| 1159 | 524 | 525 |
| 1160 | 552 | 553 |
| 1161 | 550 | 551 |
| 1162 | 538 | 539 |
| 1163 | 566 | 567 |
| 1164 | 564 | 565 |
| 1165 | 554 | 555 |
| 1166 | 582 | 583 |
| 1167 | 580 | 581 |
| 1168 | 540 | 541 |
| 1169 | 568 | 569 |
| 1170 | 566 | 567 |
| 1171 | 554 | 555 |
| 1172 | 582 | 583 |
| 1173 | 580 | 581 |
| 1174 | 570 | 571 |
| 1175 | 598 | 599 |
| 1176 | 596 | 597 |
| 1177 | 554 | 555 |
| 1178 | 582 | 583 |
| 1179 | 580 | 581 |
| 1180 | 568 | 569 |
| 1181 | 596 | 597 |
| 1182 | 594 | 595 |
| 1183 | 584 | 585 |
| 1184 | 612 | 613 |
| 1185 | 610 | 611 |
| 1186 | 583 | 584 |
| 1187 | 611 | 612 |
| 1188 | 609 | 610 |
| 1189 | 597 | 598 |
| 1190 | 625 | 626 |
| 1191 | 623 | 624 |
| 1192 | 613 | 614 |
| 1193 | 641 | 642 |
| 1194 | 639 | 640 |
| 1195 | 558 | 559 |
| 1196 | 586 | 587 |
| 1197 | 584 | 585 |
| 1198 | 572 | 573 |
| 1199 | 600 | 601 |
| 1200 | 598 | 599 |
| 1201 | 555 | 556 |
| 1202 | 573 | 574 |
| 1203 | 585 | 586 |
| 1204 | 624 | 625 |
| 1205 | 479 | 480 |
| 1206 | 521 | 522 |
| 1207 | 583 | 584 |
| 1208 | 601 | 602 |
| 1209 | 613 | 614 |
| 1210 | 652 | 653 |
| 1211 | 507 | 508 |
| 1212 | 549 | 550 |
| 1213 | 581 | 582 |
| 1214 | 599 | 600 |
| 1215 | 611 | 612 |
| 1216 | 650 | 651 |
| 1217 | 505 | 506 |
| 1218 | 547 | 548 |
| 1219 | 579 | 580 |
| 1220 | 597 | 598 |
| 1221 | 609 | 610 |
| 1222 | 648 | 649 |
| 1223 | 503 | 504 |
| 1224 | 545 | 546 |
| 1225 | 583 | 584 |
| 1226 | 601 | 602 |
| 1227 | 613 | 614 |
| 1228 | 652 | 653 |

TABLE 2-continued

| Compound No. | M.W. | Mass |
|---|---|---|
| 1229 | 507 | 508 |
| 1230 | 549 | 550 |
| 1231 | 580 | 581 |
| 1232 | 598 | 599 |
| 1233 | 610 | 611 |
| 1234 | 649 | 650 |
| 1235 | 504 | 505 |
| 1236 | 546 | 547 |
| 1237 | 569 | 570 |
| 1238 | 587 | 588 |
| 1239 | 599 | 600 |
| 1240 | 638 | 639 |
| 1241 | 493 | 494 |
| 1242 | 535 | 536 |
| 1243 | 597 | 598 |
| 1244 | 615 | 616 |
| 1245 | 627 | 628 |
| 1246 | 666 | 667 |
| 1247 | 521 | 522 |
| 1248 | 563 | 564 |
| 1249 | 595 | 596 |
| 1250 | 613 | 614 |
| 1251 | 625 | 626 |
| 1252 | 664 | 665 |
| 1253 | 519 | 520 |
| 1254 | 561 | 562 |
| 1255 | 593 | 594 |
| 1256 | 611 | 612 |
| 1257 | 623 | 624 |
| 1258 | 662 | 663 |
| 1259 | 517 | 518 |
| 1260 | 559 | 560 |
| 1261 | 597 | 598 |
| 1262 | 615 | 616 |
| 1263 | 627 | 628 |
| 1264 | 666 | 667 |
| 1265 | 521 | 522 |
| 1266 | 563 | 564 |
| 1267 | 594 | 595 |
| 1268 | 612 | 613 |
| 1269 | 624 | 625 |
| 1270 | 663 | 664 |
| 1271 | 518 | 519 |
| 1272 | 560 | 561 |
| 1273 | 585 | 586 |
| 1274 | 603 | 604 |
| 1275 | 615 | 616 |
| 1276 | 654 | 655 |
| 1277 | 509 | 510 |
| 1278 | 551 | 552 |
| 1279 | 613 | 614 |
| 1280 | 631 | 632 |
| 1281 | 643 | 644 |
| 1282 | 682 | 683 |
| 1283 | 537 | 538 |
| 1284 | 579 | 580 |
| 1285 | 611 | 612 |
| 1286 | 629 | 630 |
| 1287 | 641 | 642 |
| 1288 | 680 | 681 |
| 1289 | 535 | 536 |
| 1290 | 577 | 578 |
| 1291 | 609 | 610 |
| 1292 | 627 | 628 |
| 1293 | 639 | 640 |
| 1294 | 678 | 679 |
| 1295 | 533 | 534 |
| 1296 | 575 | 576 |
| 1297 | 613 | 614 |
| 1298 | 631 | 632 |
| 1299 | 643 | 644 |
| 1300 | 682 | 683 |
| 1301 | 537 | 538 |
| 1302 | 579 | 580 |
| 1303 | 610 | 611 |
| 1304 | 628 | 629 |
| 1305 | 640 | 641 |
| 1306 | 679 | 680 |
| 1307 | 534 | 535 |
| 1308 | 576 | 577 |
| 1309 | 601 | 602 |
| 1310 | 619 | 620 |
| 1311 | 631 | 632 |
| 1312 | 670 | 671 |
| 1313 | 525 | 526 |
| 1314 | 567 | 568 |
| 1315 | 629 | 630 |
| 1316 | 647 | 648 |
| 1317 | 659 | 660 |
| 1318 | 698 | 699 |
| 1319 | 553 | 554 |
| 1320 | 595 | 596 |
| 1321 | 627 | 628 |
| 1322 | 645 | 646 |
| 1323 | 657 | 658 |
| 1324 | 696 | 697 |
| 1325 | 551 | 552 |
| 1326 | 593 | 594 |
| 1327 | 625 | 626 |
| 1328 | 643 | 644 |
| 1329 | 655 | 656 |
| 1330 | 694 | 695 |
| 1331 | 549 | 550 |
| 1332 | 591 | 592 |
| 1333 | 629 | 630 |
| 1334 | 647 | 648 |
| 1335 | 659 | 660 |
| 1336 | 698 | 699 |
| 1337 | 553 | 554 |
| 1338 | 595 | 596 |
| 1339 | 626 | 627 |
| 1340 | 644 | 645 |
| 1341 | 656 | 657 |
| 1342 | 695 | 696 |
| 1343 | 550 | 551 |
| 1344 | 592 | 593 |
| 1345 | 584 | 585 |
| 1346 | 602 | 603 |
| 1347 | 614 | 615 |
| 1348 | 653 | 654 |
| 1349 | 508 | 509 |
| 1350 | 550 | 551 |
| 1351 | 612 | 613 |
| 1352 | 630 | 631 |
| 1353 | 642 | 643 |
| 1354 | 681 | 682 |
| 1355 | 536 | 537 |
| 1356 | 578 | 579 |
| 1357 | 610 | 611 |
| 1358 | 628 | 629 |
| 1359 | 640 | 641 |
| 1360 | 679 | 680 |
| 1361 | 534 | 535 |
| 1362 | 576 | 577 |
| 1363 | 608 | 609 |
| 1364 | 626 | 627 |
| 1365 | 638 | 639 |
| 1366 | 677 | 678 |
| 1367 | 532 | 533 |
| 1368 | 574 | 575 |
| 1369 | 612 | 613 |
| 1370 | 630 | 631 |
| 1371 | 642 | 643 |
| 1372 | 681 | 682 |
| 1373 | 536 | 537 |
| 1374 | 578 | 579 |
| 1375 | 609 | 610 |
| 1376 | 627 | 628 |
| 1377 | 639 | 640 |
| 1378 | 678 | 679 |
| 1379 | 533 | 534 |
| 1380 | 575 | 576 |
| 1381 | 612 | 613 |
| 1382 | 630 | 631 |

TABLE 2-continued

| Compound No. | M.W. | Mass |
|---|---|---|
| 1383 | 642 | 643 |
| 1384 | 681 | 682 |
| 1385 | 536 | 537 |
| 1386 | 578 | 579 |
| 1387 | 640 | 641 |
| 1388 | 658 | 659 |
| 1389 | 670 | 671 |
| 1390 | 709 | 710 |
| 1391 | 564 | 565 |
| 1392 | 606 | 607 |
| 1393 | 638 | 639 |
| 1394 | 656 | 657 |
| 1395 | 668 | 669 |
| 1396 | 707 | 708 |
| 1397 | 562 | 563 |
| 1398 | 604 | 605 |
| 1399 | 636 | 637 |
| 1400 | 654 | 655 |
| 1401 | 666 | 667 |
| 1402 | 705 | 706 |
| 1403 | 560 | 561 |
| 1404 | 602 | 603 |
| 1405 | 640 | 641 |
| 1406 | 658 | 659 |
| 1407 | 670 | 671 |
| 1408 | 709 | 710 |
| 1409 | 564 | 565 |
| 1410 | 606 | 607 |
| 1411 | 637 | 638 |
| 1412 | 655 | 656 |
| 1413 | 667 | 668 |
| 1414 | 706 | 707 |
| 1415 | 561 | 562 |
| 1416 | 603 | 604 |
| 1417 | 688 | 689 |
| 1418 | 706 | 707 |
| 1419 | 718 | 719 |
| 1420 | 757 | 758 |
| 1421 | 612 | 613 |
| 1422 | 654 | 655 |
| 1423 | 716 | 717 |
| 1424 | 734 | 735 |
| 1425 | 746 | 747 |
| 1426 | 785 | 786 |
| 1427 | 640 | 641 |
| 1428 | 682 | 683 |
| 1429 | 714 | 715 |
| 1430 | 732 | 733 |
| 1431 | 744 | 745 |
| 1432 | 783 | 784 |
| 1433 | 638 | 639 |
| 1434 | 680 | 681 |
| 1435 | 712 | 713 |
| 1436 | 730 | 731 |
| 1437 | 742 | 743 |
| 1438 | 781 | 782 |
| 1439 | 636 | 637 |
| 1440 | 678 | 679 |
| 1441 | 716 | 717 |
| 1442 | 734 | 735 |
| 1443 | 746 | 747 |
| 1444 | 785 | 786 |
| 1445 | 640 | 641 |
| 1446 | 682 | 683 |
| 1447 | 713 | 714 |
| 1448 | 731 | 732 |
| 1449 | 743 | 744 |
| 1450 | 782 | 783 |
| 1451 | 637 | 638 |
| 1452 | 679 | 680 |
| 1453 | 718 | 719 |
| 1454 | 736 | 737 |
| 1455 | 748 | 749 |
| 1456 | 787 | 788 |
| 1457 | 642 | 643 |
| 1458 | 684 | 685 |
| 1459 | 746 | 747 |

TABLE 2-continued

| Compound No. | M.W. | Mass |
|---|---|---|
| 1460 | 764 | 765 |
| 1461 | 776 | 777 |
| 1462 | 815 | 816 |
| 1463 | 670 | 671 |
| 1464 | 712 | 713 |
| 1465 | 744 | 745 |
| 1466 | 762 | 763 |
| 1467 | 774 | 775 |
| 1468 | 813 | 814 |
| 1469 | 668 | 669 |
| 1470 | 710 | 711 |
| 1471 | 742 | 743 |
| 1472 | 760 | 761 |
| 1473 | 772 | 773 |
| 1474 | 811 | 812 |
| 1475 | 666 | 667 |
| 1476 | 708 | 709 |
| 1477 | 746 | 747 |
| 1478 | 764 | 765 |
| 1479 | 776 | 777 |
| 1480 | 815 | 816 |
| 1481 | 670 | 671 |
| 1482 | 712 | 713 |
| 1483 | 743 | 744 |
| 1484 | 761 | 762 |
| 1485 | 773 | 774 |
| 1486 | 812 | 813 |
| 1487 | 667 | 668 |
| 1488 | 709 | 710 |
| 1489 | 612 | 613 |
| 1490 | 630 | 631 |
| 1491 | 642 | 643 |
| 1492 | 681 | 682 |
| 1493 | 536 | 537 |
| 1494 | 578 | 579 |
| 1495 | 640 | 641 |
| 1496 | 658 | 659 |
| 1497 | 670 | 671 |
| 1498 | 709 | 710 |
| 1499 | 564 | 565 |
| 1500 | 606 | 607 |
| 1501 | 638 | 639 |
| 1502 | 656 | 657 |
| 1503 | 668 | 669 |
| 1504 | 707 | 708 |
| 1505 | 562 | 563 |
| 1506 | 604 | 605 |
| 1507 | 636 | 637 |
| 1508 | 654 | 655 |
| 1509 | 666 | 667 |
| 1510 | 705 | 706 |
| 1511 | 560 | 561 |
| 1512 | 602 | 603 |
| 1513 | 640 | 641 |
| 1514 | 658 | 659 |
| 1515 | 670 | 671 |
| 1516 | 709 | 710 |
| 1517 | 564 | 565 |
| 1518 | 606 | 607 |
| 1519 | 637 | 638 |
| 1520 | 655 | 656 |
| 1521 | 667 | 668 |
| 1522 | 706 | 707 |
| 1523 | 561 | 562 |
| 1524 | 603 | 604 |
| 1525 | 614 | 615 |
| 1526 | 632 | 633 |
| 1527 | 644 | 645 |
| 1528 | 683 | 684 |
| 1529 | 538 | 539 |
| 1530 | 580 | 581 |
| 1531 | 642 | 643 |
| 1532 | 660 | 661 |
| 1533 | 672 | 673 |
| 1534 | 711 | 712 |
| 1535 | 566 | 567 |
| 1536 | 608 | 609 |

TABLE 2-continued

| Compound No. | M.W. | Mass |
|---|---|---|
| 1537 | 640 | 641 |
| 1538 | 658 | 659 |
| 1539 | 670 | 671 |
| 1540 | 709 | 710 |
| 1541 | 564 | 565 |
| 1542 | 606 | 607 |
| 1543 | 638 | 639 |
| 1544 | 656 | 657 |
| 1545 | 668 | 669 |
| 1546 | 707 | 708 |
| 1547 | 562 | 563 |
| 1548 | 604 | 605 |
| 1549 | 642 | 643 |
| 1550 | 660 | 661 |
| 1551 | 672 | 673 |
| 1552 | 711 | 712 |
| 1553 | 566 | 567 |
| 1554 | 608 | 609 |
| 1555 | 639 | 640 |
| 1556 | 657 | 658 |
| 1557 | 669 | 670 |
| 1558 | 708 | 709 |
| 1559 | 563 | 564 |
| 1560 | 605 | 606 |
| 1561 | 599 | 600 |
| 1562 | 617 | 618 |
| 1563 | 629 | 630 |
| 1564 | 668 | 669 |
| 1565 | 523 | 524 |
| 1566 | 565 | 566 |
| 1567 | 627 | 628 |
| 1568 | 645 | 646 |
| 1569 | 657 | 658 |
| 1570 | 696 | 697 |
| 1571 | 551 | 552 |
| 1572 | 593 | 594 |
| 1573 | 625 | 626 |
| 1574 | 643 | 644 |
| 1575 | 655 | 656 |
| 1576 | 694 | 695 |
| 1577 | 549 | 550 |
| 1578 | 591 | 592 |
| 1579 | 623 | 624 |
| 1580 | 641 | 642 |
| 1581 | 653 | 654 |
| 1582 | 692 | 693 |
| 1583 | 547 | 548 |
| 1584 | 589 | 590 |
| 1585 | 627 | 628 |
| 1586 | 645 | 646 |
| 1587 | 657 | 658 |
| 1588 | 696 | 697 |
| 1589 | 551 | 552 |
| 1590 | 593 | 594 |
| 1591 | 624 | 625 |
| 1592 | 642 | 643 |
| 1593 | 654 | 655 |
| 1594 | 693 | 694 |
| 1595 | 548 | 549 |
| 1596 | 590 | 591 |
| 1597 | 657 | 658 |
| 1598 | 675 | 676 |
| 1599 | 687 | 688 |
| 1600 | 726 | 727 |
| 1601 | 581 | 582 |
| 1602 | 623 | 624 |
| 1603 | 685 | 686 |
| 1604 | 703 | 704 |
| 1605 | 715 | 716 |
| 1606 | 754 | 755 |
| 1607 | 609 | 610 |
| 1608 | 651 | 652 |
| 1609 | 683 | 684 |
| 1610 | 701 | 702 |
| 1611 | 713 | 714 |
| 1612 | 752 | 753 |
| 1613 | 607 | 608 |

TABLE 2-continued

| Compound No. | M.W. | Mass |
|---|---|---|
| 1614 | 649 | 650 |
| 1615 | 681 | 682 |
| 1616 | 699 | 700 |
| 1617 | 711 | 712 |
| 1618 | 750 | 751 |
| 1619 | 605 | 606 |
| 1620 | 647 | 648 |
| 1621 | 685 | 686 |
| 1622 | 703 | 704 |
| 1623 | 715 | 716 |
| 1624 | 754 | 755 |
| 1625 | 609 | 610 |
| 1626 | 651 | 652 |
| 1627 | 682 | 683 |
| 1628 | 700 | 701 |
| 1629 | 712 | 713 |
| 1630 | 751 | 752 |
| 1631 | 606 | 607 |
| 1632 | 648 | 649 |
| 1633 | 738 | 739 |
| 1634 | 756 | 757 |
| 1635 | 768 | 769 |
| 1636 | 807 | 808 |
| 1637 | 662 | 663 |
| 1638 | 704 | 705 |
| 1639 | 766 | 767 |
| 1640 | 784 | 785 |
| 1641 | 796 | 797 |
| 1642 | 835 | 836 |
| 1643 | 690 | 691 |
| 1644 | 732 | 733 |
| 1645 | 764 | 765 |
| 1646 | 782 | 783 |
| 1647 | 794 | 795 |
| 1648 | 833 | 834 |
| 1649 | 688 | 689 |
| 1650 | 730 | 731 |
| 1651 | 762 | 763 |
| 1652 | 780 | 781 |
| 1653 | 792 | 793 |
| 1654 | 831 | 832 |
| 1655 | 686 | 687 |
| 1656 | 728 | 729 |
| 1657 | 766 | 767 |
| 1658 | 784 | 785 |
| 1659 | 796 | 797 |
| 1660 | 835 | 836 |
| 1661 | 690 | 691 |
| 1662 | 732 | 733 |
| 1663 | 763 | 764 |
| 1664 | 781 | 782 |
| 1665 | 793 | 794 |
| 1666 | 832 | 833 |
| 1667 | 687 | 688 |
| 1668 | 729 | 730 |
| 1669 | 587 | 588 |
| 1670 | 605 | 606 |
| 1671 | 617 | 618 |
| 1672 | 656 | 657 |
| 1673 | 511 | 512 |
| 1674 | 553 | 554 |
| 1675 | 615 | 616 |
| 1676 | 633 | 634 |
| 1677 | 645 | 646 |
| 1678 | 684 | 685 |
| 1679 | 539 | 540 |
| 1680 | 581 | 582 |
| 1681 | 613 | 614 |
| 1682 | 631 | 632 |
| 1683 | 643 | 644 |
| 1684 | 682 | 683 |
| 1685 | 537 | 538 |
| 1686 | 579 | 580 |
| 1687 | 611 | 612 |
| 1688 | 629 | 630 |
| 1689 | 641 | 642 |
| 1690 | 680 | 681 |

TABLE 2-continued

| Compound No. | M.W. | Mass |
|---|---|---|
| 1691 | 535 | 536 |
| 1692 | 577 | 578 |
| 1693 | 615 | 616 |
| 1694 | 633 | 634 |
| 1695 | 645 | 646 |
| 1696 | 684 | 685 |
| 1697 | 539 | 540 |
| 1698 | 581 | 582 |
| 1699 | 612 | 613 |
| 1700 | 630 | 631 |
| 1701 | 642 | 643 |
| 1702 | 681 | 682 |
| 1703 | 536 | 537 |
| 1704 | 578 | 579 |
| 1705 | 600 | 601 |
| 1706 | 618 | 619 |
| 1707 | 630 | 631 |
| 1708 | 669 | 670 |
| 1709 | 524 | 525 |
| 1710 | 566 | 567 |
| 1711 | 628 | 629 |
| 1712 | 646 | 647 |
| 1713 | 658 | 659 |
| 1714 | 697 | 698 |
| 1715 | 552 | 553 |
| 1716 | 594 | 595 |
| 1717 | 626 | 627 |
| 1718 | 644 | 645 |
| 1719 | 656 | 657 |
| 1720 | 695 | 696 |
| 1721 | 550 | 551 |
| 1722 | 592 | 593 |
| 1723 | 624 | 625 |
| 1724 | 642 | 643 |
| 1725 | 654 | 655 |
| 1726 | 693 | 694 |
| 1727 | 548 | 549 |
| 1728 | 590 | 591 |
| 1729 | 628 | 629 |
| 1730 | 646 | 647 |
| 1731 | 658 | 659 |
| 1732 | 697 | 698 |
| 1733 | 552 | 553 |
| 1734 | 594 | 595 |
| 1735 | 625 | 626 |
| 1736 | 643 | 644 |
| 1737 | 655 | 656 |
| 1738 | 694 | 695 |
| 1739 | 549 | 550 |
| 1740 | 591 | 592 |
| 1741 | 656 | 657 |
| 1742 | 674 | 675 |
| 1743 | 686 | 687 |
| 1744 | 725 | 726 |
| 1745 | 580 | 581 |
| 1746 | 622 | 623 |
| 1747 | 684 | 685 |
| 1748 | 702 | 703 |
| 1749 | 714 | 715 |
| 1750 | 753 | 754 |
| 1751 | 608 | 609 |
| 1752 | 650 | 651 |
| 1753 | 682 | 683 |
| 1754 | 700 | 701 |
| 1755 | 712 | 713 |
| 1756 | 751 | 752 |
| 1757 | 606 | 607 |
| 1758 | 648 | 649 |
| 1759 | 680 | 681 |
| 1760 | 698 | 699 |
| 1761 | 710 | 711 |
| 1762 | 749 | 750 |
| 1763 | 604 | 605 |
| 1764 | 646 | 647 |
| 1765 | 684 | 685 |
| 1766 | 702 | 703 |
| 1767 | 714 | 715 |
| 1768 | 753 | 754 |
| 1769 | 608 | 609 |
| 1770 | 650 | 651 |
| 1771 | 681 | 682 |
| 1772 | 699 | 700 |
| 1773 | 711 | 712 |
| 1774 | 750 | 751 |
| 1775 | 605 | 606 |
| 1776 | 647 | 648 |
| 1777 | 699 | 700 |
| 1778 | 717 | 718 |
| 1779 | 729 | 730 |
| 1780 | 768 | 769 |
| 1781 | 623 | 624 |
| 1782 | 665 | 666 |
| 1783 | 727 | 728 |
| 1784 | 745 | 746 |
| 1785 | 757 | 758 |
| 1786 | 796 | 797 |
| 1787 | 651 | 652 |
| 1788 | 693 | 694 |
| 1789 | 725 | 726 |
| 1790 | 743 | 744 |
| 1791 | 755 | 756 |
| 1792 | 794 | 795 |
| 1793 | 649 | 650 |
| 1794 | 691 | 692 |
| 1795 | 723 | 724 |
| 1796 | 741 | 742 |
| 1797 | 753 | 754 |
| 1798 | 792 | 793 |
| 1799 | 647 | 648 |
| 1800 | 689 | 690 |
| 1801 | 727 | 728 |
| 1802 | 745 | 746 |
| 1803 | 757 | 758 |
| 1804 | 796 | 797 |
| 1805 | 651 | 652 |
| 1806 | 693 | 694 |
| 1807 | 724 | 725 |
| 1808 | 742 | 743 |
| 1809 | 754 | 755 |
| 1810 | 793 | 794 |
| 1811 | 648 | 649 |
| 1812 | 690 | 691 |
| 1813 | 629 | 630 |
| 1814 | 647 | 648 |
| 1815 | 659 | 660 |
| 1816 | 698 | 699 |
| 1817 | 553 | 554 |
| 1818 | 595 | 596 |
| 1819 | 657 | 658 |
| 1820 | 675 | 676 |
| 1821 | 687 | 688 |
| 1822 | 726 | 727 |
| 1823 | 581 | 582 |
| 1824 | 623 | 624 |
| 1825 | 655 | 656 |
| 1826 | 673 | 674 |
| 1827 | 685 | 686 |
| 1828 | 724 | 725 |
| 1829 | 579 | 580 |
| 1830 | 621 | 622 |
| 1831 | 653 | 654 |
| 1832 | 671 | 672 |
| 1833 | 683 | 684 |
| 1834 | 722 | 723 |
| 1835 | 577 | 578 |
| 1836 | 619 | 620 |
| 1837 | 657 | 658 |
| 1838 | 675 | 676 |
| 1839 | 687 | 688 |
| 1840 | 726 | 727 |
| 1841 | 581 | 582 |
| 1842 | 623 | 624 |
| 1843 | 654 | 655 |
| 1844 | 672 | 673 |

TABLE 2-continued

| Compound No. | M.W. | Mass |
|---|---|---|
| 1845 | 684 | 685 |
| 1846 | 723 | 724 |
| 1847 | 578 | 579 |
| 1848 | 620 | 621 |
| 1849 | 662 | 663 |
| 1850 | 680 | 681 |
| 1851 | 692 | 693 |
| 1852 | 731 | 732 |
| 1853 | 586 | 587 |
| 1854 | 628 | 629 |
| 1855 | 690 | 691 |
| 1856 | 708 | 709 |
| 1857 | 720 | 721 |
| 1858 | 759 | 760 |
| 1859 | 614 | 615 |
| 1860 | 656 | 657 |
| 1861 | 688 | 689 |
| 1862 | 706 | 707 |
| 1863 | 718 | 719 |
| 1864 | 757 | 758 |
| 1865 | 612 | 613 |
| 1866 | 654 | 655 |
| 1867 | 686 | 687 |
| 1868 | 704 | 705 |
| 1869 | 716 | 717 |
| 1870 | 755 | 756 |
| 1871 | 610 | 611 |
| 1872 | 652 | 653 |
| 1873 | 690 | 691 |
| 1874 | 708 | 709 |
| 1875 | 720 | 721 |
| 1876 | 759 | 760 |
| 1877 | 614 | 615 |
| 1878 | 656 | 657 |
| 1879 | 687 | 688 |
| 1880 | 705 | 706 |
| 1881 | 717 | 718 |
| 1882 | 756 | 757 |
| 1883 | 611 | 612 |
| 1884 | 653 | 654 |
| 1885 | 609 | 610 |
| 1886 | 627 | 628 |
| 1887 | 639 | 640 |
| 1888 | 678 | 679 |
| 1889 | 533 | 534 |
| 1890 | 575 | 576 |
| 1891 | 637 | 638 |
| 1892 | 655 | 656 |
| 1893 | 667 | 668 |
| 1894 | 706 | 707 |
| 1895 | 561 | 562 |
| 1896 | 603 | 604 |
| 1897 | 635 | 636 |
| 1898 | 653 | 654 |
| 1899 | 665 | 666 |
| 1900 | 704 | 705 |
| 1901 | 559 | 560 |
| 1902 | 601 | 602 |
| 1903 | 633 | 634 |
| 1904 | 651 | 652 |
| 1905 | 663 | 664 |
| 1906 | 702 | 703 |
| 1907 | 557 | 558 |
| 1908 | 599 | 600 |
| 1909 | 637 | 638 |
| 1910 | 655 | 656 |
| 1911 | 667 | 668 |
| 1912 | 706 | 707 |
| 1913 | 561 | 562 |
| 1914 | 603 | 604 |
| 1915 | 634 | 635 |
| 1916 | 652 | 653 |
| 1917 | 664 | 665 |
| 1918 | 703 | 704 |
| 1919 | 558 | 559 |
| 1920 | 600 | 601 |
| 1921 | 609 | 610 |
| 1922 | 627 | 628 |
| 1923 | 639 | 640 |
| 1924 | 678 | 679 |
| 1925 | 533 | 534 |
| 1926 | 575 | 576 |
| 1927 | 637 | 638 |
| 1928 | 655 | 656 |
| 1929 | 667 | 668 |
| 1930 | 706 | 707 |
| 1931 | 561 | 562 |
| 1932 | 603 | 604 |
| 1933 | 635 | 636 |
| 1934 | 653 | 654 |
| 1935 | 665 | 666 |
| 1936 | 704 | 705 |
| 1937 | 559 | 560 |
| 1938 | 601 | 602 |
| 1939 | 633 | 634 |
| 1940 | 651 | 652 |
| 1941 | 663 | 664 |
| 1942 | 702 | 703 |
| 1943 | 557 | 558 |
| 1944 | 599 | 600 |
| 1945 | 637 | 638 |
| 1946 | 655 | 656 |
| 1947 | 667 | 668 |
| 1948 | 706 | 707 |
| 1949 | 561 | 562 |
| 1950 | 603 | 604 |
| 1951 | 634 | 635 |
| 1952 | 652 | 653 |
| 1953 | 664 | 665 |
| 1954 | 703 | 704 |
| 1955 | 558 | 559 |
| 1956 | 600 | 601 |
| 1957 | 626 | 627 |
| 1958 | 644 | 645 |
| 1959 | 656 | 657 |
| 1960 | 695 | 696 |
| 1961 | 550 | 551 |
| 1962 | 592 | 593 |
| 1963 | 654 | 655 |
| 1964 | 672 | 673 |
| 1965 | 684 | 685 |
| 1966 | 723 | 724 |
| 1967 | 578 | 579 |
| 1968 | 620 | 621 |
| 1969 | 652 | 653 |
| 1970 | 670 | 671 |
| 1971 | 682 | 683 |
| 1972 | 721 | 722 |
| 1973 | 576 | 577 |
| 1974 | 618 | 619 |
| 1975 | 650 | 651 |
| 1976 | 668 | 669 |
| 1977 | 680 | 681 |
| 1978 | 719 | 720 |
| 1979 | 574 | 575 |
| 1980 | 616 | 617 |
| 1981 | 654 | 655 |
| 1982 | 672 | 673 |
| 1983 | 684 | 685 |
| 1984 | 723 | 724 |
| 1985 | 578 | 579 |
| 1986 | 620 | 621 |
| 1987 | 651 | 652 |
| 1988 | 669 | 670 |
| 1989 | 681 | 682 |
| 1990 | 720 | 721 |
| 1991 | 575 | 576 |
| 1992 | 617 | 618 |
| 1993 | 626 | 627 |
| 1994 | 644 | 645 |
| 1995 | 656 | 657 |
| 1996 | 695 | 696 |
| 1997 | 550 | 551 |
| 1998 | 592 | 593 |

TABLE 2-continued

| Compound No. | M.W. | Mass |
|---|---|---|
| 1999 | 654 | 655 |
| 2000 | 672 | 673 |
| 2001 | 684 | 685 |
| 2002 | 723 | 724 |
| 2003 | 578 | 579 |
| 2004 | 620 | 621 |
| 2005 | 652 | 653 |
| 2006 | 670 | 671 |
| 2007 | 682 | 683 |
| 2008 | 721 | 722 |
| 2009 | 576 | 577 |
| 2010 | 618 | 619 |
| 2011 | 650 | 651 |
| 2012 | 668 | 669 |
| 2013 | 680 | 681 |
| 2014 | 719 | 720 |
| 2015 | 574 | 575 |
| 2016 | 616 | 617 |
| 2017 | 654 | 655 |
| 2018 | 672 | 673 |
| 2019 | 684 | 685 |
| 2020 | 723 | 724 |
| 2021 | 578 | 579 |
| 2022 | 620 | 621 |
| 2023 | 651 | 652 |
| 2024 | 669 | 670 |
| 2025 | 681 | 682 |
| 2026 | 720 | 721 |
| 2027 | 575 | 576 |
| 2028 | 617 | 618 |
| 2029 | 586 | 587 |
| 2030 | 604 | 605 |
| 2031 | 616 | 617 |
| 2032 | 655 | 656 |
| 2033 | 510 | 511 |
| 2034 | 552 | 553 |
| 2035 | 614 | 615 |
| 2036 | 632 | 633 |
| 2037 | 644 | 645 |
| 2038 | 683 | 684 |
| 2039 | 538 | 539 |
| 2040 | 580 | 581 |
| 2041 | 612 | 613 |
| 2042 | 630 | 631 |
| 2043 | 642 | 643 |
| 2044 | 681 | 682 |
| 2045 | 536 | 537 |
| 2046 | 578 | 579 |
| 2047 | 610 | 611 |
| 2048 | 628 | 629 |
| 2049 | 640 | 641 |
| 2050 | 679 | 680 |
| 2051 | 534 | 535 |
| 2052 | 576 | 577 |
| 2053 | 614 | 615 |
| 2054 | 632 | 633 |
| 2055 | 644 | 645 |
| 2056 | 683 | 684 |
| 2057 | 538 | 539 |
| 2058 | 580 | 581 |
| 2059 | 611 | 612 |
| 2060 | 629 | 630 |
| 2061 | 641 | 642 |
| 2062 | 680 | 681 |
| 2063 | 535 | 536 |
| 2064 | 577 | 578 |
| 2065 | 640 | 641 |
| 2066 | 658 | 659 |
| 2067 | 670 | 671 |
| 2068 | 709 | 710 |
| 2069 | 564 | 565 |
| 2070 | 606 | 607 |
| 2071 | 668 | 669 |
| 2072 | 686 | 687 |
| 2073 | 698 | 699 |
| 2074 | 737 | 738 |
| 2075 | 592 | 593 |

TABLE 2-continued

| Compound No. | M.W. | Mass |
|---|---|---|
| 2076 | 634 | 635 |
| 2077 | 666 | 667 |
| 2078 | 684 | 685 |
| 2079 | 696 | 697 |
| 2080 | 735 | 736 |
| 2081 | 590 | 591 |
| 2082 | 632 | 633 |
| 2083 | 664 | 665 |
| 2084 | 682 | 683 |
| 2085 | 694 | 695 |
| 2086 | 733 | 734 |
| 2087 | 588 | 589 |
| 2088 | 630 | 631 |
| 2089 | 668 | 669 |
| 2090 | 686 | 687 |
| 2091 | 698 | 699 |
| 2092 | 737 | 738 |
| 2093 | 592 | 593 |
| 2094 | 634 | 635 |
| 2095 | 665 | 666 |
| 2096 | 683 | 684 |
| 2097 | 695 | 696 |
| 2098 | 734 | 735 |
| 2099 | 589 | 590 |
| 2100 | 631 | 632 |
| 2101 | 637 | 638 |
| 2102 | 655 | 656 |
| 2103 | 667 | 668 |
| 2104 | 706 | 707 |
| 2105 | 561 | 562 |
| 2106 | 603 | 604 |
| 2107 | 665 | 666 |
| 2108 | 683 | 684 |
| 2109 | 695 | 696 |
| 2110 | 734 | 735 |
| 2111 | 589 | 590 |
| 2112 | 631 | 632 |
| 2113 | 663 | 664 |
| 2114 | 681 | 682 |
| 2115 | 693 | 694 |
| 2116 | 732 | 733 |
| 2117 | 587 | 588 |
| 2118 | 629 | 630 |
| 2119 | 661 | 662 |
| 2120 | 679 | 680 |
| 2121 | 691 | 692 |
| 2122 | 730 | 731 |
| 2123 | 585 | 586 |
| 2124 | 627 | 628 |
| 2125 | 665 | 666 |
| 2126 | 683 | 684 |
| 2127 | 695 | 696 |
| 2128 | 734 | 735 |
| 2129 | 589 | 590 |
| 2130 | 631 | 632 |
| 2131 | 662 | 663 |
| 2132 | 680 | 681 |
| 2133 | 692 | 693 |
| 2134 | 731 | 732 |
| 2135 | 586 | 587 |
| 2136 | 628 | 629 |
| 2137 | 659 | 660 |
| 2138 | 677 | 678 |
| 2139 | 689 | 690 |
| 2140 | 728 | 729 |
| 2141 | 583 | 584 |
| 2142 | 625 | 626 |
| 2143 | 687 | 688 |
| 2144 | 705 | 706 |
| 2145 | 717 | 718 |
| 2146 | 756 | 757 |
| 2147 | 611 | 612 |
| 2148 | 653 | 654 |
| 2149 | 685 | 686 |
| 2150 | 703 | 704 |
| 2151 | 715 | 716 |
| 2152 | 754 | 755 |

TABLE 2-continued

| Compound No. | M.W. | Mass |
|---|---|---|
| 2153 | 609 | 610 |
| 2154 | 651 | 652 |
| 2155 | 683 | 684 |
| 2156 | 701 | 702 |
| 2157 | 713 | 714 |
| 2158 | 752 | 753 |
| 2159 | 607 | 608 |
| 2160 | 649 | 650 |
| 2161 | 687 | 688 |
| 2162 | 705 | 706 |
| 2163 | 717 | 718 |
| 2164 | 756 | 757 |
| 2165 | 611 | 612 |
| 2166 | 653 | 654 |
| 2167 | 684 | 685 |
| 2168 | 702 | 703 |
| 2169 | 714 | 715 |
| 2170 | 753 | 754 |
| 2171 | 608 | 609 |
| 2172 | 650 | 651 |
| 2173 | 559 | 560 |
| 2174 | 577 | 578 |
| 2175 | 589 | 590 |
| 2176 | 628 | 629 |
| 2177 | 483 | 484 |
| 2178 | 525 | 526 |
| 2179 | 587 | 588 |
| 2180 | 605 | 606 |
| 2181 | 617 | 618 |
| 2182 | 656 | 657 |
| 2183 | 511 | 512 |
| 2184 | 553 | 554 |
| 2185 | 585 | 586 |
| 2186 | 603 | 604 |
| 2187 | 615 | 616 |
| 2188 | 654 | 655 |
| 2189 | 509 | 510 |
| 2190 | 551 | 552 |
| 2191 | 583 | 584 |
| 2192 | 601 | 602 |
| 2193 | 613 | 614 |
| 2194 | 652 | 653 |
| 2195 | 507 | 508 |
| 2196 | 549 | 550 |
| 2197 | 587 | 588 |
| 2198 | 605 | 606 |
| 2199 | 617 | 618 |
| 2200 | 656 | 657 |
| 2203 | 661 | 662 |
| 2204 | 673 | 674 |
| 2205 | 671 | 672 |
| 2206 | 669 | 670 |
| 2207 | 687 | 688 |
| 2208 | 683 | 684 |
| 2209 | 695 | 696 |
| 2210 | 693 | 592 |
| 2211 | 691 | 692 |
| 2212 | 709 | 710 |
| 2213 | 559 | 560 |
| 2214 | 701 | 702 |
| 2215 | 713 | 714 |
| 2216 | 711 | 712 |
| 2217 | 709 | 710 |

EXAMPLE 3

Effect of ICG-001 and Imatinib on Cancer Cell Lines

Figure 14:
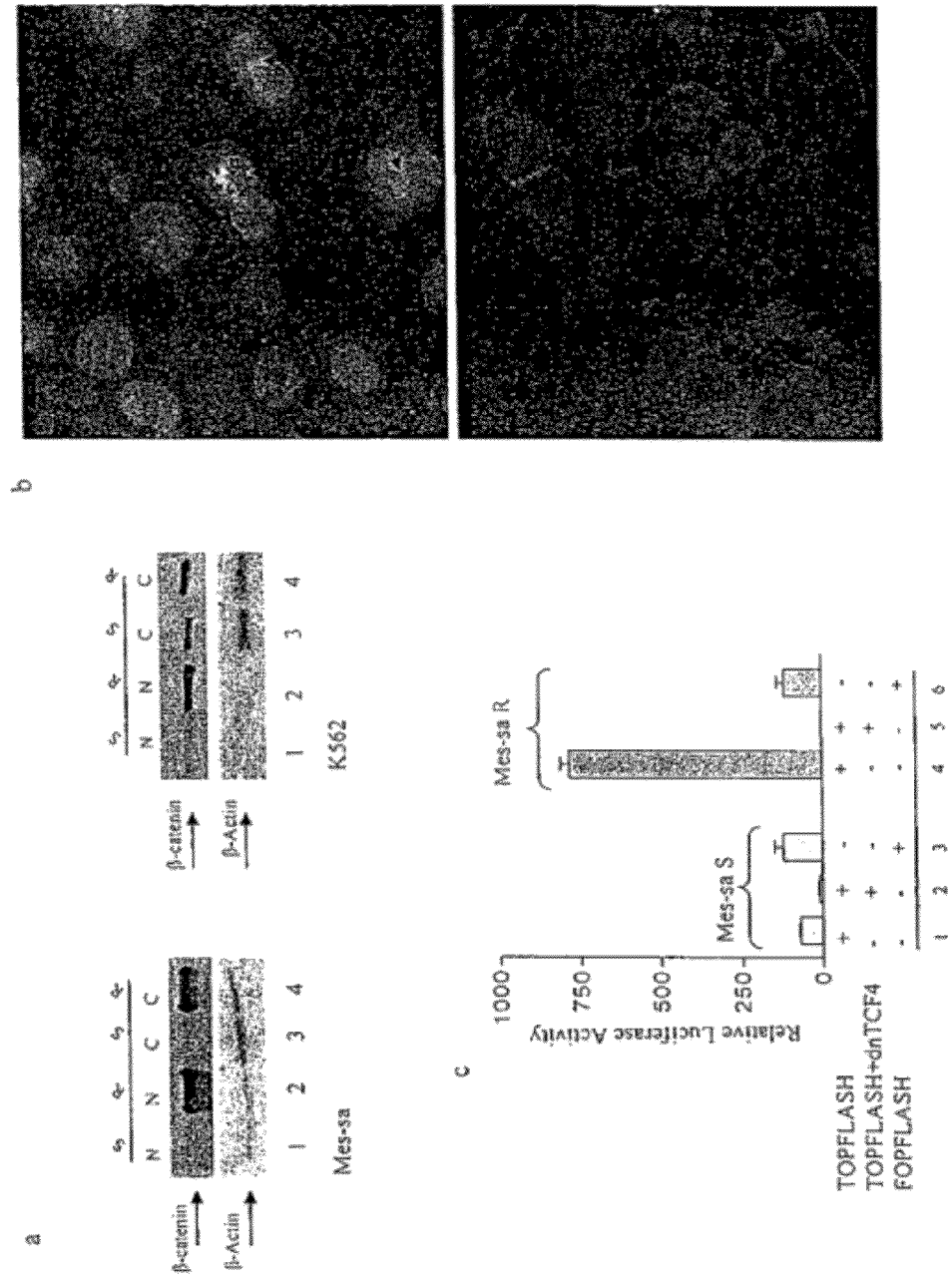
FIGS. 14A-C shows the levels of cytosolic and nuclear β-catenin as measured by immunoblotting (FIG. 14A), and immunofluorescence microscopy (FIG. 14B) as compared to drug sensitive counterparts. The increased nuclear β-catenin was blocked using a dominant negative TCF4 construct (FIG. 14C).

The human ovarian sarcoma cells MES-SA and the corresponding doxorubicin-resistant line MES-SA/Dx5 (Hua J et al Gynecologic Oncol. 2005) and the CML derived cell line K562 and the corresponding imatinib mesylate resistant K562 cells (Dai Y et al JBC 279, 34227, 2004) were used for this example. Both resistant (R) cell lines showed dramatically increased levels of both cytosolic and nuclear β-catenin as judged by both immunoblotting (FIG. 14A) and immunofluorescence microscopy (FIG. 14B) compared to their drug sensitive (S) counterparts. The increased nuclear β-catenin was reflected in dramatically increased TCF/β-catenin transcriptional activity as judged by the TOPFLASH reporter, which could be completely blocked using a dominant negative TCF4 construct (FIG. 14C).

Figure 15:
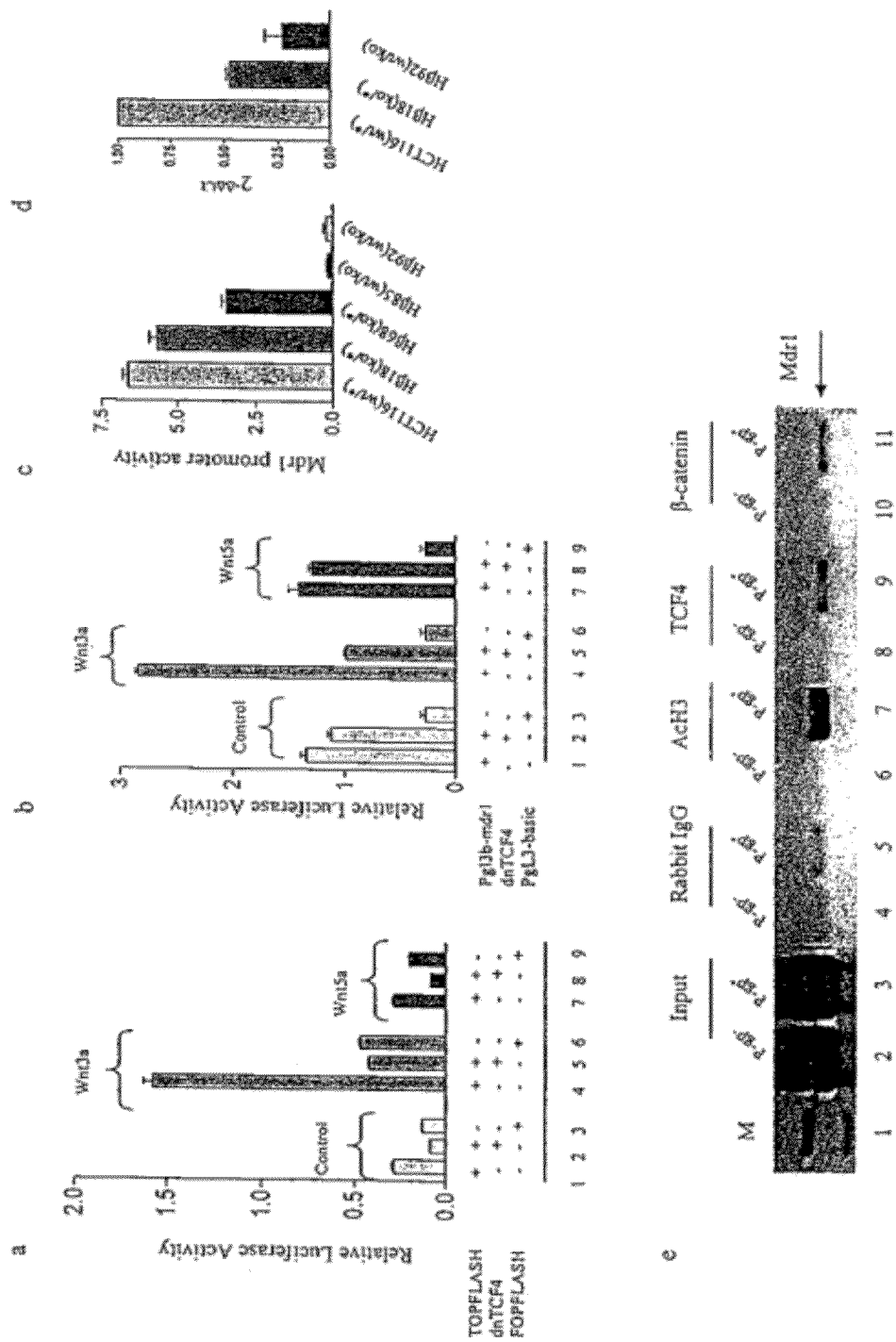
FIGS. 15A-E shows that in MES-SA cells, Wnt3a but not Wnt5a increased luciferase activity, which was blocked by cotransfection with a dominant negative TCF4 construct (FIG. 15A). Wnt5a conditioned media showed no enhancement of expression of the MDR-1/luciferase reporter construct (FIG. 15B). MDR-1 wild-type HCT-116 cells and Hβ18 (KO/*) cells is shown in FIG. 15C (MDR-1/luciferase activity) and FIG. 15D (RT-PCR). Recruitment of TCF4 and β-catenin to the MDR-1 promoter is shown in FIG. 15E.

To confirm that activation of the Wnt/β-catenin pathway was critical for the activation of MDR-1 expression in MES-SA cells, the following set of experiments were performed. MES-SA cells were transfected with either the TOPFLASH or FOPFLASH reporters and treated with media alone, or with added Wnt3a or Wnt5a. Addition of "canonical" Wnt3a but not "non-canonical" Wnt5a increased luciferase activity ~4 fold and the increased activation was completely blocked by cotransfection of a dnTCF4 construct (FIG. 15A). Similarly, an ~2 fold increase in MDR-1/luciferase activity was observed upon treatment with Wnt3a. This activation was also completely inhibited by cotransfection of the dnTCF4 construct. Wnt5a conditioned media showed no enhancement of expression of the MDR-1 luciferase reporter construct (FIG. 15B).

To further confirm the importance of the role of nuclear β-catenin in driving MDR-1 expression, isogenic HCT-116 cell lines were utilized (Waldmann 2002). Wild-type HCT-116 cells demonstrated the highest MDR-1 expression as judged by both MDR-1/luciferase activity and real time RT-PCR (FIG. 15C, D). Hβ18(ko/*) cells, in which the wild type allele of β-catenin is deleted but the oncogenic allele is maintained, and have somewhat lower levels of nuclear fβ-catenin, showed slightly reduced MDR-1 luciferase activity and a reduction in MDR-1 message (FIG. 15C, D). Hβ92 (wt/ko) cells, in which the wild type allele is retained and the oncogenic allele is deleted, showed even more dramatic reduction of MDR-1 luciferase activity and message (FIG. 15C, D).

TCF/β-catenin recruitment at the MDR-1 promoter in MES-SA and MES-SA/Dx5 cells was investigated. In the MES-SA/Dx5 cells, in which MDR-1 is actively transcribed as judged by the level of acetylated Histone H3 at the promoter, and expressed, there was obvious recruitment of both TCF4 and β-catenin to the promoter, which was absent in the parental MES-SA cell line (FIG. 15E).

Figure 16:
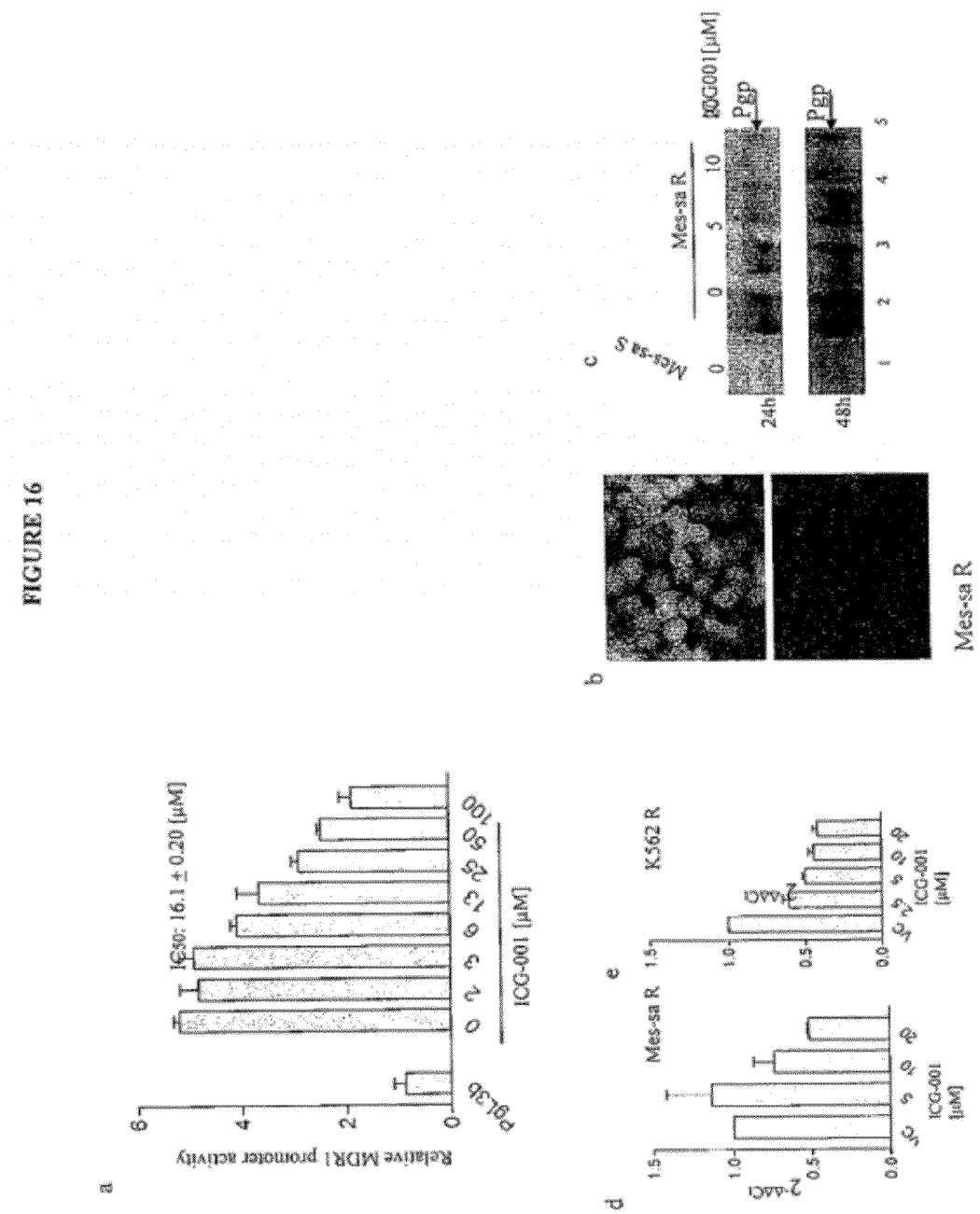
FIGS. 16A-E shows the effect of ICG-001 on transcriptional regulation of the MDR-1 gene in MES-SA cells: MDR-1/luciferase activity (16A); MDR-1 protein expression by immunofluorescence (16B) and immunoblotting (16C); message level by RT-PCR in MES-SA/Dx5 cells (16D) and K562 cells (16E).

To investigate differential coactivator usage for the transcriptional regulation of the MDR-1 gene in MES-SA cells, the chemogenomic tool ICG-001 was used (Emami et al. 2004). ICG-001 reduced MDR-1 luciferase activity in MES-SA/Dx5 cells with an $IC_{50}$~16 uM (FIG. 16A). The level of MDR-1 protein expression in the MES-SA/Dx5 cells was also significantly reduced by ICG-001 as judged by immunofluorescence (FIG. 16B) and immunoblotting (FIG. 16C) in a dose dependent manner. This effect was reflected at the message level as judged by real time RT-PCR in both MES-SA/Dx5 cells (FIG. 16D) and the imatinib mesylate resistant K562 cells (FIG. 16E).

Figure 17:
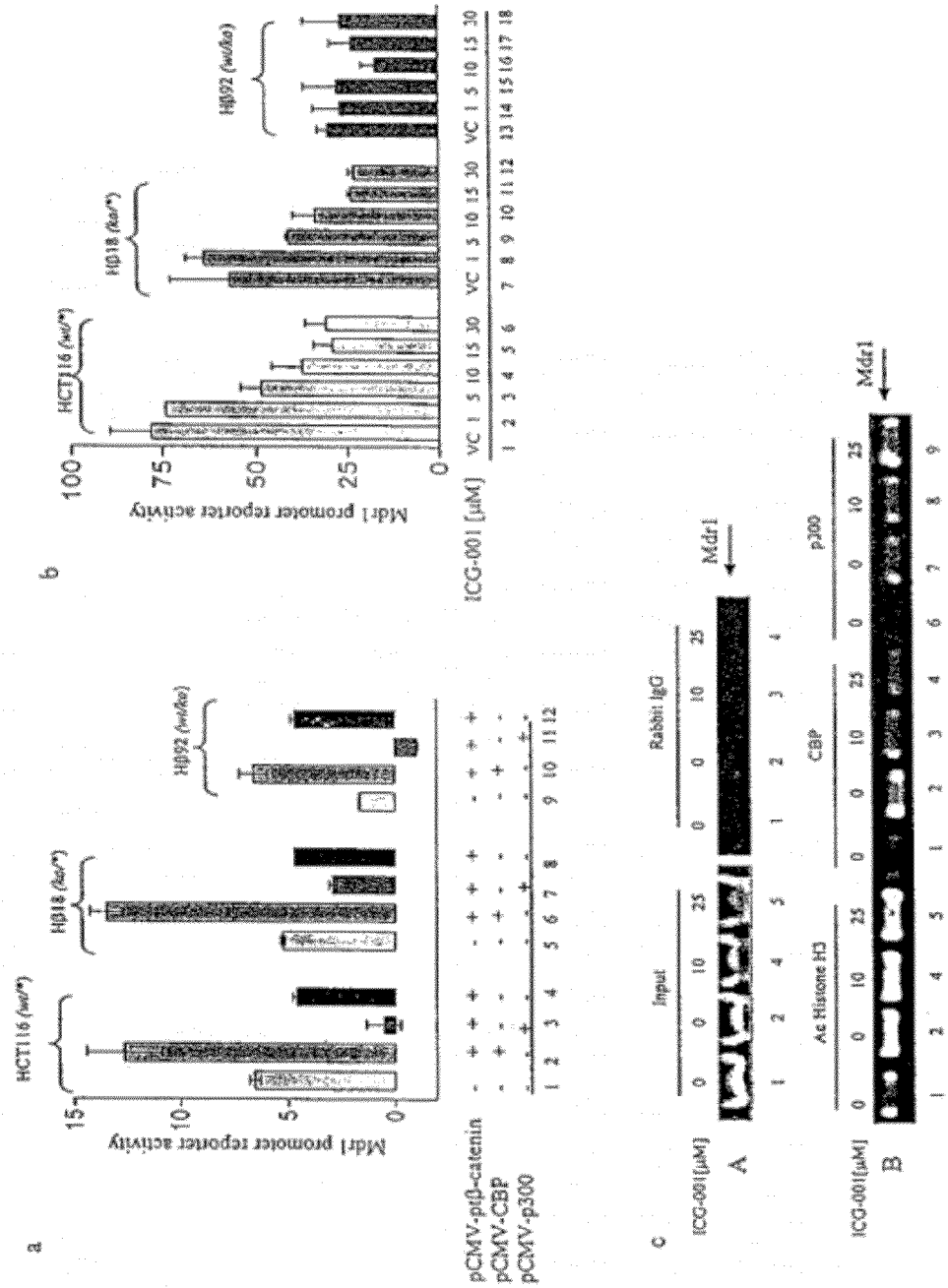
FIGS. 17A-C shows MDR-1 transcriptional regulation in HCT116 cell lines: MDR-1/luciferase expression (17A); effect of ICG-001 (17B); and blocking occupancy of the MDR-1 promoter by CBP (17C).

MDR-1 transcriptional regulation in the isogenic HCT116 cell lines was also investigated. In all of the isogenic HCT116 cell lines, cotransfection of point mutant constitutively translocating β-catenin and CBP increased MDR-1 luciferase expression (FIG. 17A), whereas transfection of point mutant β-catenin alone only increased luciferase activity compared to non-transfected control in the Hβ92(wt/ko) cells (FIG. 17A), which have severely limiting amounts of nuclear β-catenin. Transfection of p300 decreased MDR-1/luciferase activity below control levels in all 3 cell lines (FIG. 17A). ICG-001 dose dependently decreased MDR-1/luciferase activity in the HCT-116 wild type and Hβ18(ko/*) cell lines, whereas essentially no further reduction below basal levels was observed in the Hβ92(wt/ko) cells (FIG. 17B), consistent with a lack of β-catenin/CBP driven transcription in these cells (H Ma et al Oncogene 2005).

ChIP assay in the MES-SA/Dx5 cells demonstrated that in untreated cells, there was significant occupancy of the MDR-1 promoter by CBP, which was blocked in a dose dependent fashion by ICG-001 (FIG. 17C). On the contrary, in the absence of ICG-001, there was minimal occupancy of the MDR-1 promoter by p300, however occupancy increased with 25 uM ICG-001 treatment (FIG. 17C). Similar ICG-001 induced p300 recruitment at the survivin promoter has been previously observed, which was associated with recruitment of proteins associated with transcriptional repression (i.e., HDAC6 and PML) (H Ma et al. Oncogene 2005). A proposed non-binding mechanism is repressive transcriptional apparatus recruitment to the MDR-1 promoter by p300.

Figure 18:
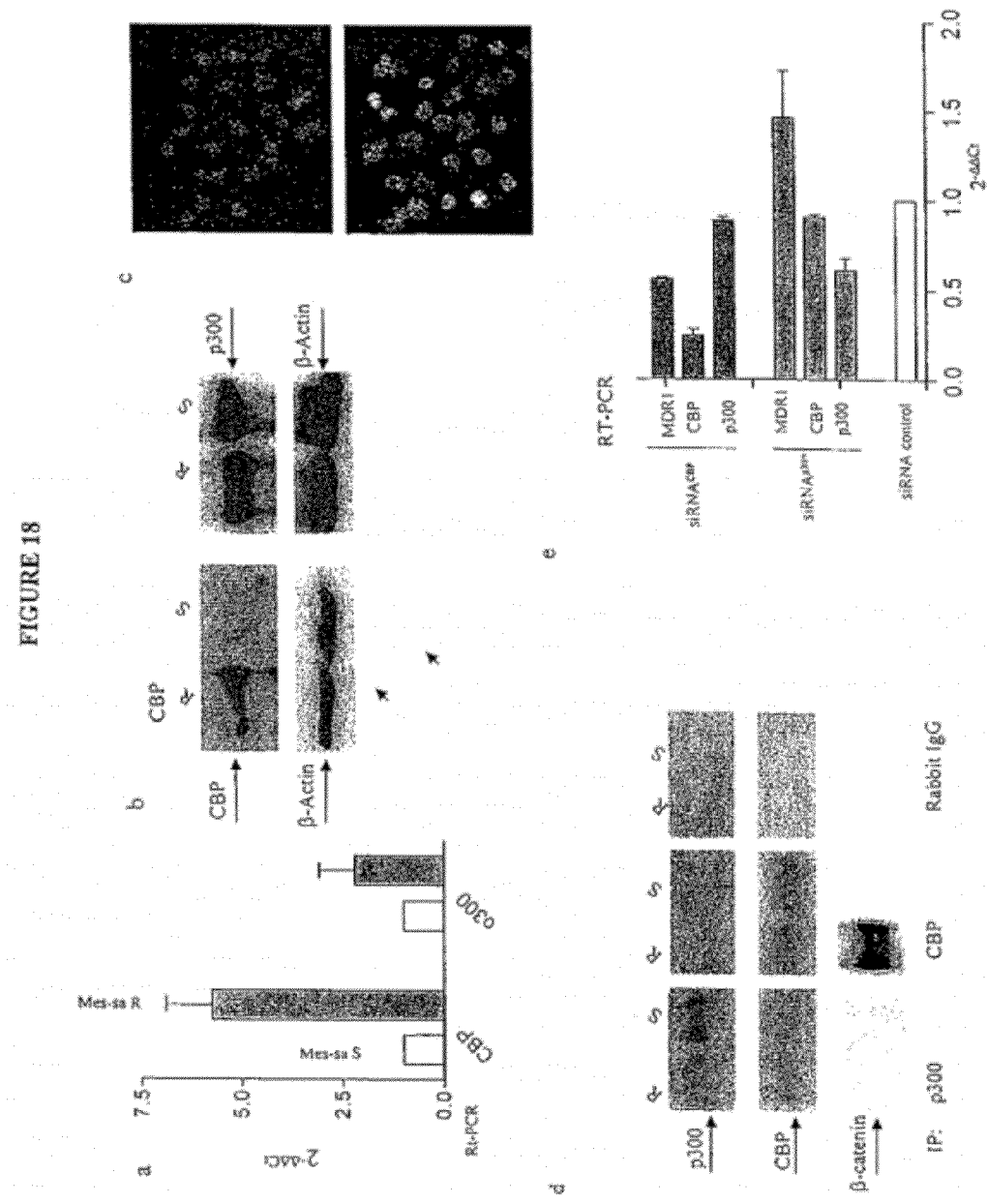
FIGS. 18A-E shows the mRNA level of endogenous CBPP coactivator compared to p300 (FIG. 18A); the level of CBP (FIG. 18B); the association of β-catenin with p300 (FIG. 18C); the level of p300 (FIG. 18D); and the effect of p300 siRNA (FIG. 18E).

The mRNA level of endogenous CBP coactivator was also significantly increased in the MES-SA/Dx5 cells compared to the MES-SA cells, whereas p300 levels message remained essentially equal (FIG. 18A). Immunofluorescence also demonstrated a substantial increase in CBP (FIG. 18B) as did immunoblotting in the MES-SA/Dx5 compared to the MES-SA parental line; although p300 protein levels remained essentially equal (FIG. 18C).

Figure 19:
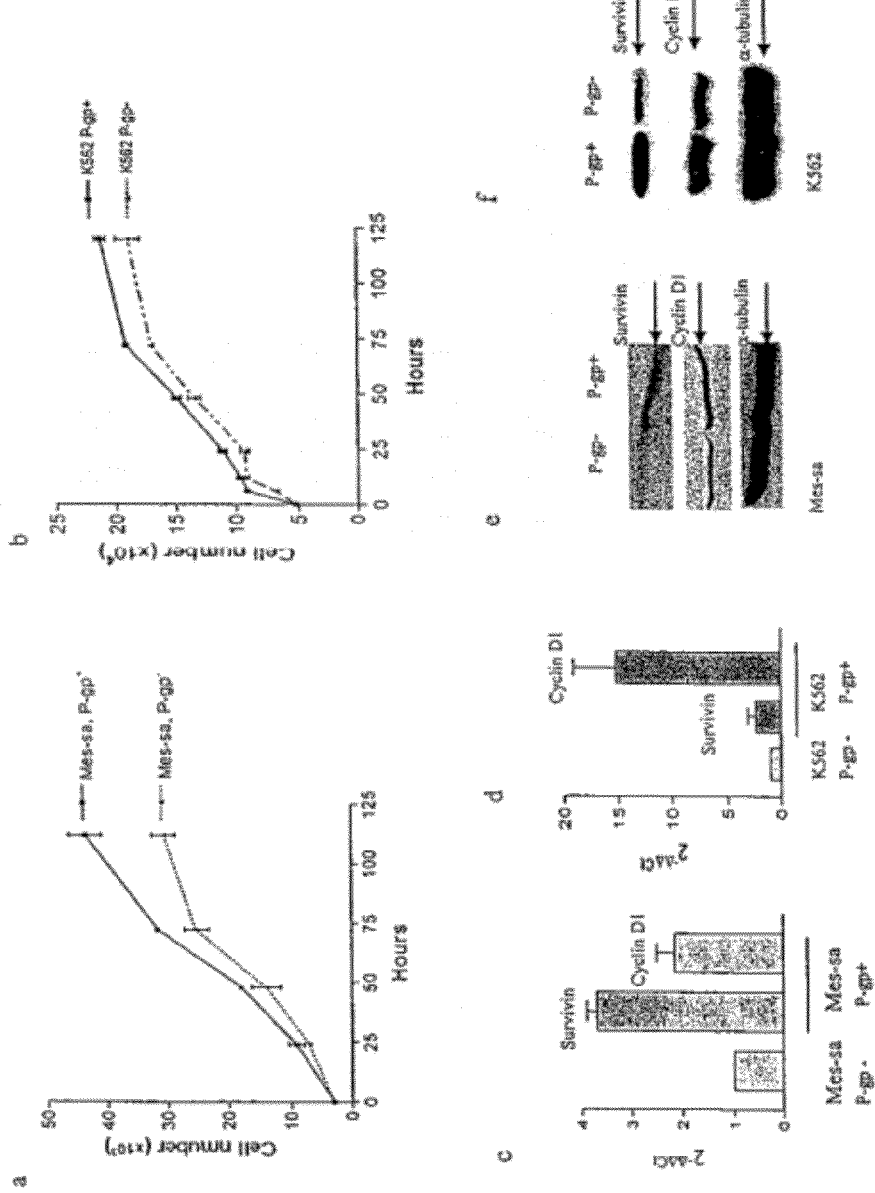
FIGS. 19A-F compares MES-SA/Dx5 cells with K562 cells: growth rate (19A, 19B); message levels for survivin and cyclin D1 (19C, 19D); and protein levels for survivin and cyclin D1 (19E, 19F).
Figure 20:
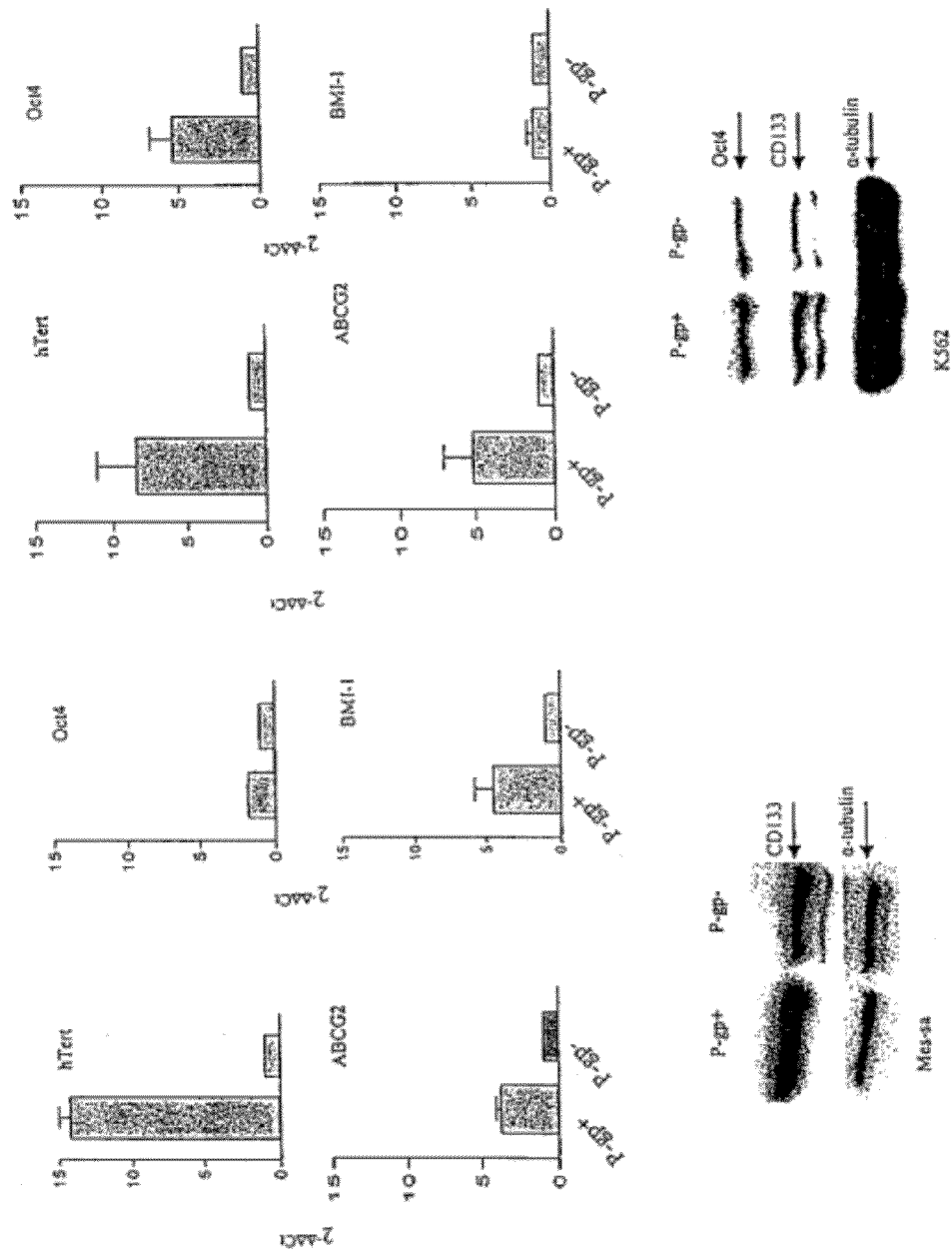

Communoprecipitation of CBP or p300 showed a strong association of β-catenin with CBP in the MES-SA/Dx5 cells that was not present in the MES-SA cells while virtually no association of β-catenin with p300 could be detected in either cell line (FIG. 18D). Finally, coactivator specific siRNA was utilized (H Ma Oncogene 2005) to knockdown either CBP or p300 in the MES-SA/Dx5 cells. MDR-1 message was specifically decreased by treatment with siRNA to CBP compared to the siRNA control treated cells, whereas p300 siRNA increased MDR-1 message levels compared to control (FIG. 18E). In culture, the MES-SA/Dx5 and K562 imatinib resistant cells grew at a somewhat faster rate than the corresponding sensitive cell lines (FIG. 19A, B). Consistent with previous data (Emami et al PNAS 2004, H. Ma et al Oncogene 2005, and J Teo et al 2005), enhanced β-catenin/CBP driven transcription was reflected at both the message (FIG. 19C, D) and protein levels (FIG. 19E, F) for both survivin and cyclin D1, in both resistant cell lines compared to their sensitive counterparts.

Figure 20:
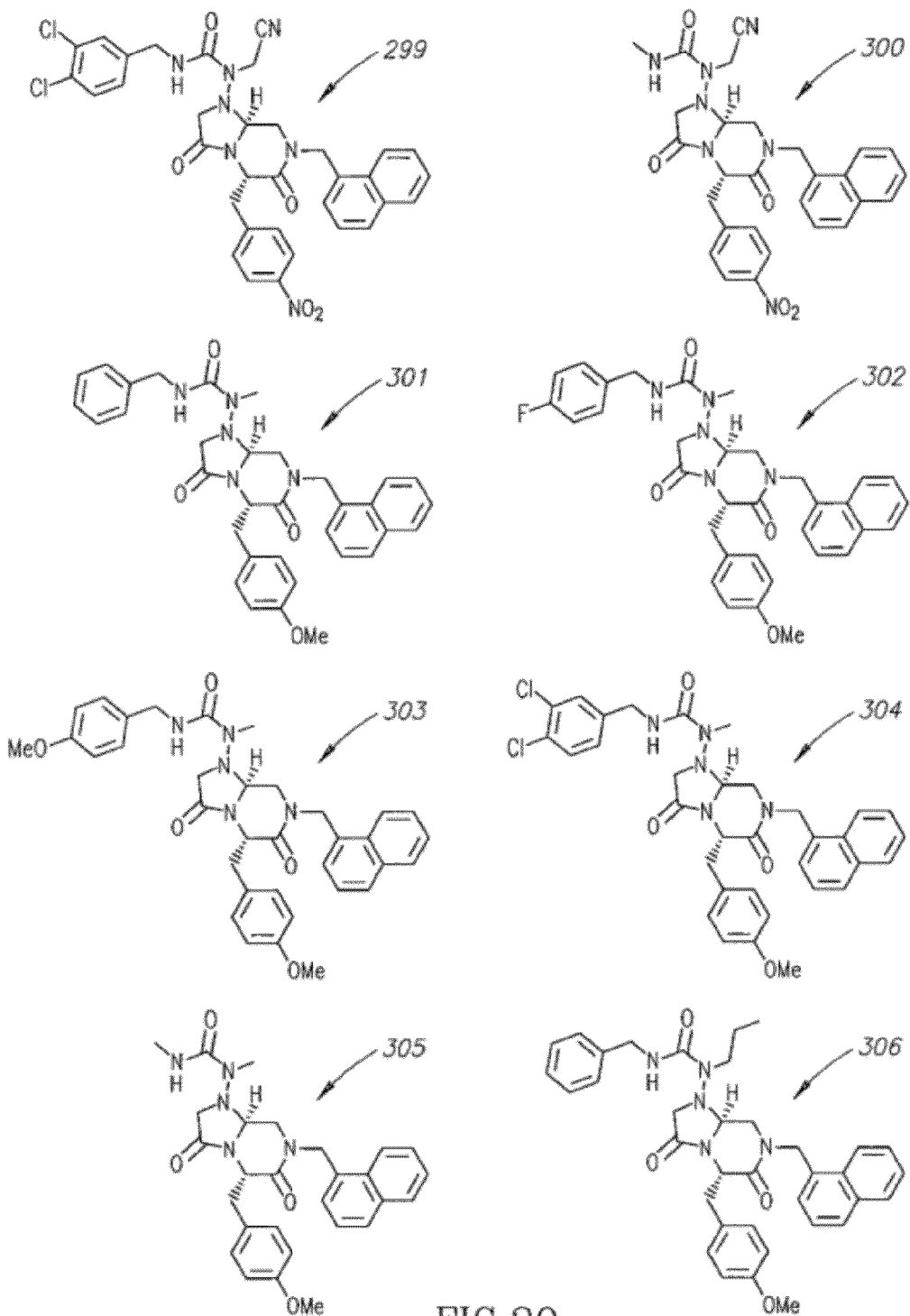
FIG. 20. RT-PCR shows an increased expression of Oct 4, hTert, Bmi-1 and ABCG-2 in MES-SA/Dx5 and K562 cells. Protein levels for Oct 4 and CD133 were increased in these cell lines.
Figure 2P:
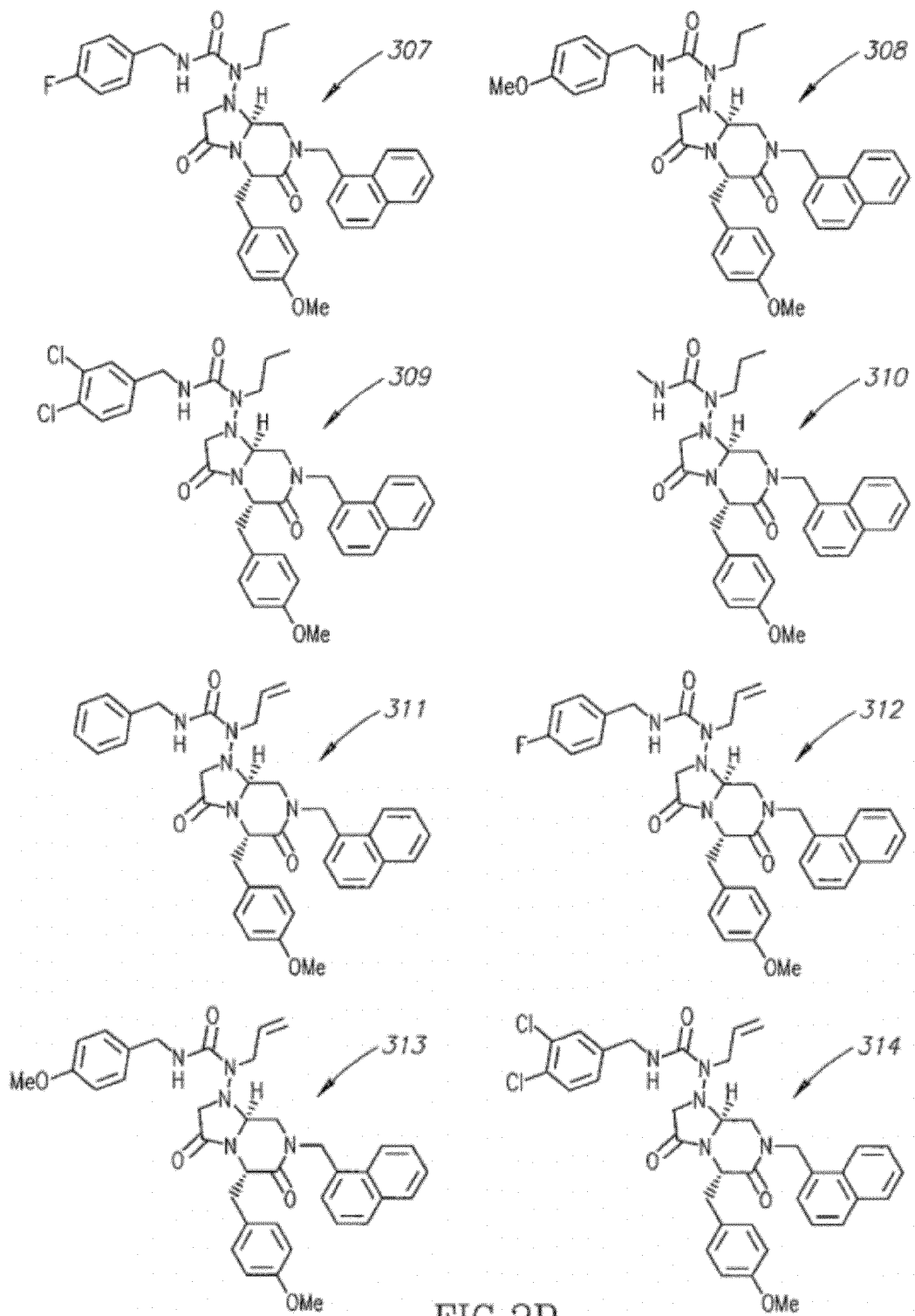
Figure 2Q:
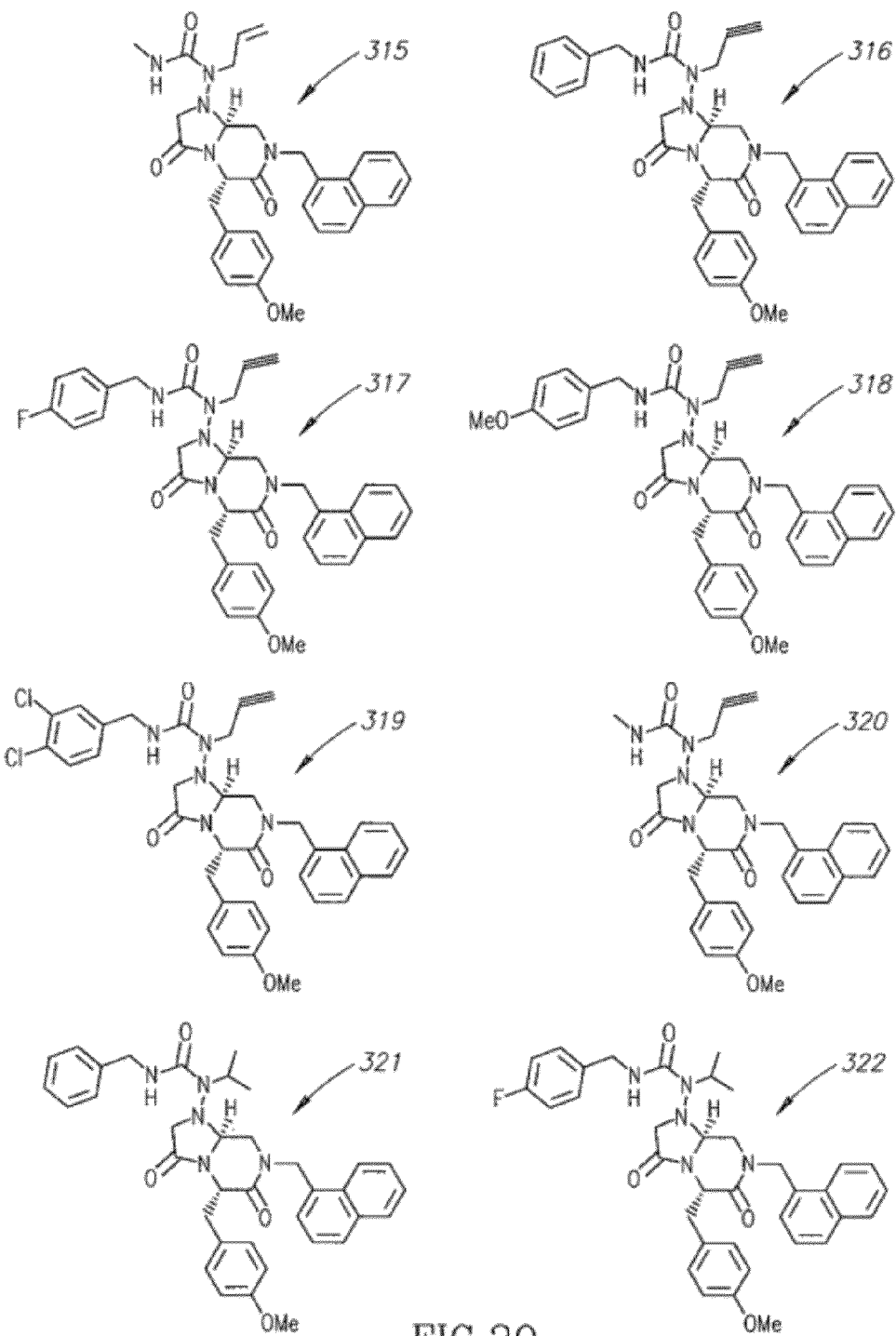
Figure 2R:
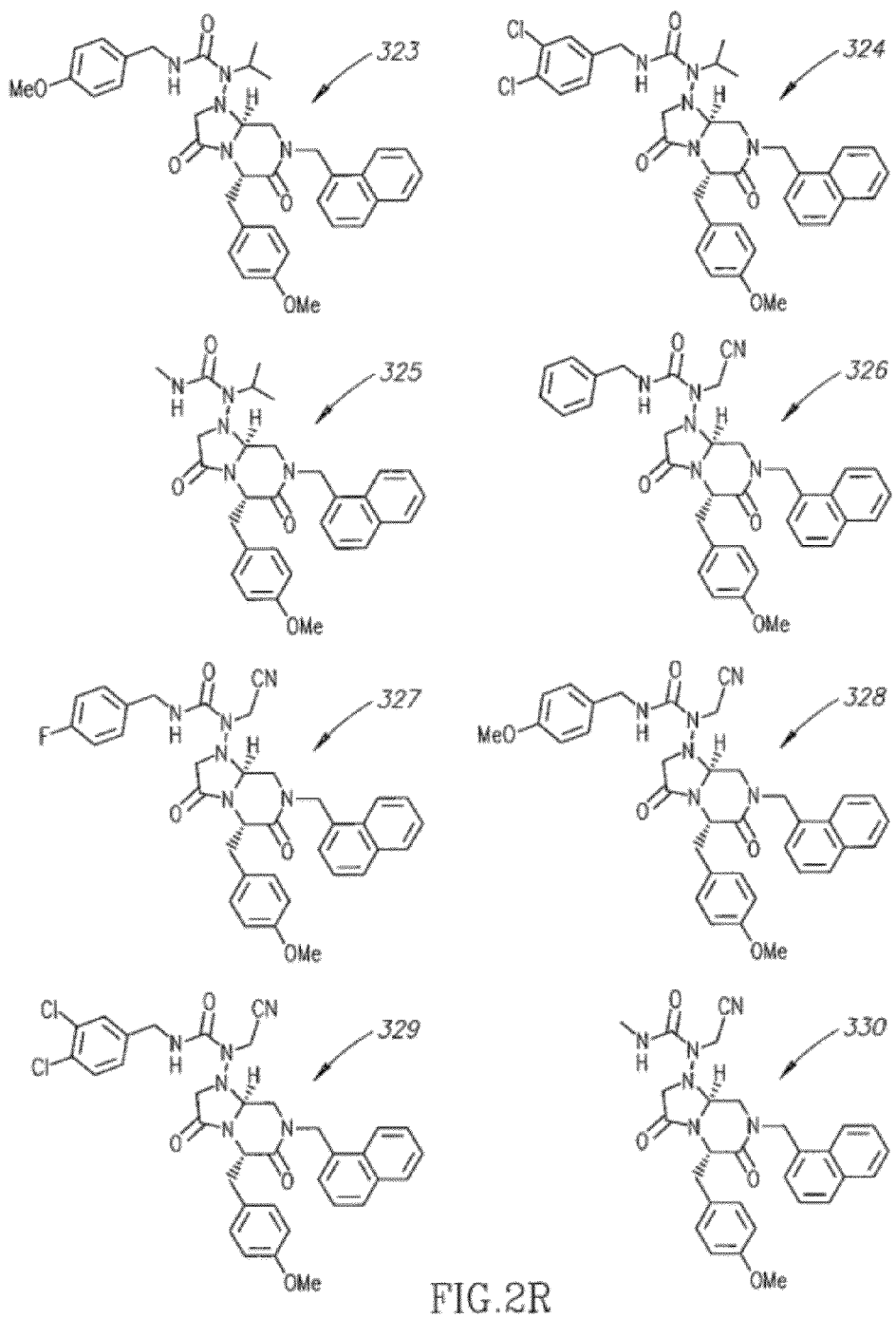
Figure 2S:
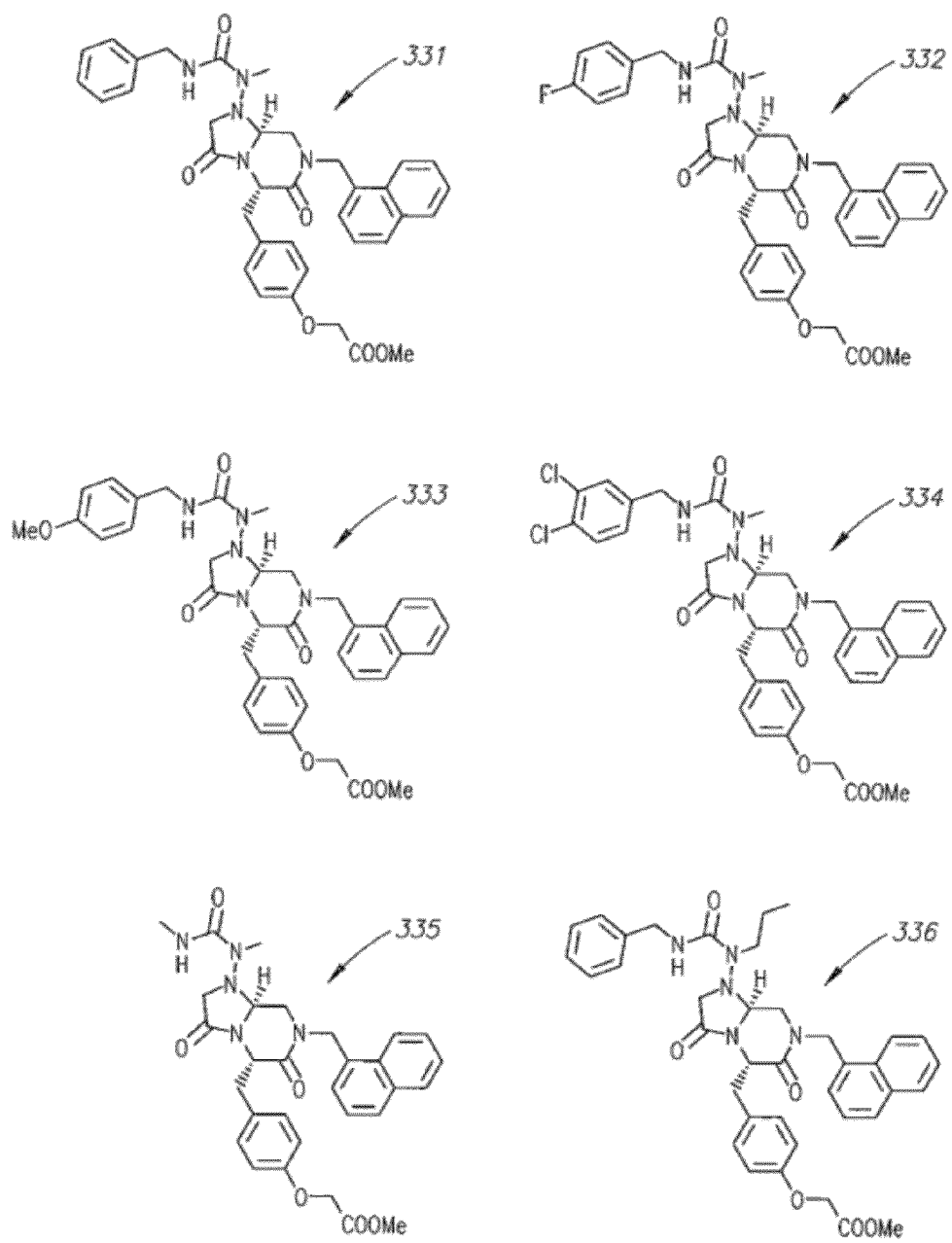
Figure 2T:
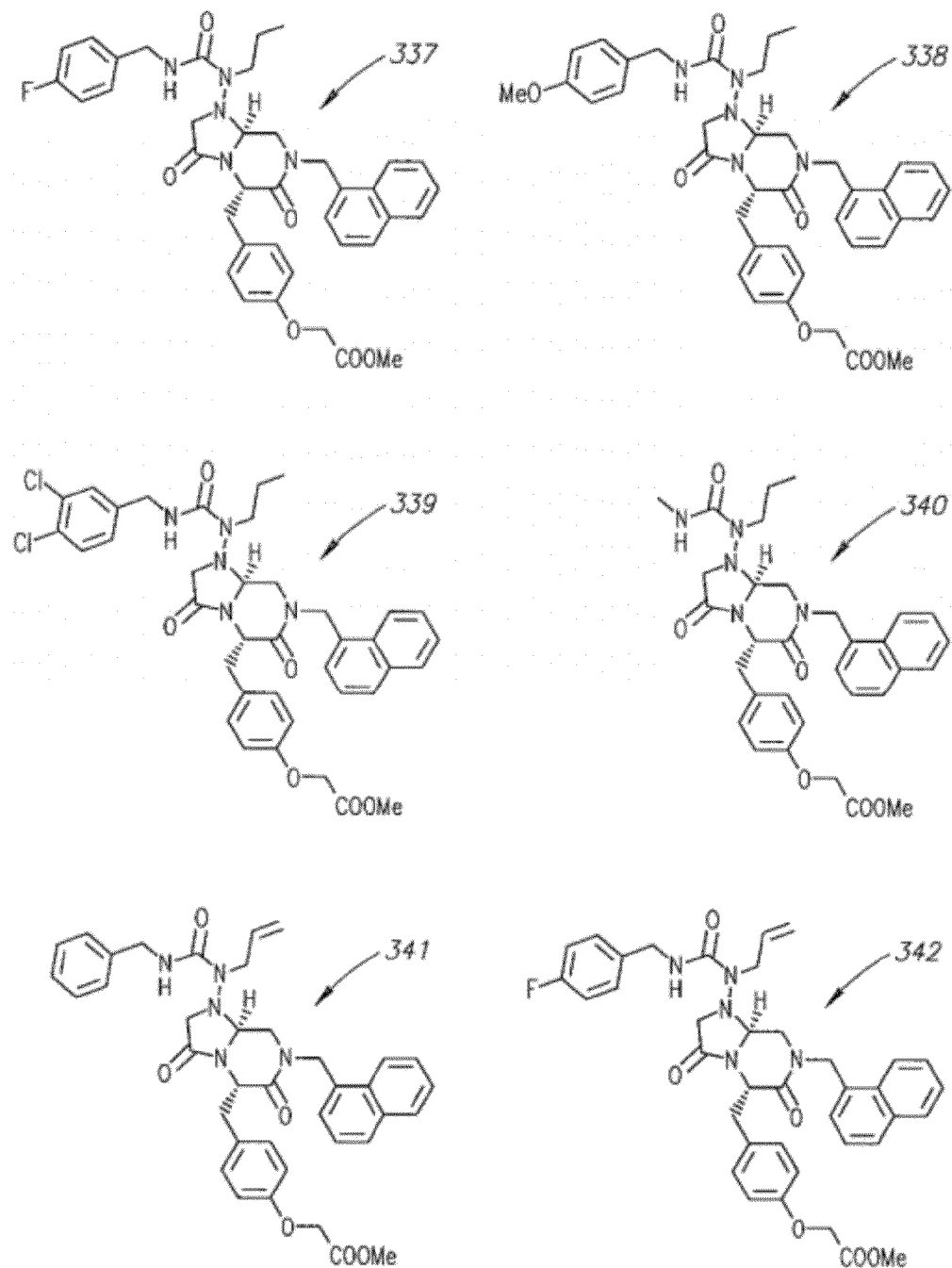
Figure 2U:
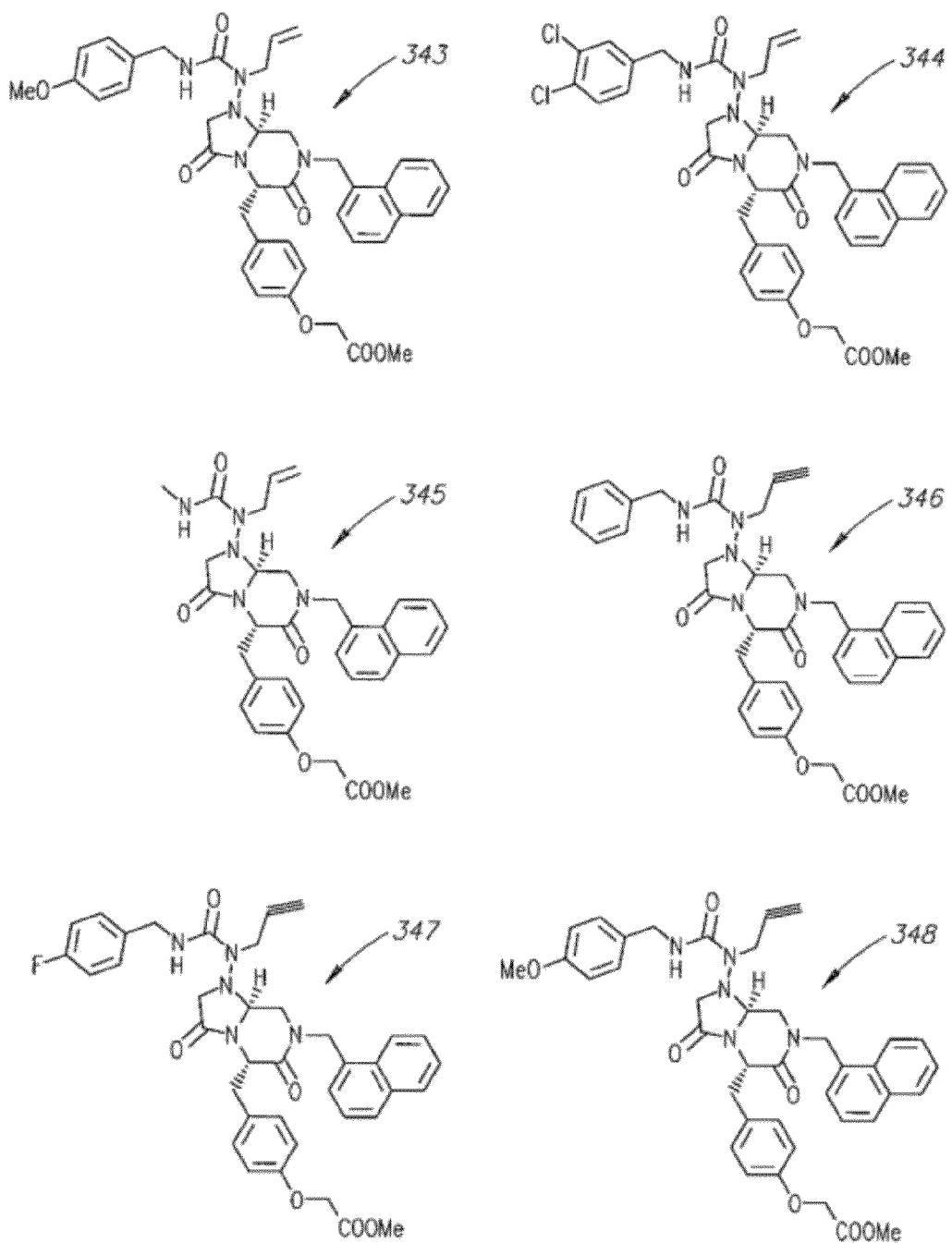
Figure 2V:
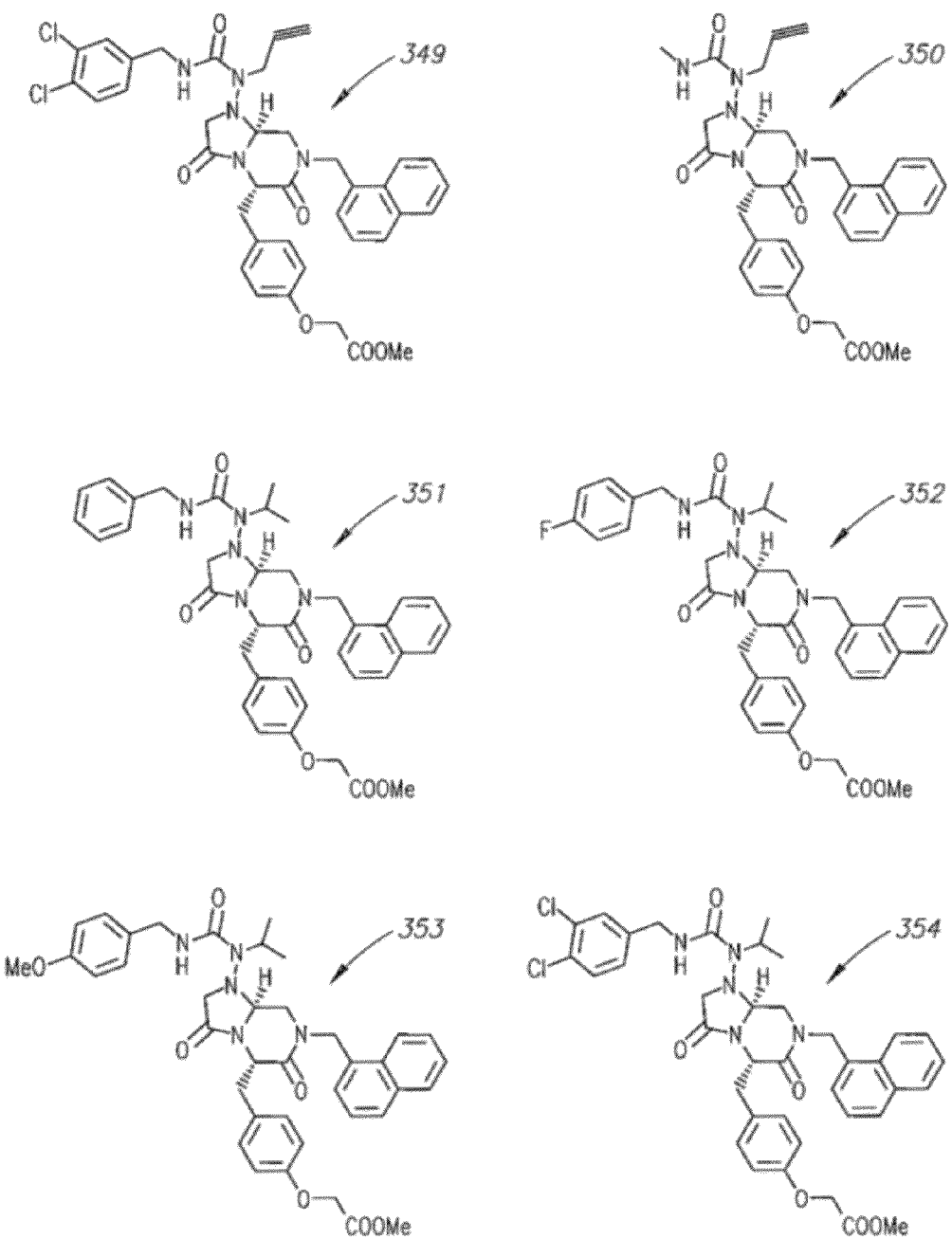
Figure 2W:
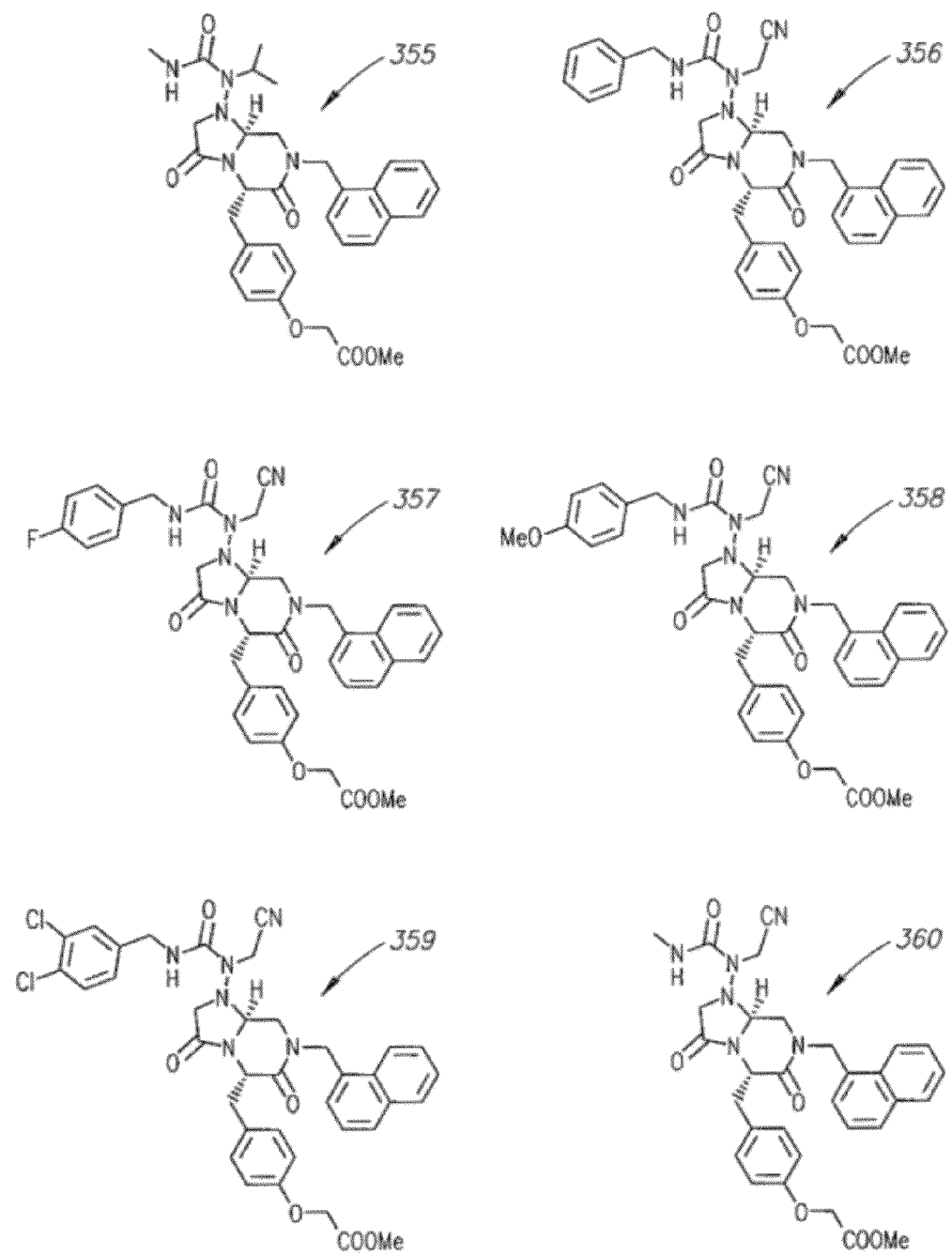
Figure 2X:
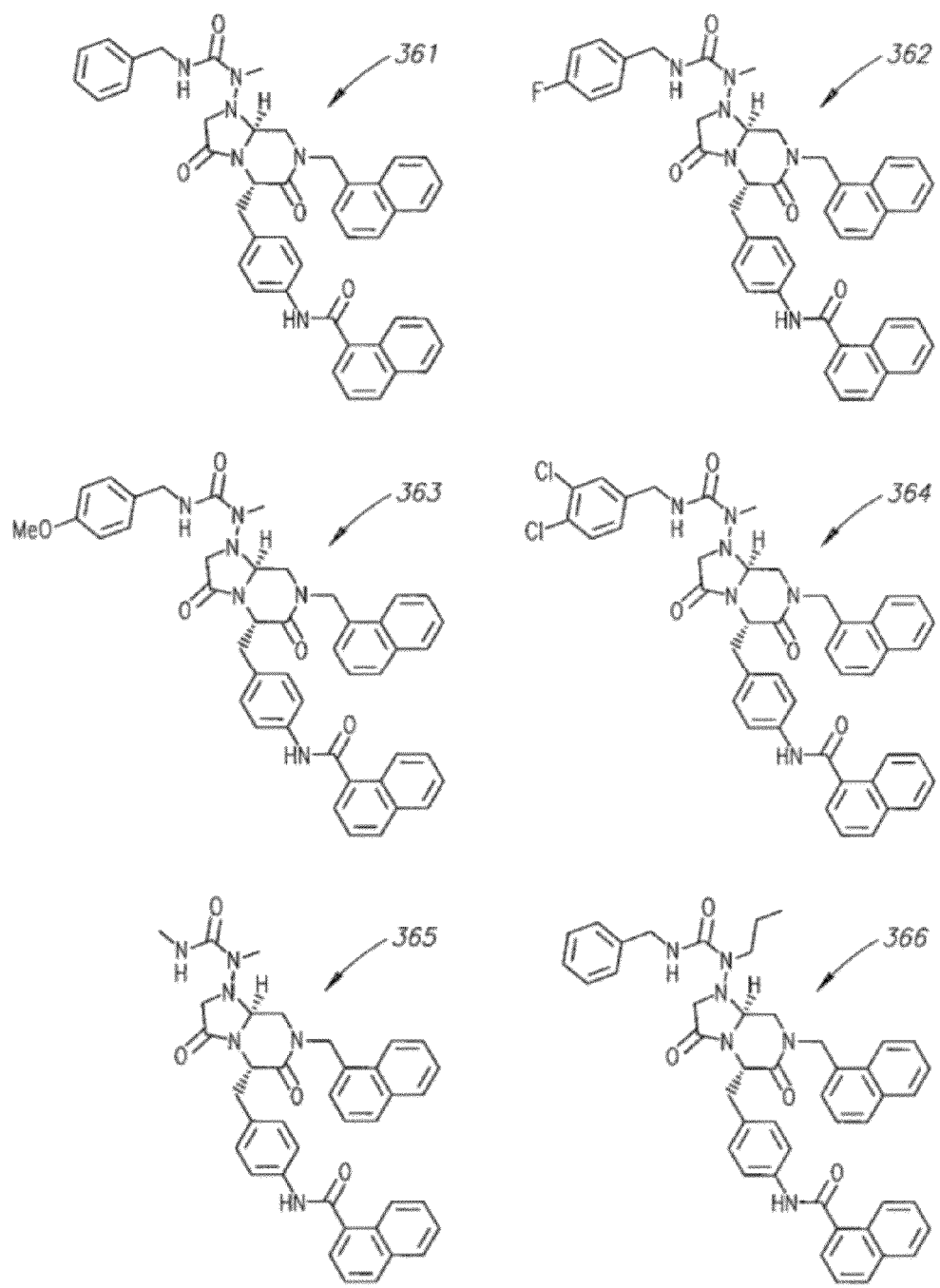
Figure 2Y:
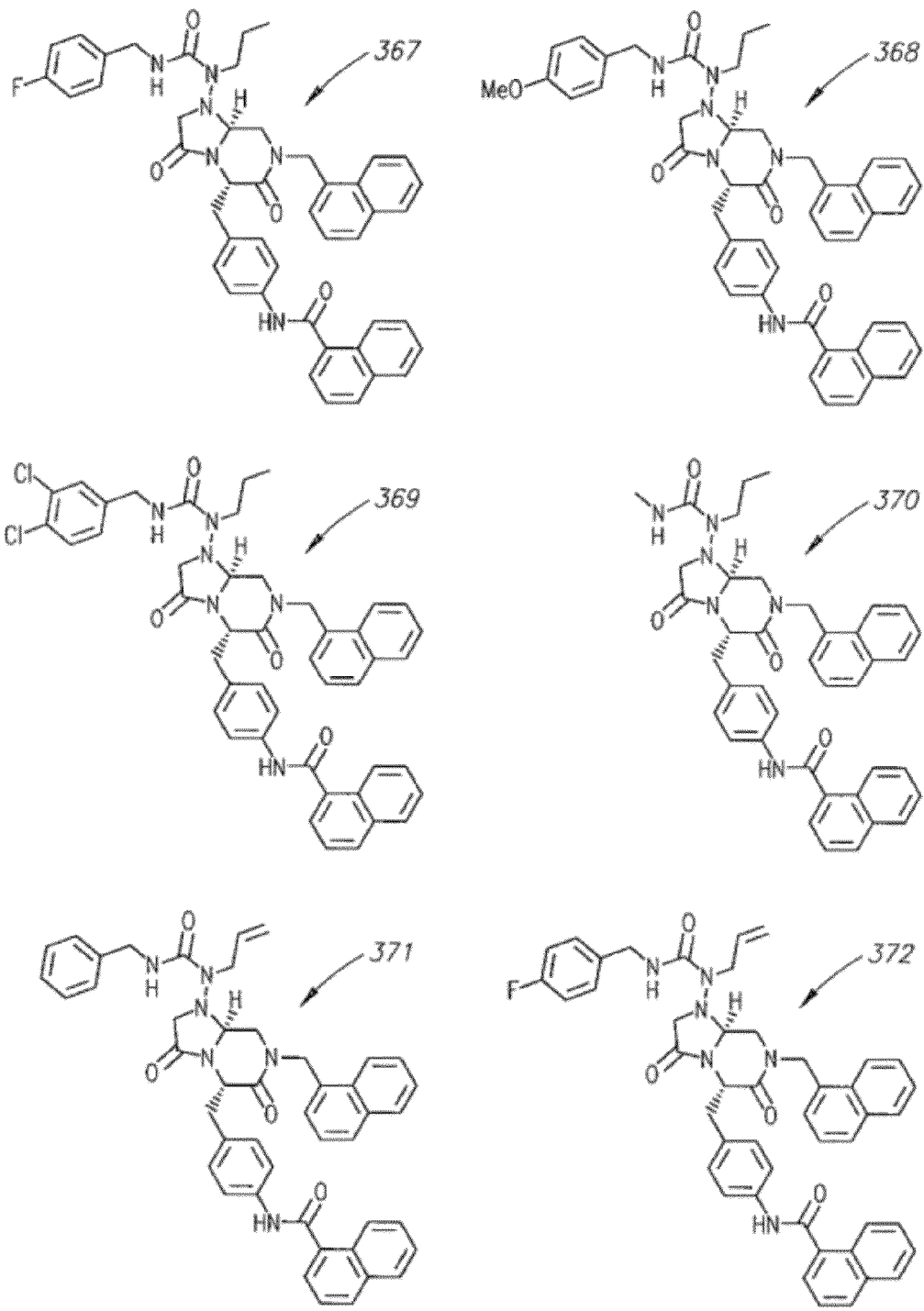
Figure 2Z:
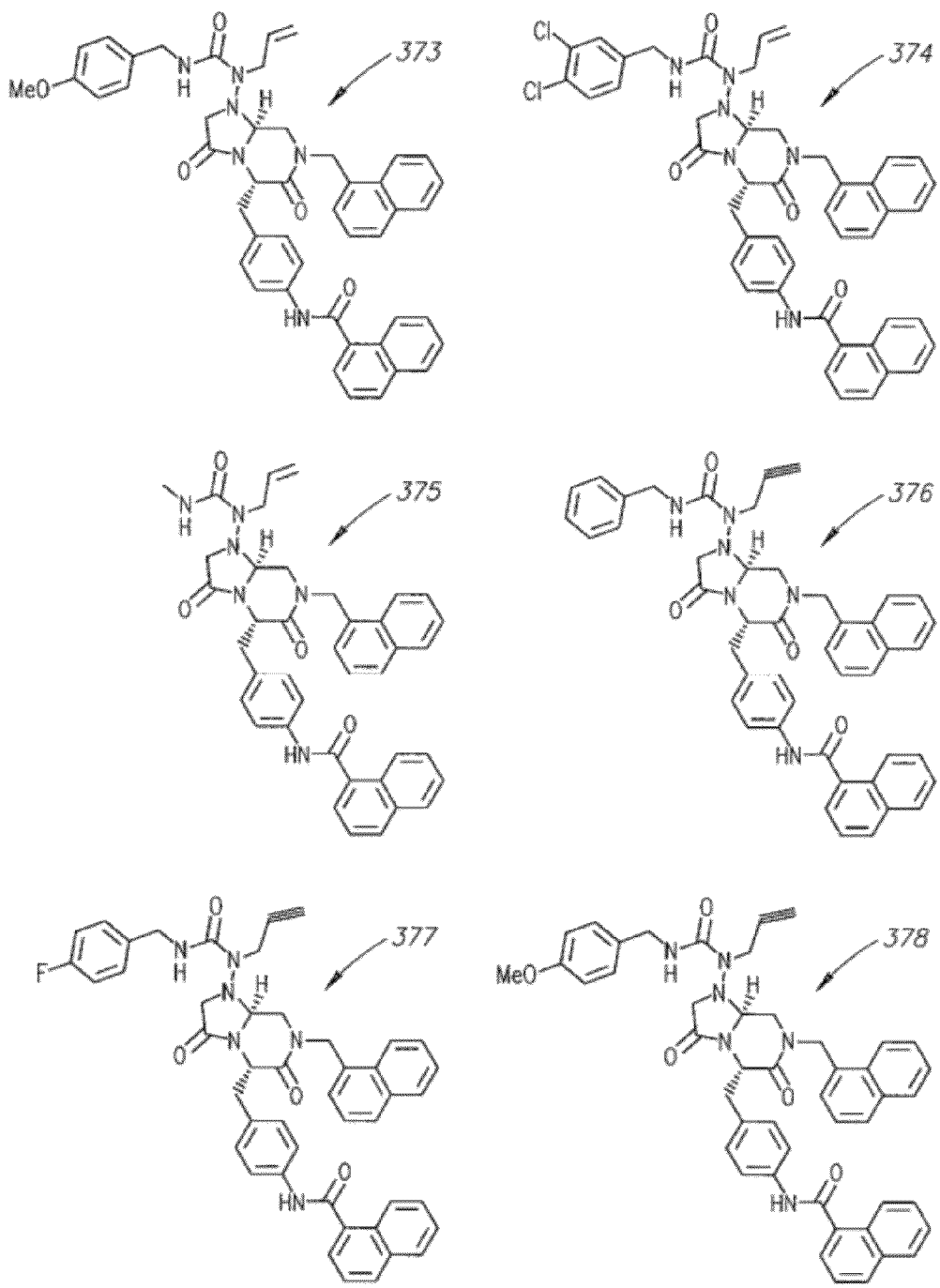
Figure 2A:
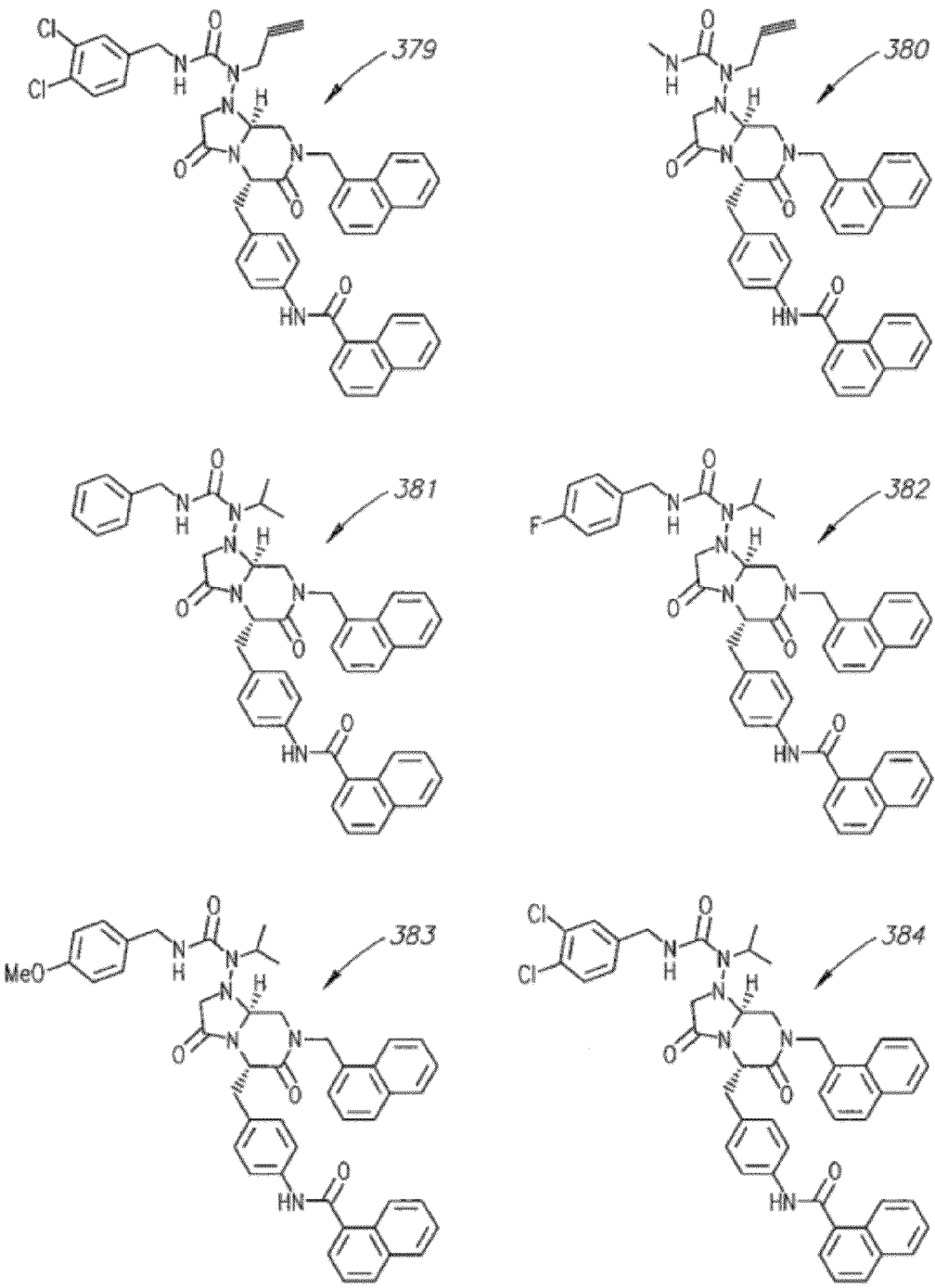
Figure 2A:
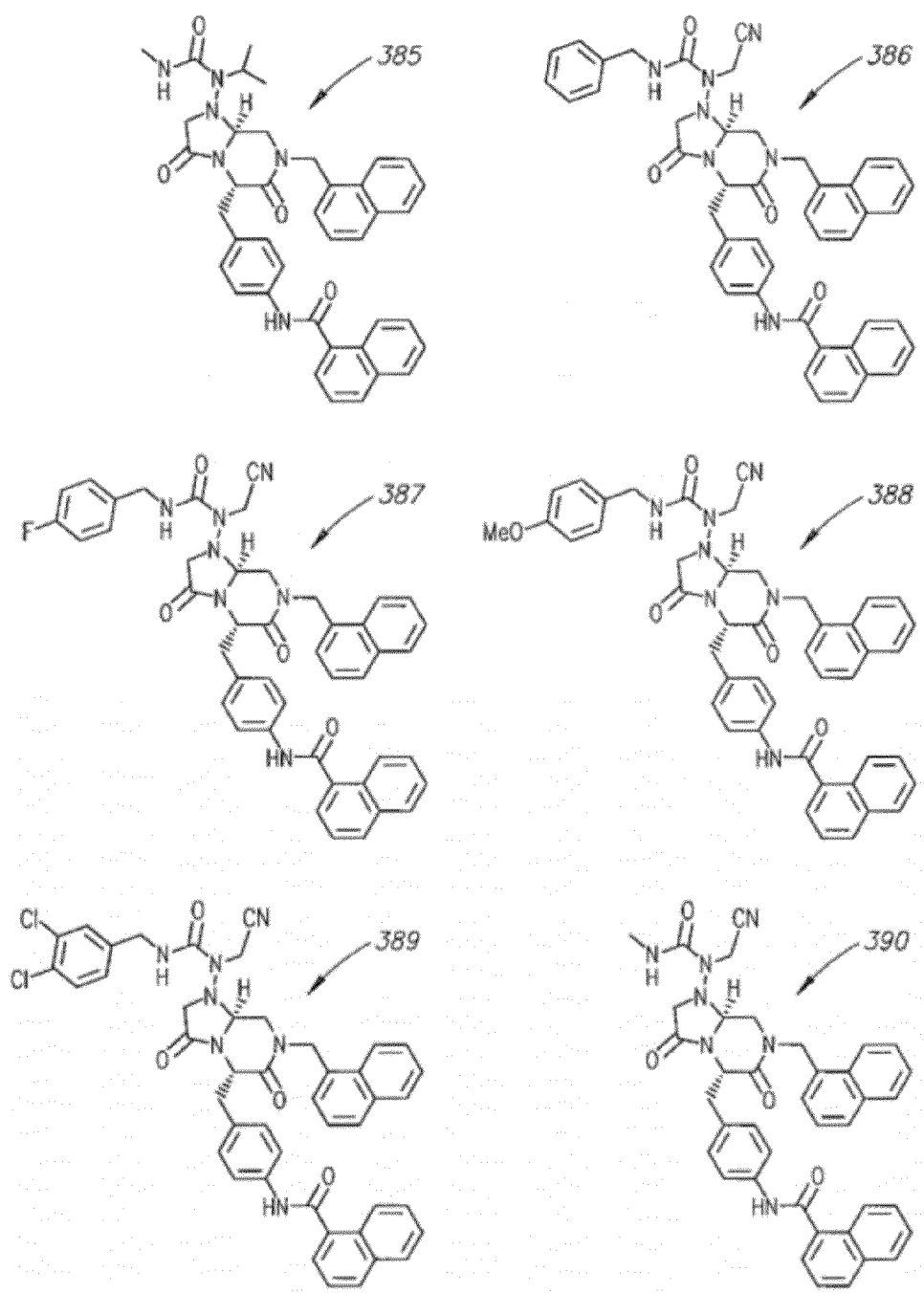
Figure 2A:
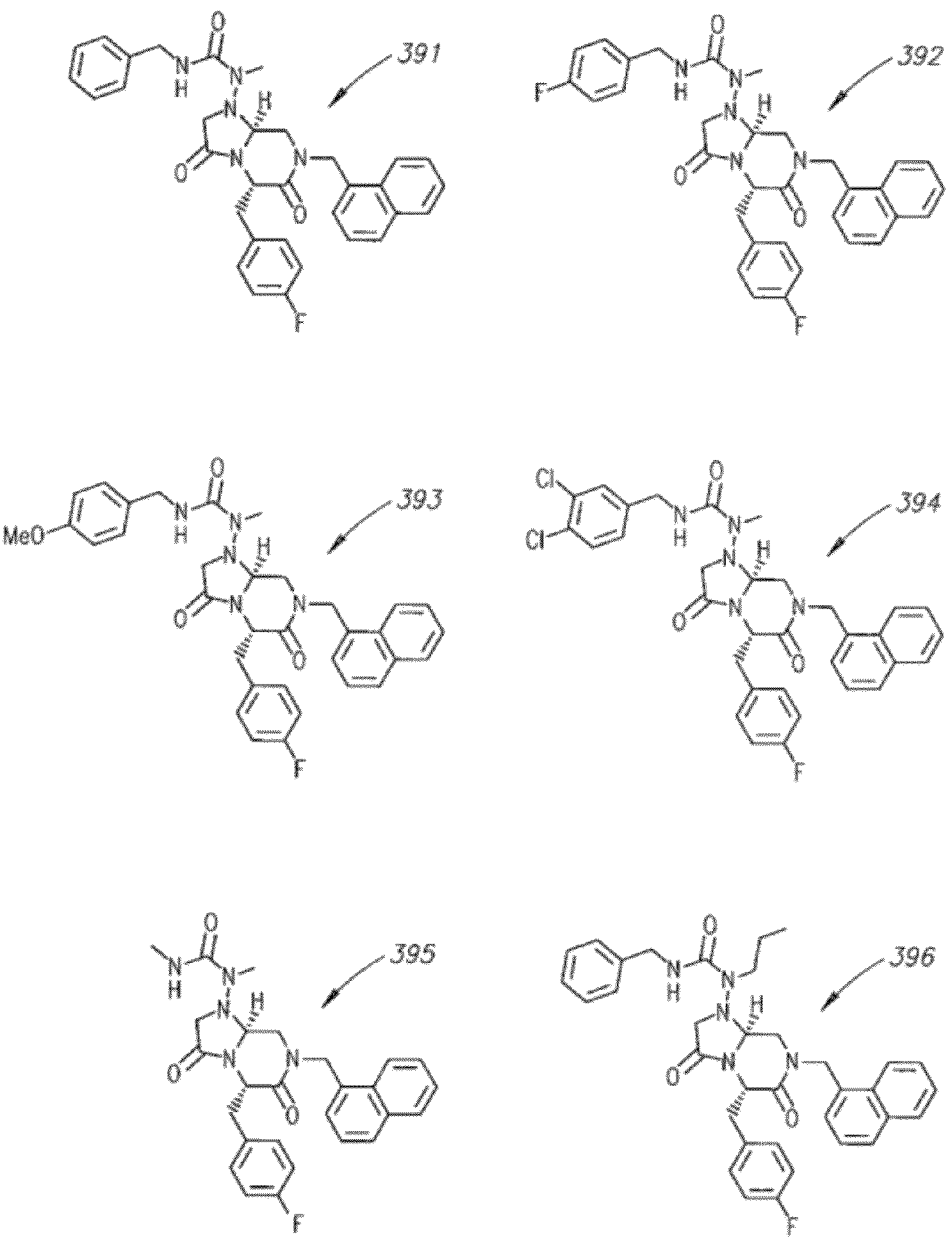
Figure 2A:
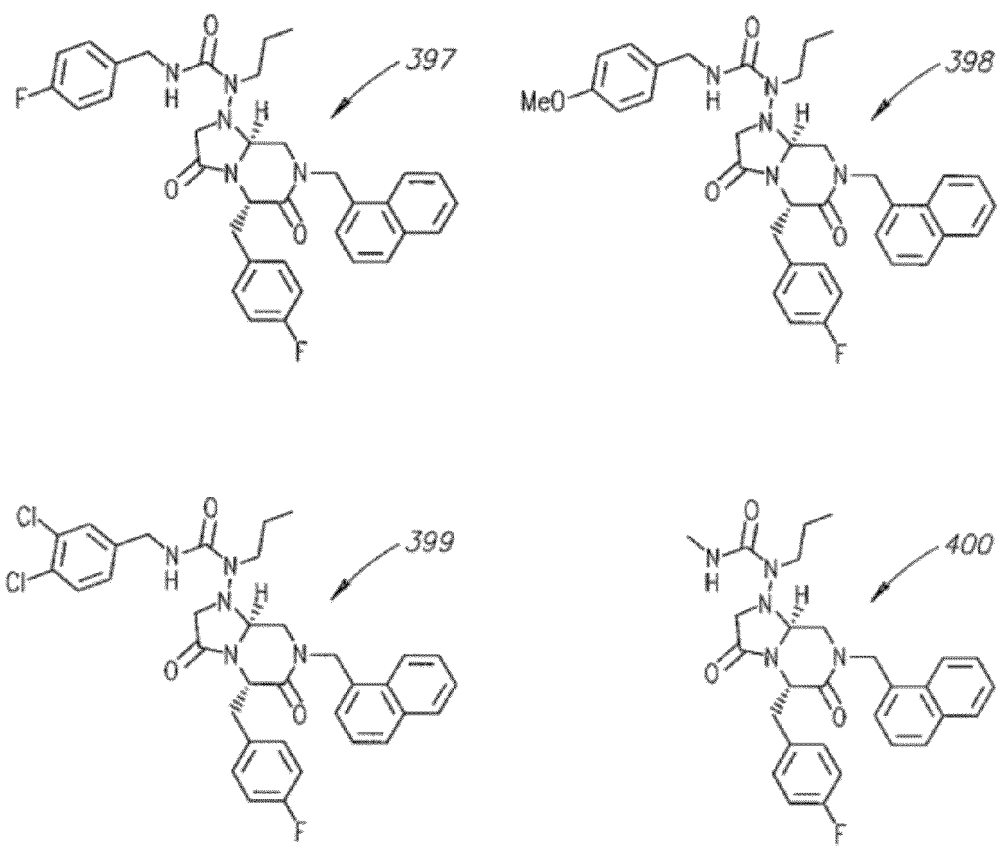
Figure 3A:
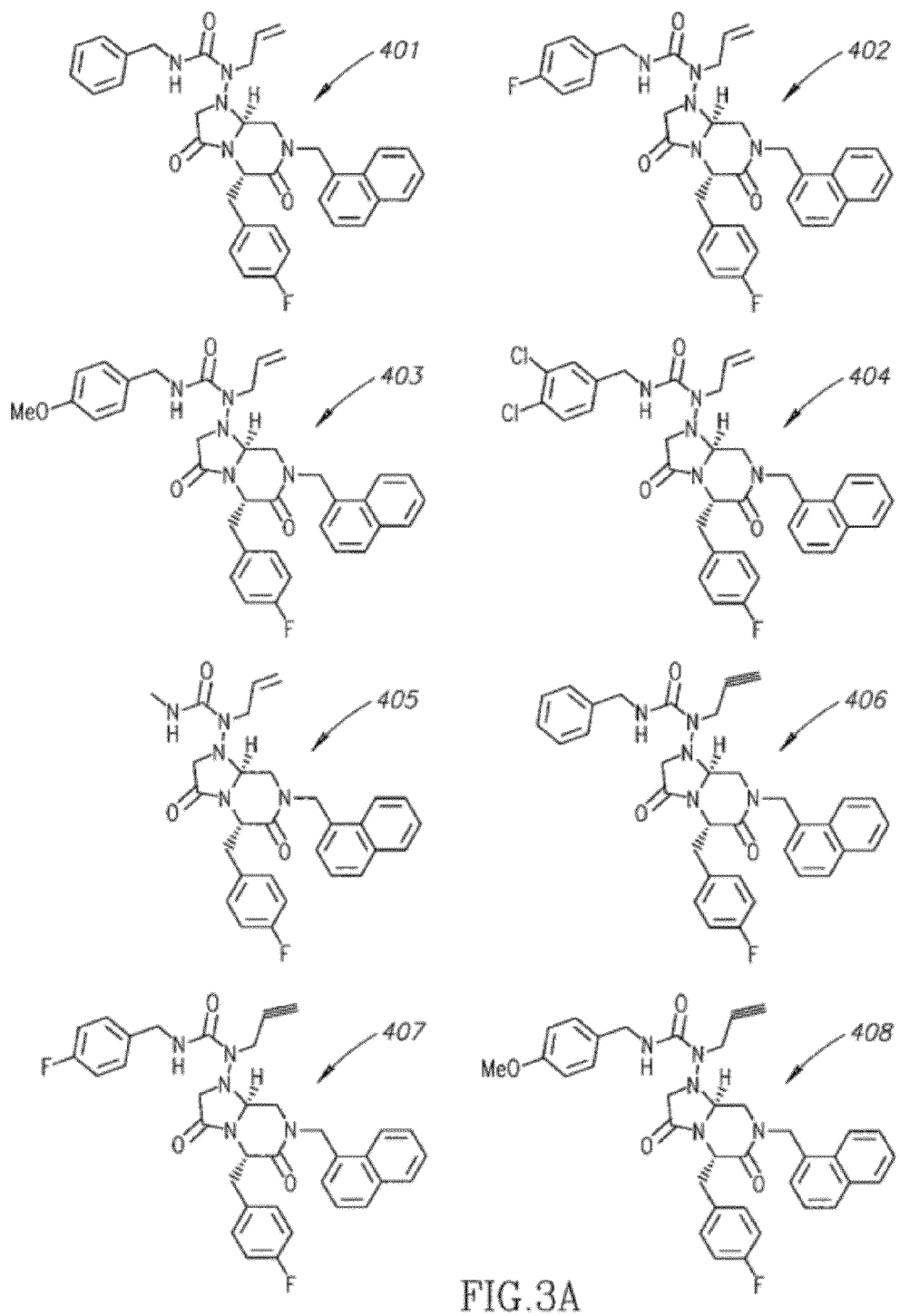
FIGS. 3A-3AC shows the chemical structures of compounds 401-600.
Figure 3B:
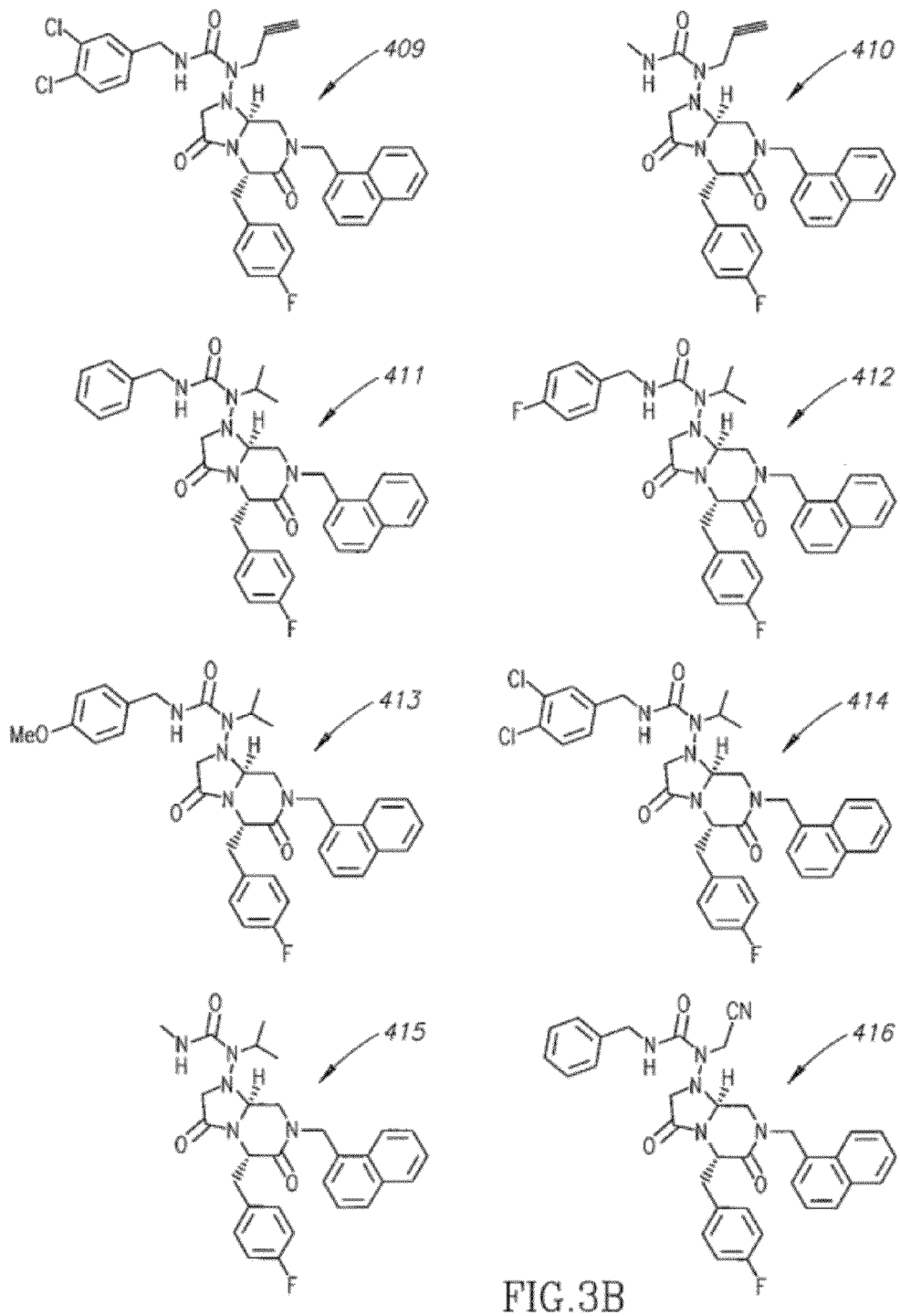
Figure 3C:
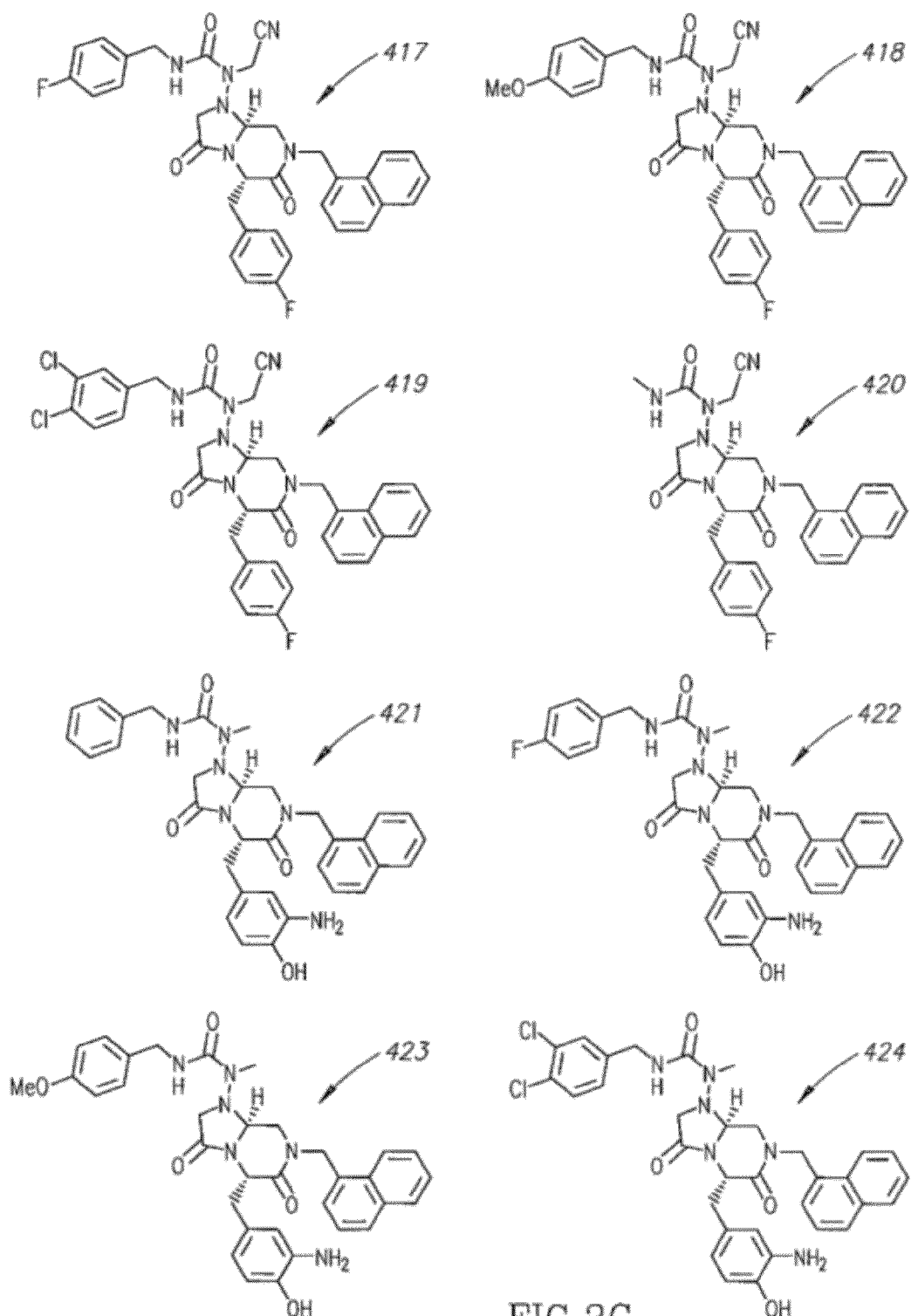
Figure 3D:
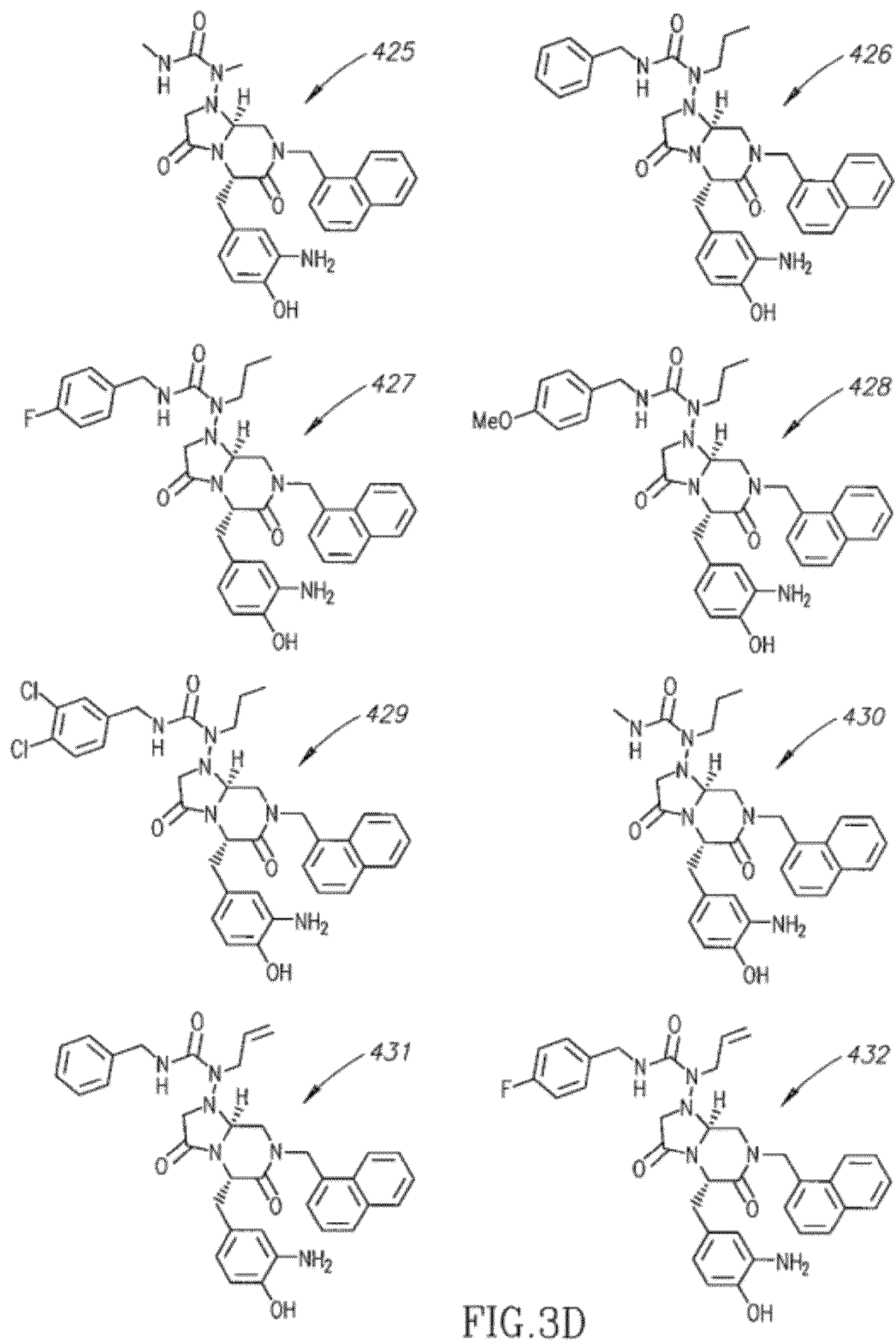
Figure 3E:
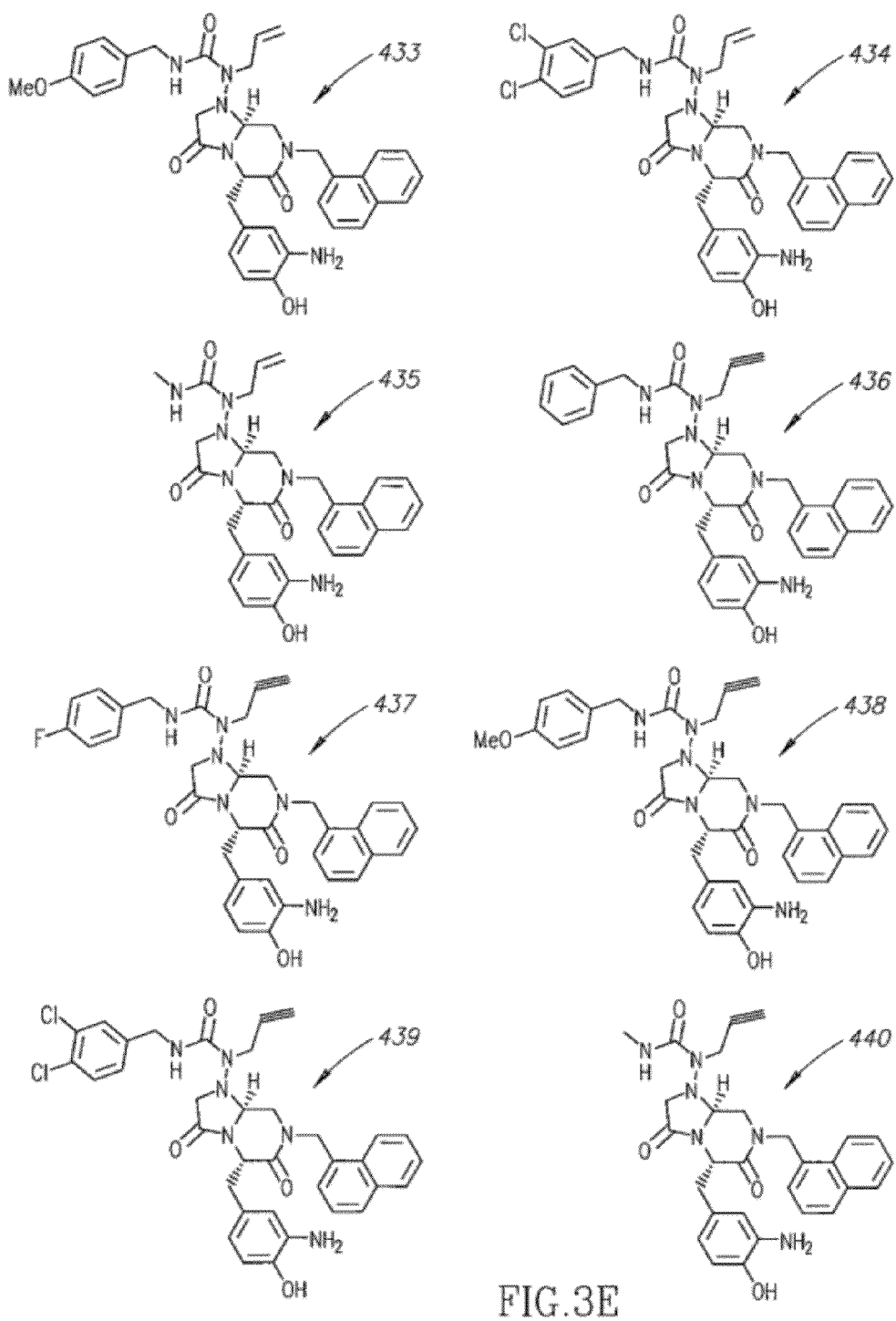
Figure 3F:
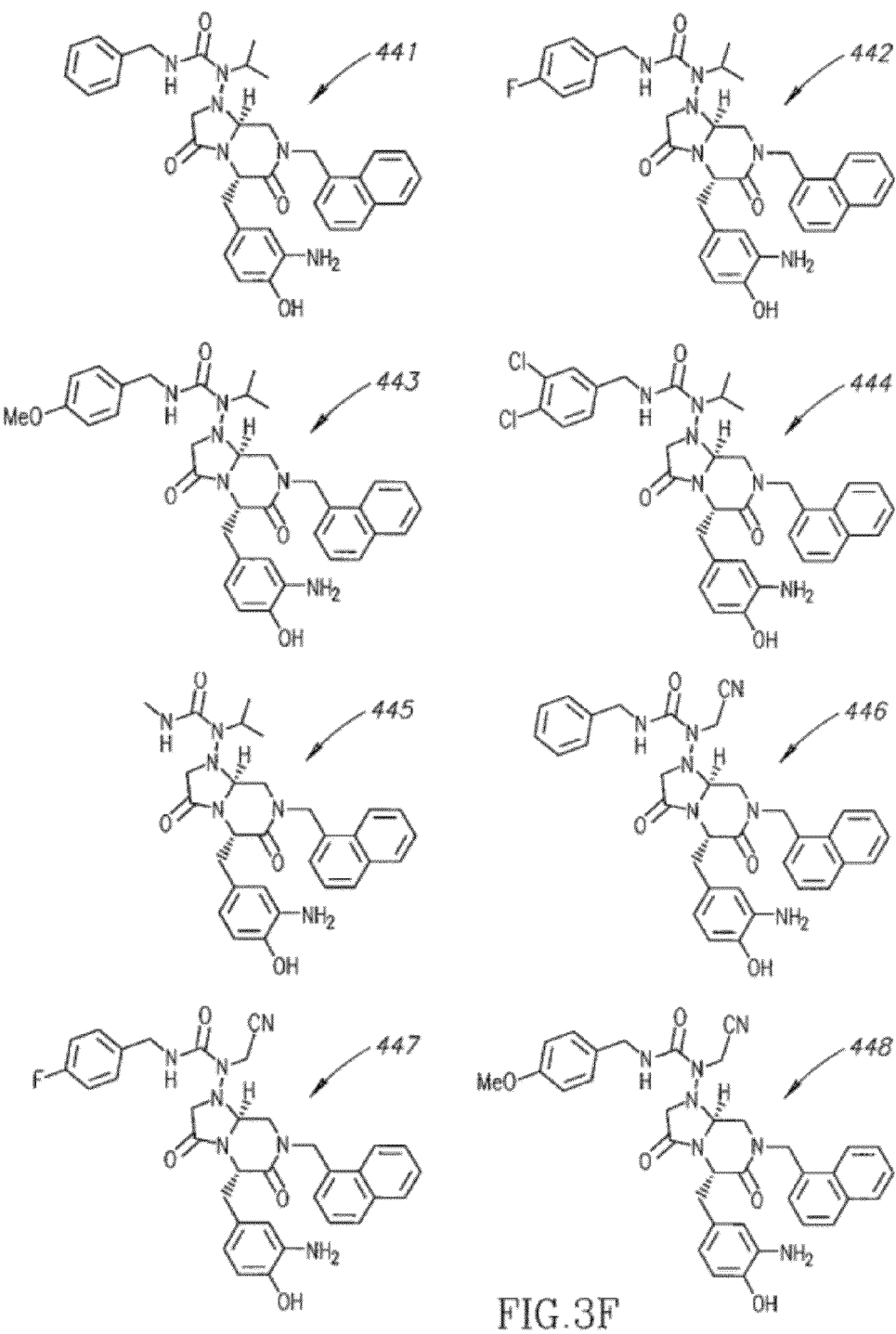
Figure 3G:
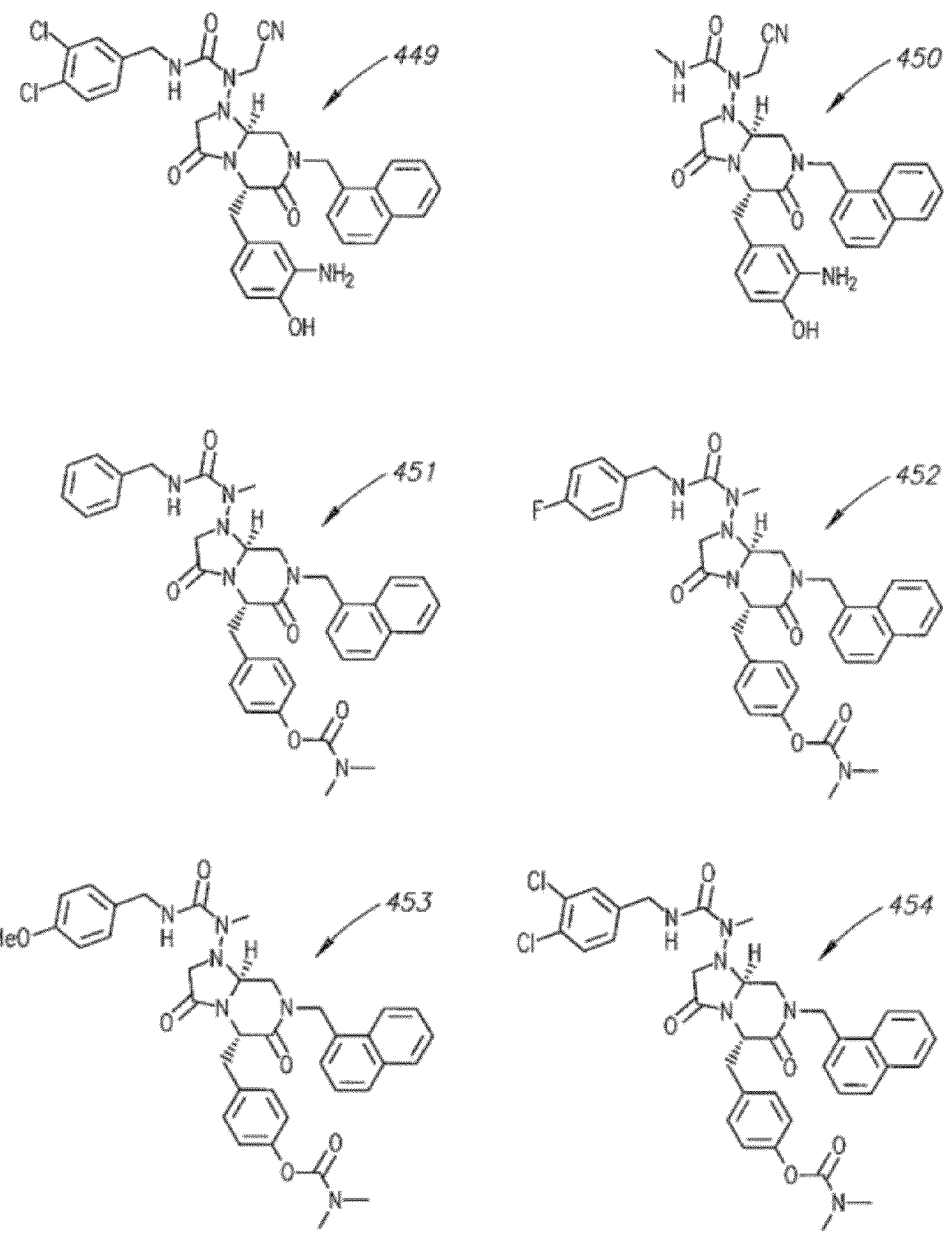
Figure 3H:
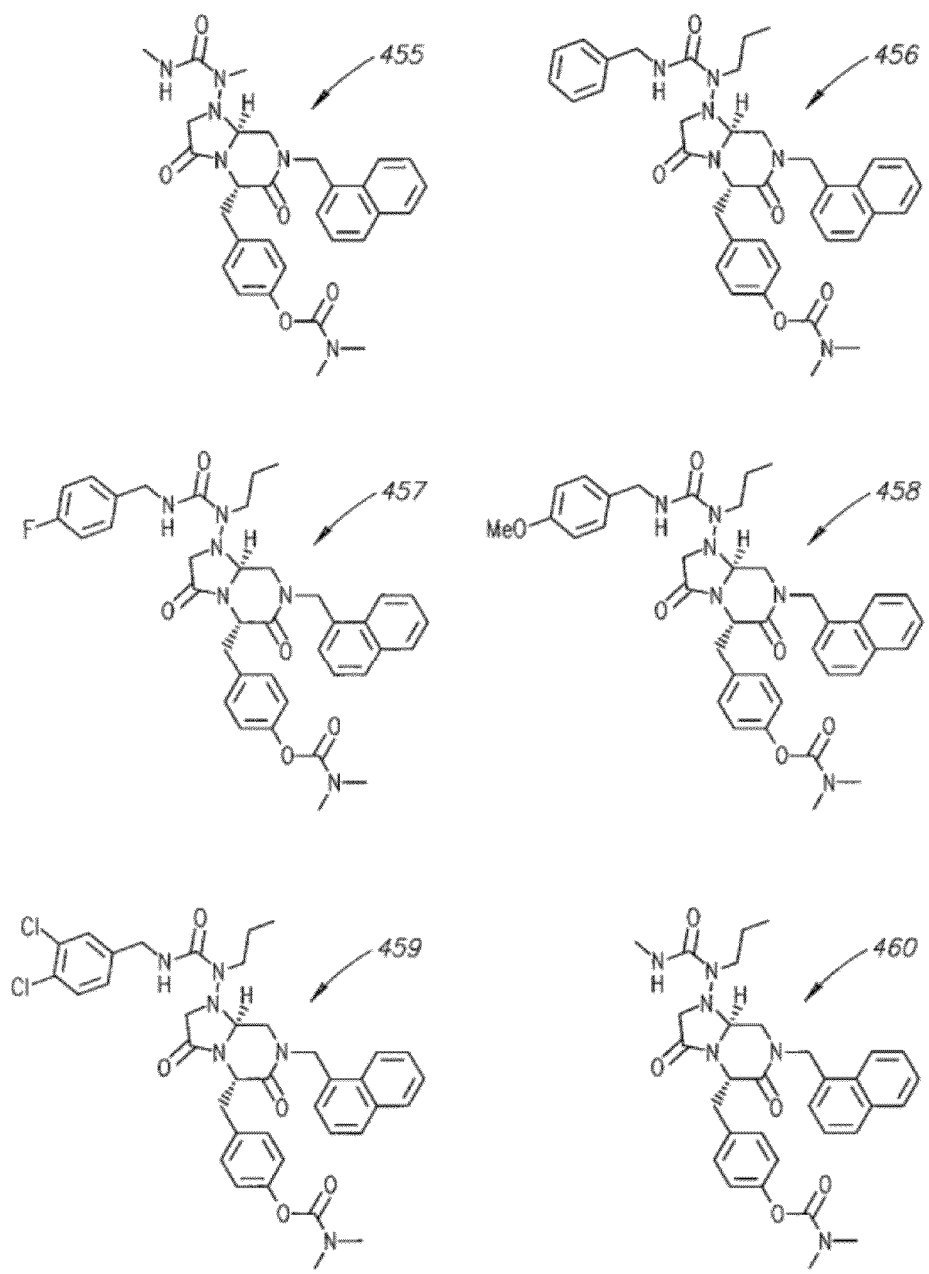
Figure 3I:
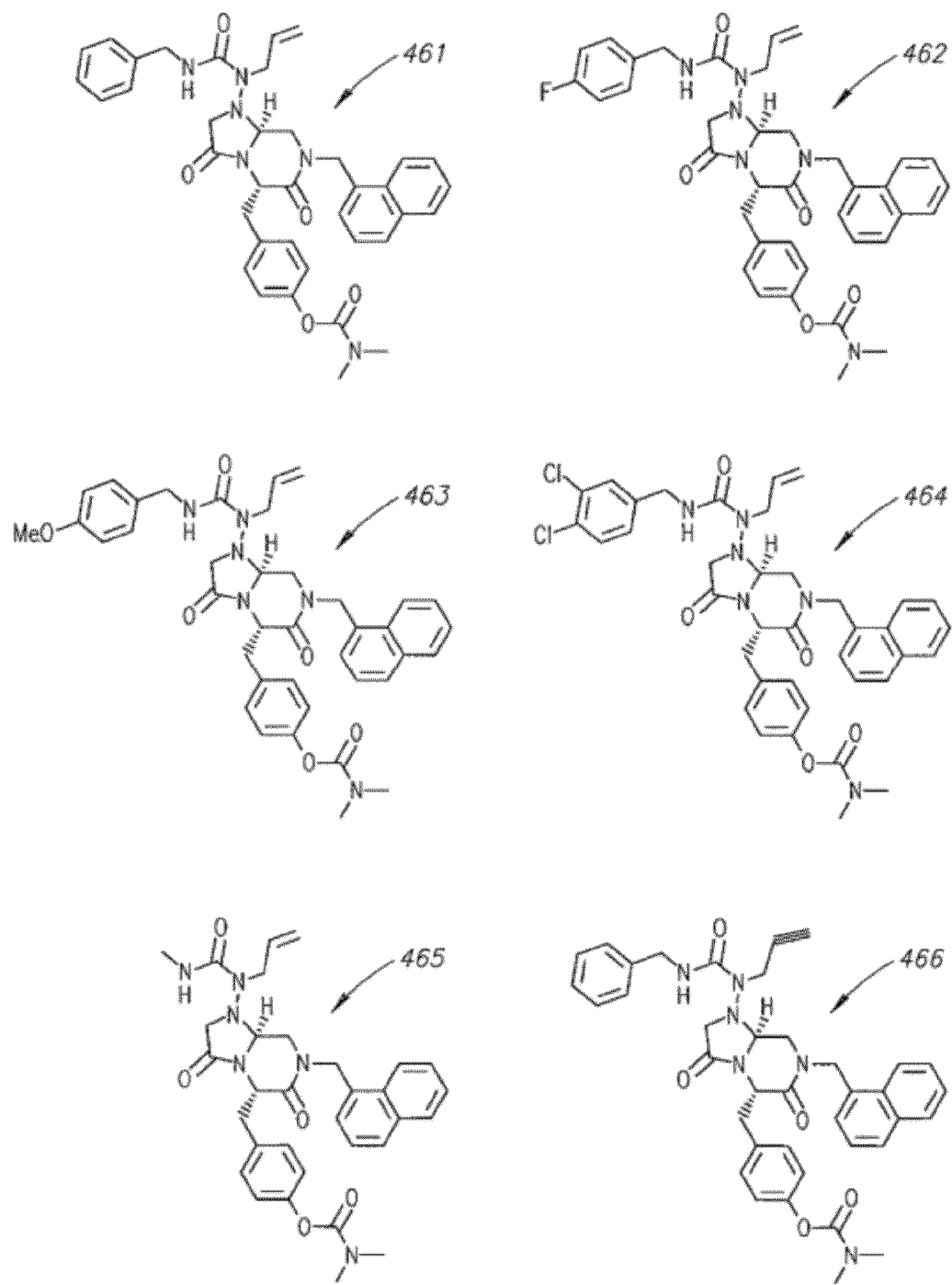
Figure 3J:
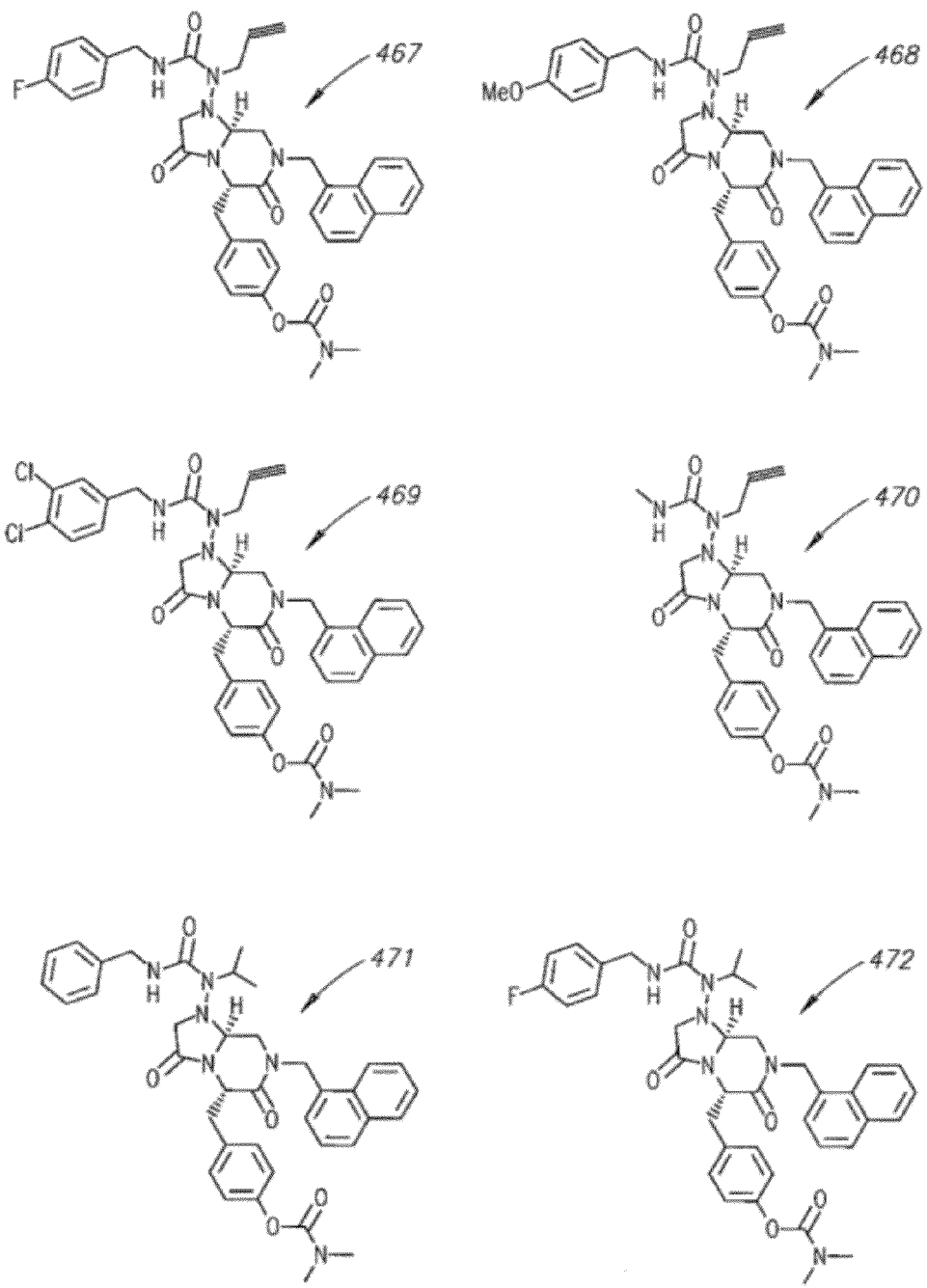
Figure 3L:
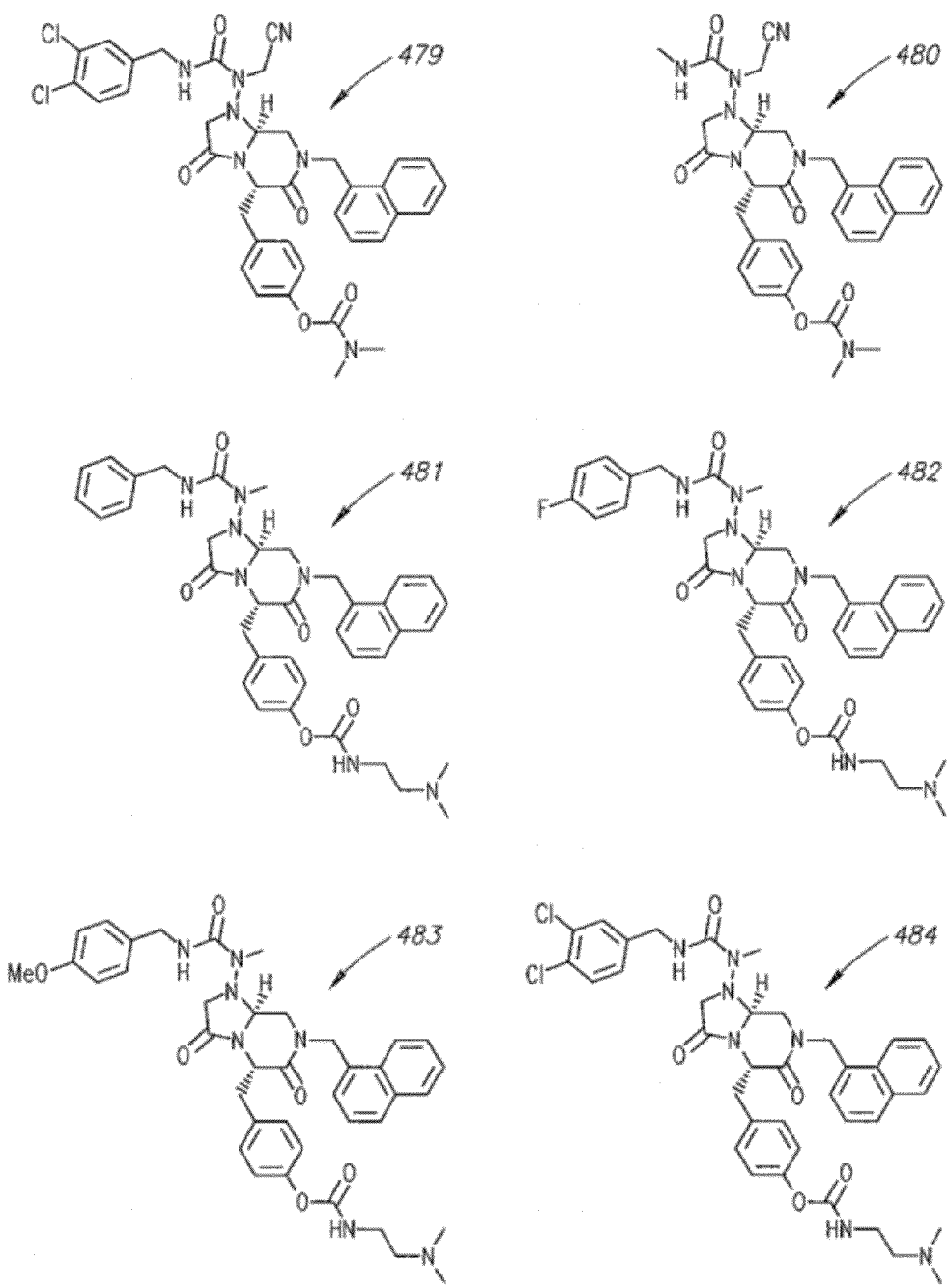
Figure 3M:
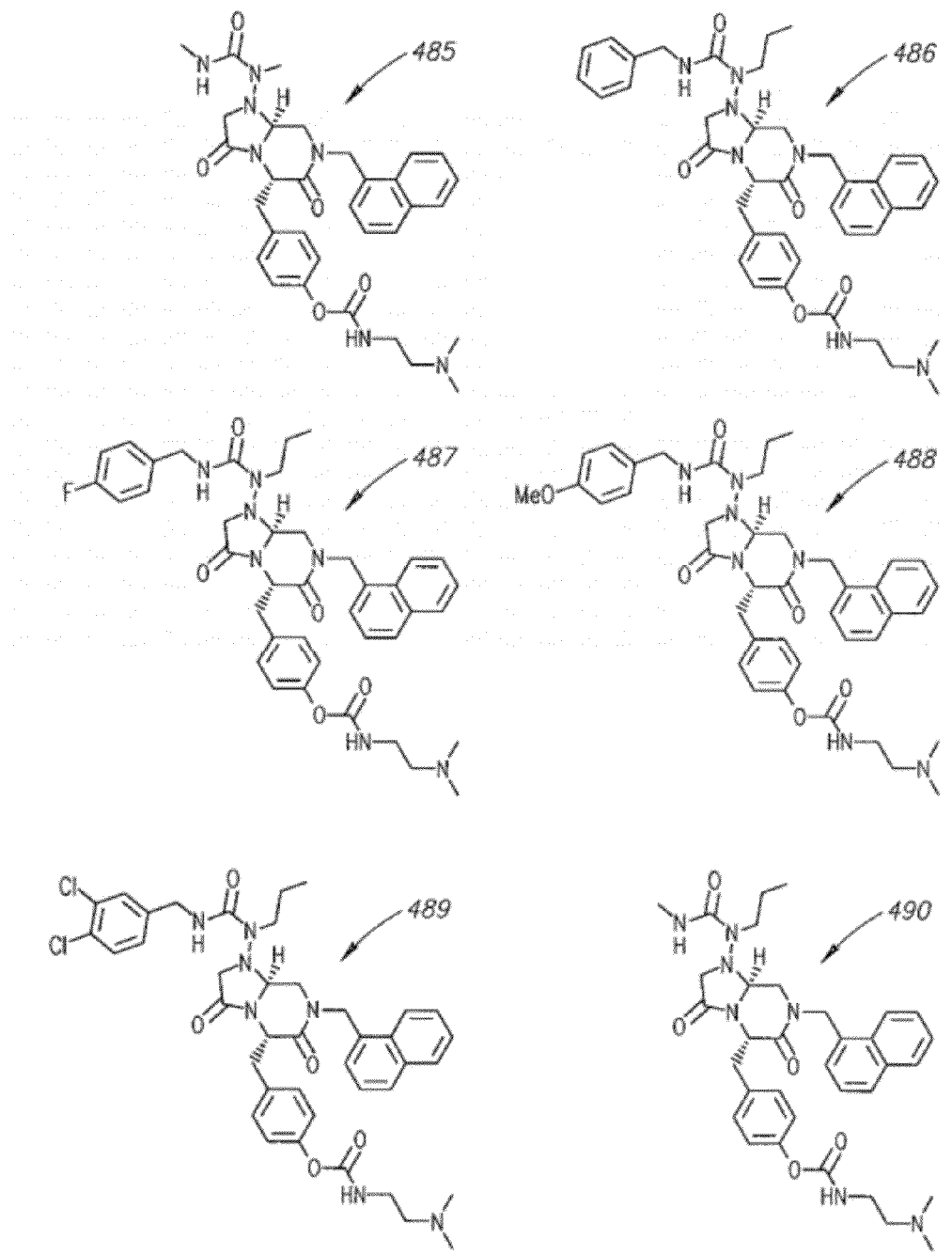
Figure 3N:
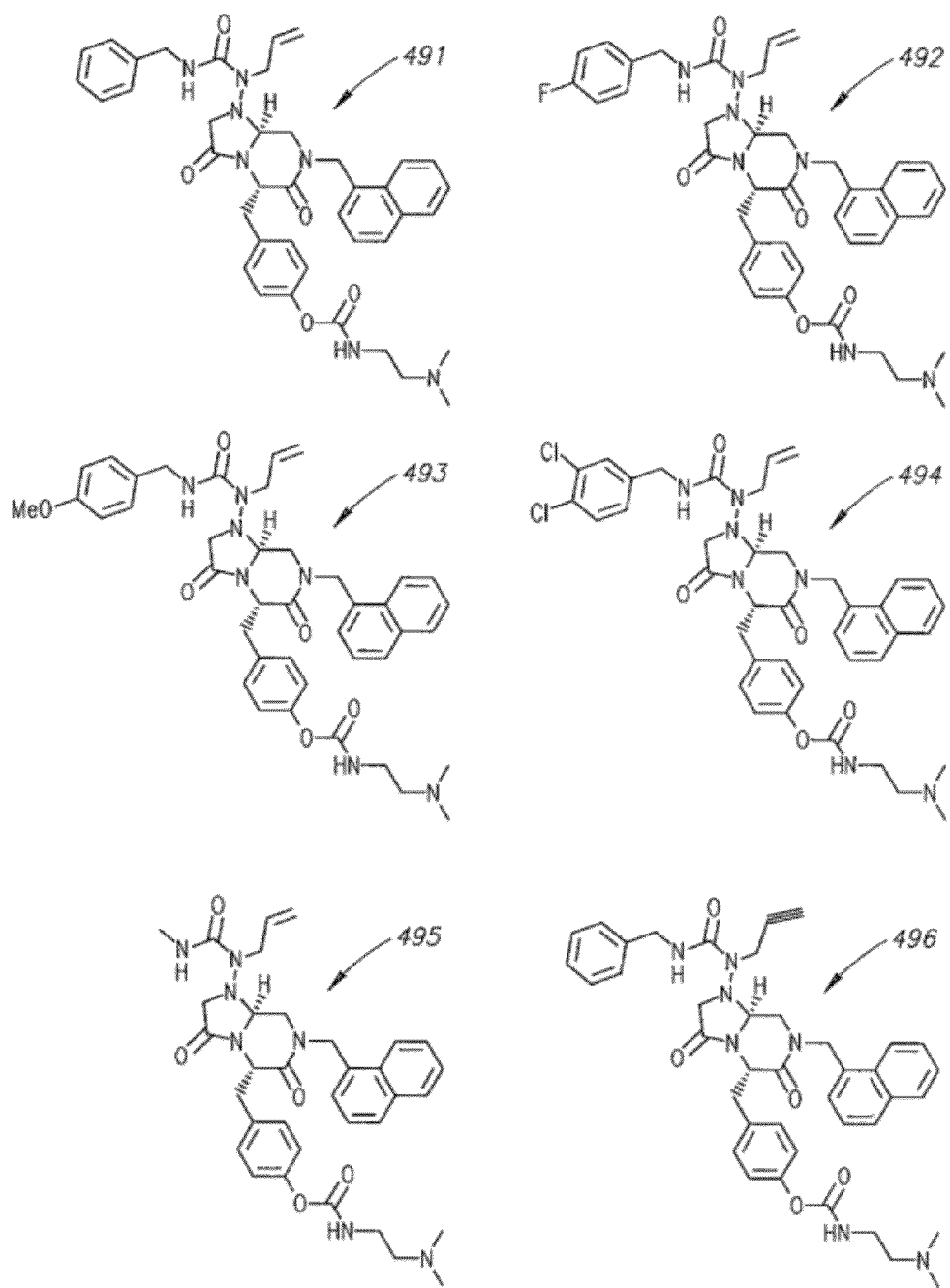
Figure 30:
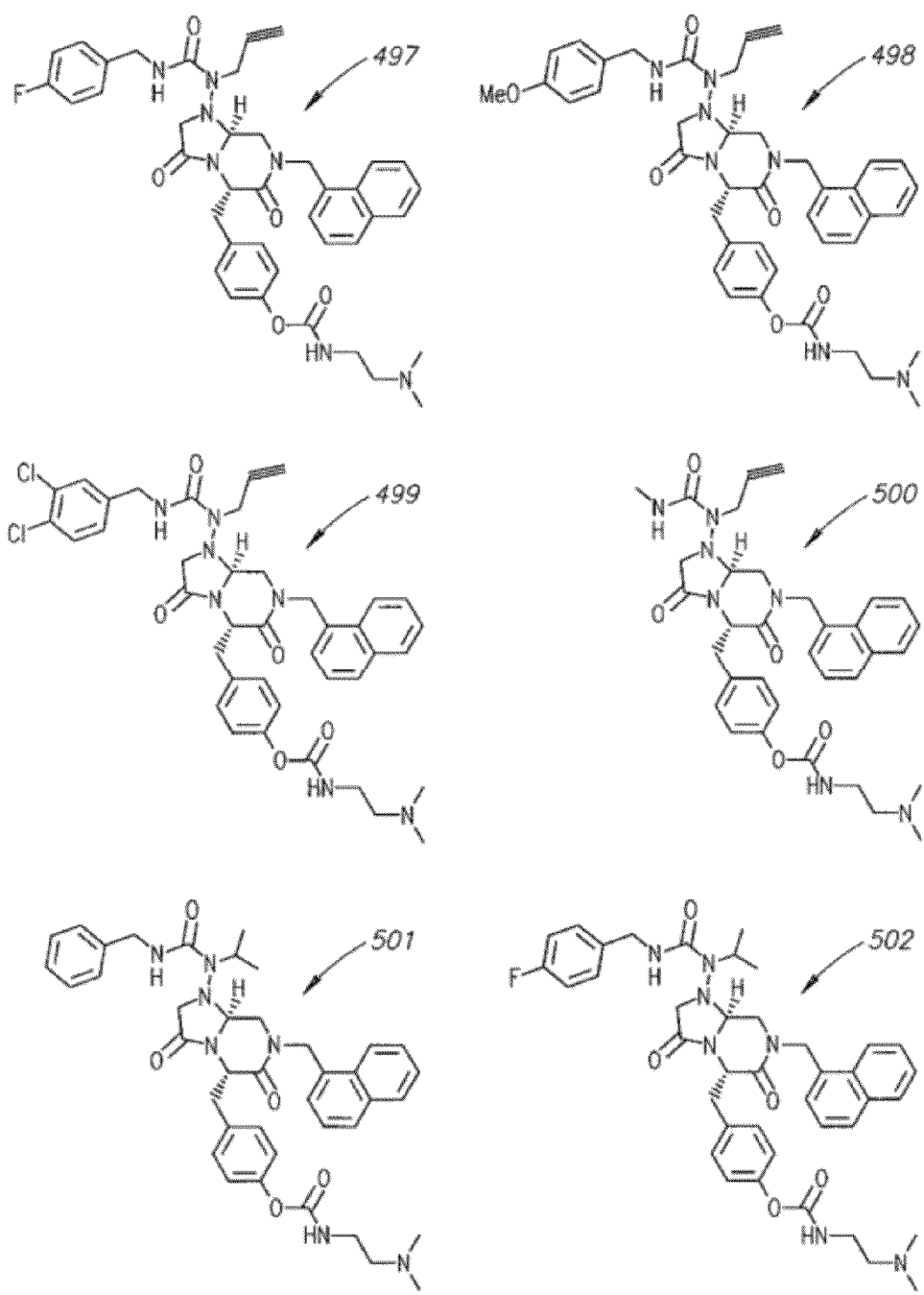
Figure 3P:
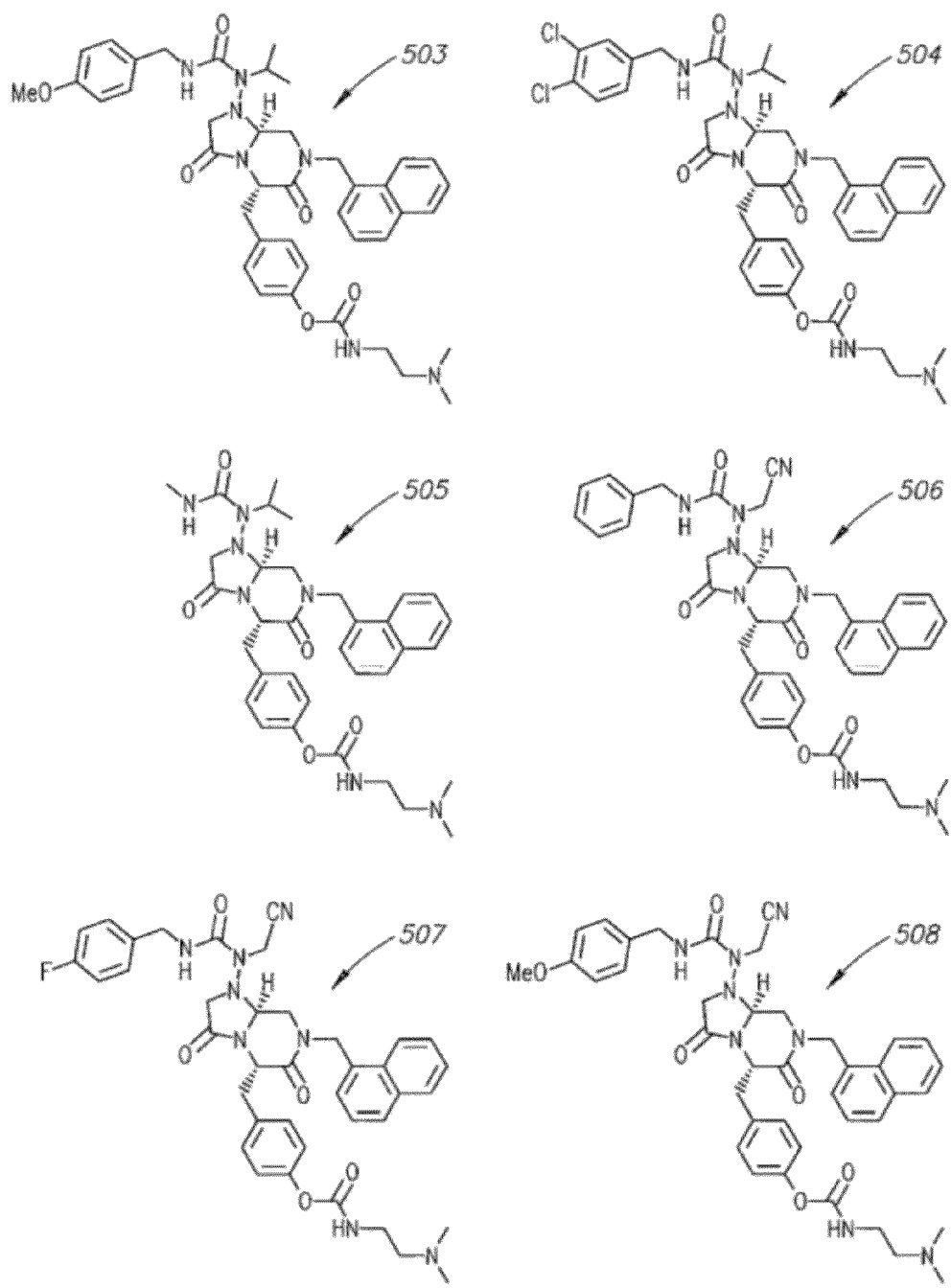
Figure 3Q:
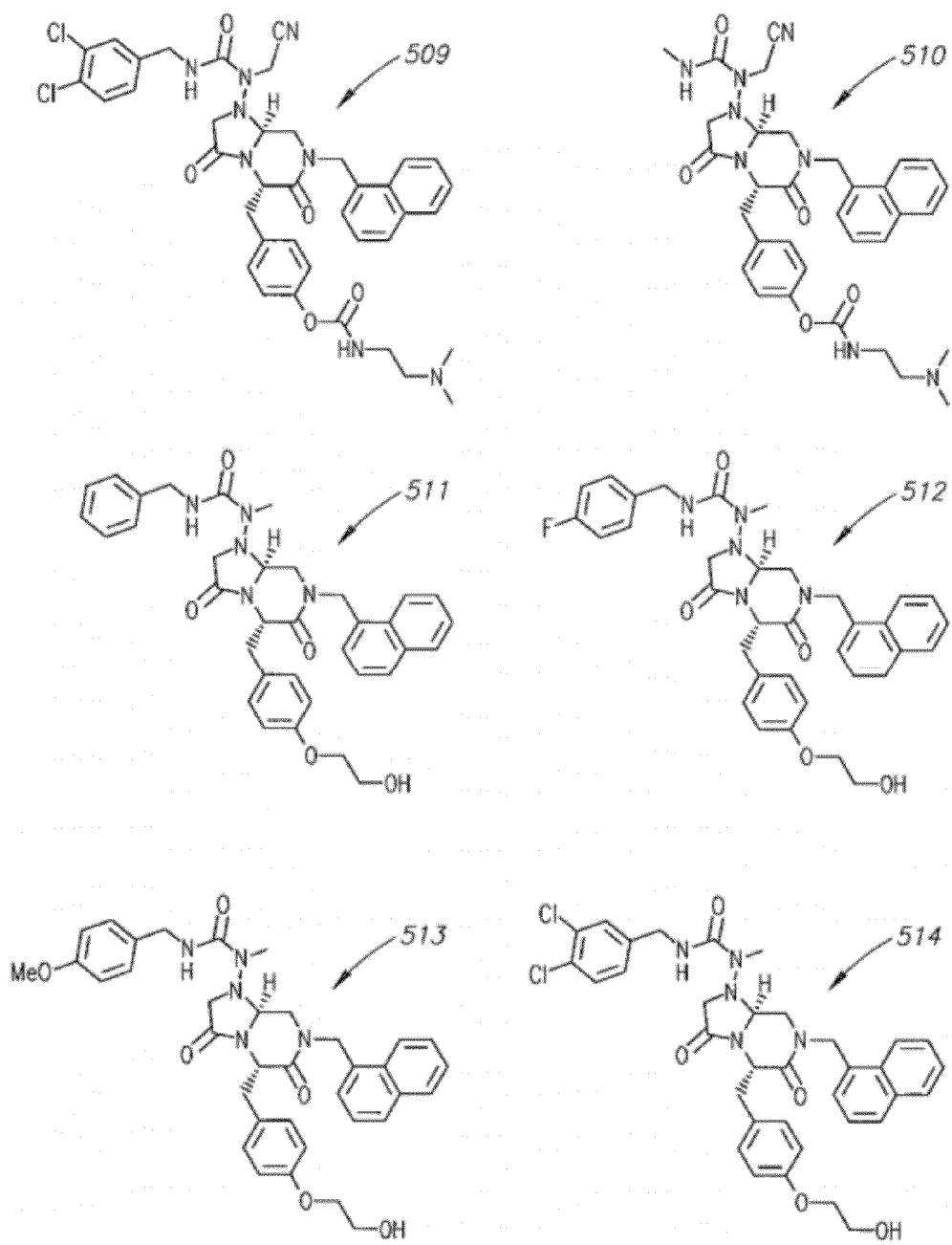
Figure 3R:
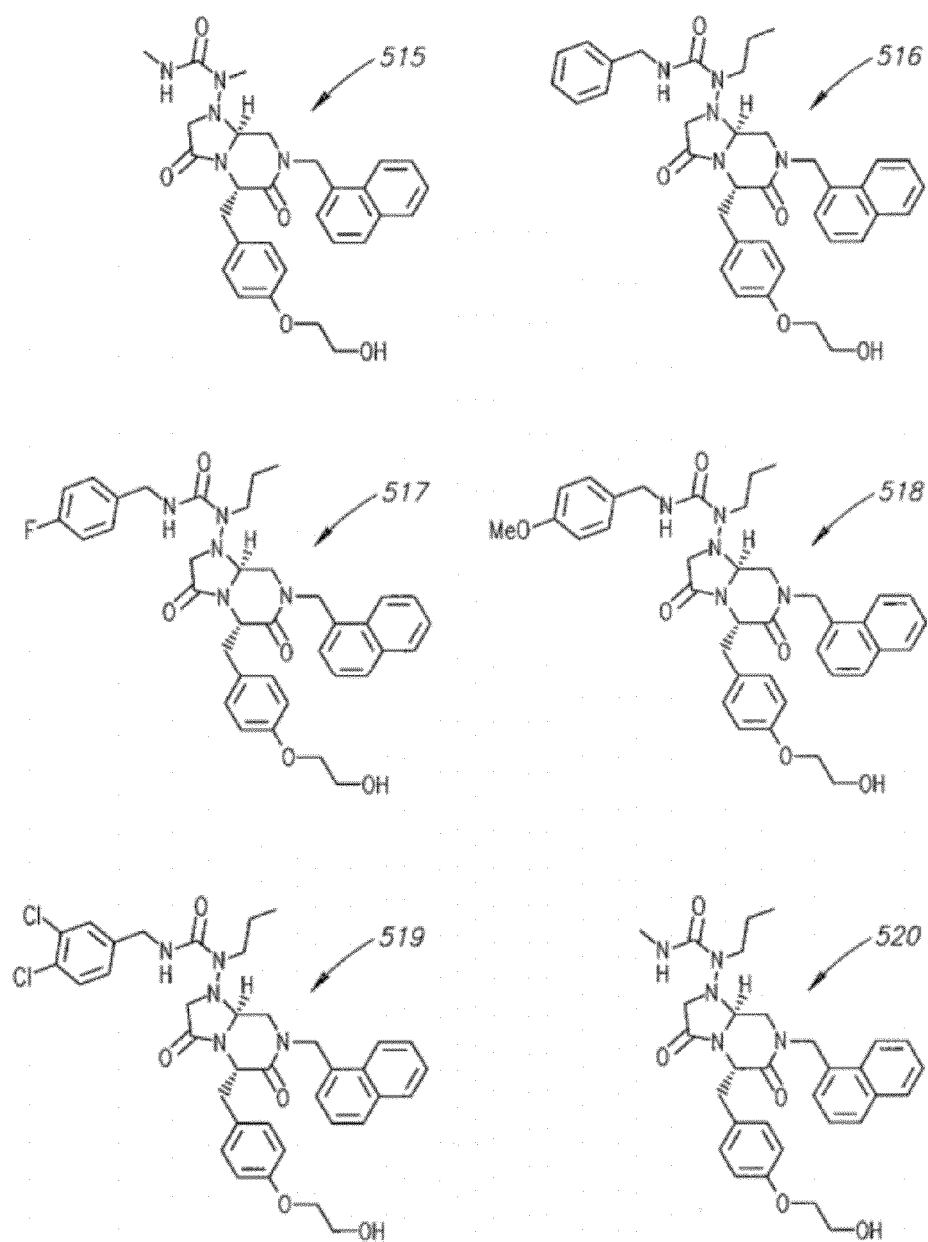
Figure 3S:
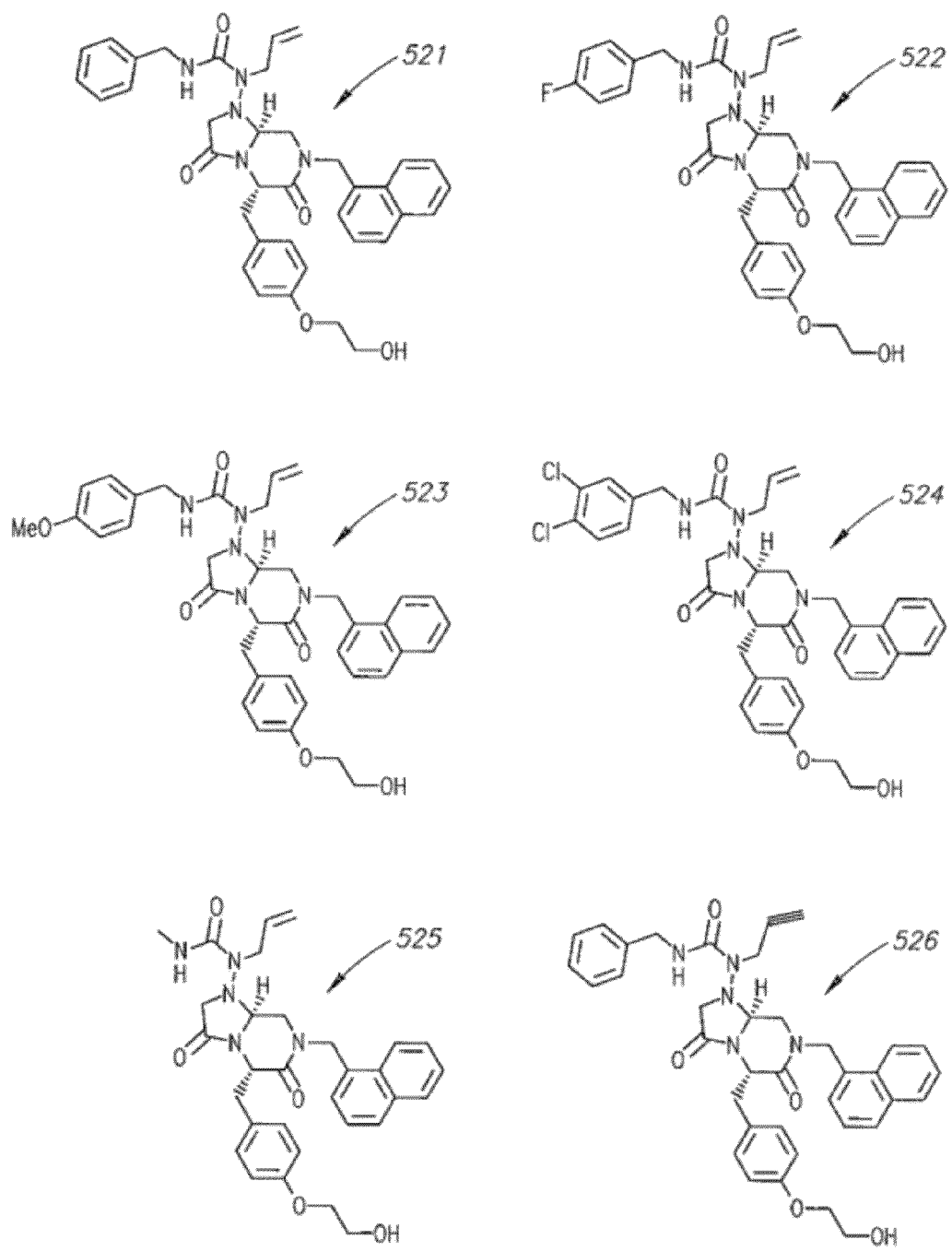
Figure 3T:
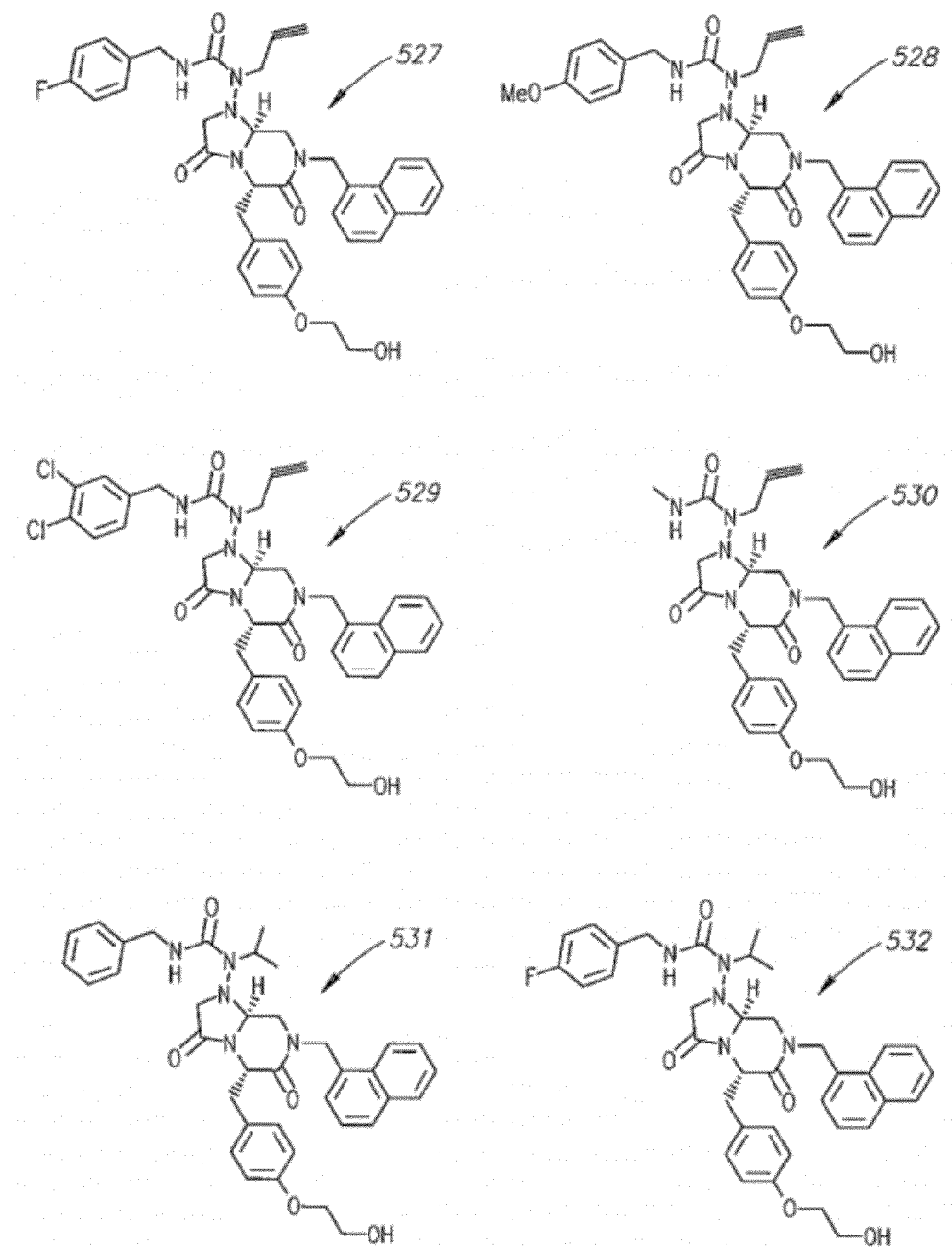
Figure 3U:
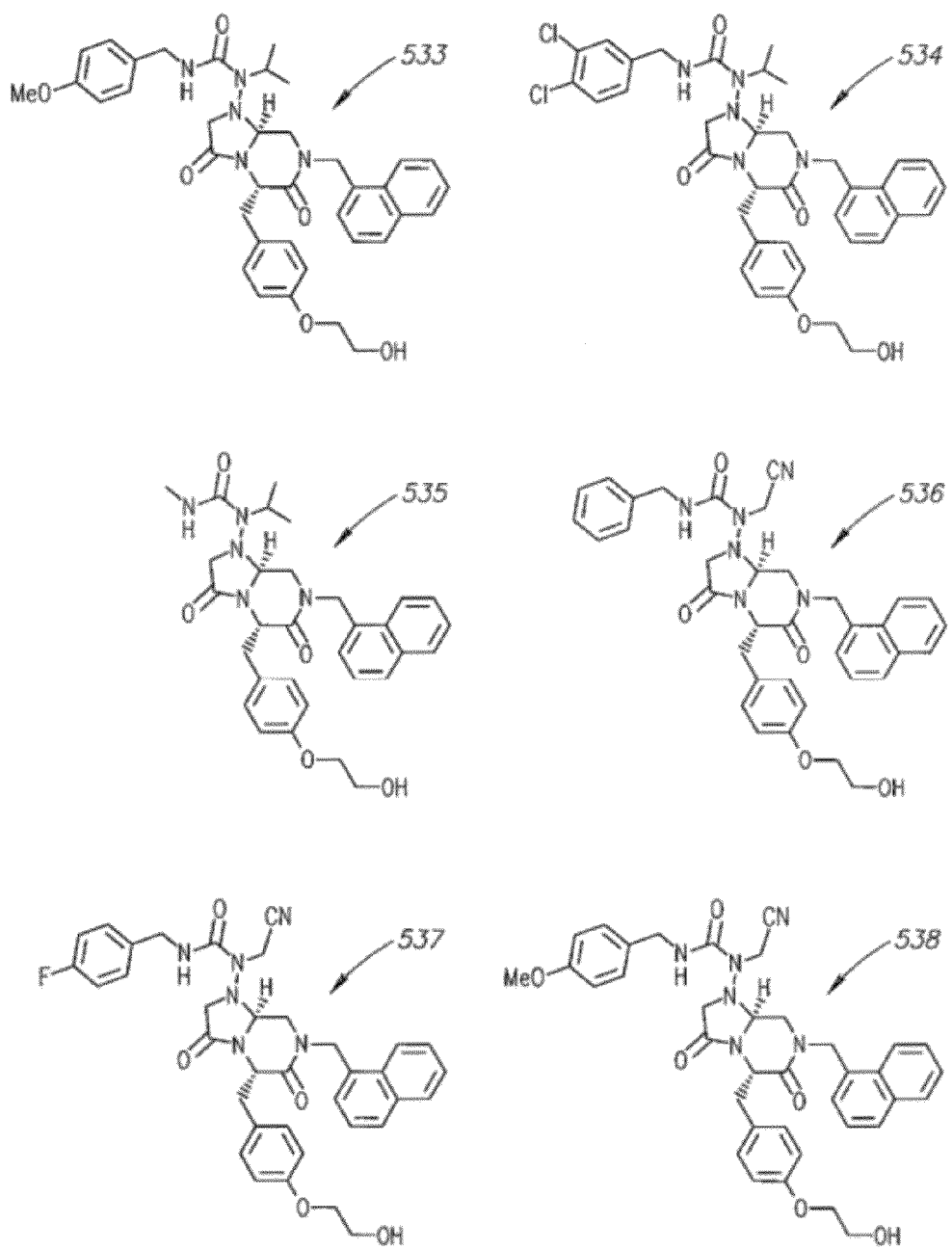
Figure 3V:
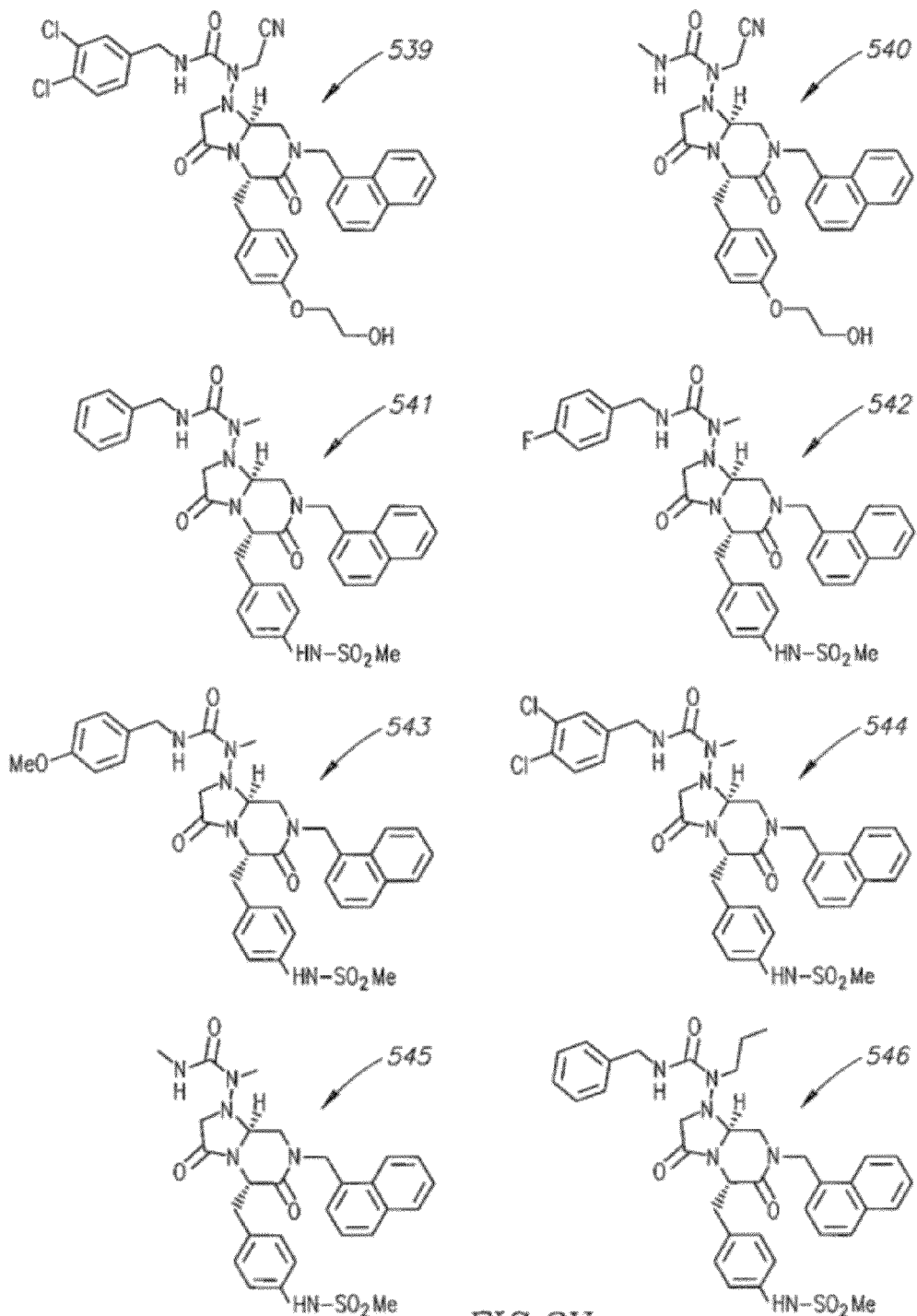
Figure 3W:
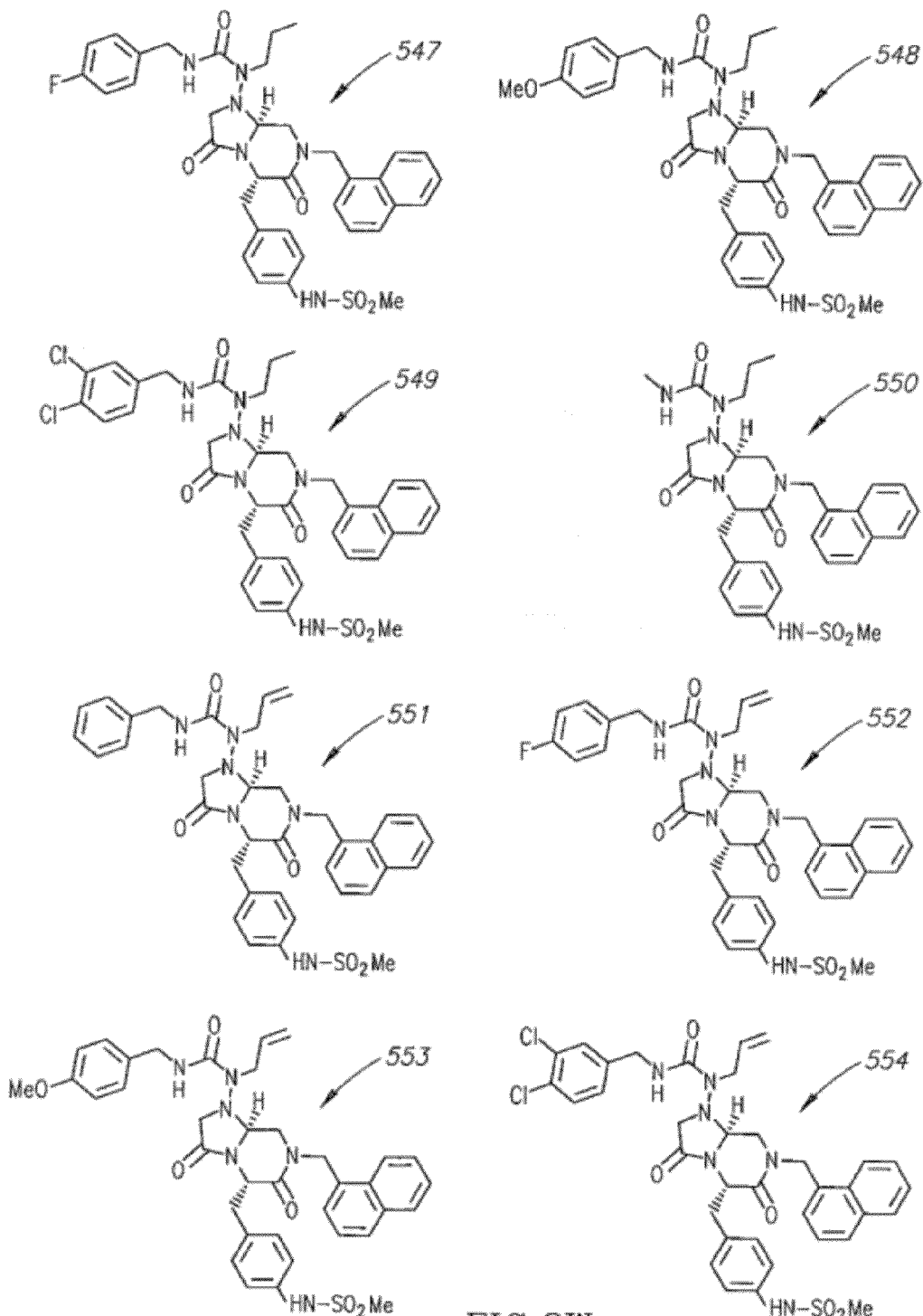
Figure 3X:
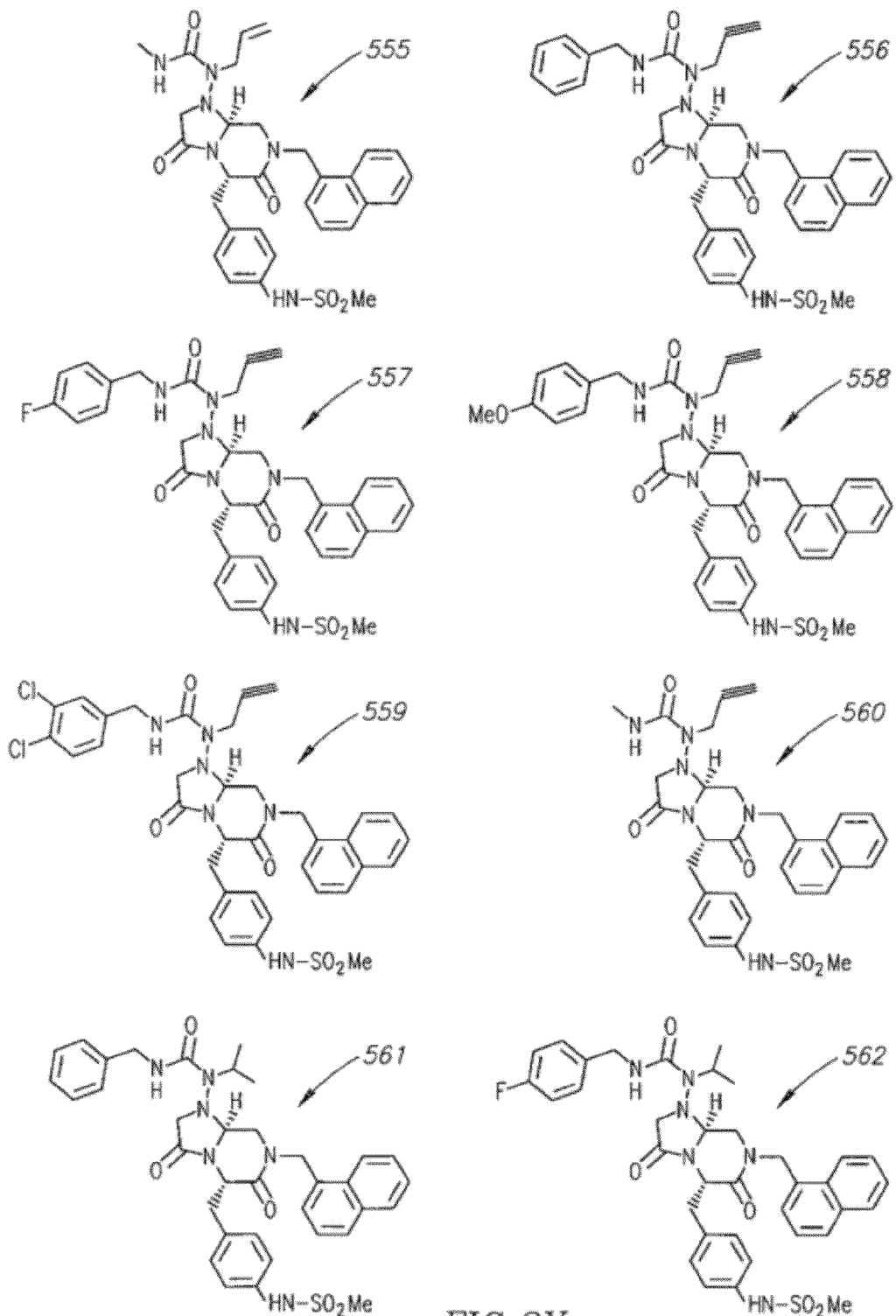
Figure 3Y:
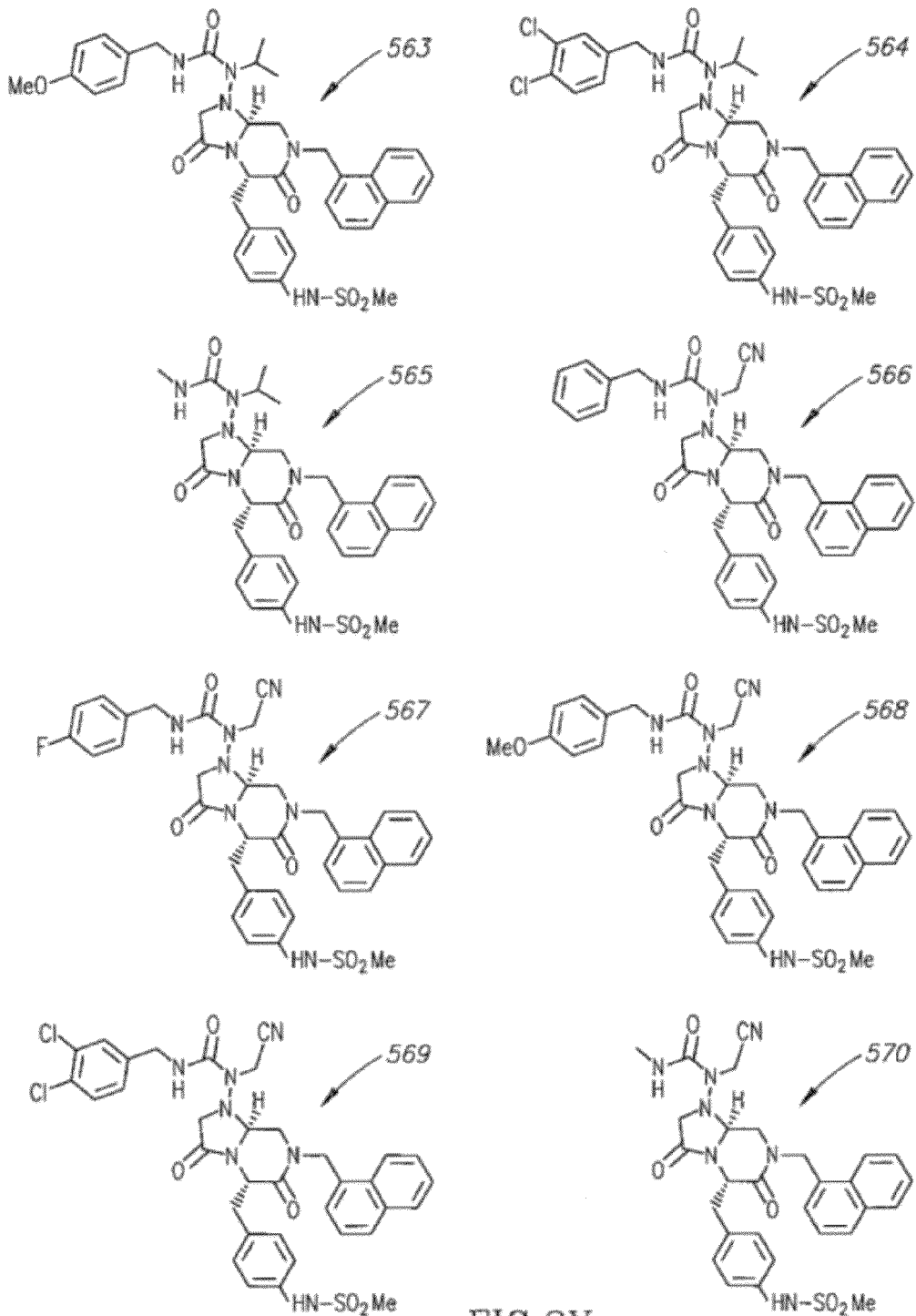
Figure 3Z:
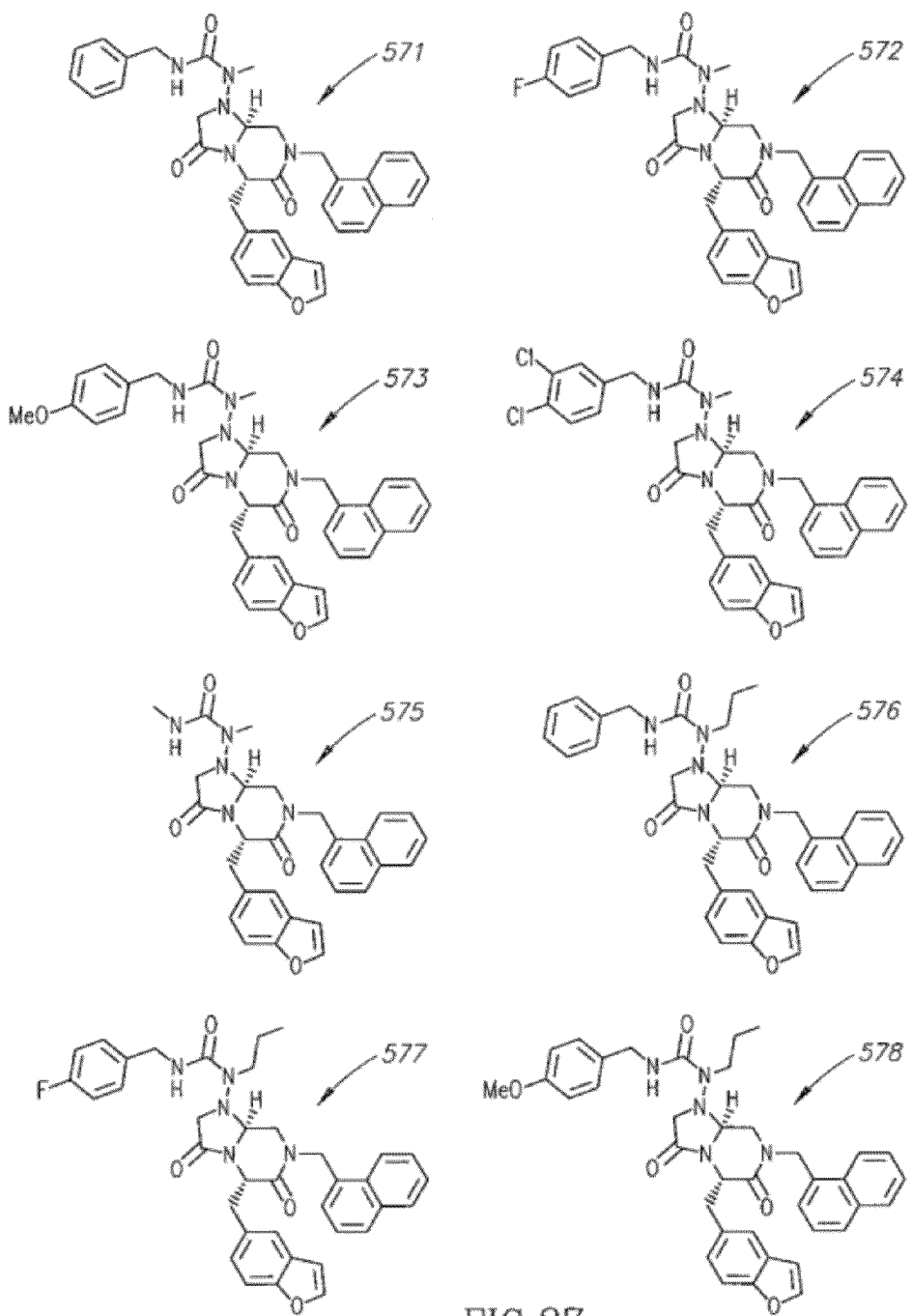
Figure 3A:
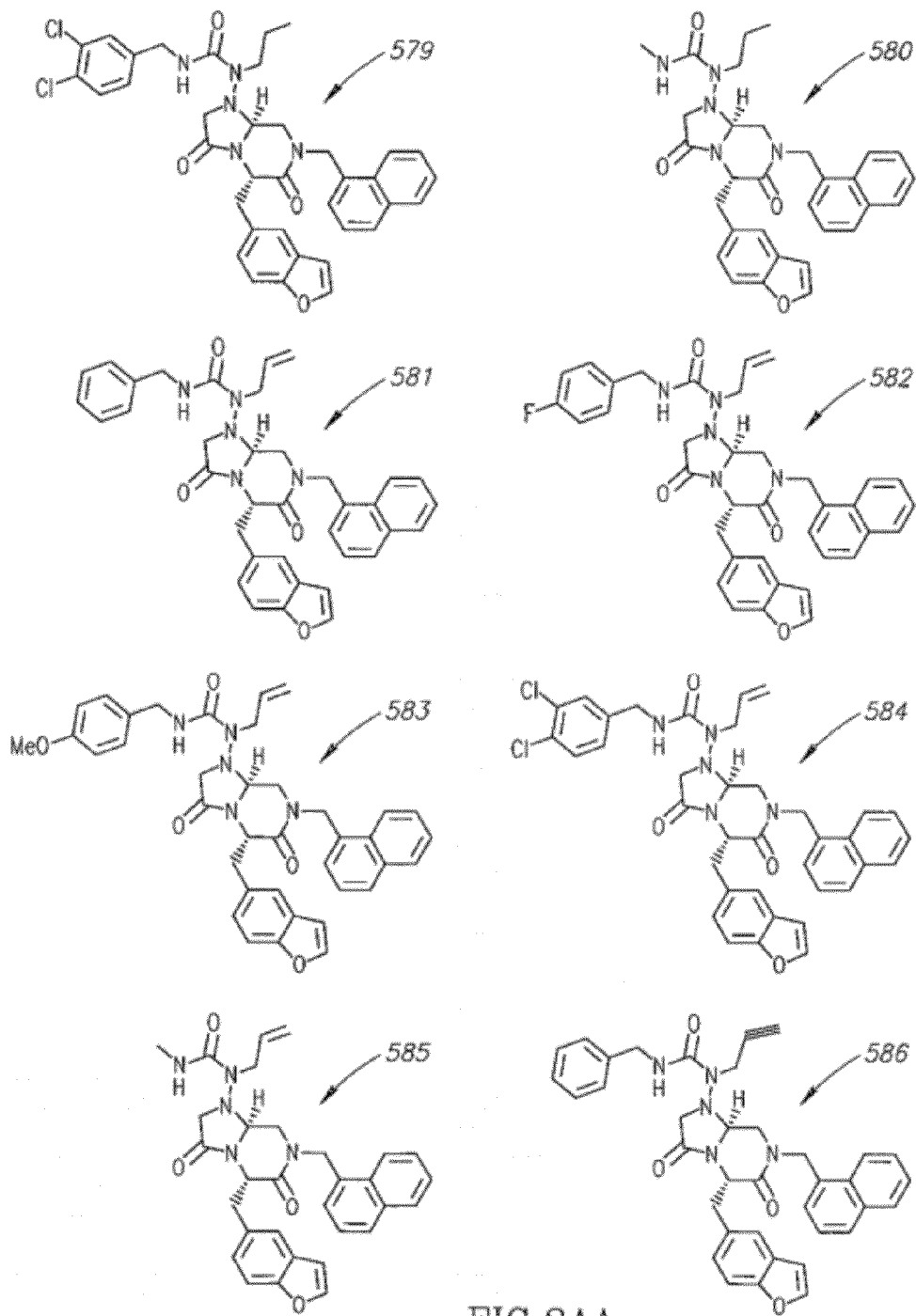
Figure 3A:
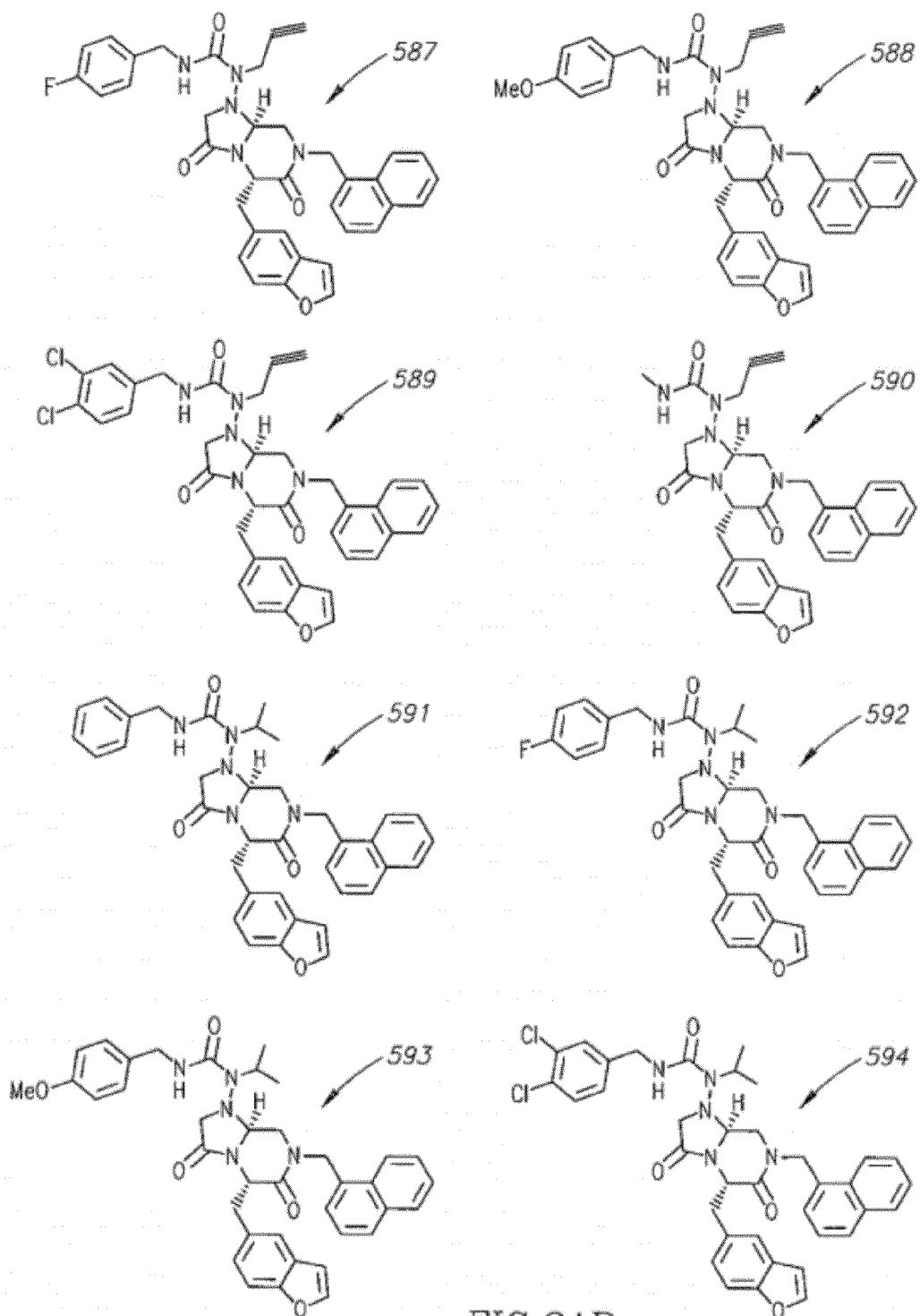
Figure 4A:
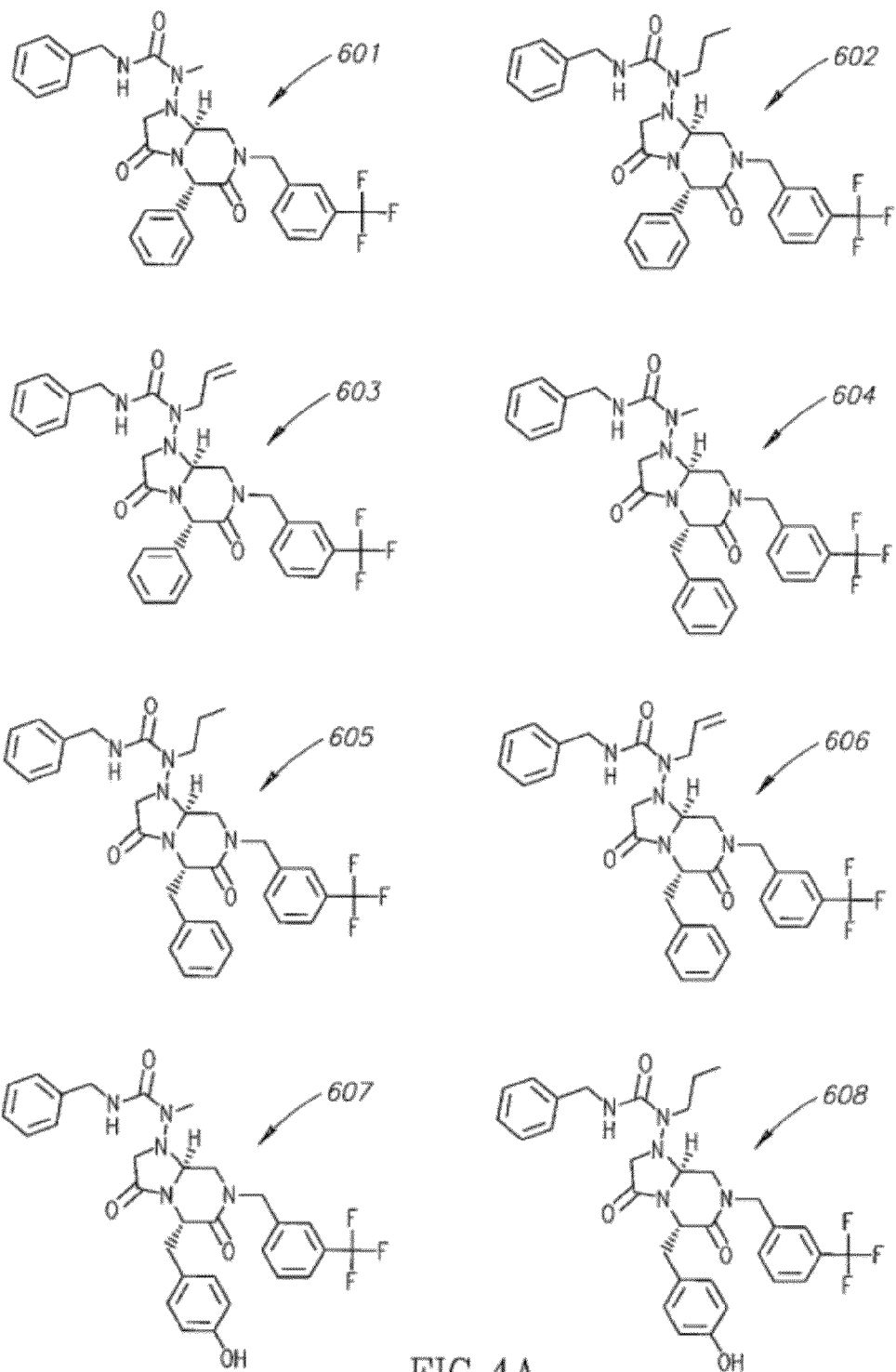
FIGS. 4A-4Y shows the chemical structures of compounds 601-800.
Figure 4B:
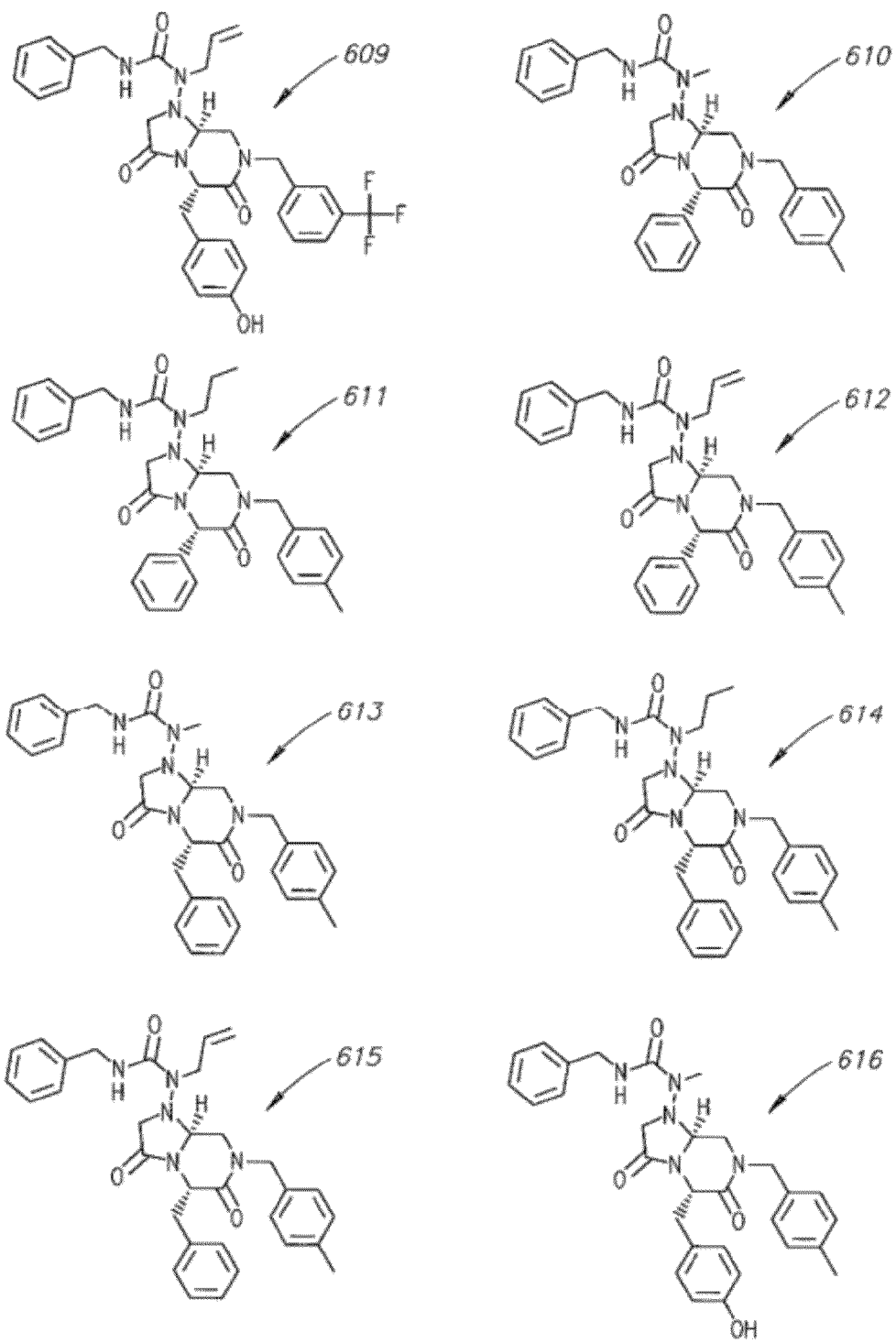
Figure 4C:
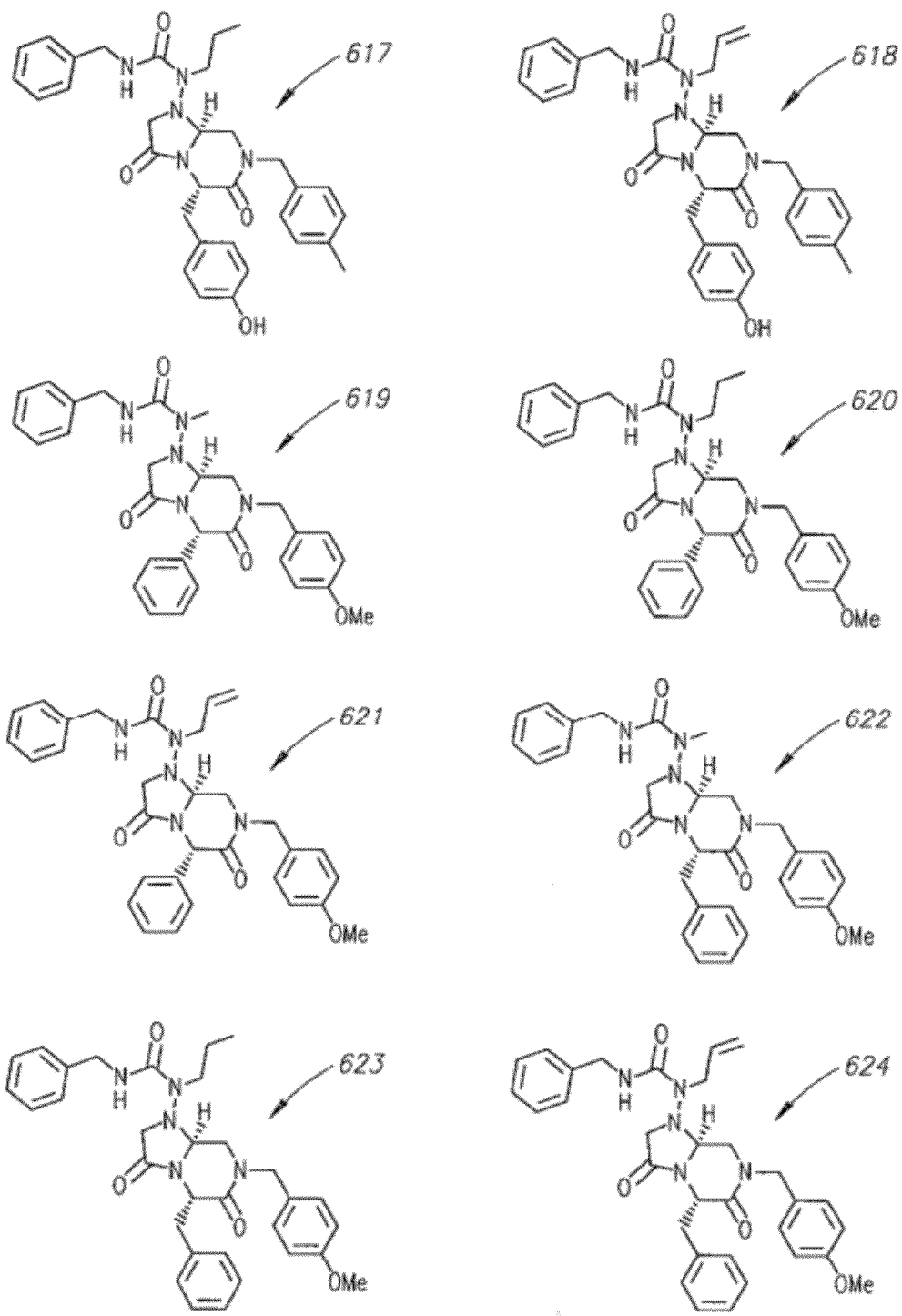
Figure 4D:
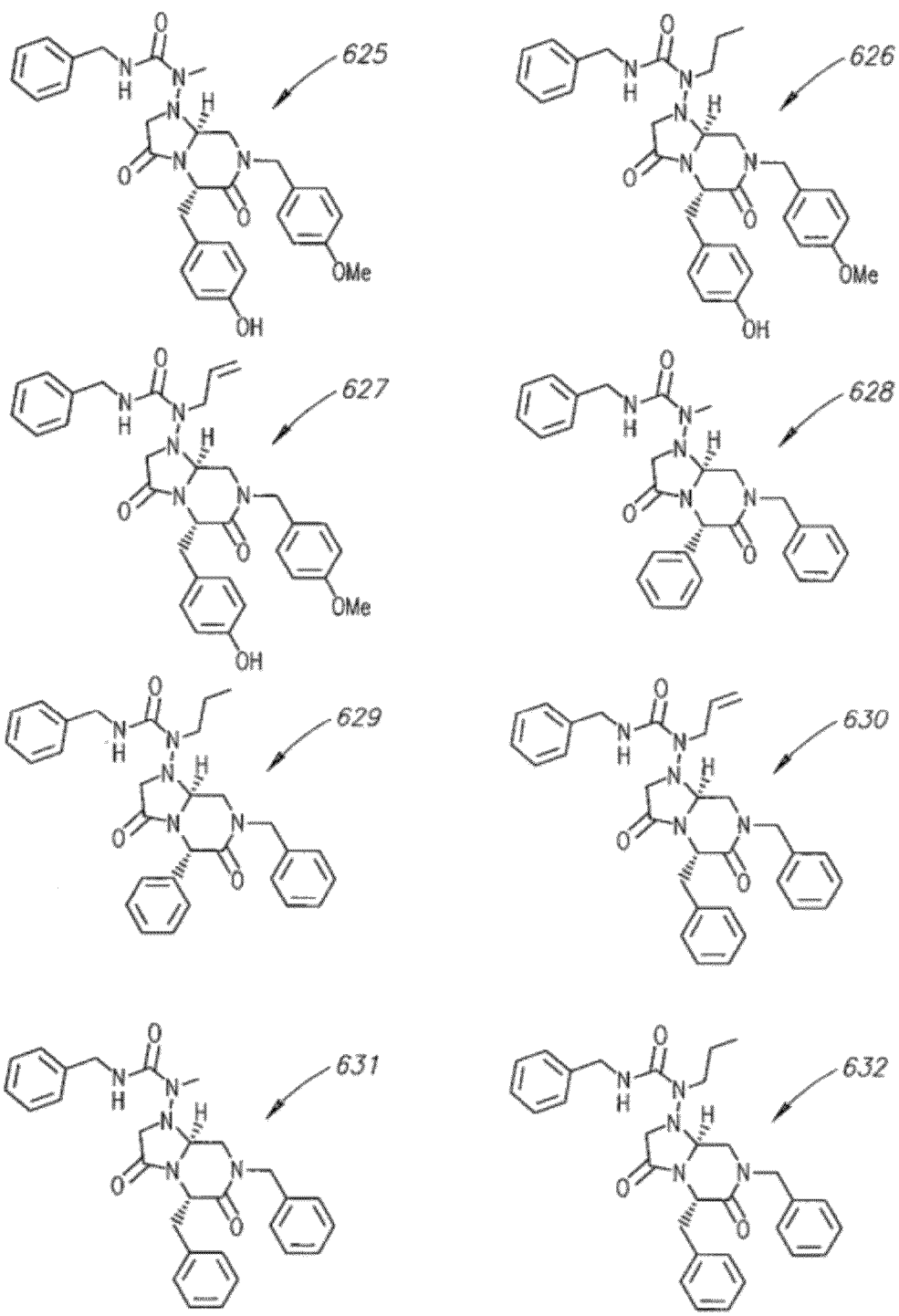
Figure 4E:
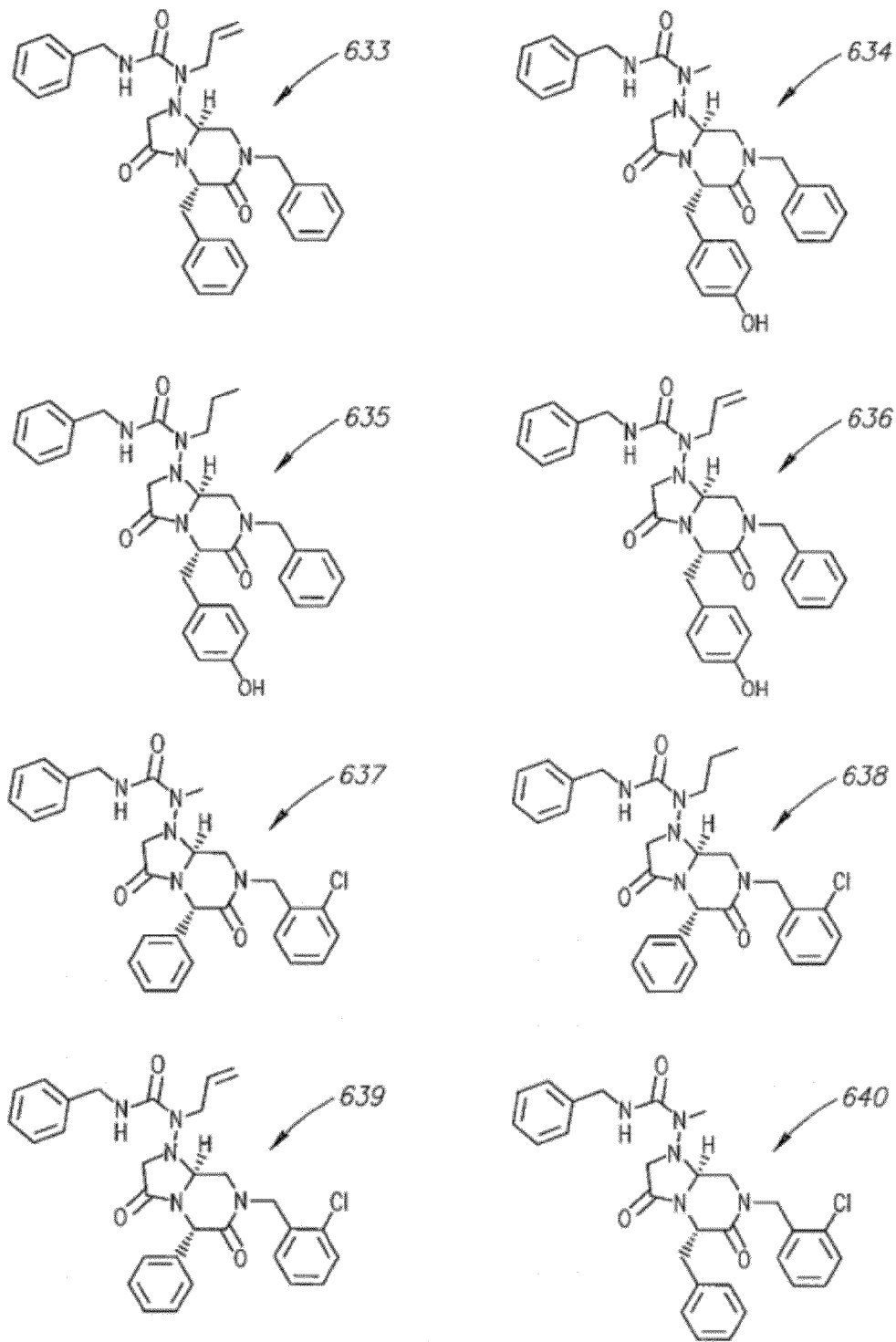
Figure 4F:
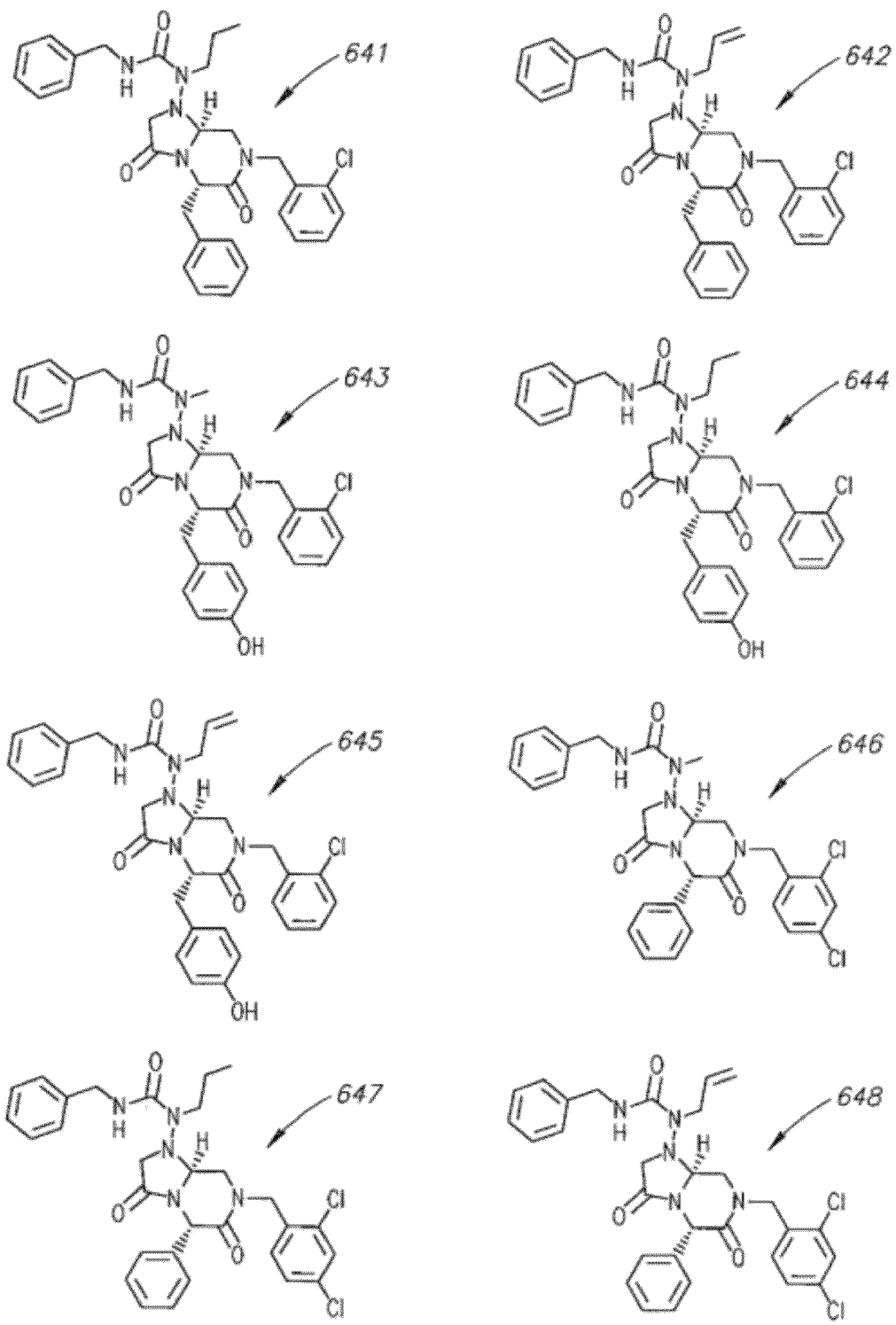
Figure 4I:
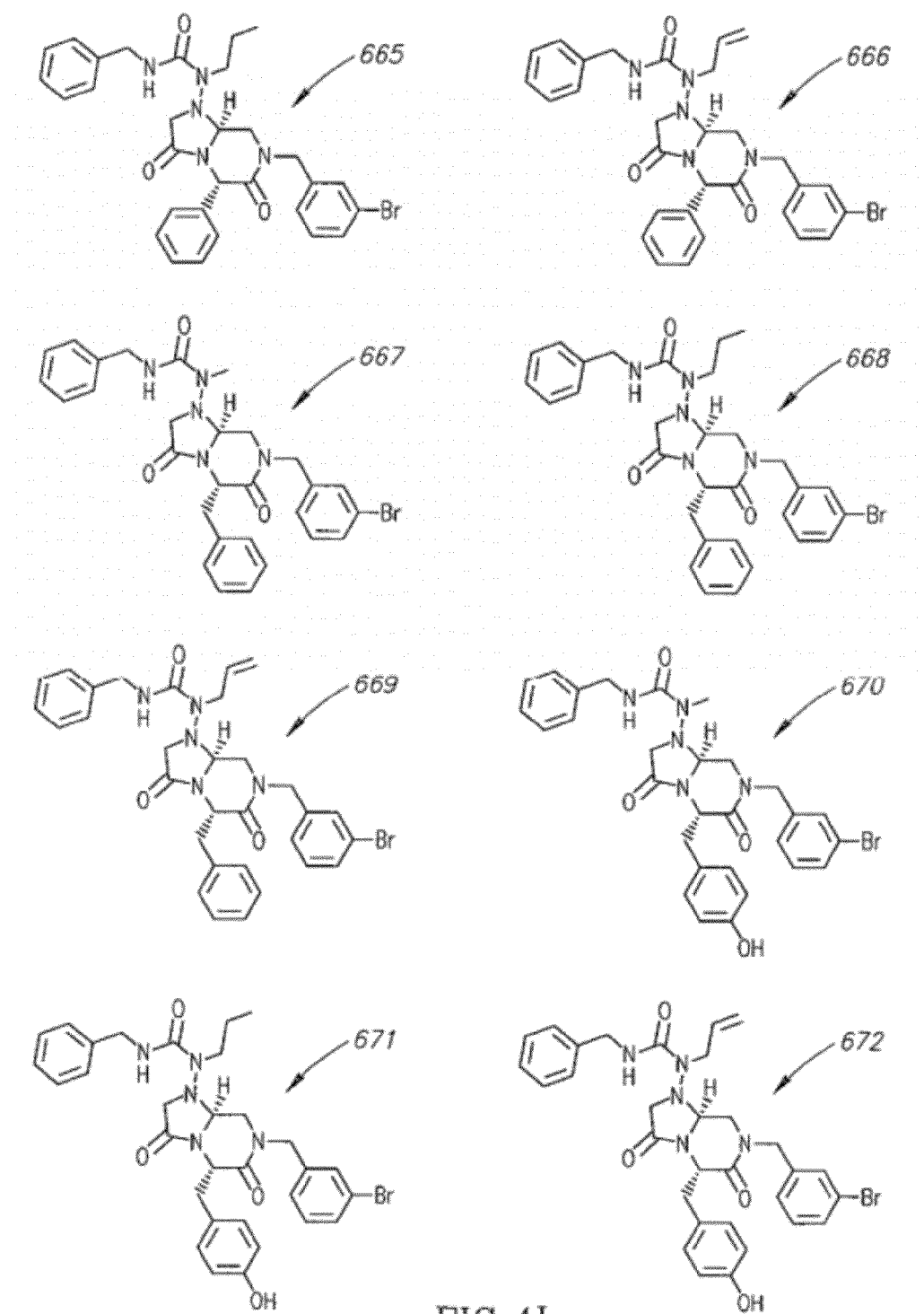
Figure 4J:
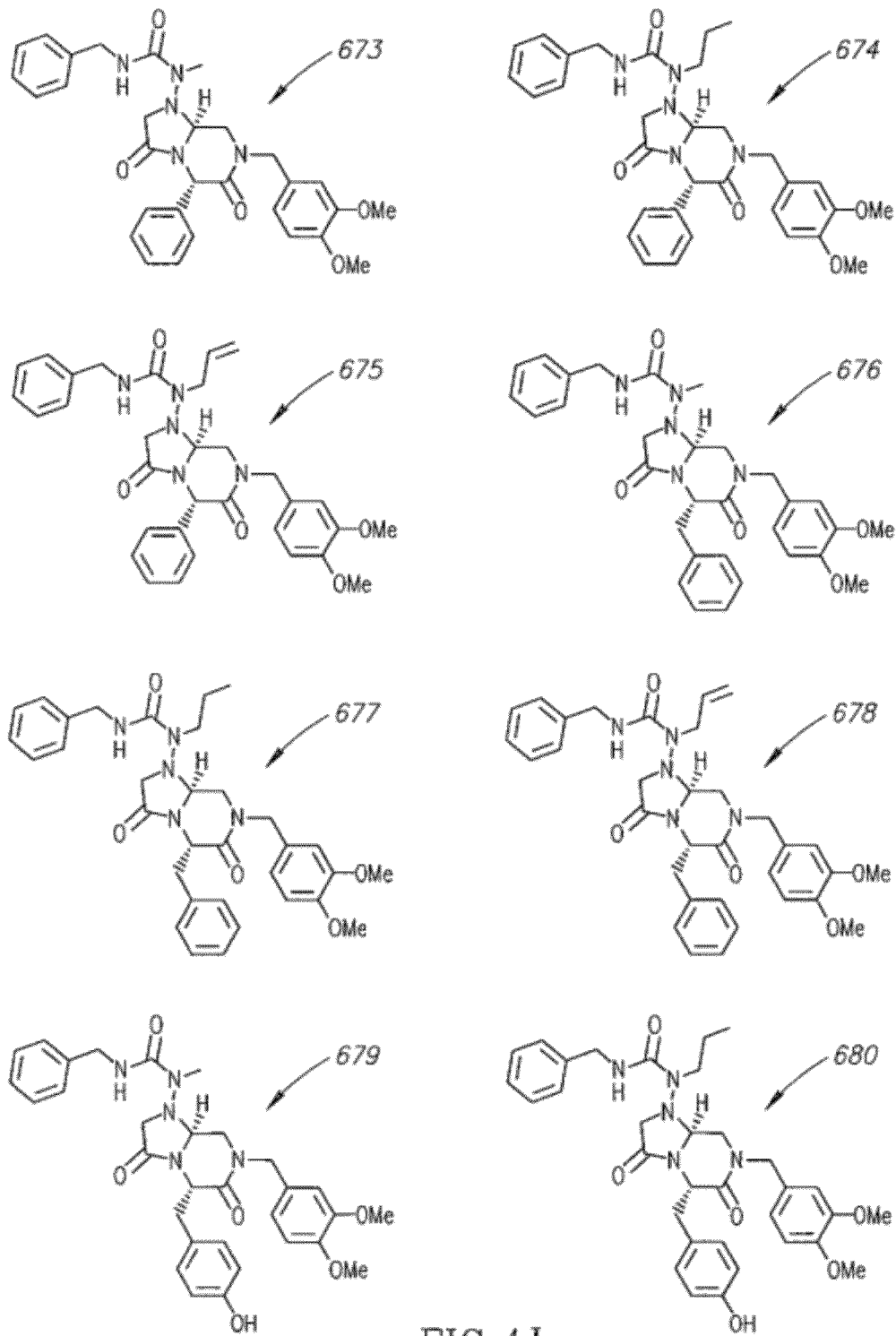
Figure 4K:
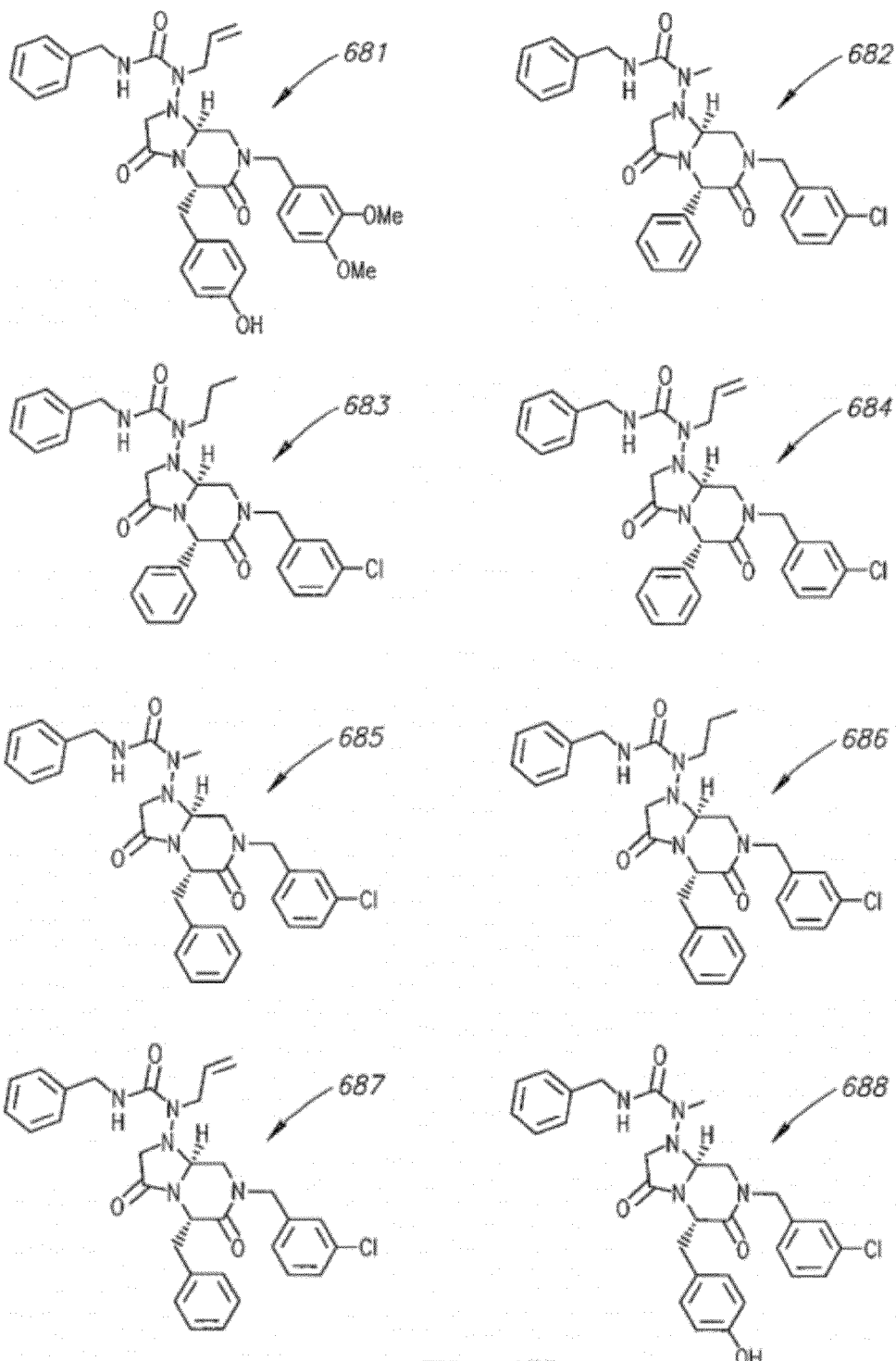
Figure 4L:
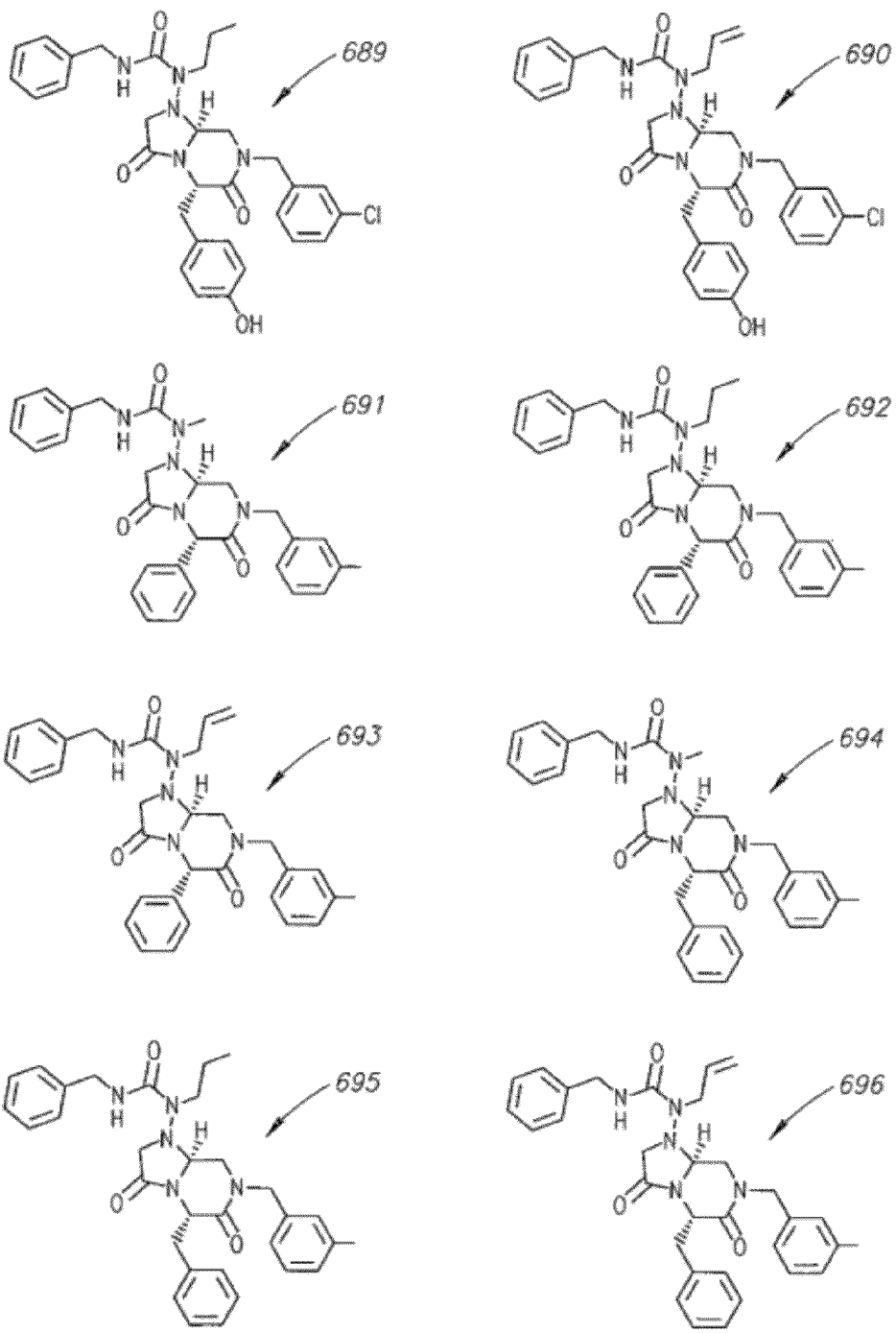
Figure 4M:
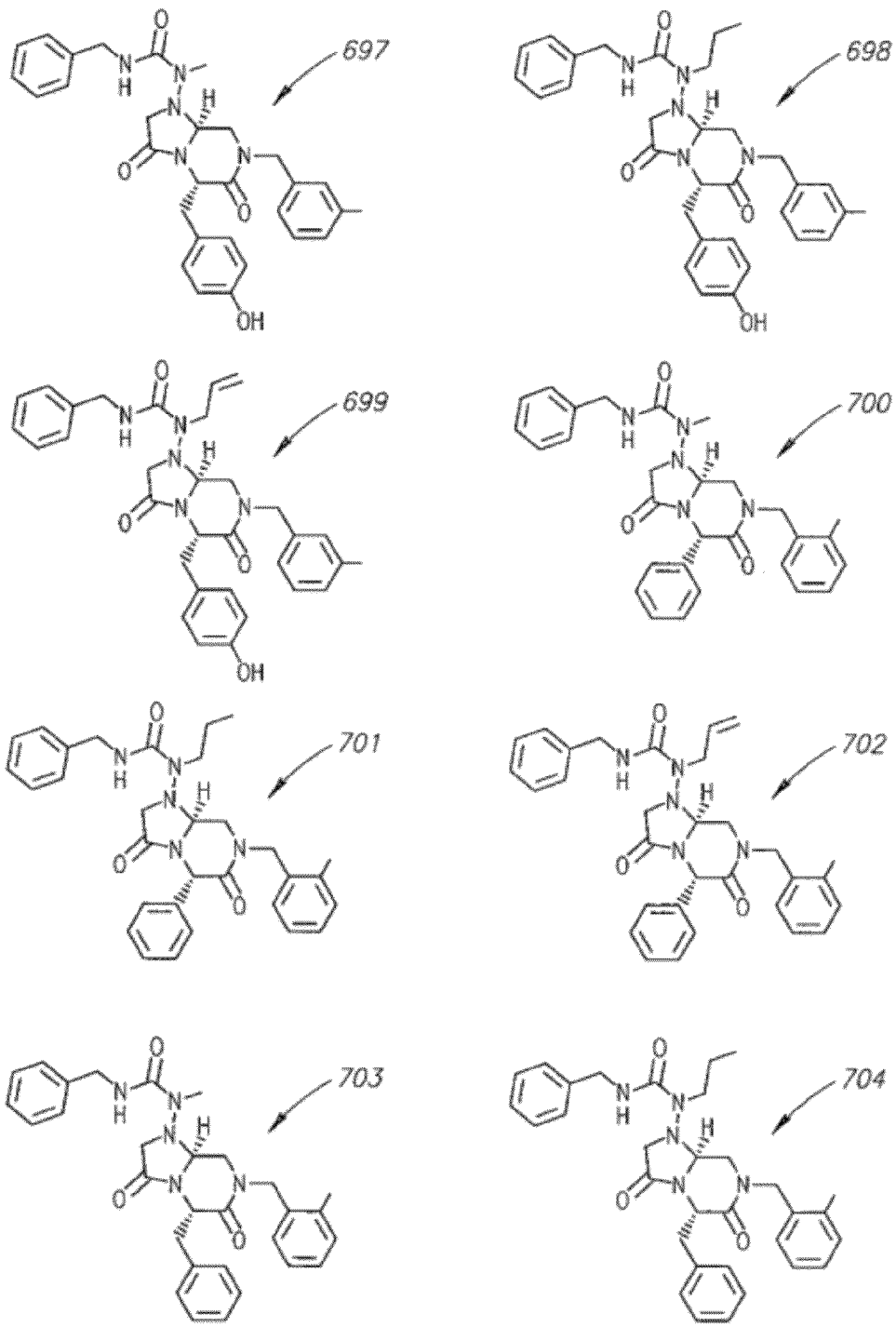
Figure 4N:
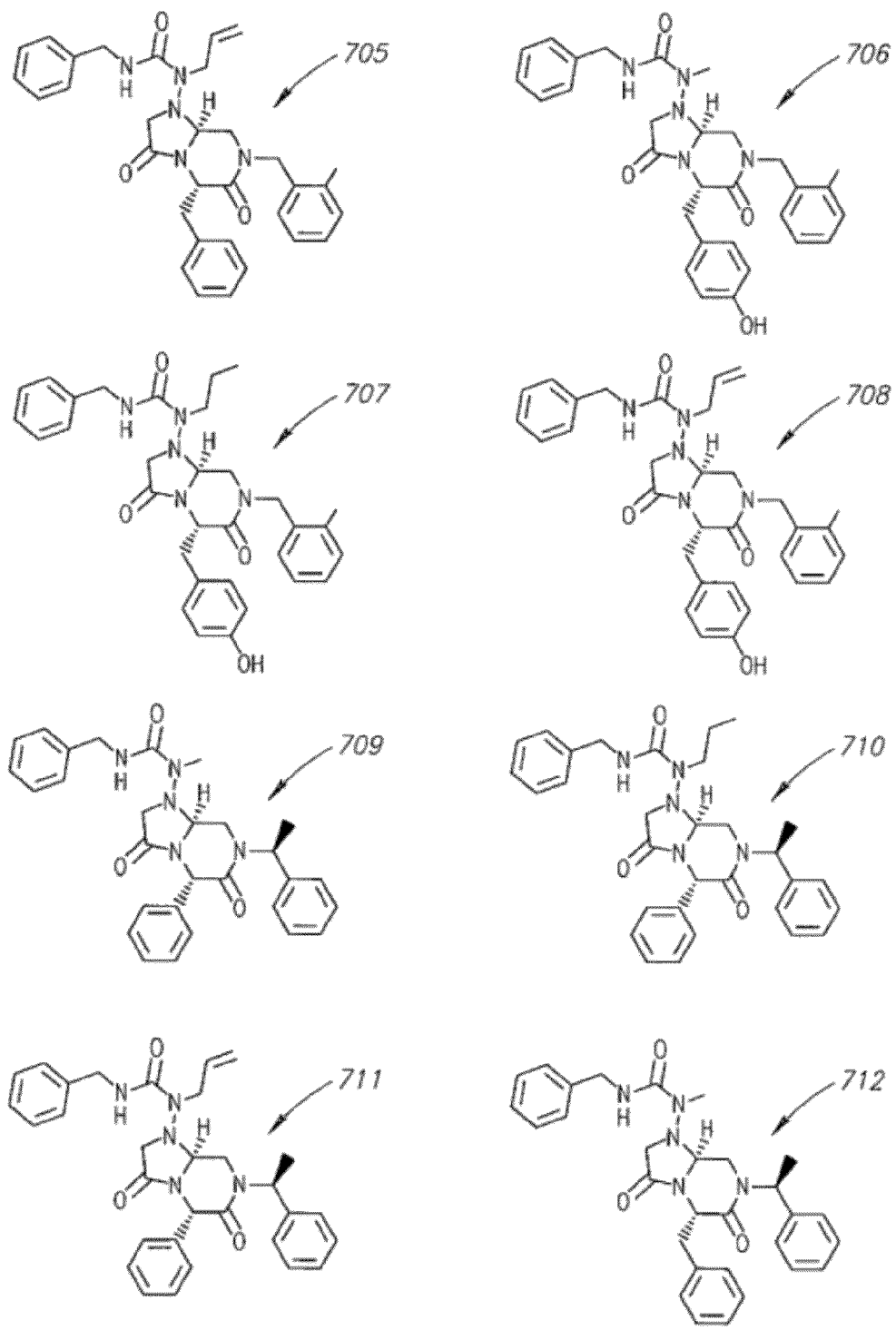
Figure 40:
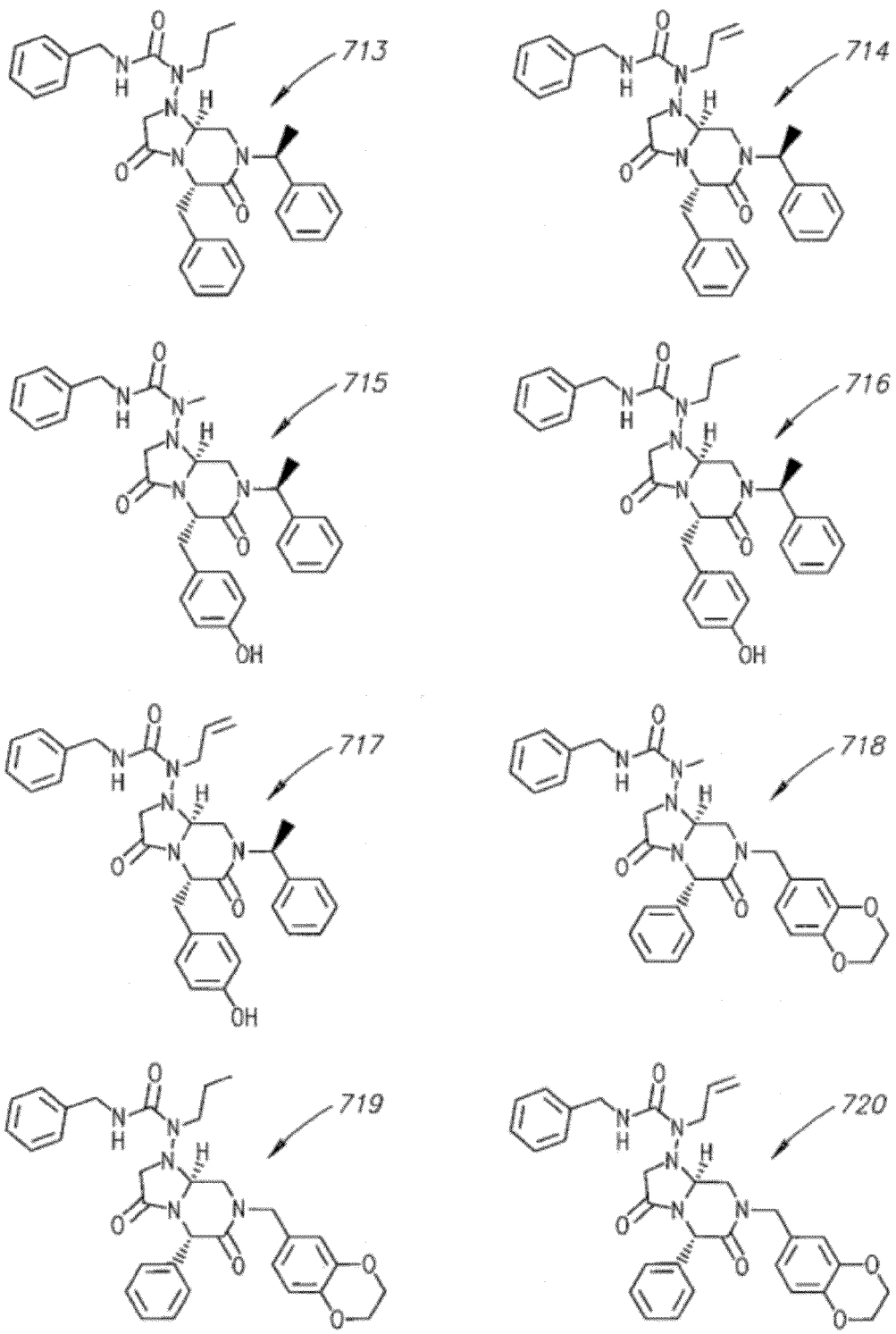
Figure 4Q:
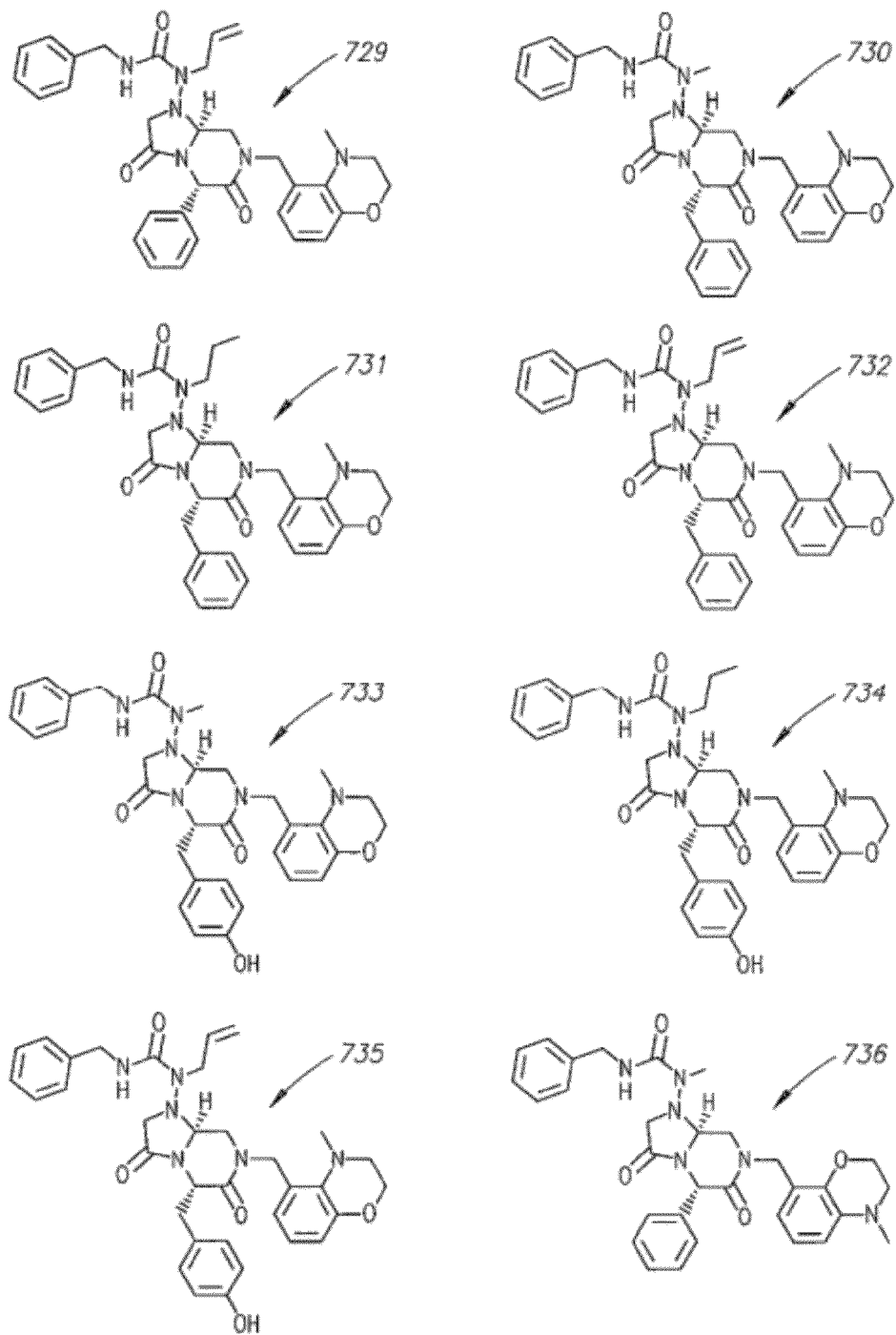
Figure 4V:
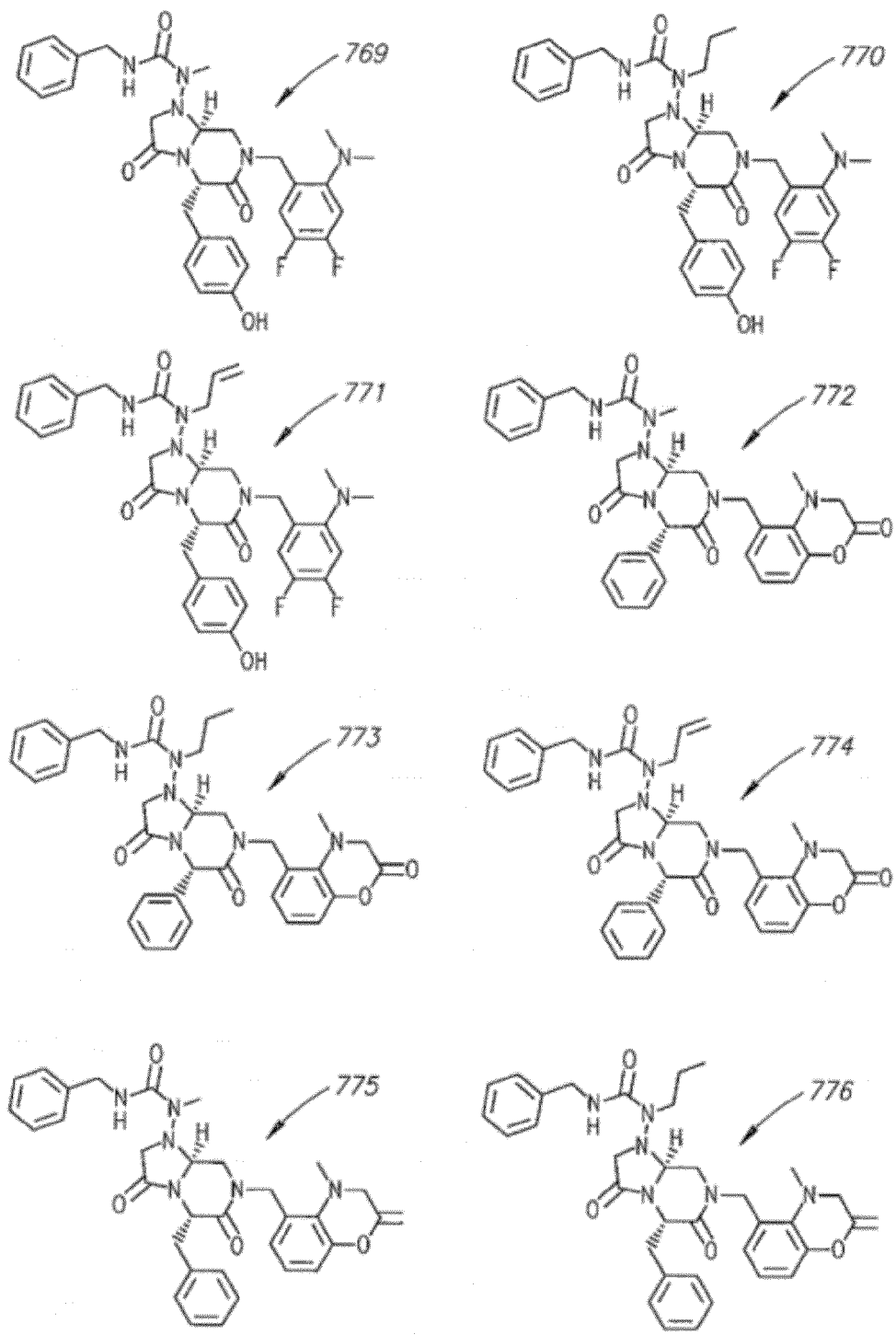
Figure 4W:
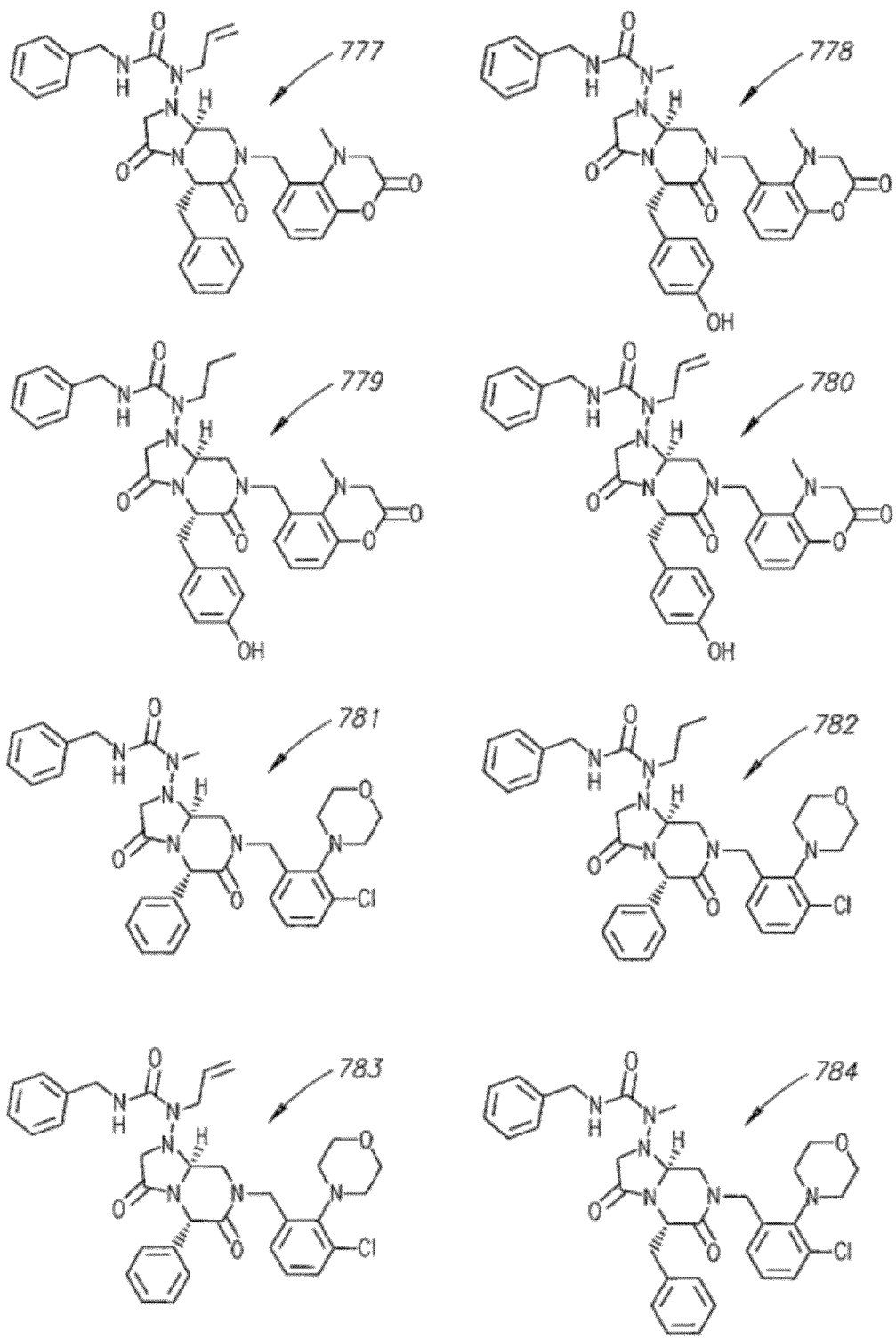
Figure 4X:
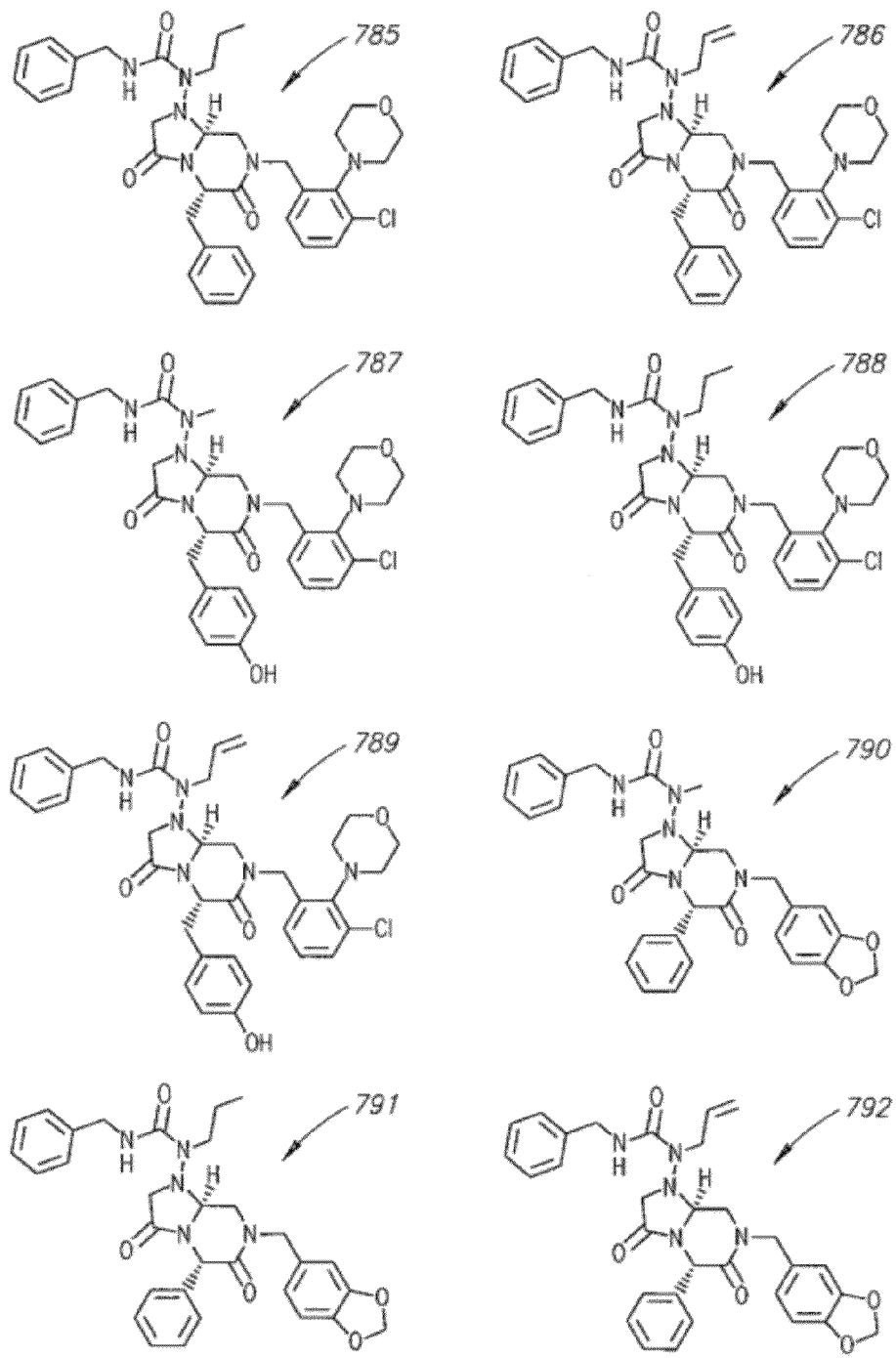
Figure 4Y:
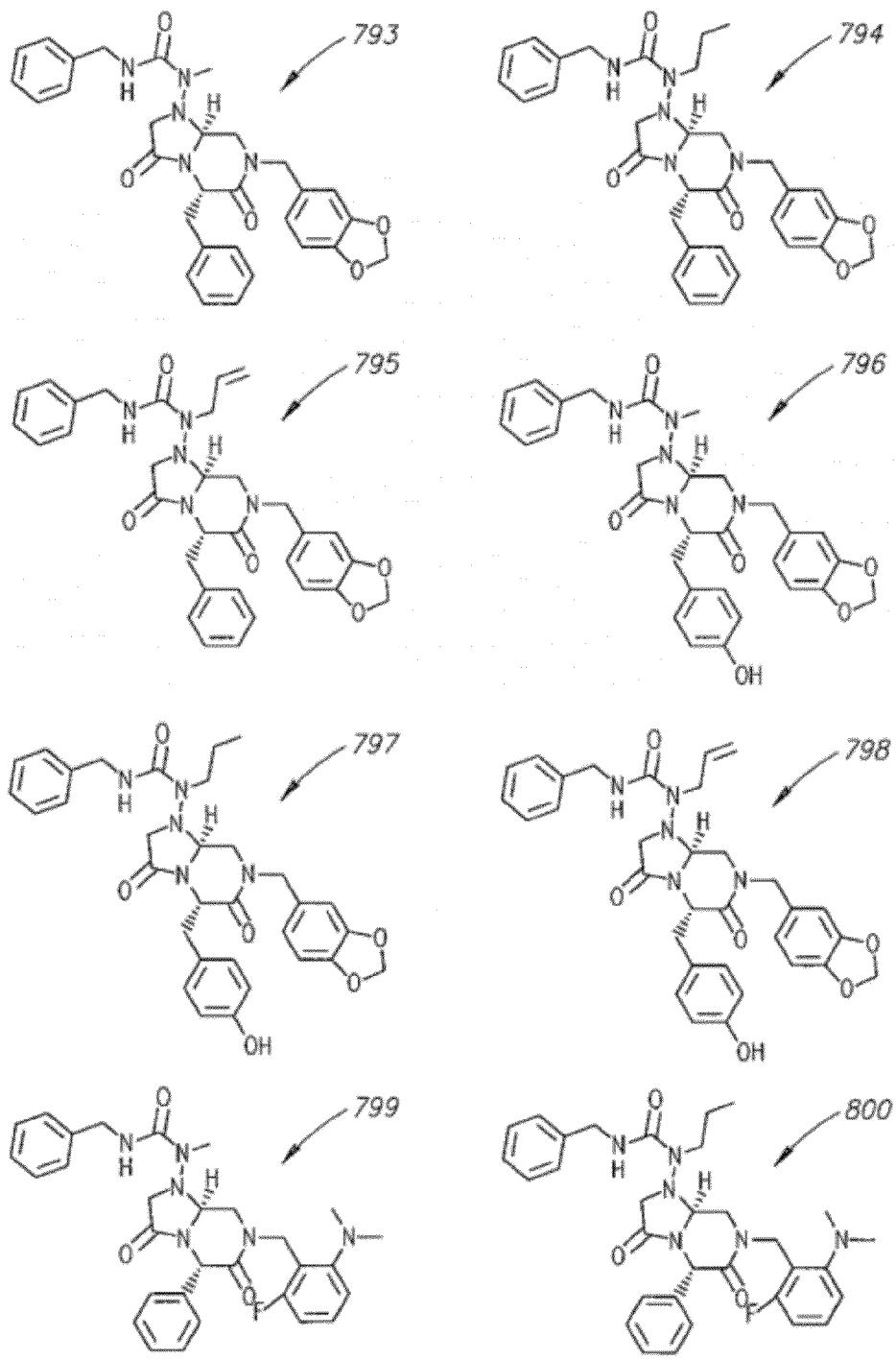
Figure 5A:
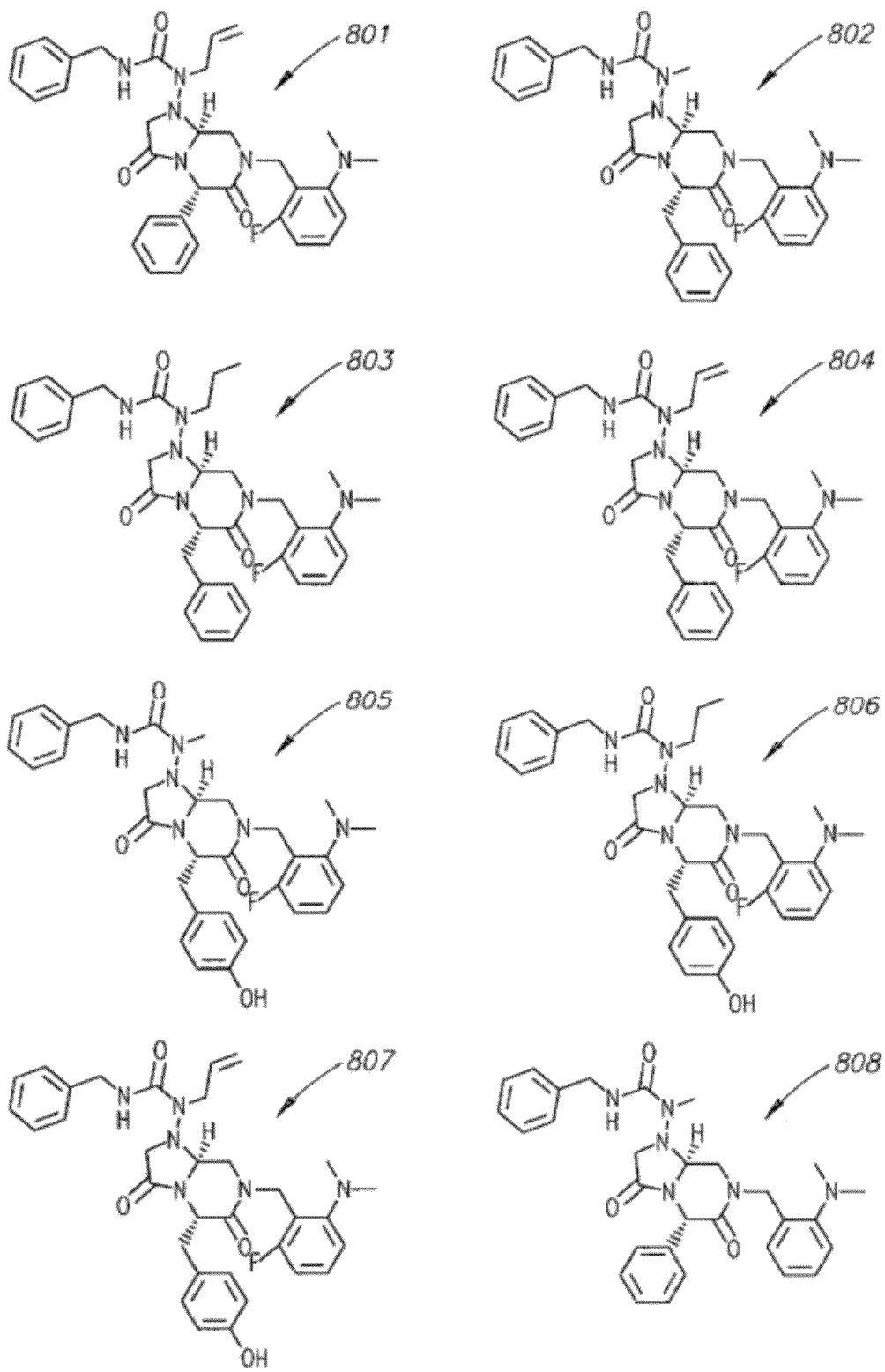
FIGS. 5A-5Y shows the chemical structures of compounds 801-1000.
Figure 5B:
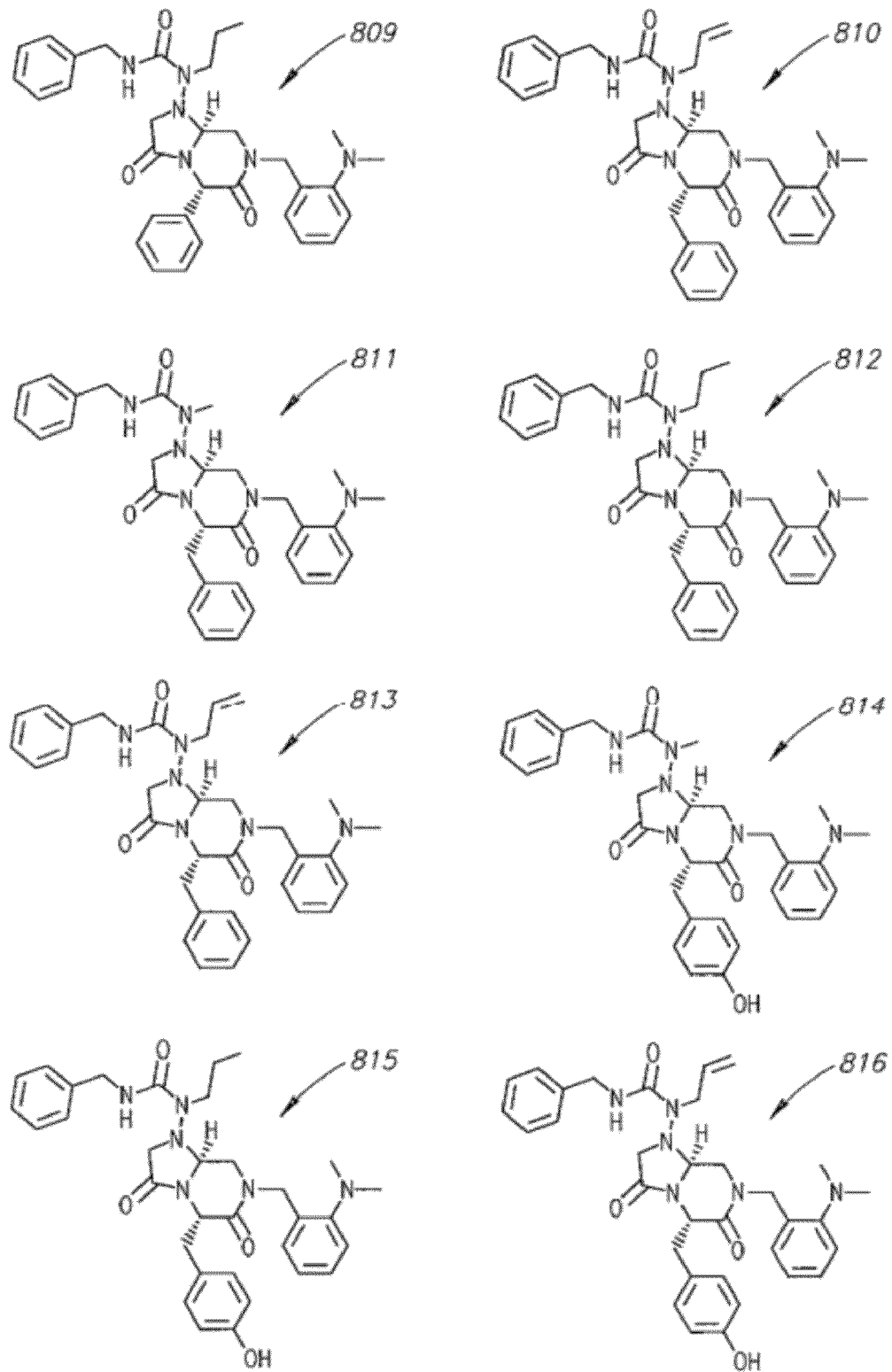
Figure 5C:
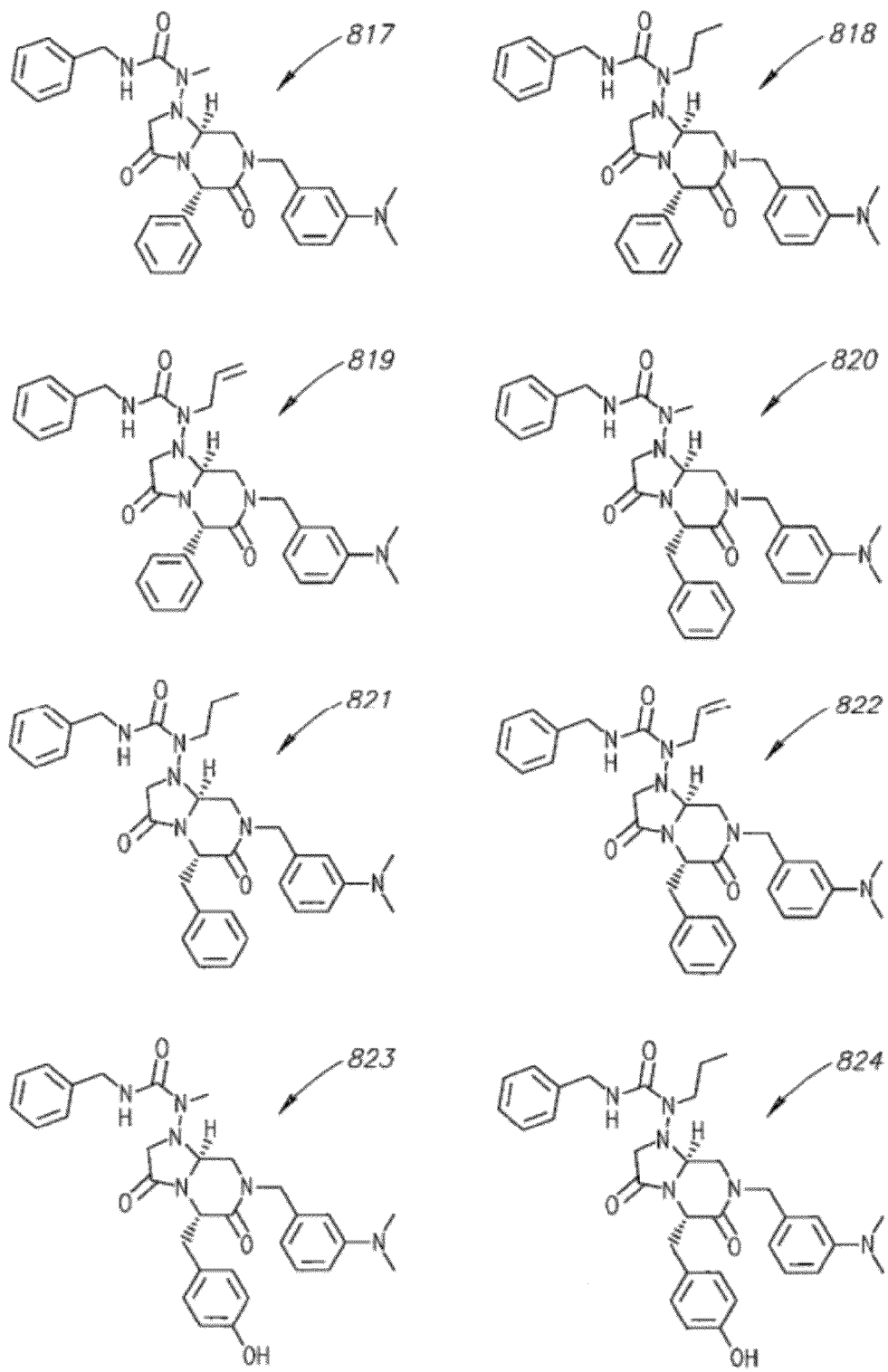
Figure 5D:
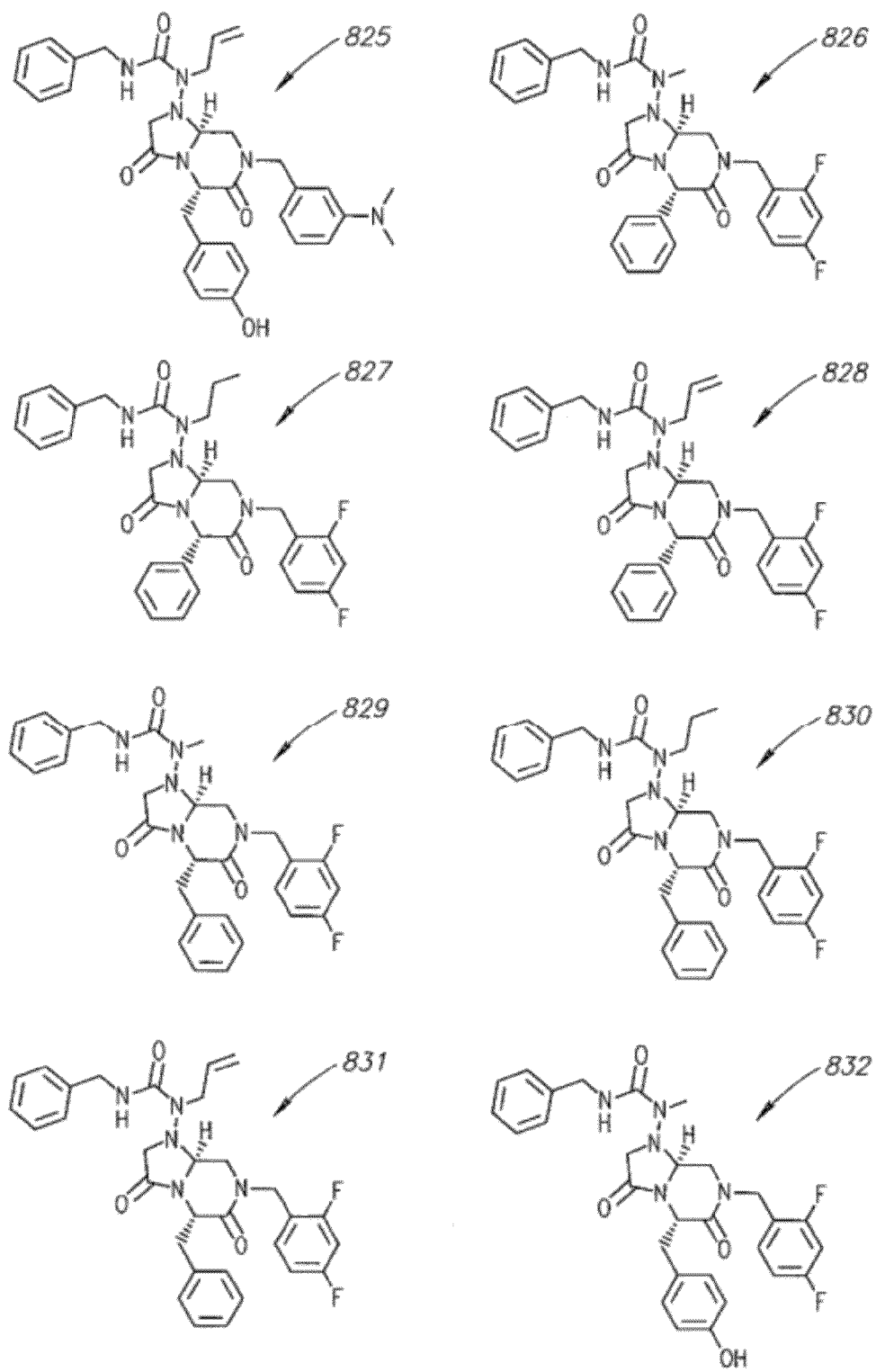
Figure 5E:
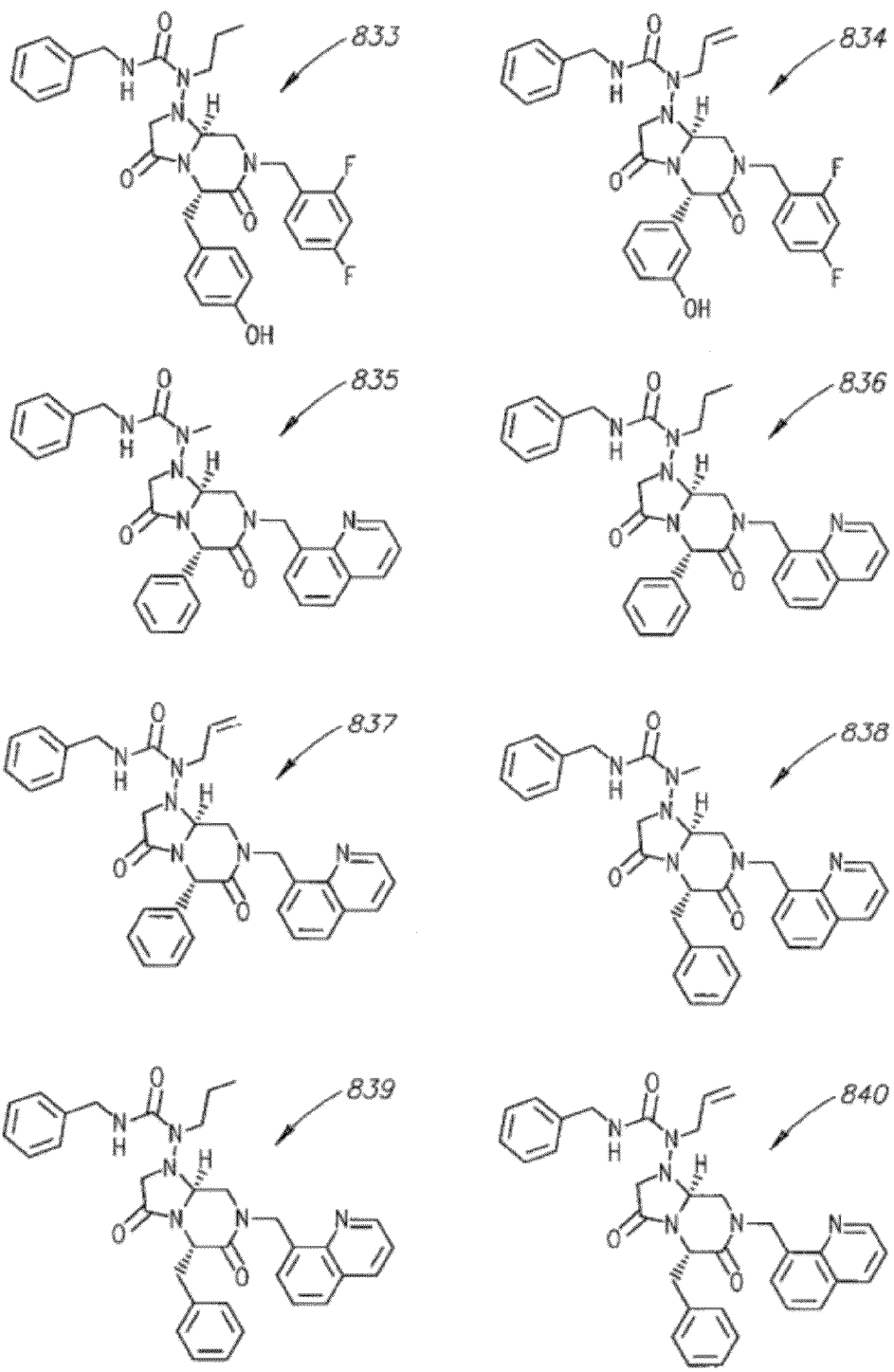
Figure 5F:
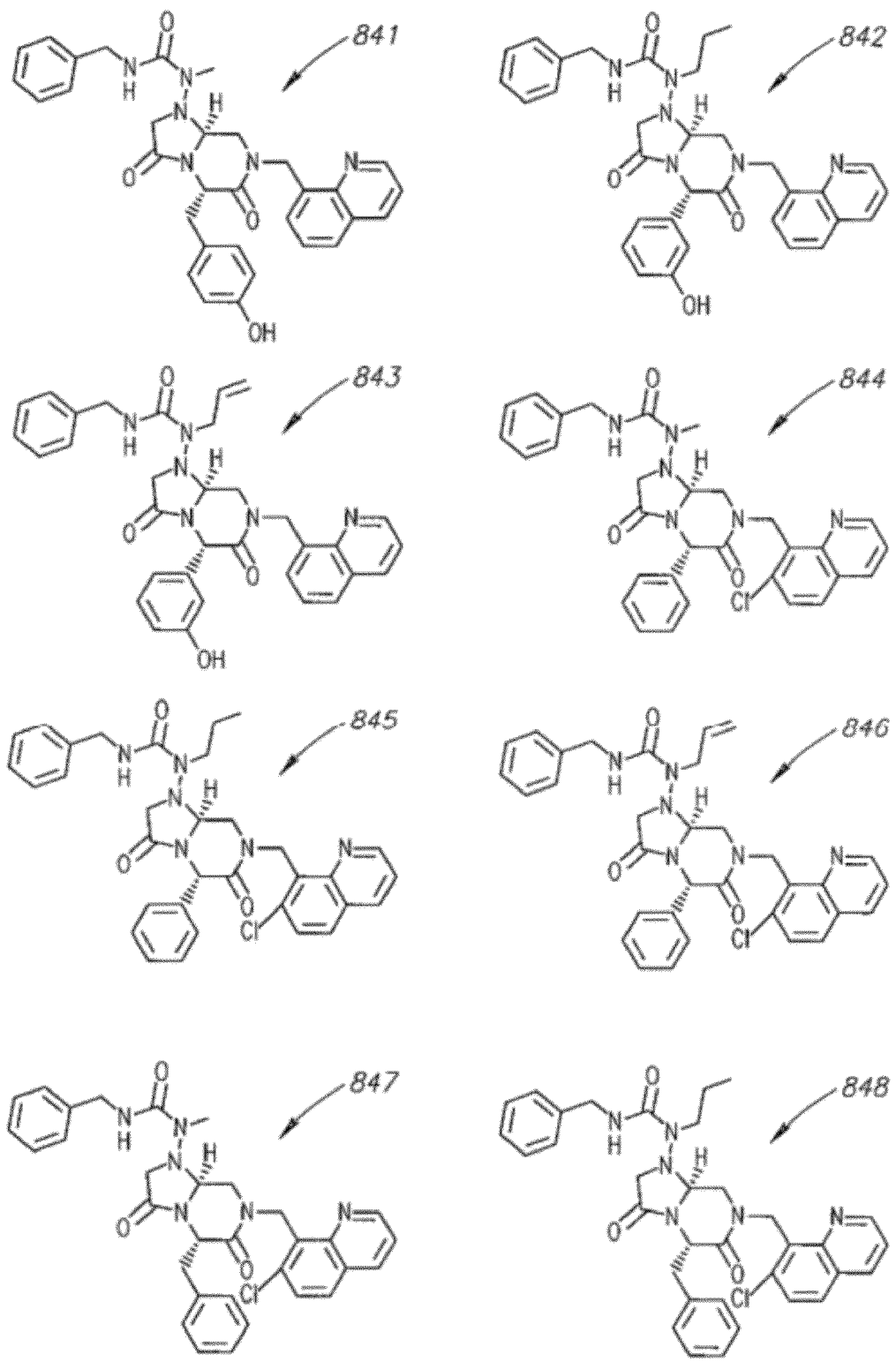
Figure 5G:
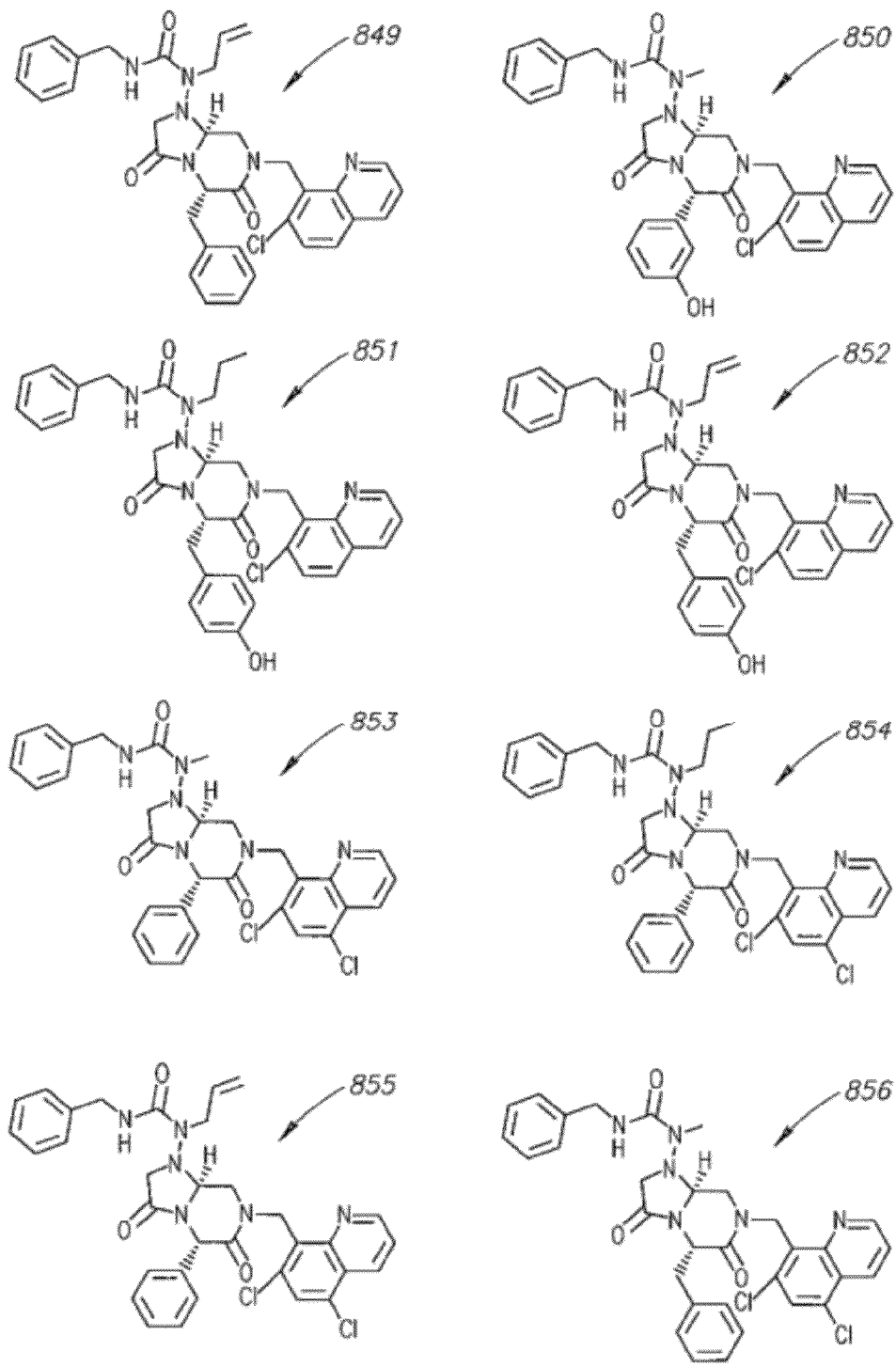
Figure 5H:
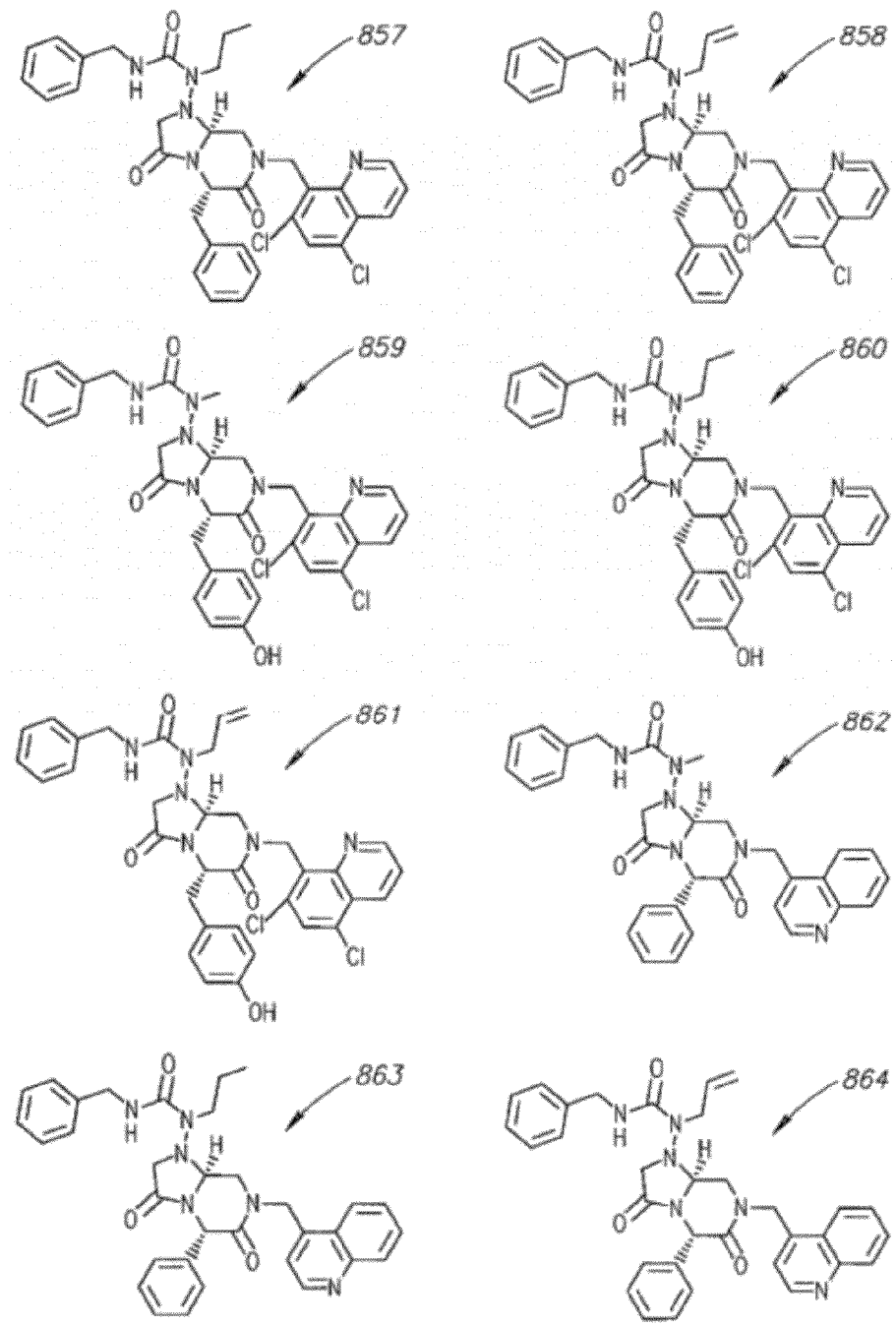
Figure 5I:
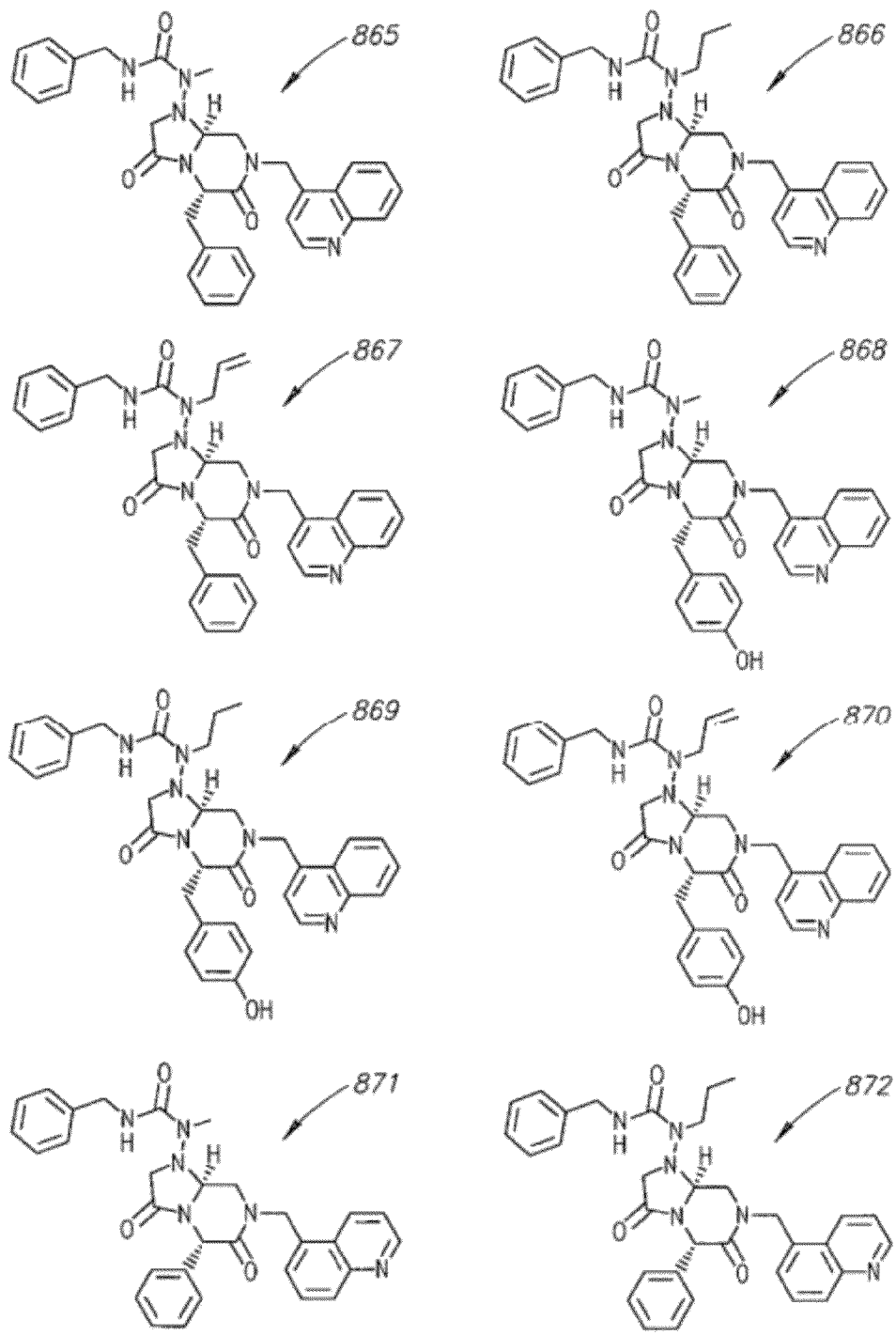
Figure 5J:
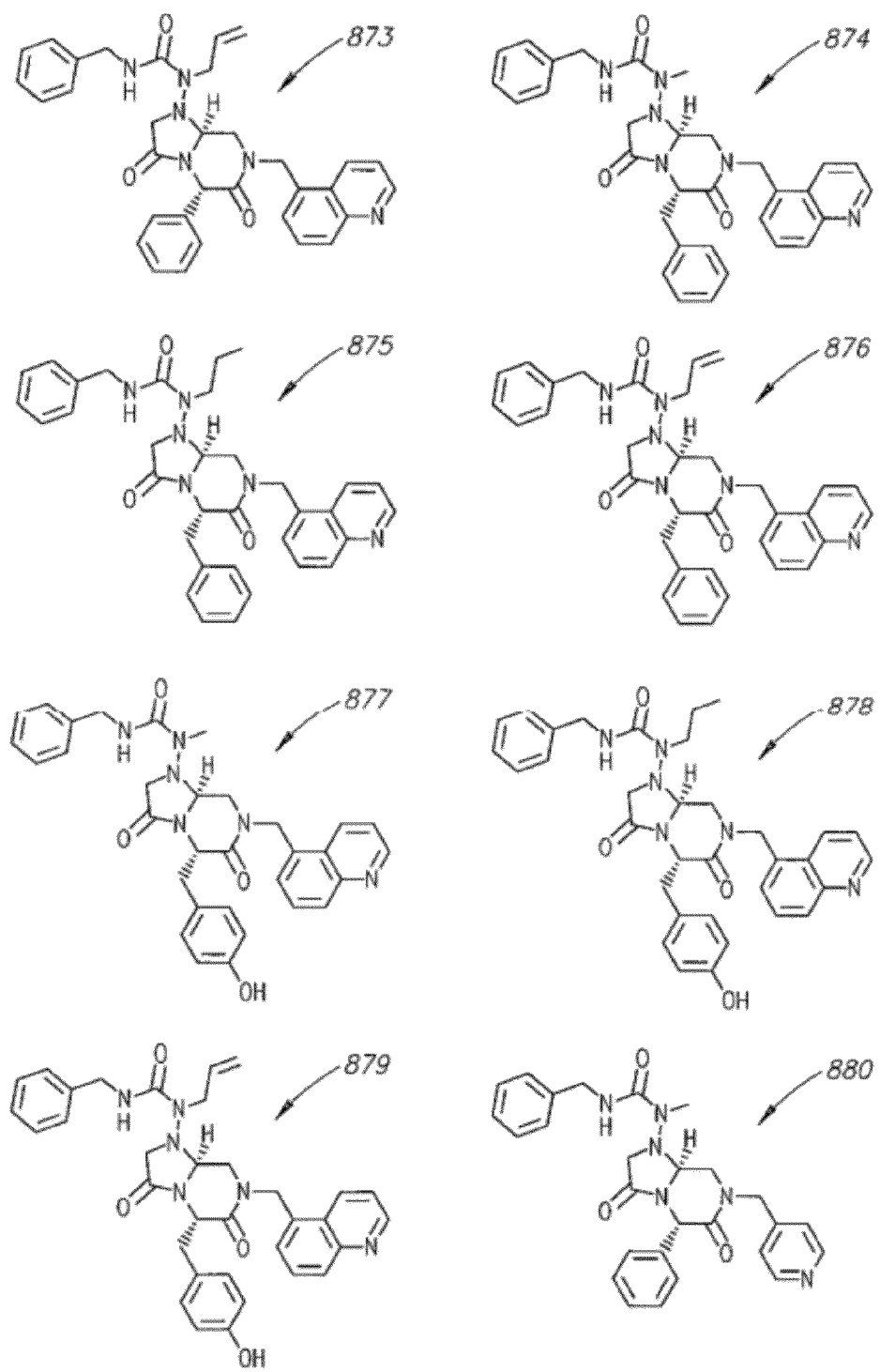
Figure 5K:
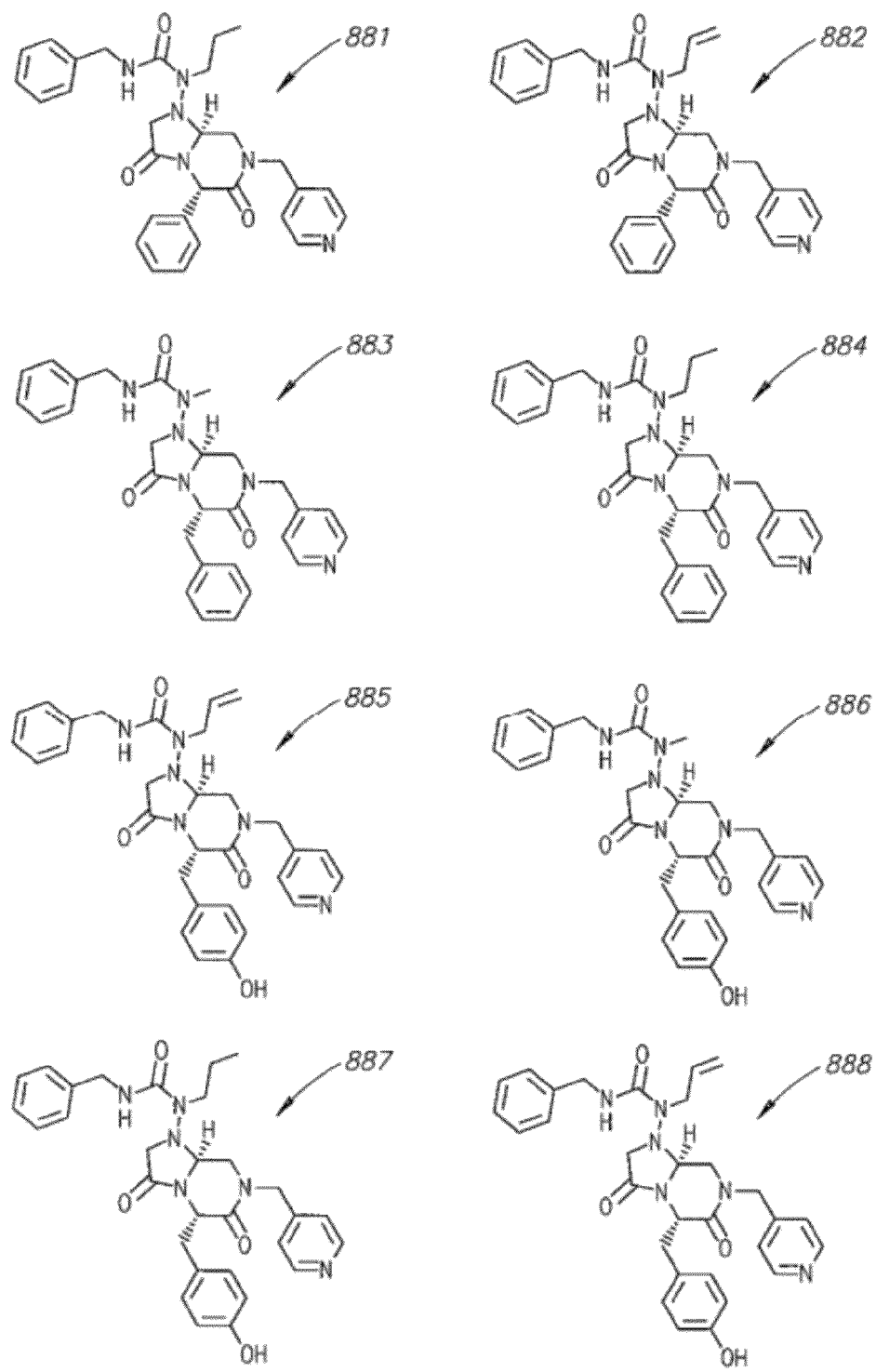
Figure 5L:
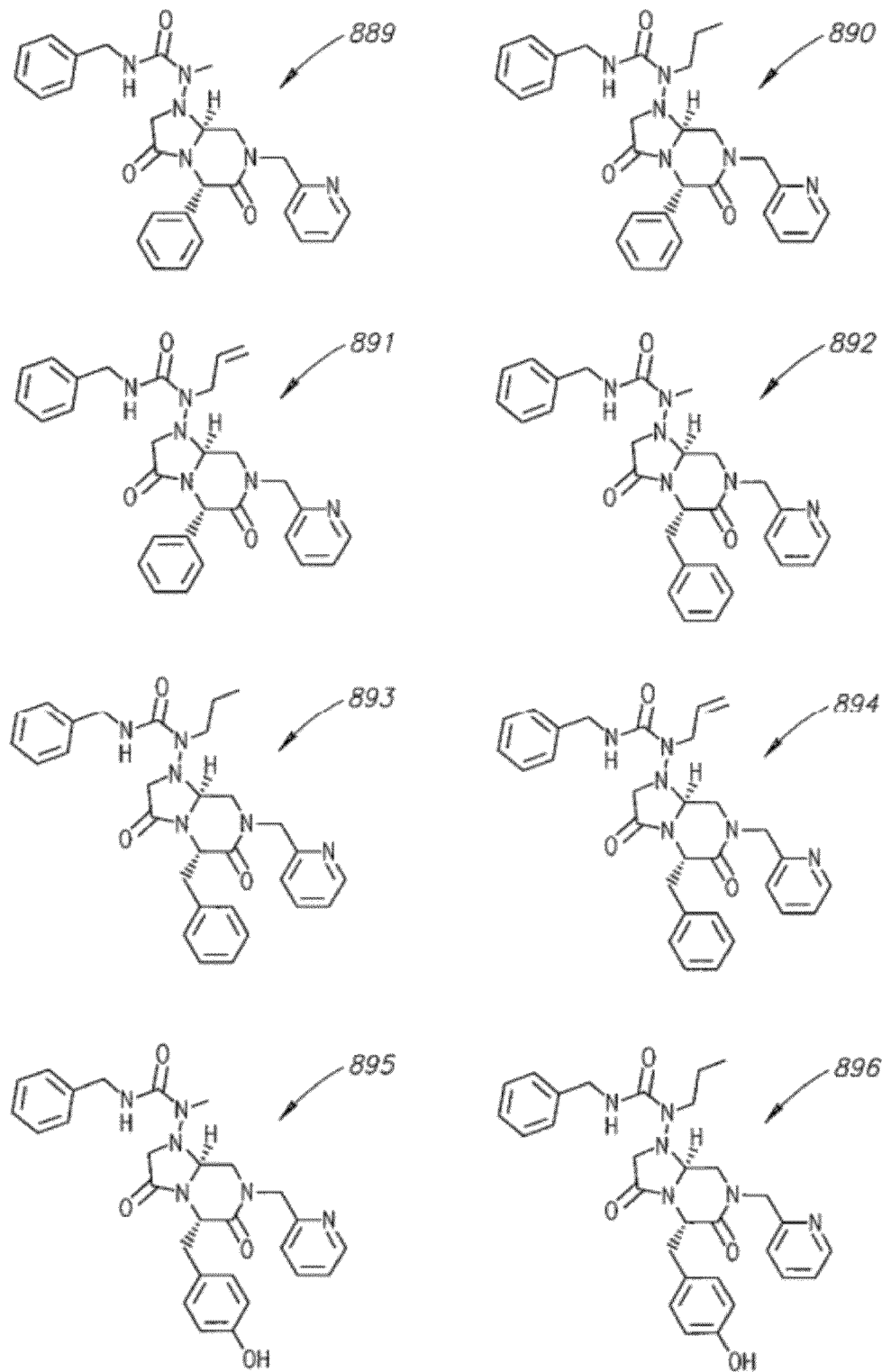
Figure 5M:
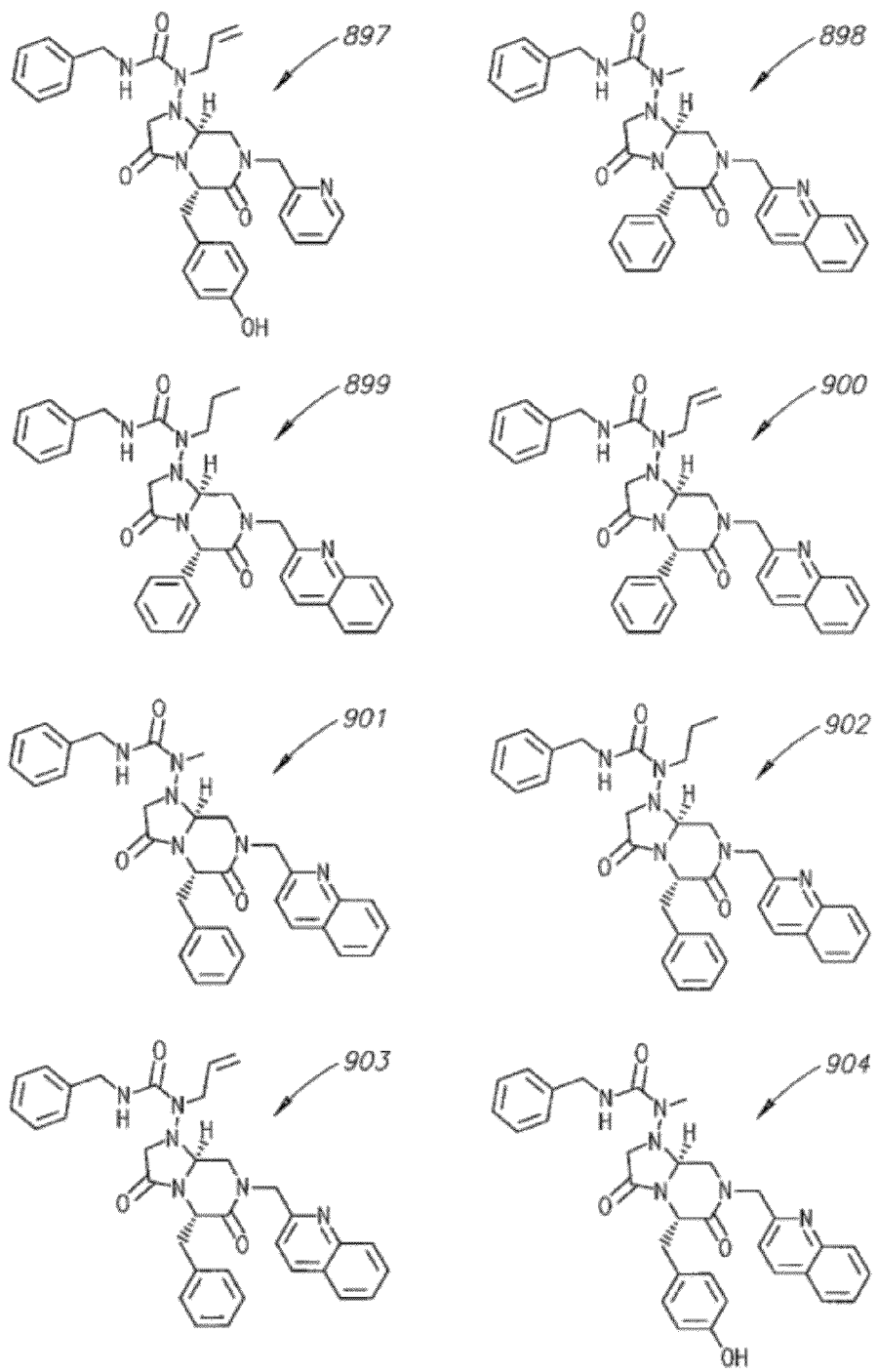
Figure 5N:
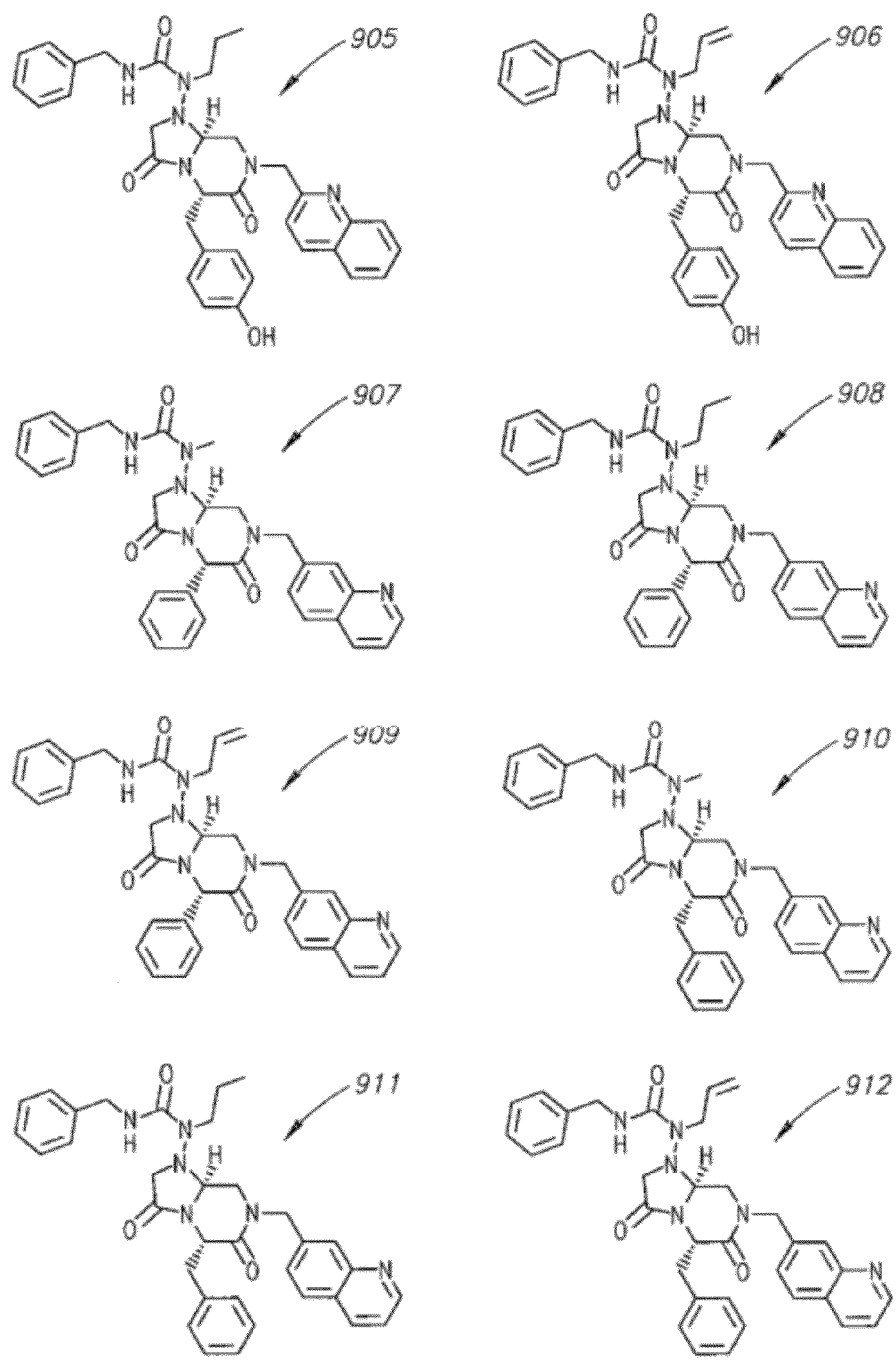
Figure 50:
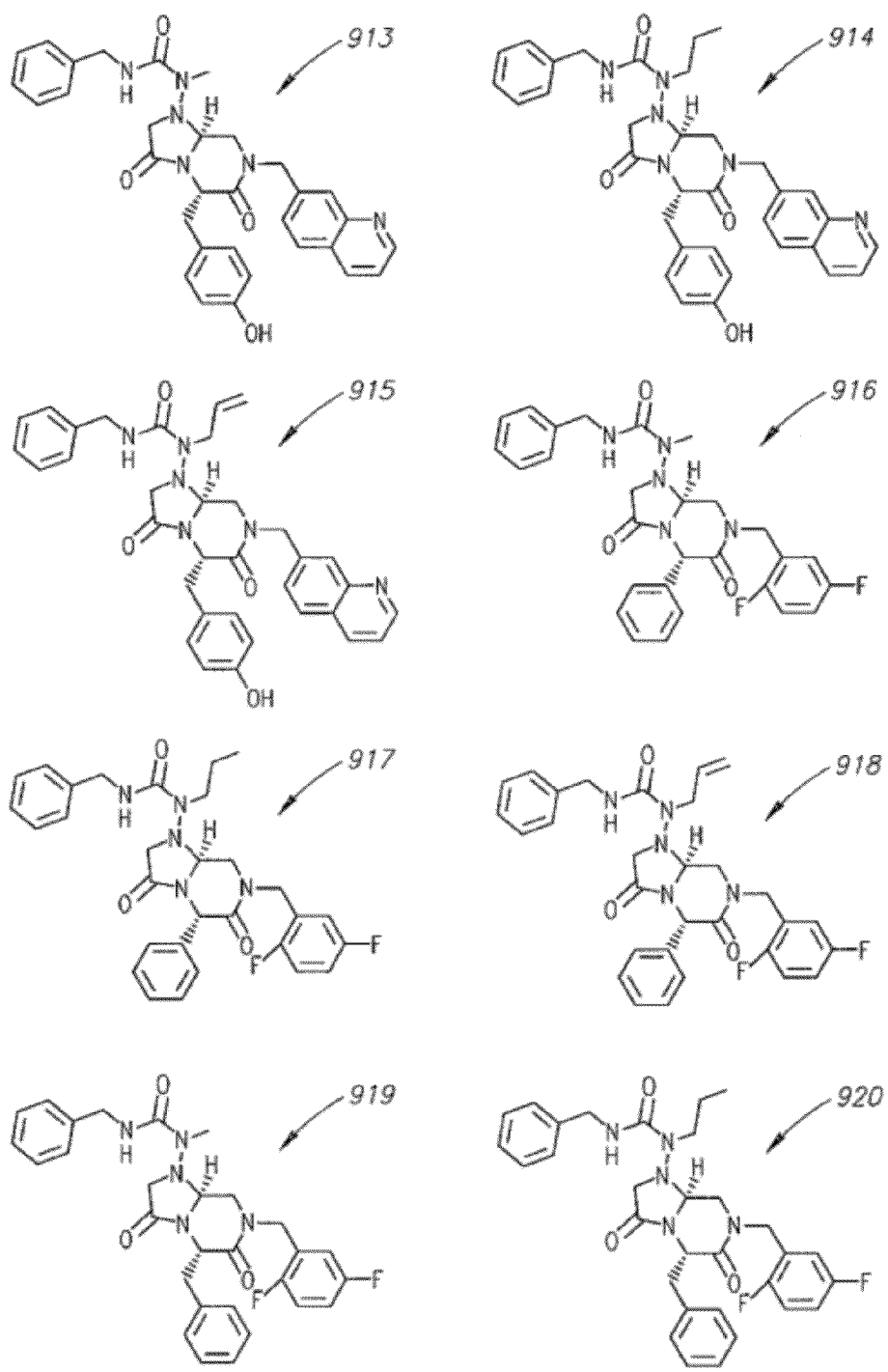
Figure 5P:
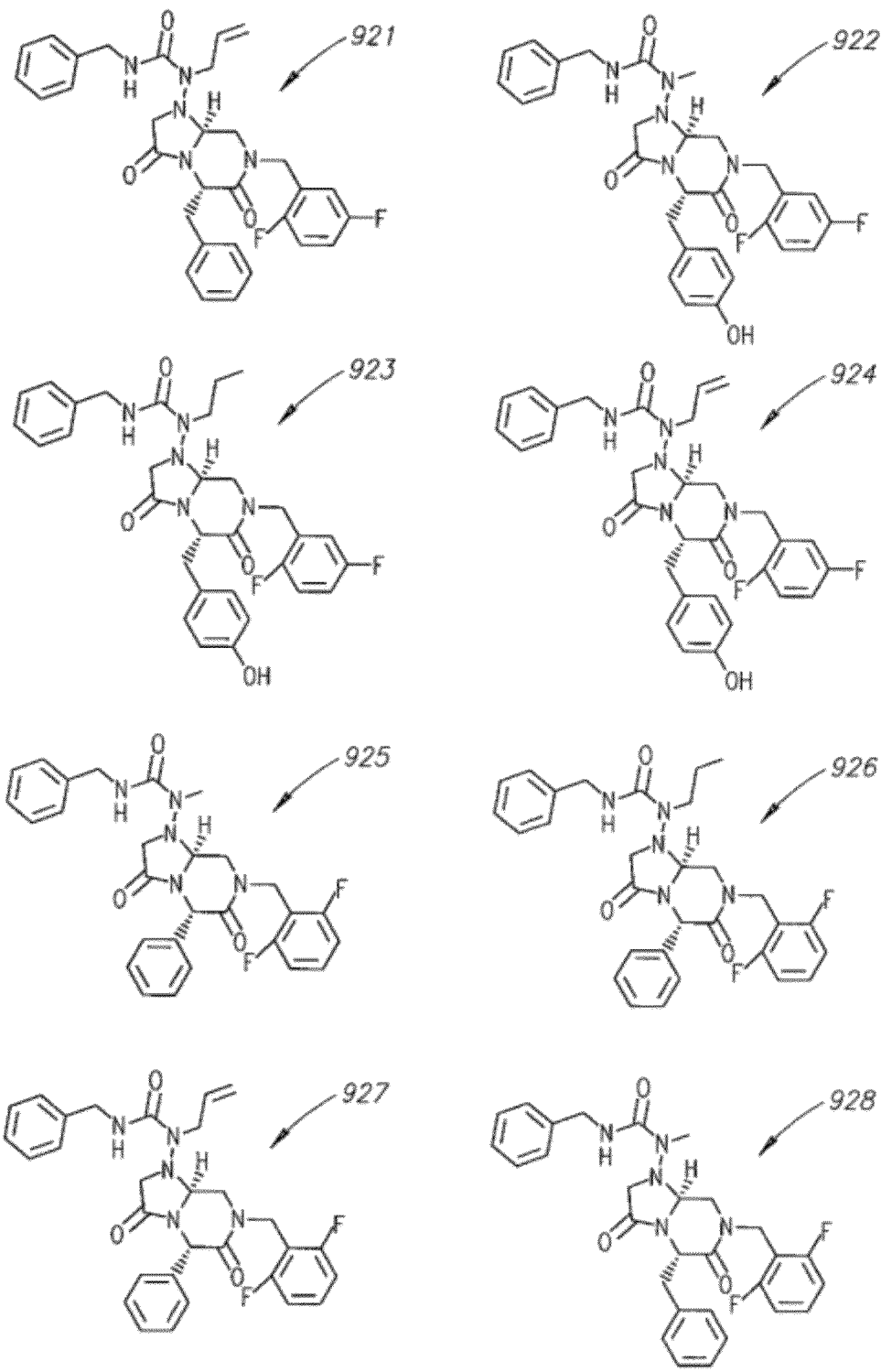
Figure 5Q:
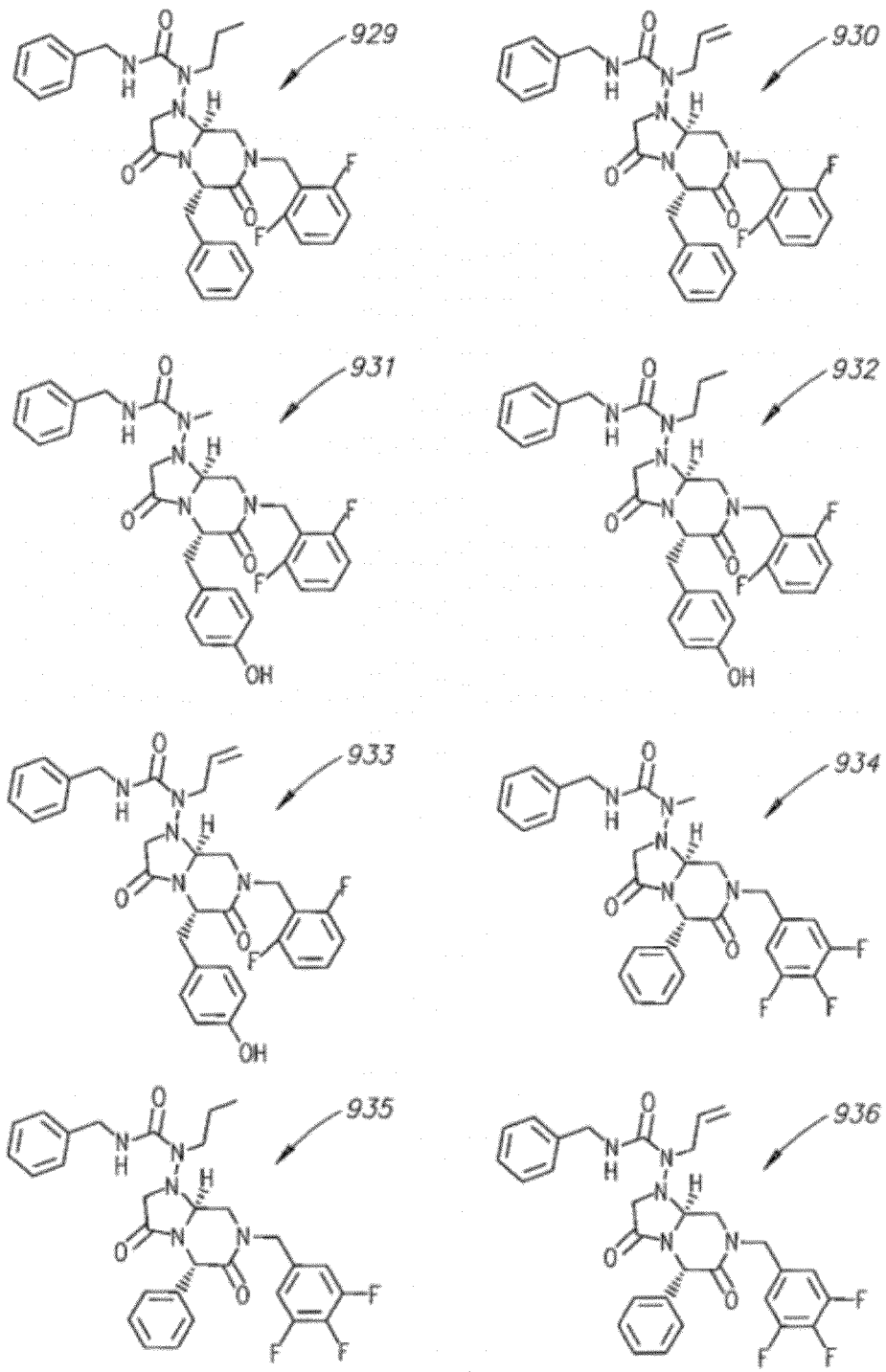
Figure 5R:
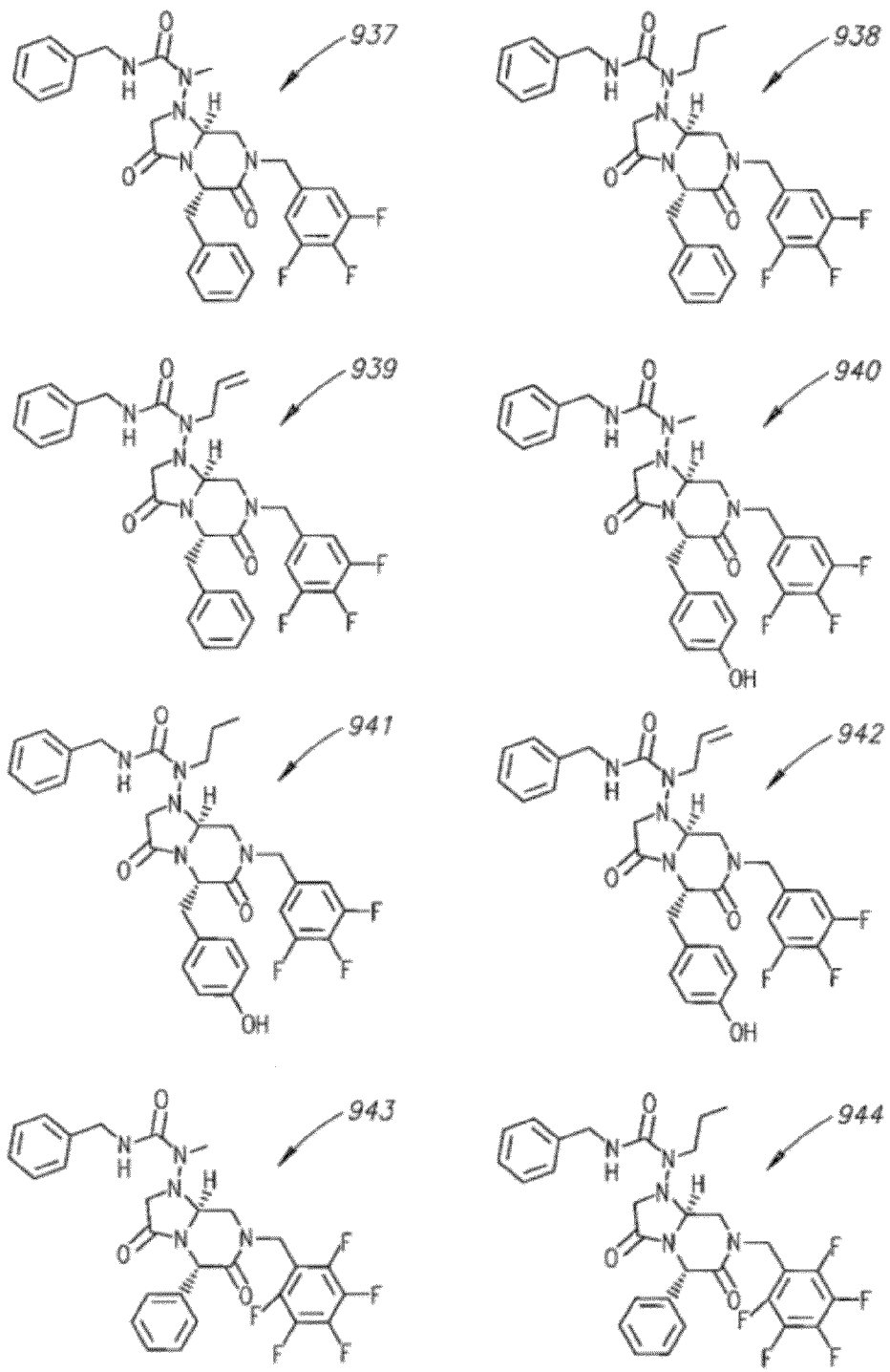
Figure 5S:
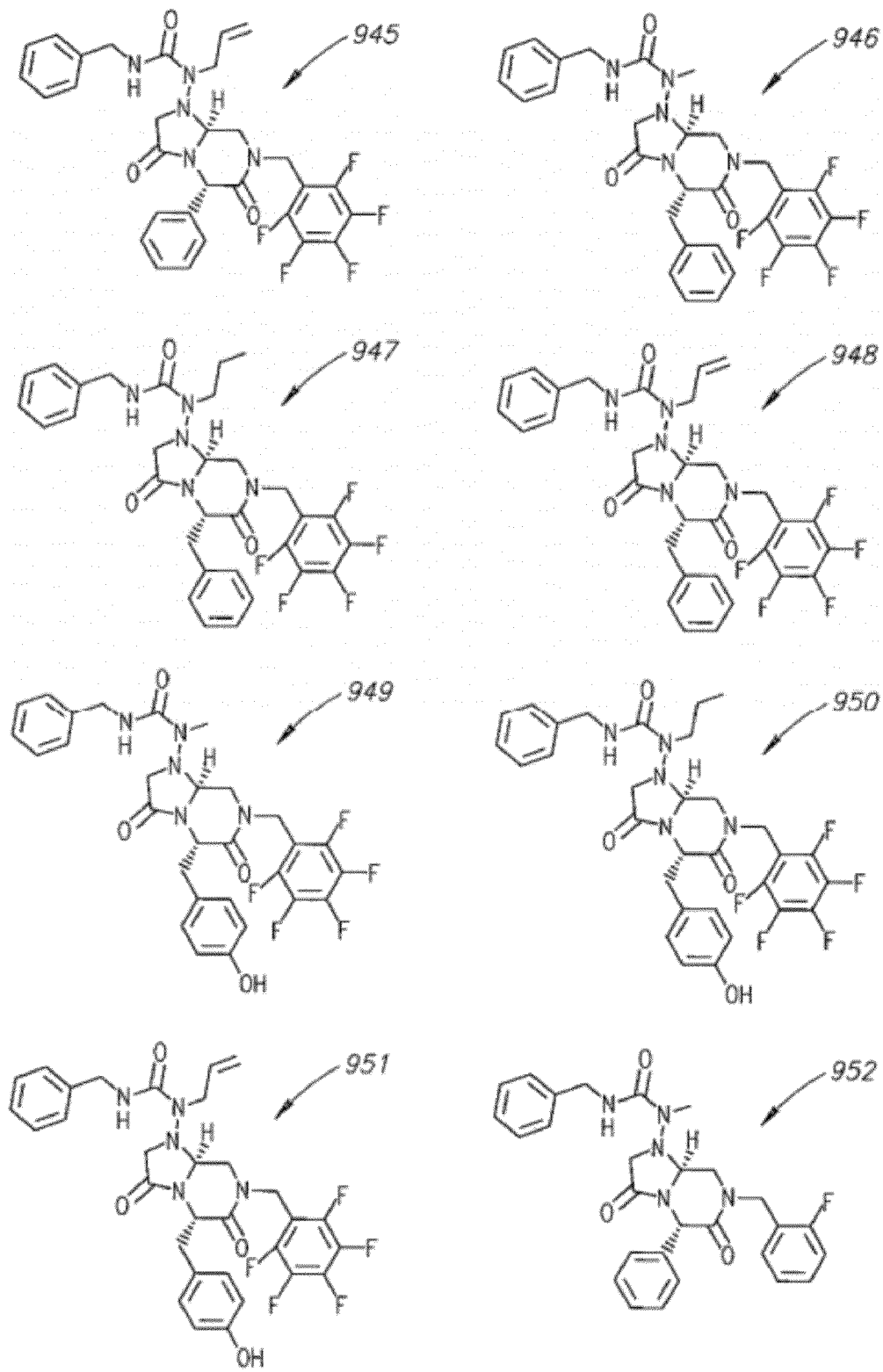
Figure 5T:
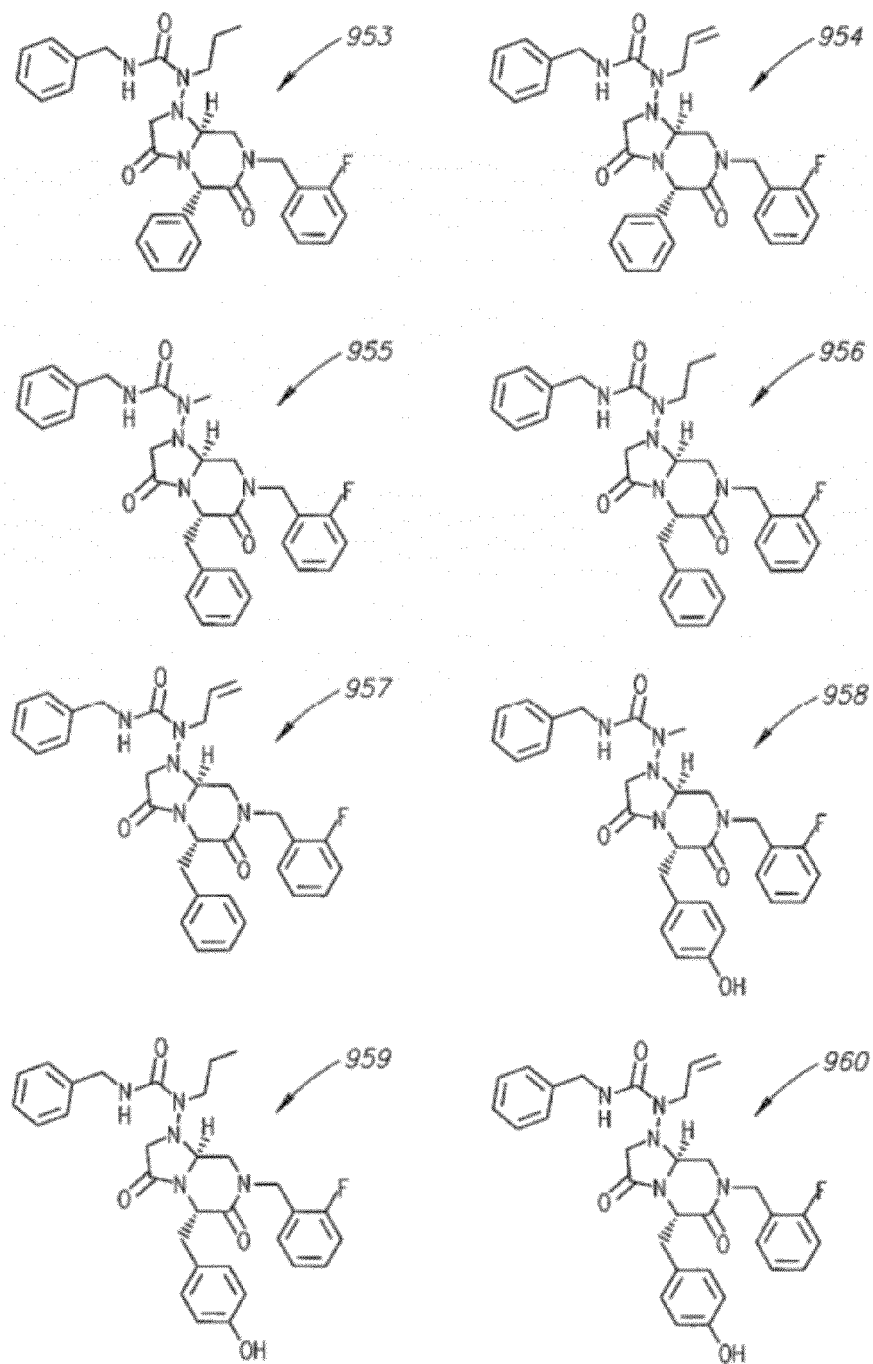
Figure 5U:
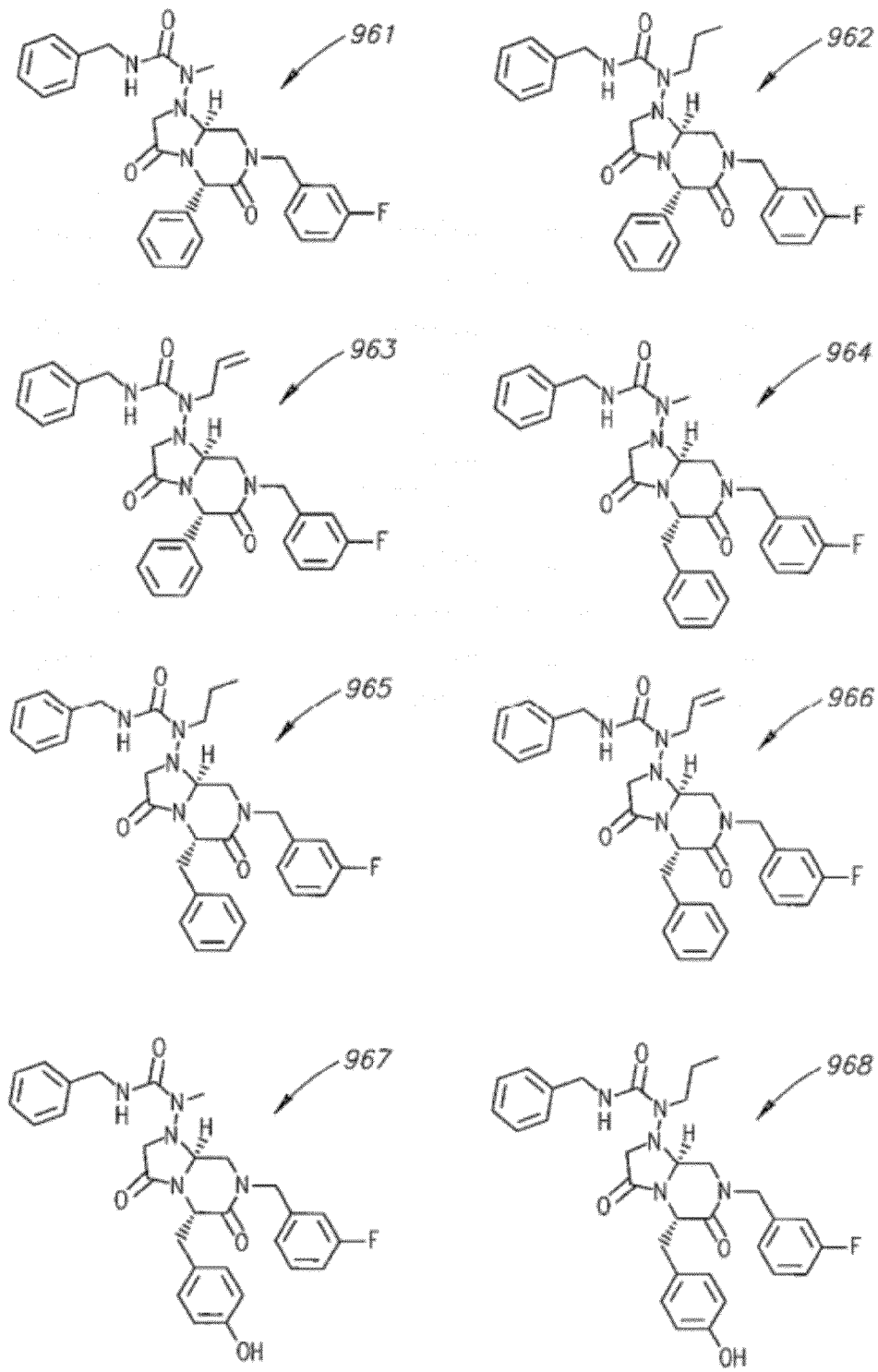
Figure 5V:
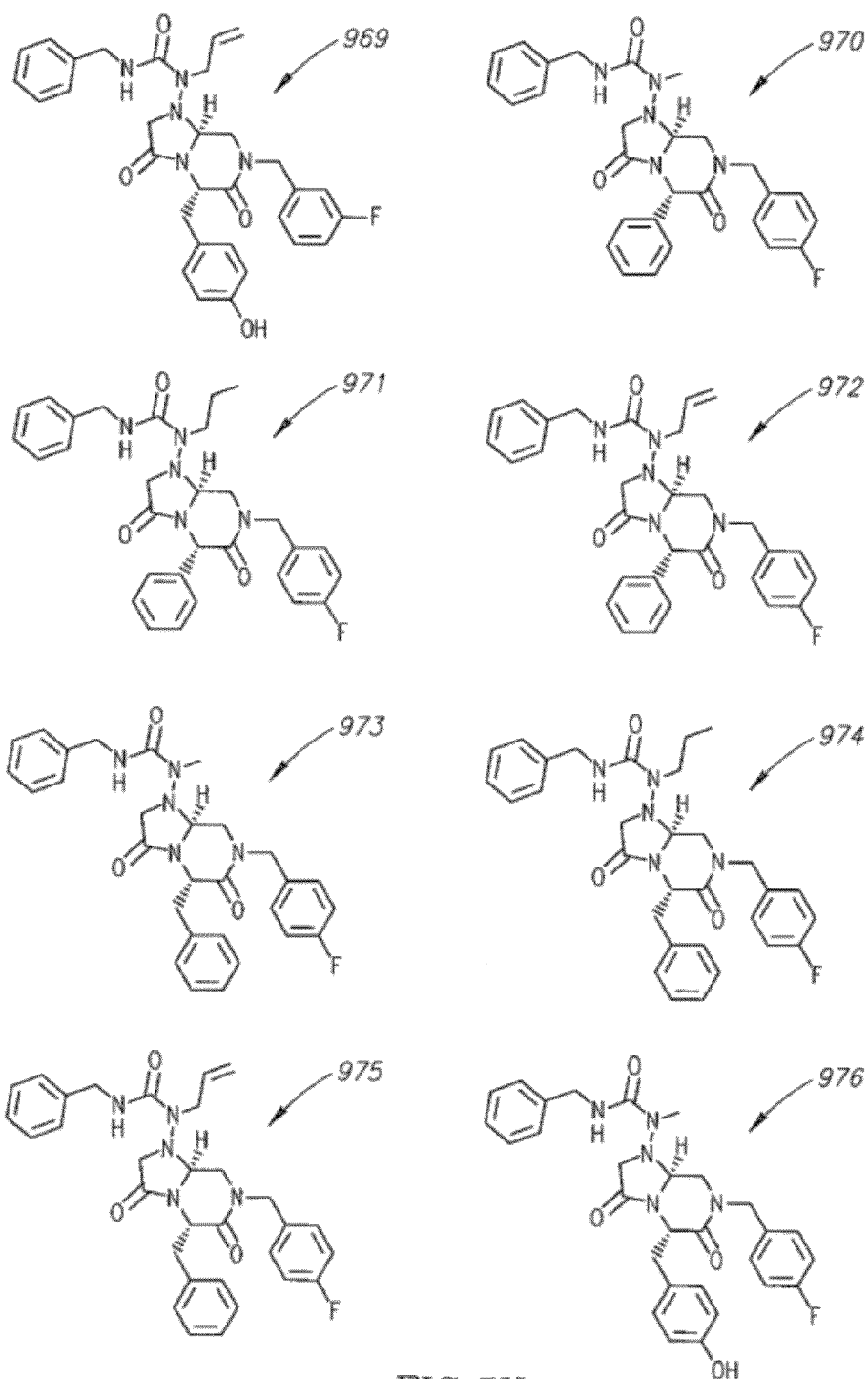
Figure 5W:
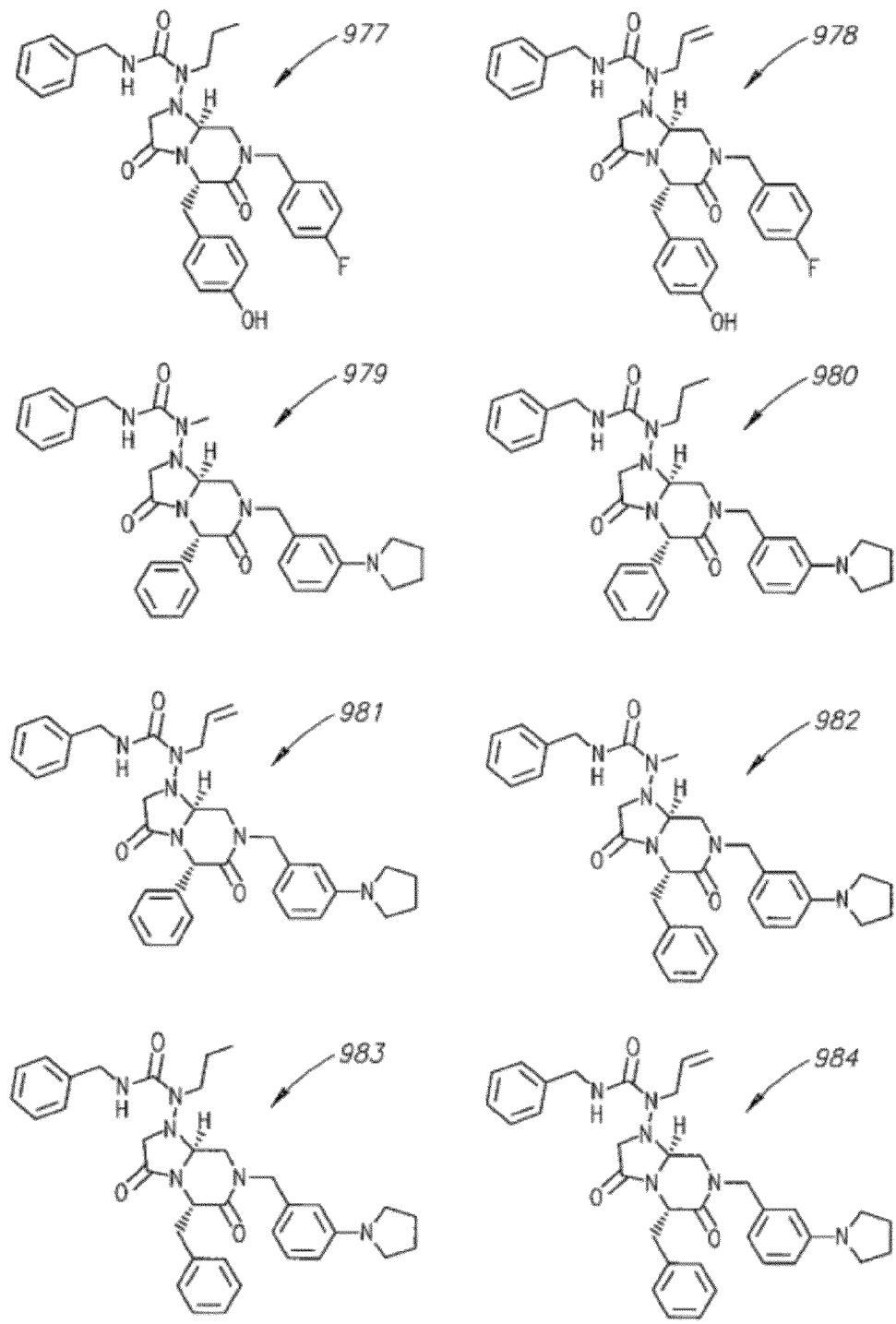
Figure 5X:
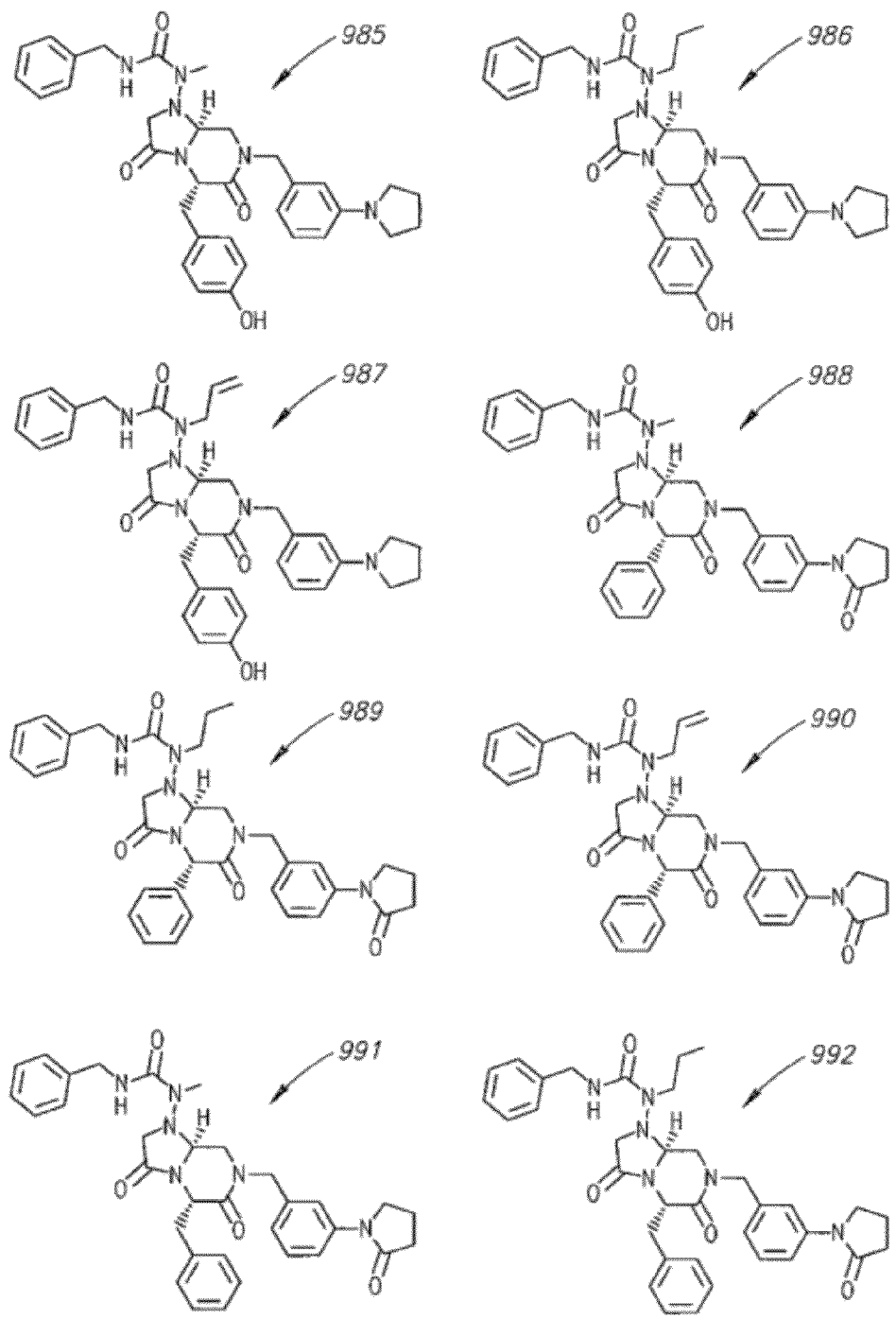
Figure 5Y:
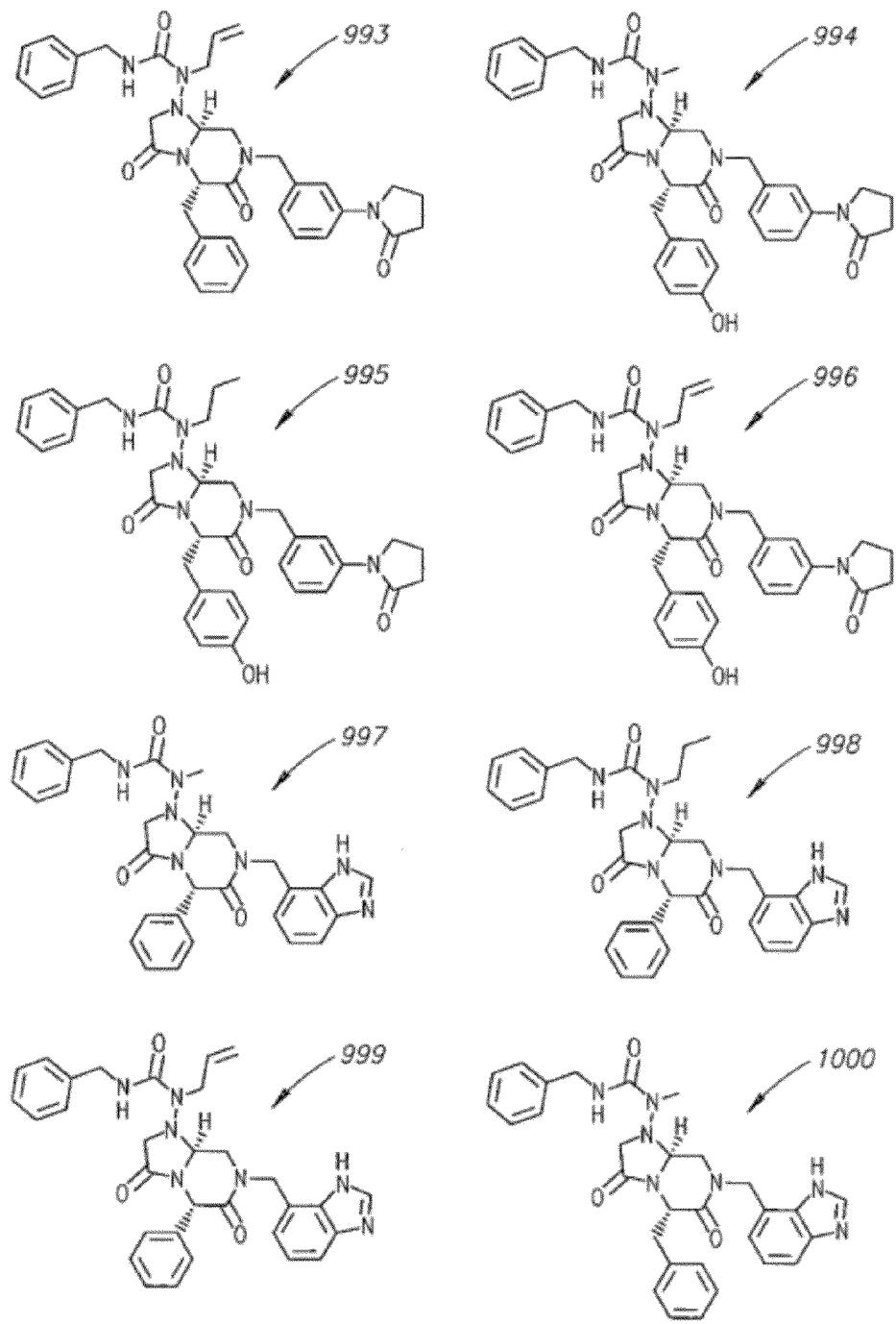
Figure 6A:
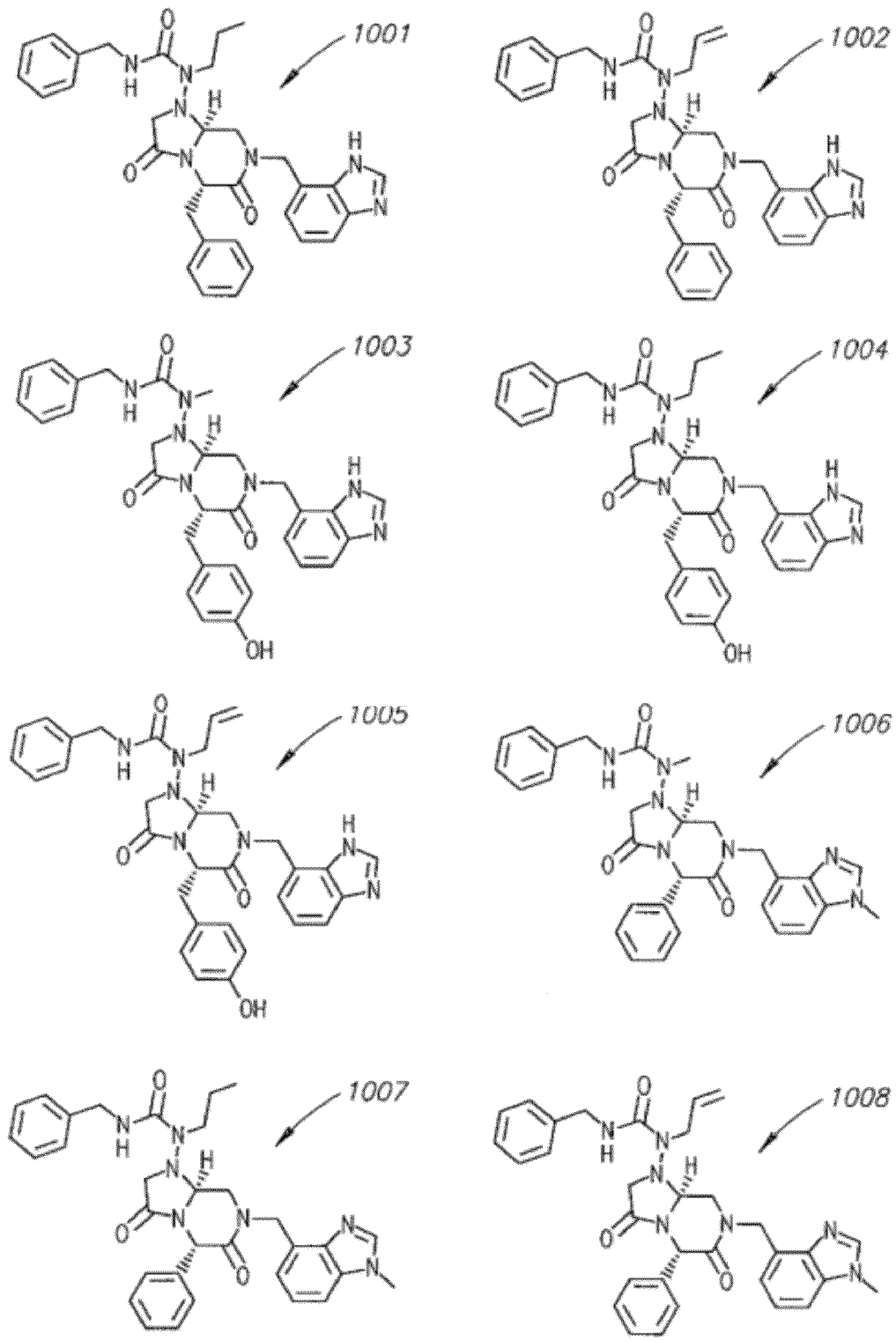
FIGS. 6A-6Y shows the chemical structures of compounds 1001-1200.
Figure 6B:
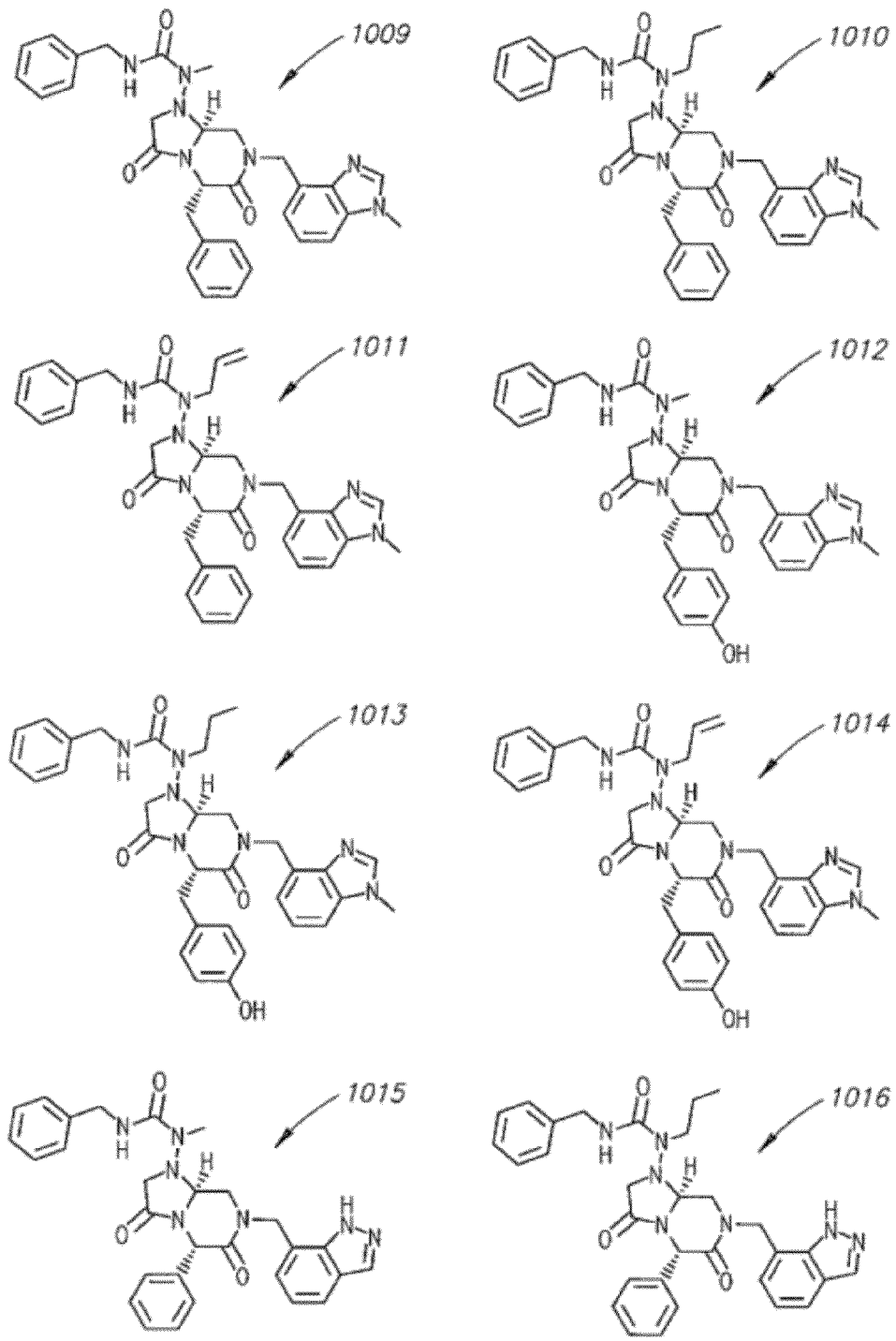
Figure 6C:
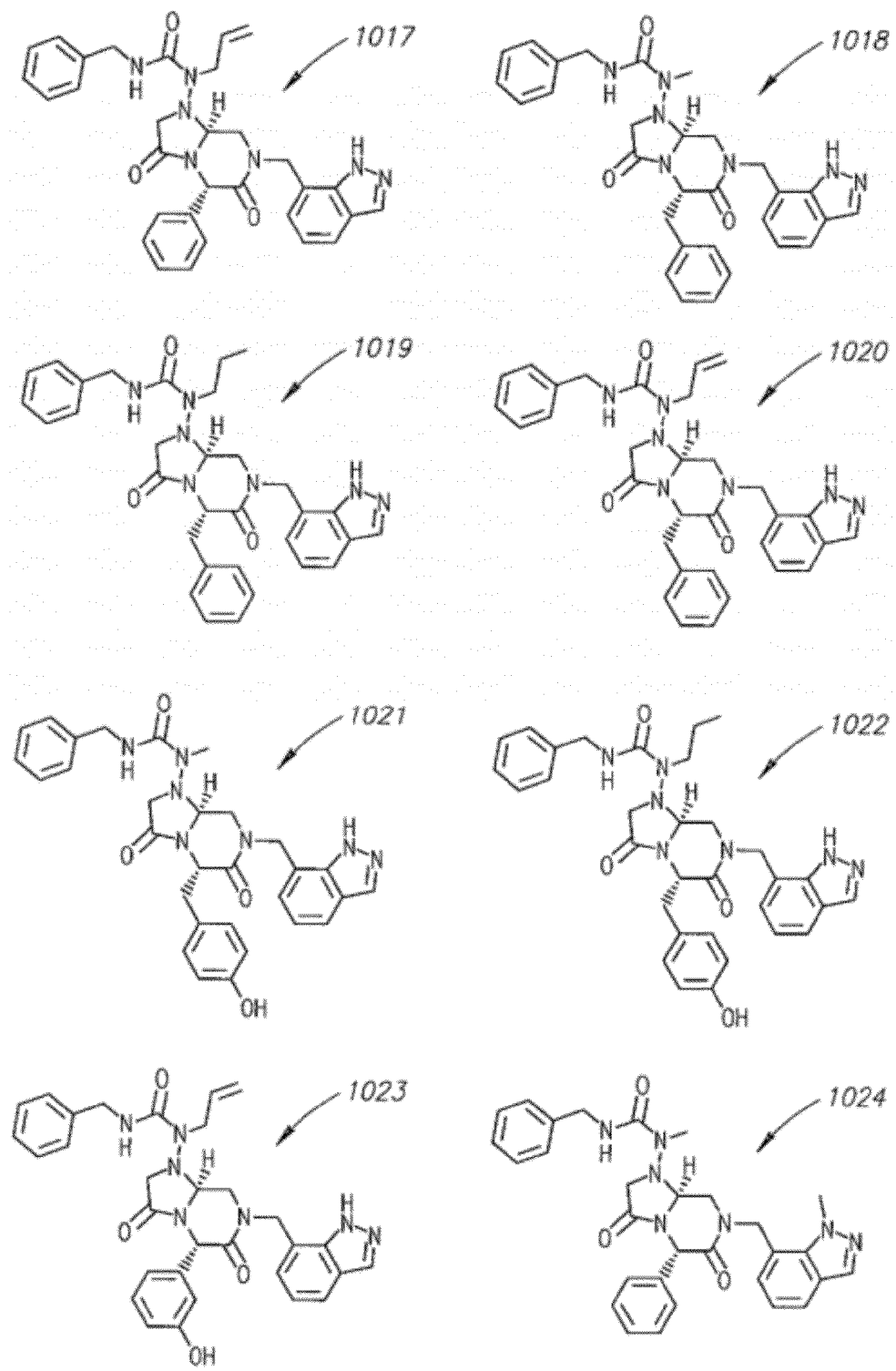
Figure 6D:
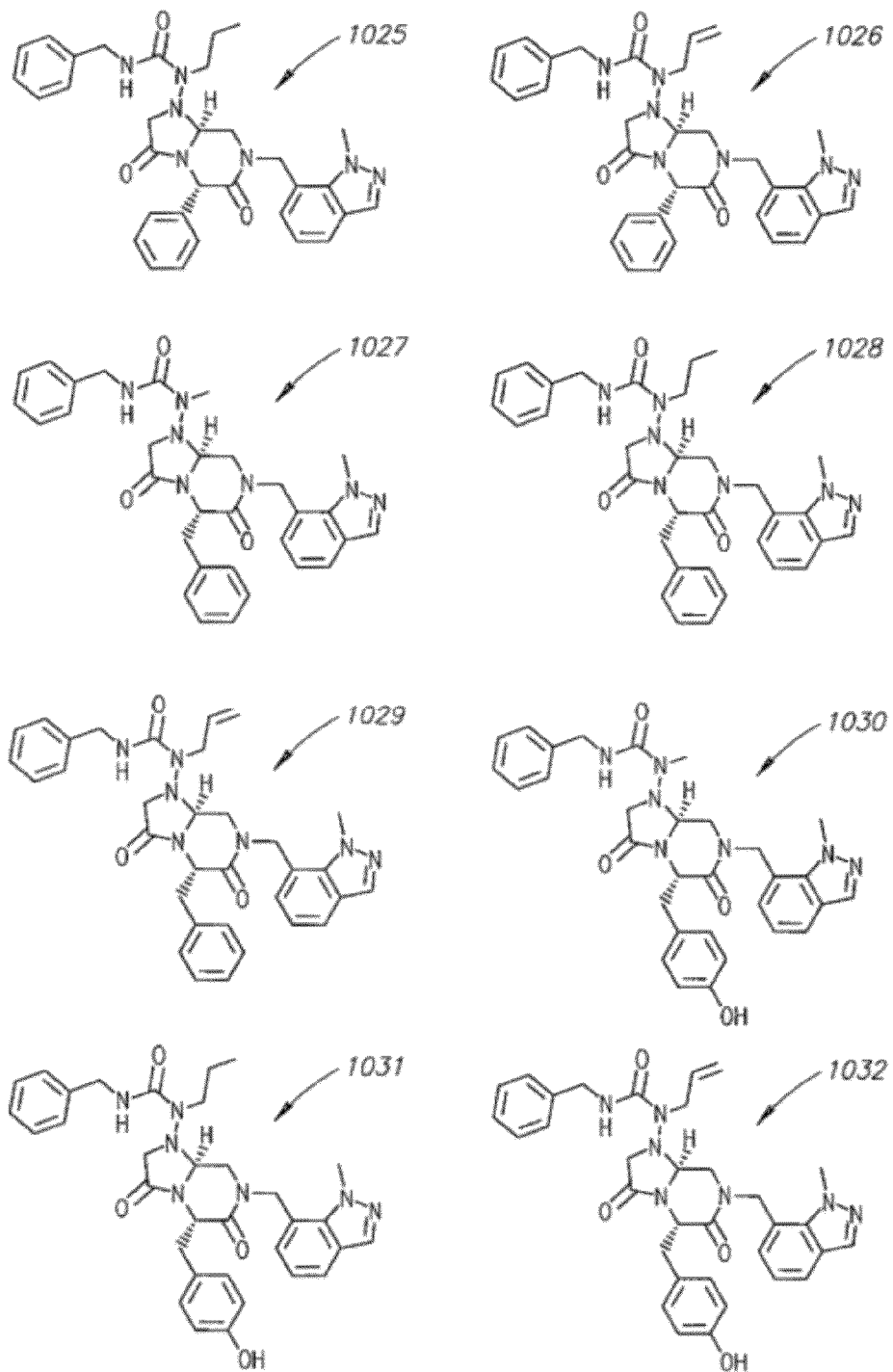
Figure 6E:
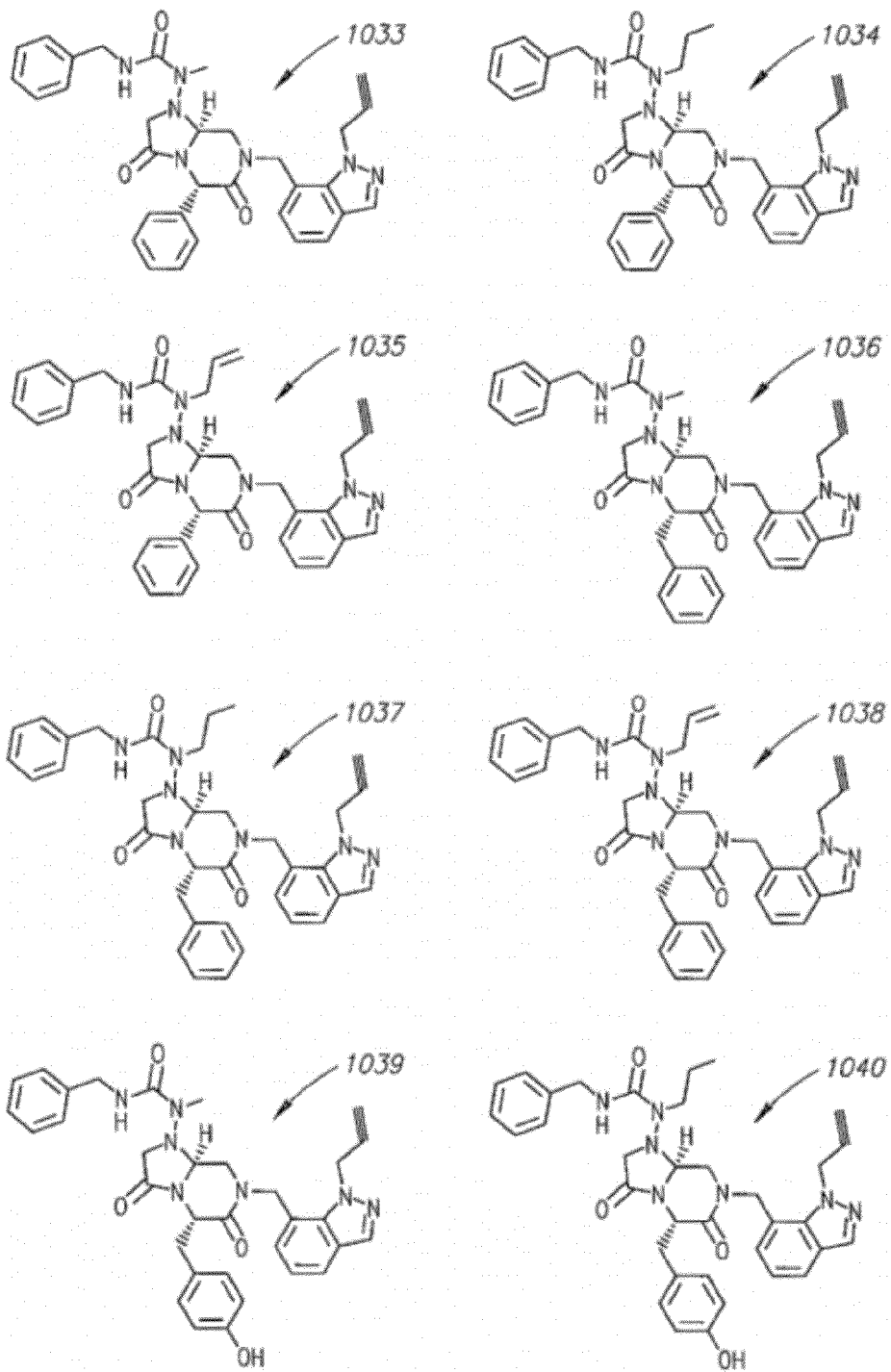
Figure 6F:
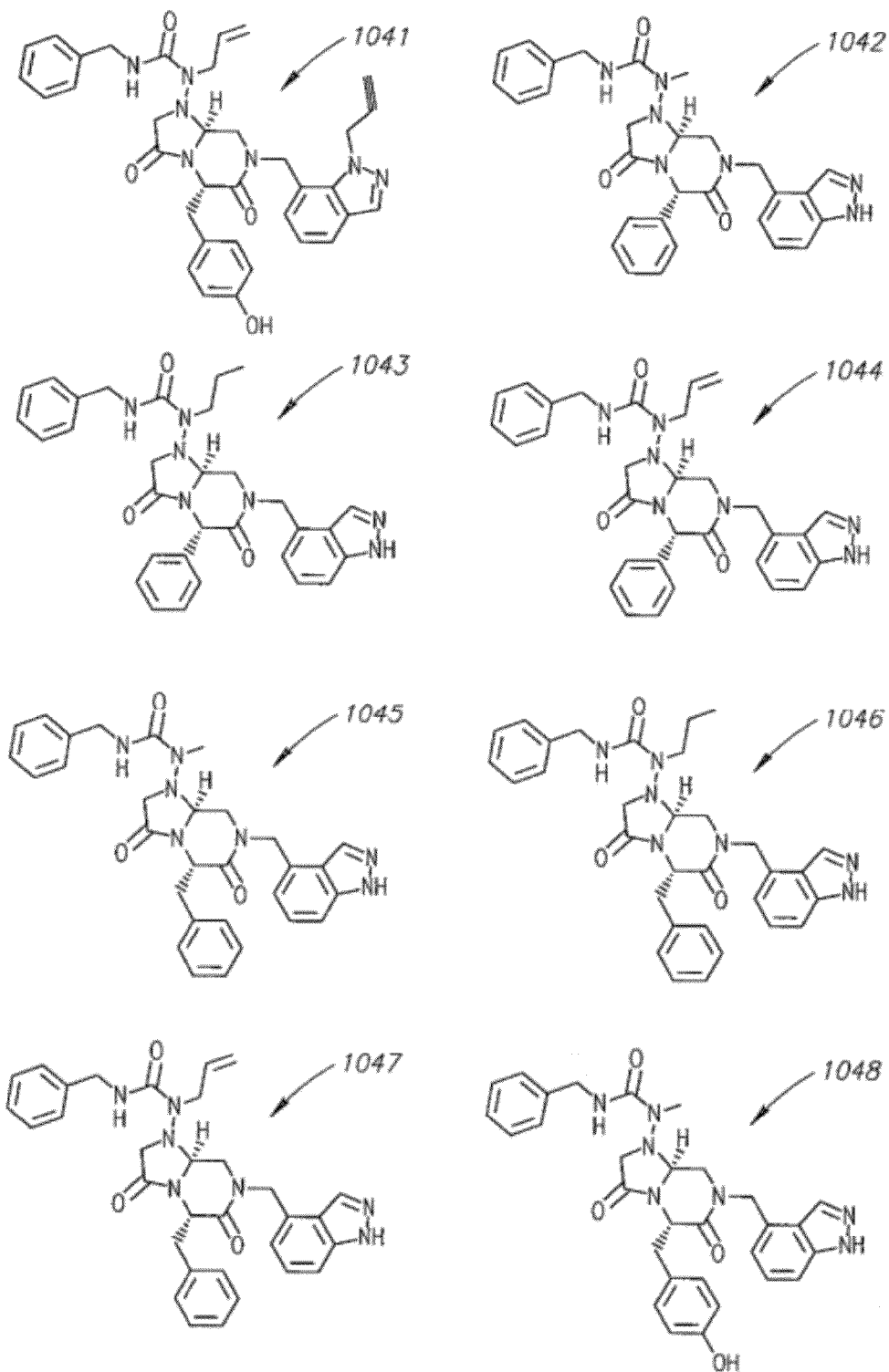
Figure 6G:
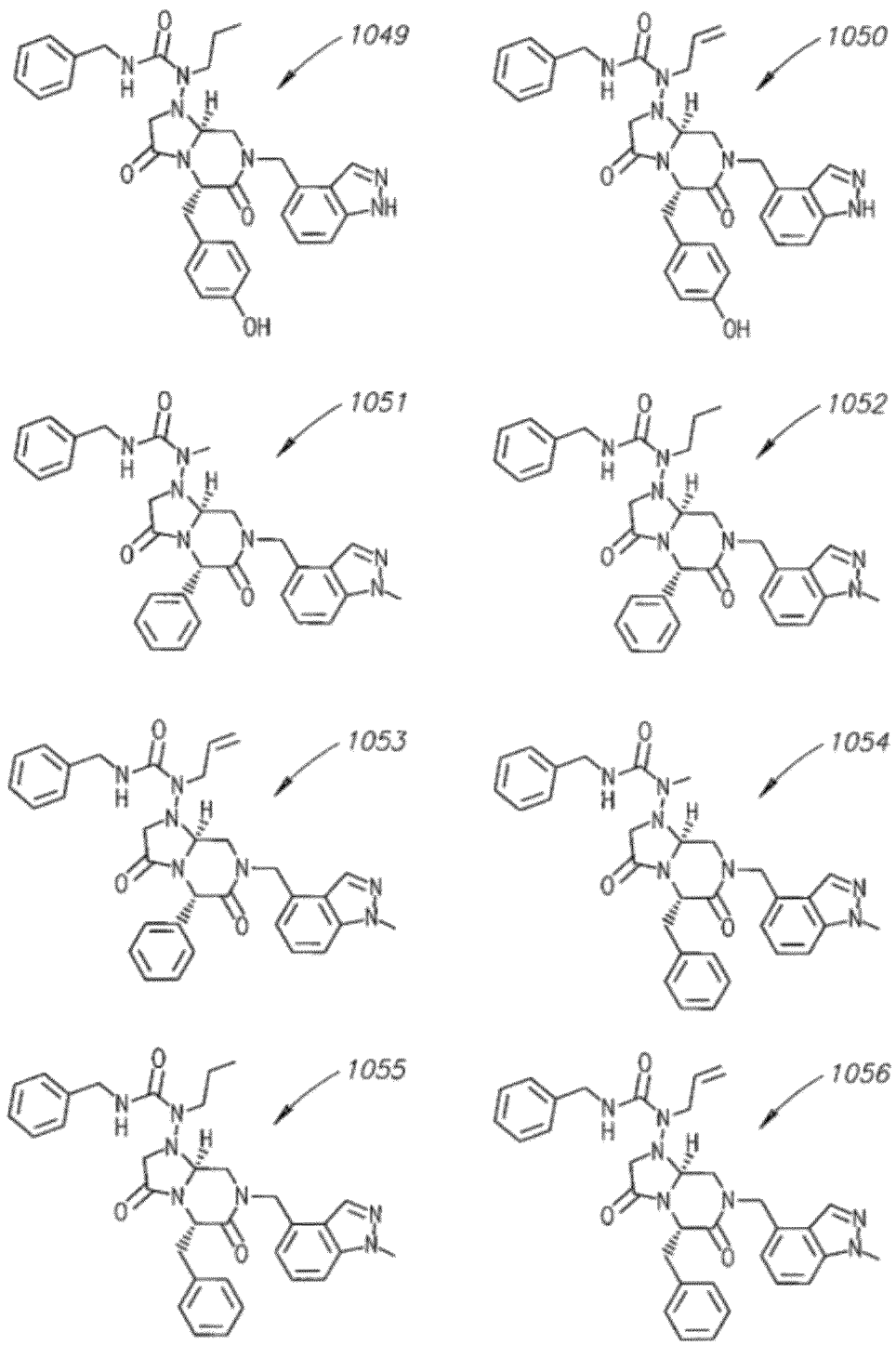
Figure 6H:
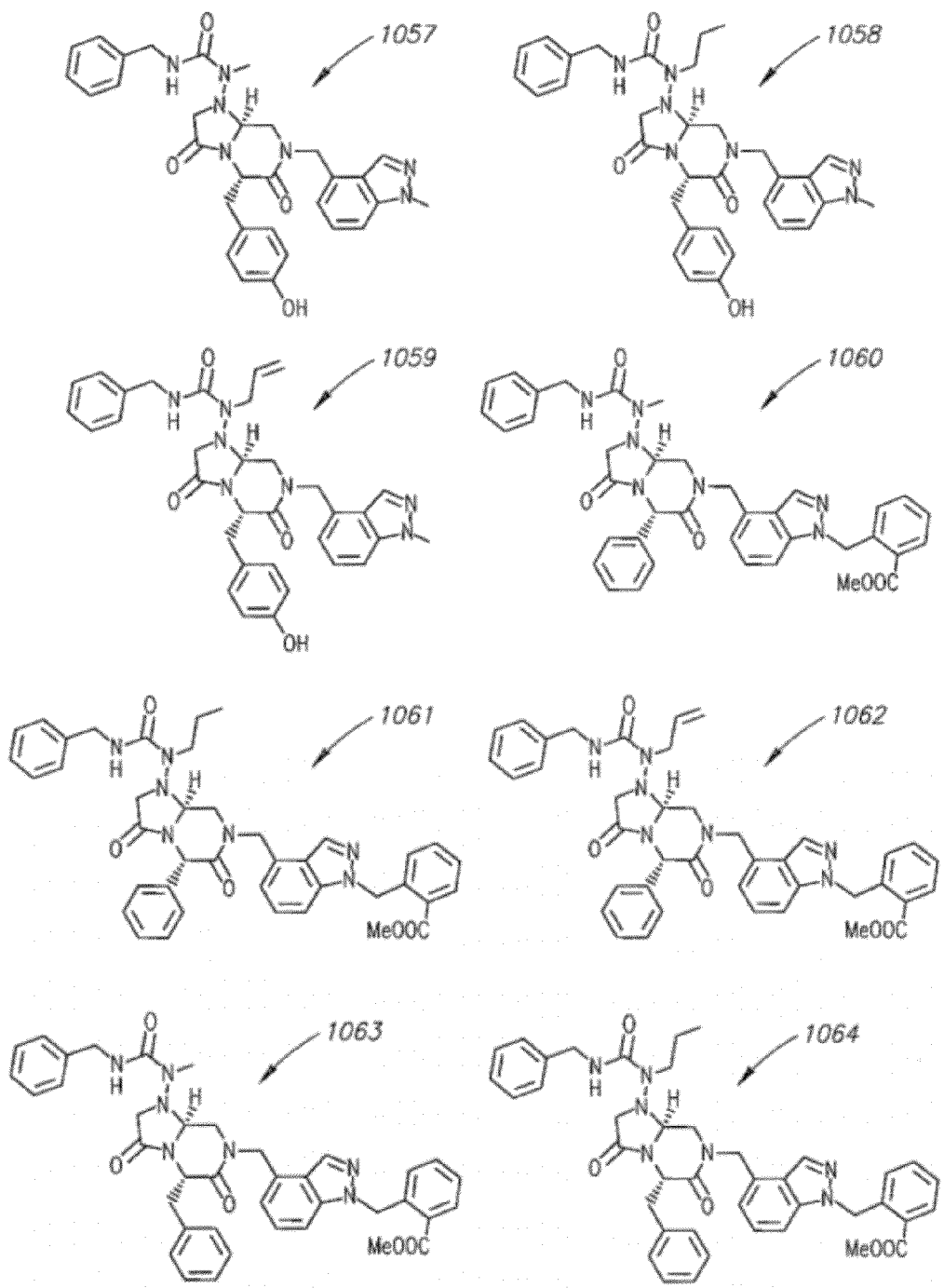
Figure 6I:
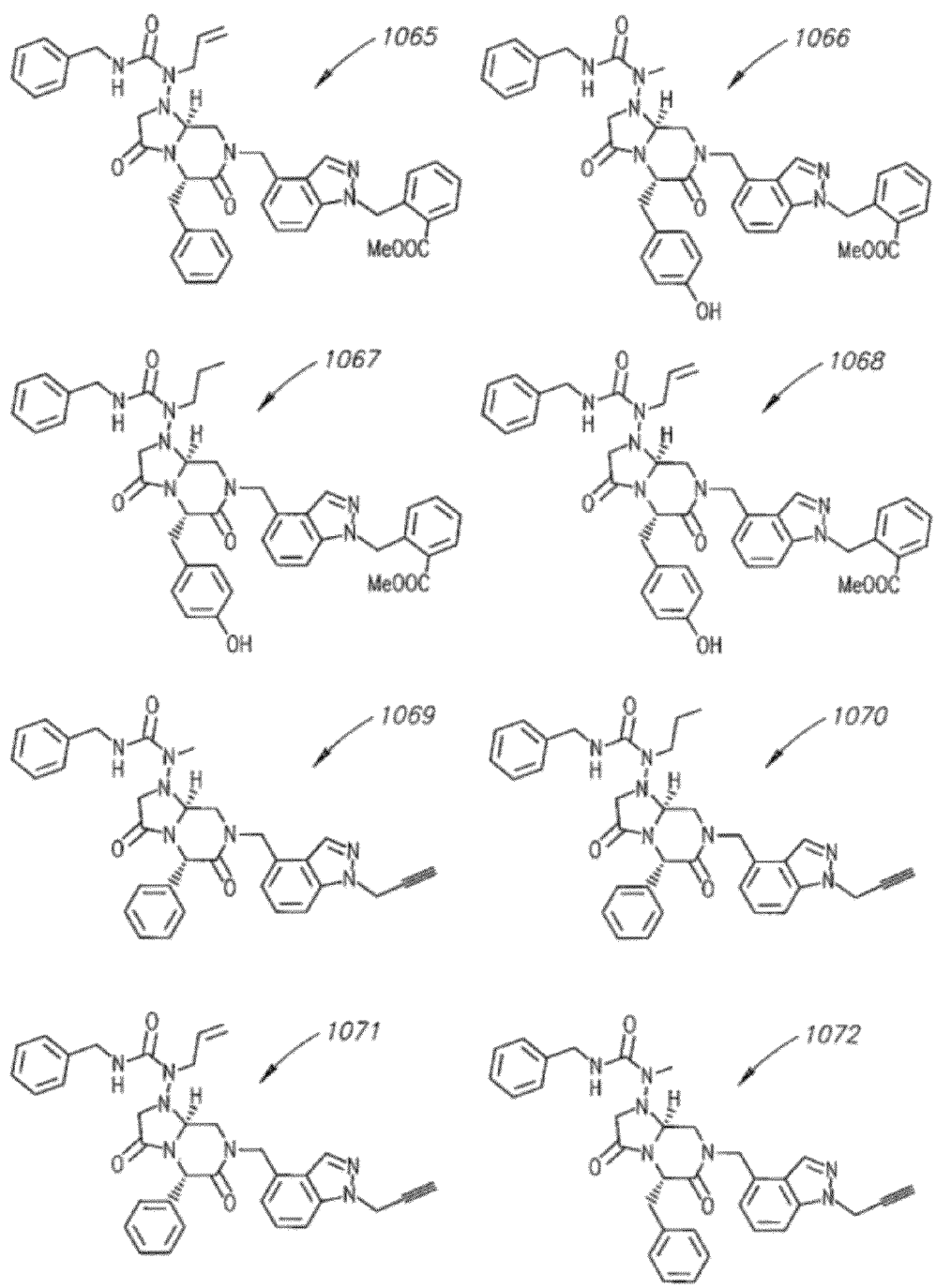
Figure 6J:
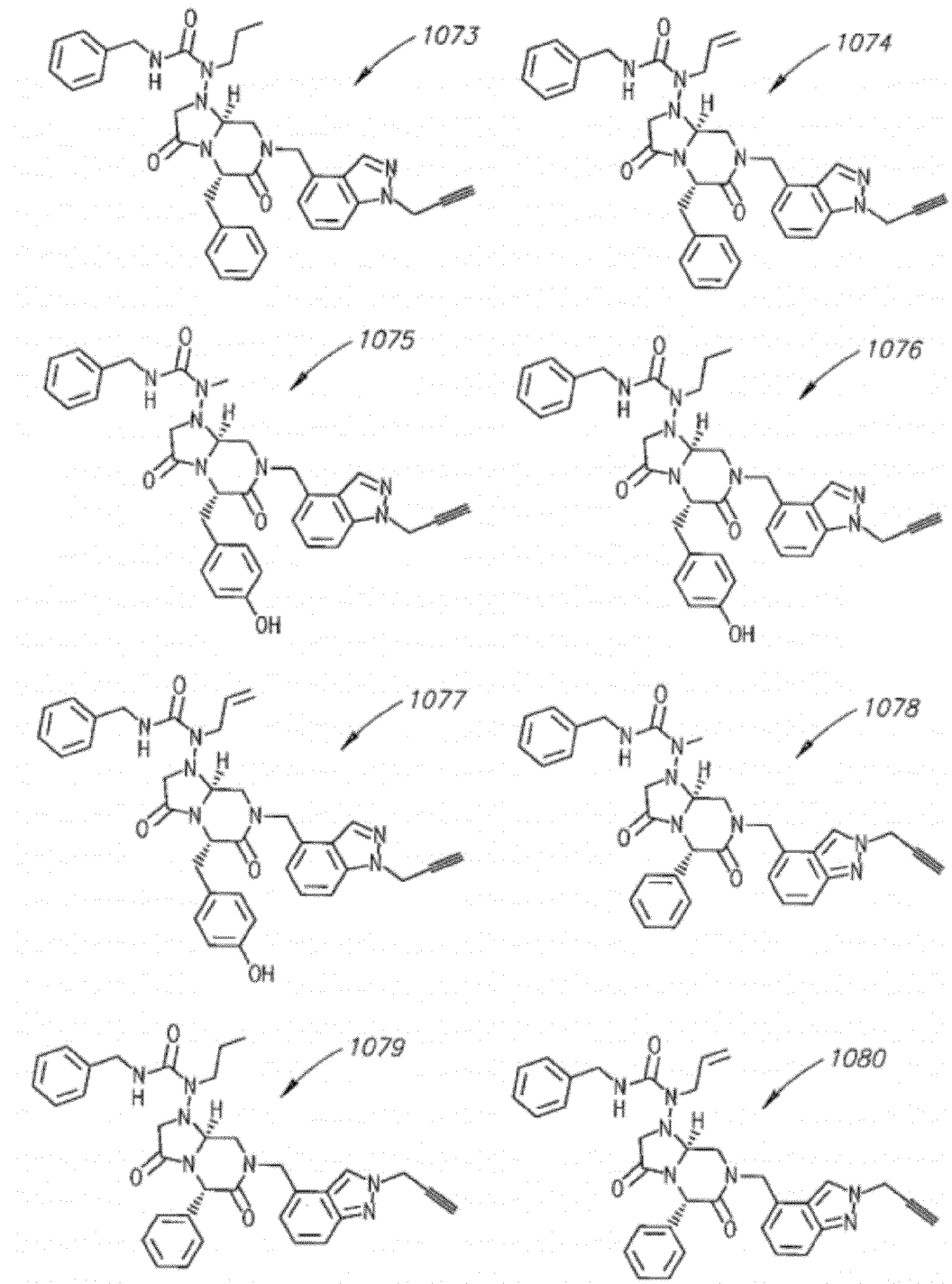
Figure 6K:
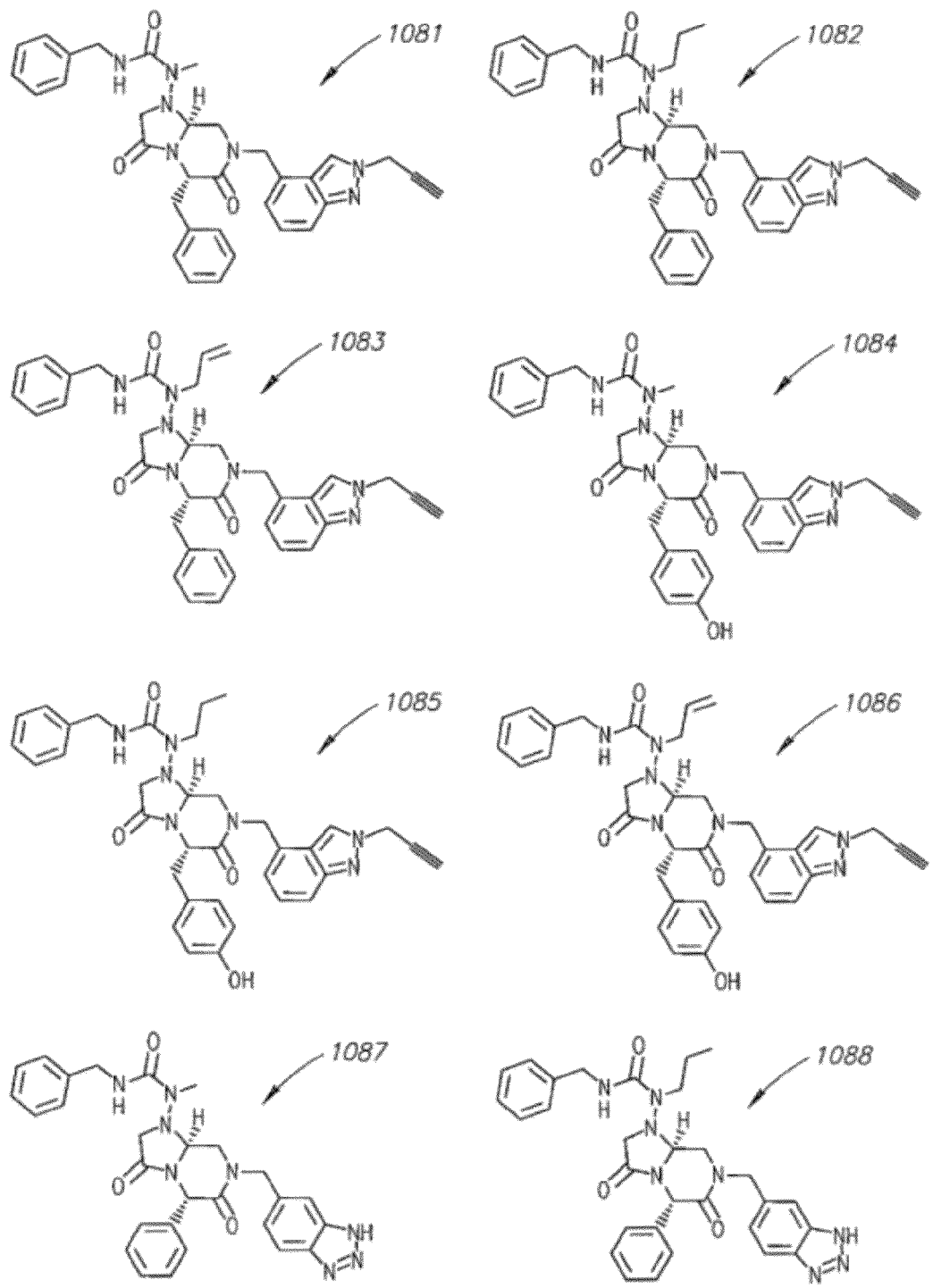
Figure 6L:
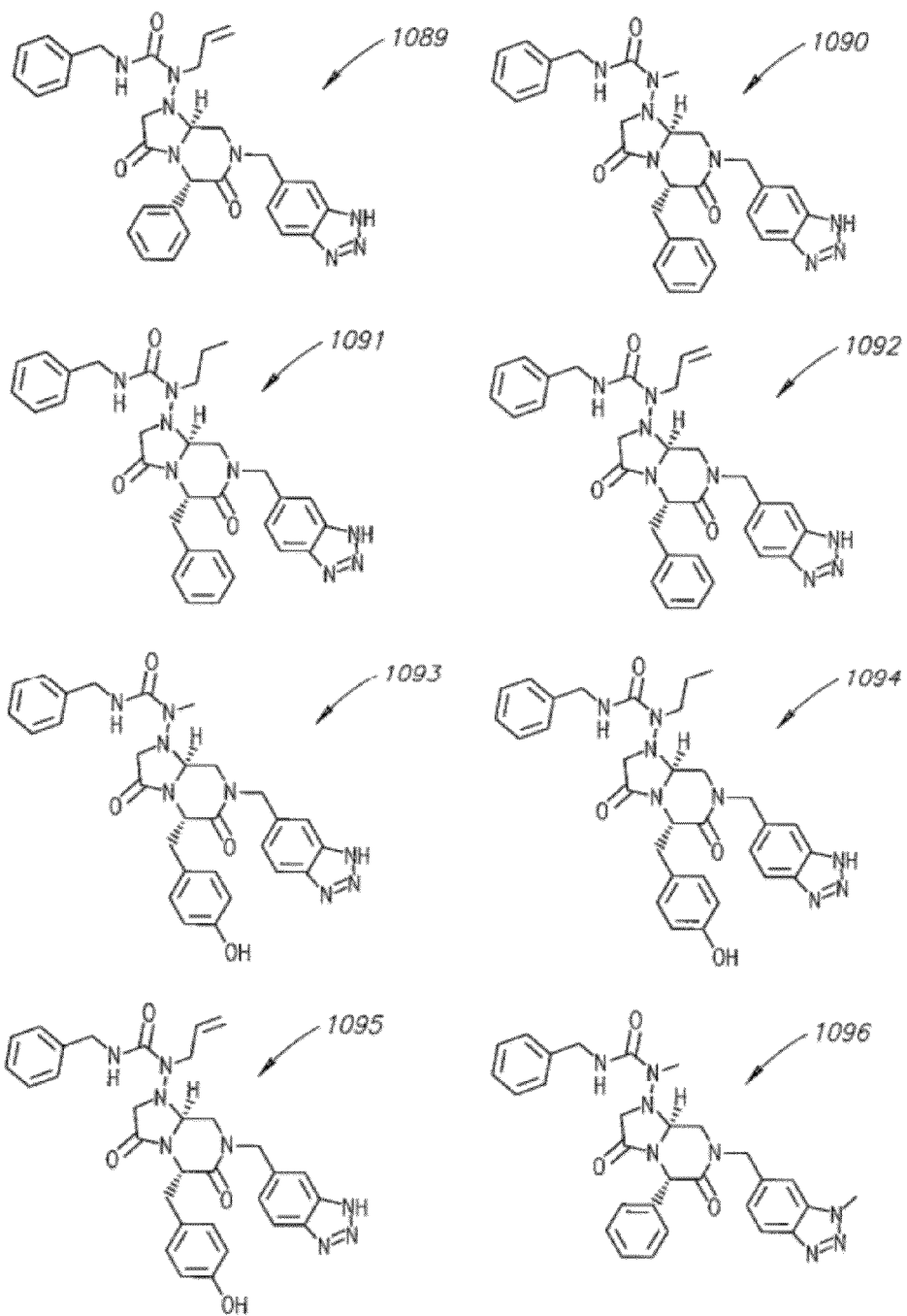
Figure 6M:
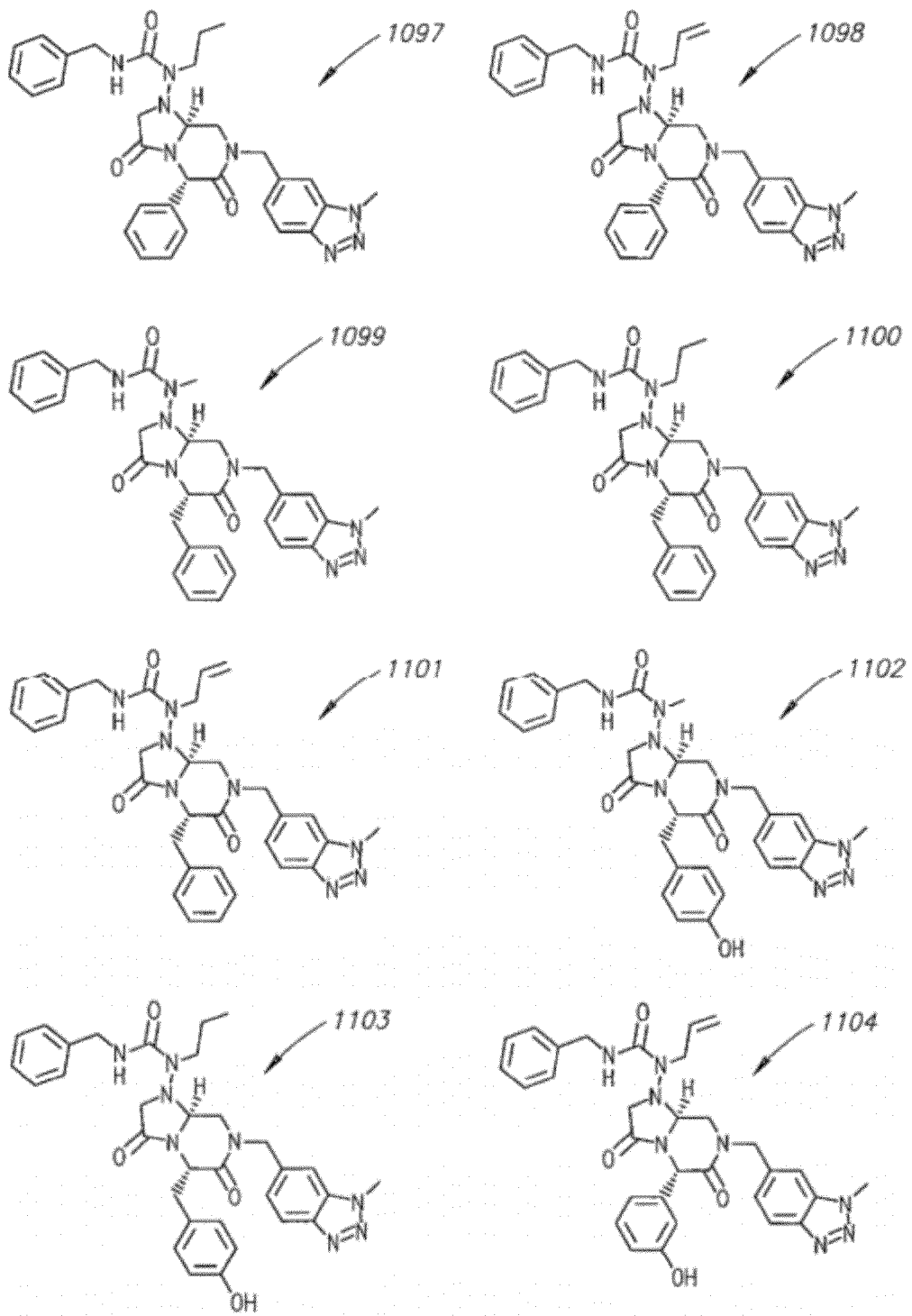
Figure 6N:
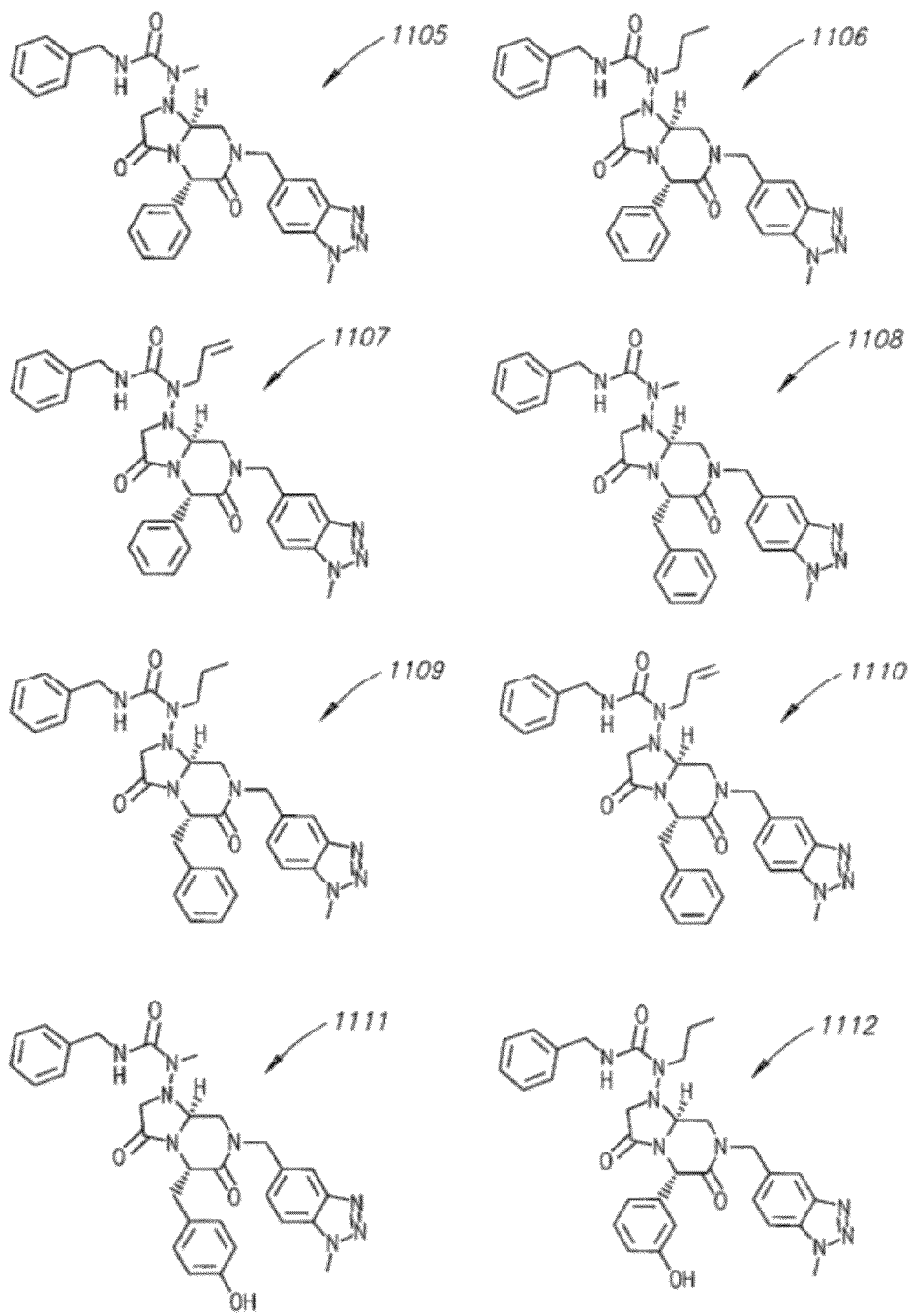
Figure 60:
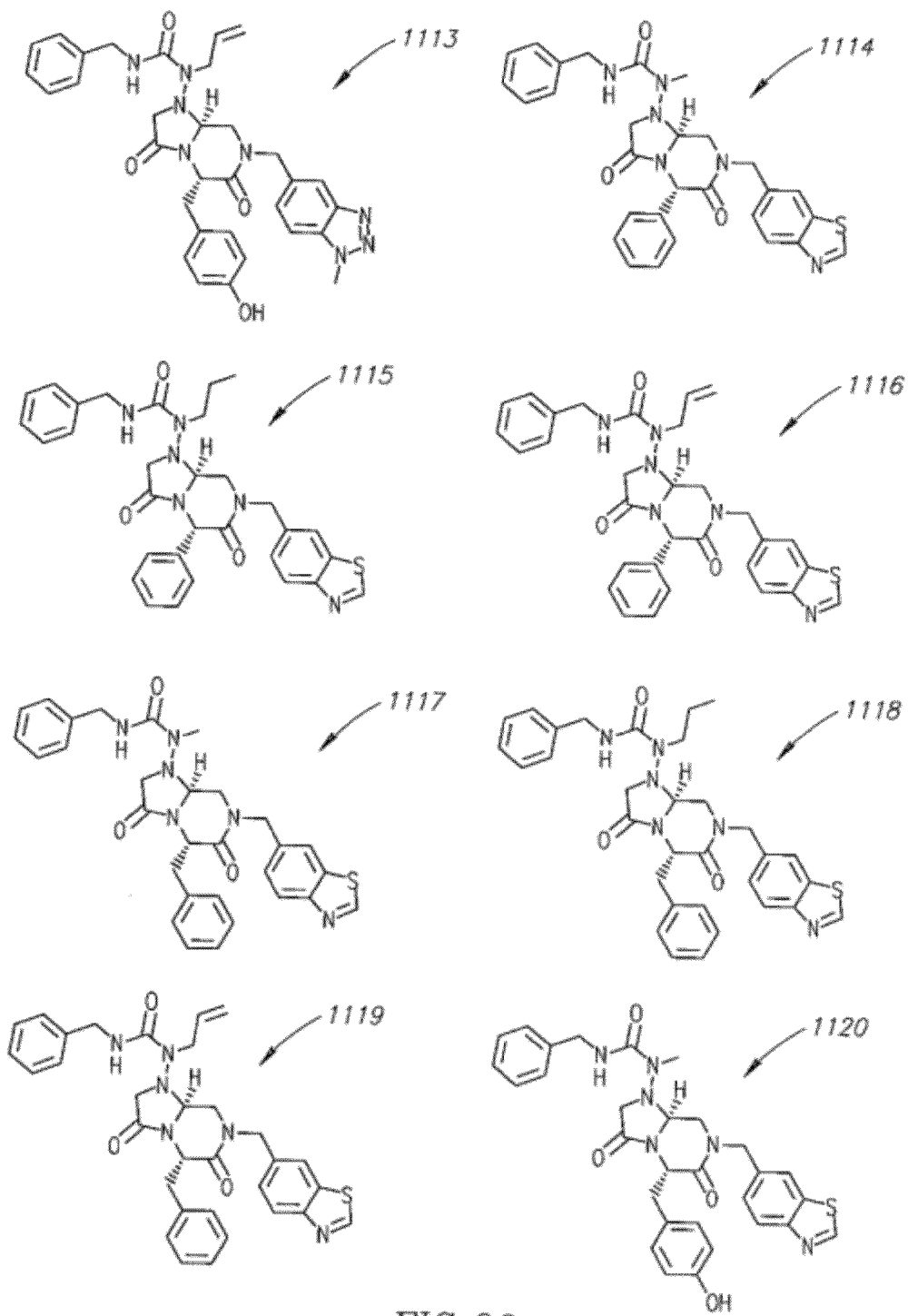
Figure 6P:
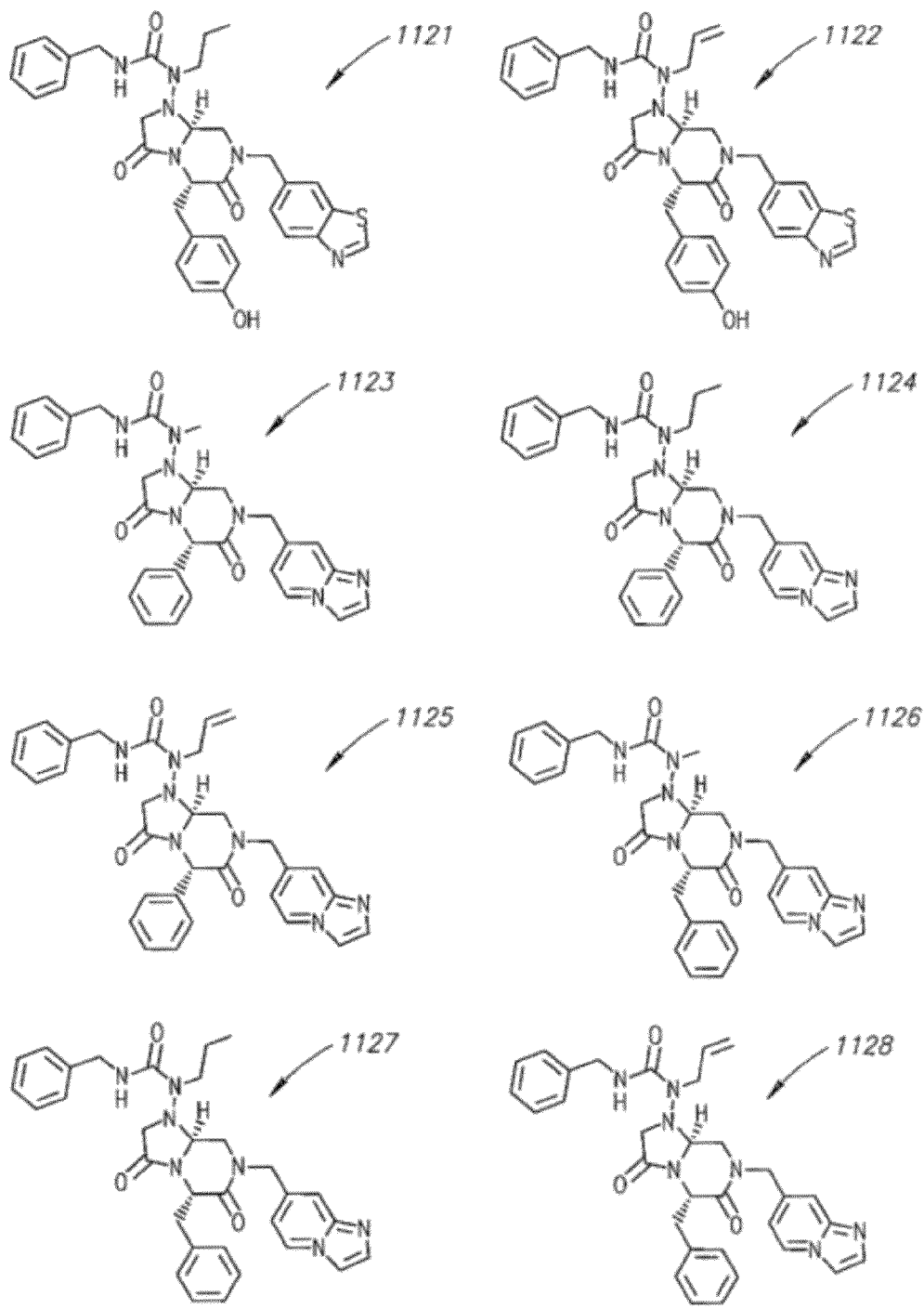
Figure 6Q:
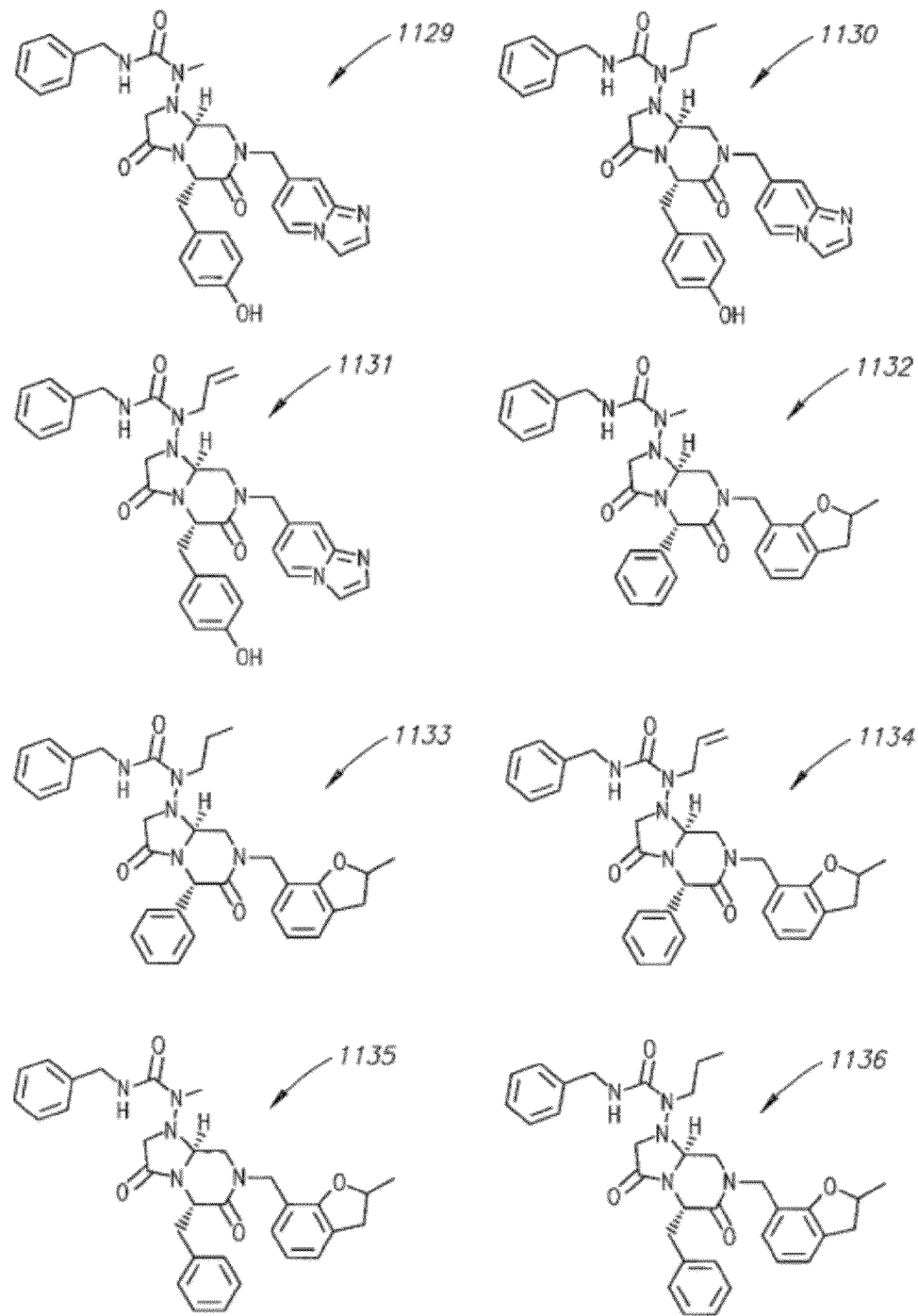
Figure 6R:
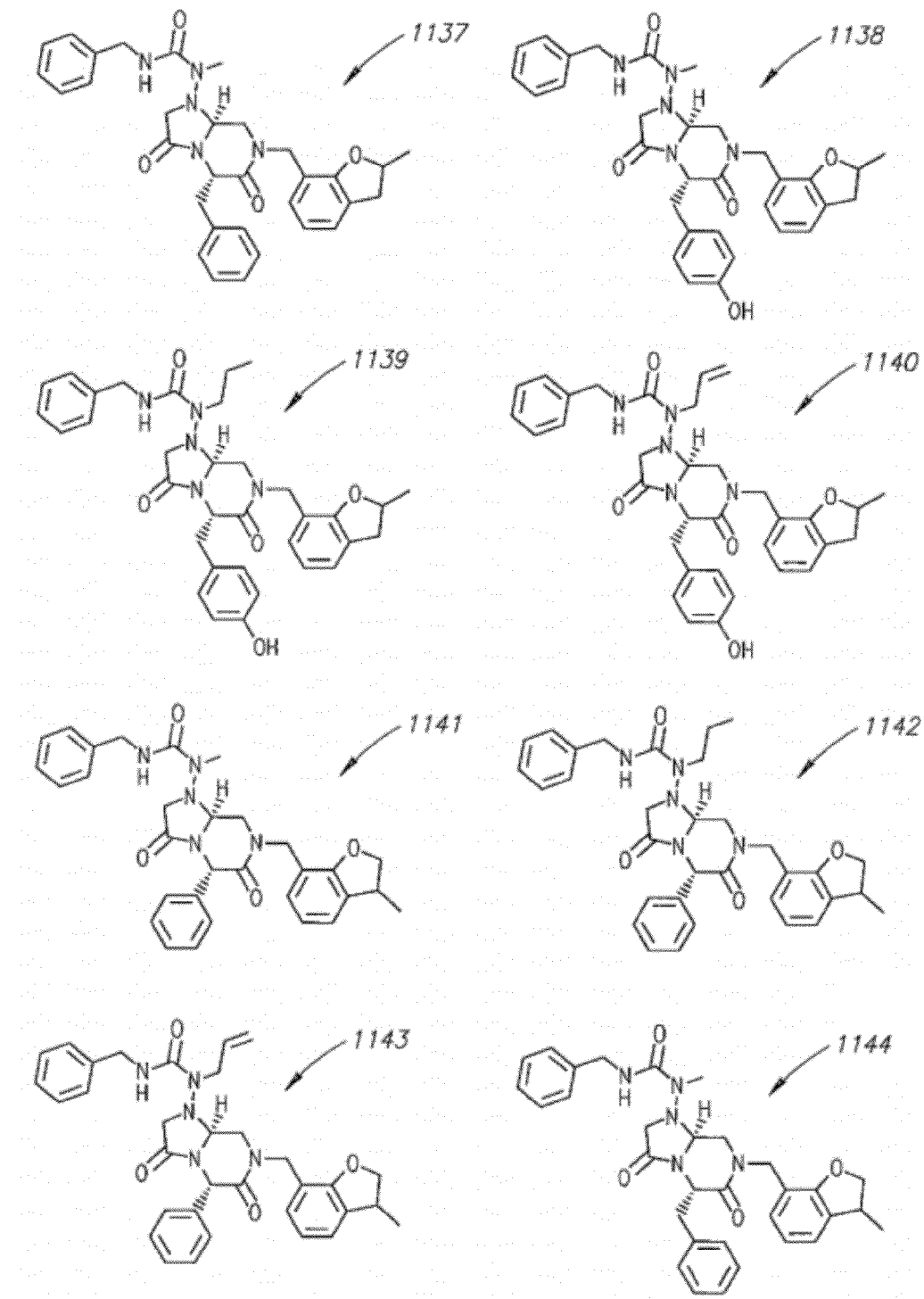
Figure 6S:
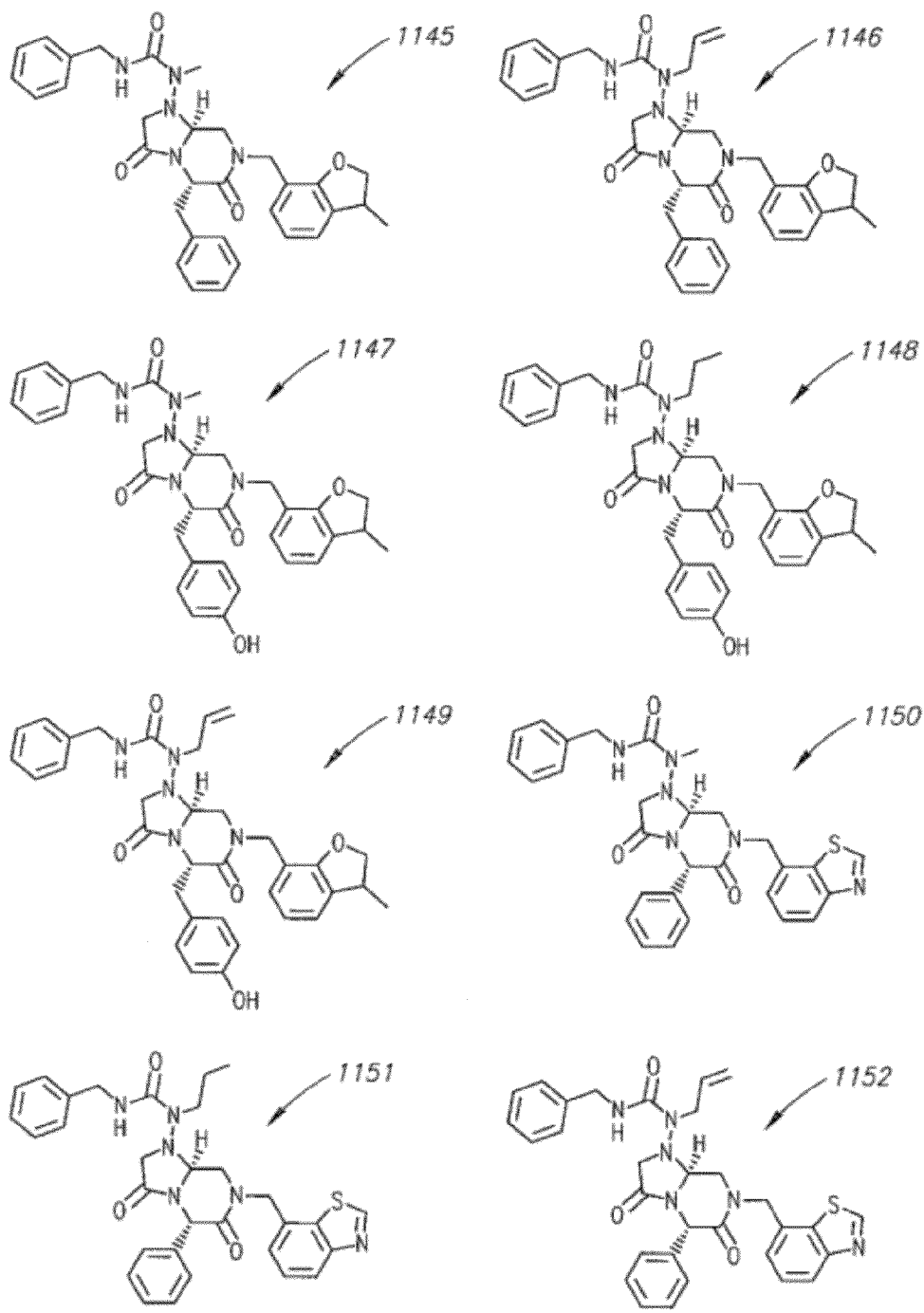
Figure 6T:
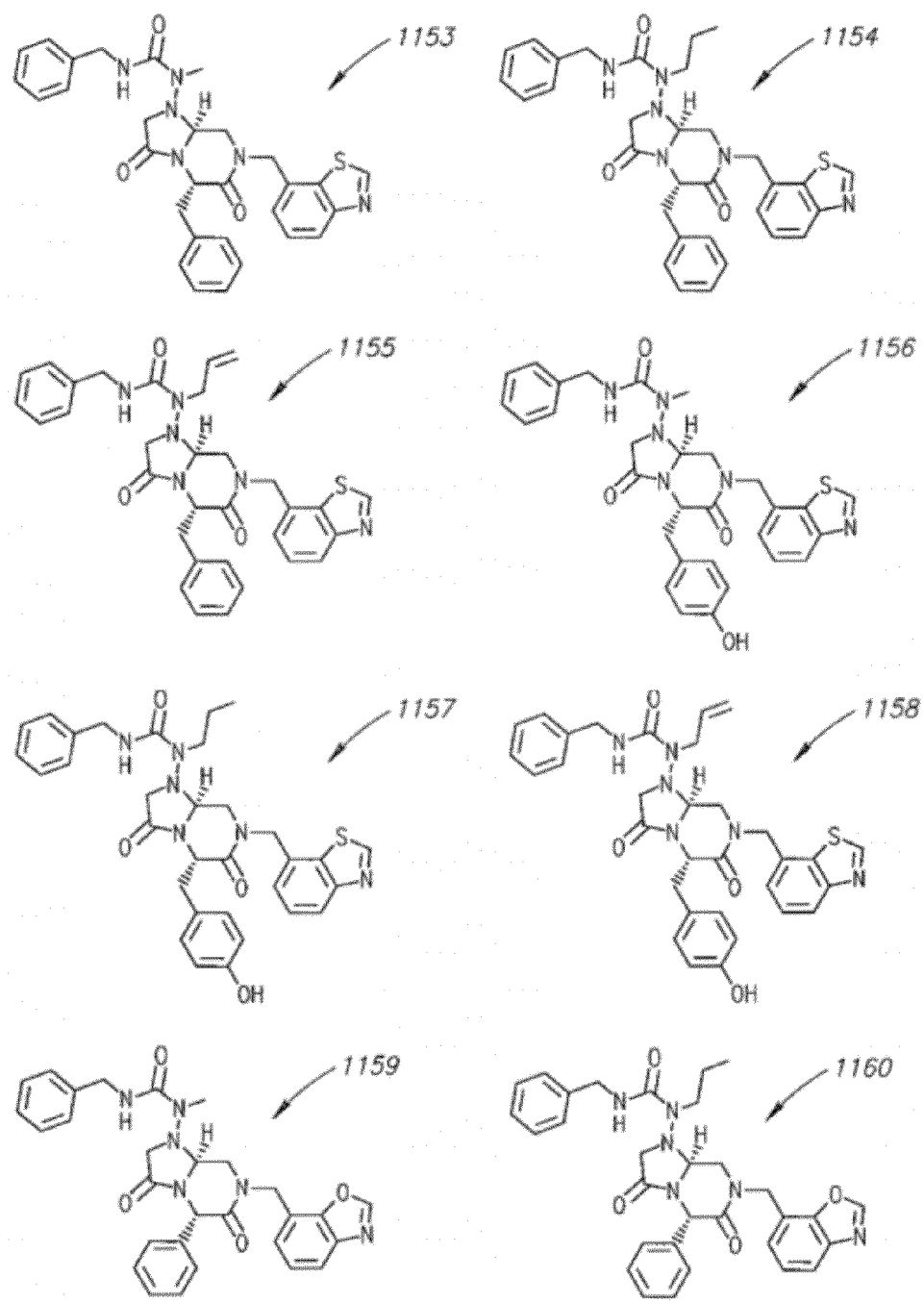
Figure 6U:
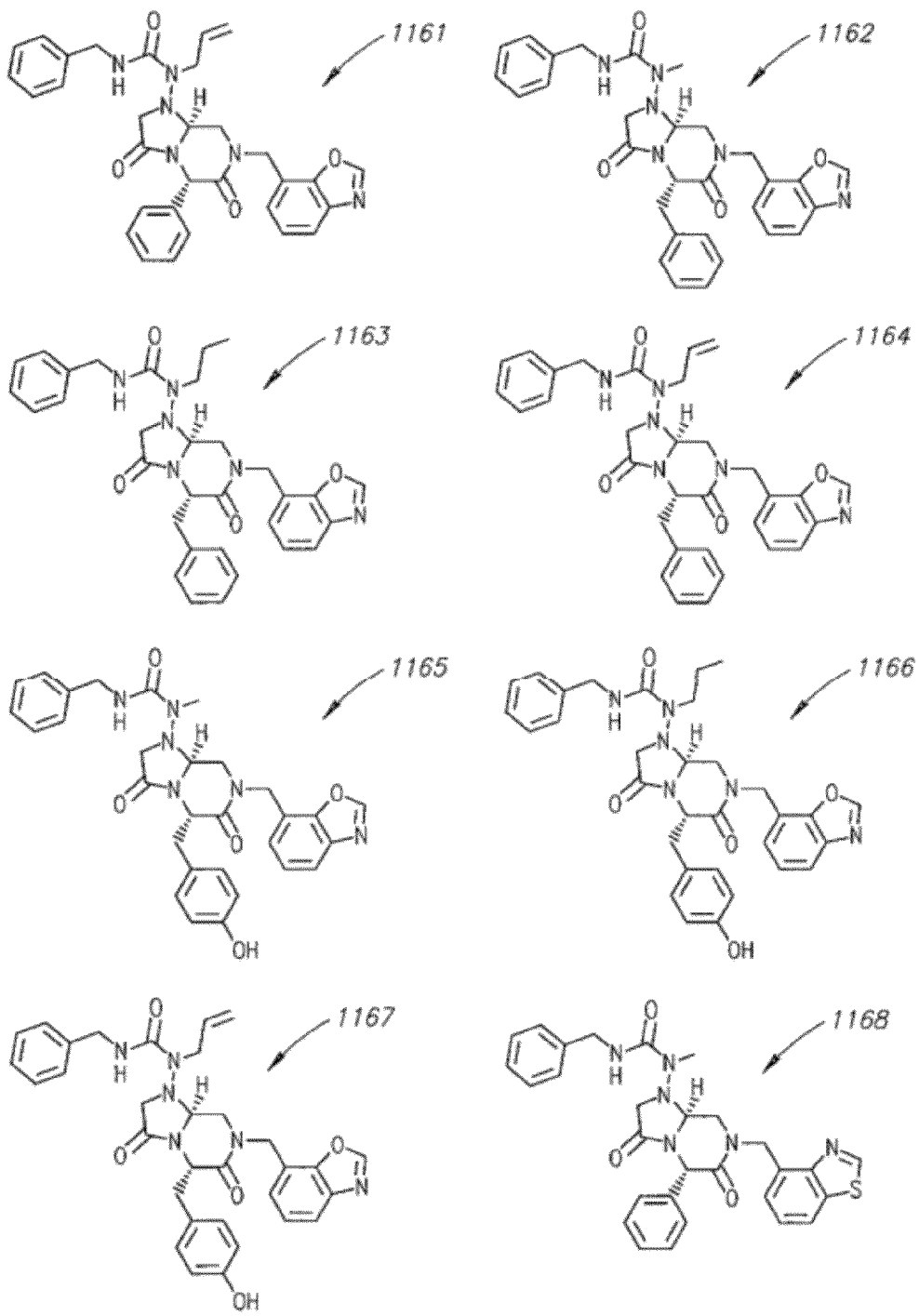
Figure 6V:
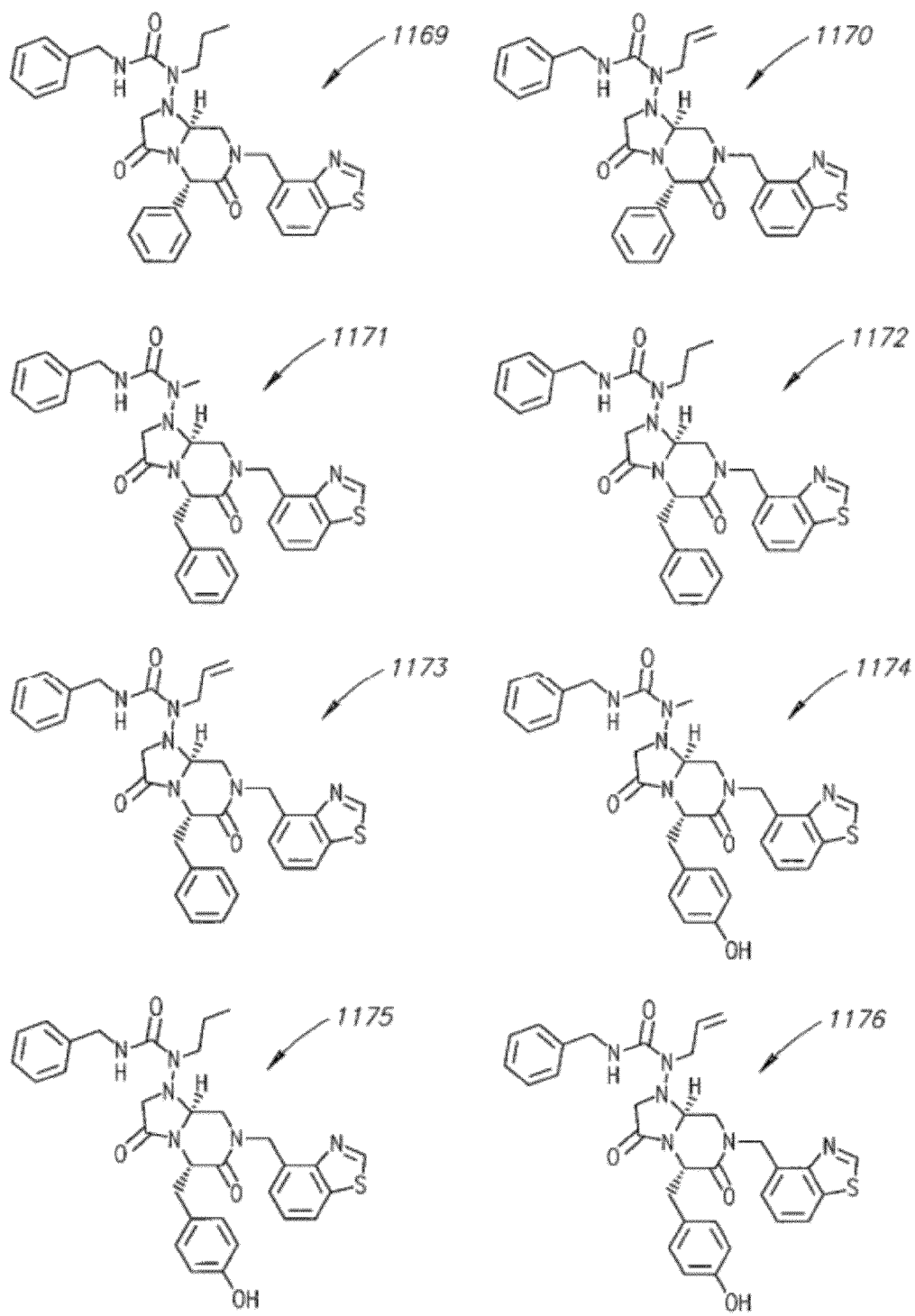
Figure 6W:
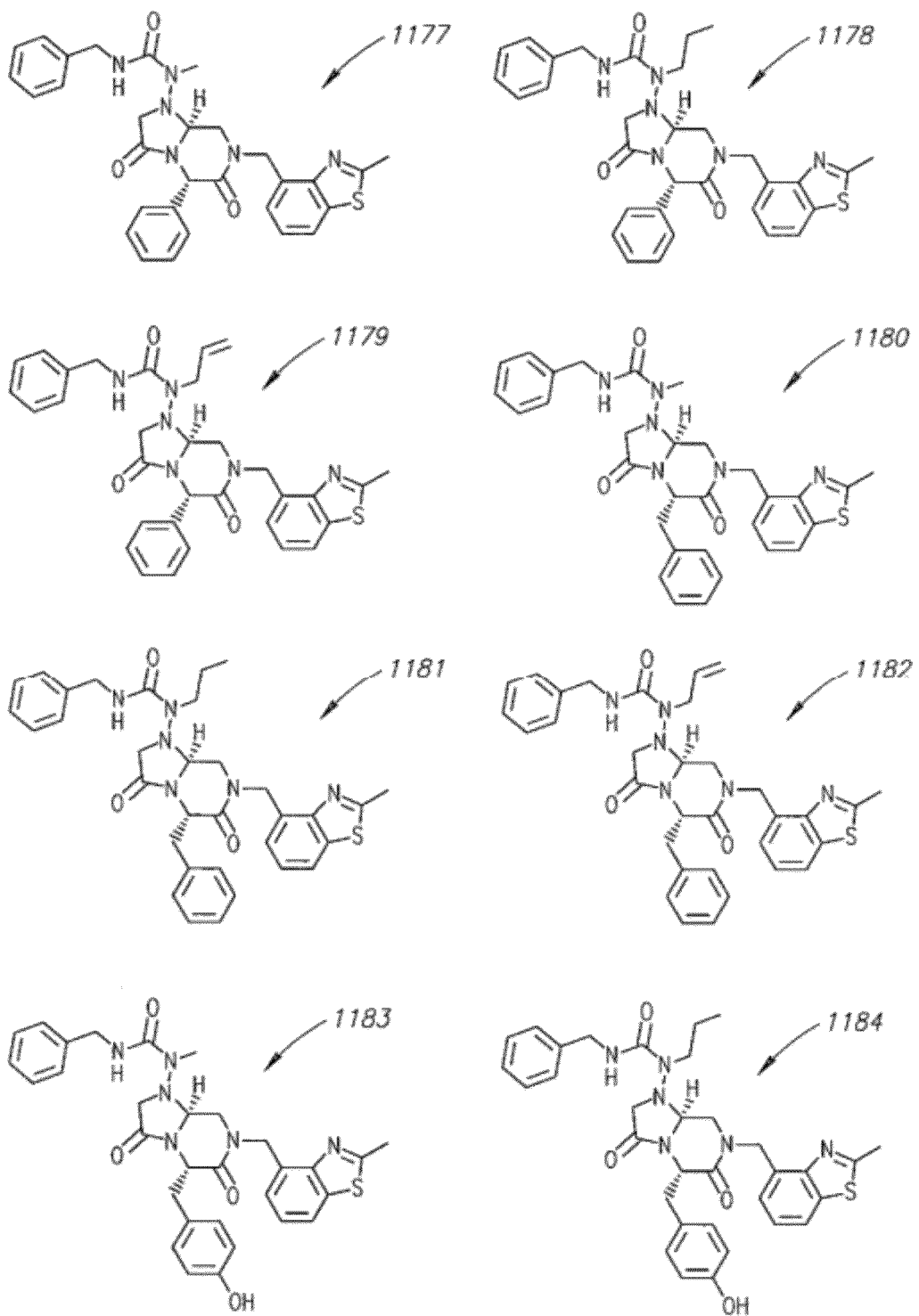
Figure 6X:
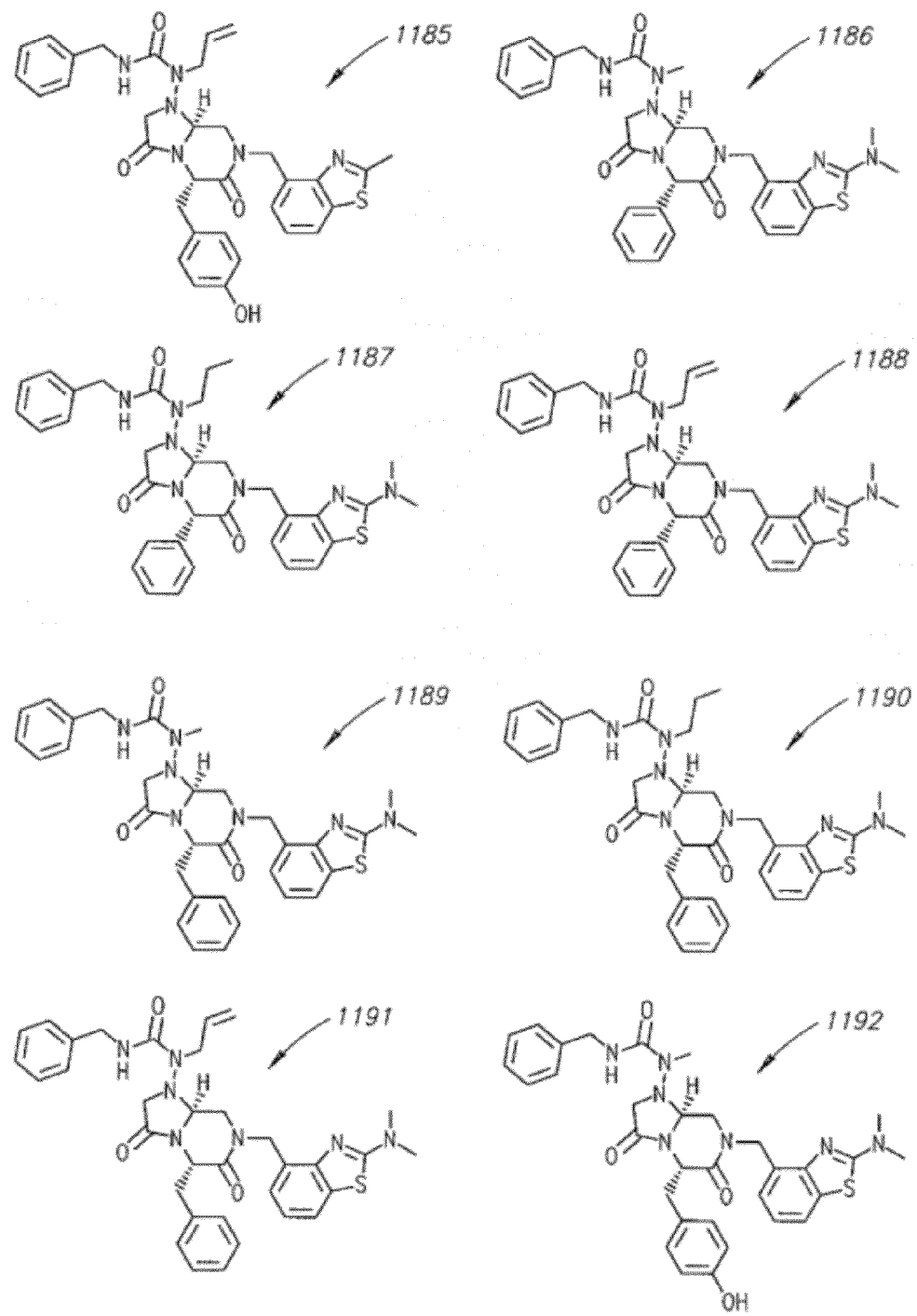
Figure 6Y:
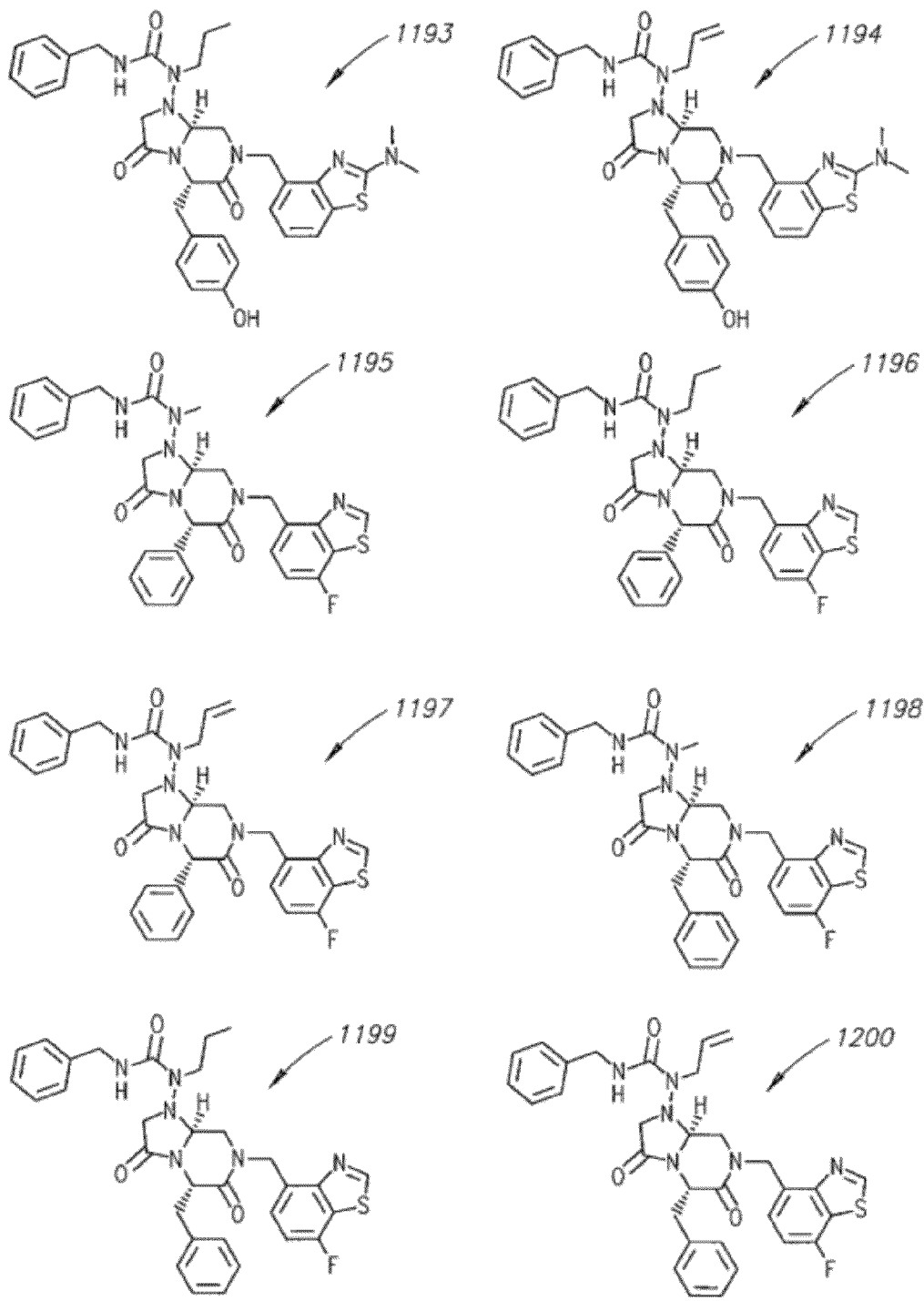
Figure 7A:
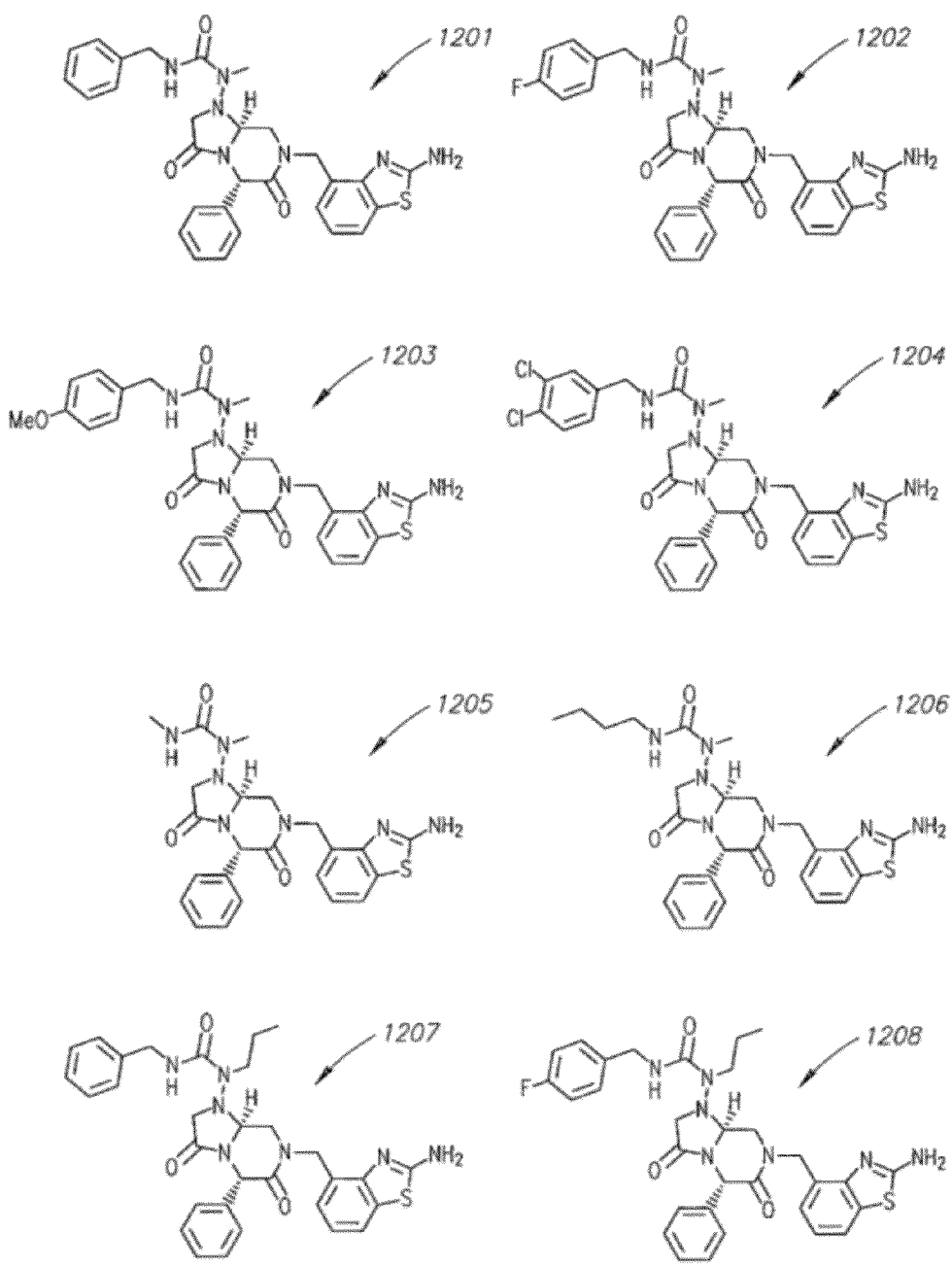
FIGS. 7A-7Z shows the chemical structures of compounds 1201-1400.
Figure 7B:
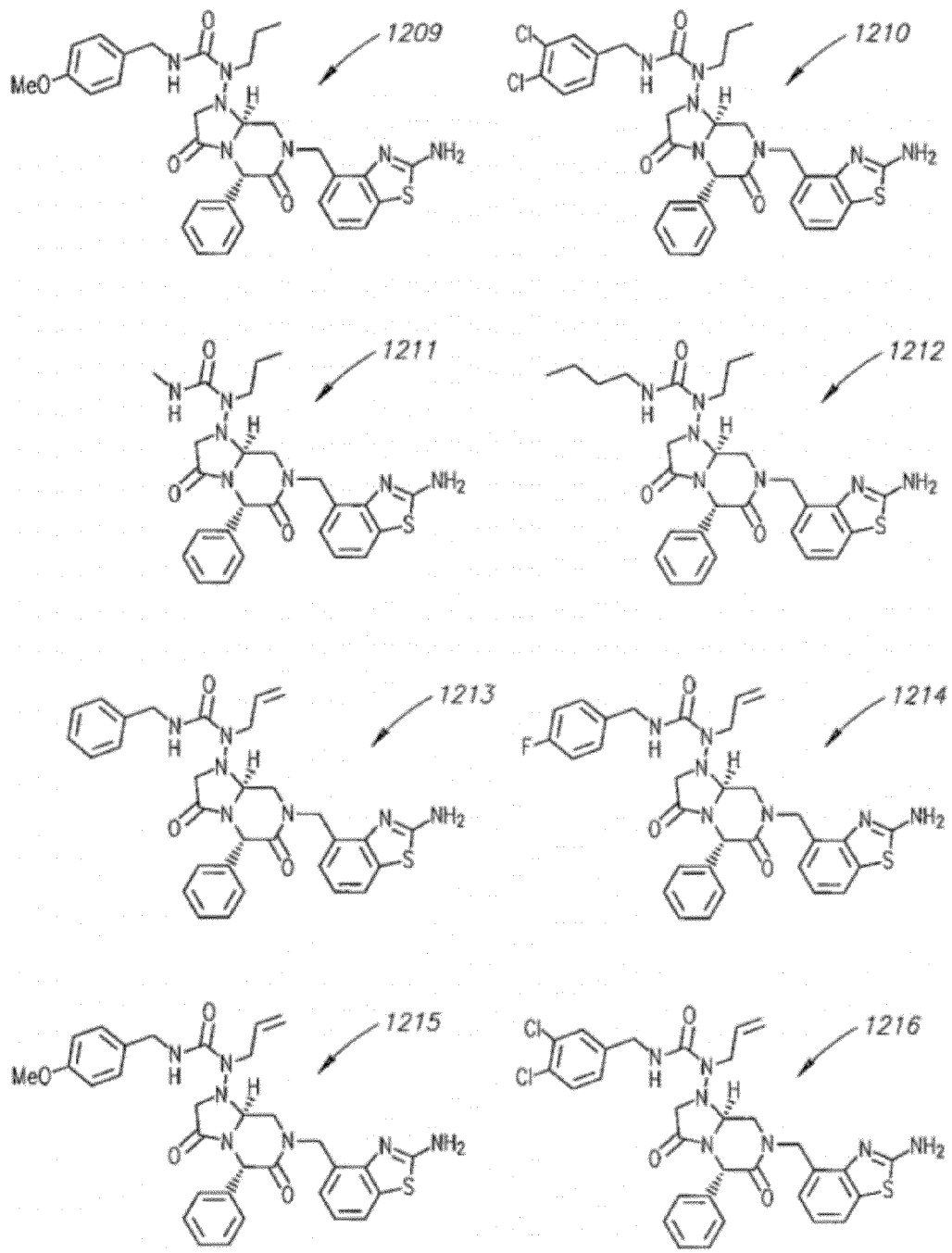
Figure 7C:
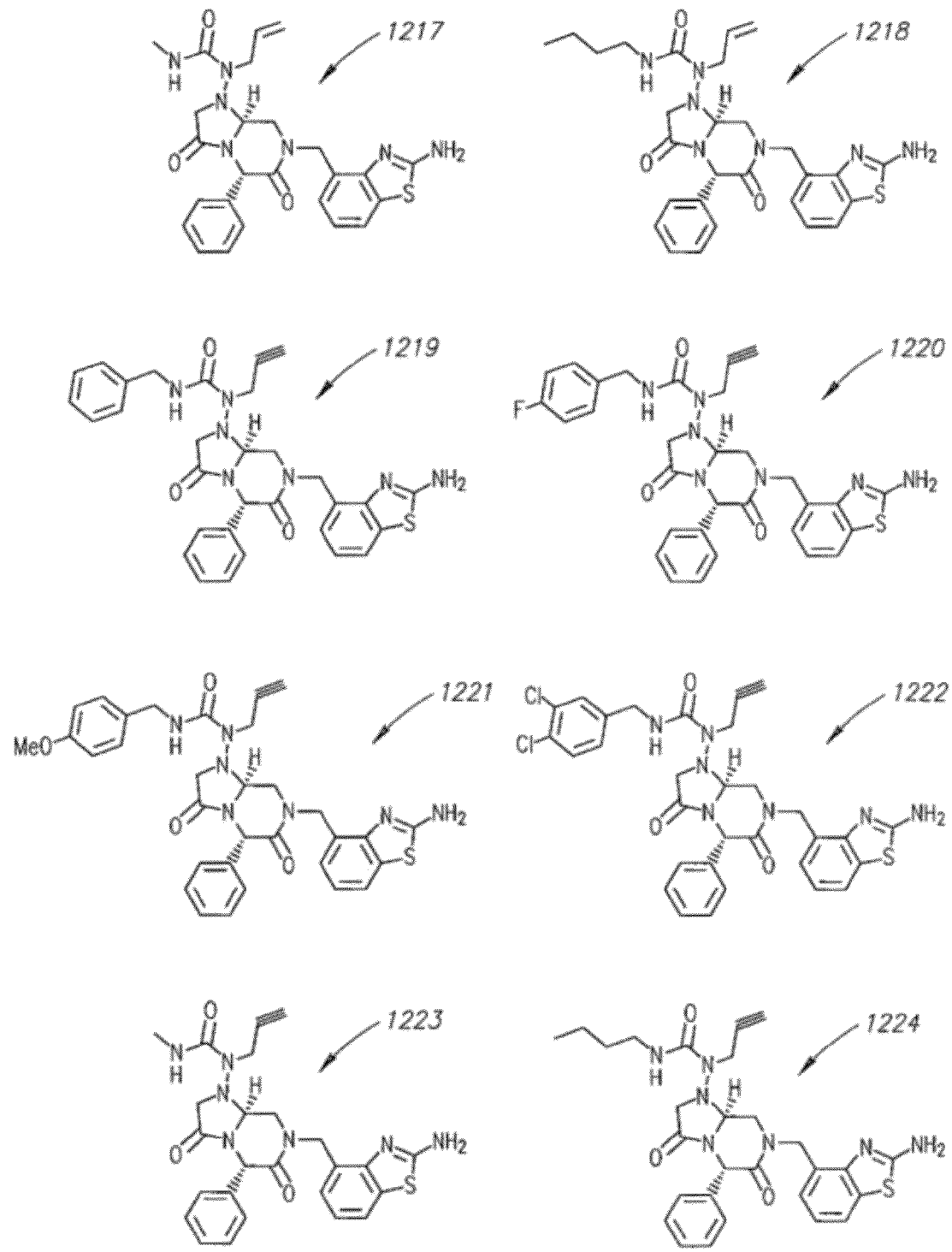
Figure 7E:
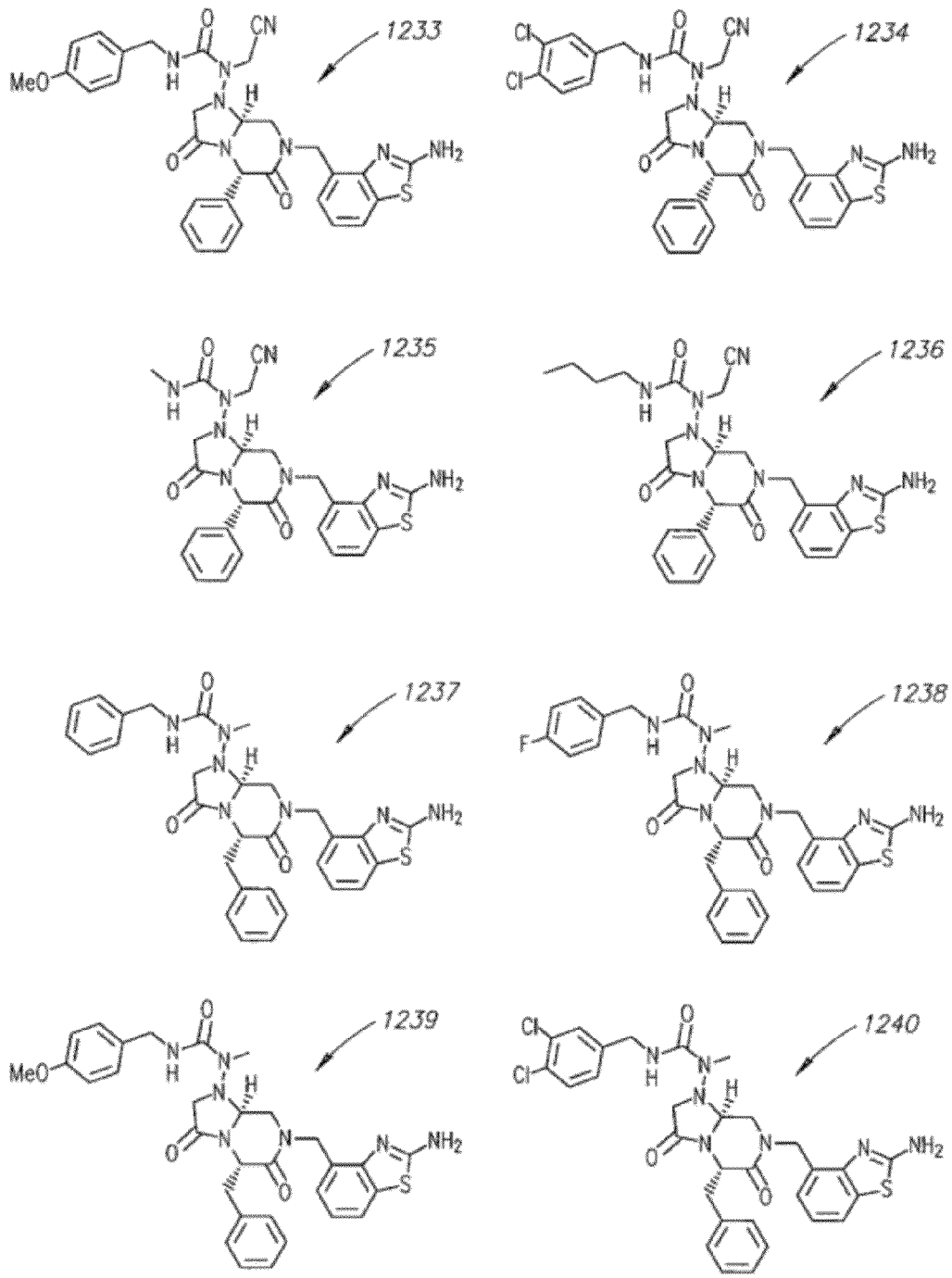
Figure 7F:
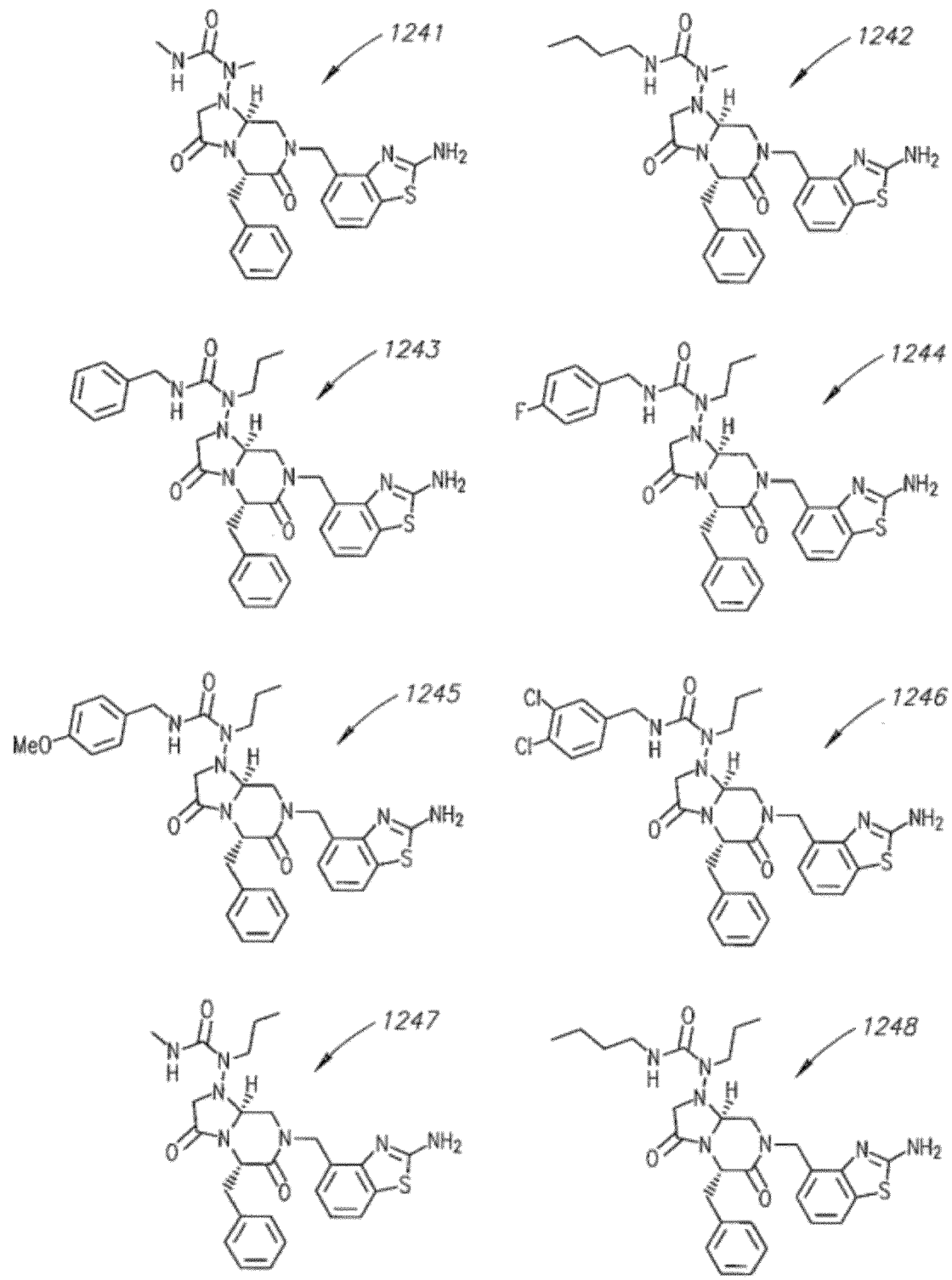
Figure 7G:
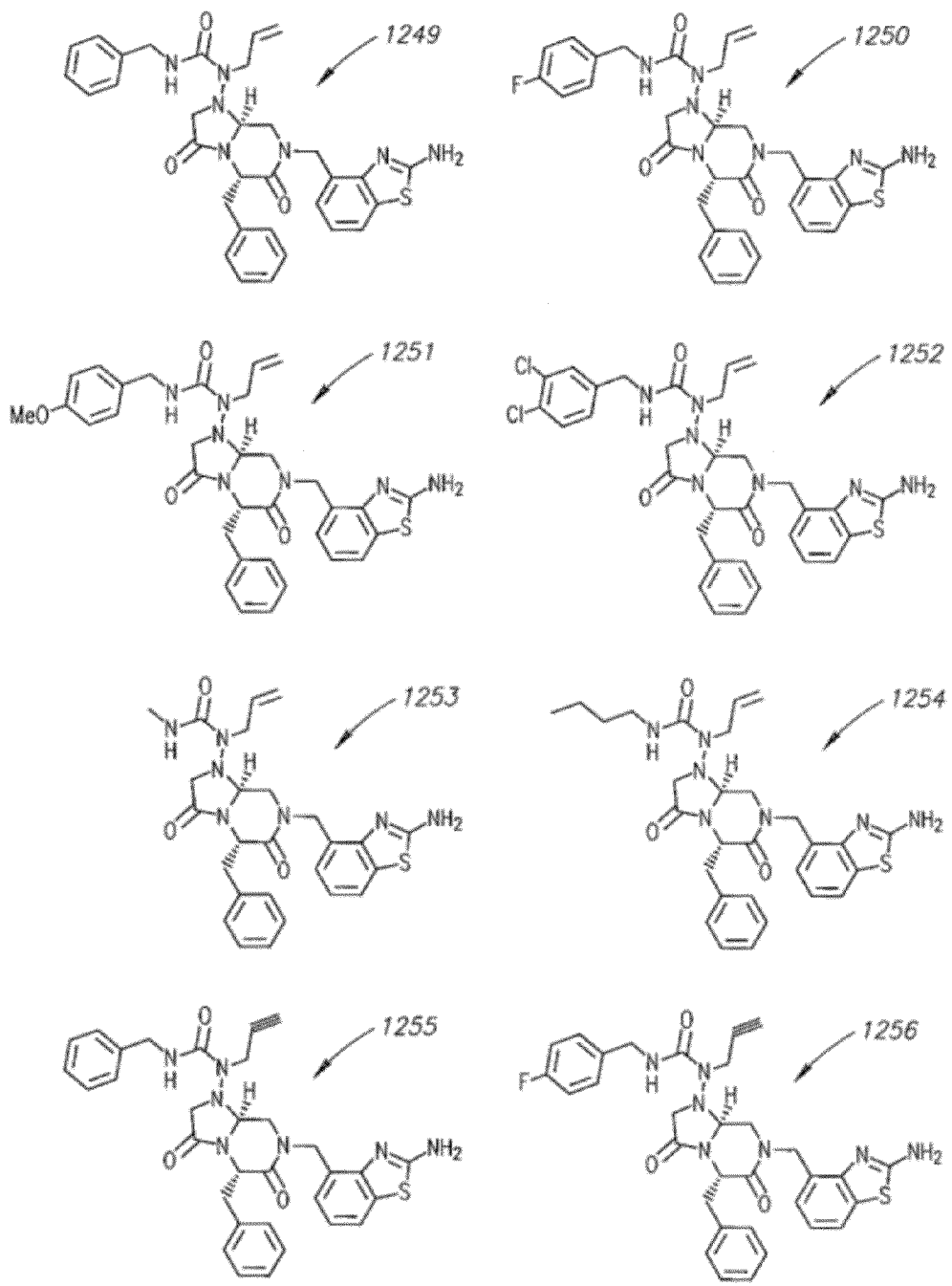
Figure 7H:
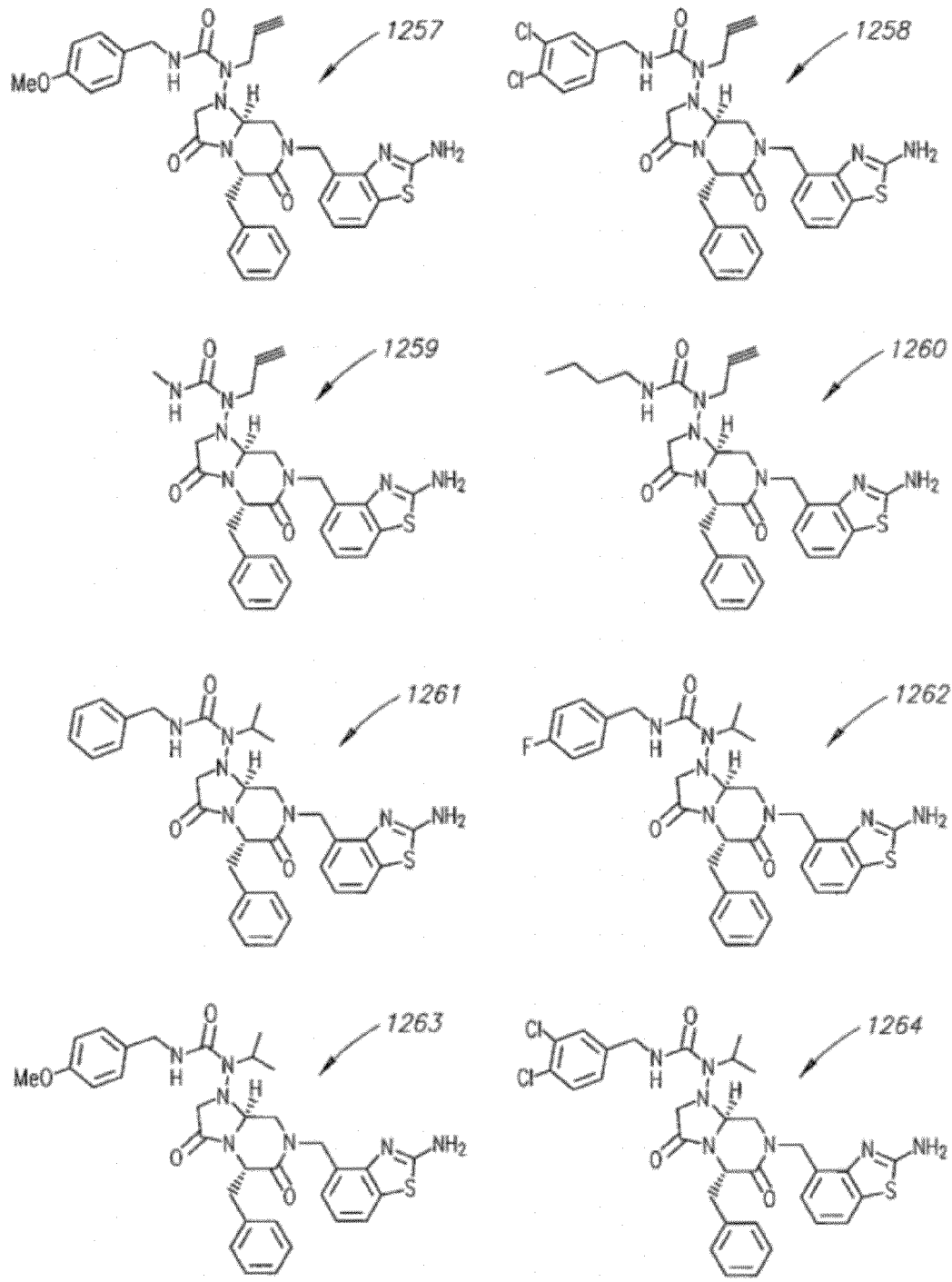
Figure 7I:
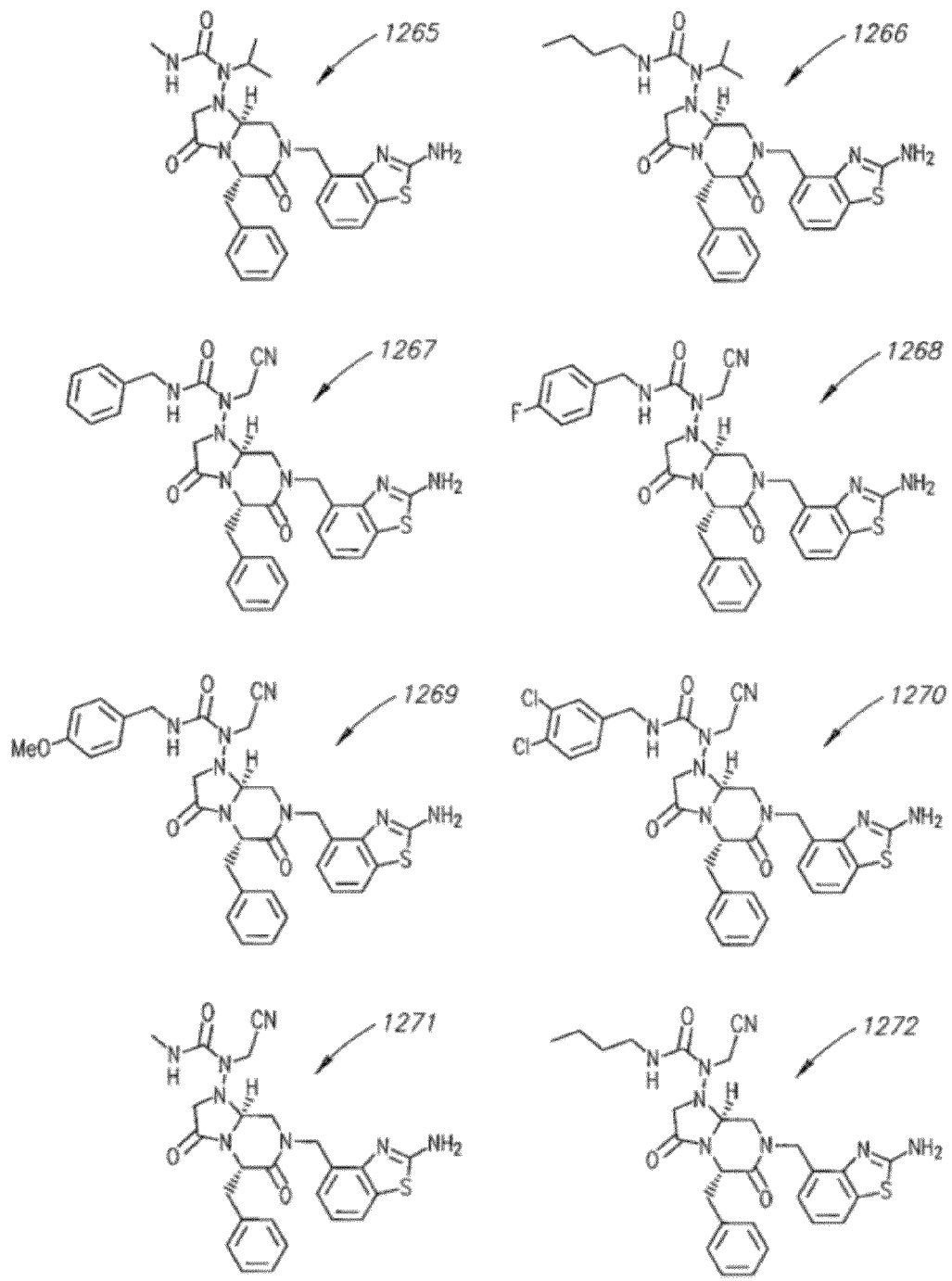
Figure 7J:
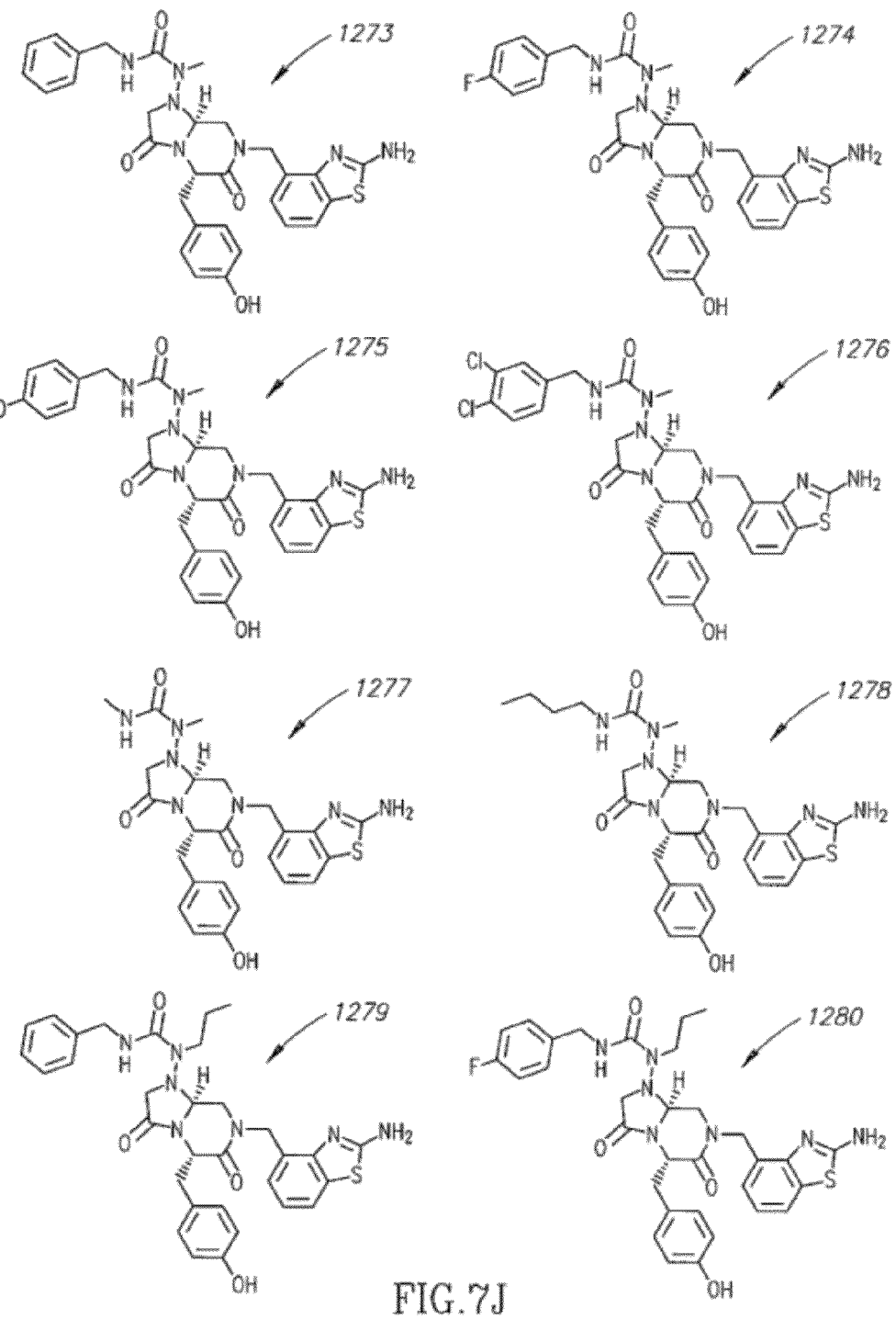
Figure 7K:
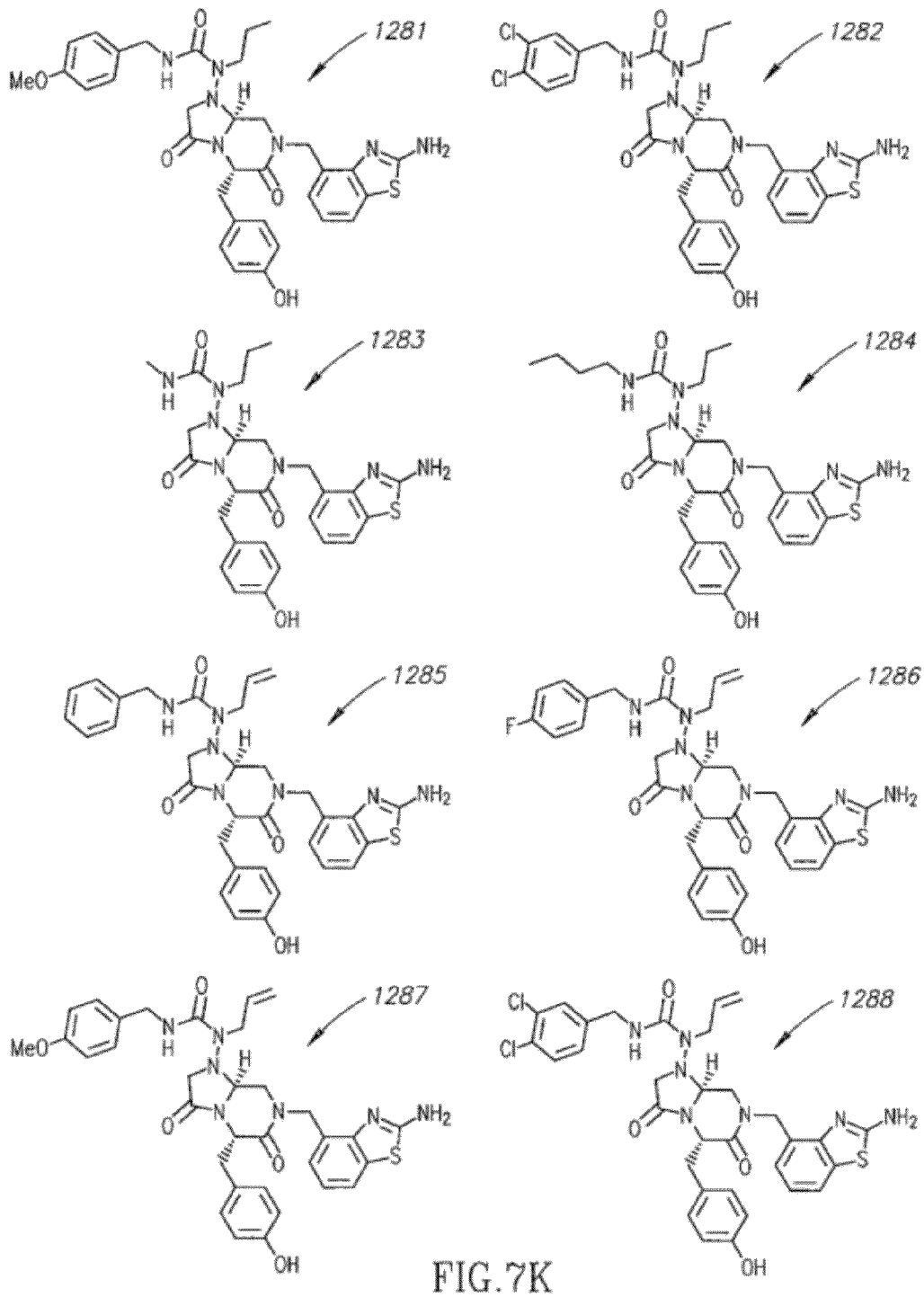
Figure 7L:
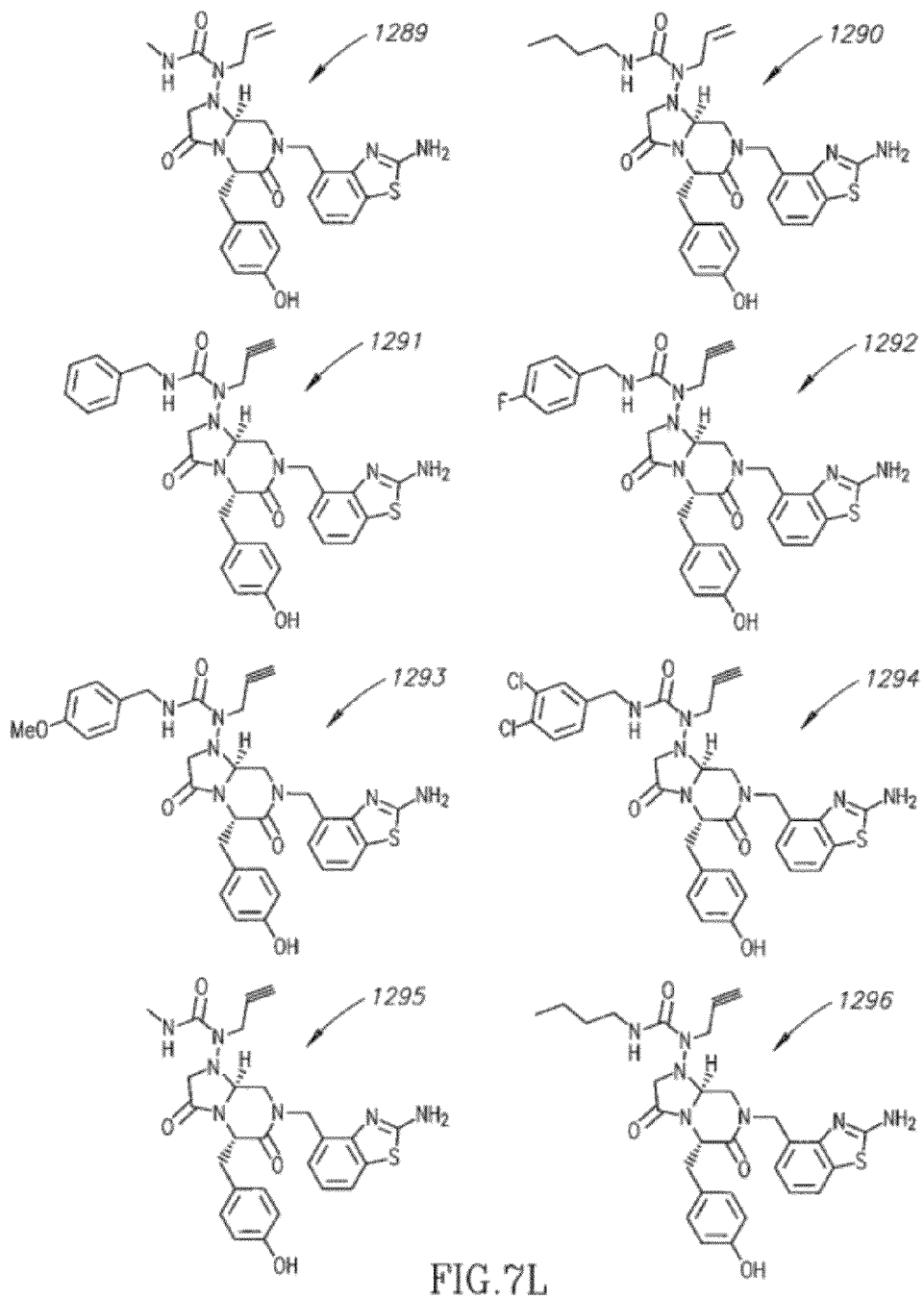
Figure 7M:
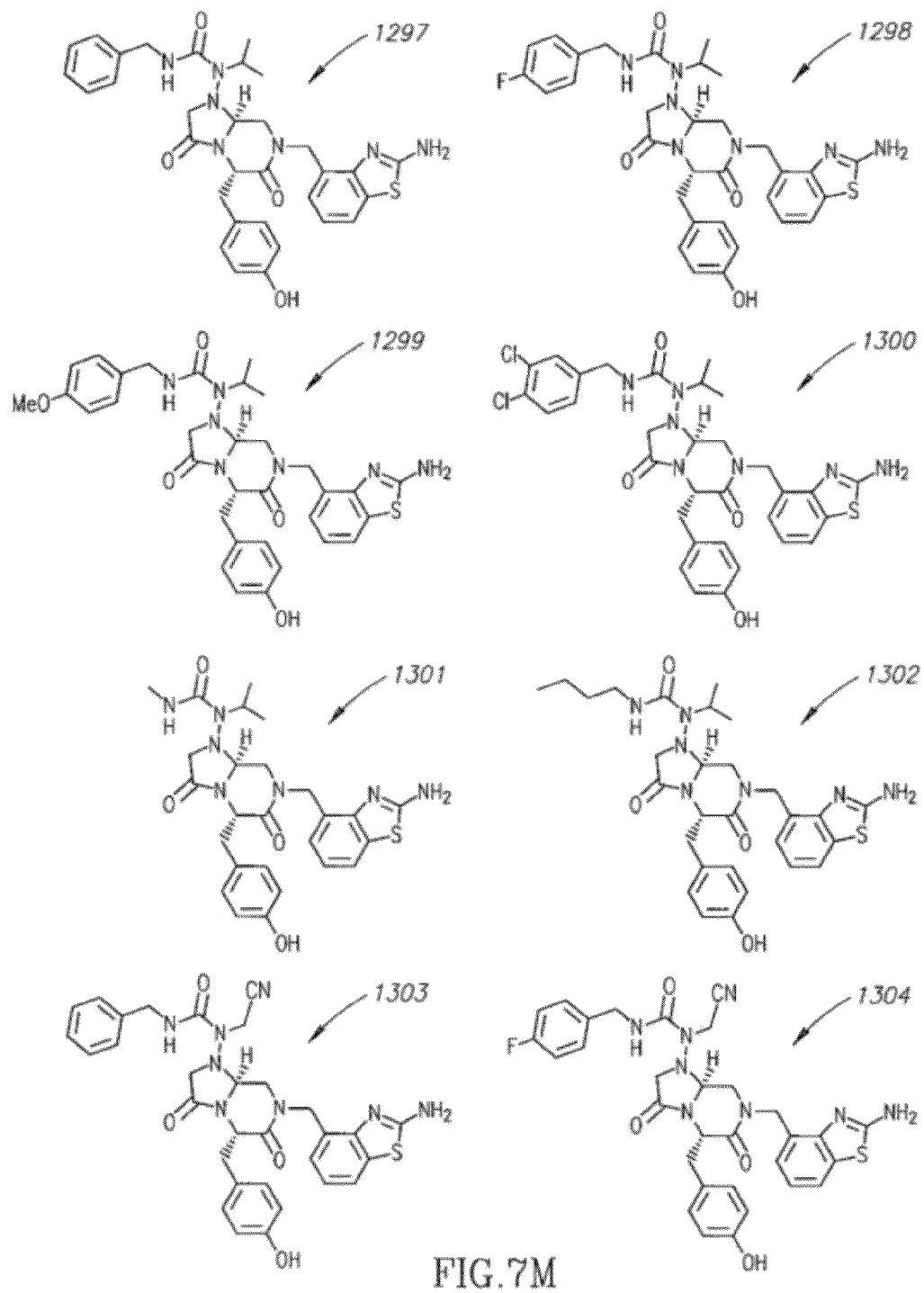
Figure 7N:
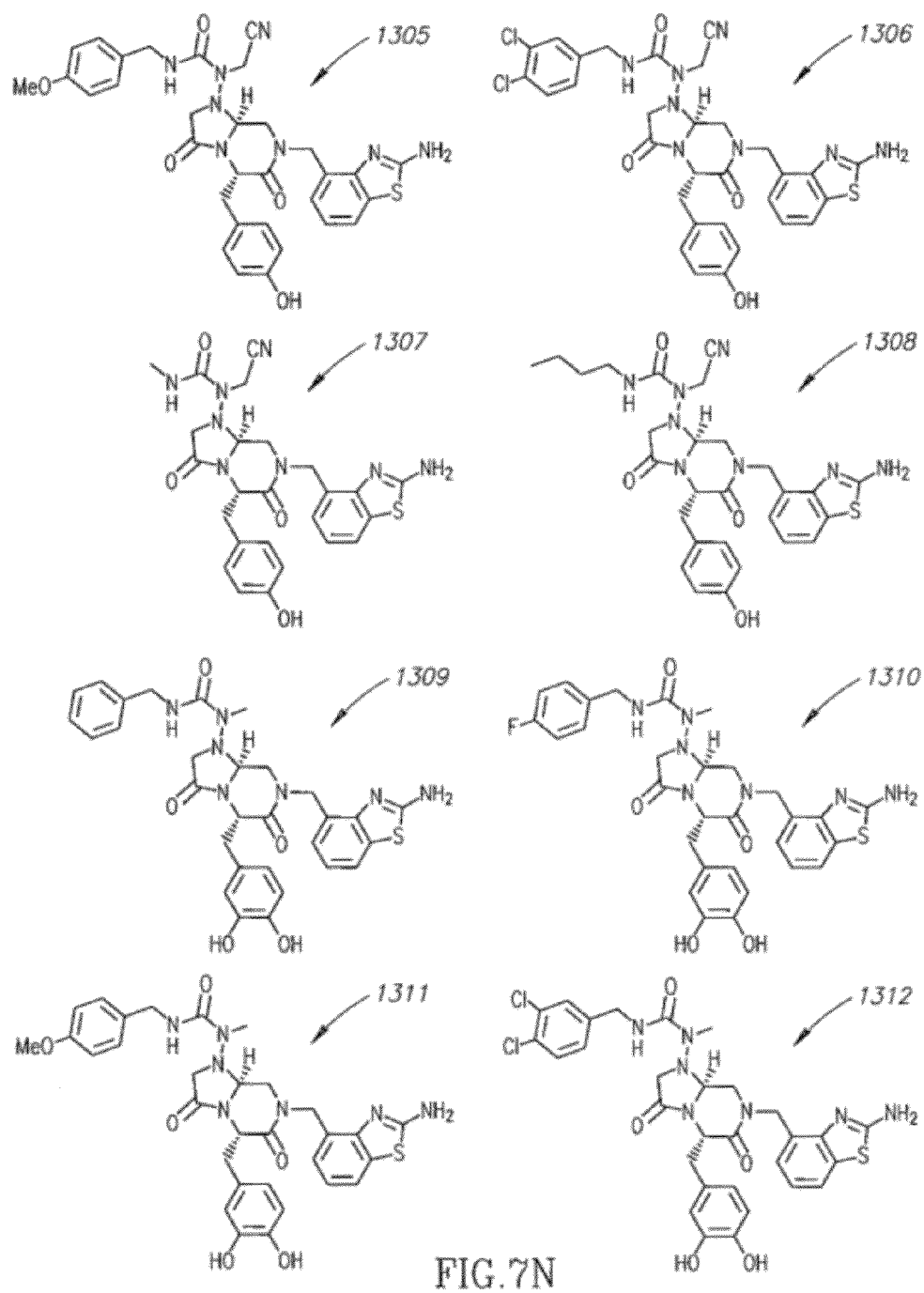
Figure 70:
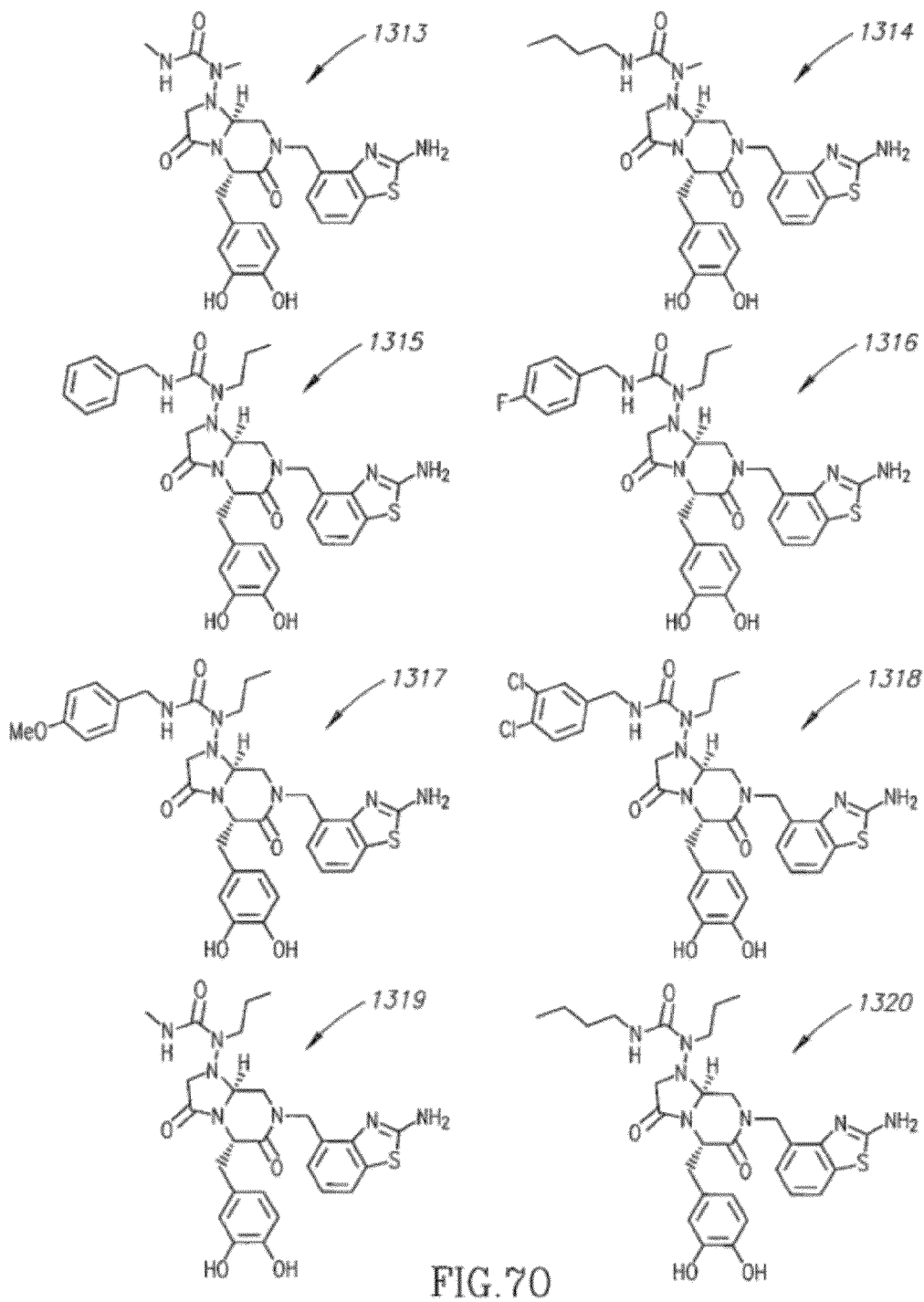
Figure 7P:
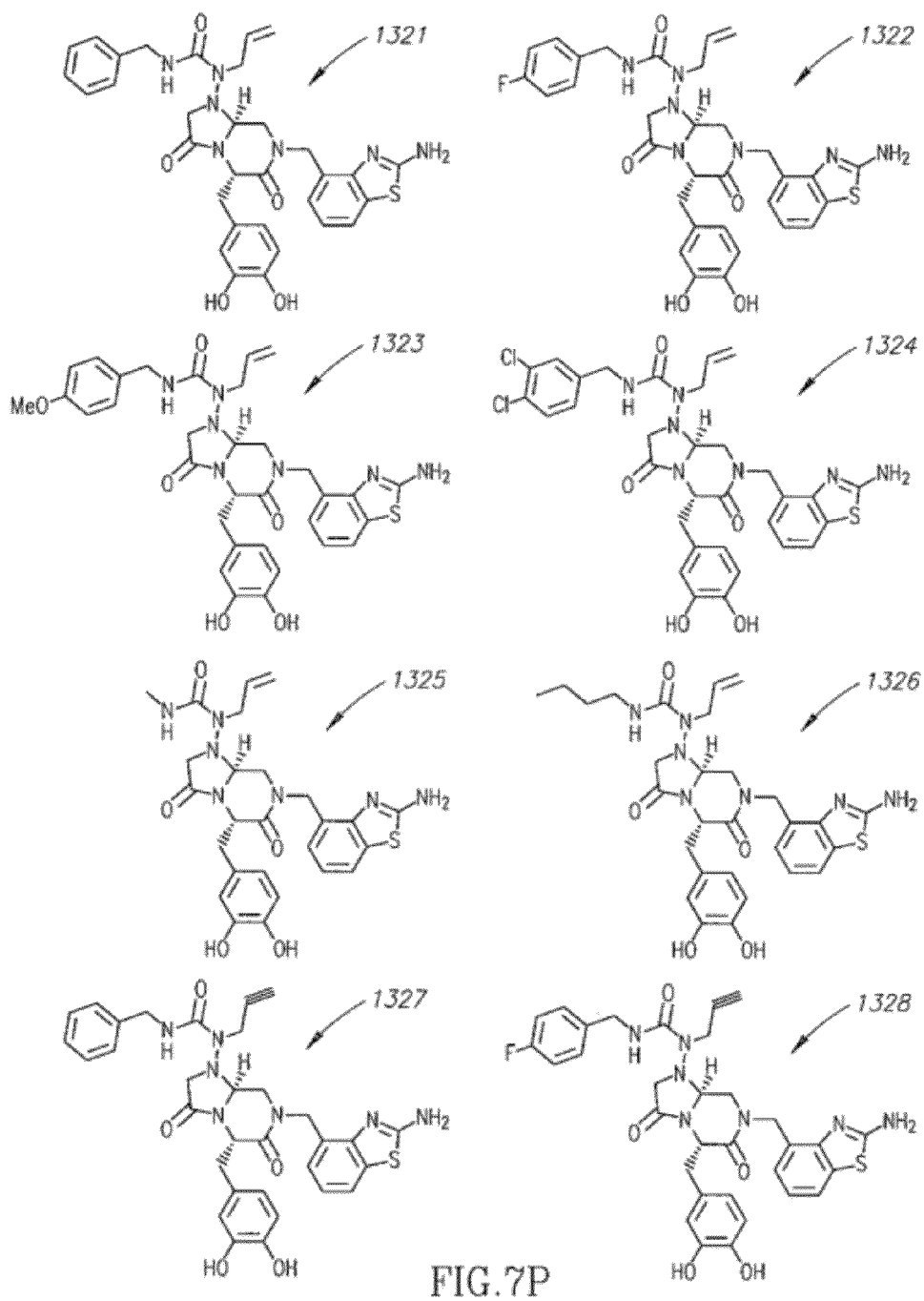
Figure 7Q:
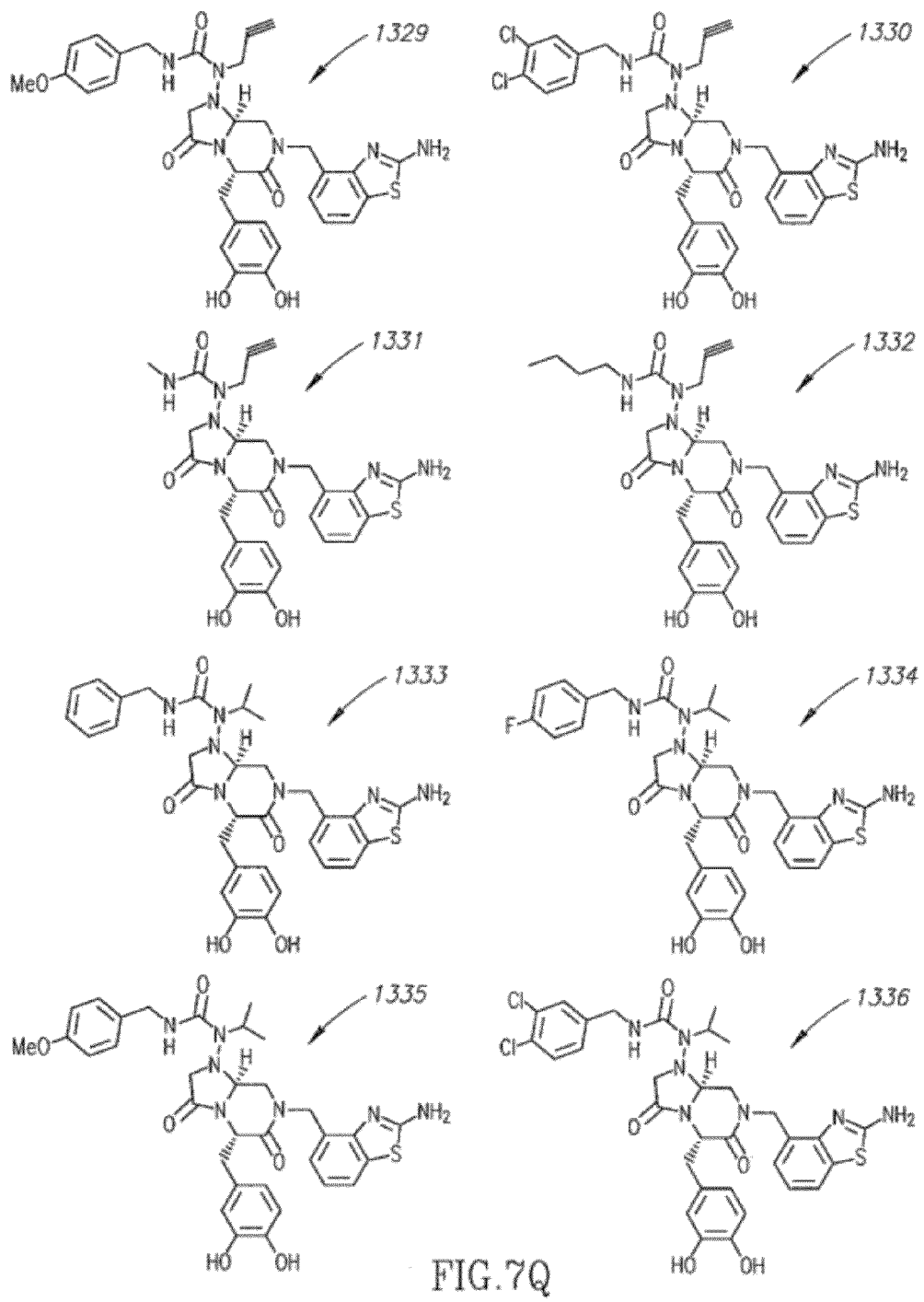
Figure 7R:
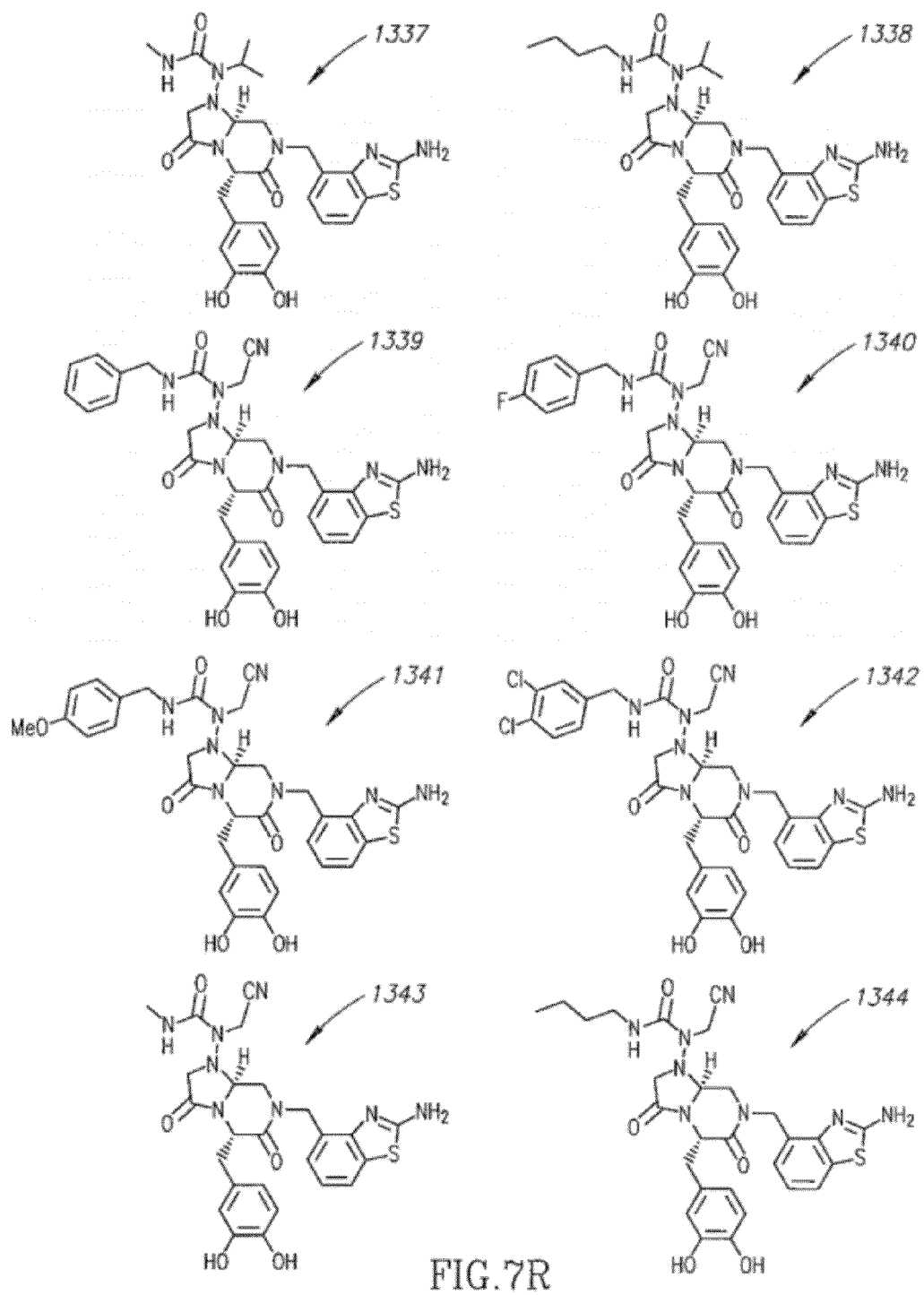
Figure 7S:
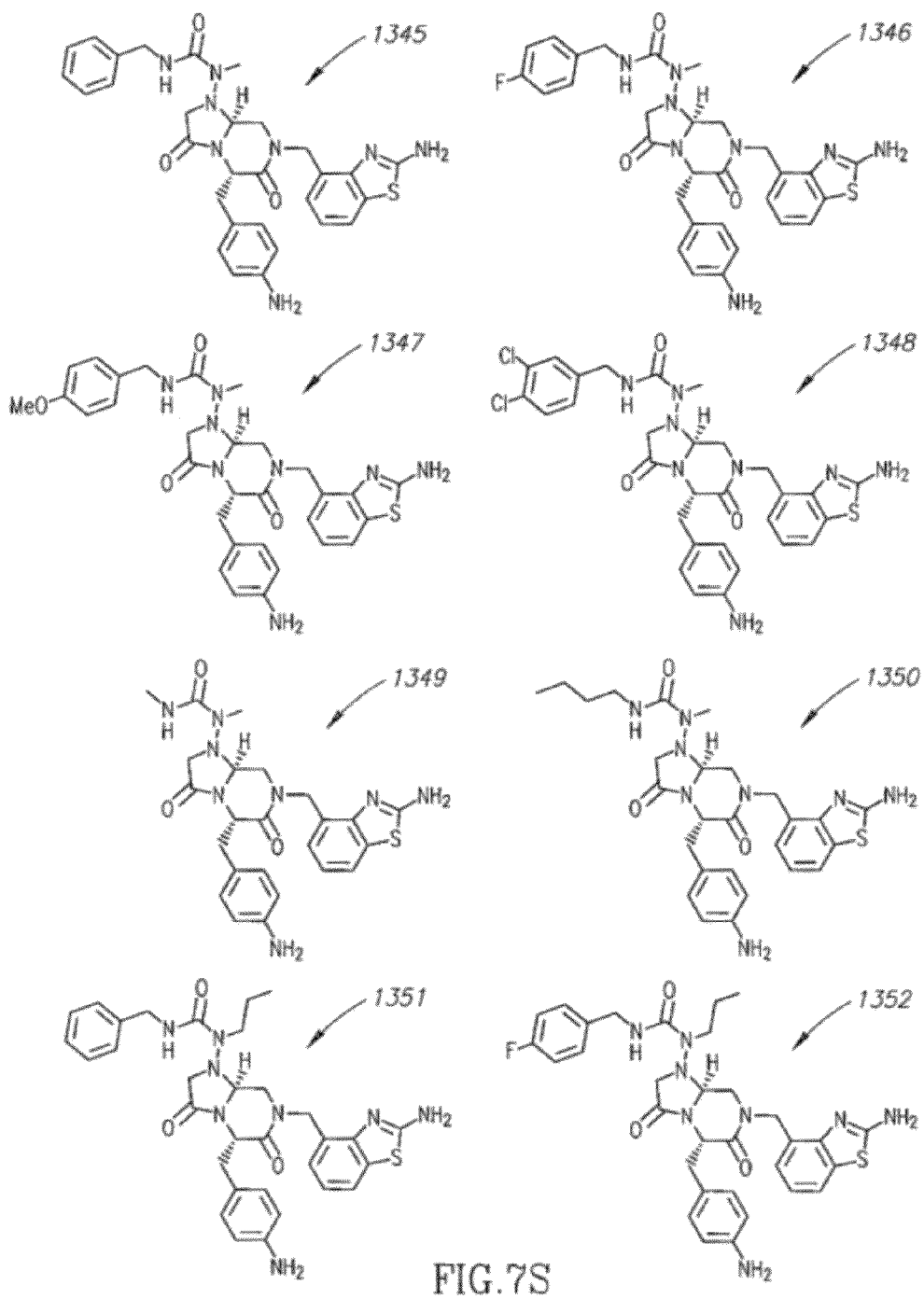
Figure 7T:
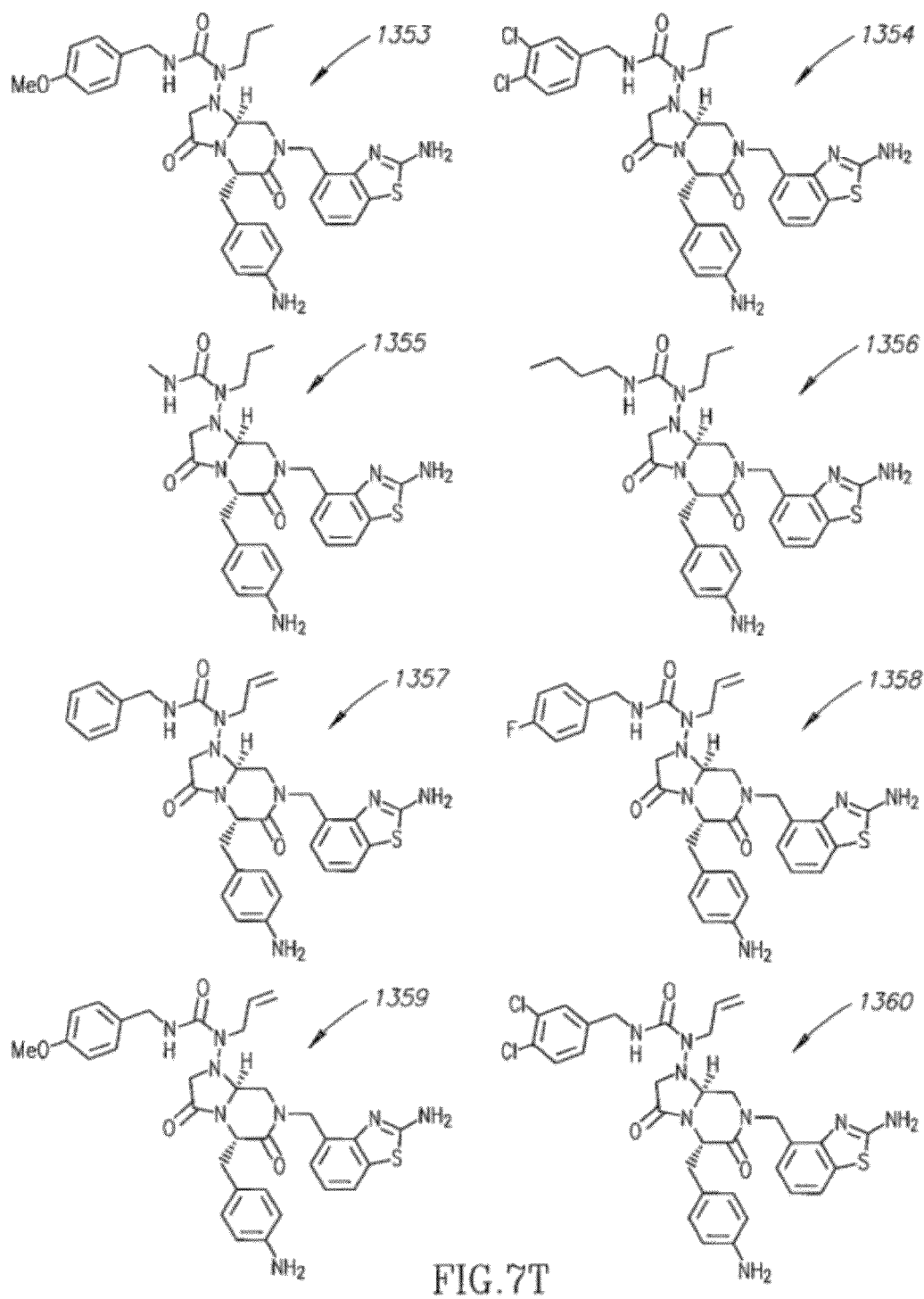
Figure 7U:
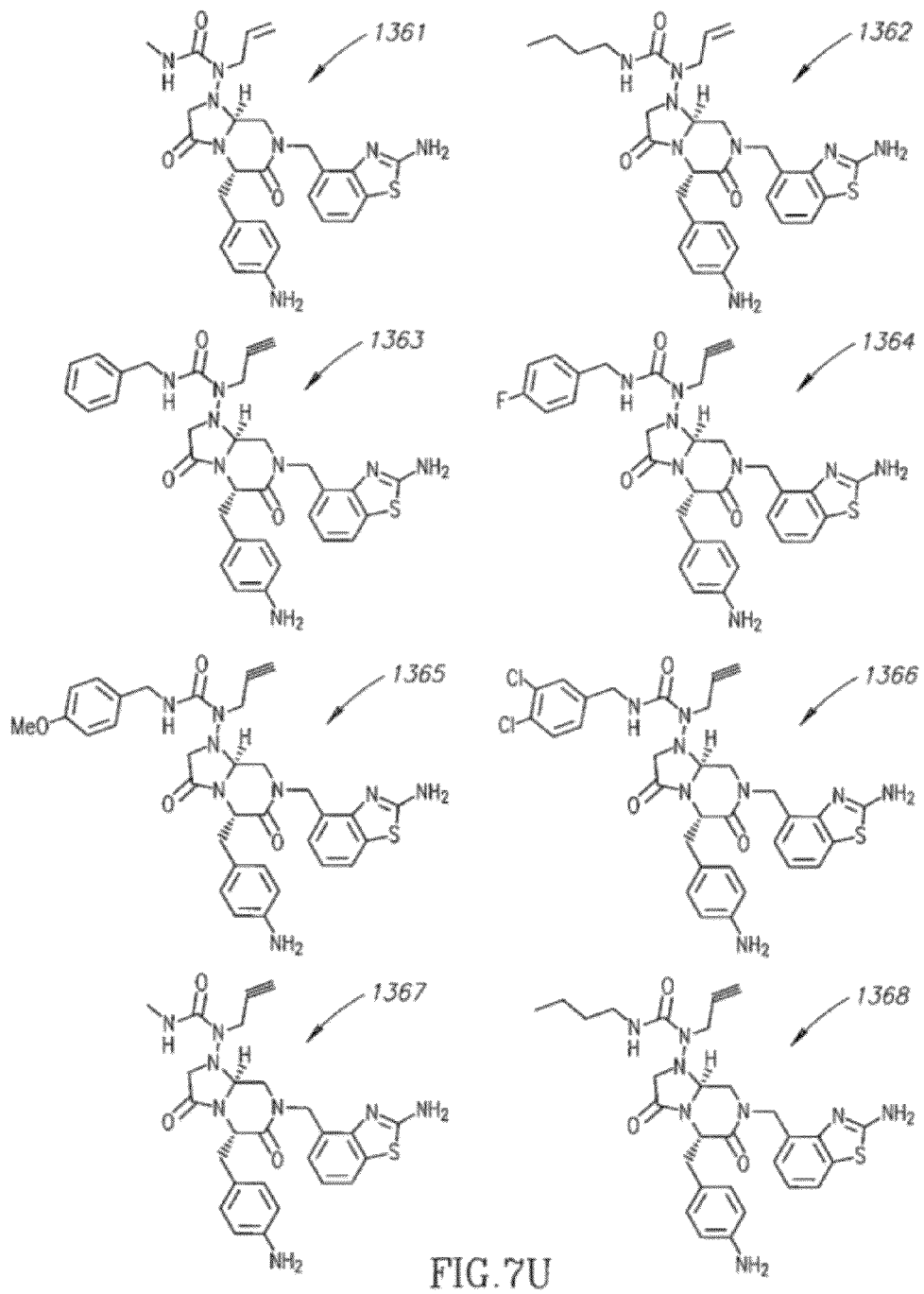
Figure 7V:
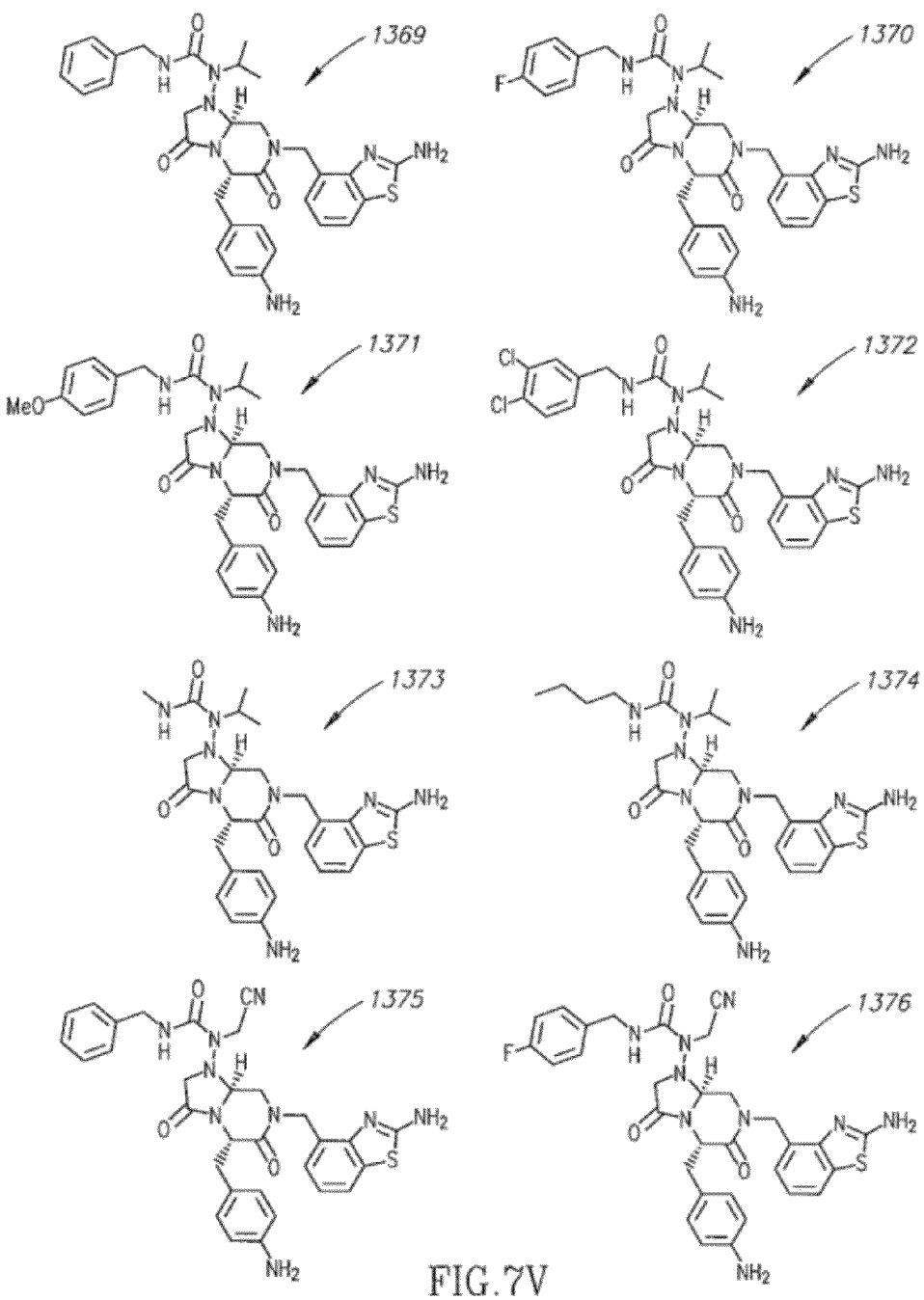
Figure 7W:
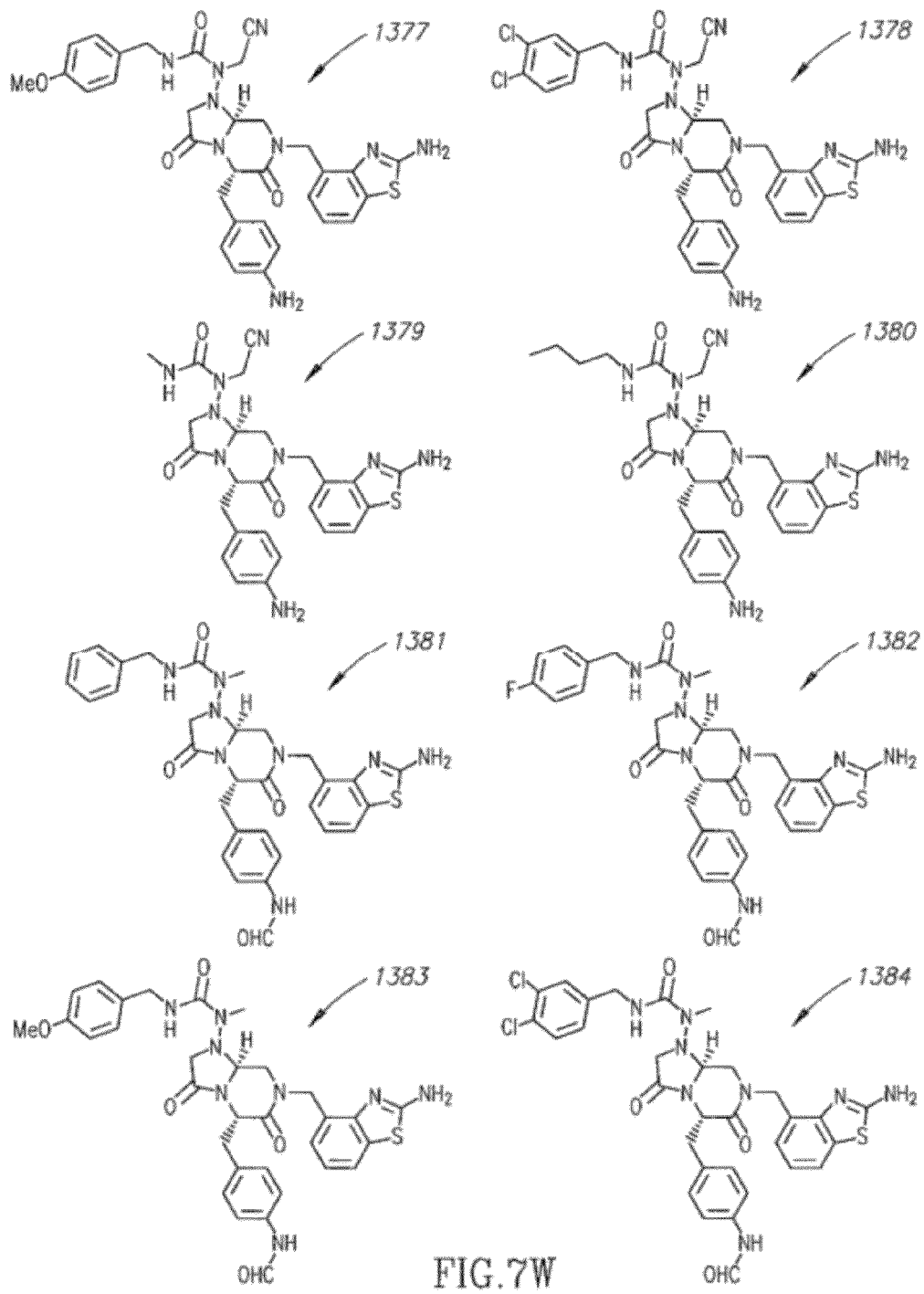
Figure 7X:
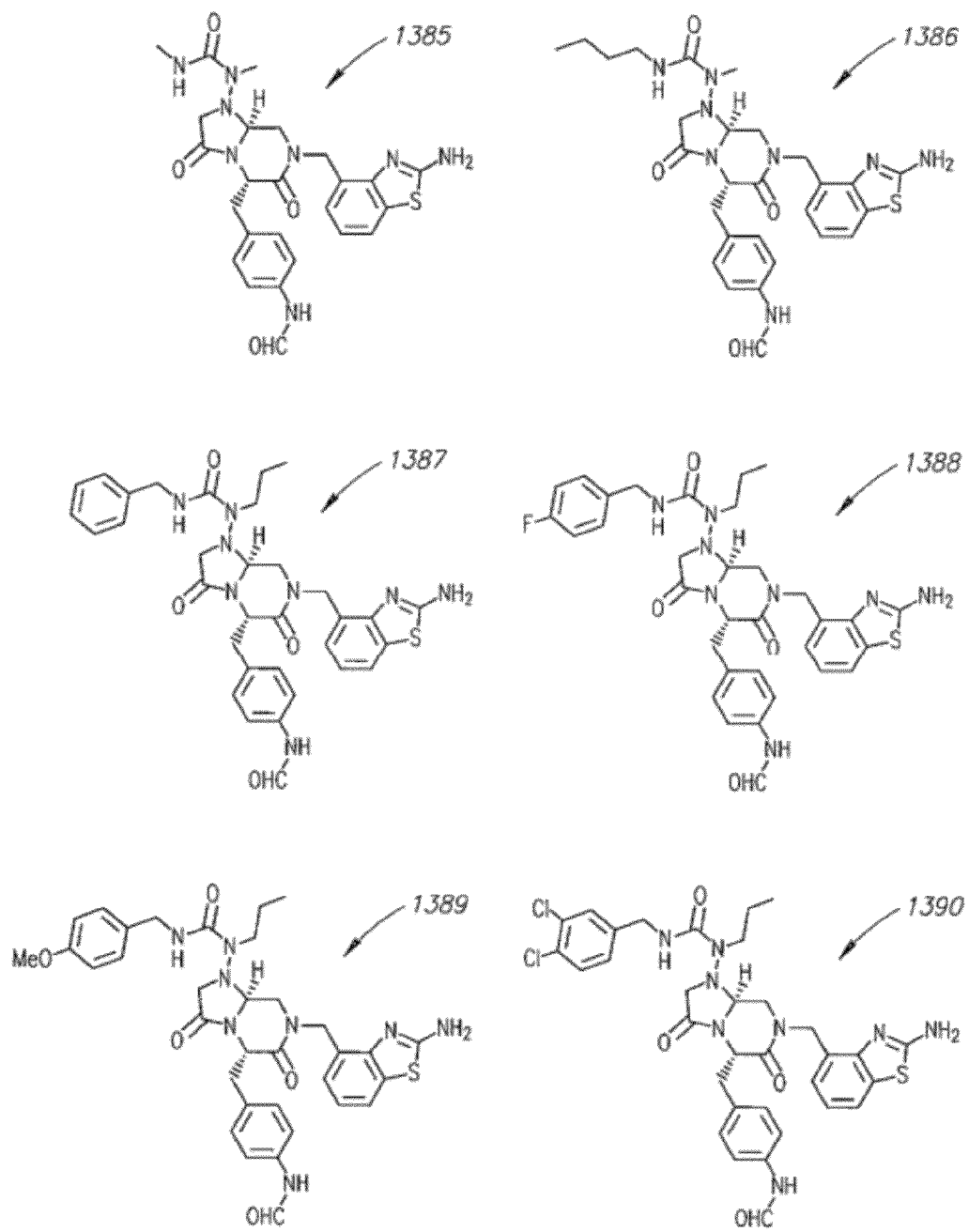
Figure 7Y:
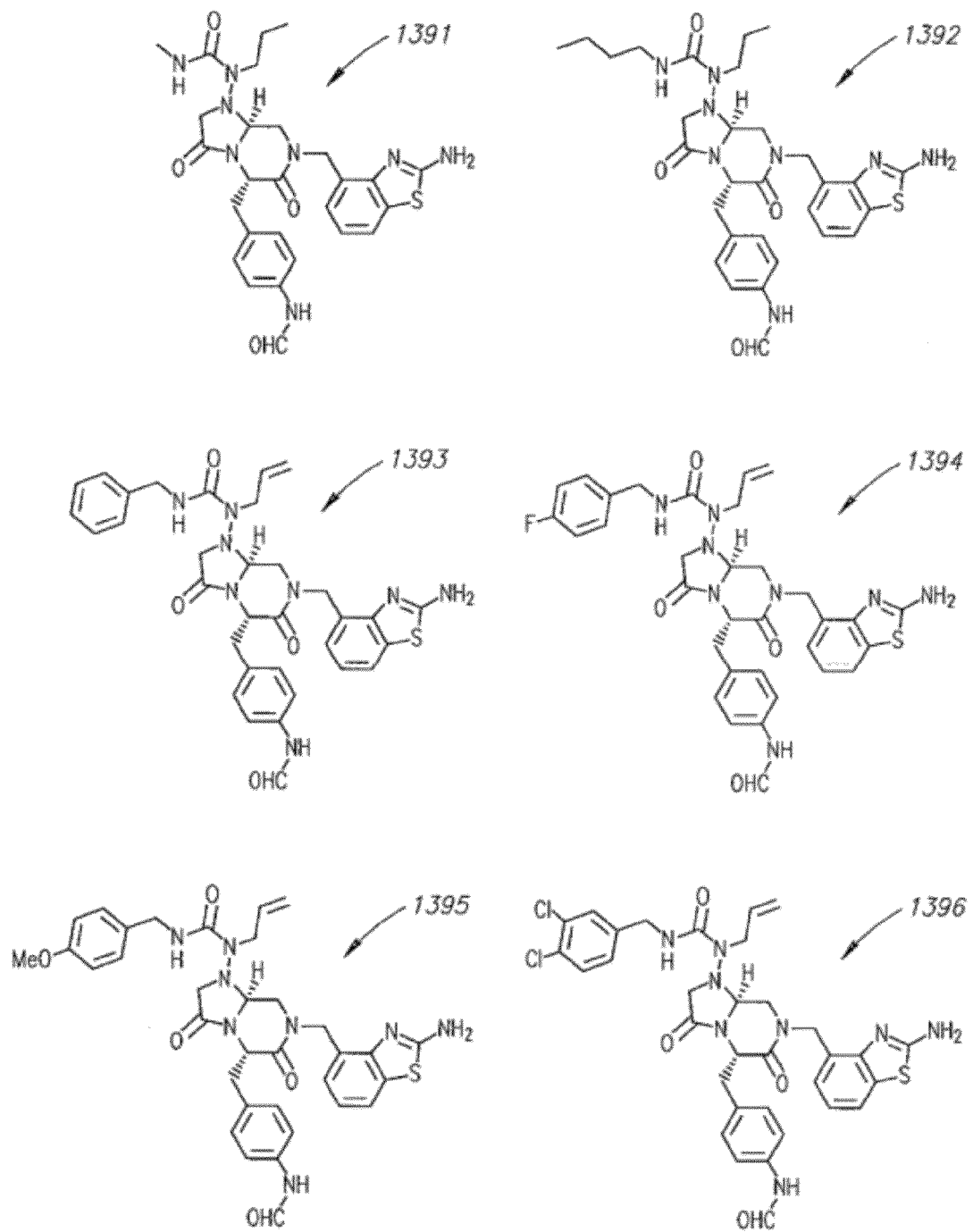
Figure 7Z:
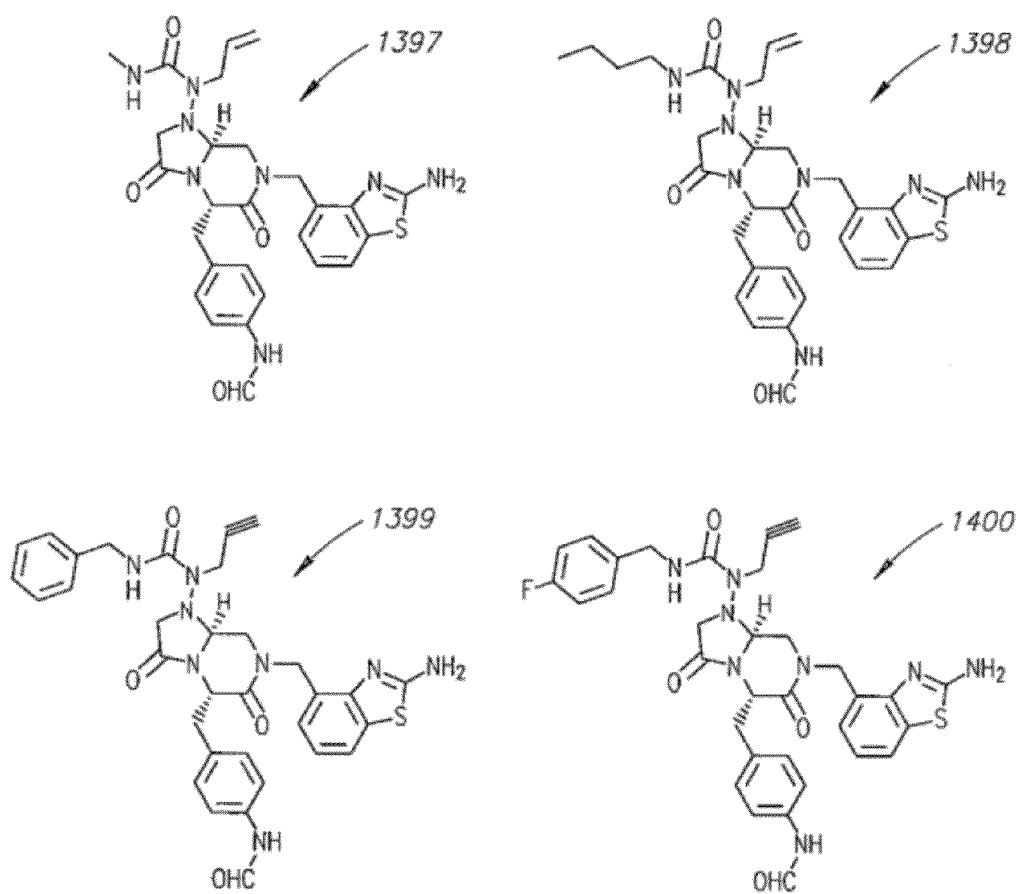
Figure 8A:
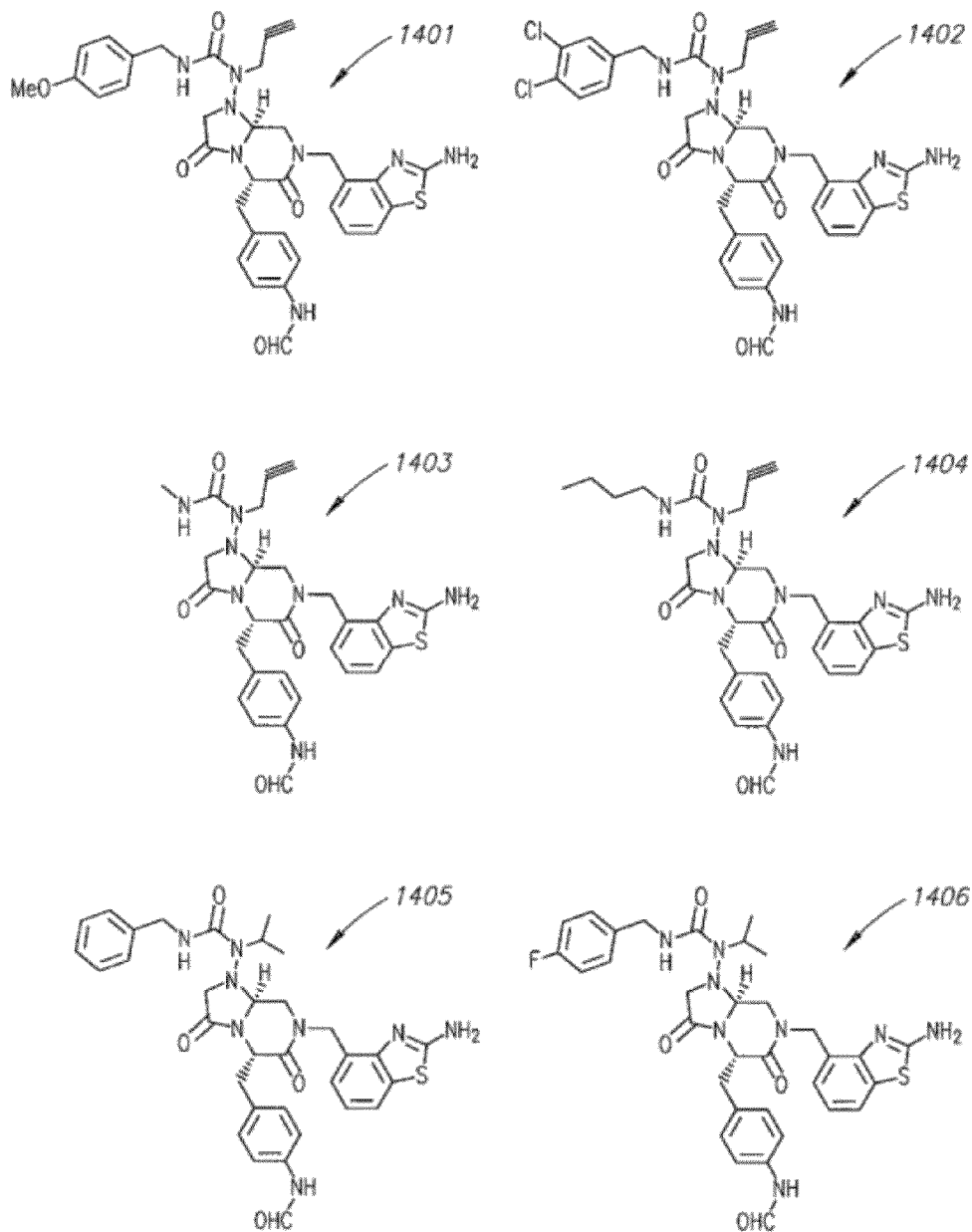
FIGS. 8A-8AC shows the chemical structures of compounds 1401-1600.
Figure 8B:
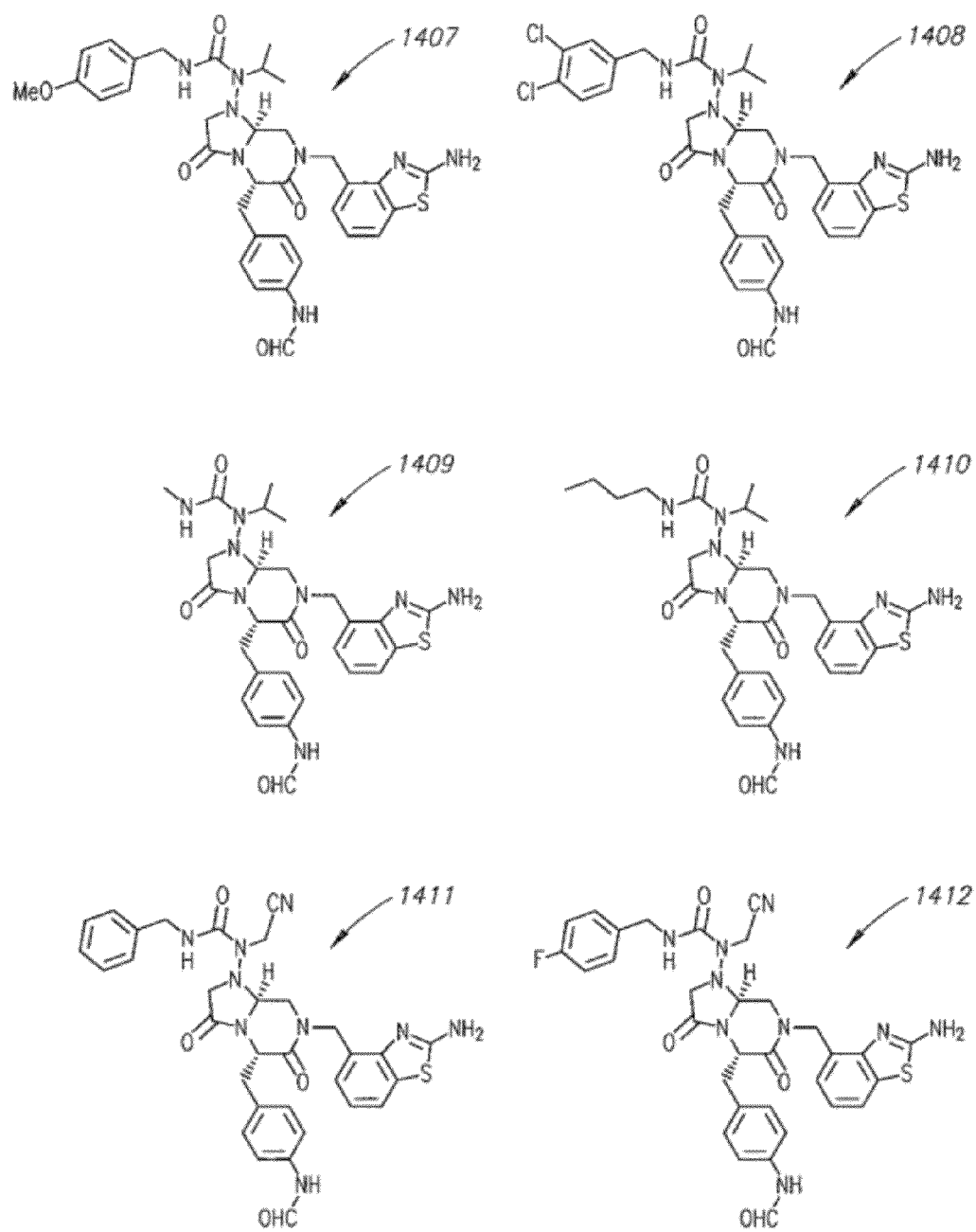
Figure 8C:
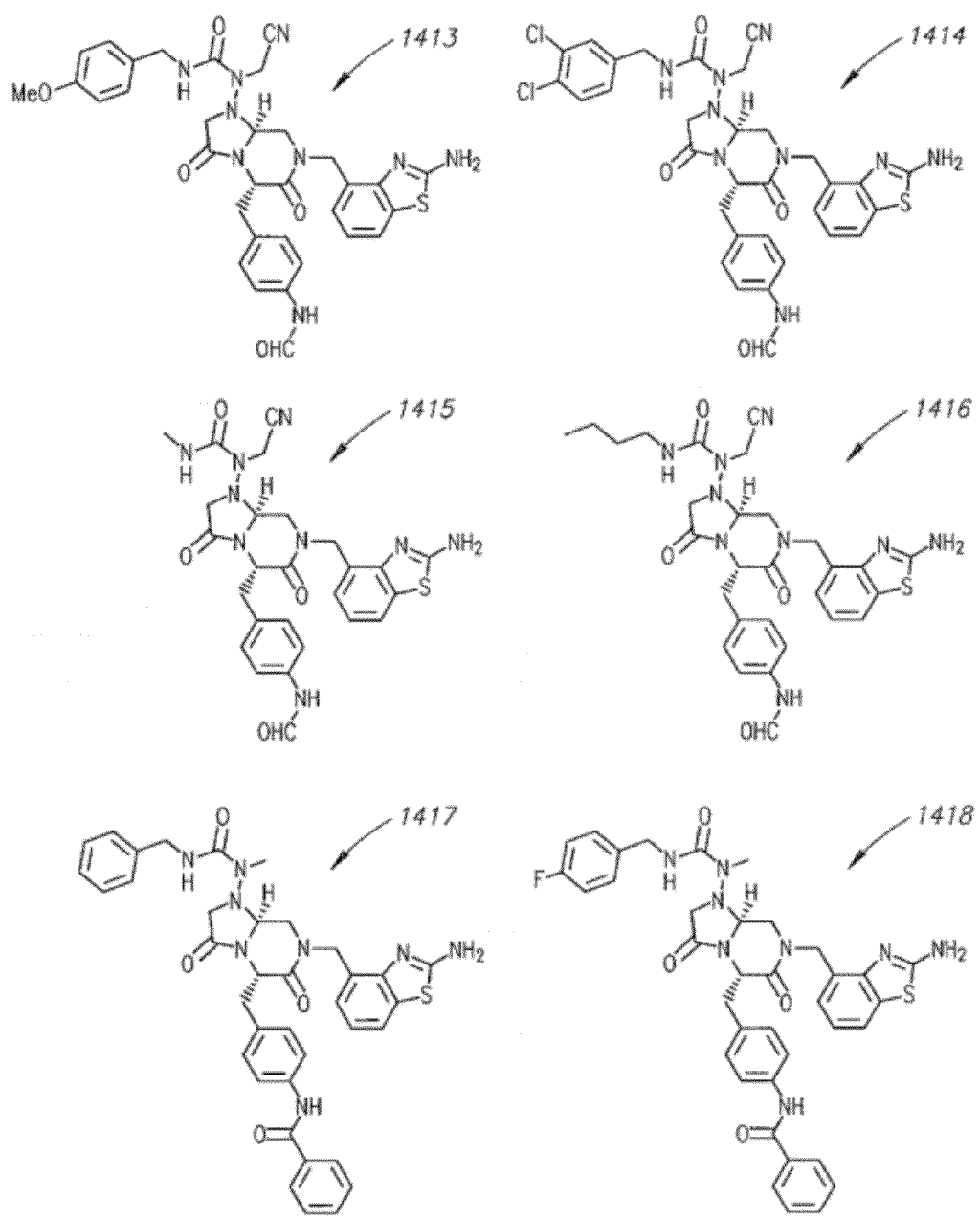
Figure 8D:
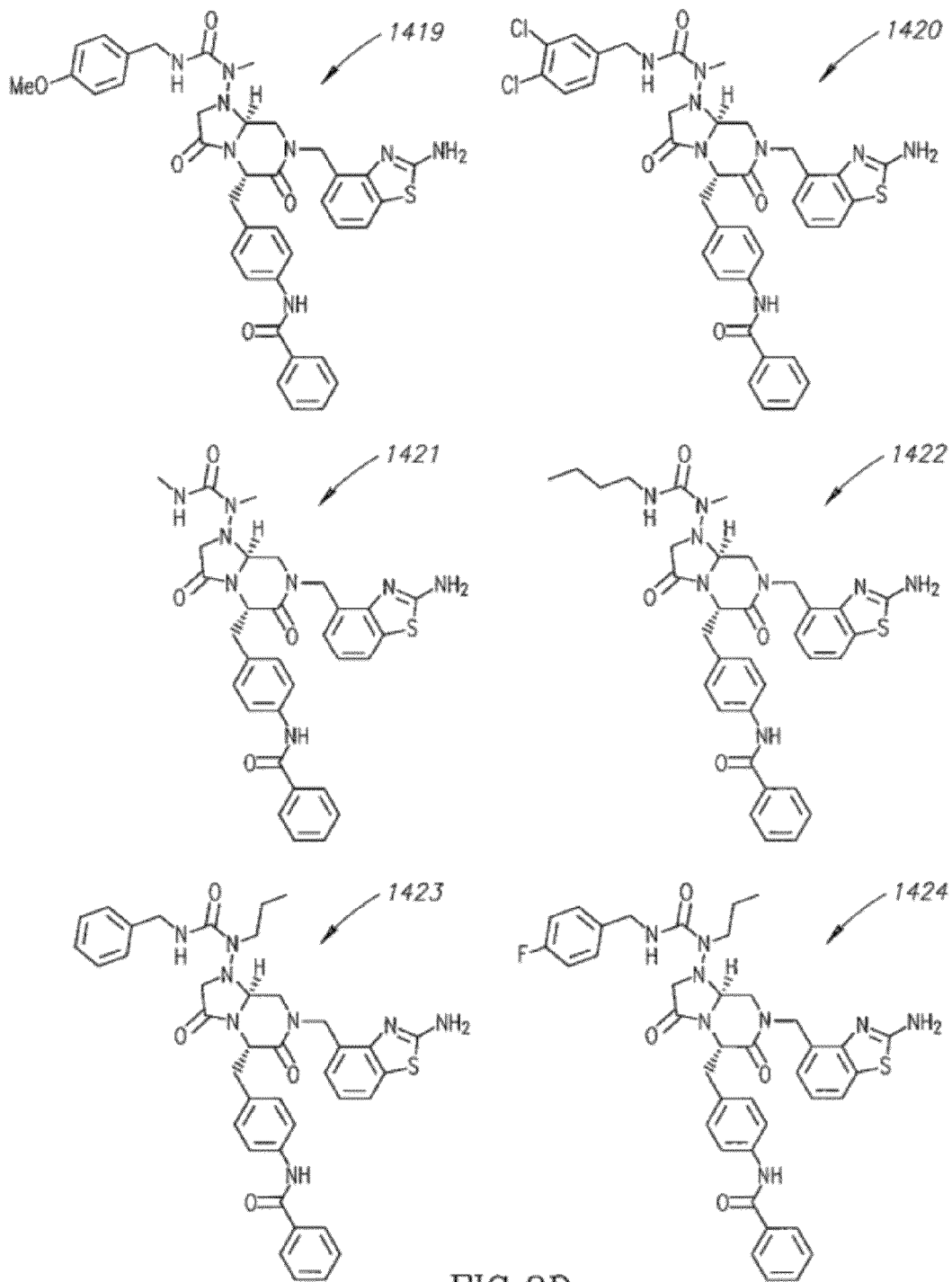
Figure 8E:
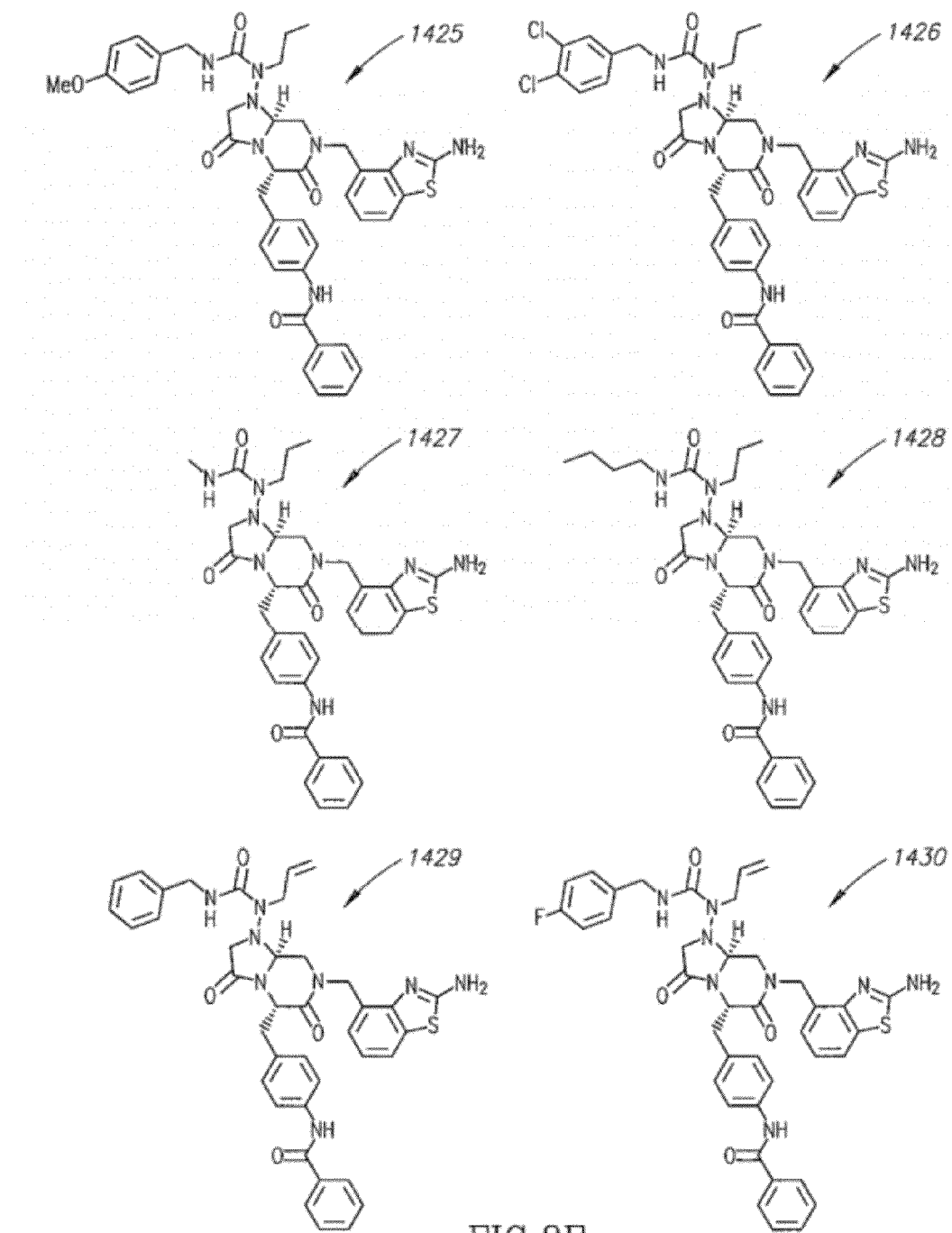
Figure 8F:
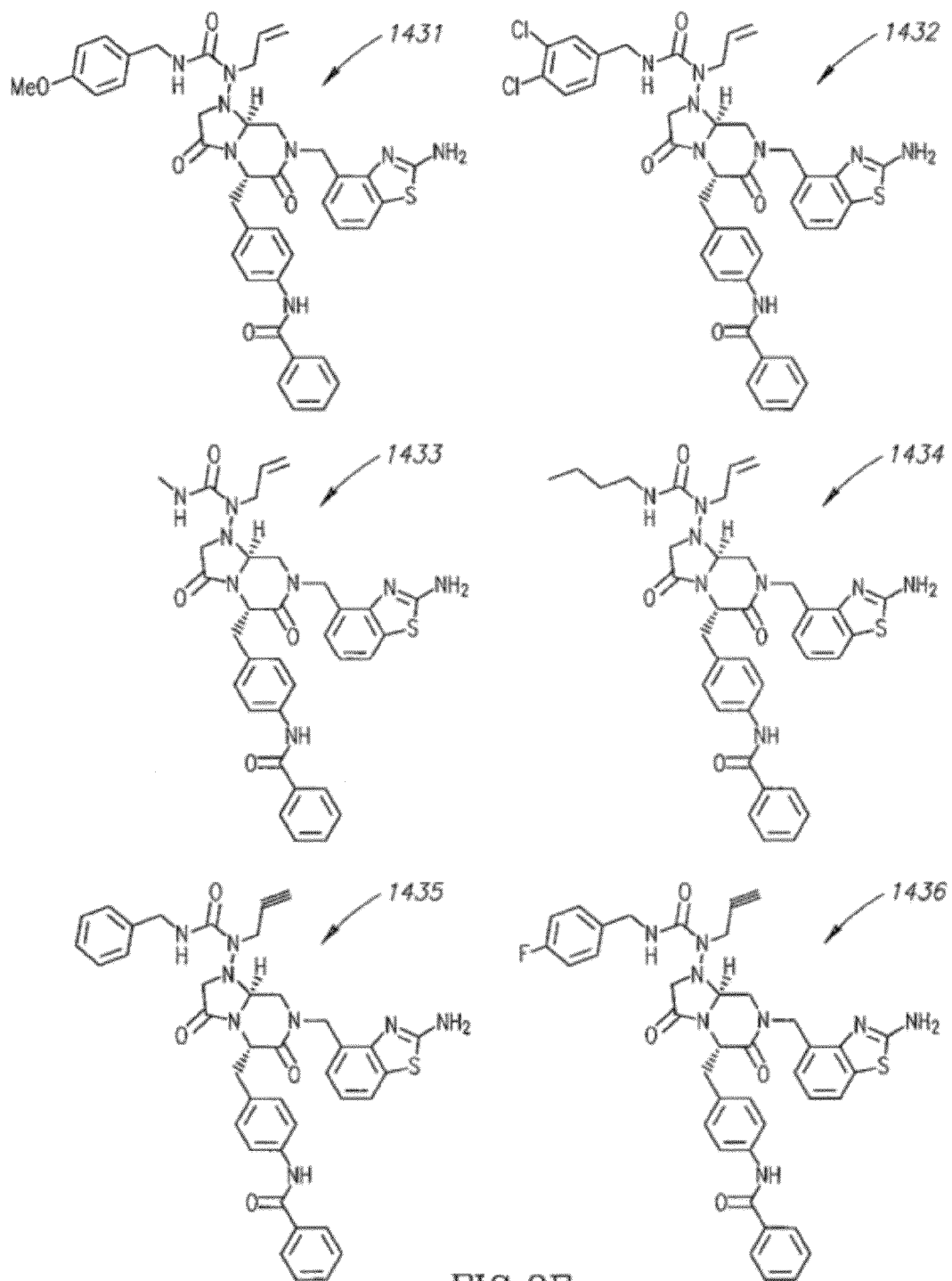
Figure 8G:
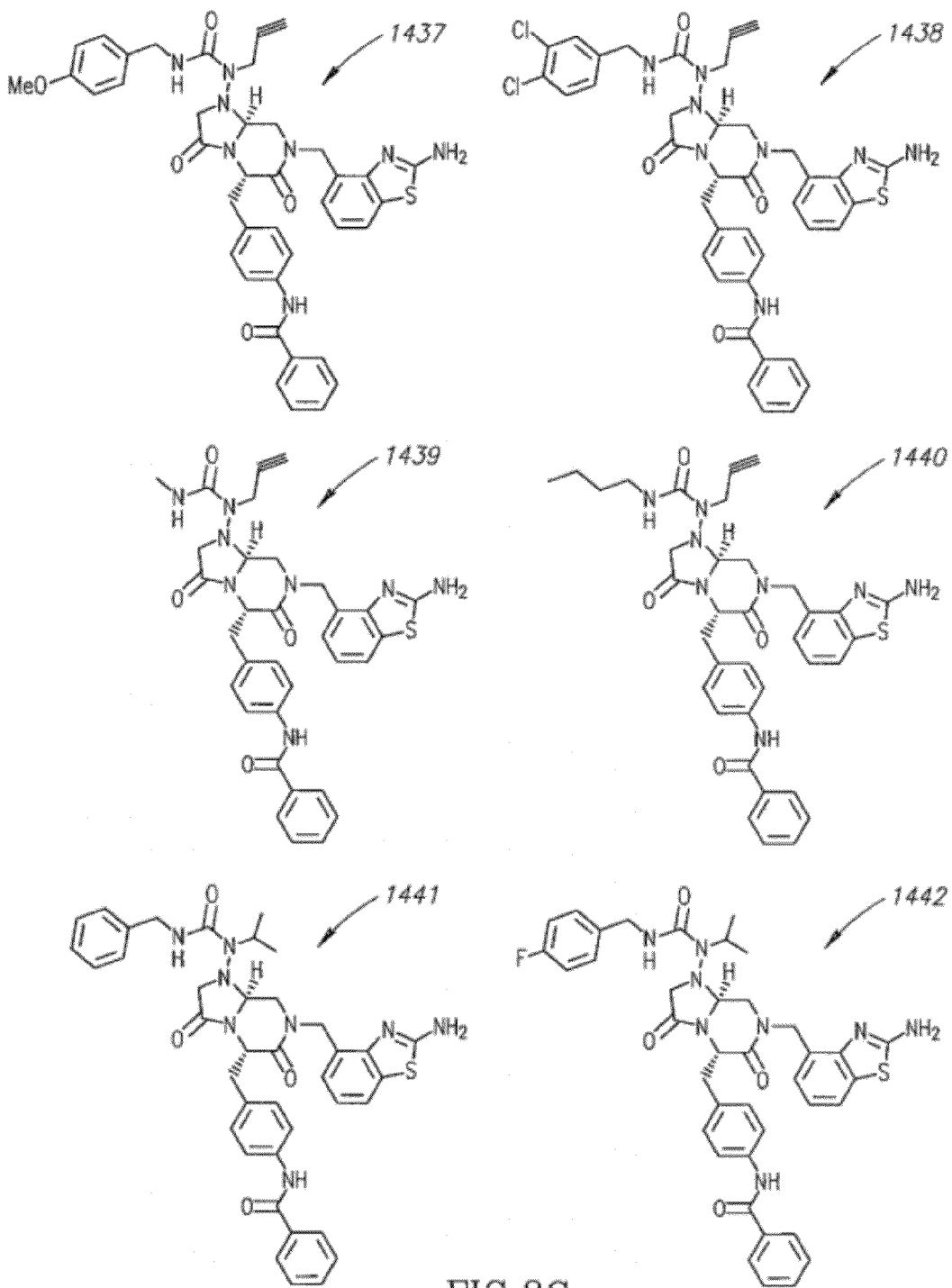
Figure 8H:
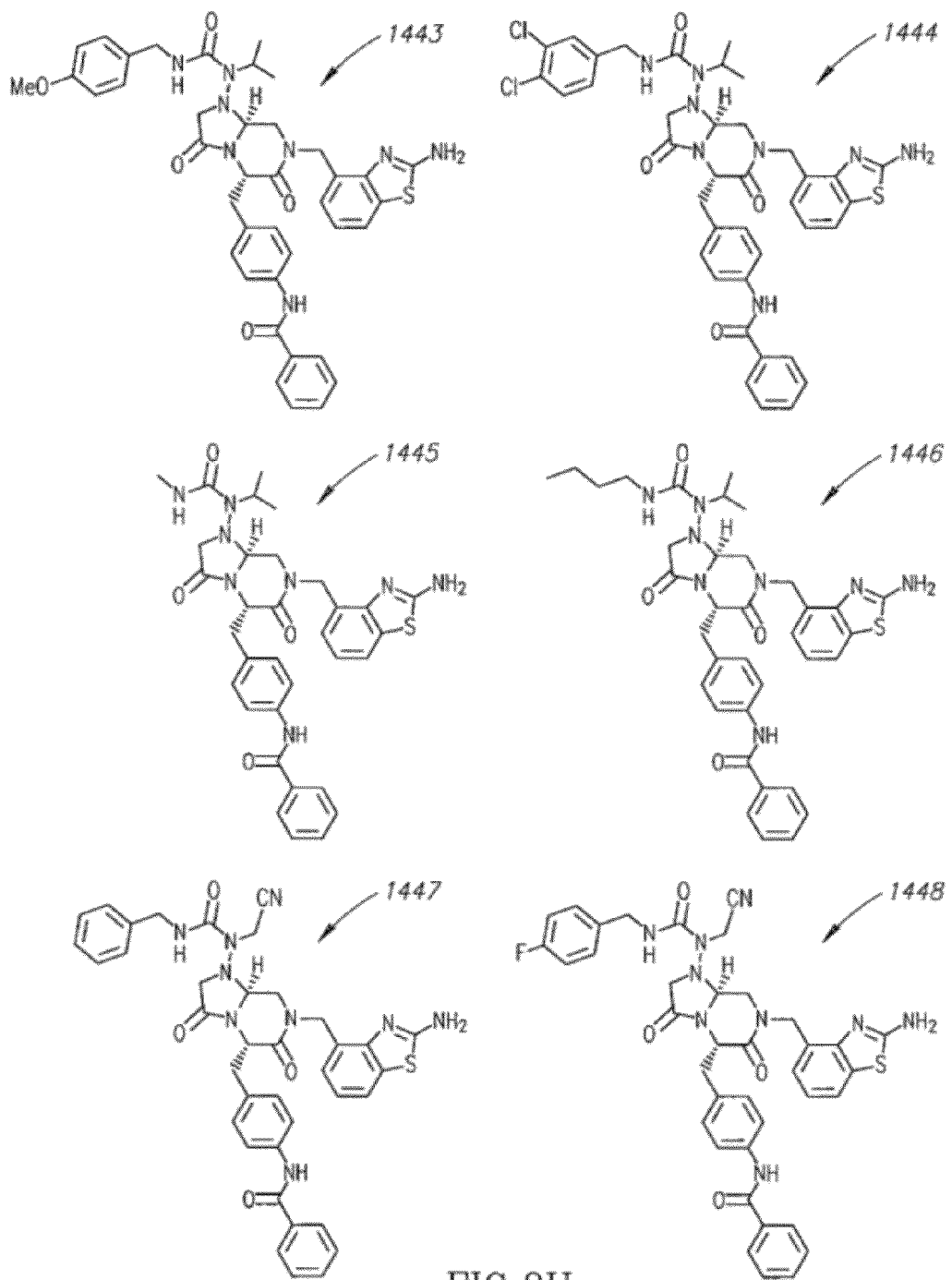
Figure 8I:
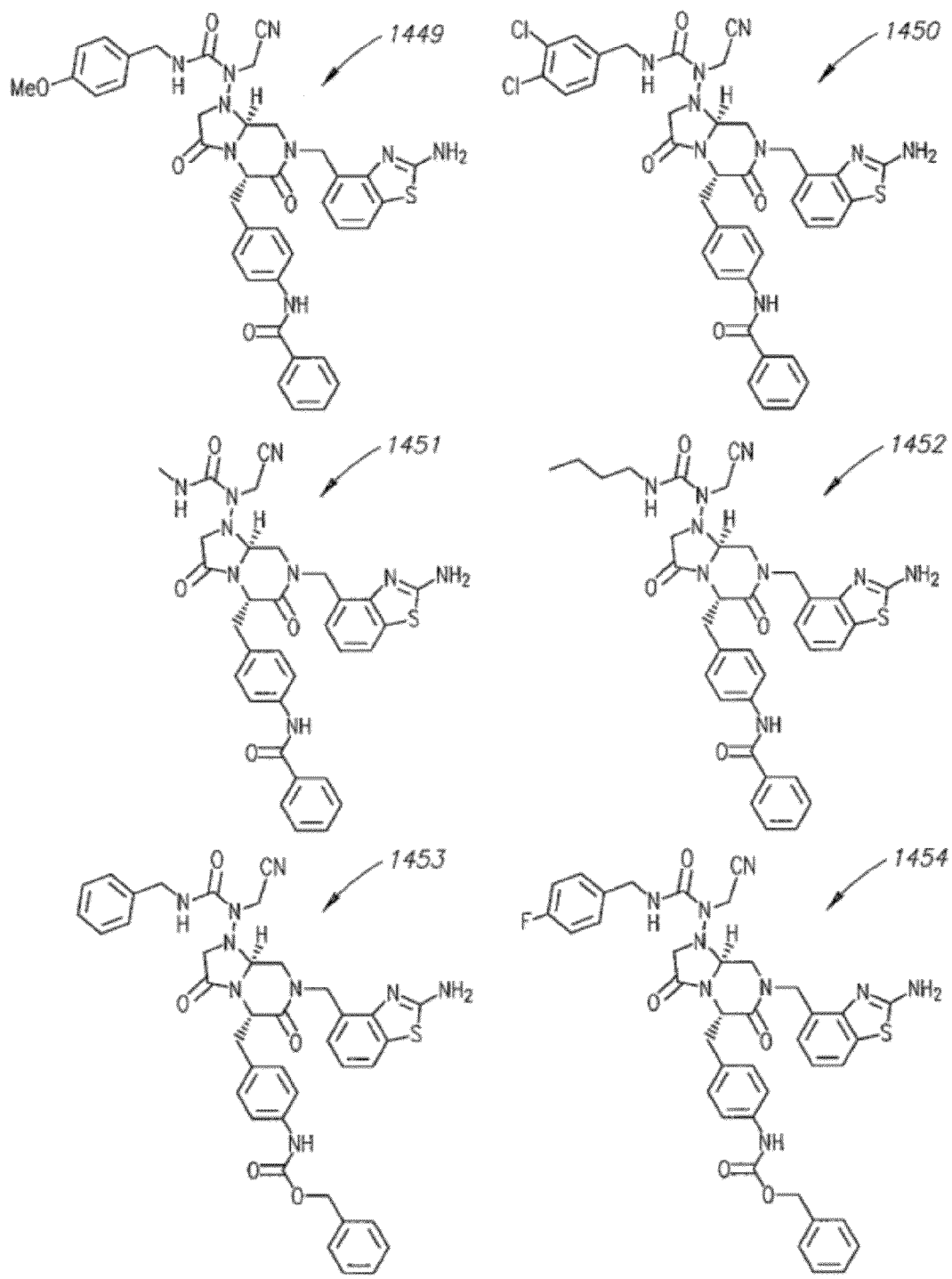
Figure 8J:
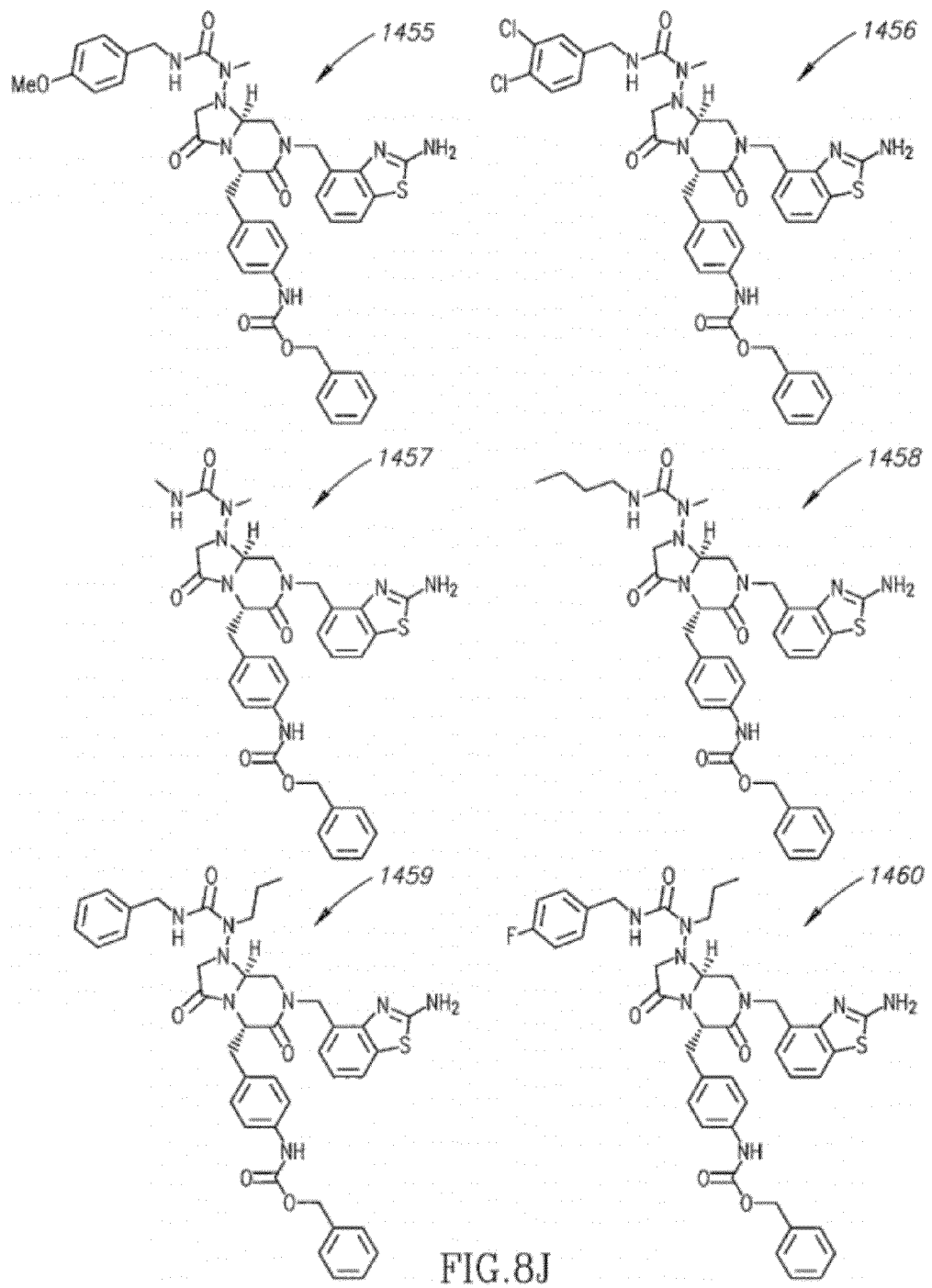
Figure 8K:
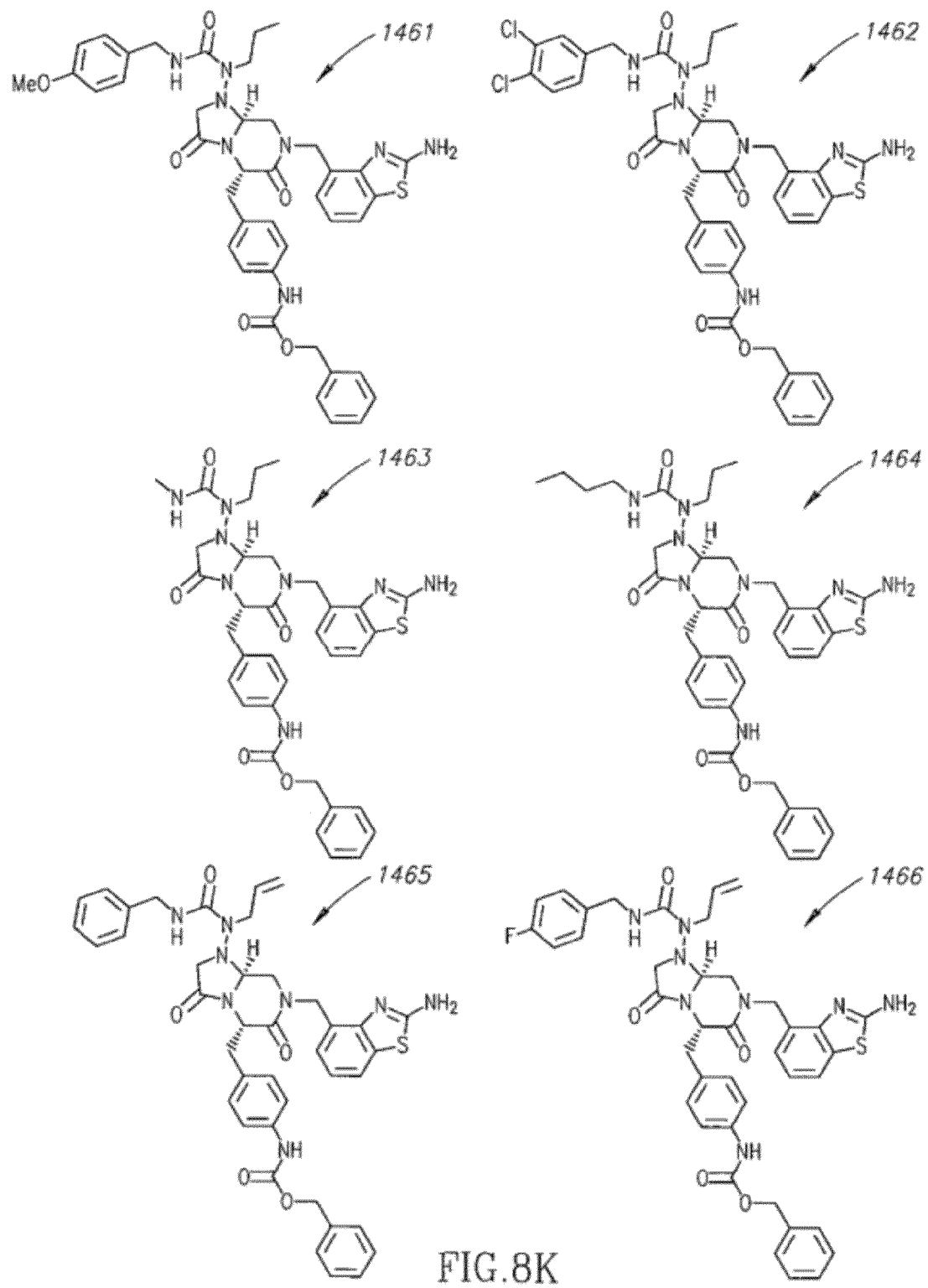
Figure 8L:
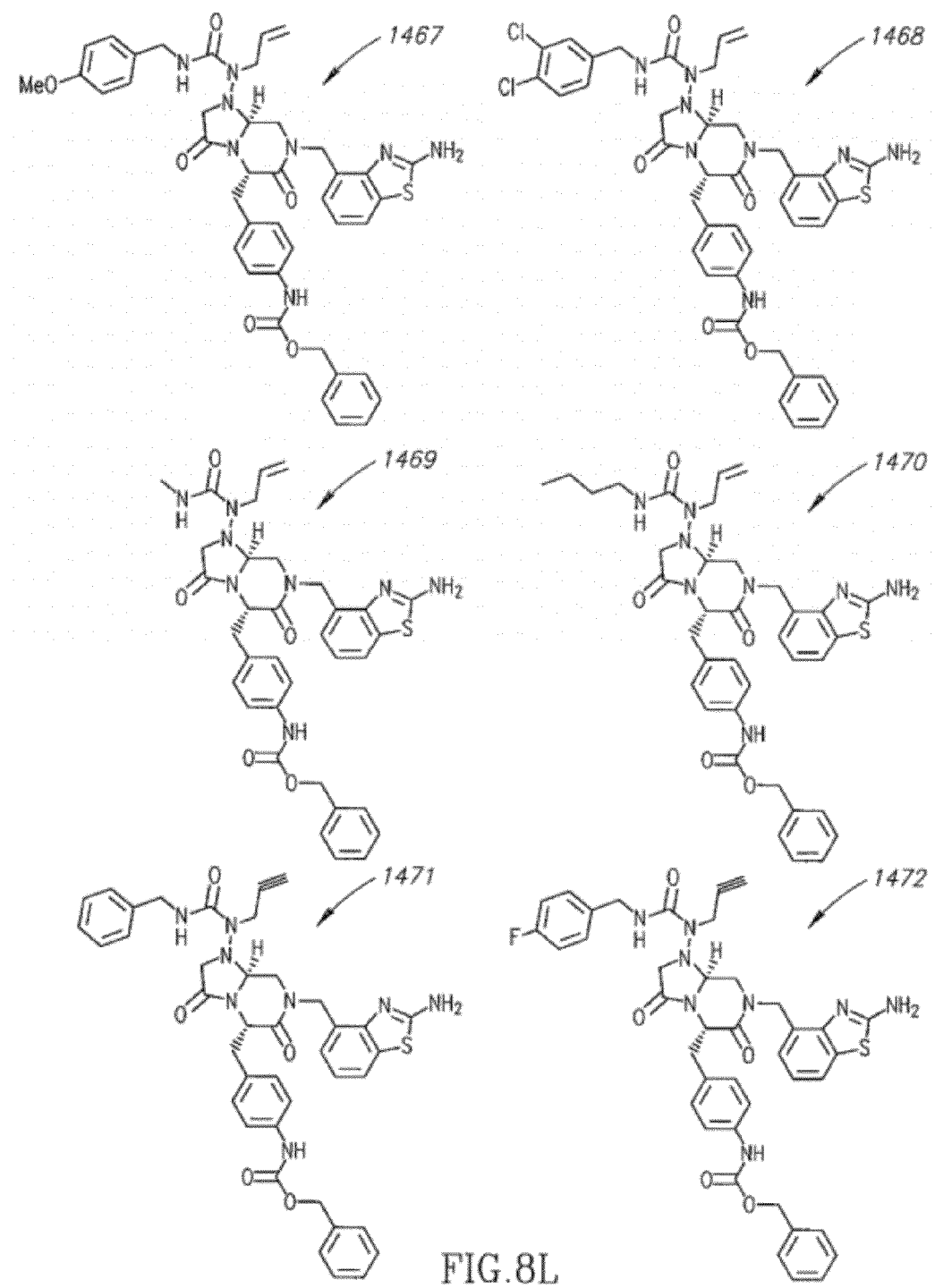
Figure 8M:
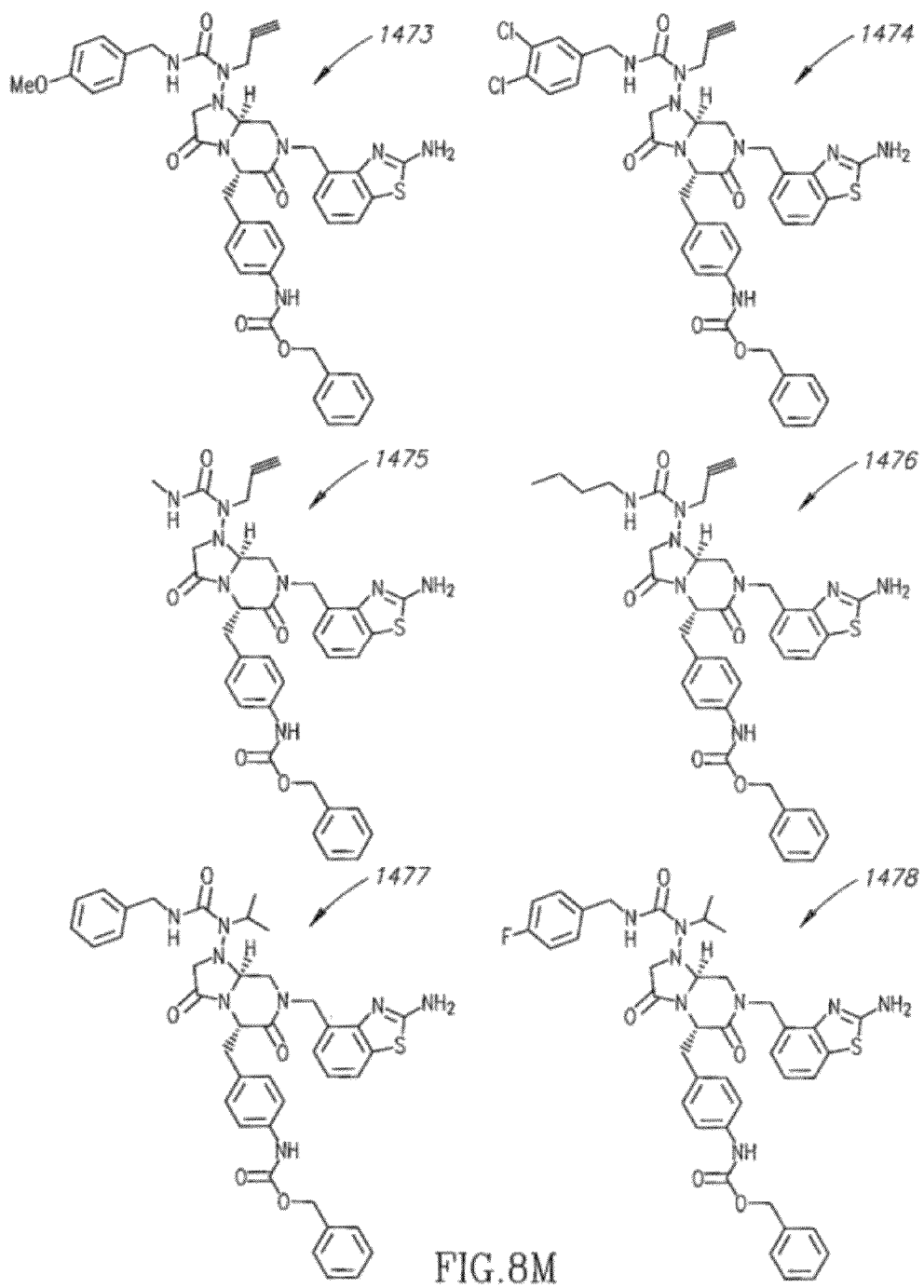
Figure 8N:
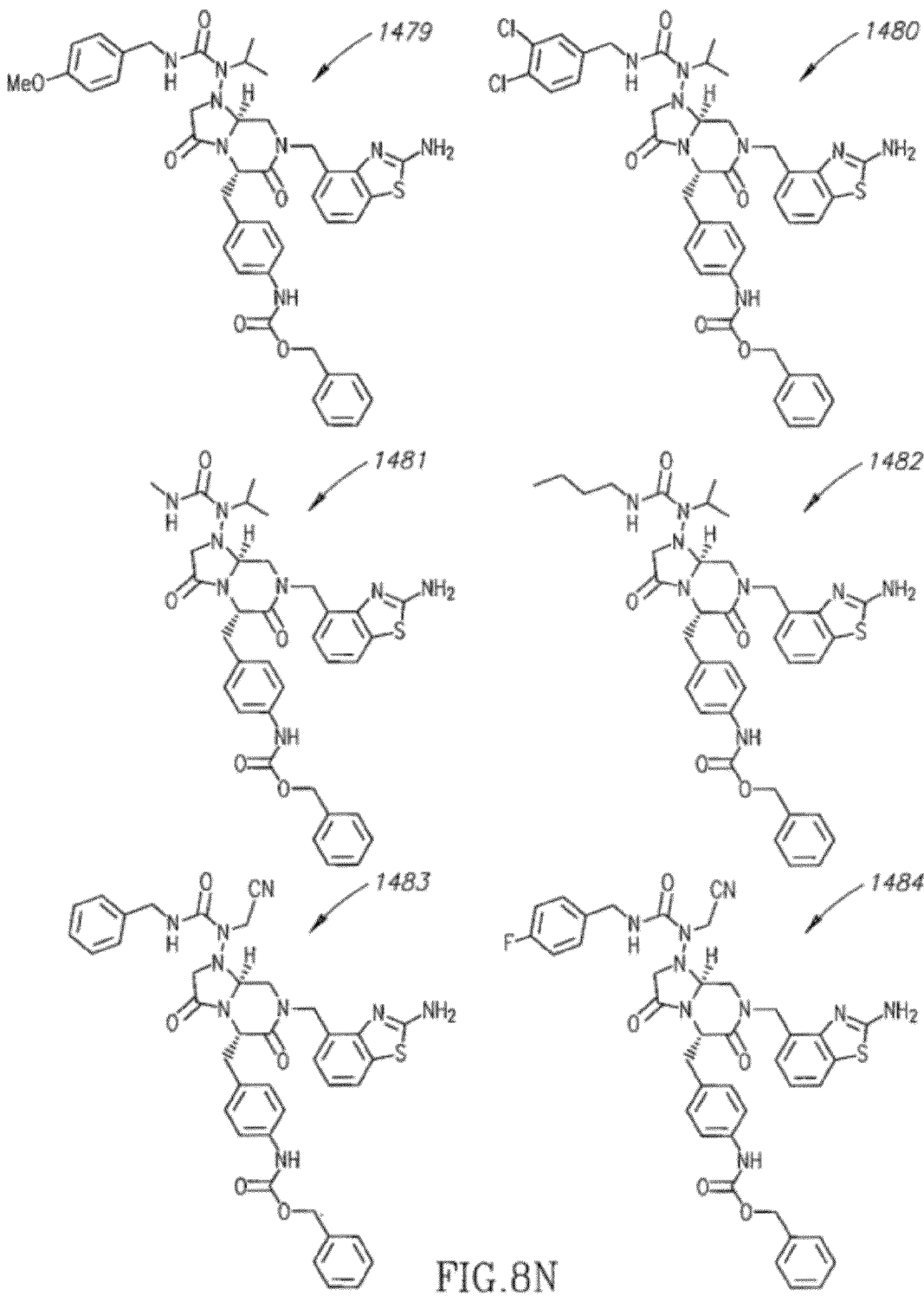
Figure 80:
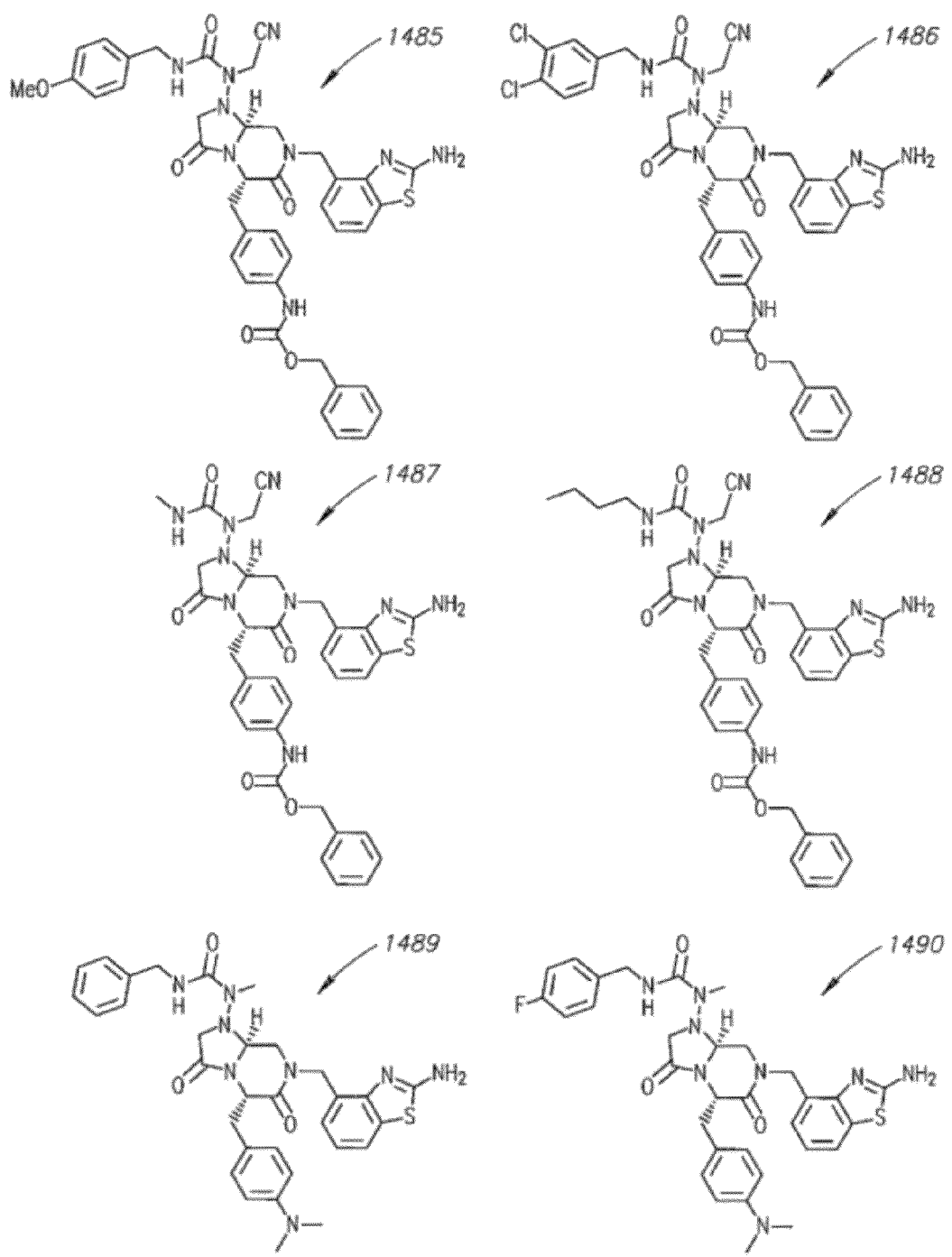
Figure 8P:
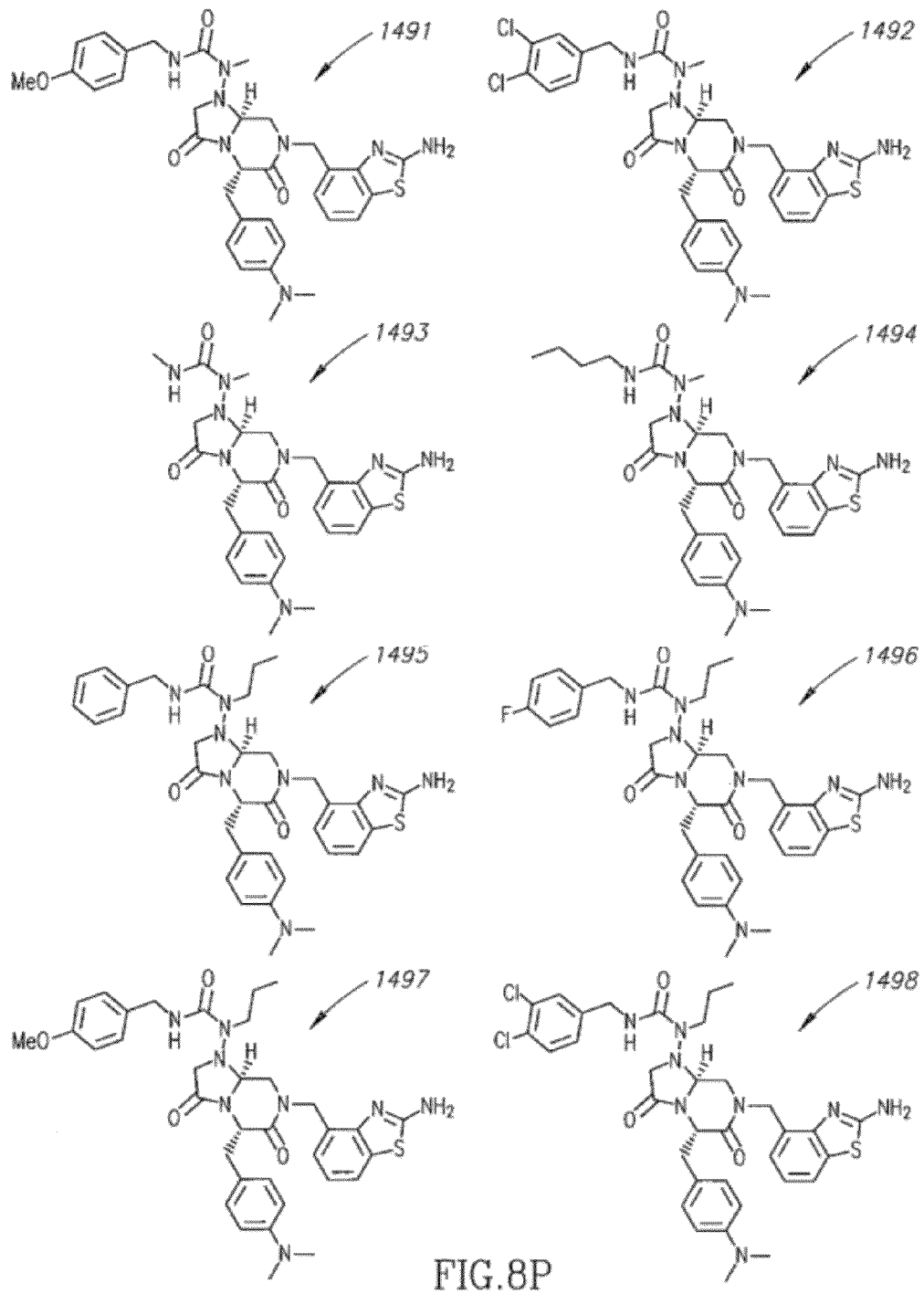
Figure 8Q:
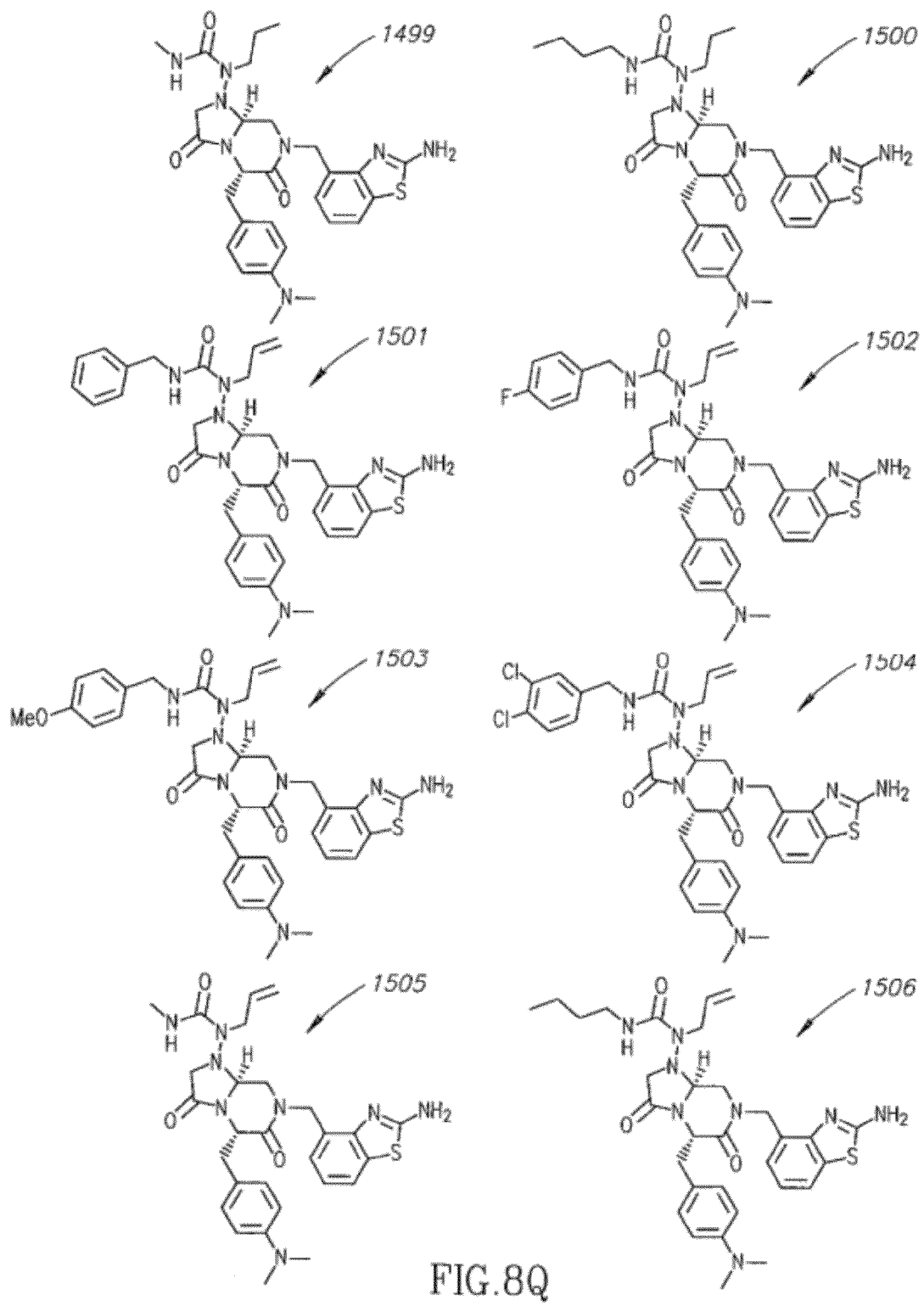
Figure 8R:
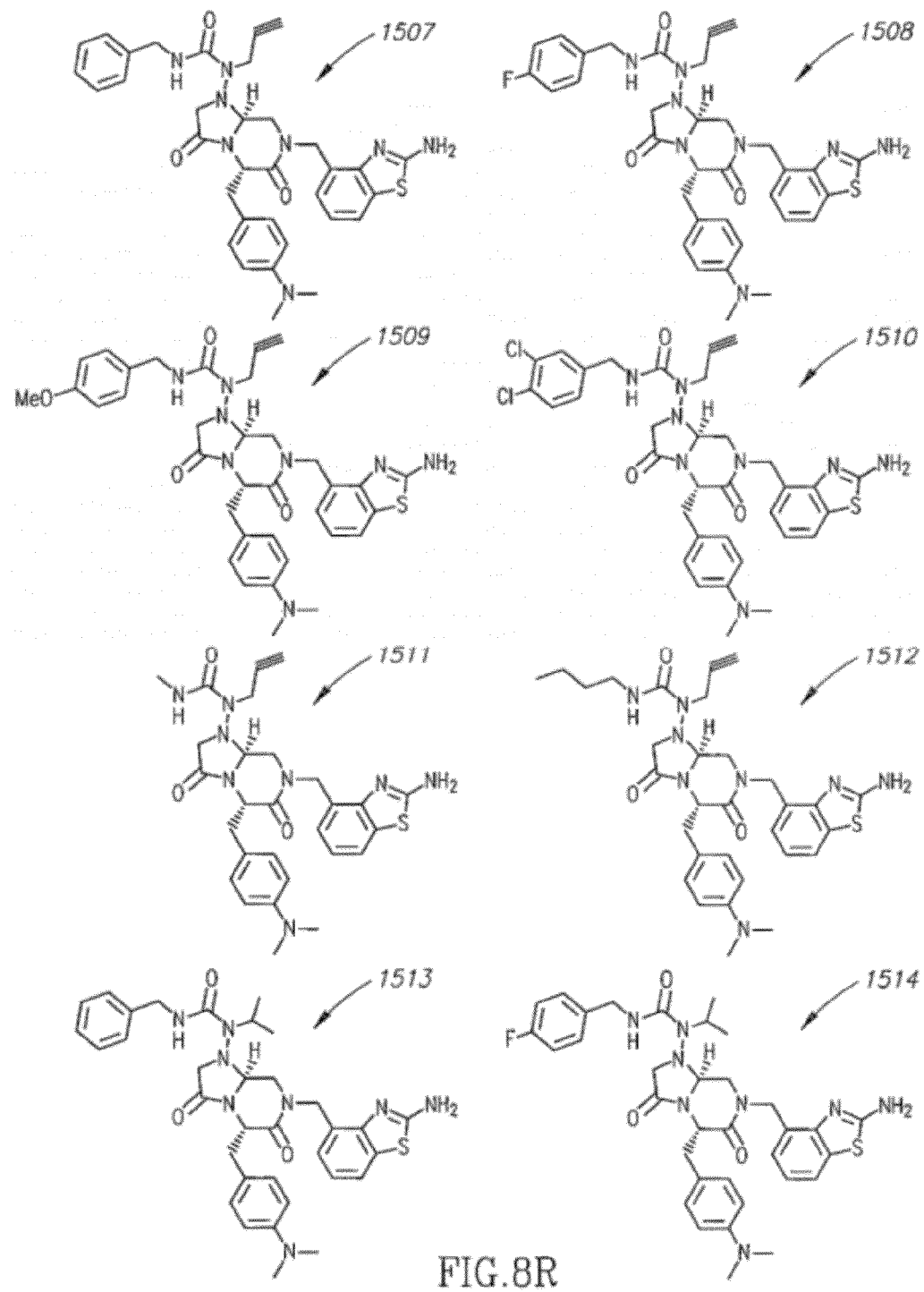
Figure 8S:
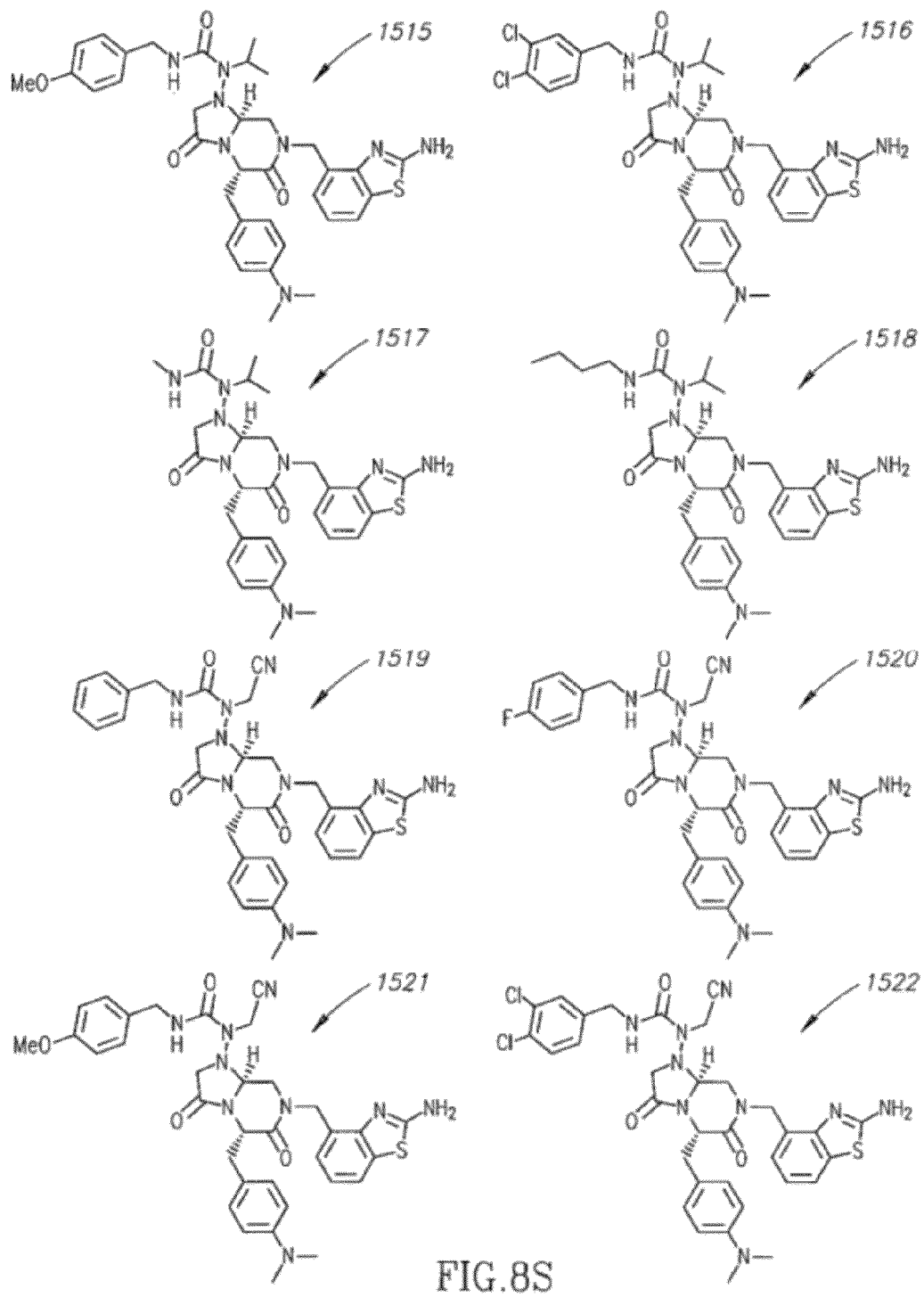
Figure 8T:
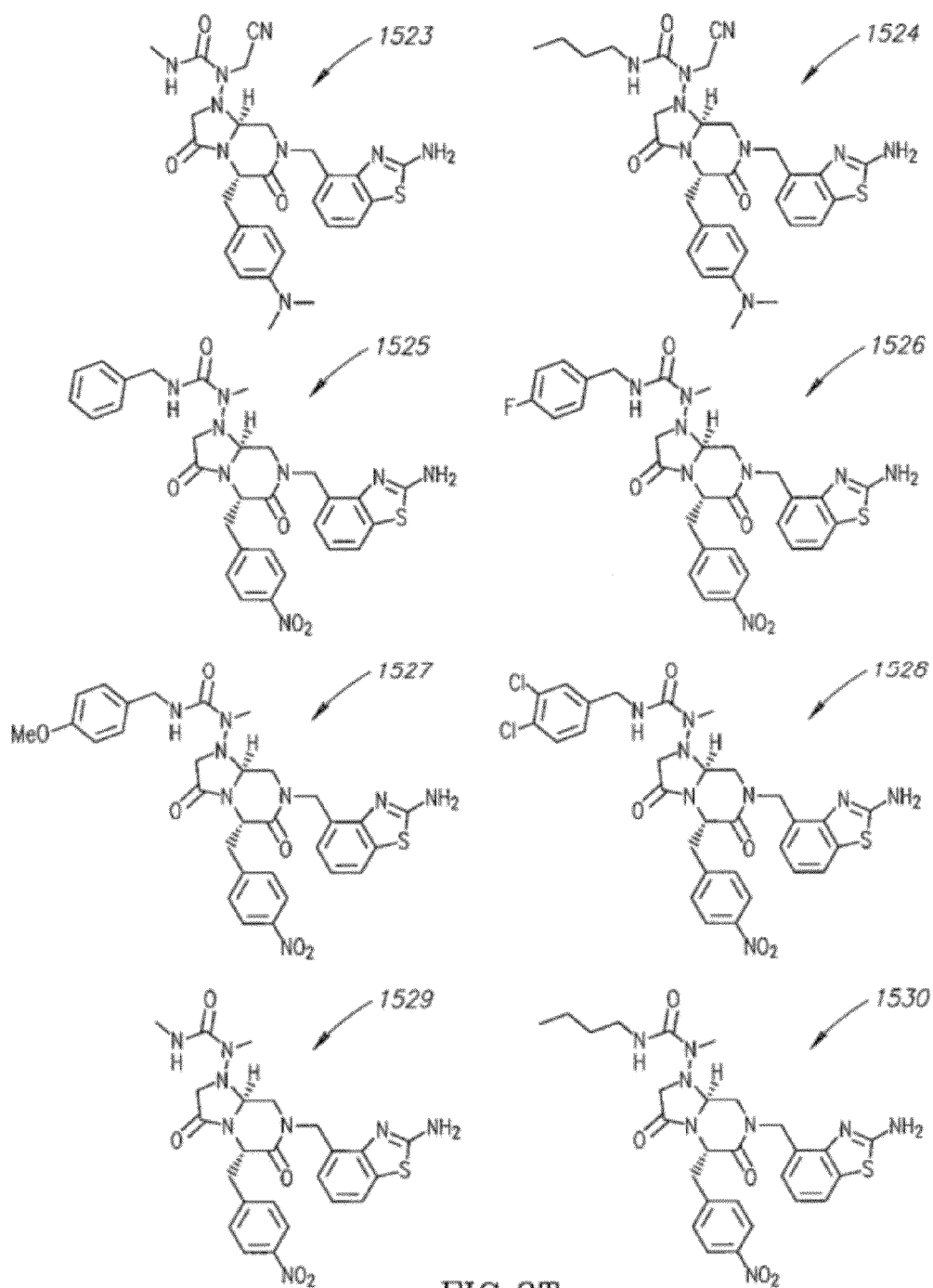
Figure 8U:
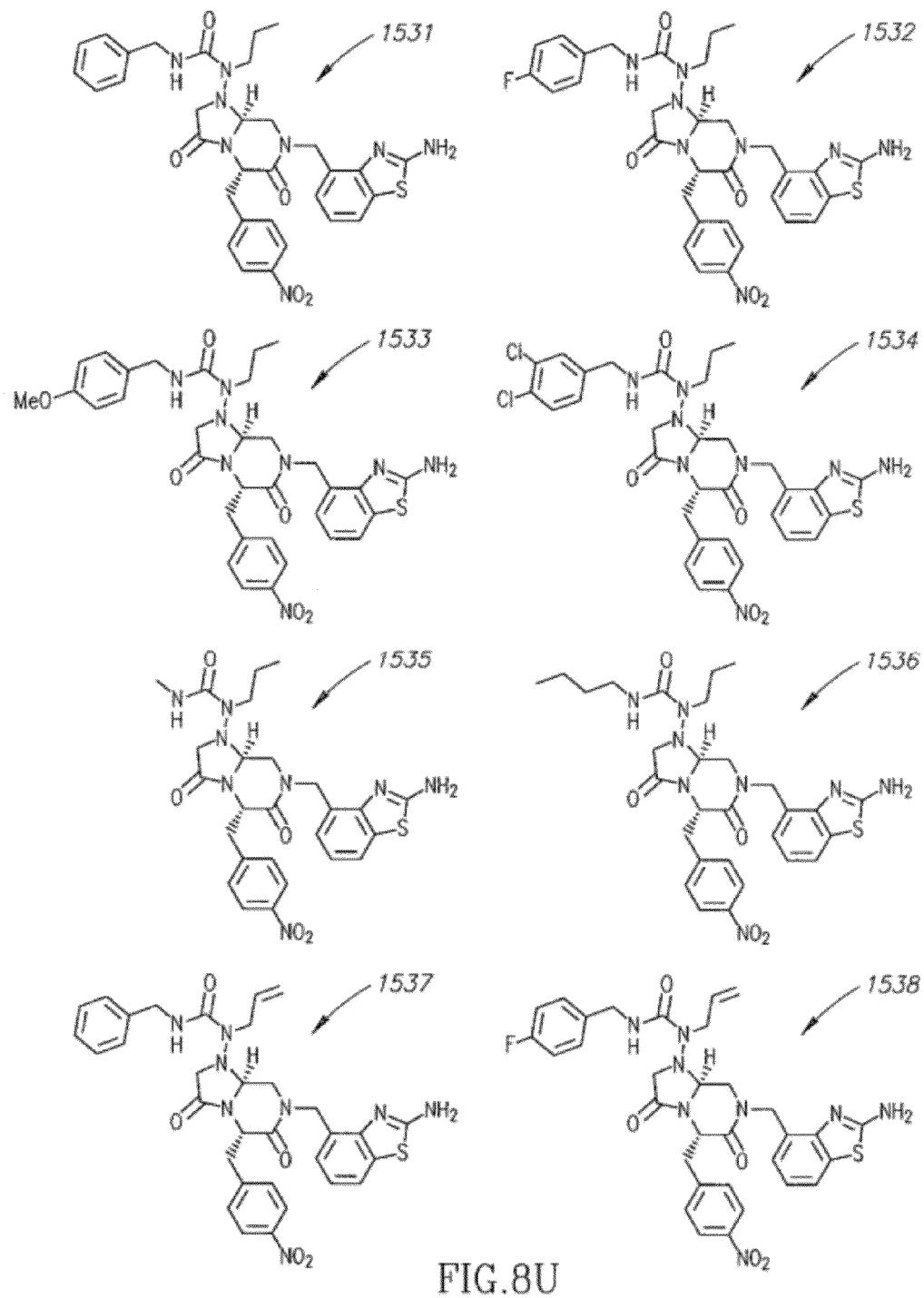
Figure 8V:
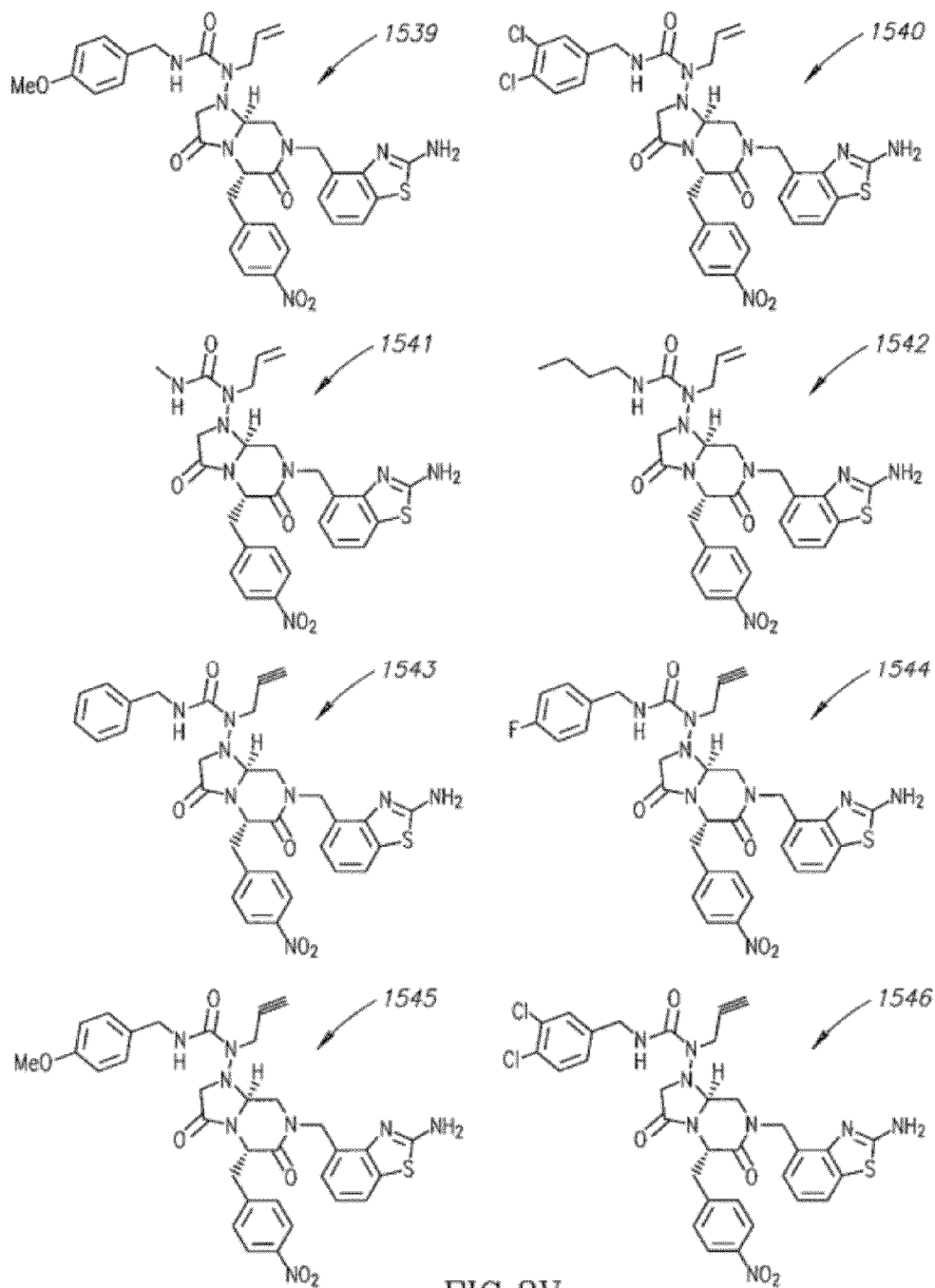
Figure 8W:
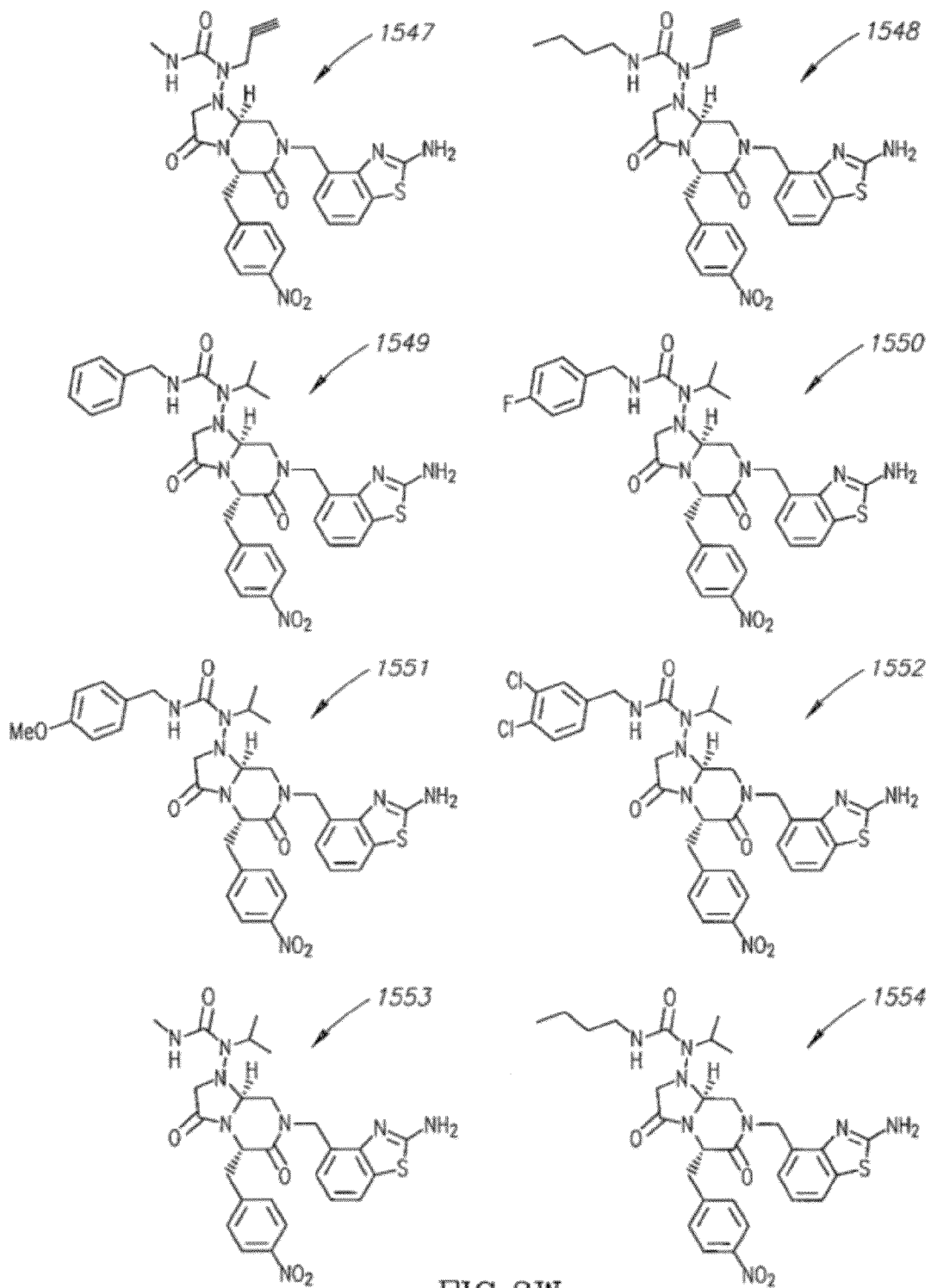
Figure 8X:
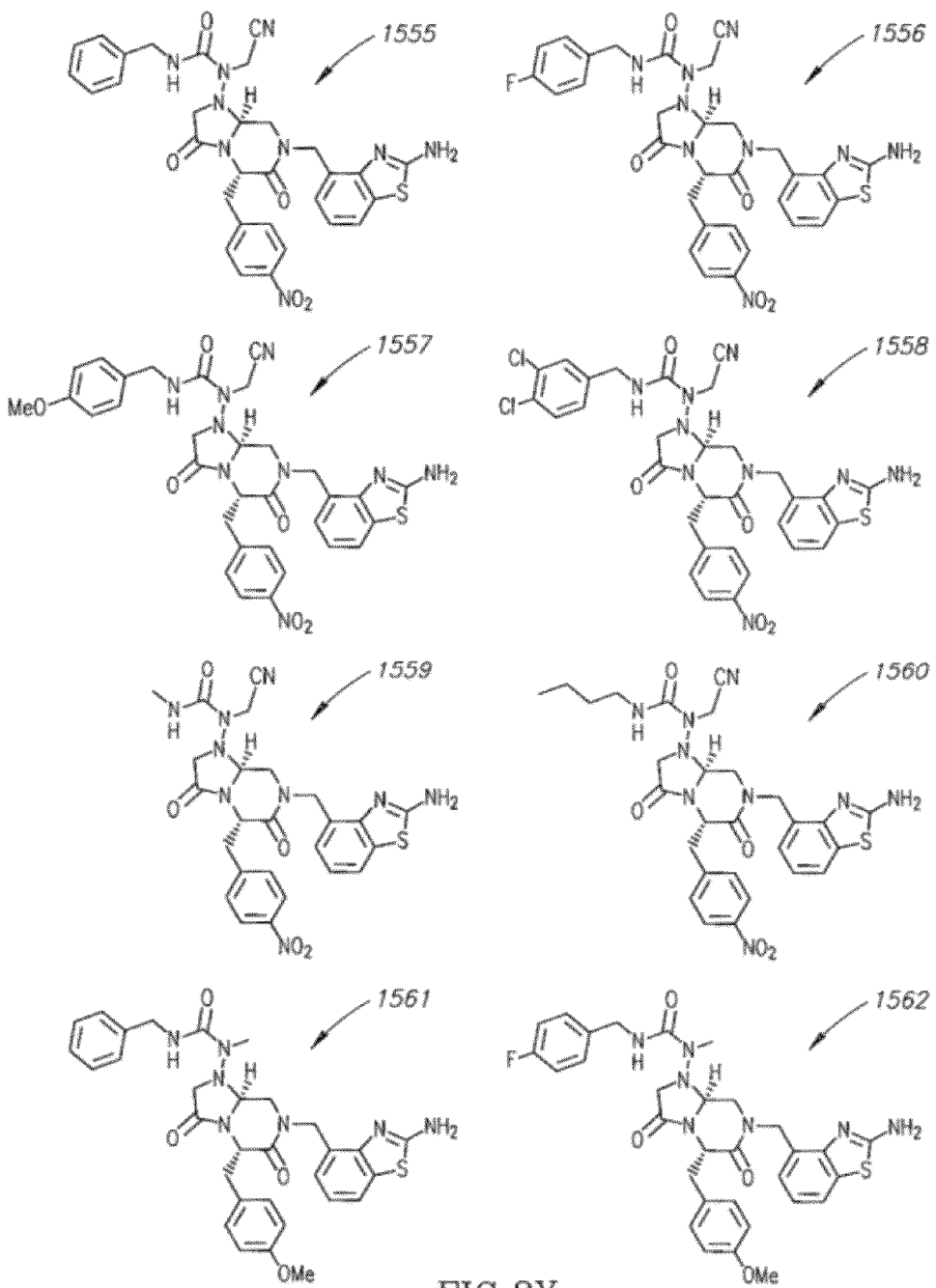
Figure 8Y:
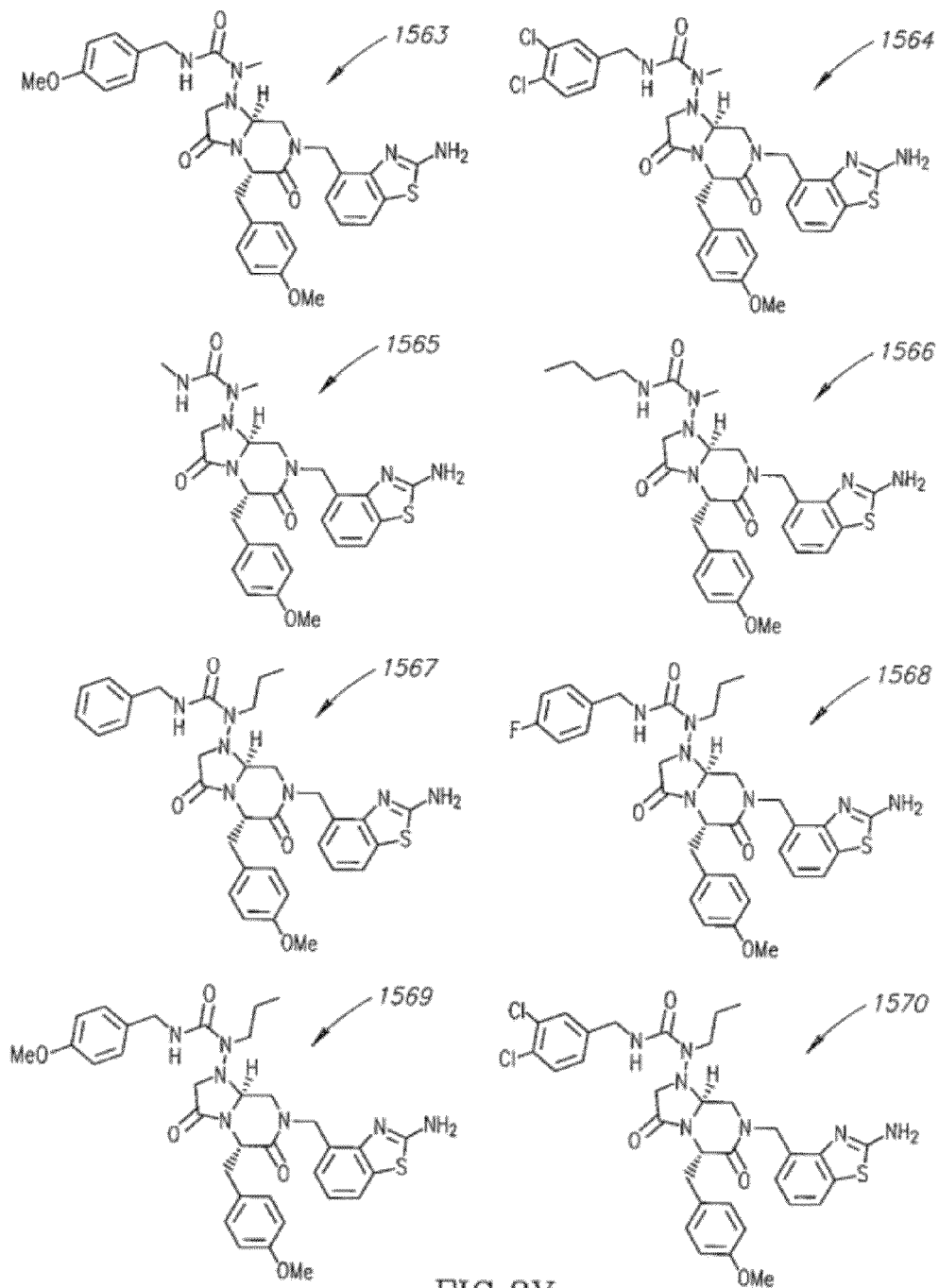
Figure 8Z:
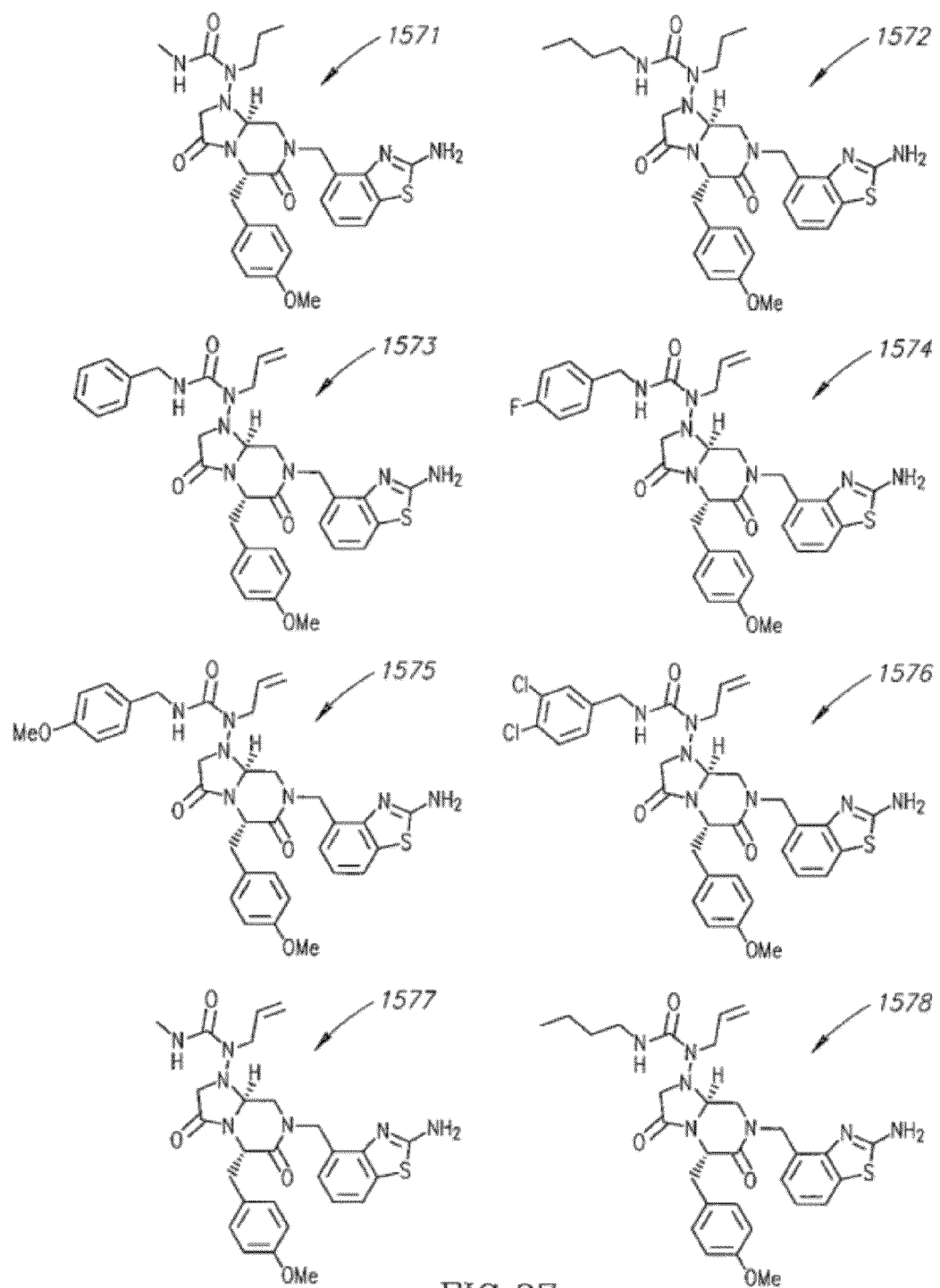
Figure 8A:
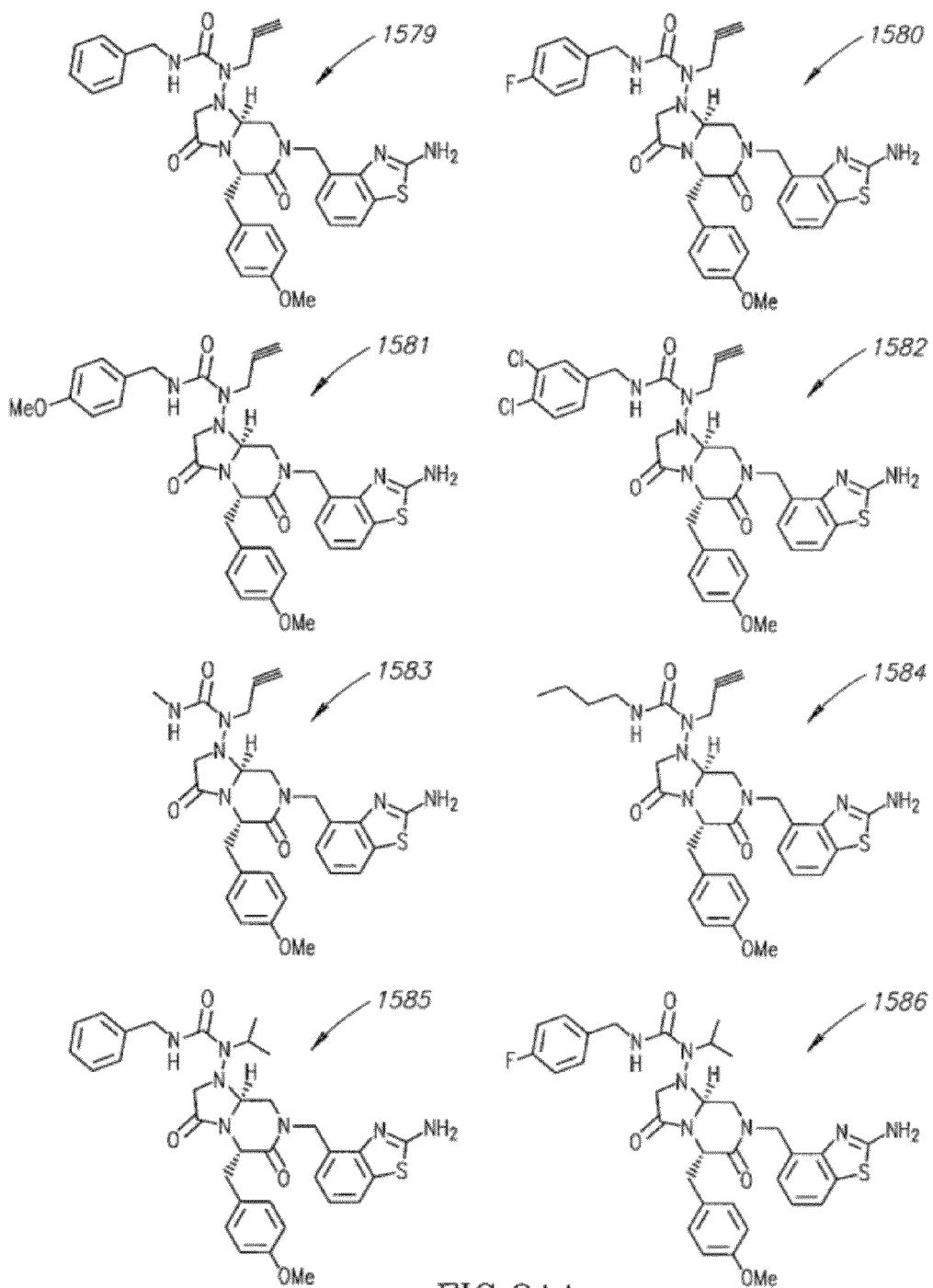
Figure 8A:
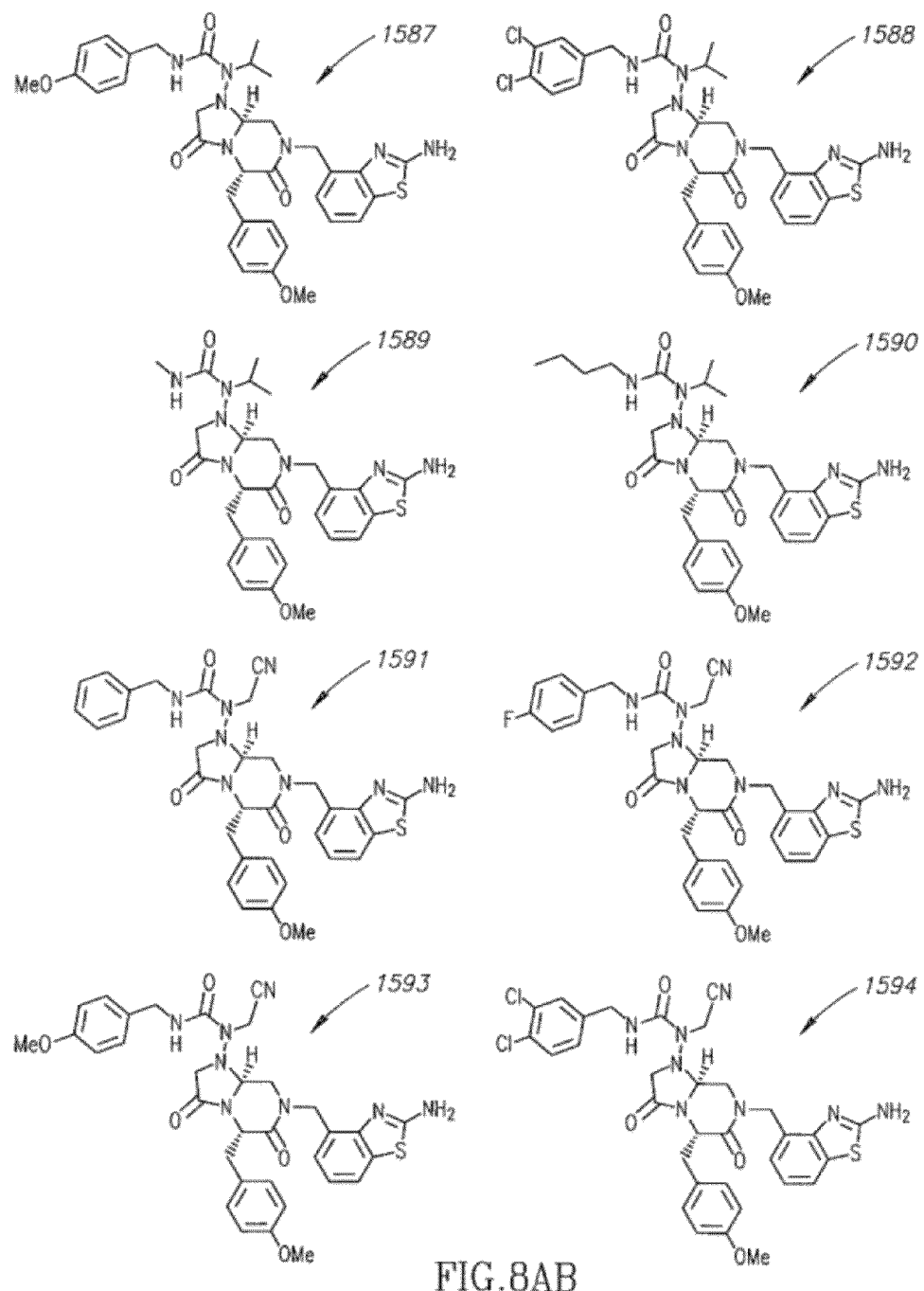
Figure 8A:
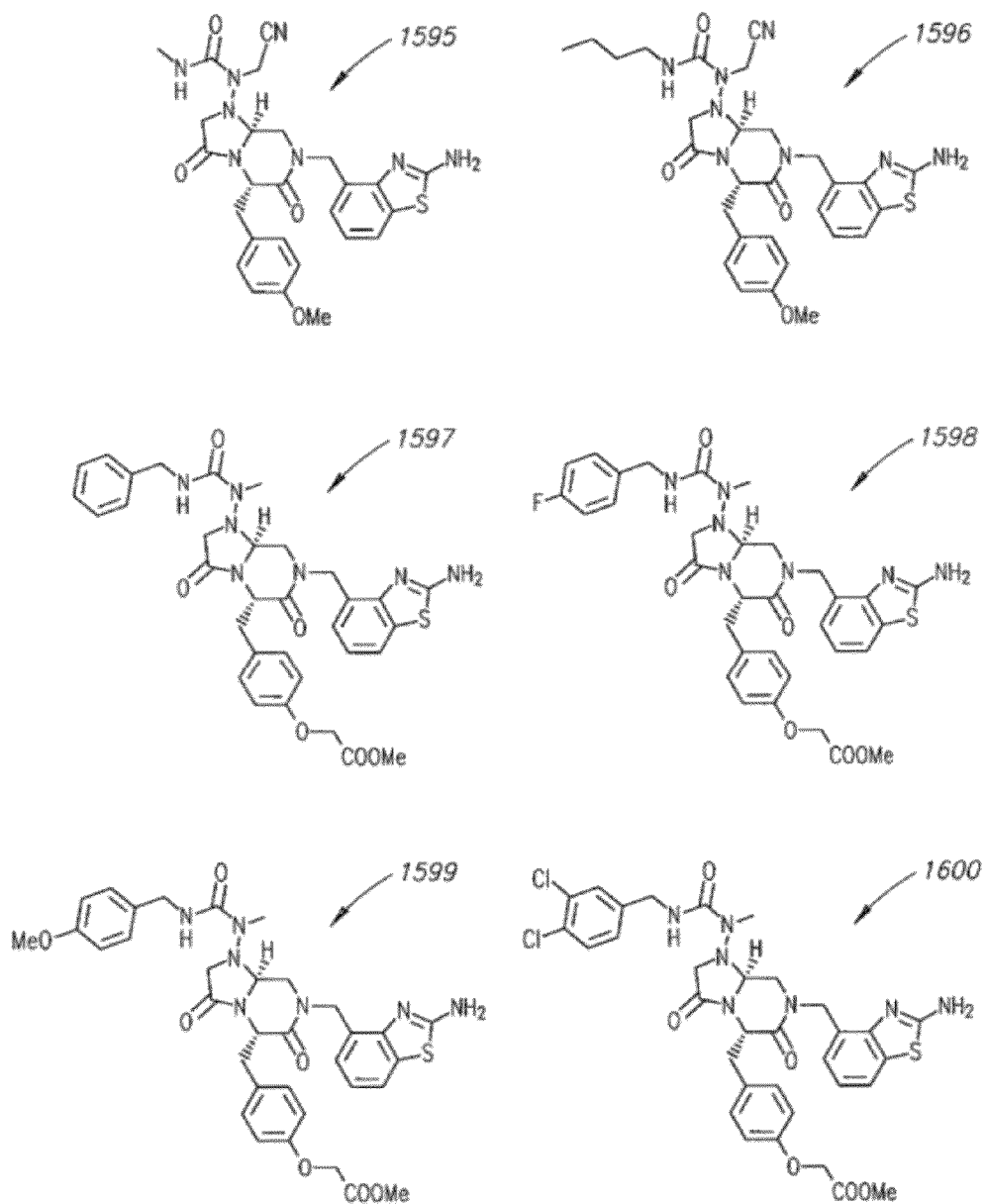
Figure 9A:
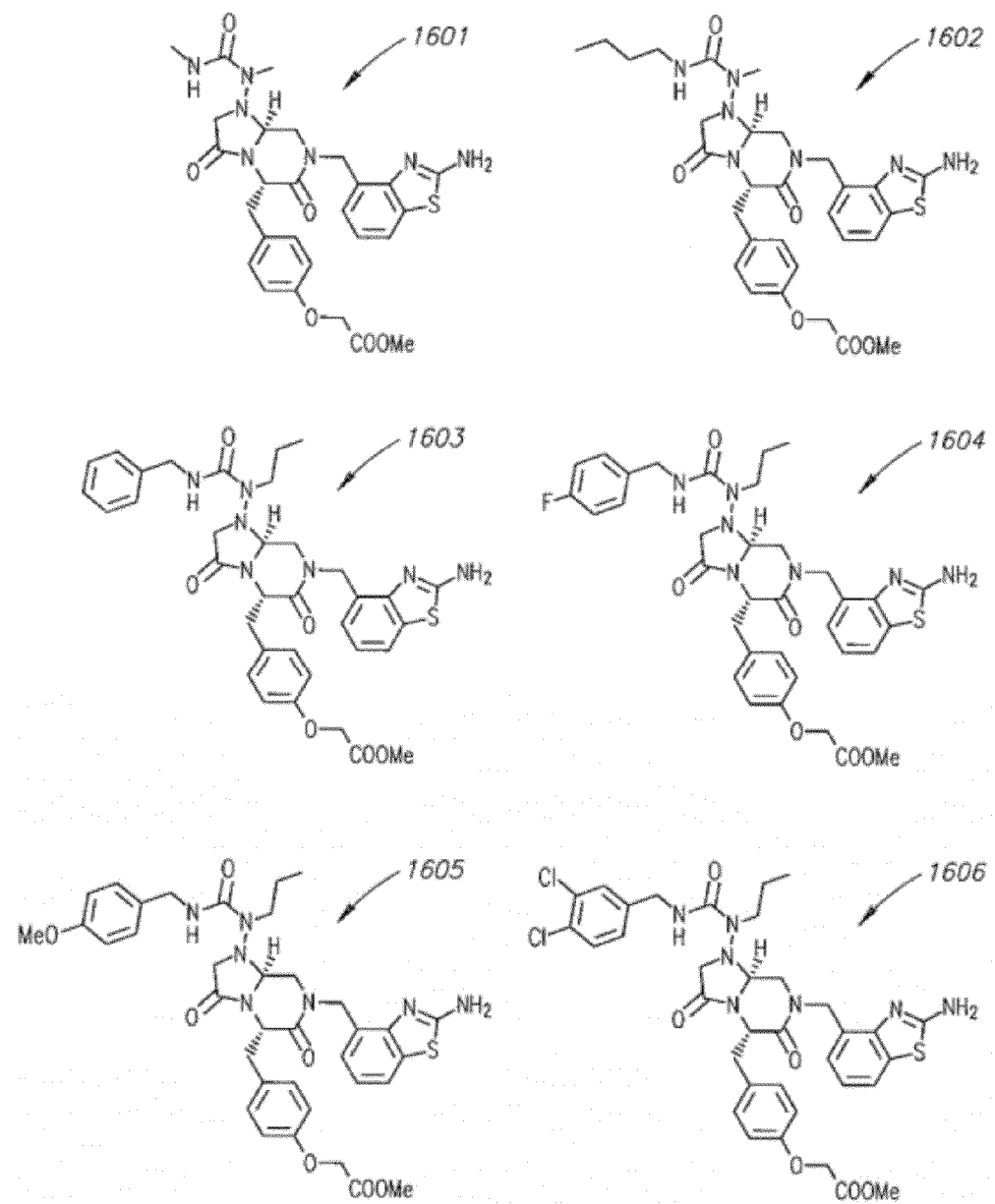
FIGS. 9A-9AE shows the chemical structures of compounds 1601-1800.
Figure 9B:
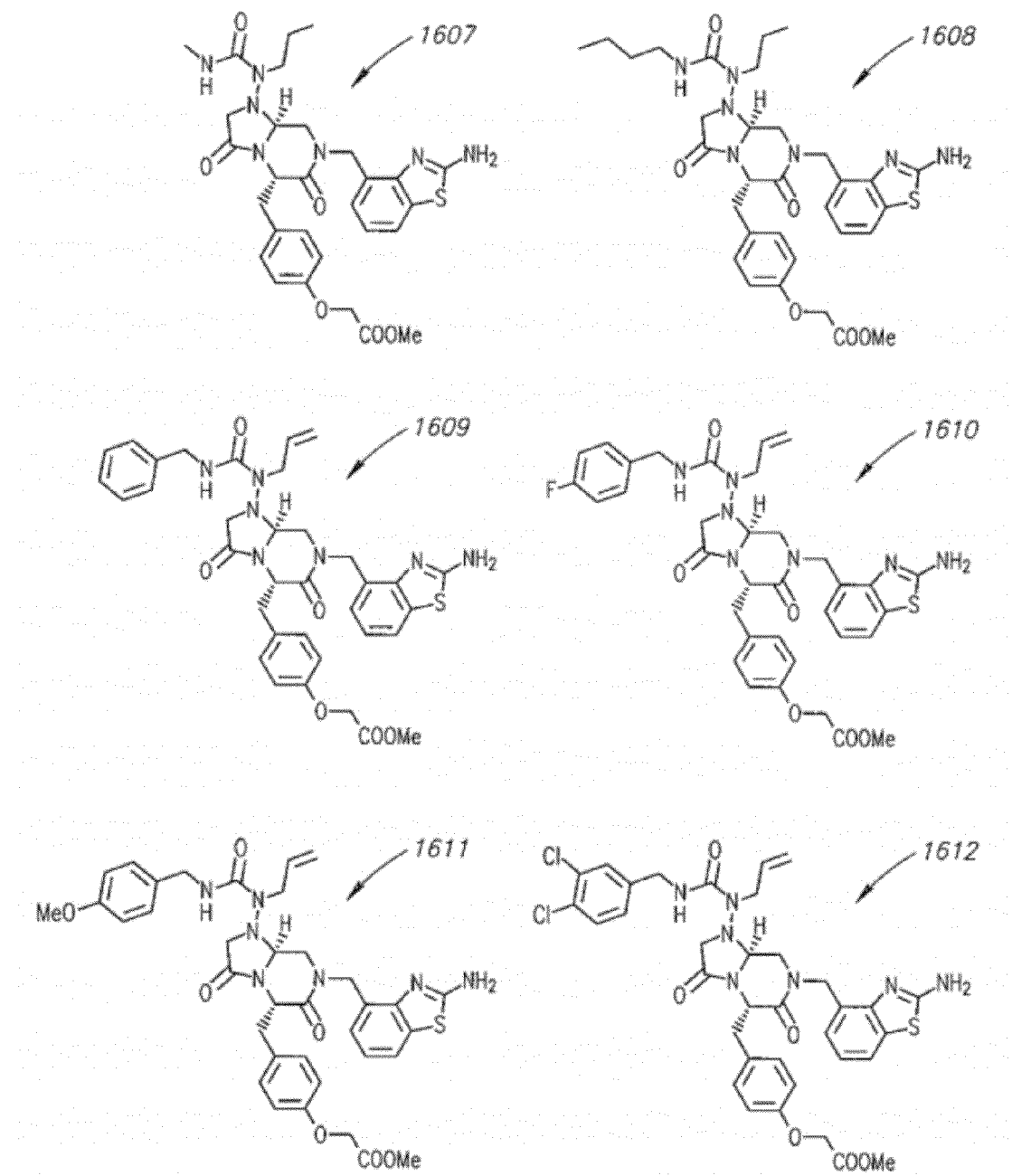
Figure 9C:
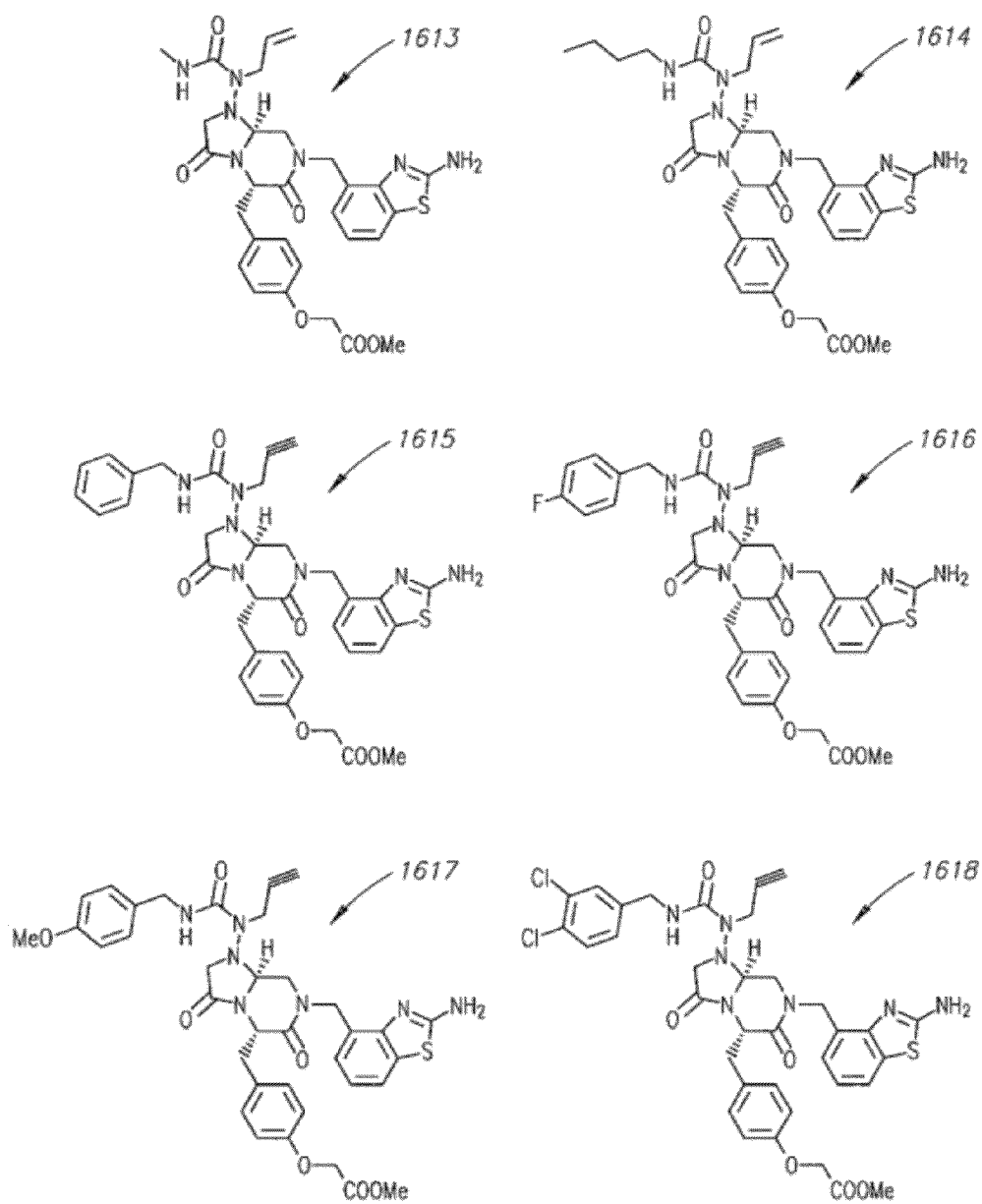
Figure 9D:
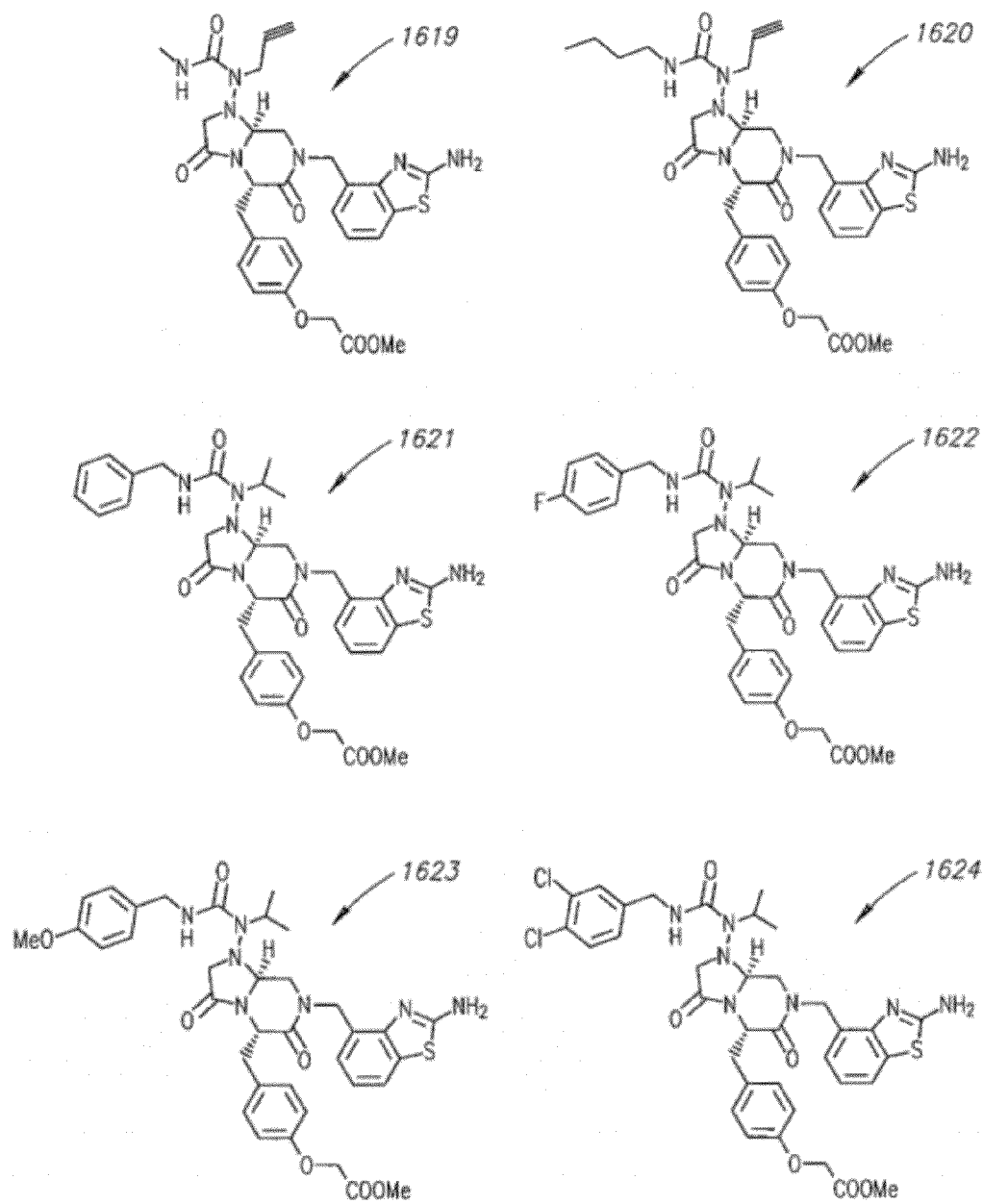
Figure 9E:
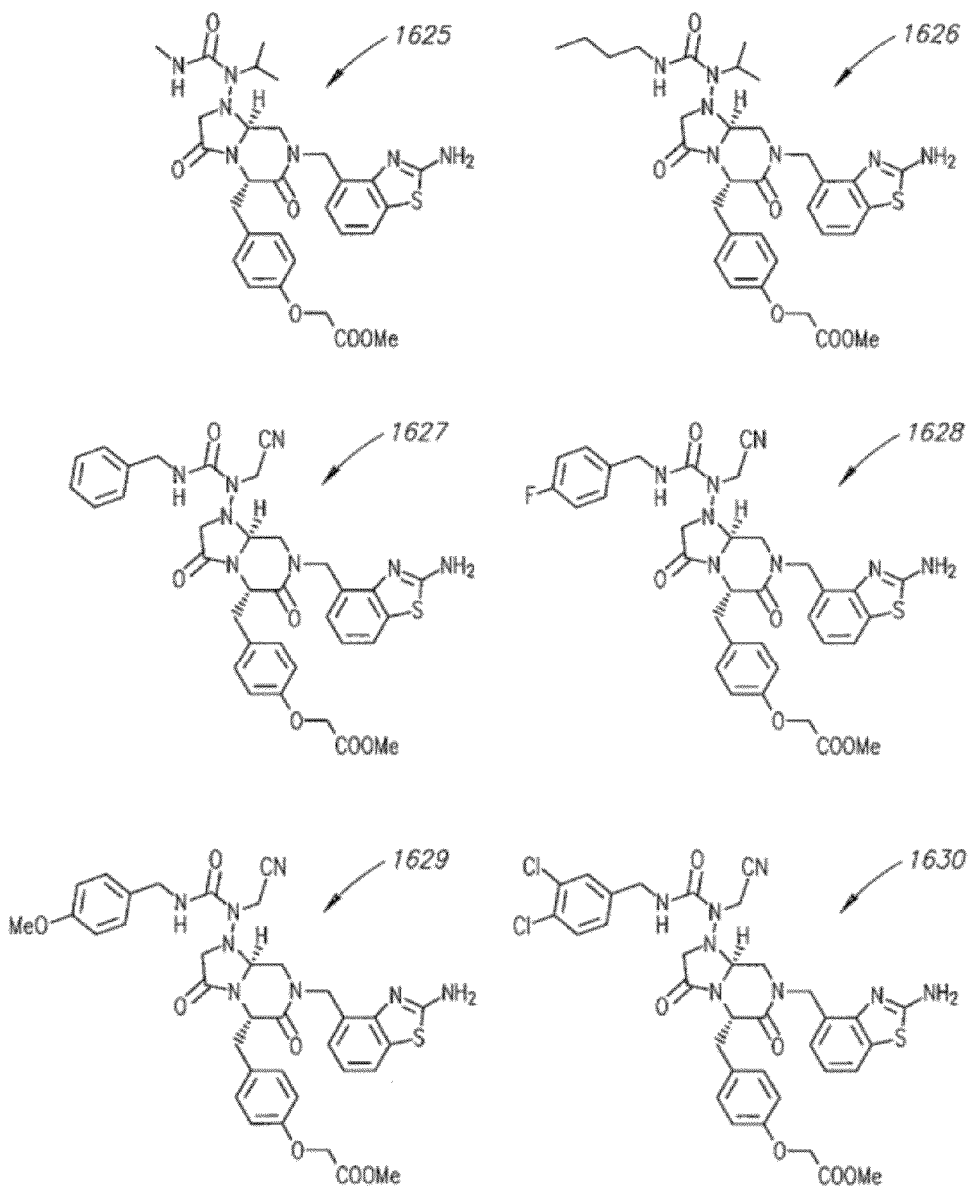
Figure 9F:
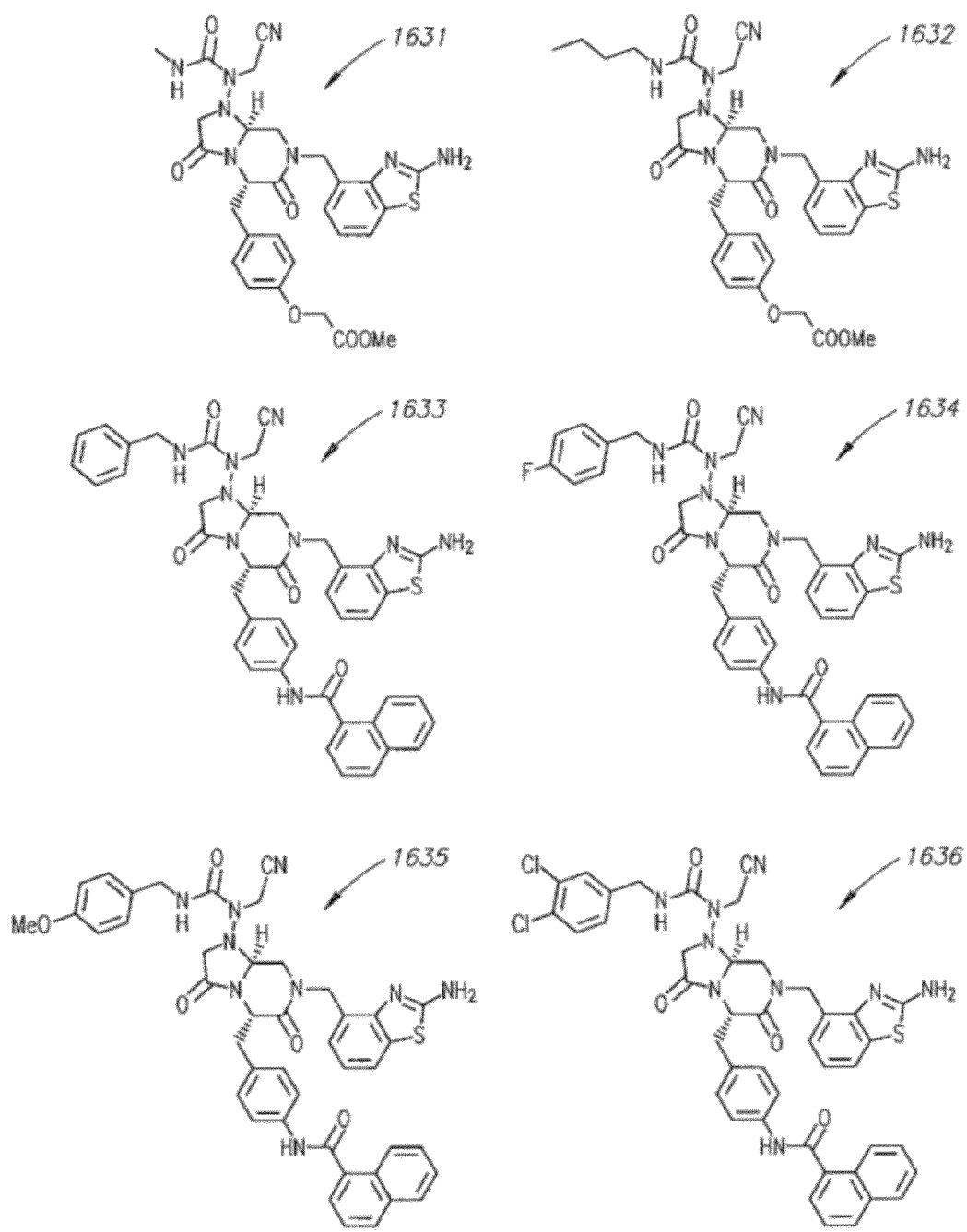
Figure 9G:
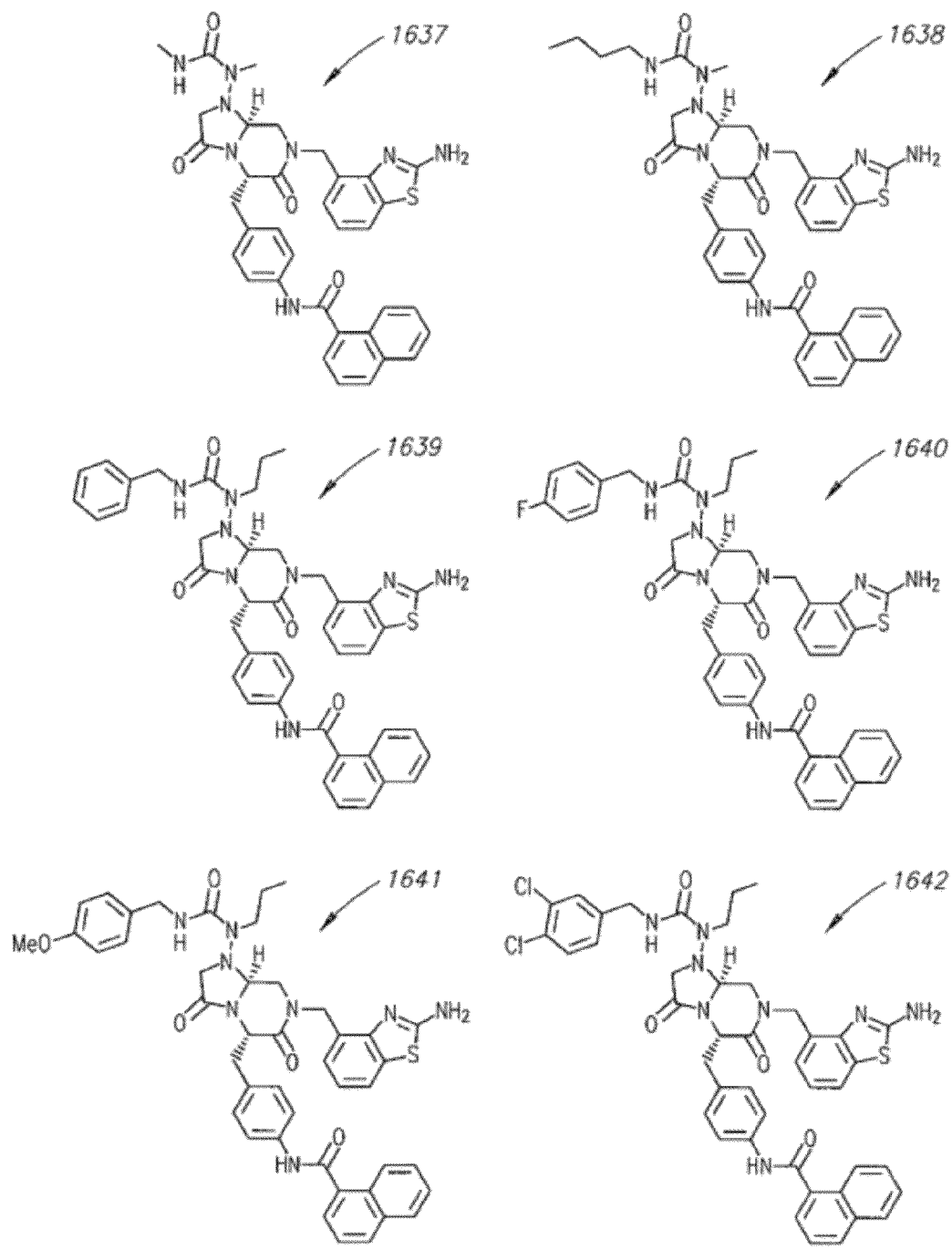
Figure 9H:
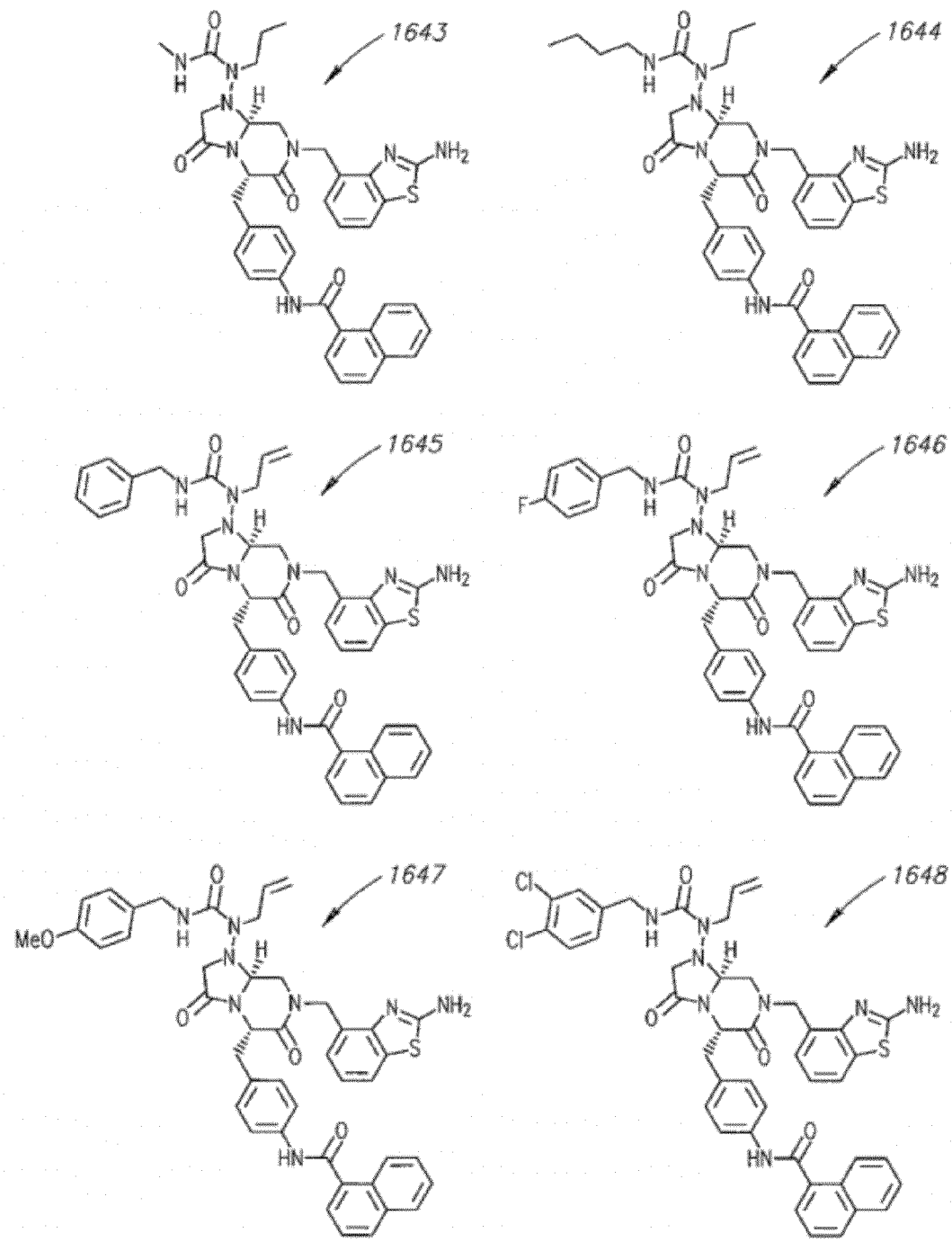
Figure 9I:
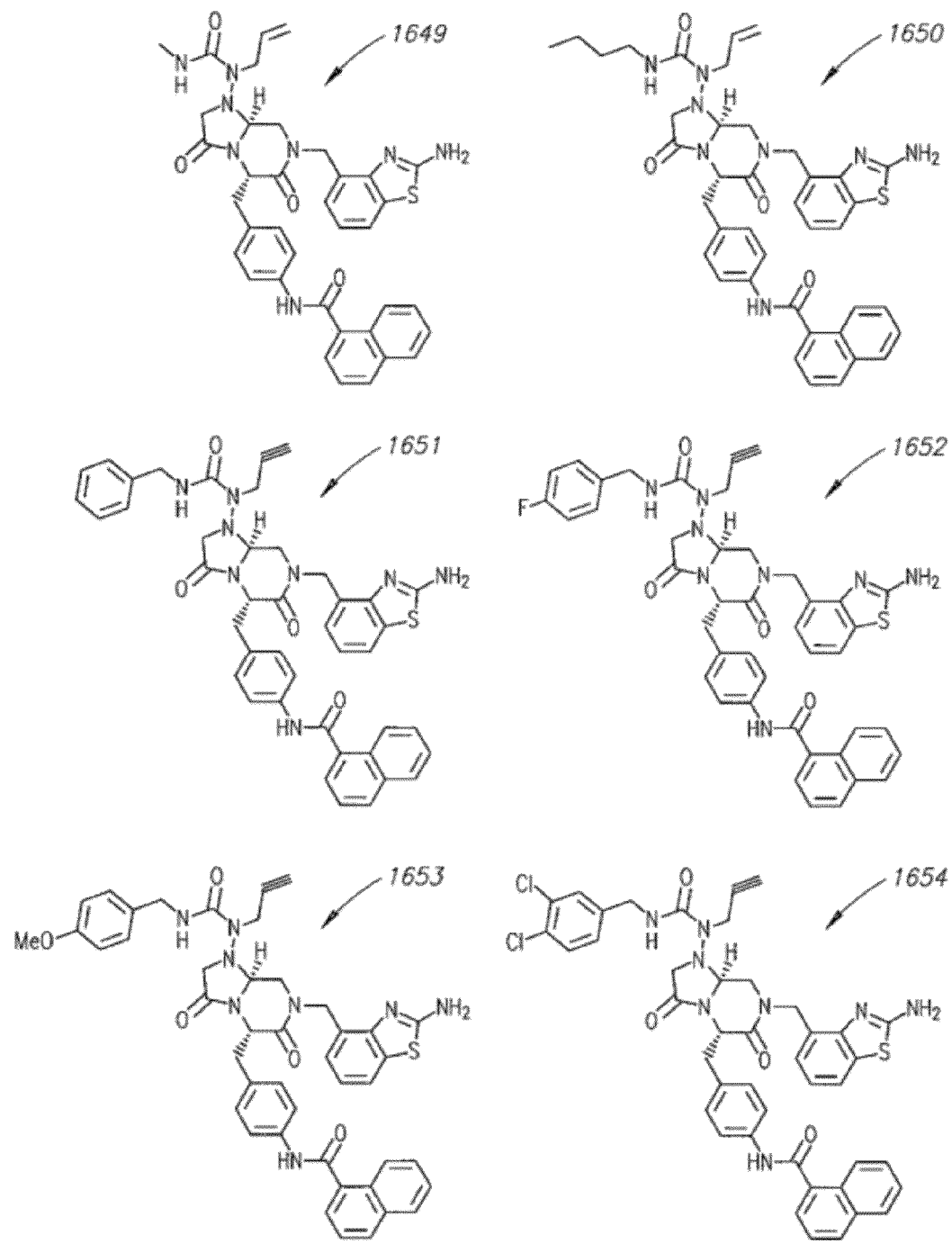
Figure 9J:
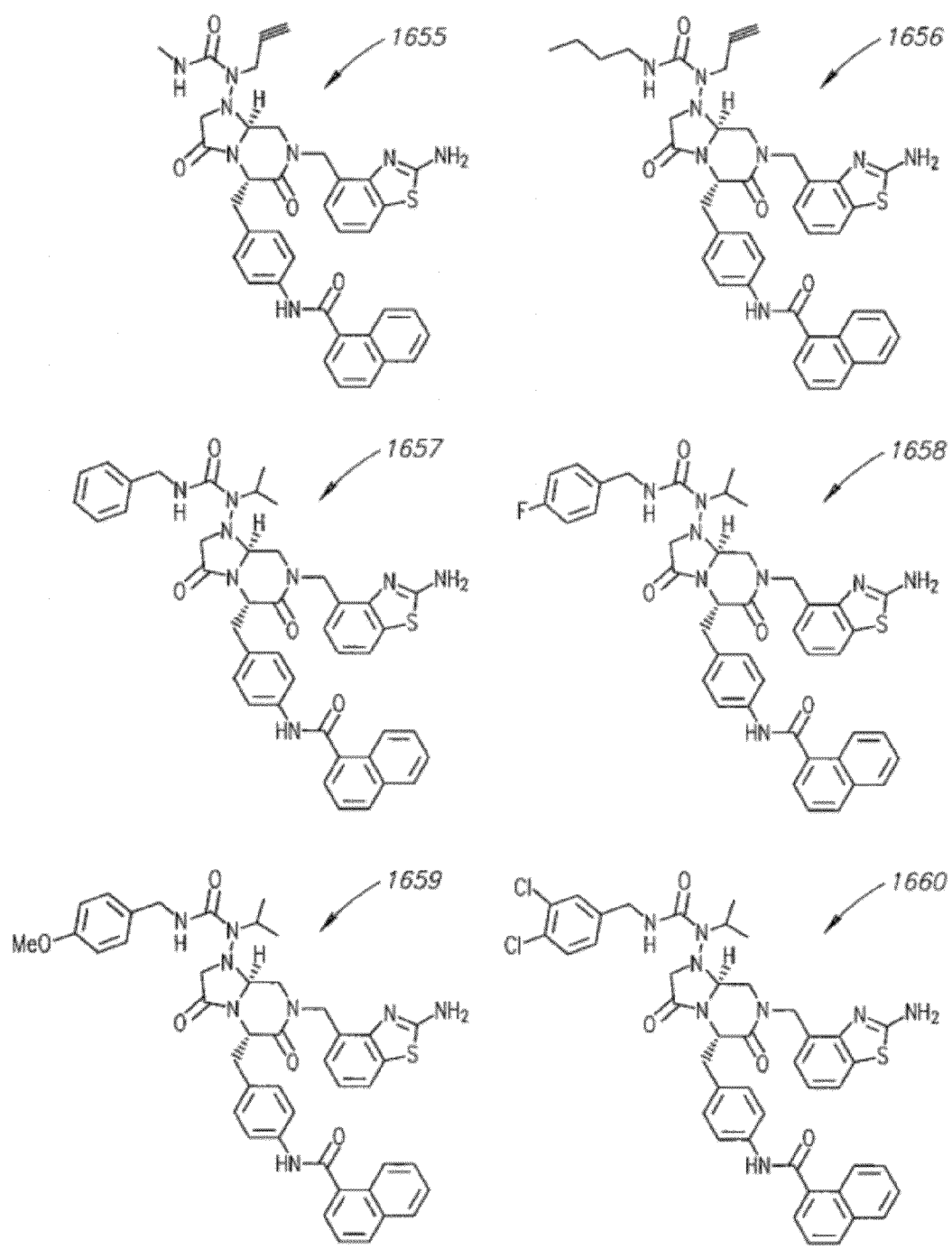
Figure 9K:
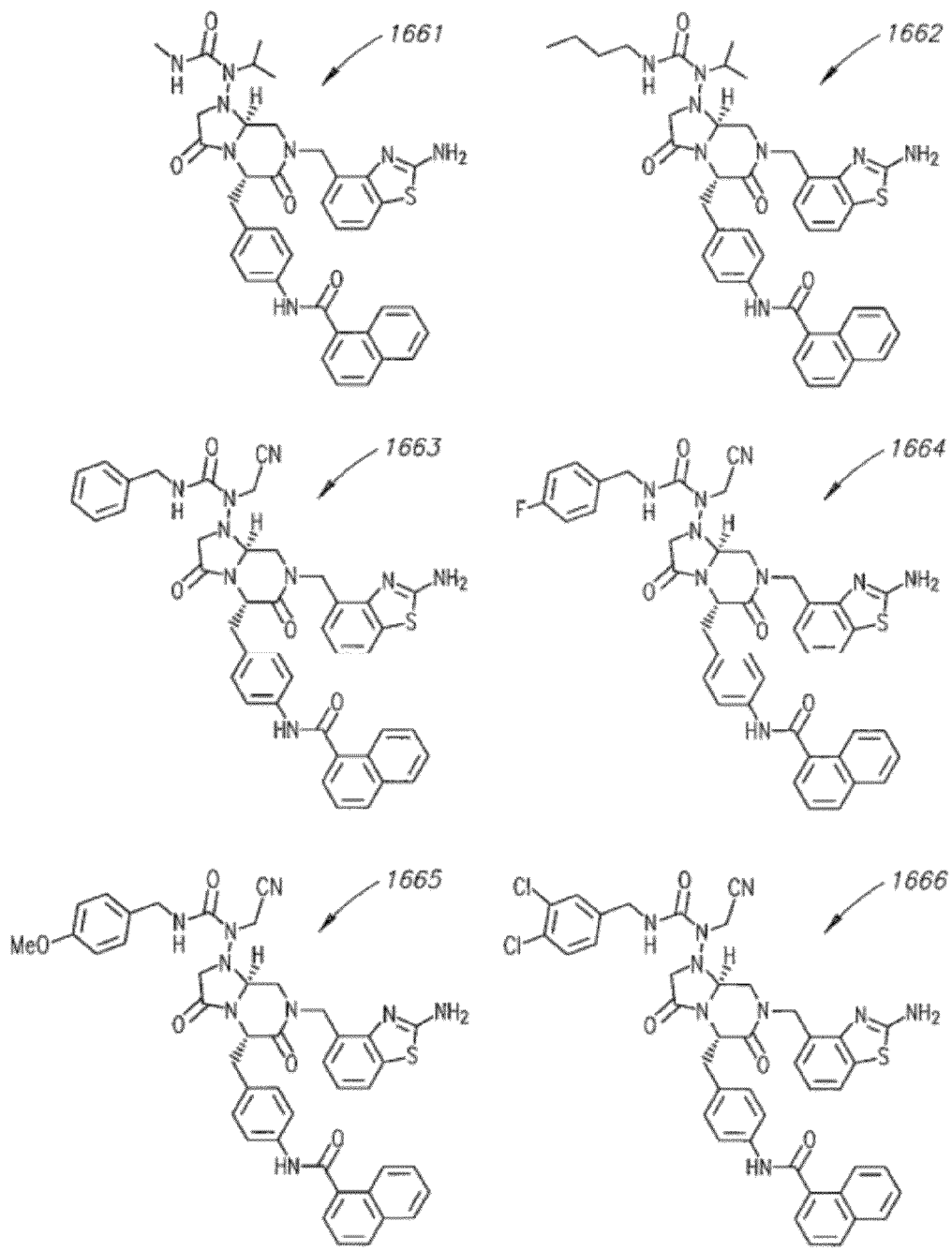
Figure 9L:
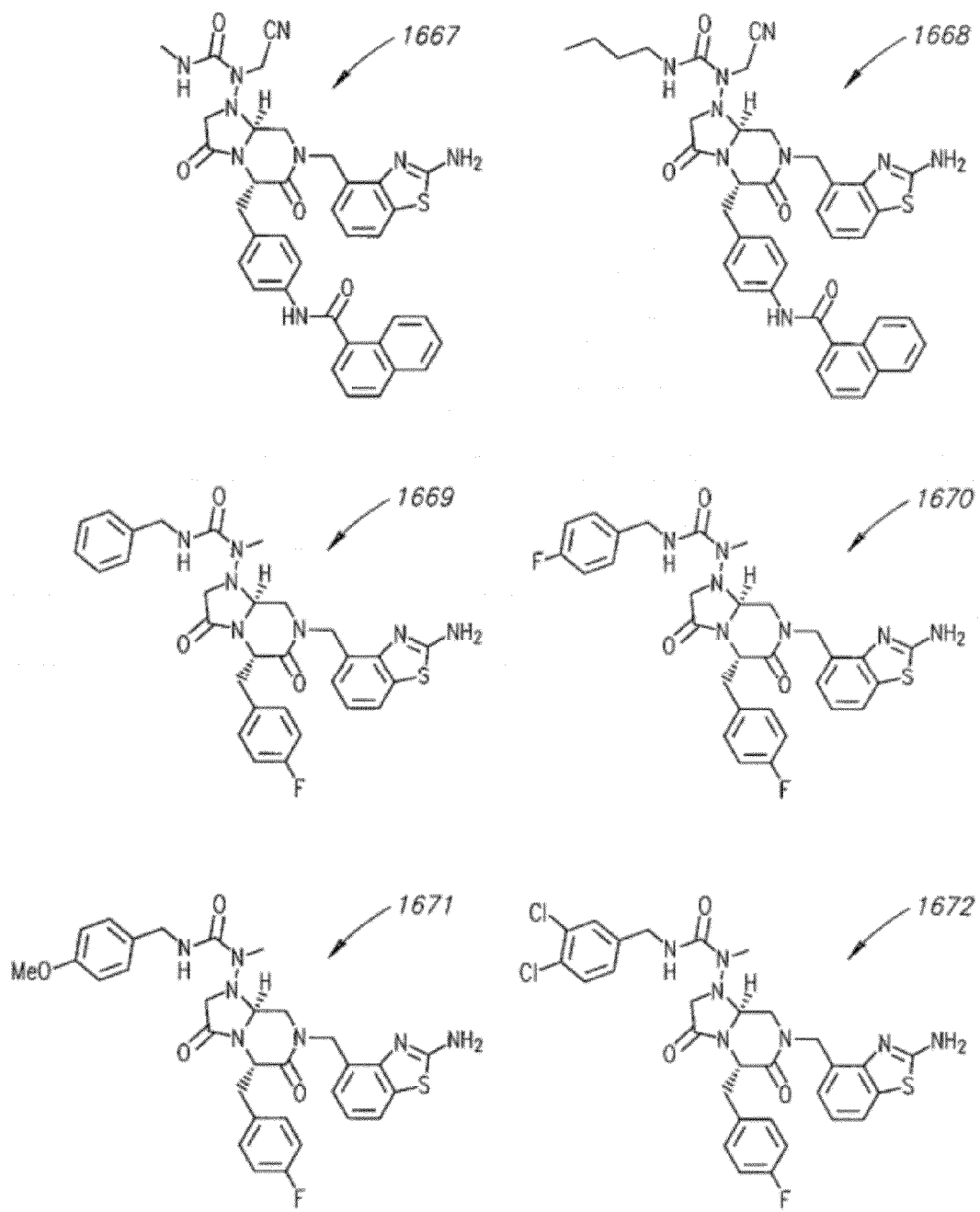
Figure 9M:
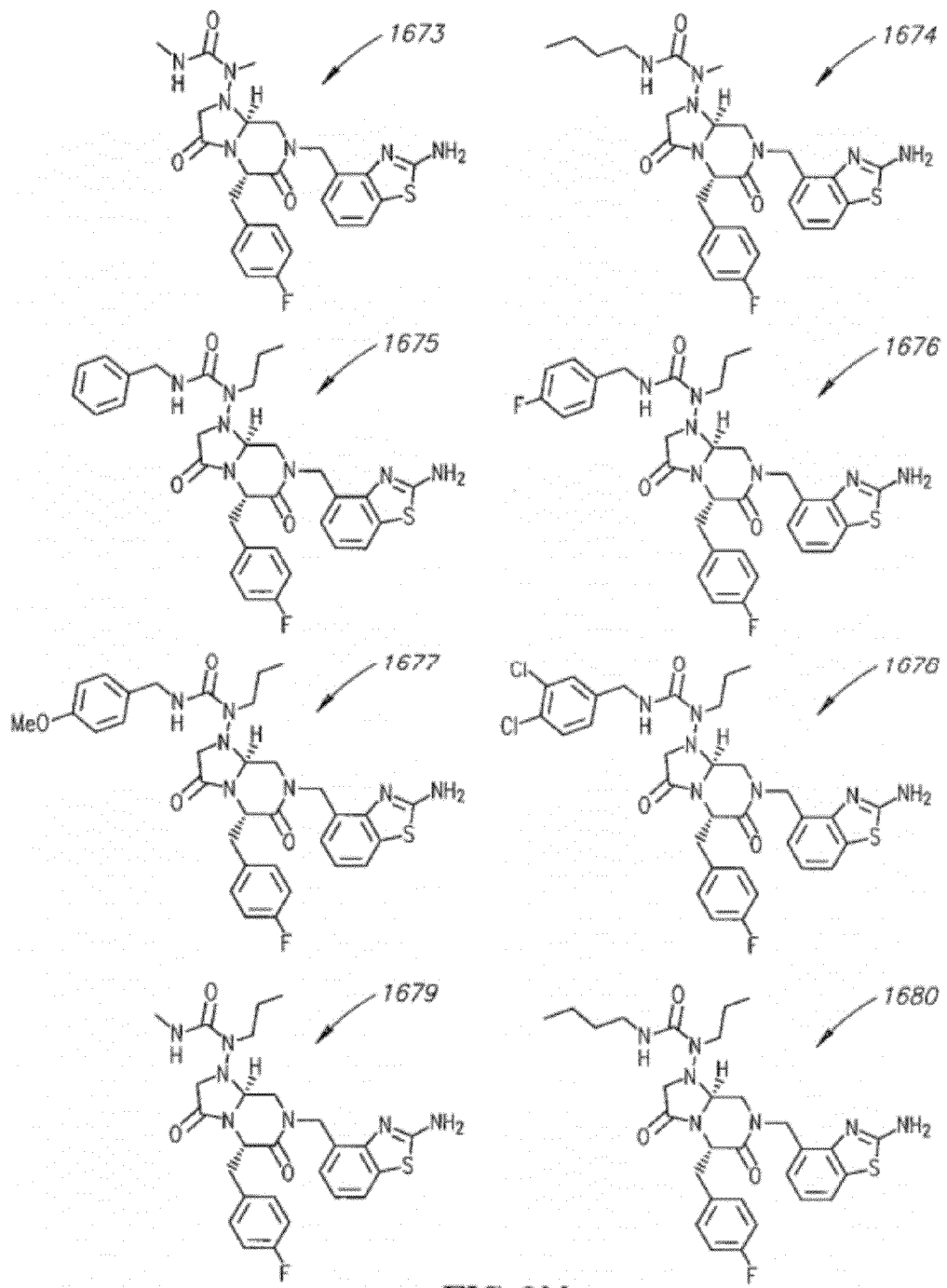
Figure 9N:
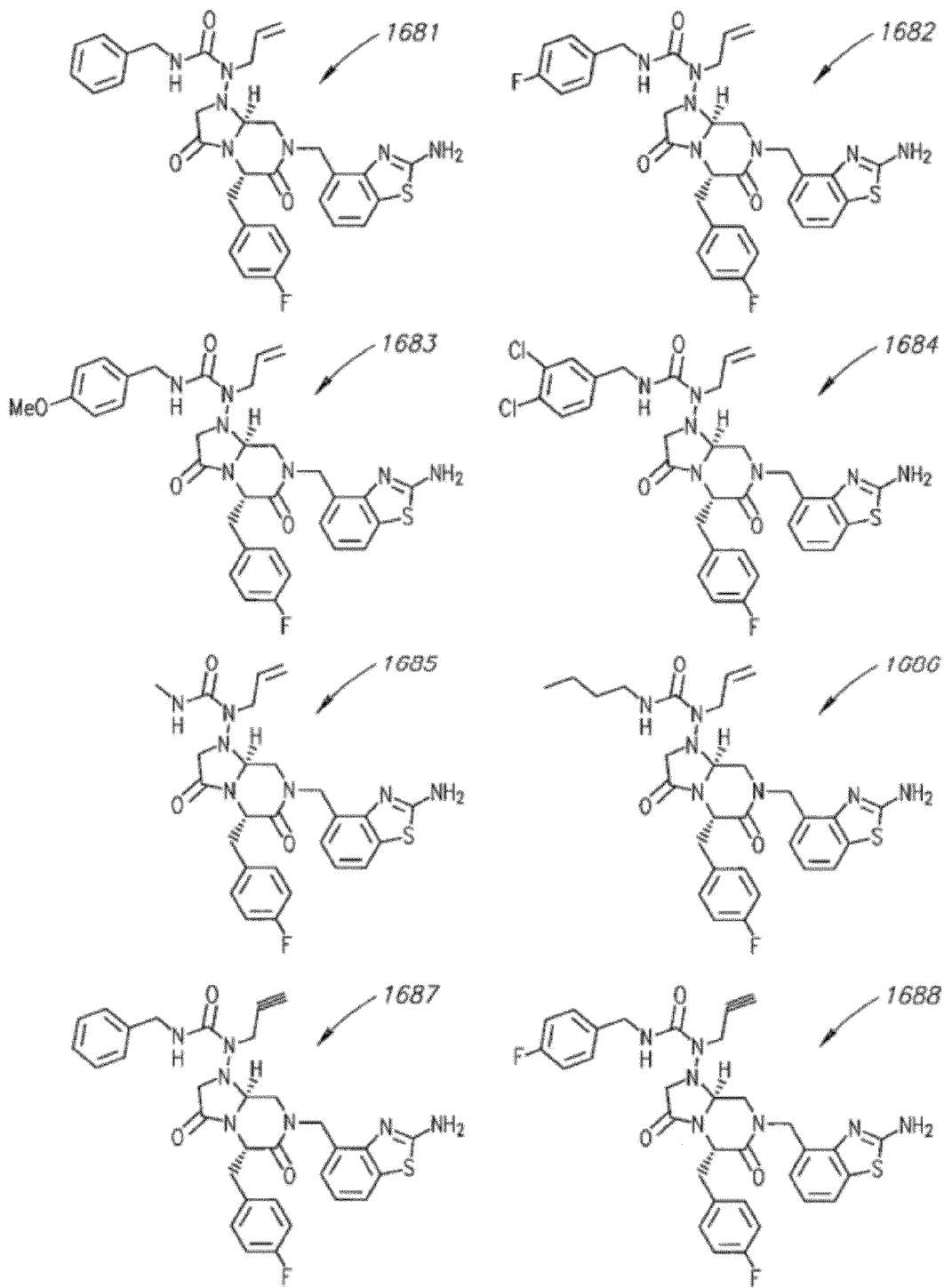
Figure 90:
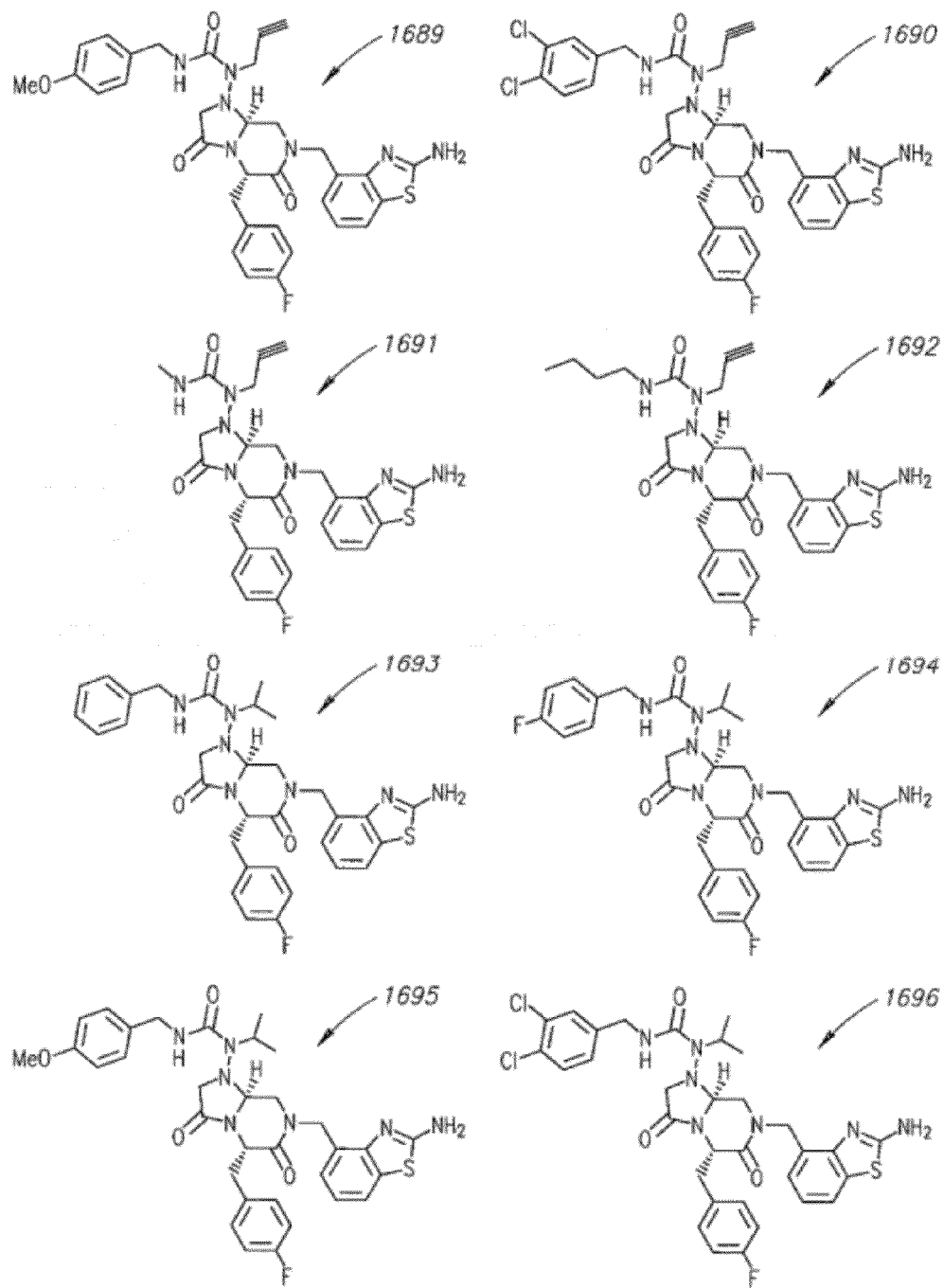
Figure 9P:
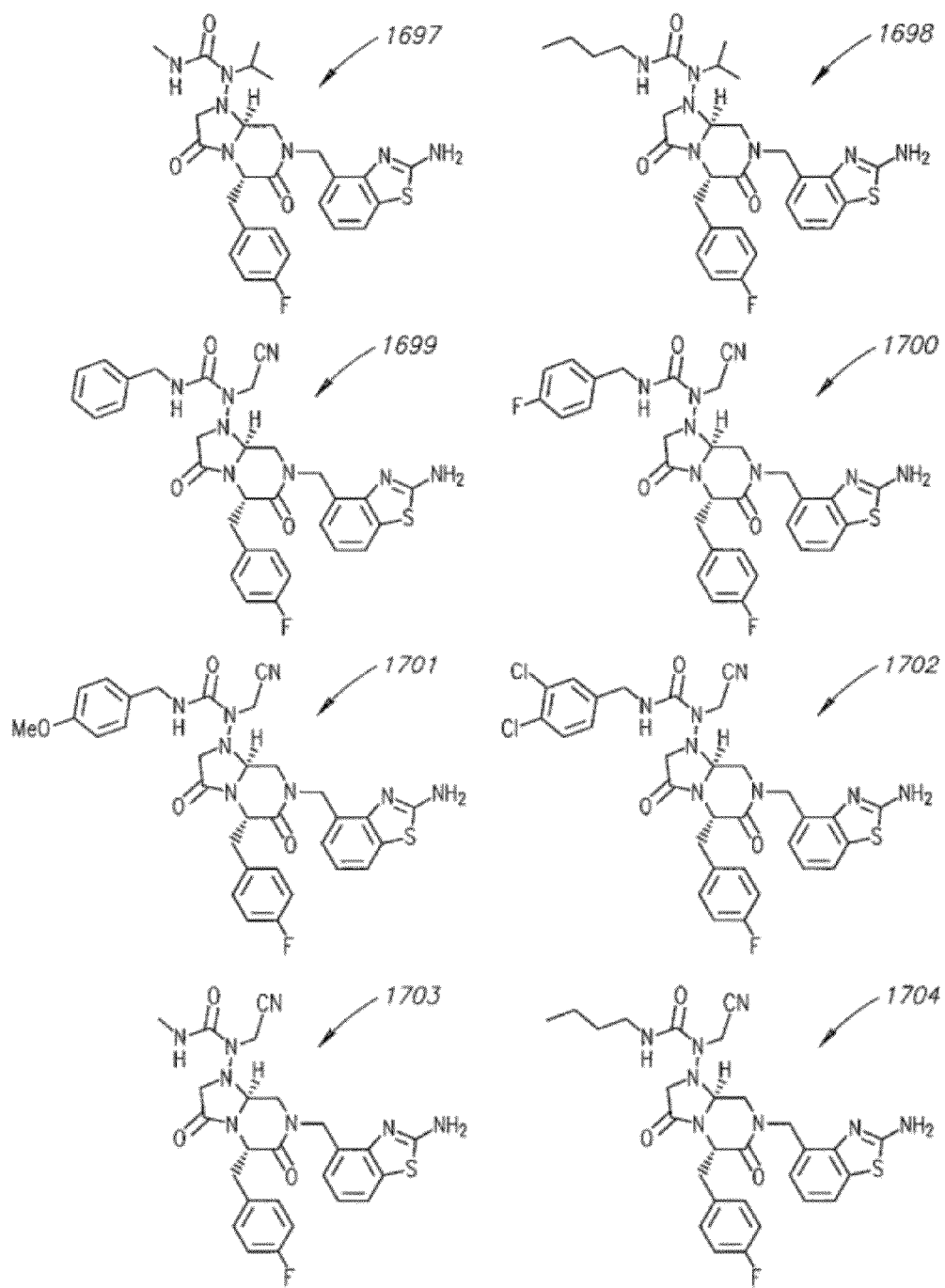
Figure 9Q:
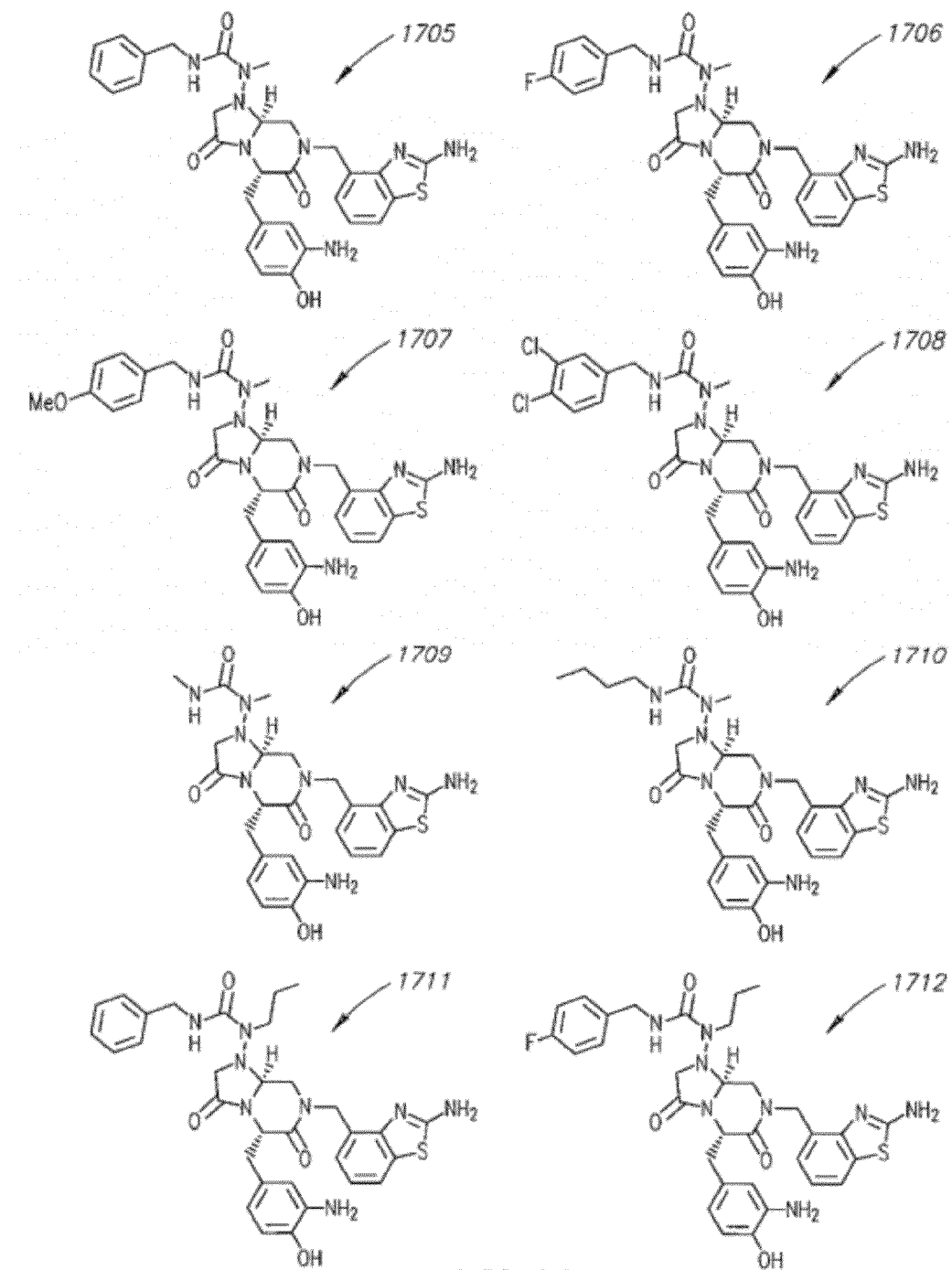
Figure 9R:
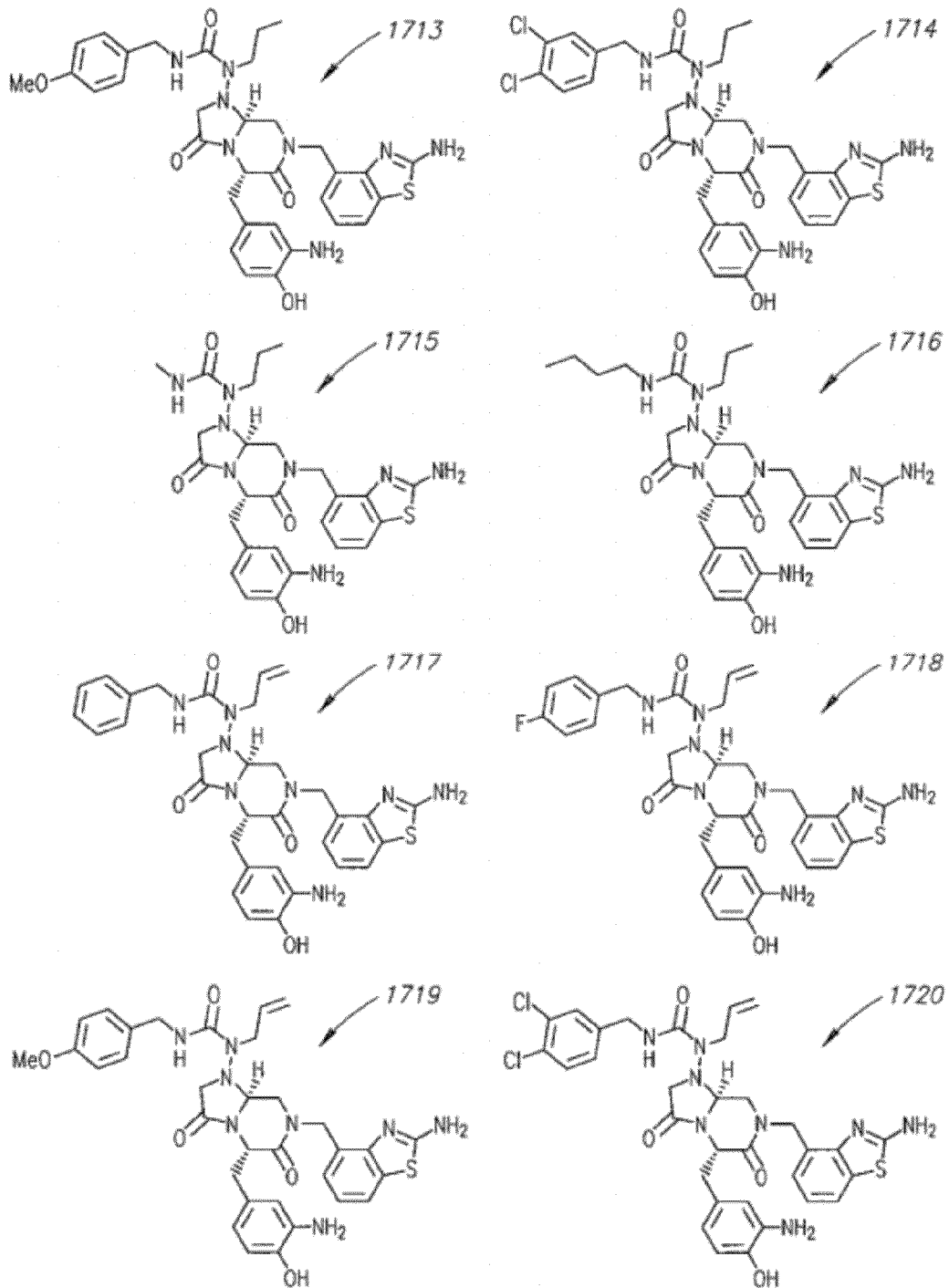
Figure 9S:
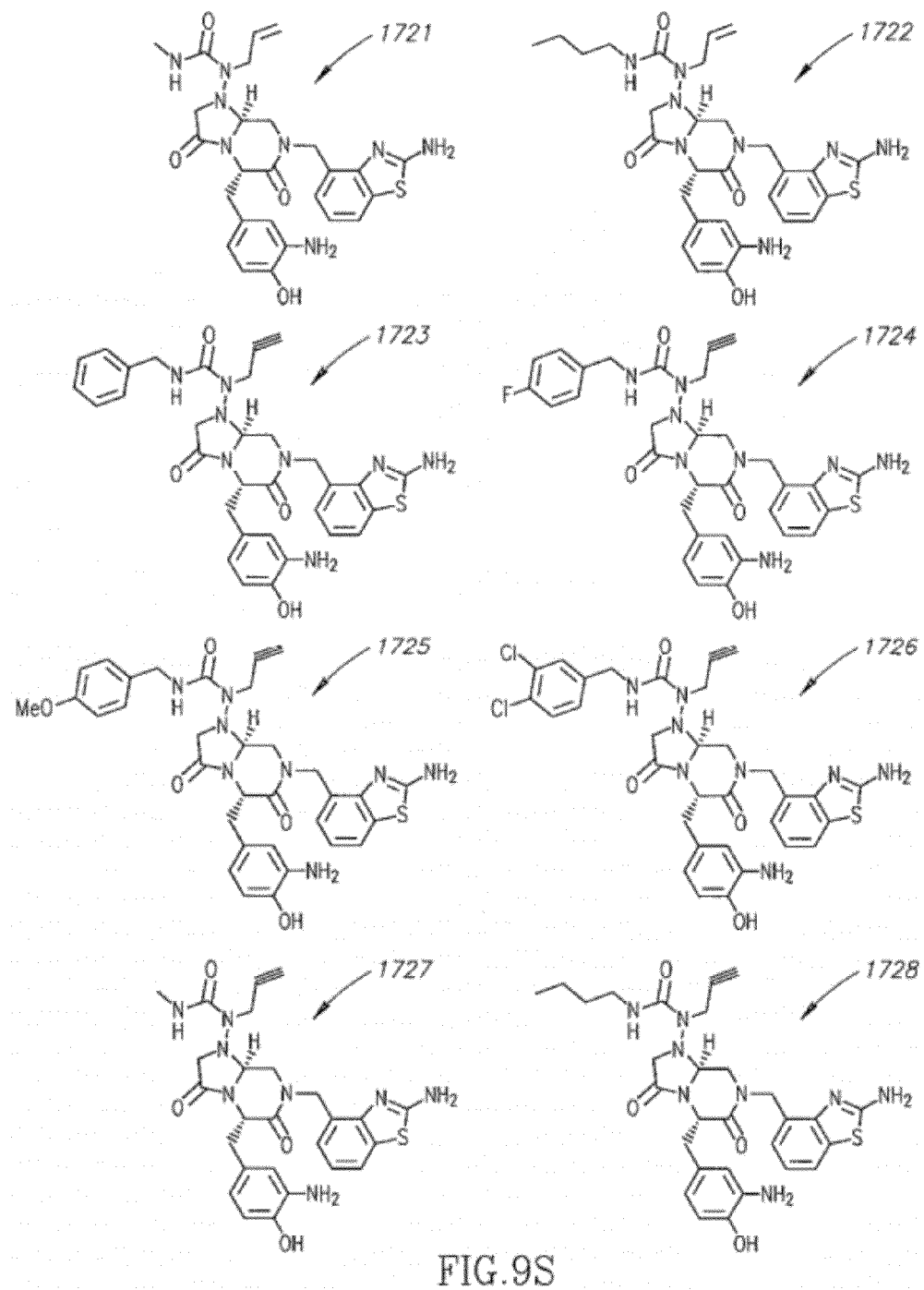
Figure 9T:
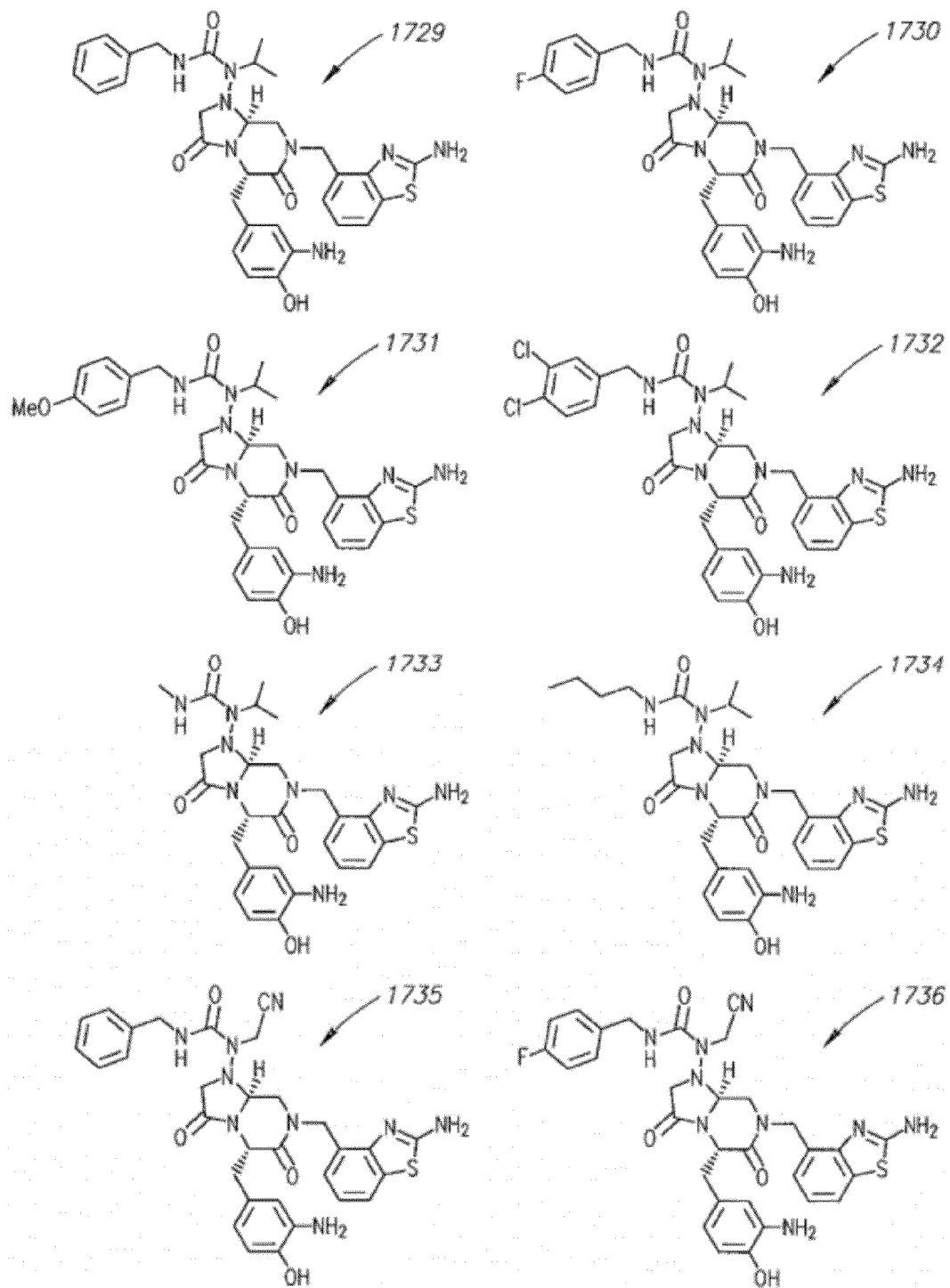
Figure 9U:
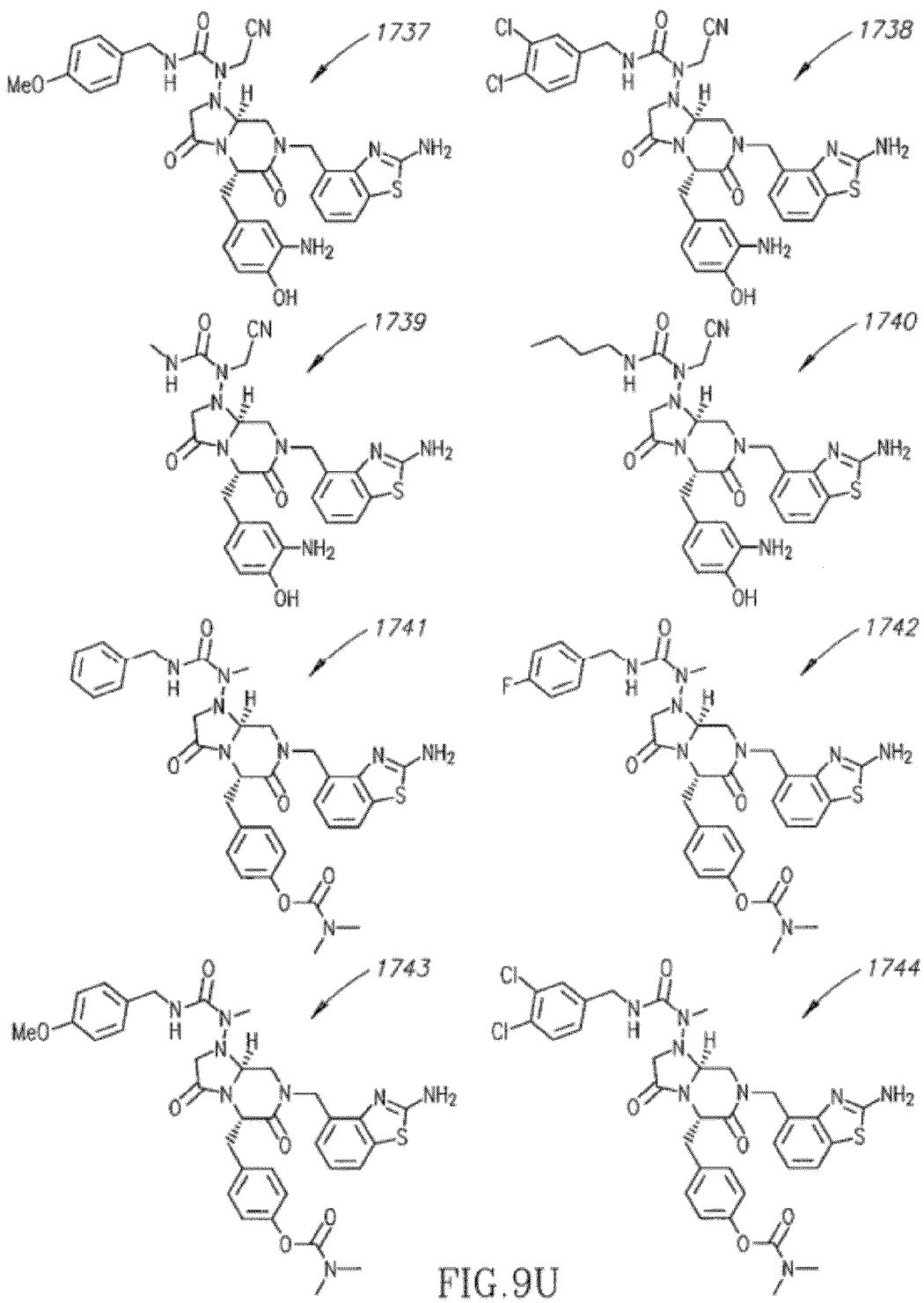
Figure 9V:
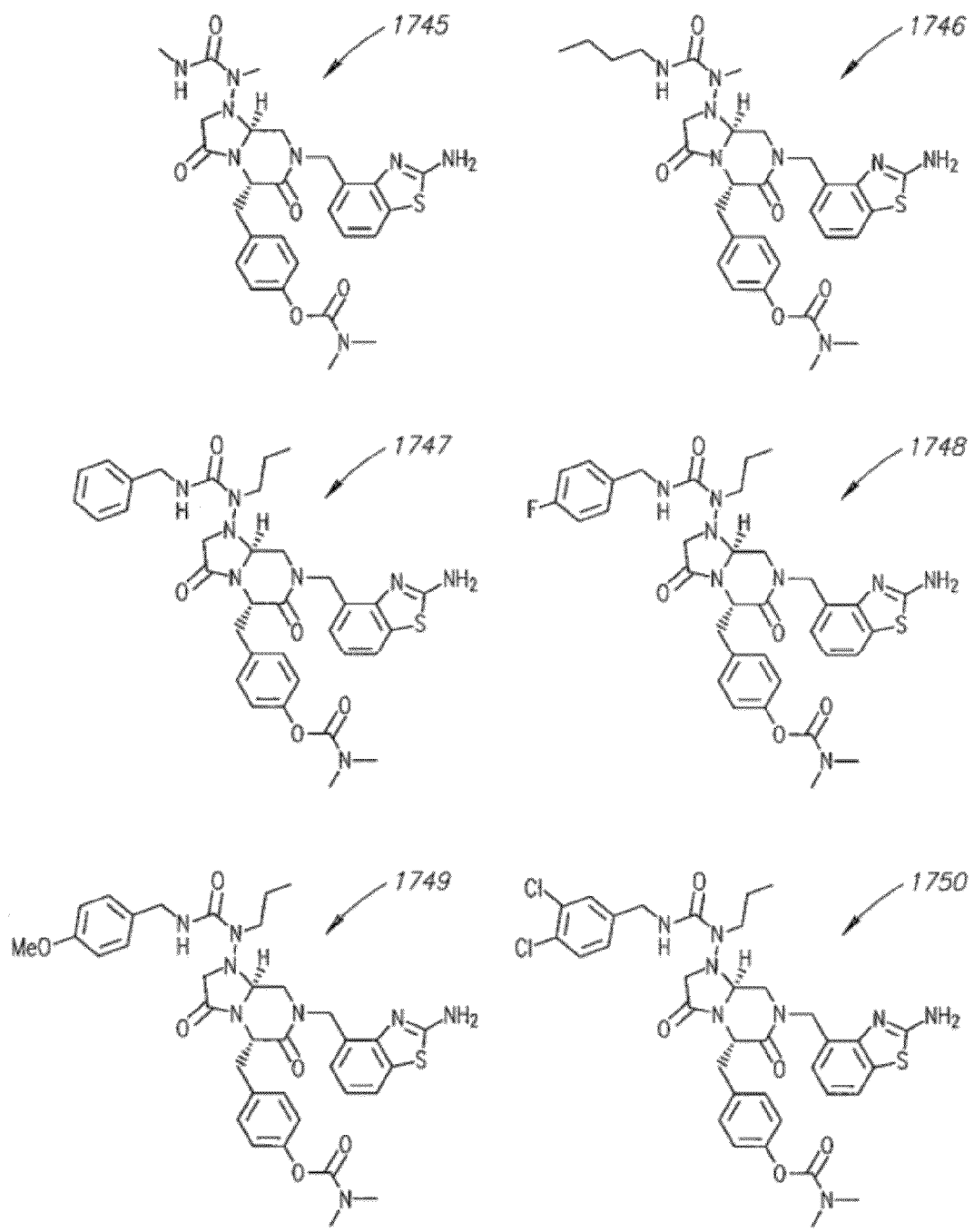
Figure 9W:
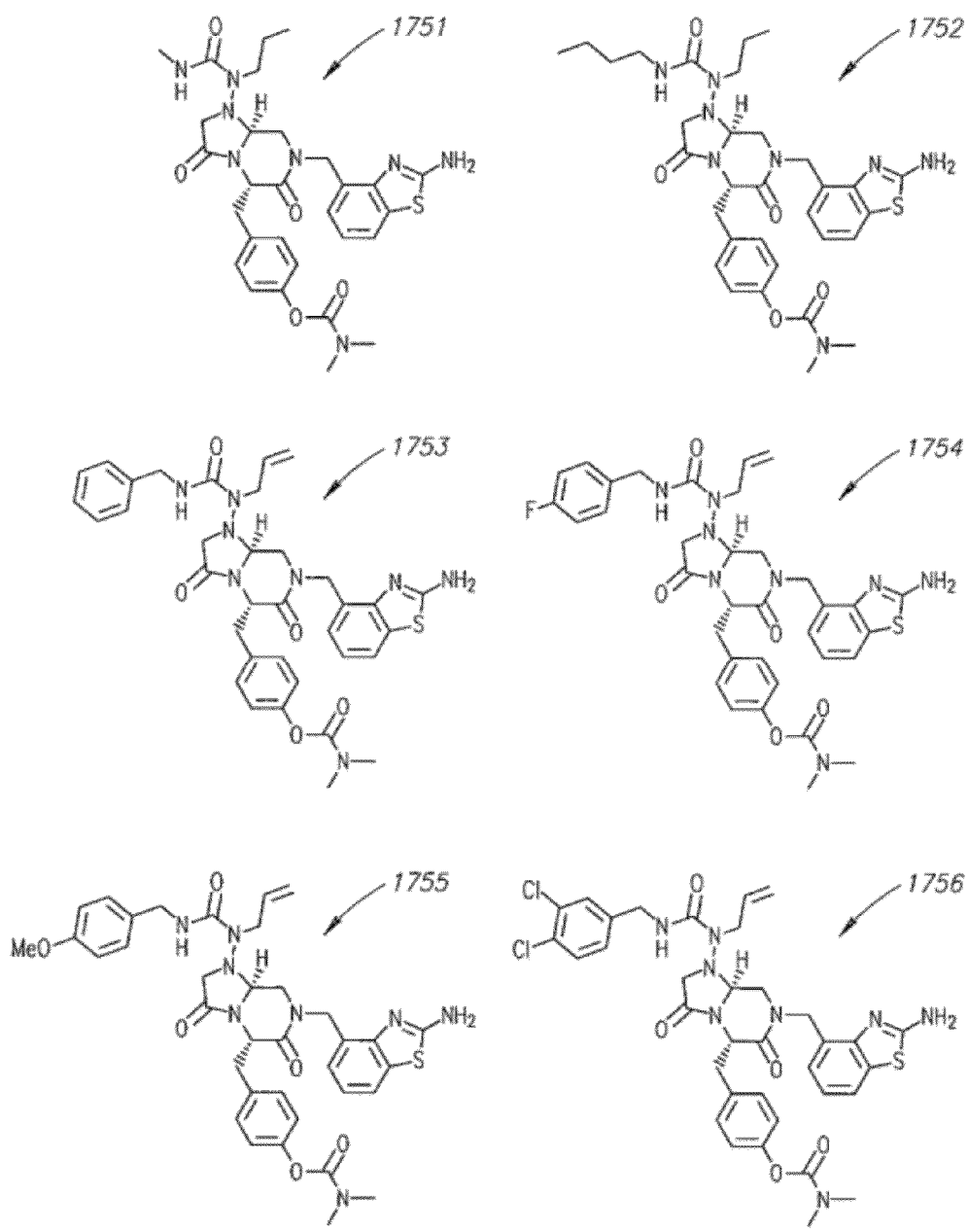
Figure 9X:
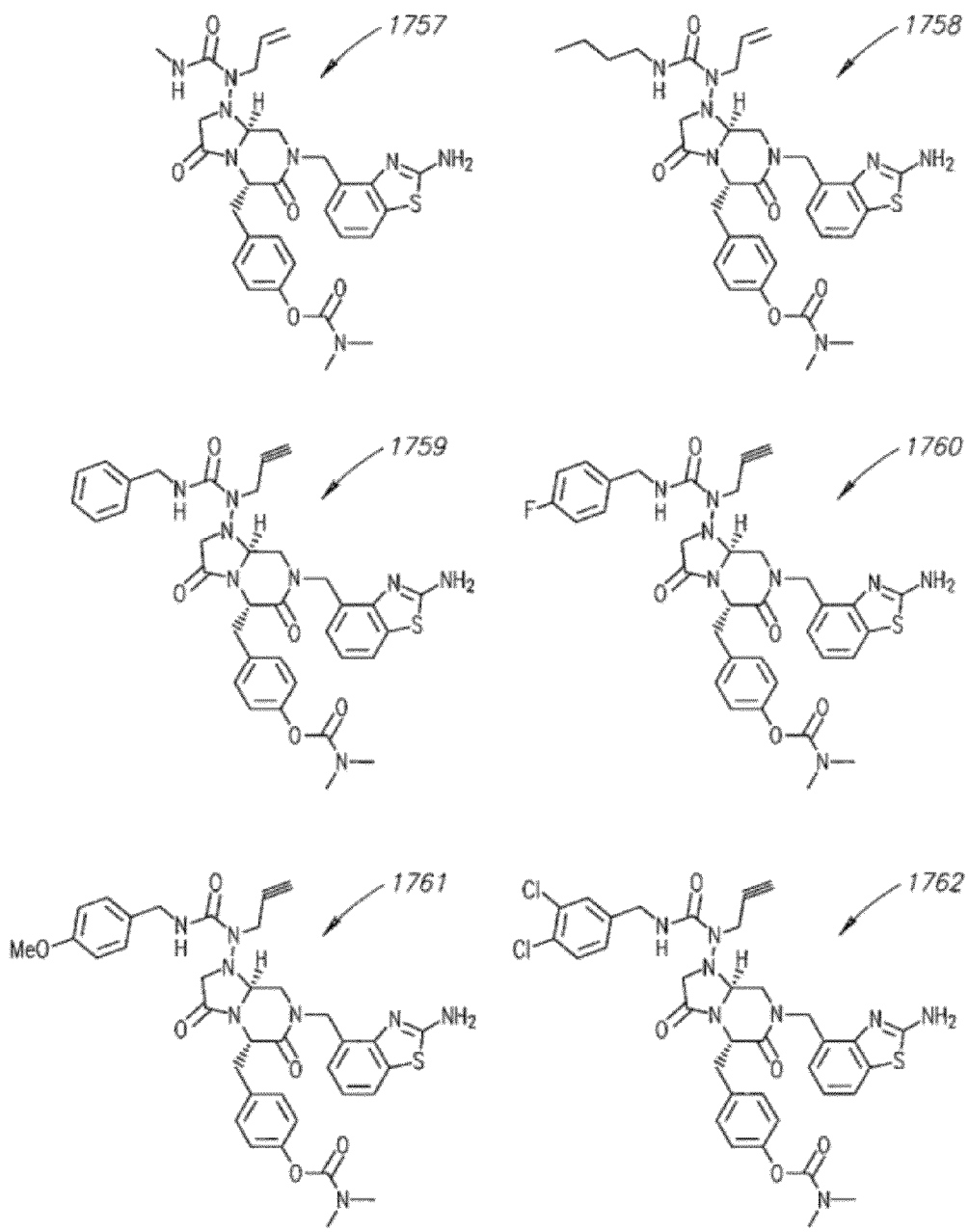
Figure 9Y:
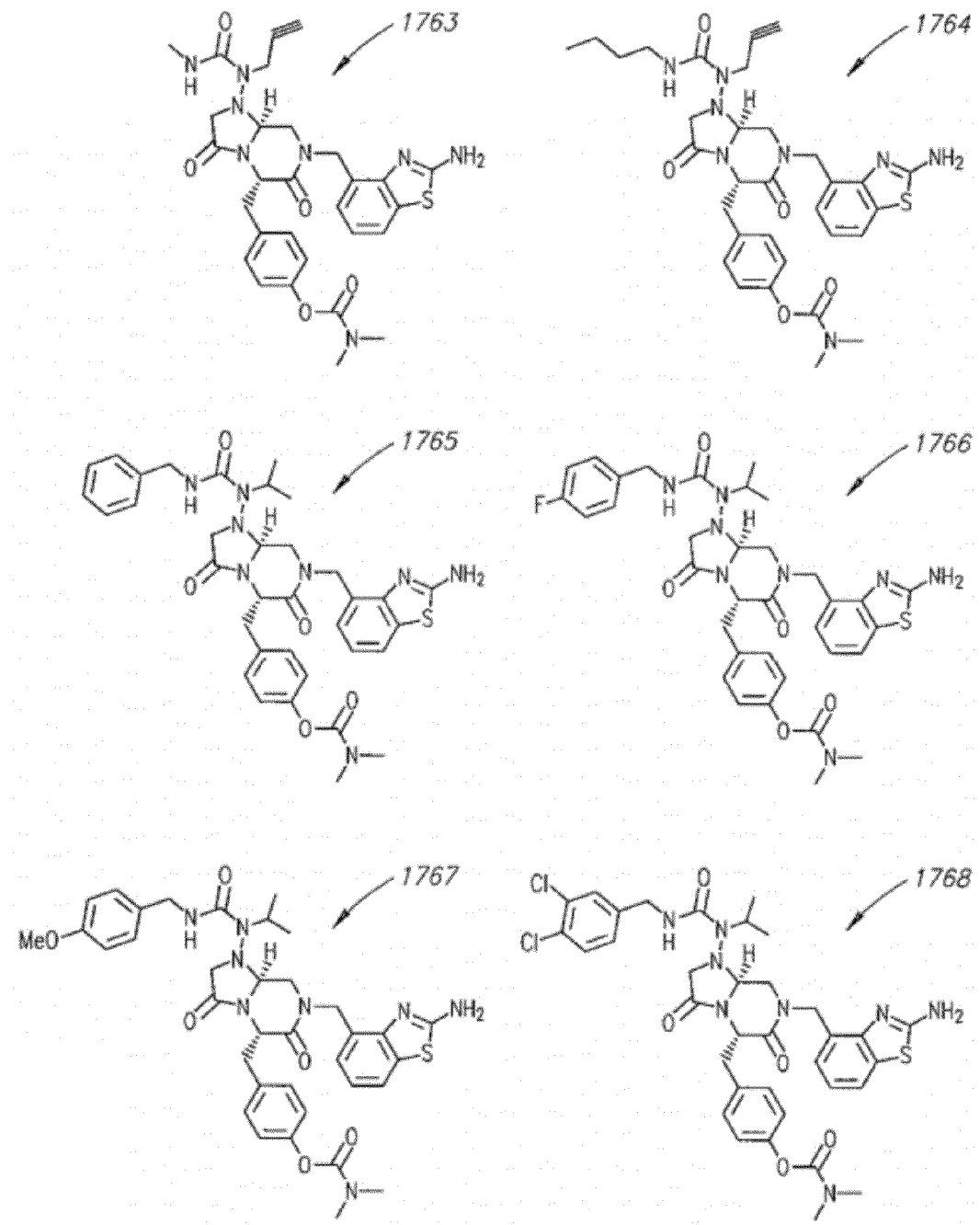
Figure 9Z:
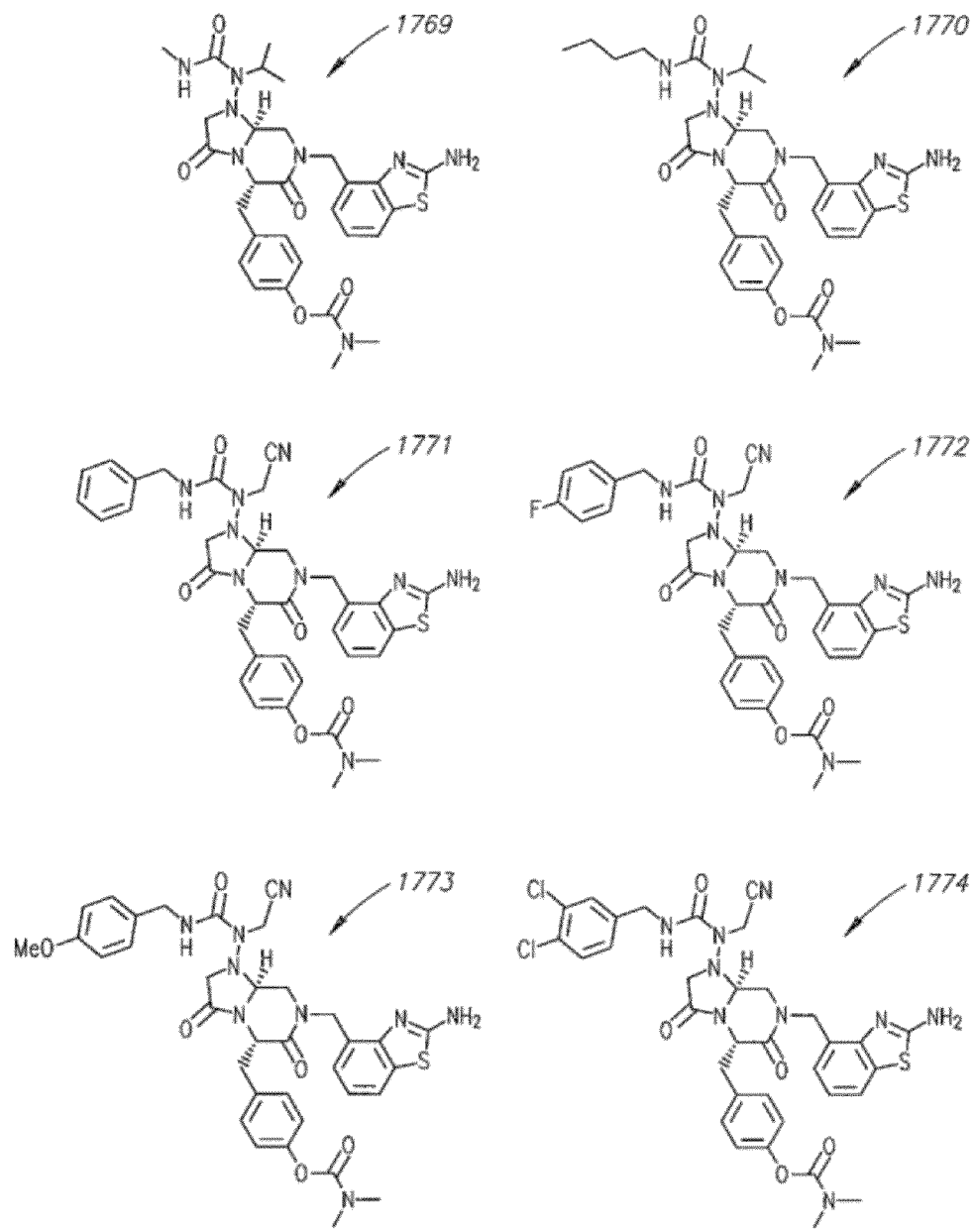
Figure 9A:
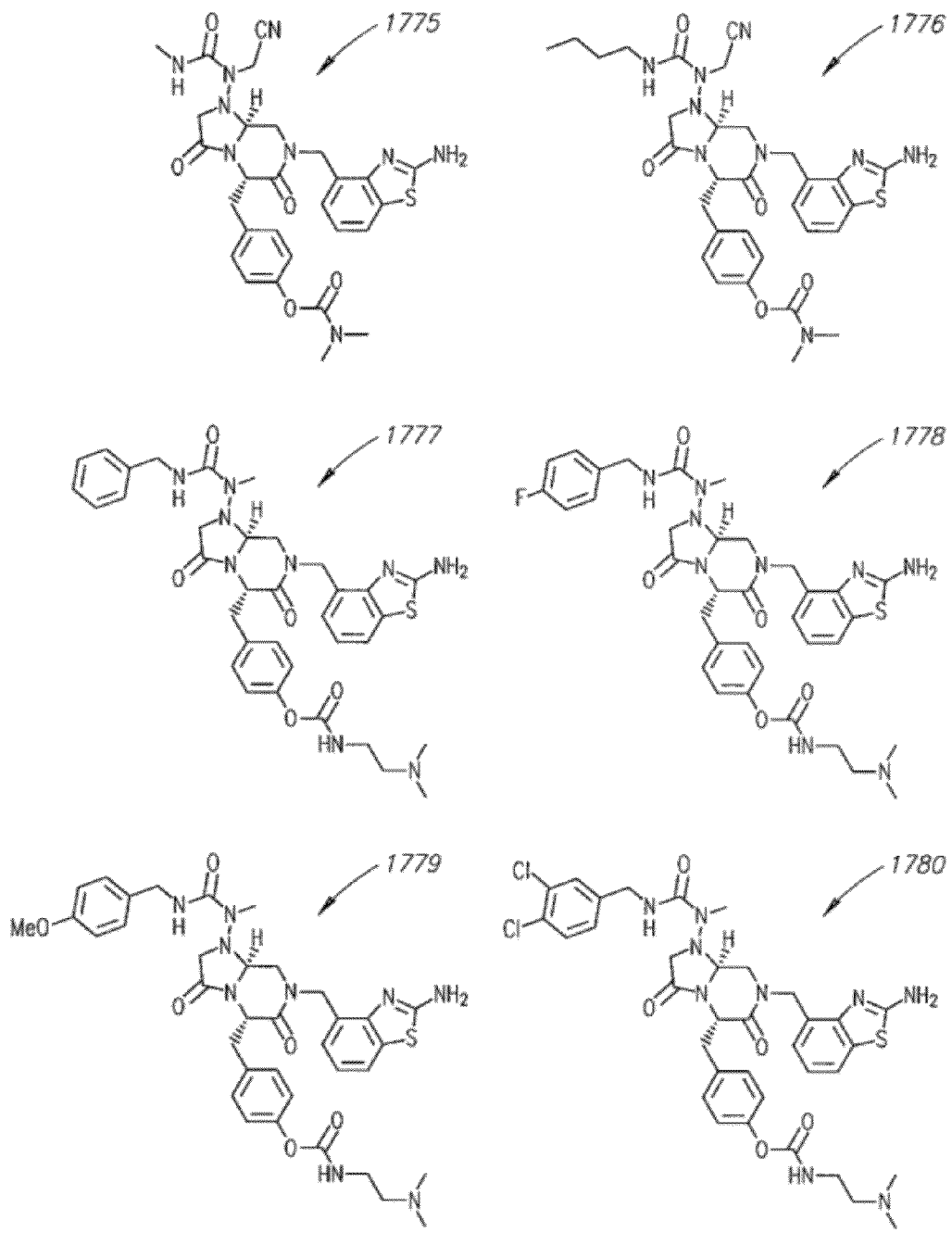
Figure 9A:
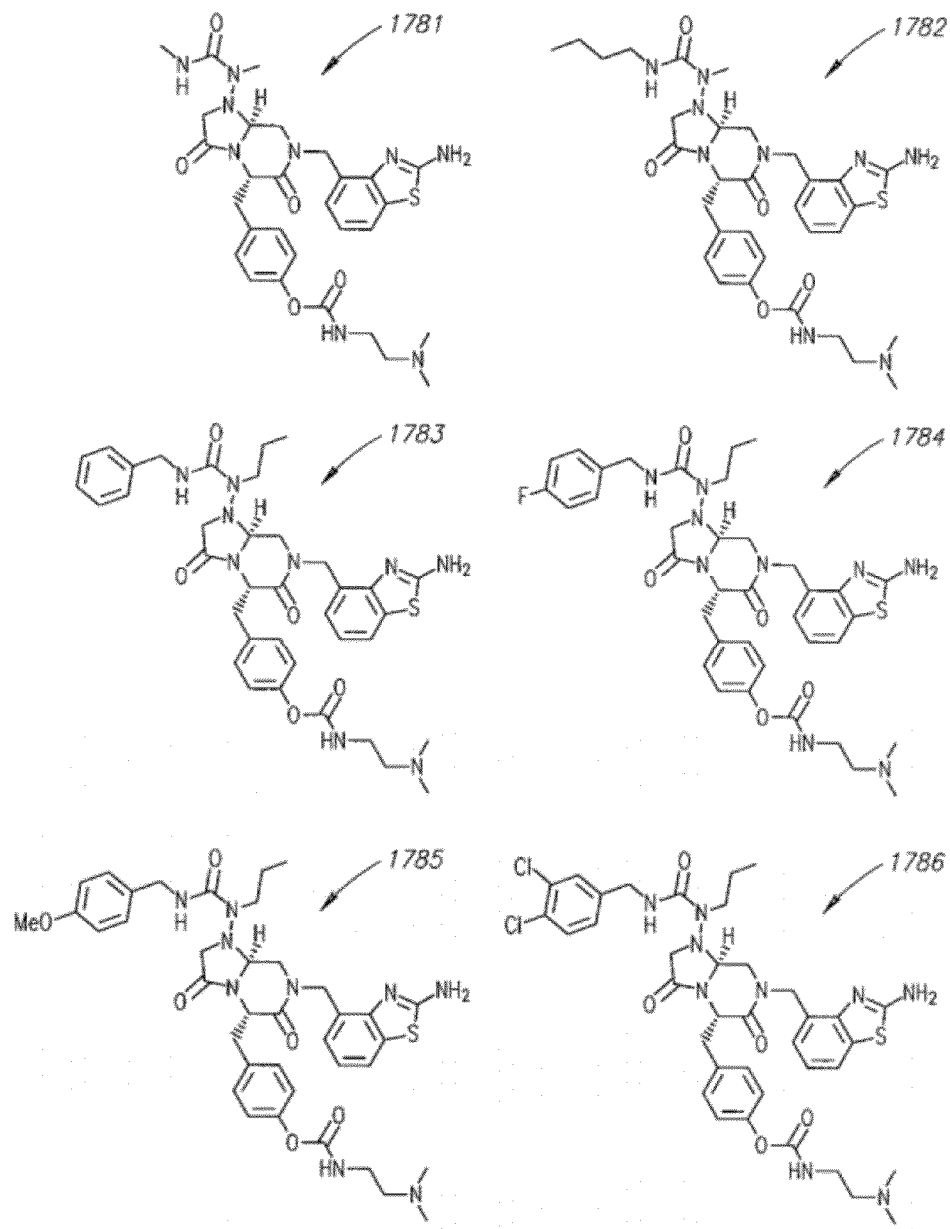
Figure 9A:
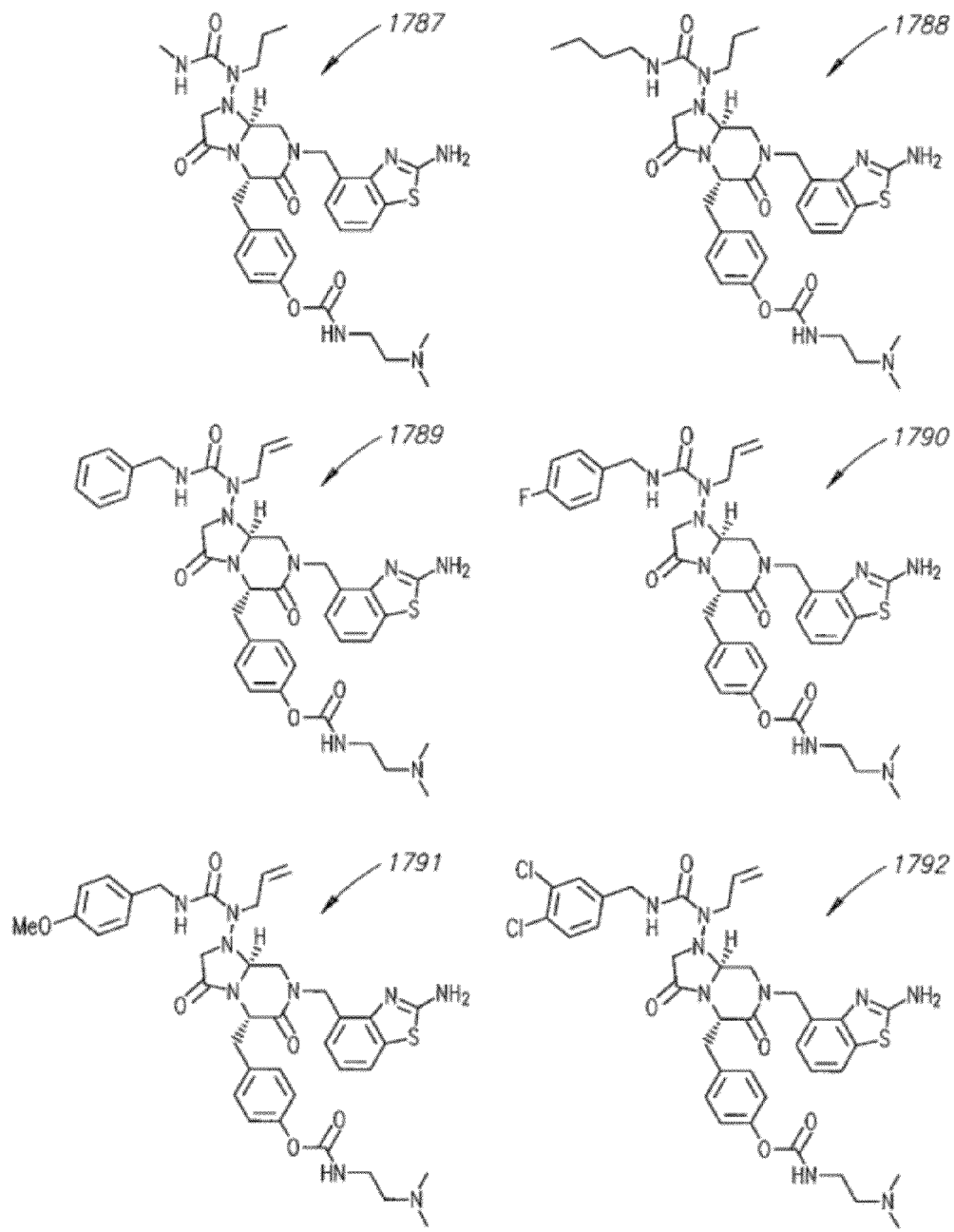
Figure 9A:
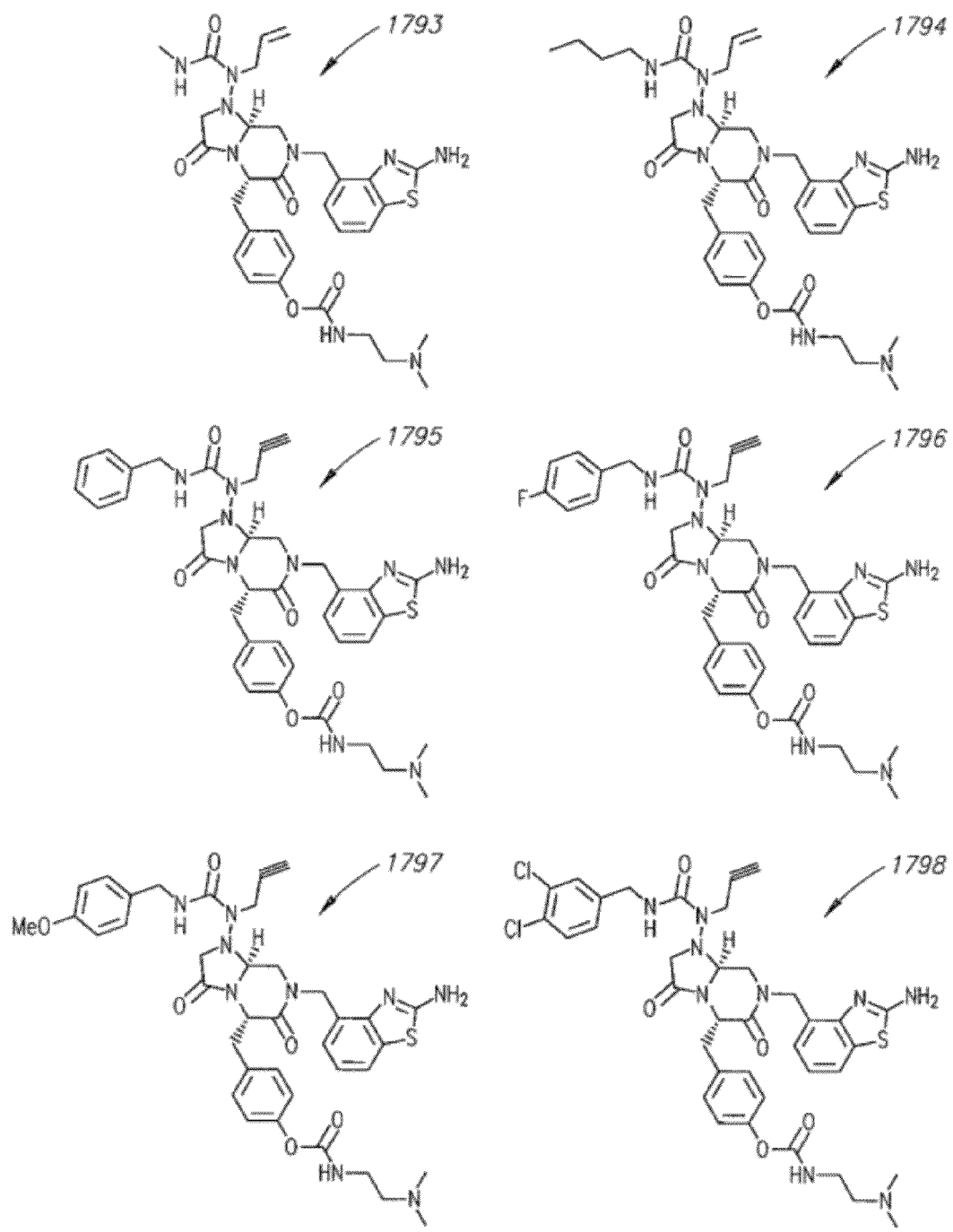
Figure 9A:
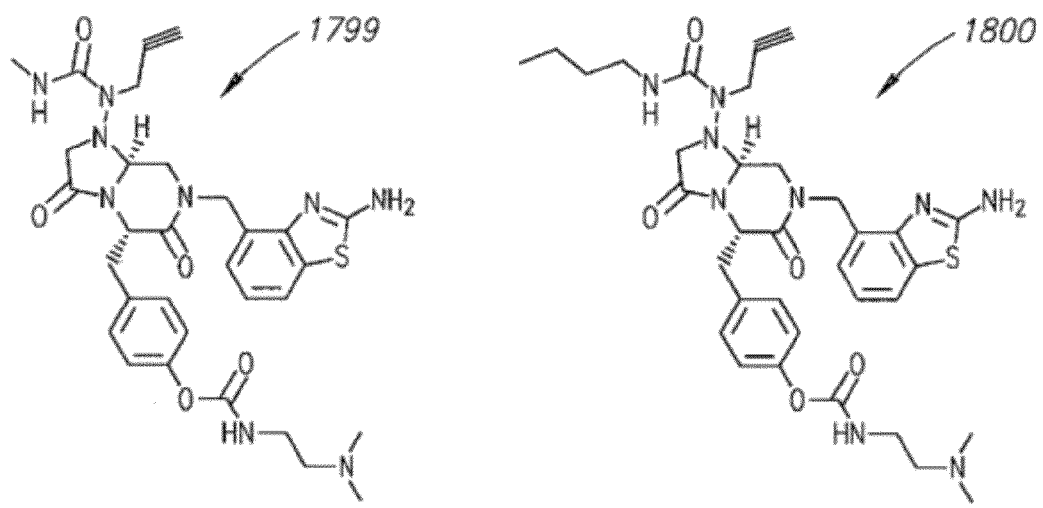
Figure 10A:
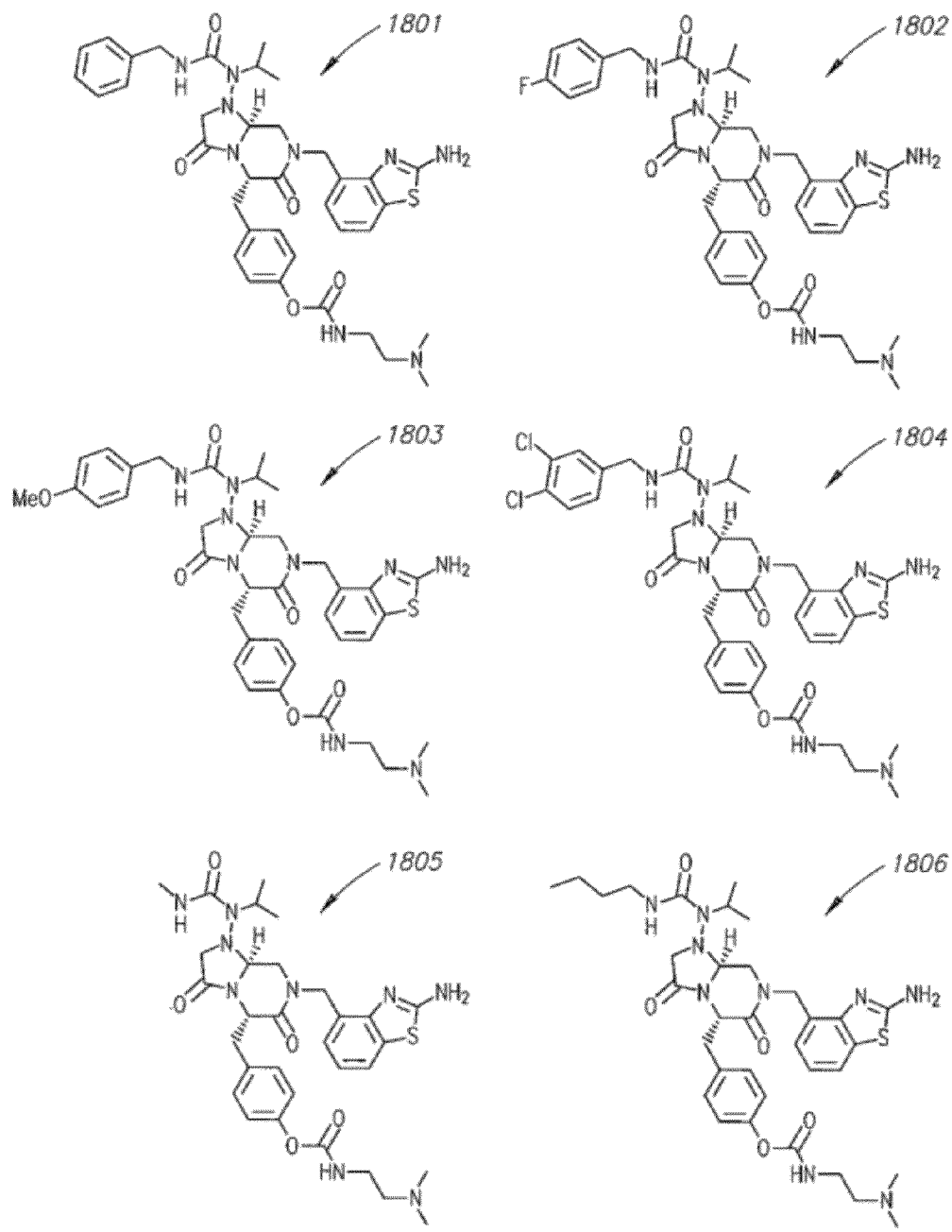
Figure 10B:
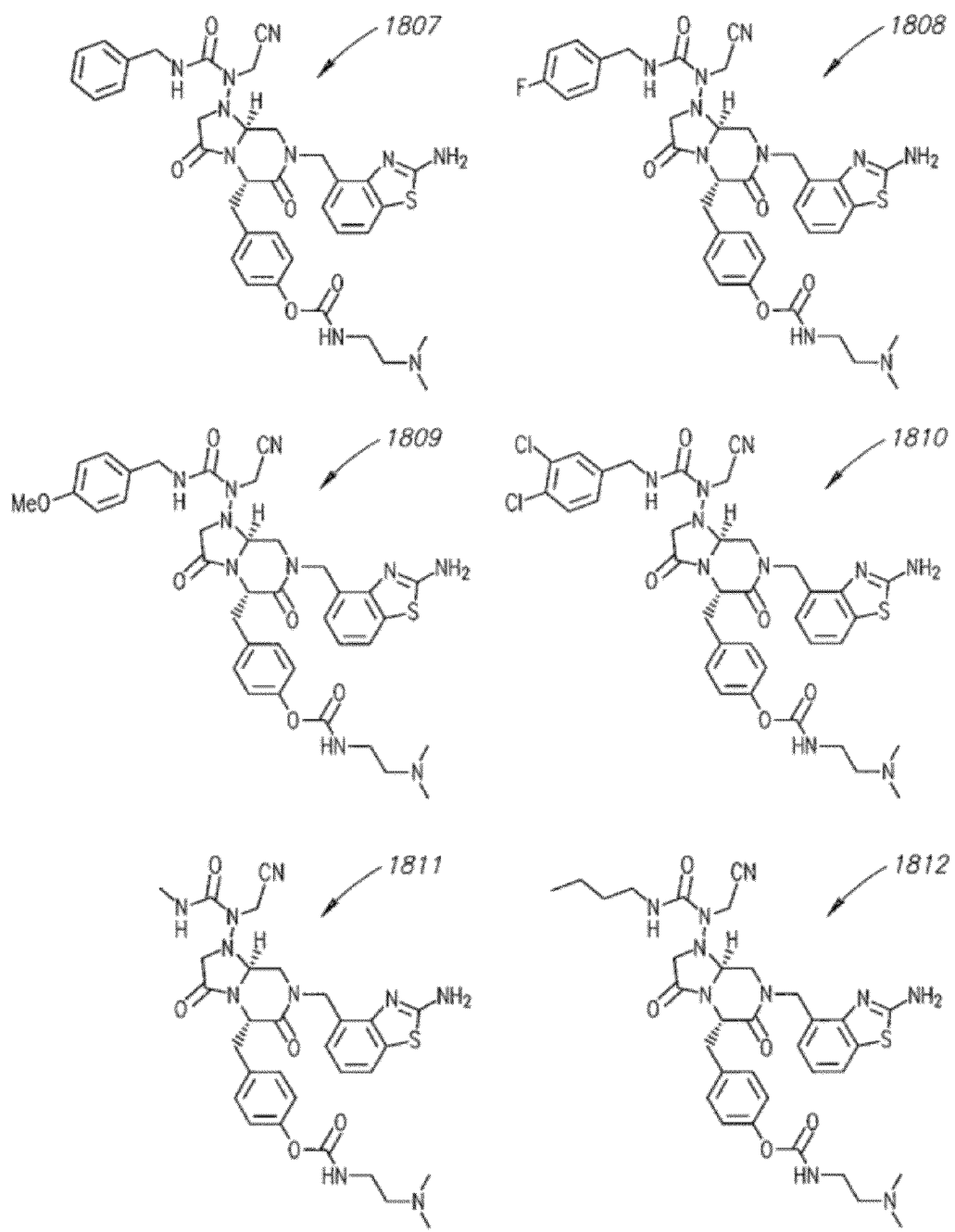
Figure 10C:
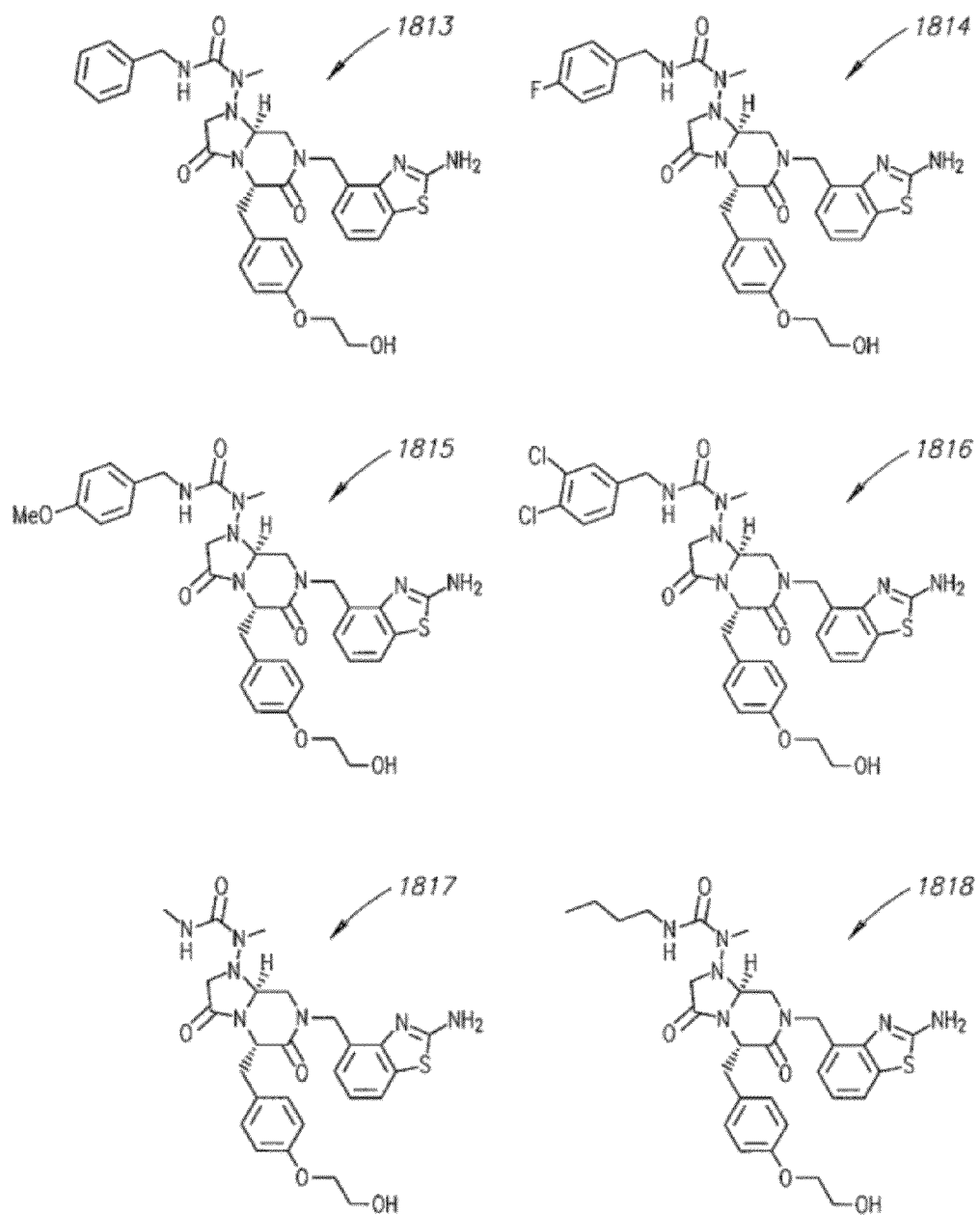
Figure 10D:
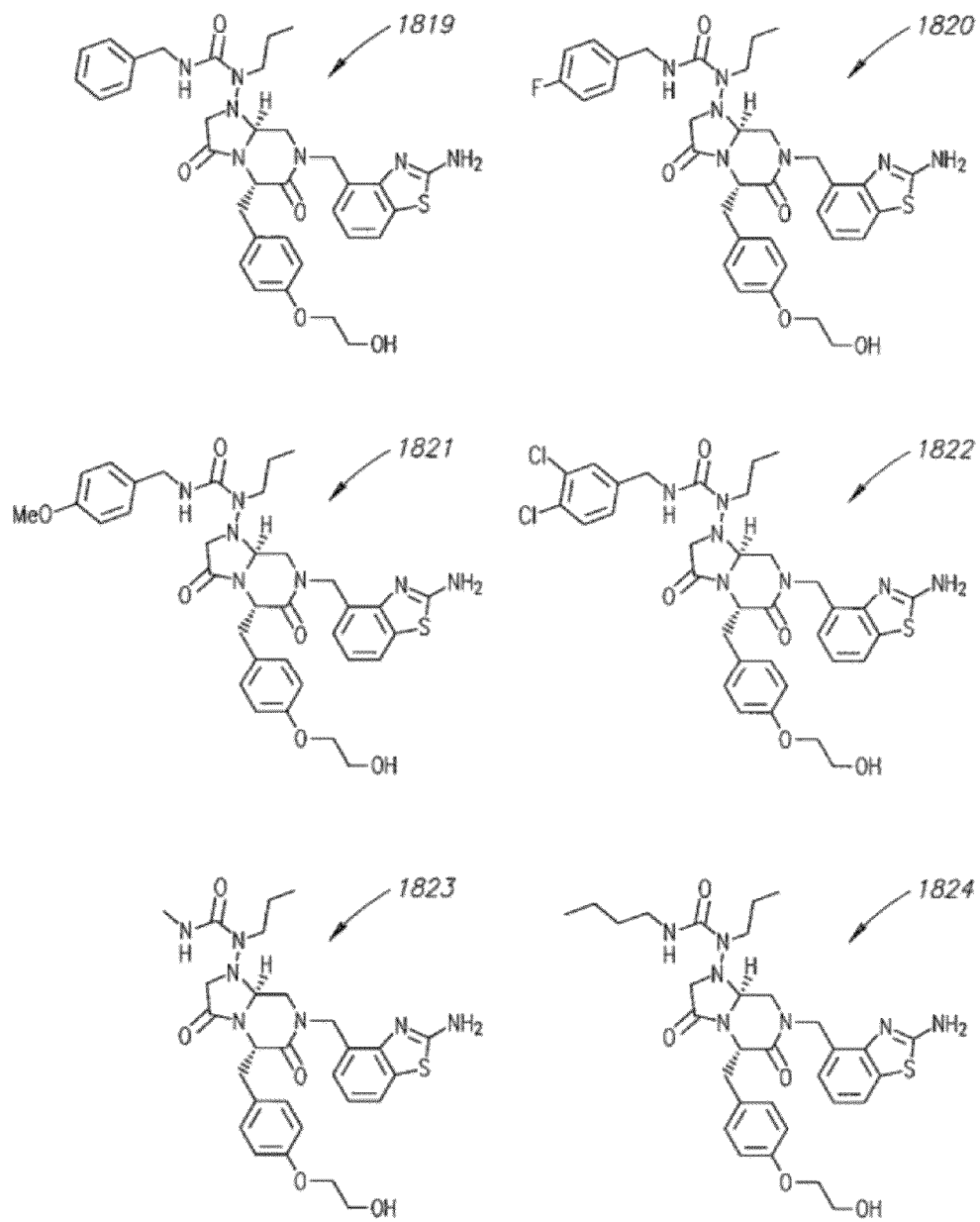
Figure 10E:
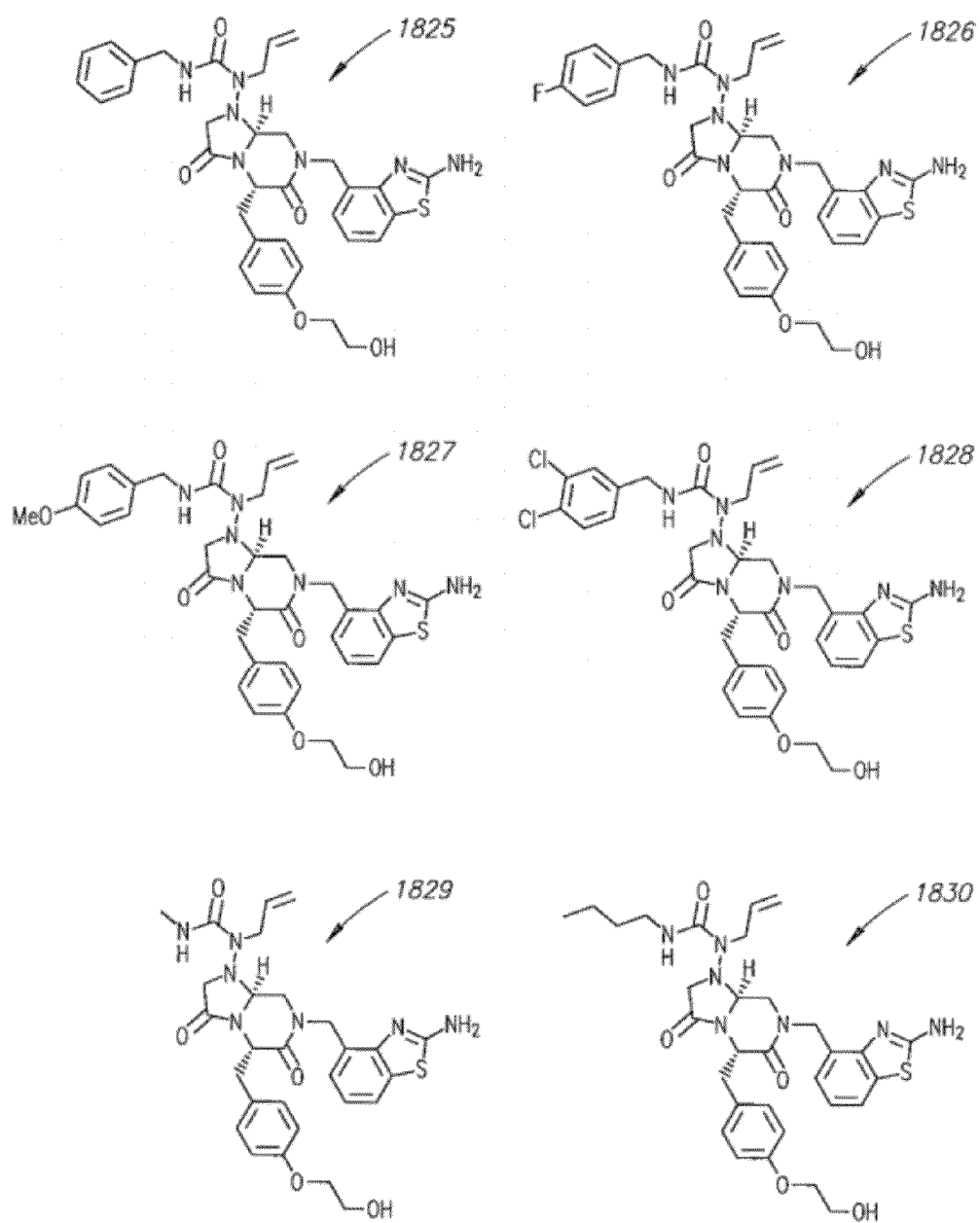
Figure 10F:
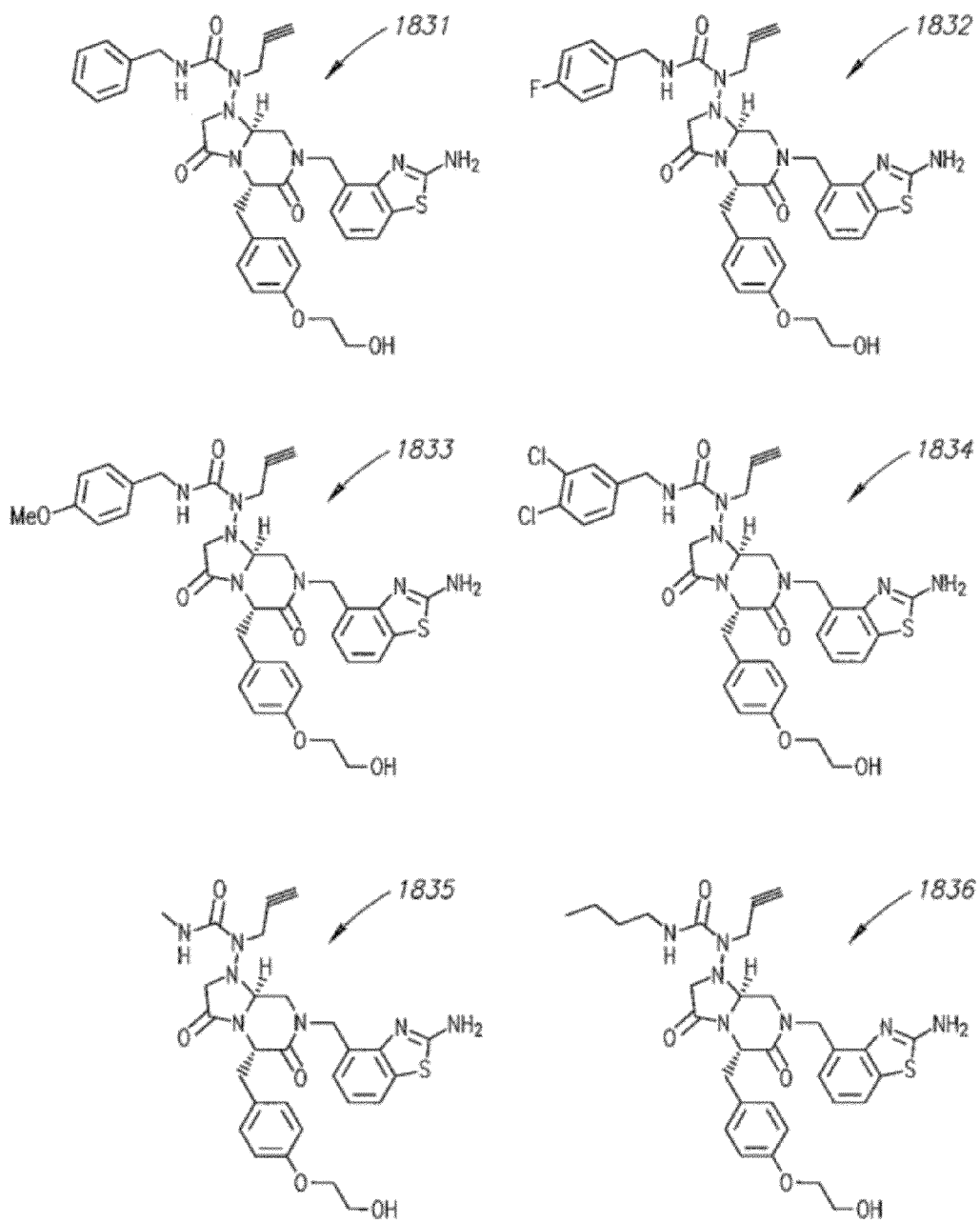
Figure 10G:
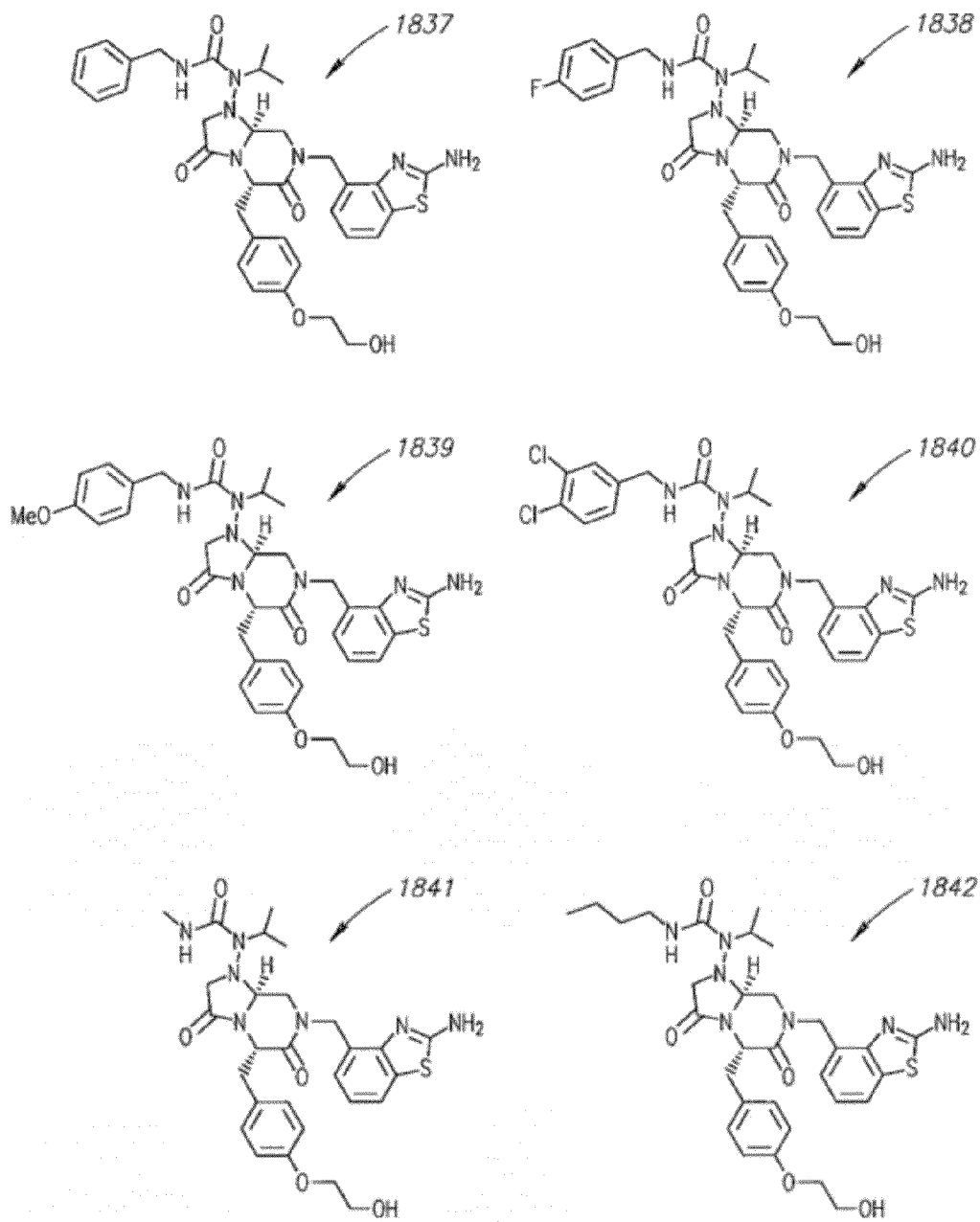
Figure 10H:
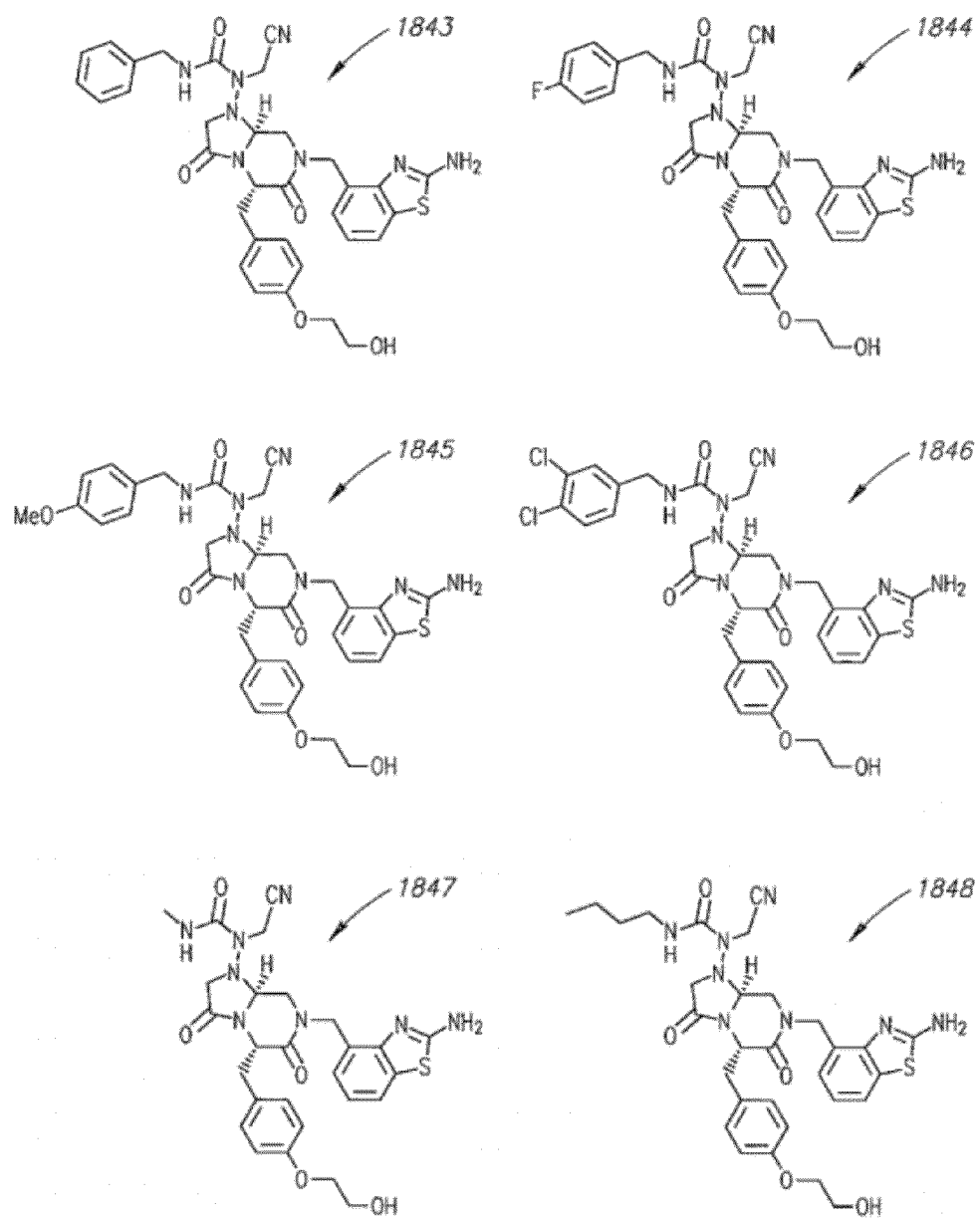
Figure 10I:
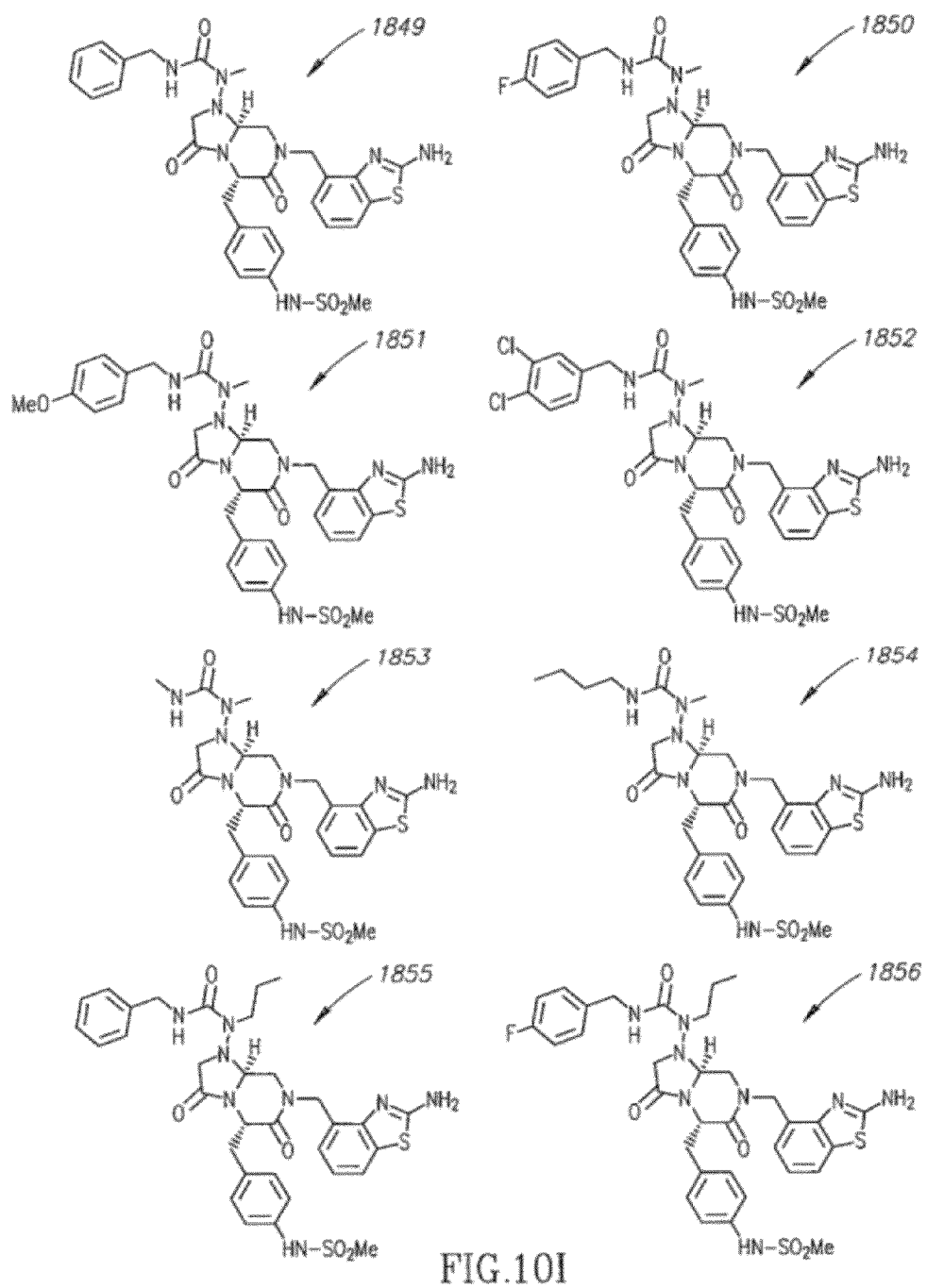
Figure 10J:
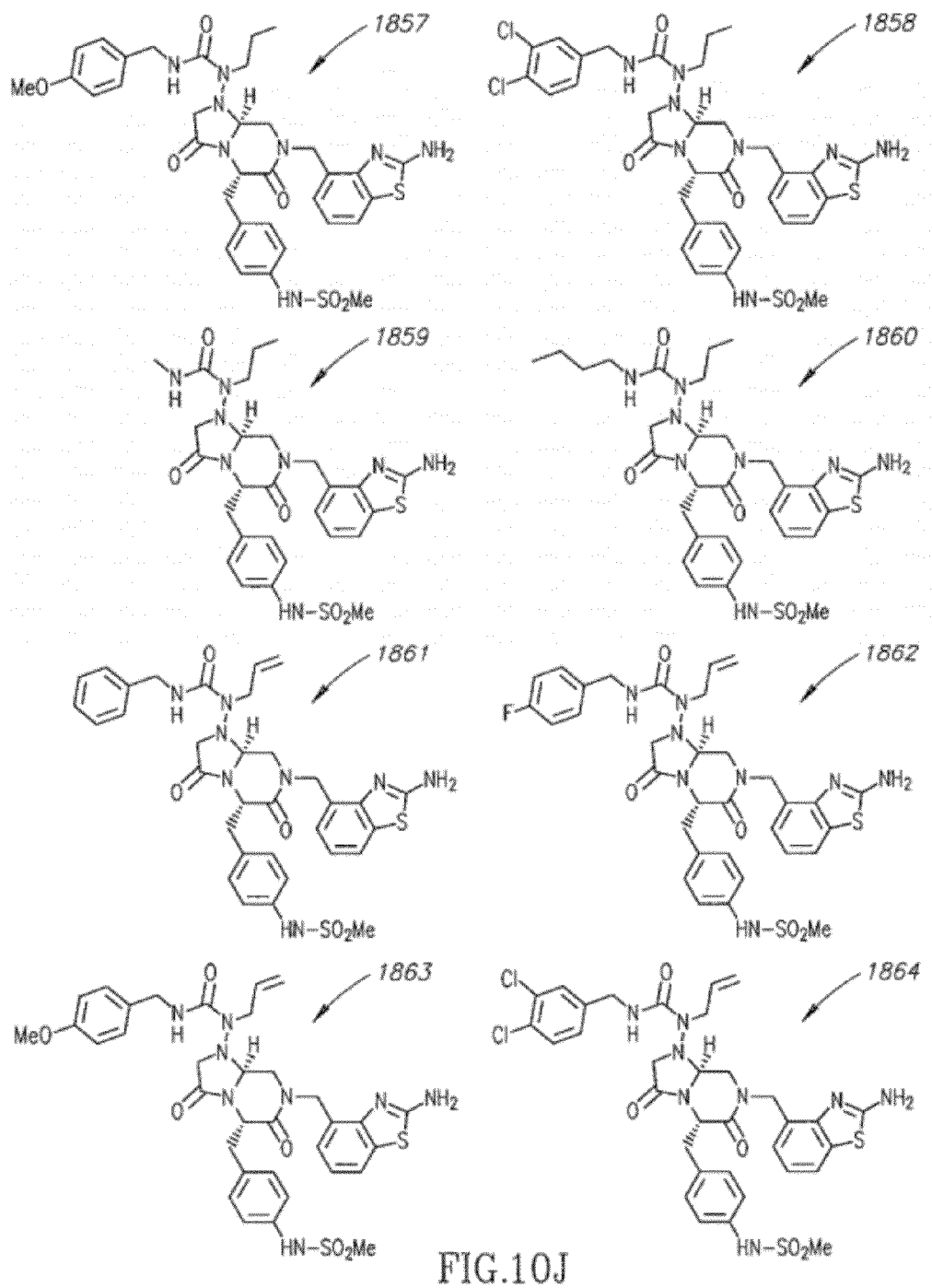
Figure 10K:
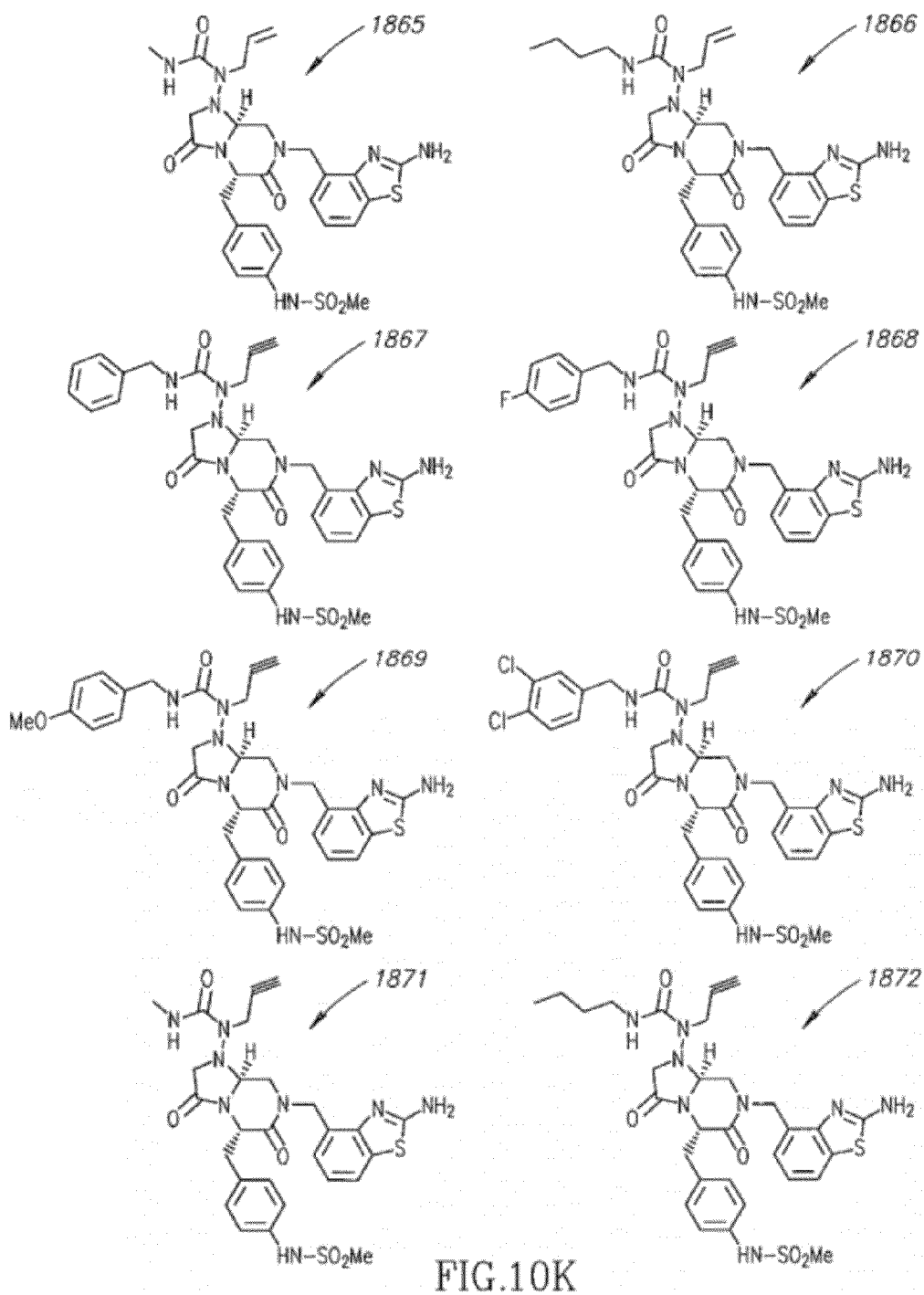
Figure 10L:
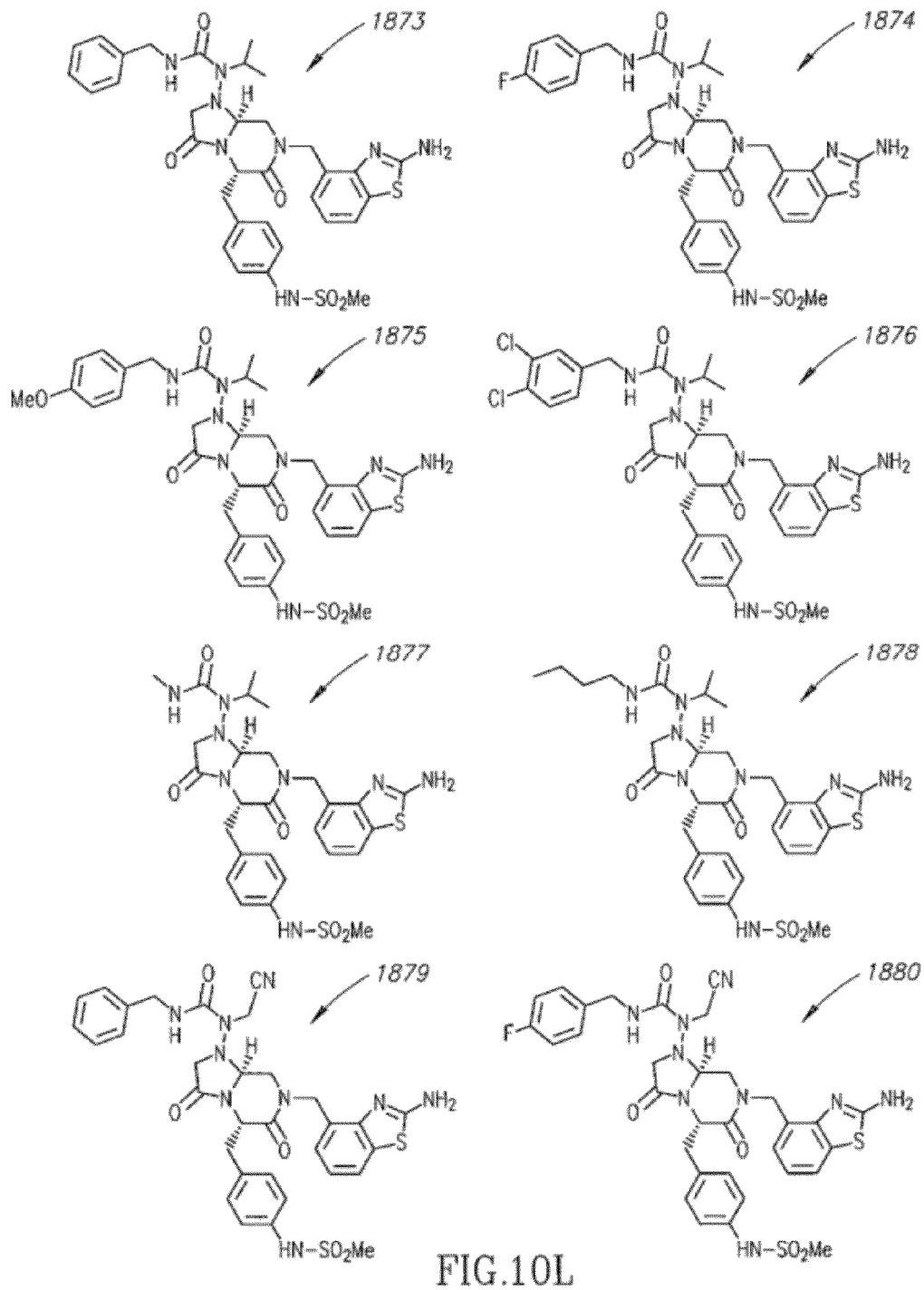
Figure 10M:
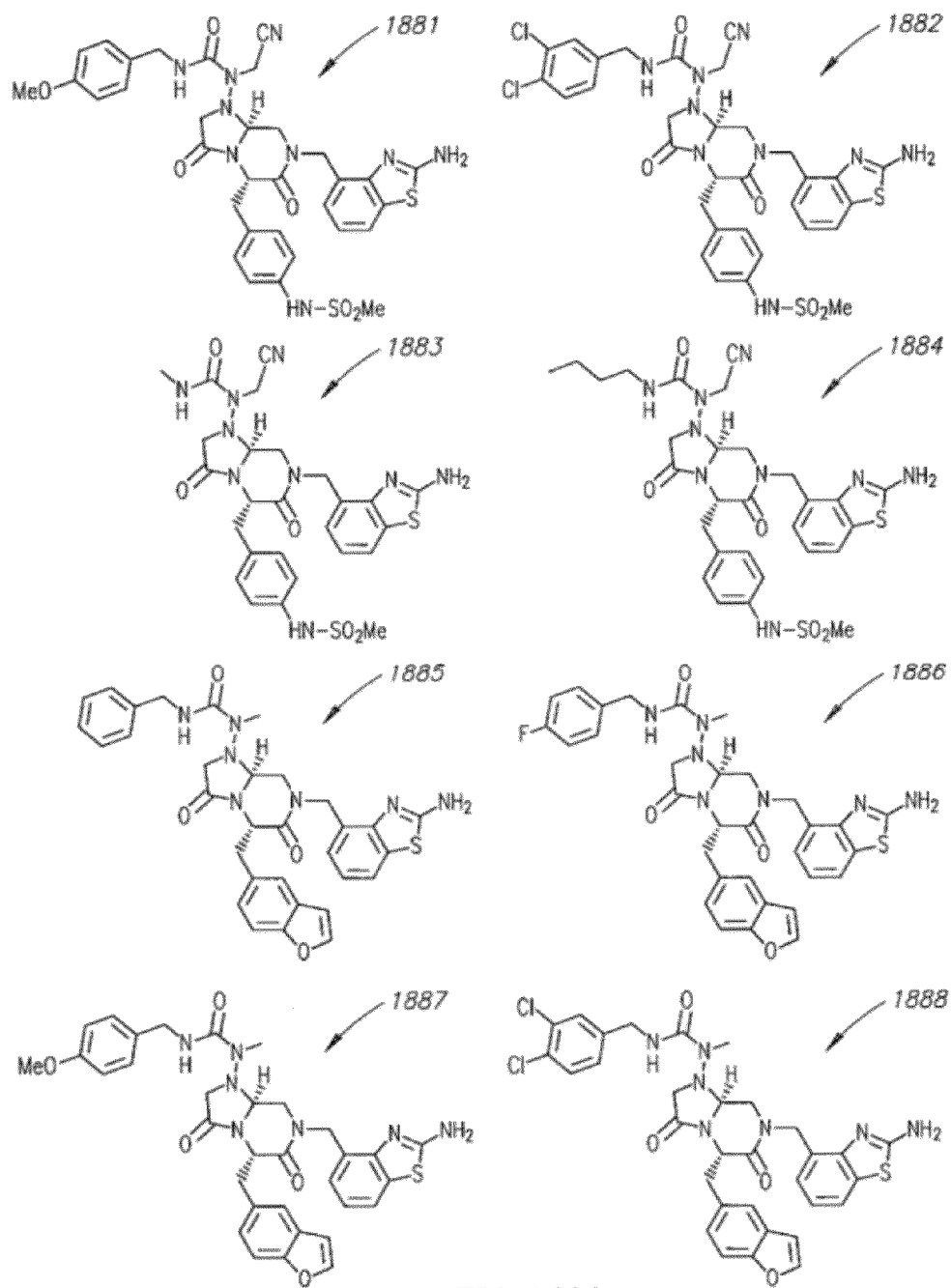
Figure 10N:
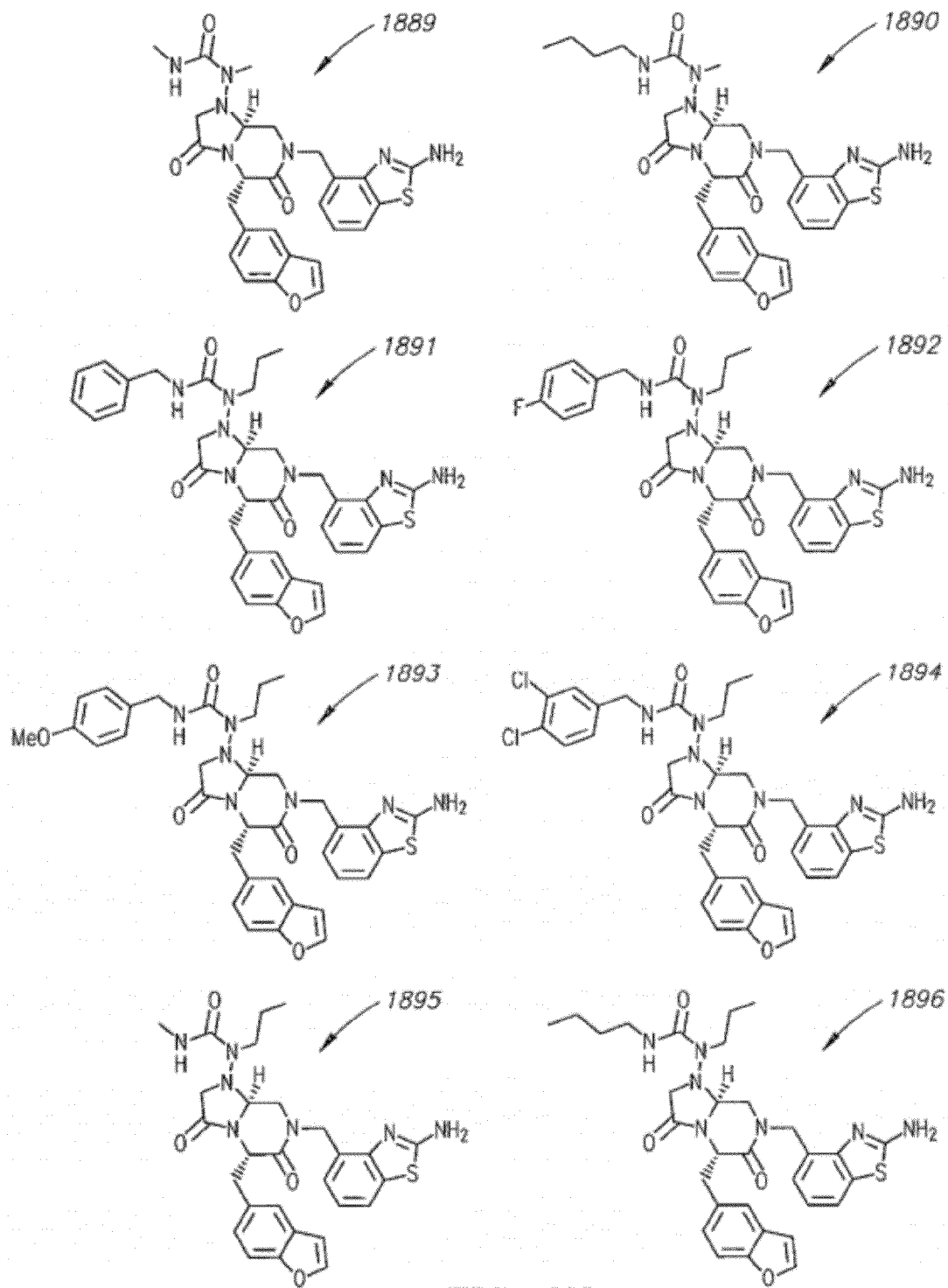
Figure 100:
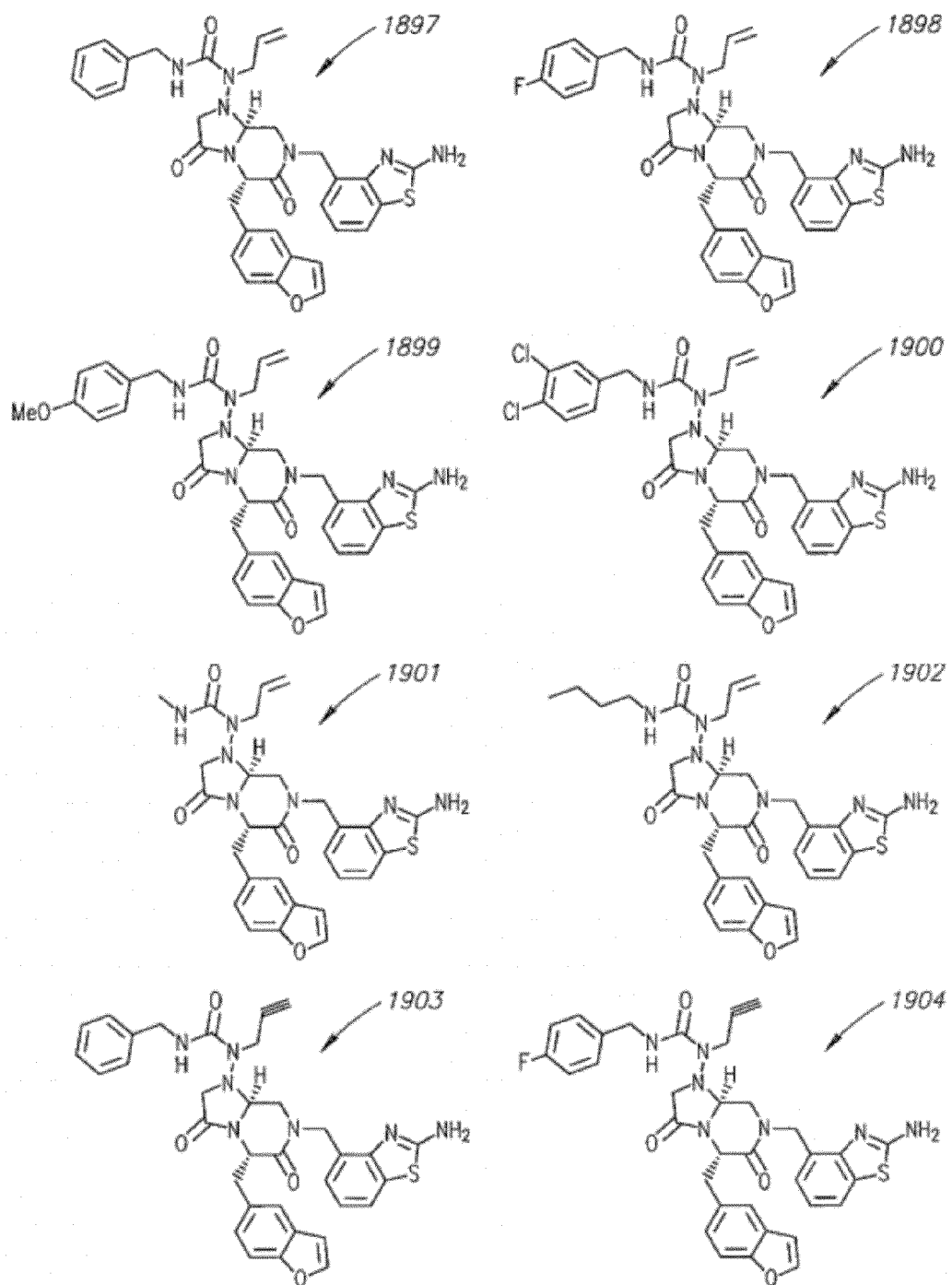
Figure 10P:
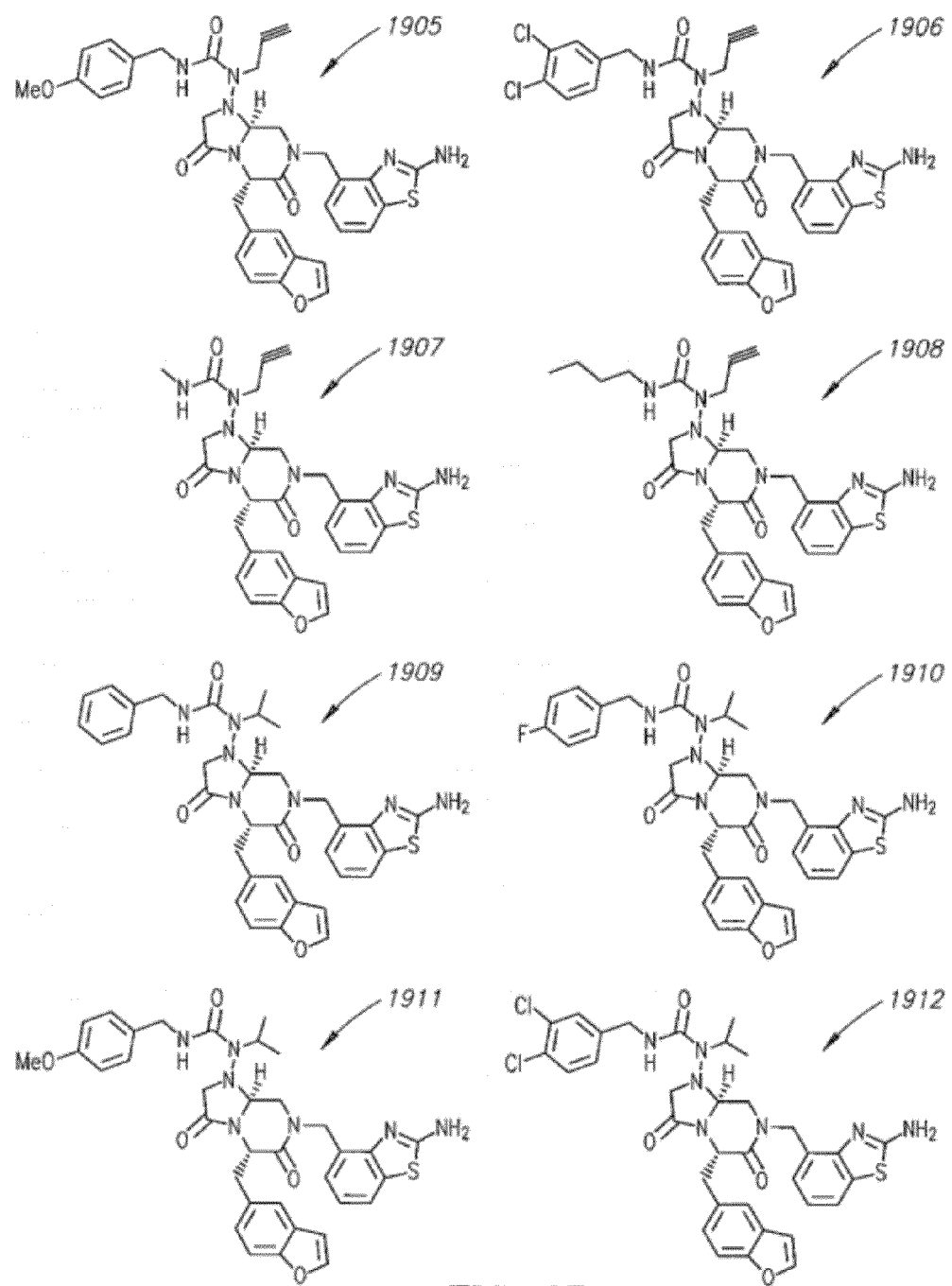
Figure 10Q:
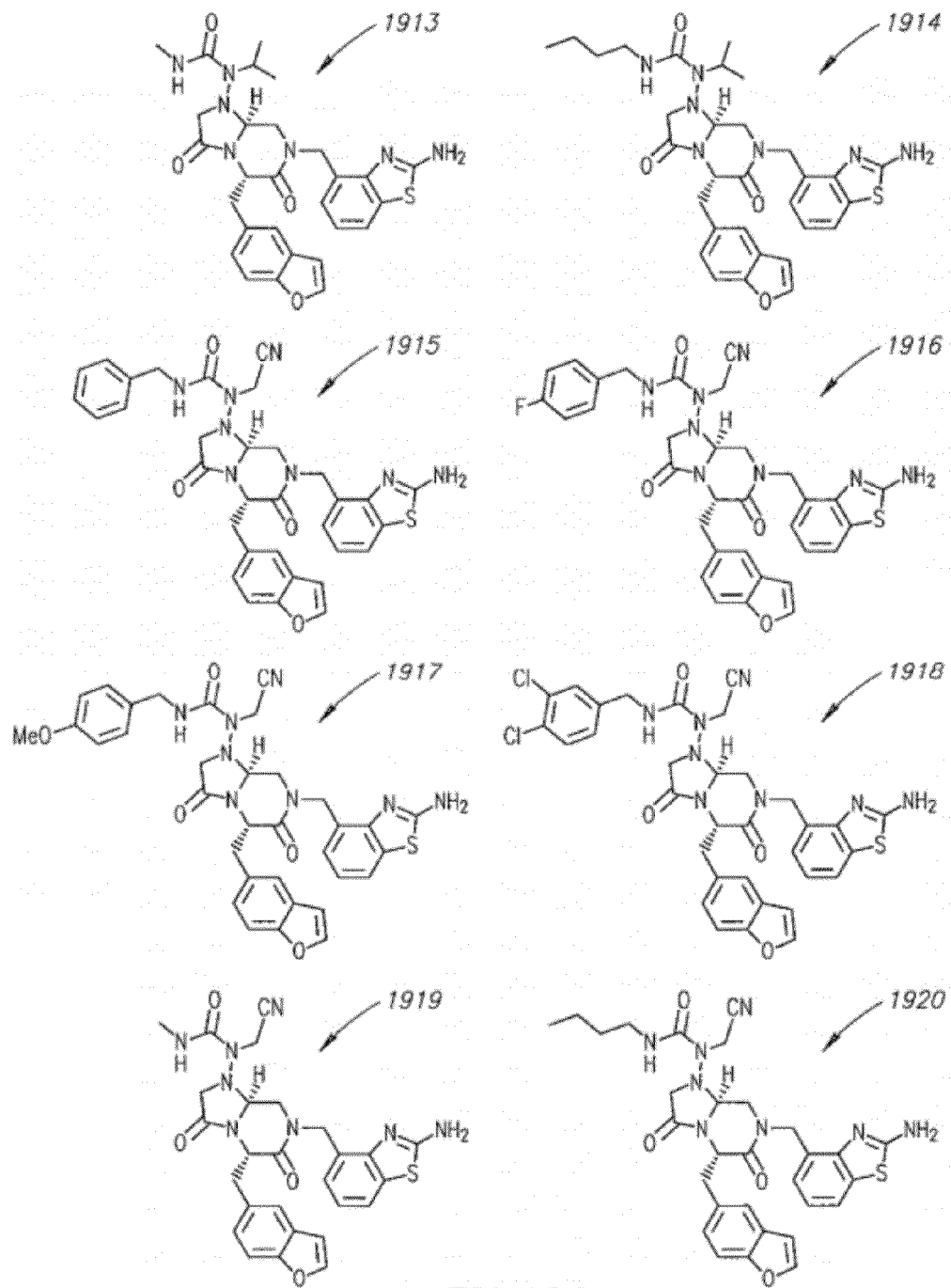
Figure 10R:
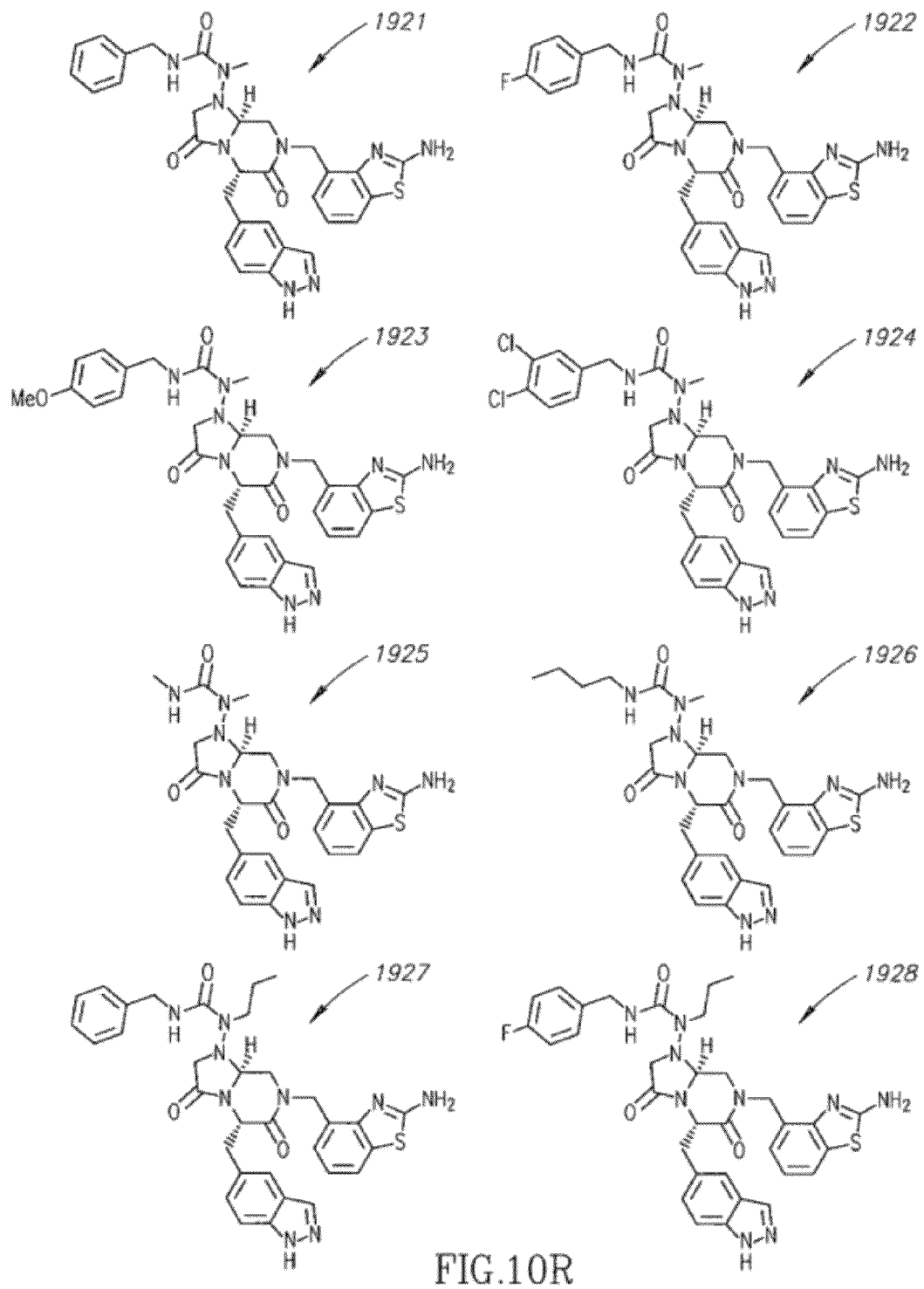
Figure 10S:
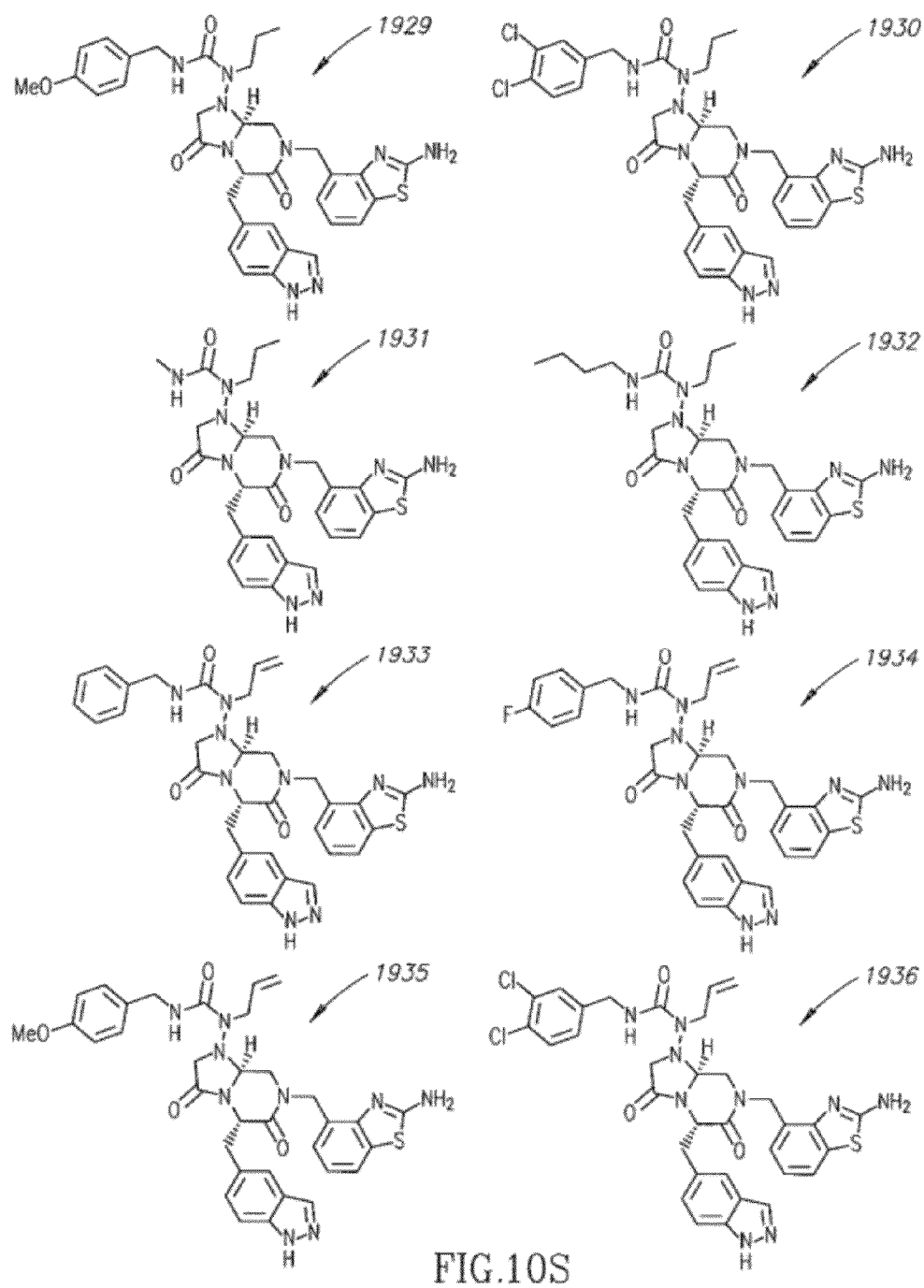
Figure 10T:
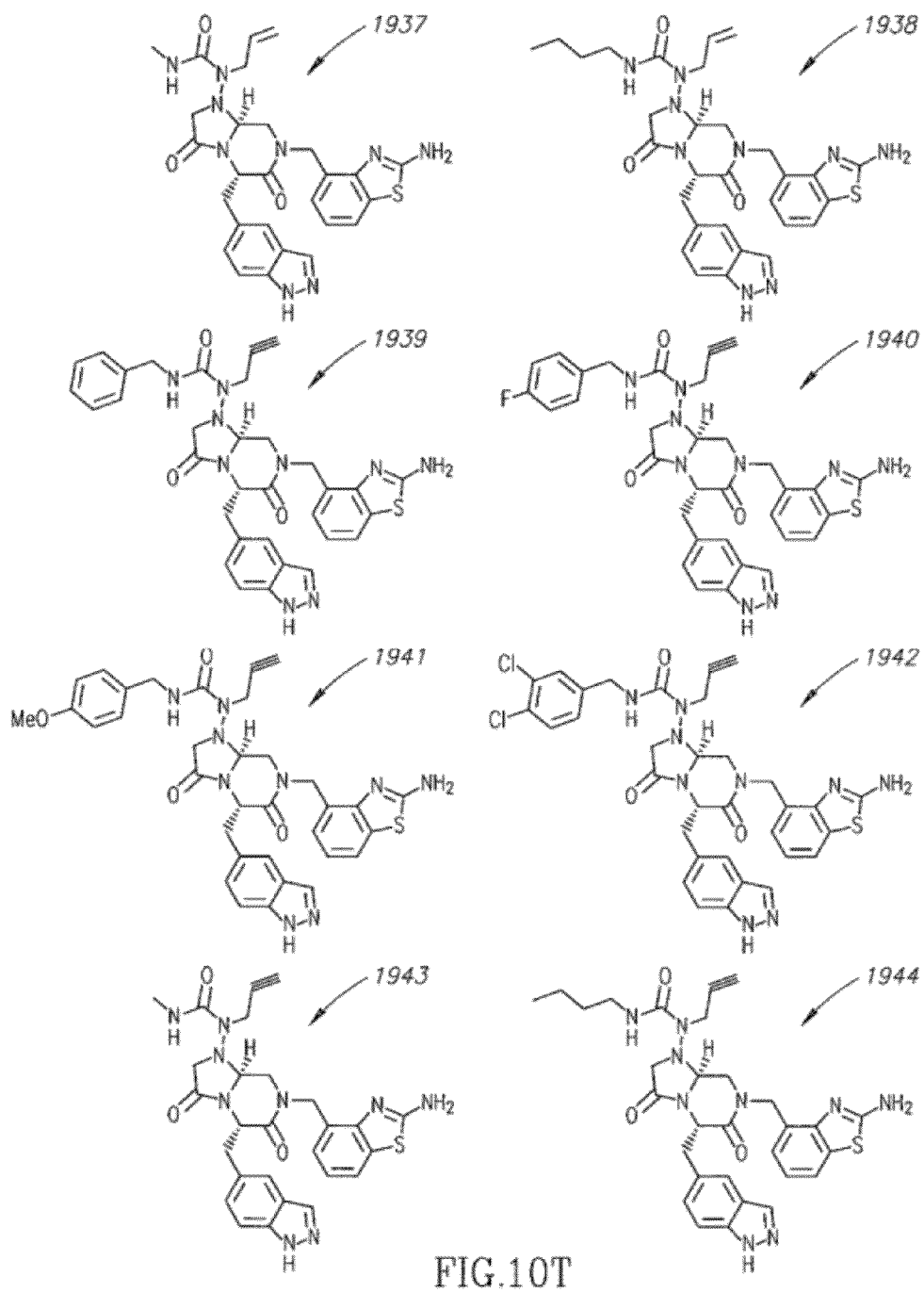
Figure 10U:
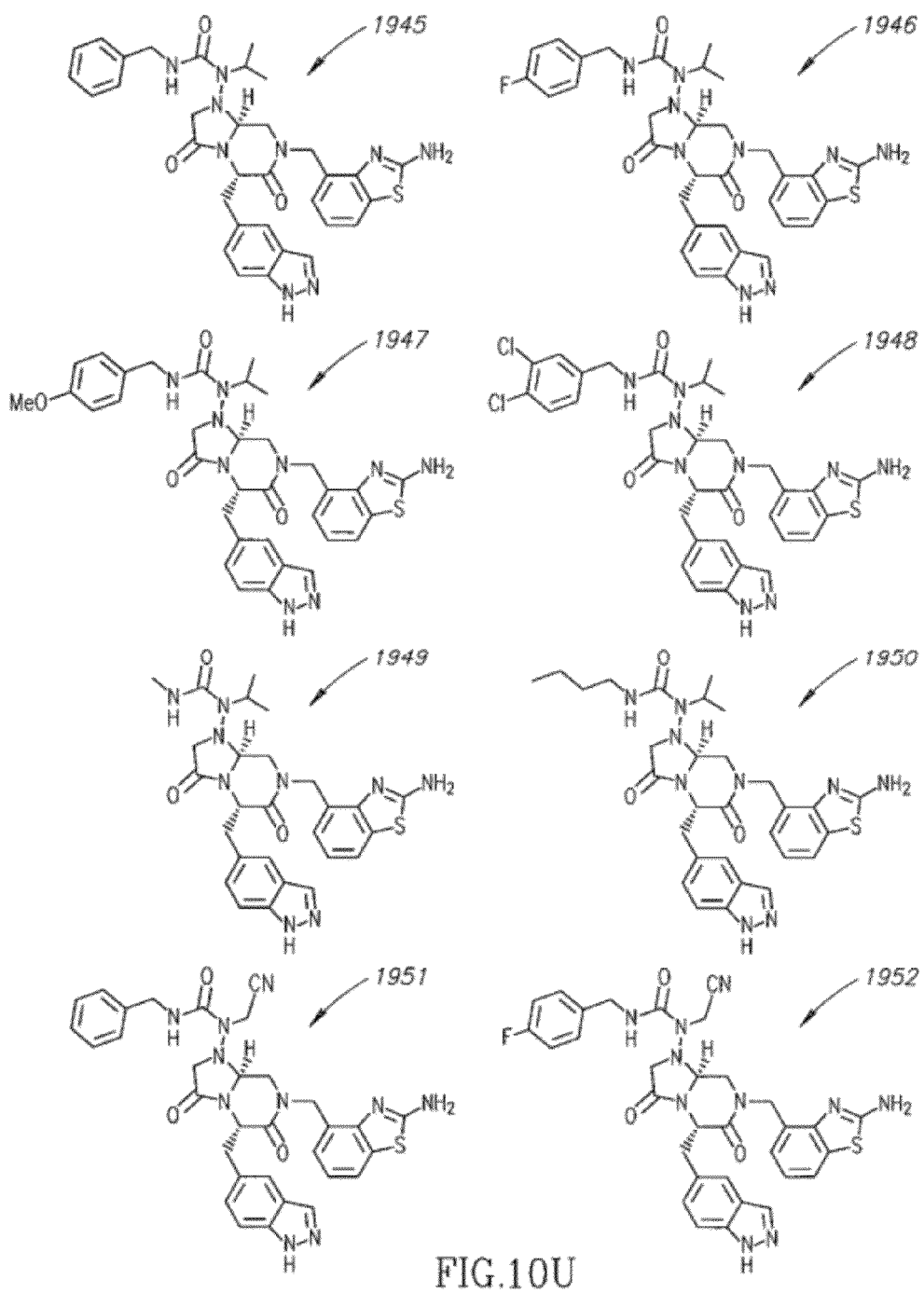
Figure 10V:
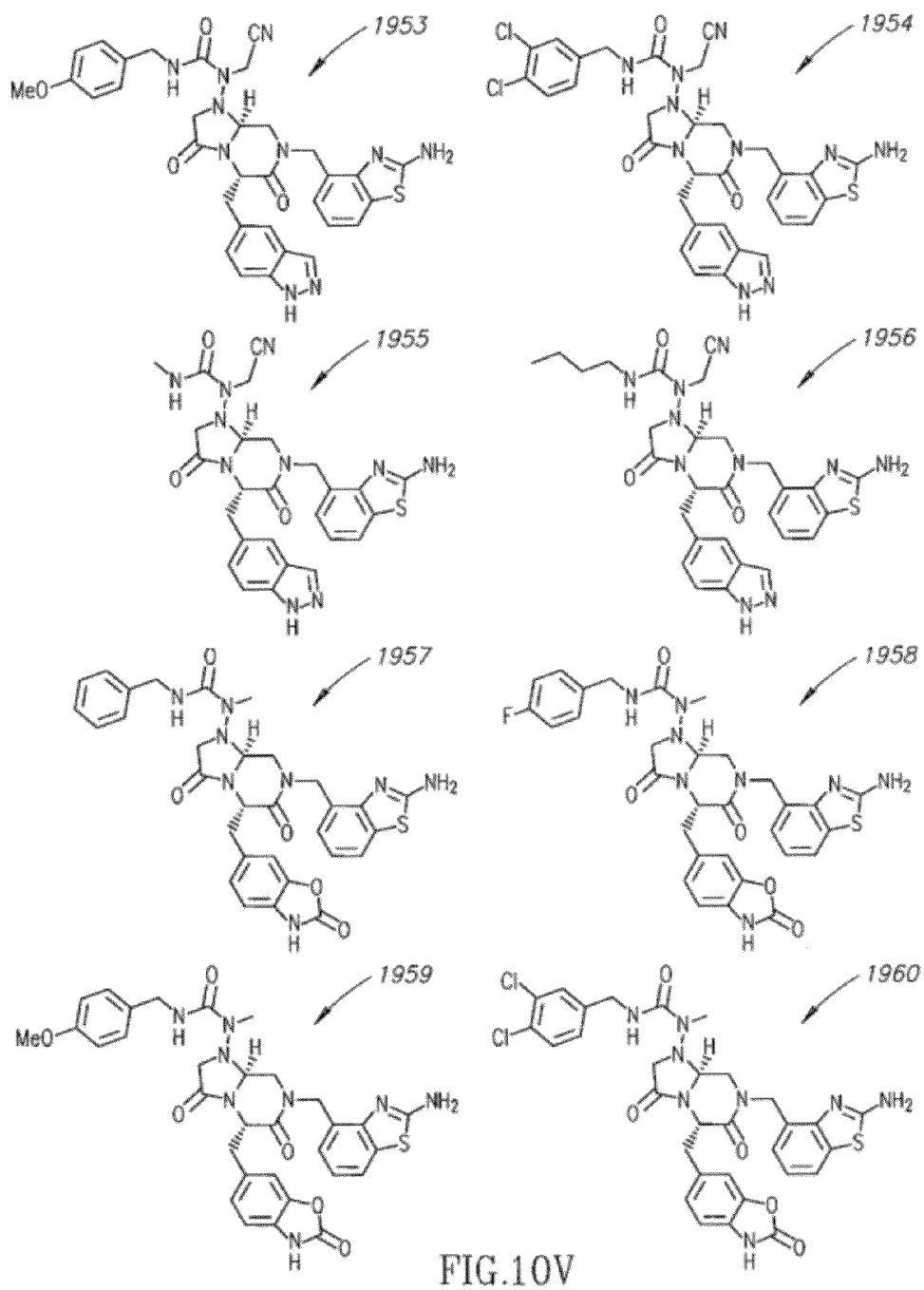
Figure 10W:
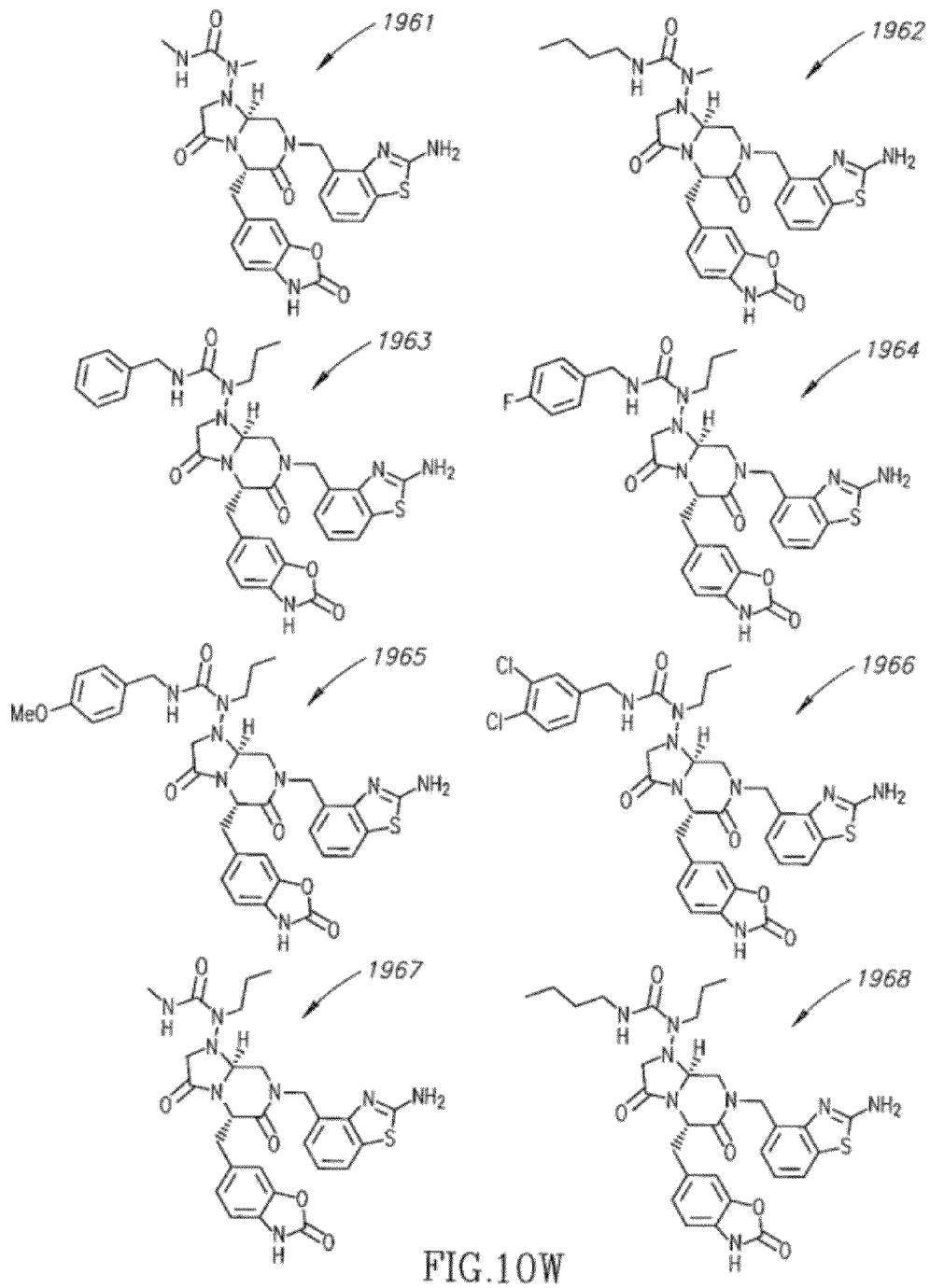
Figure 10X:
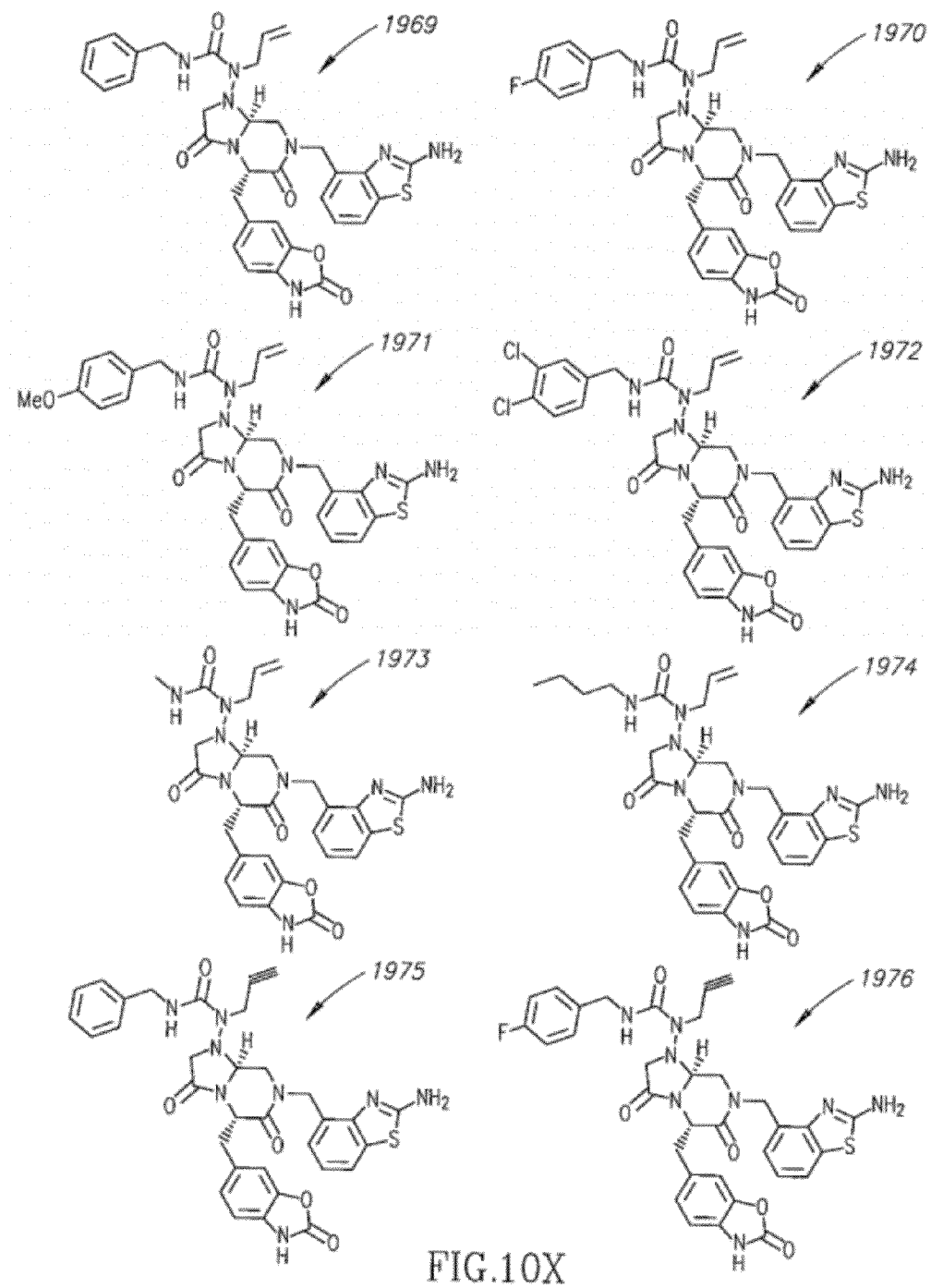
Figure 10Y:
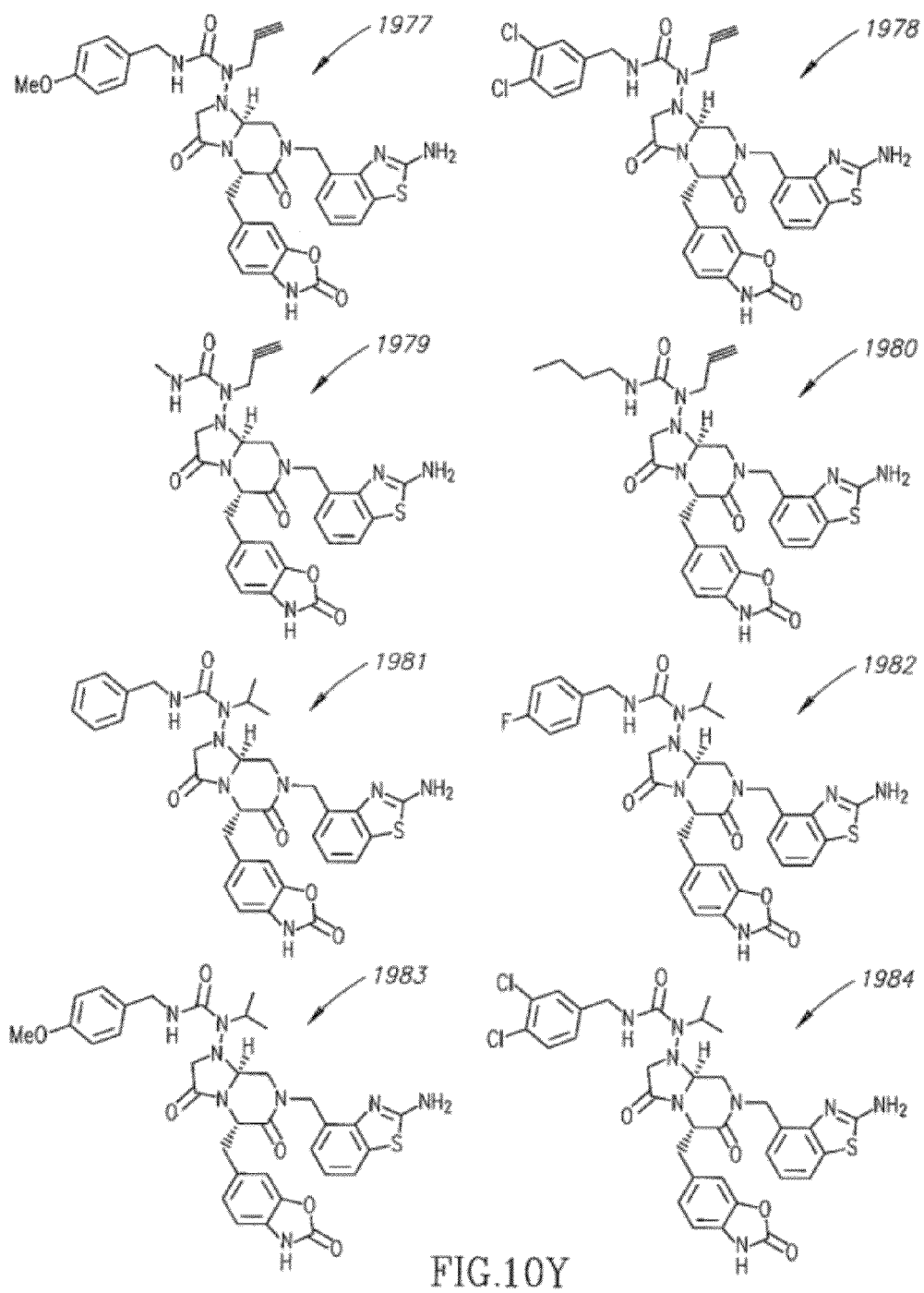
Figure 10Z:
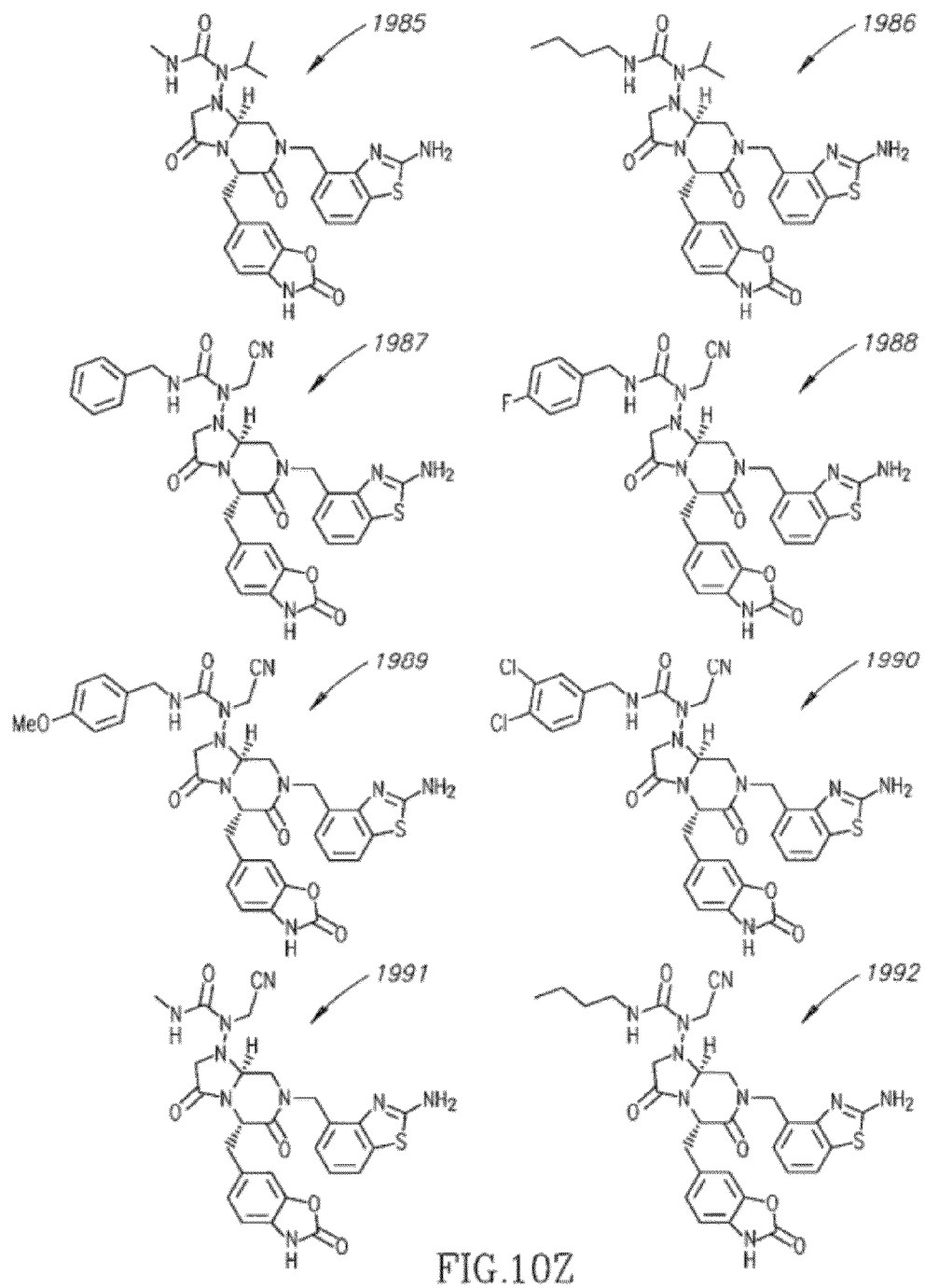
Figure 10A:
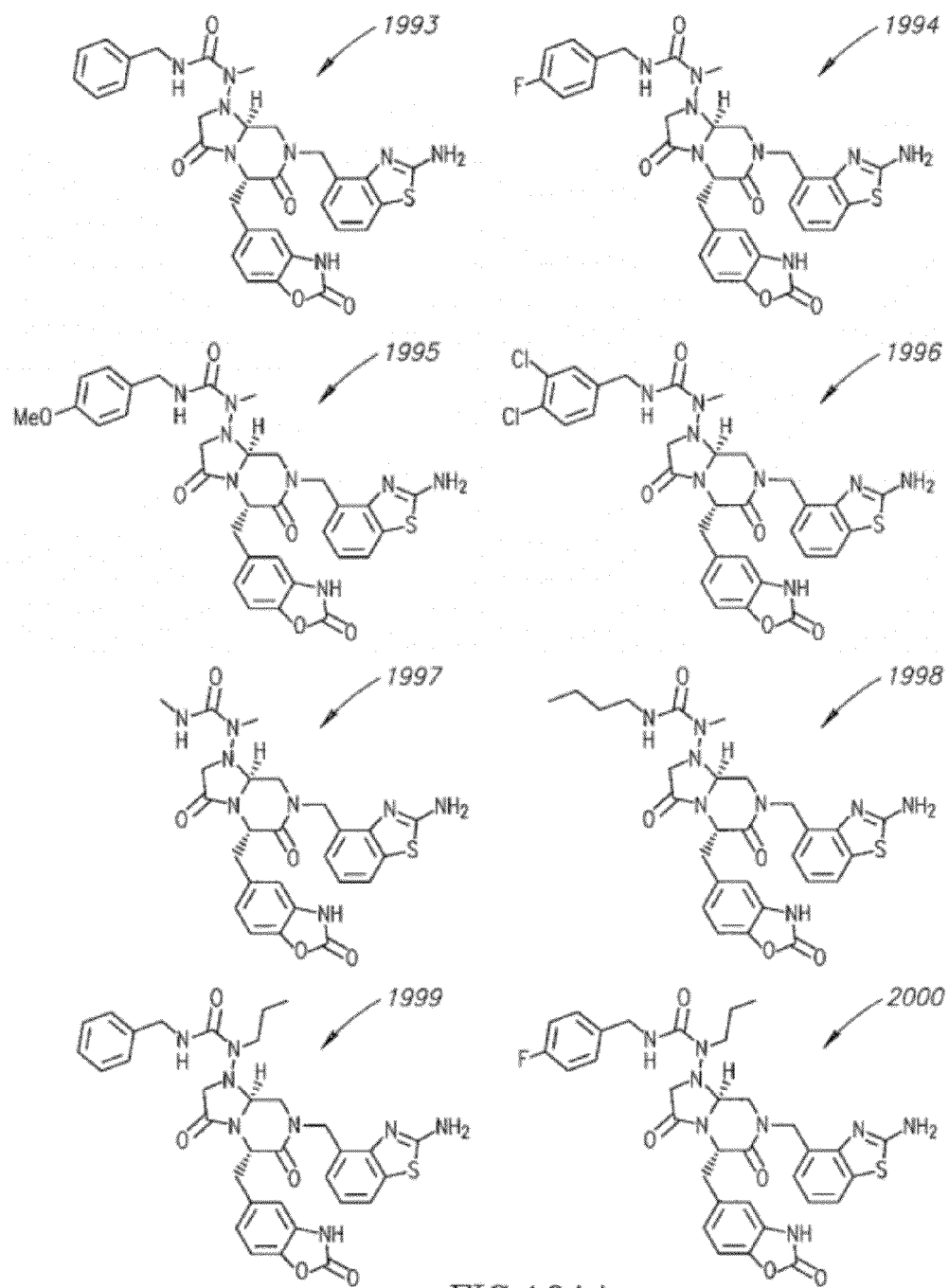
Figure 11A:
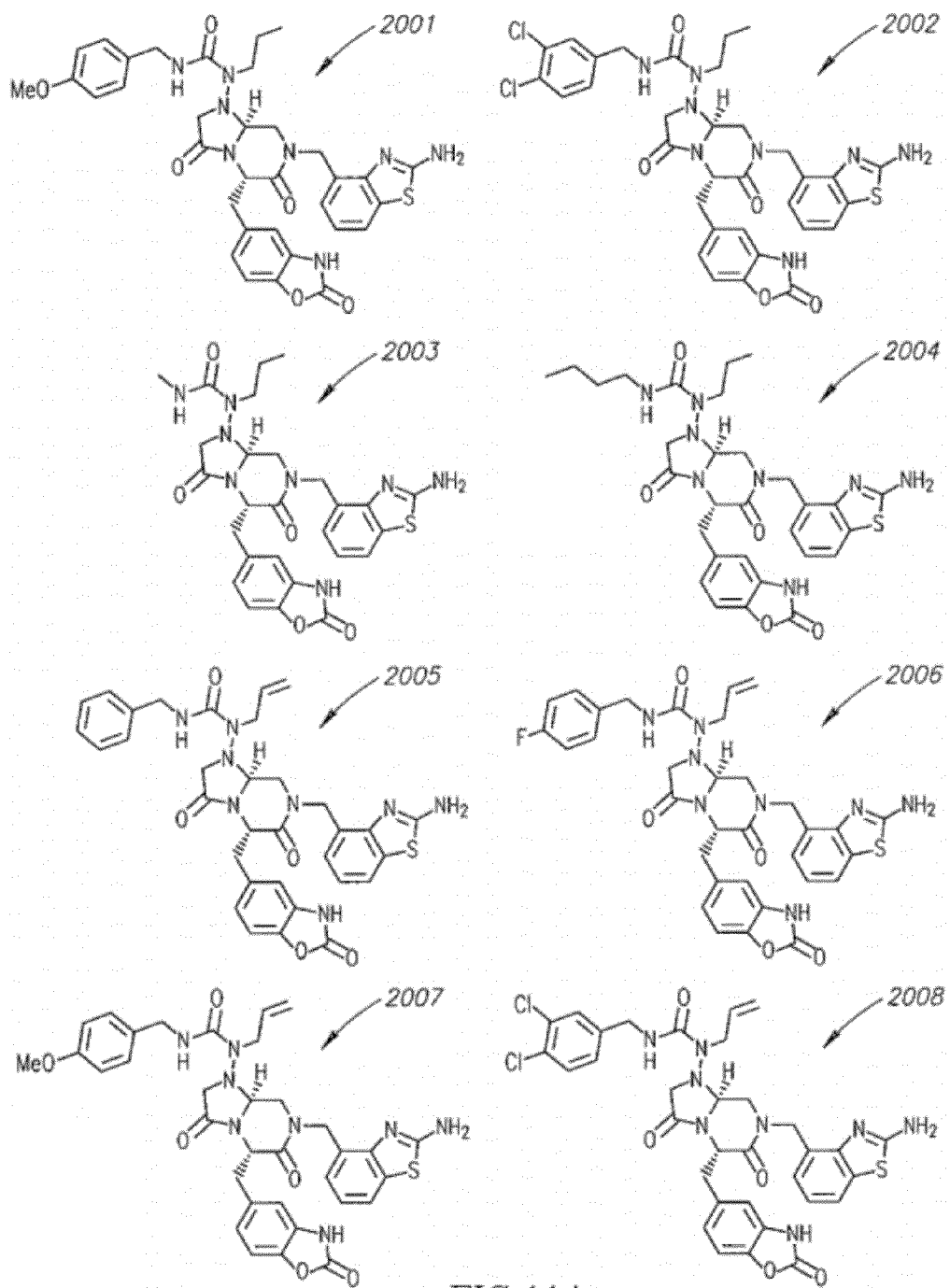
FIGS. 11A-11AA shows the chemical structures of compounds 2001-2200.
Figure 11B:
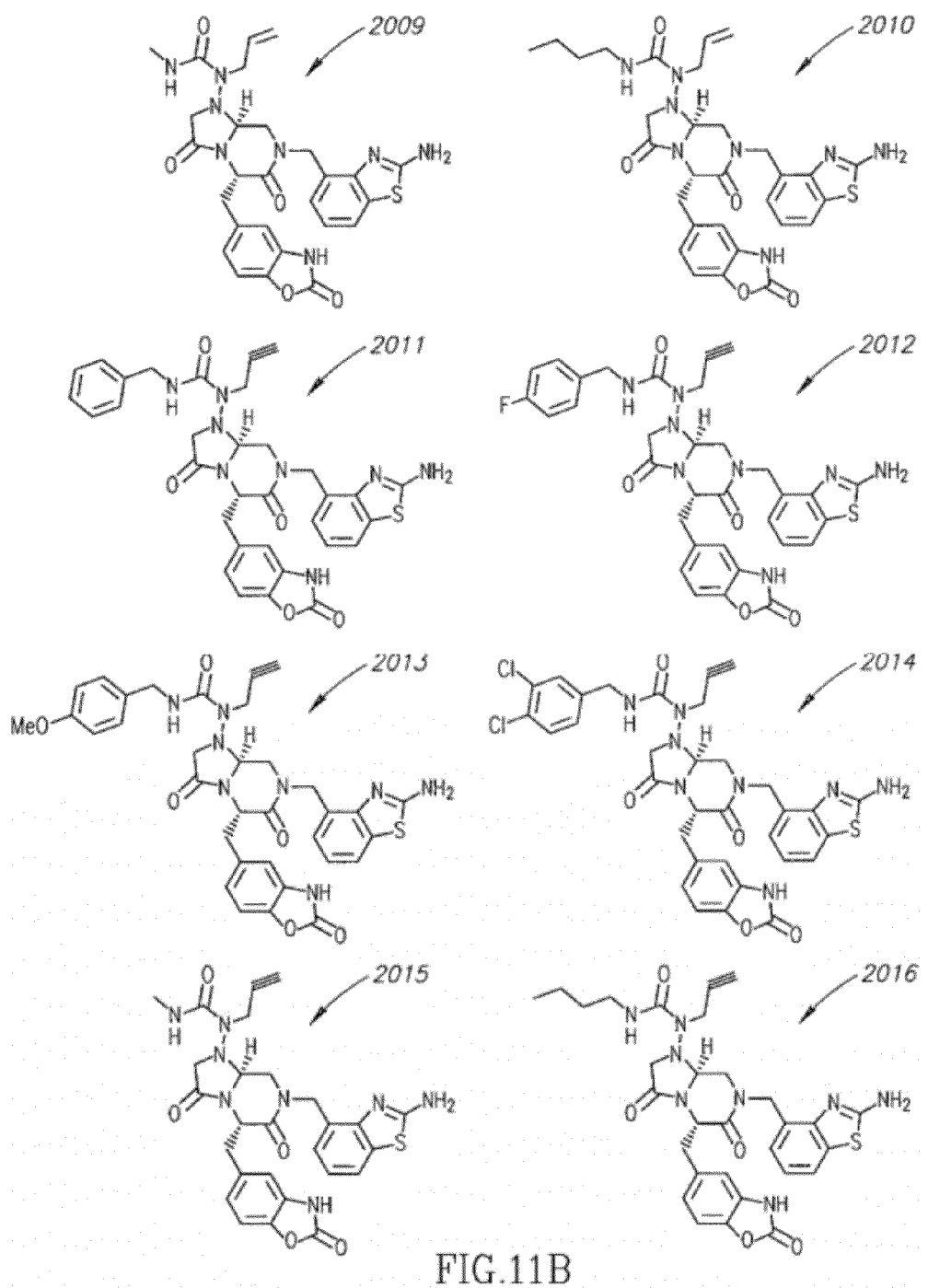
Figure 11C:
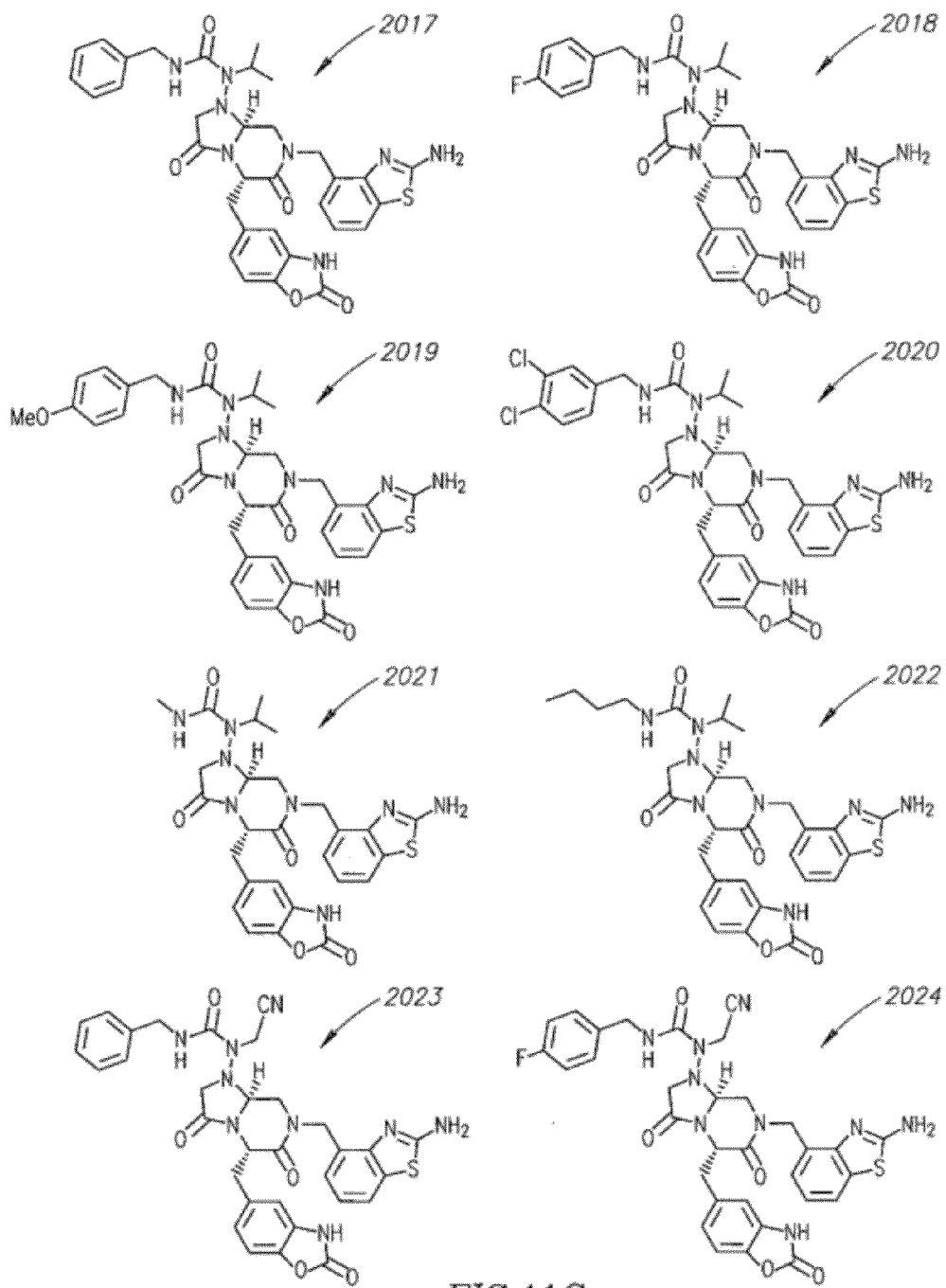
Figure 11D:
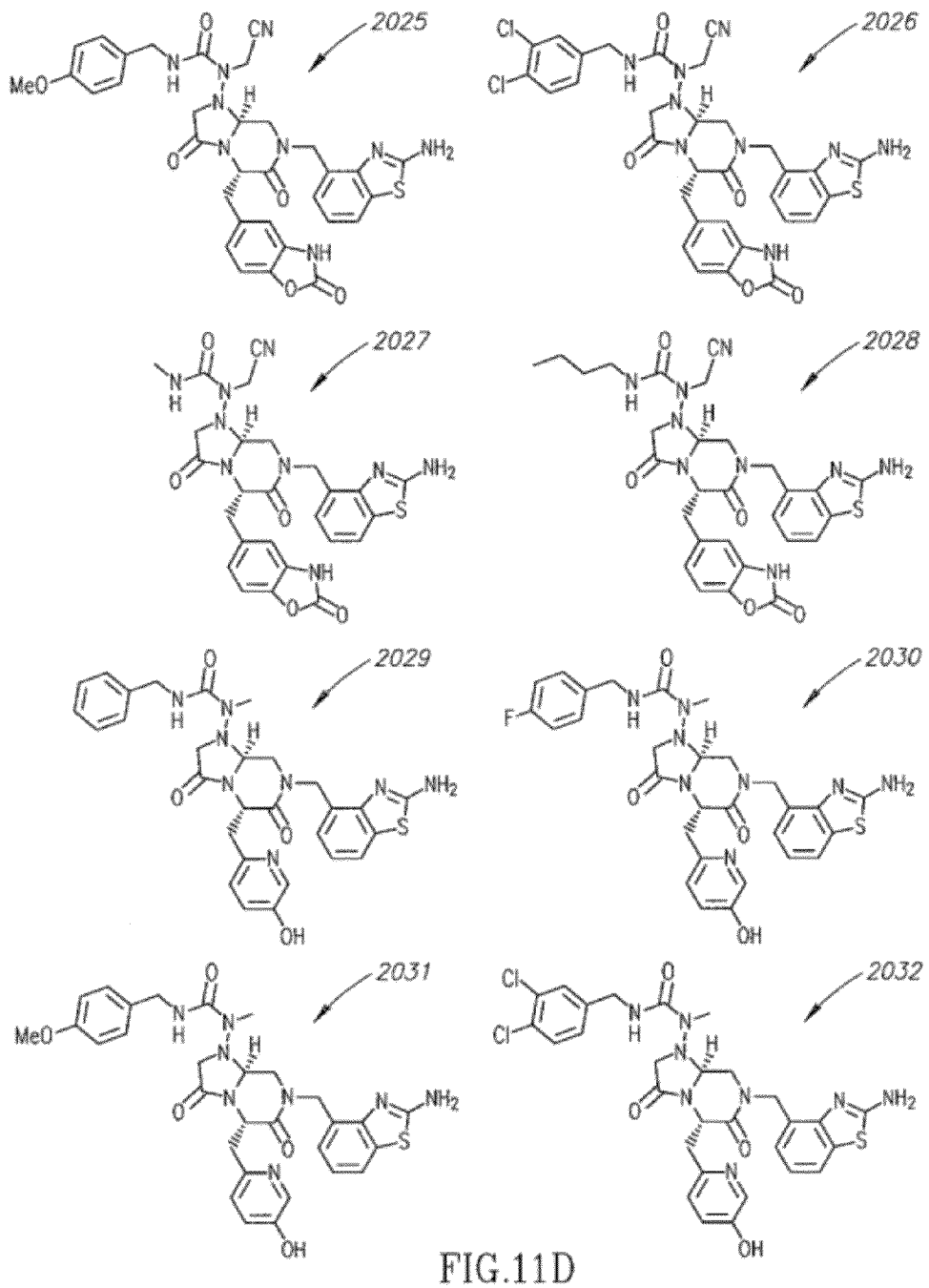
Figure 11E:
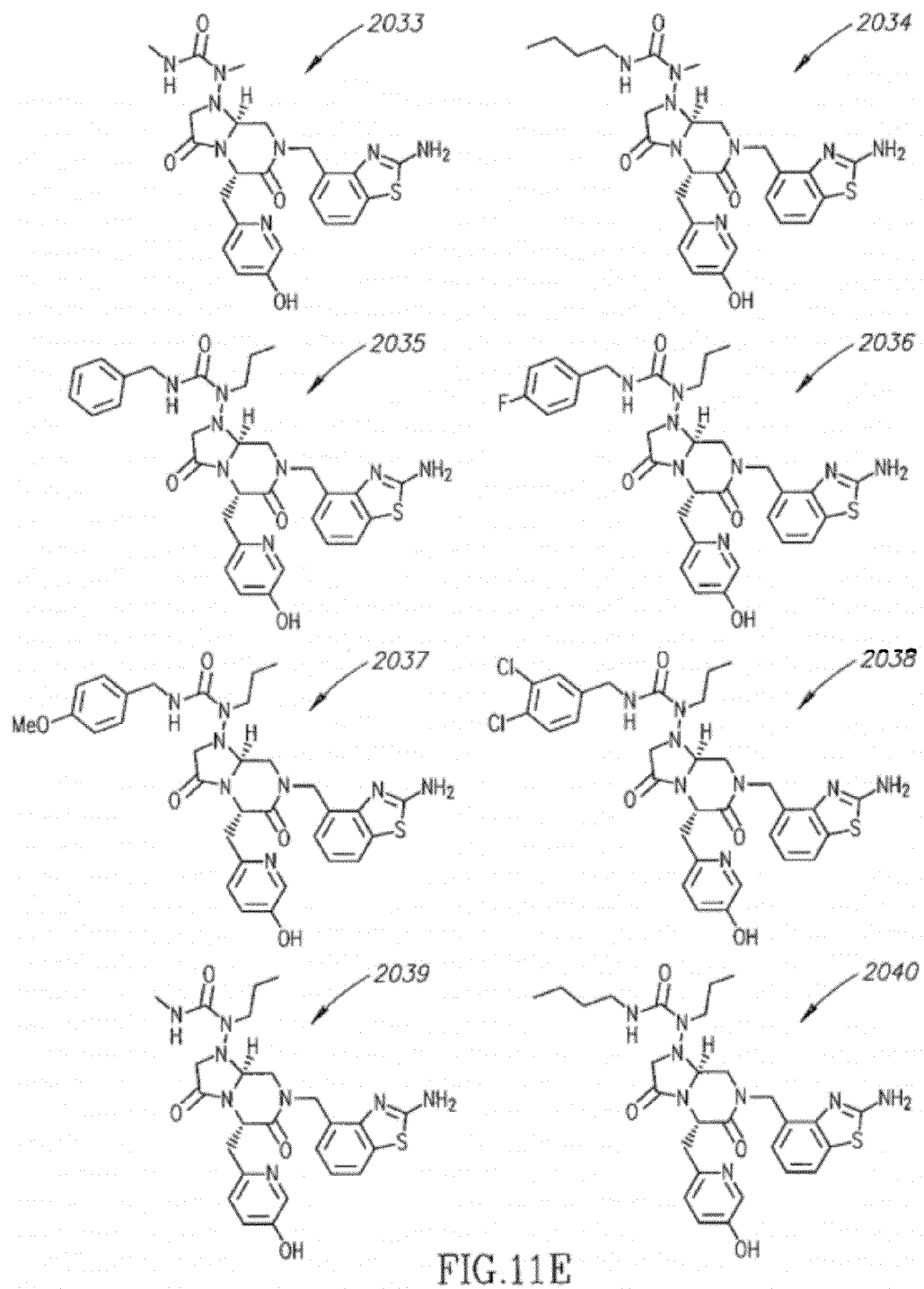
Figure 11F:
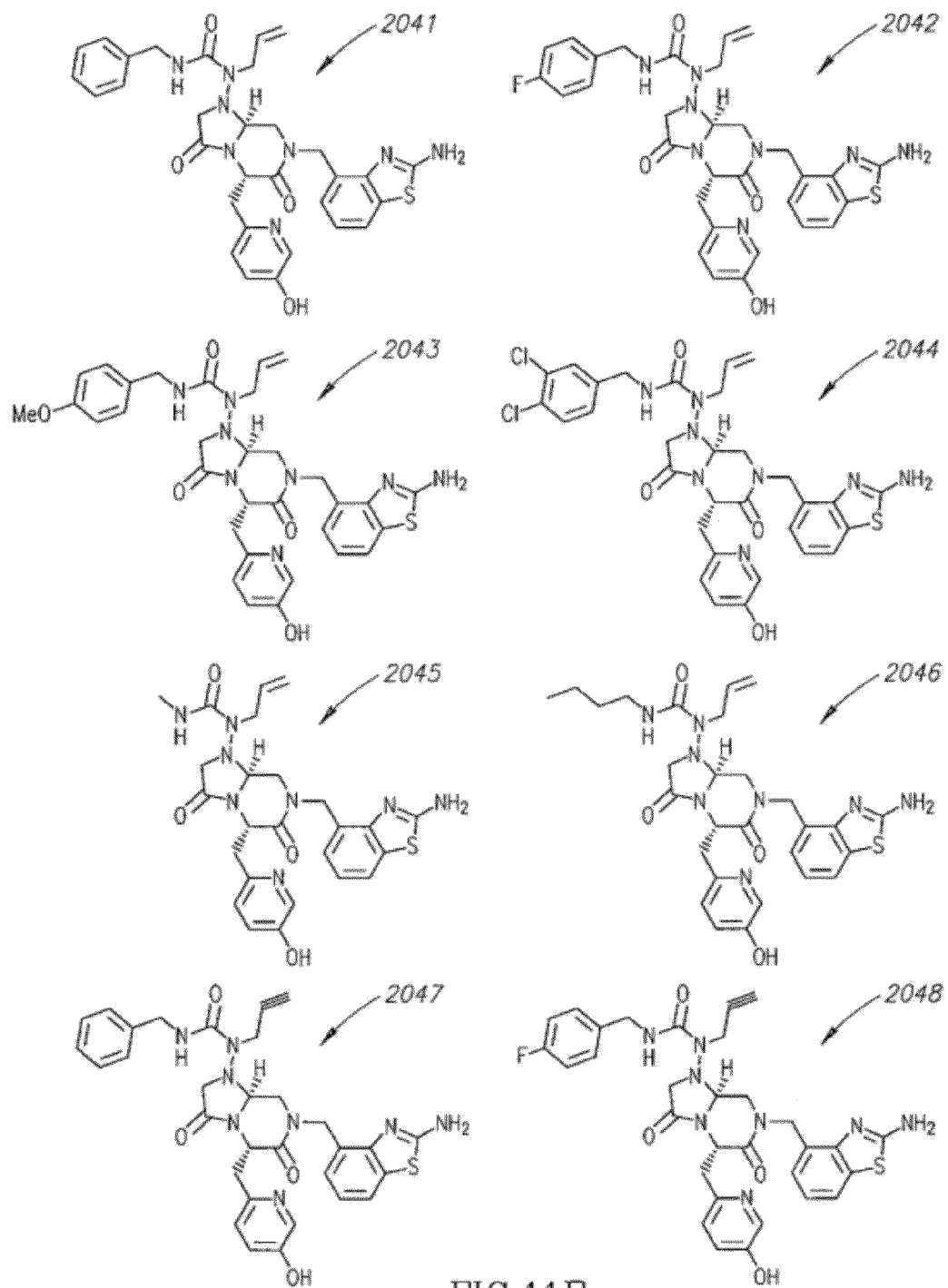
Figure 11G:
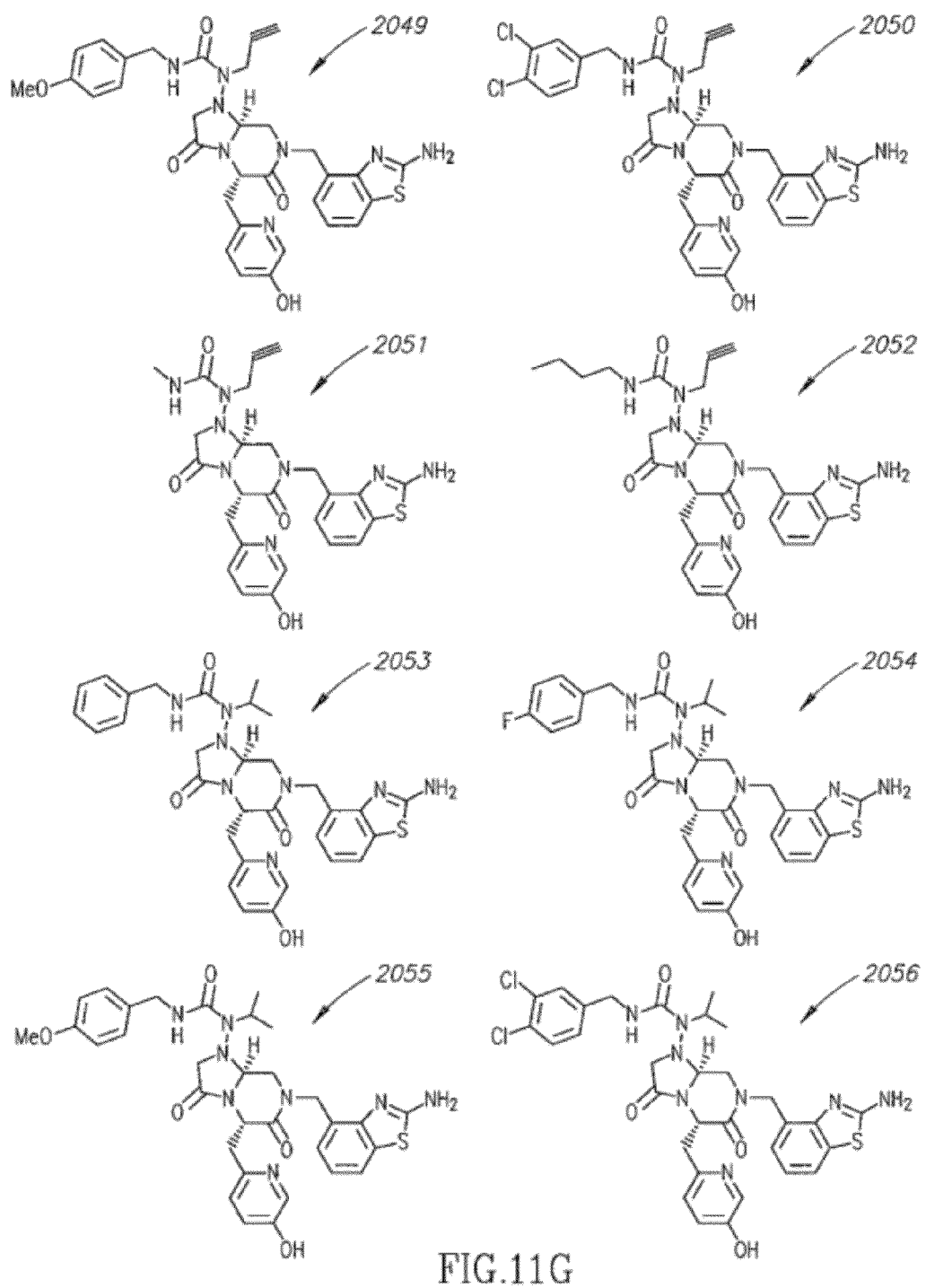
Figure 11H:
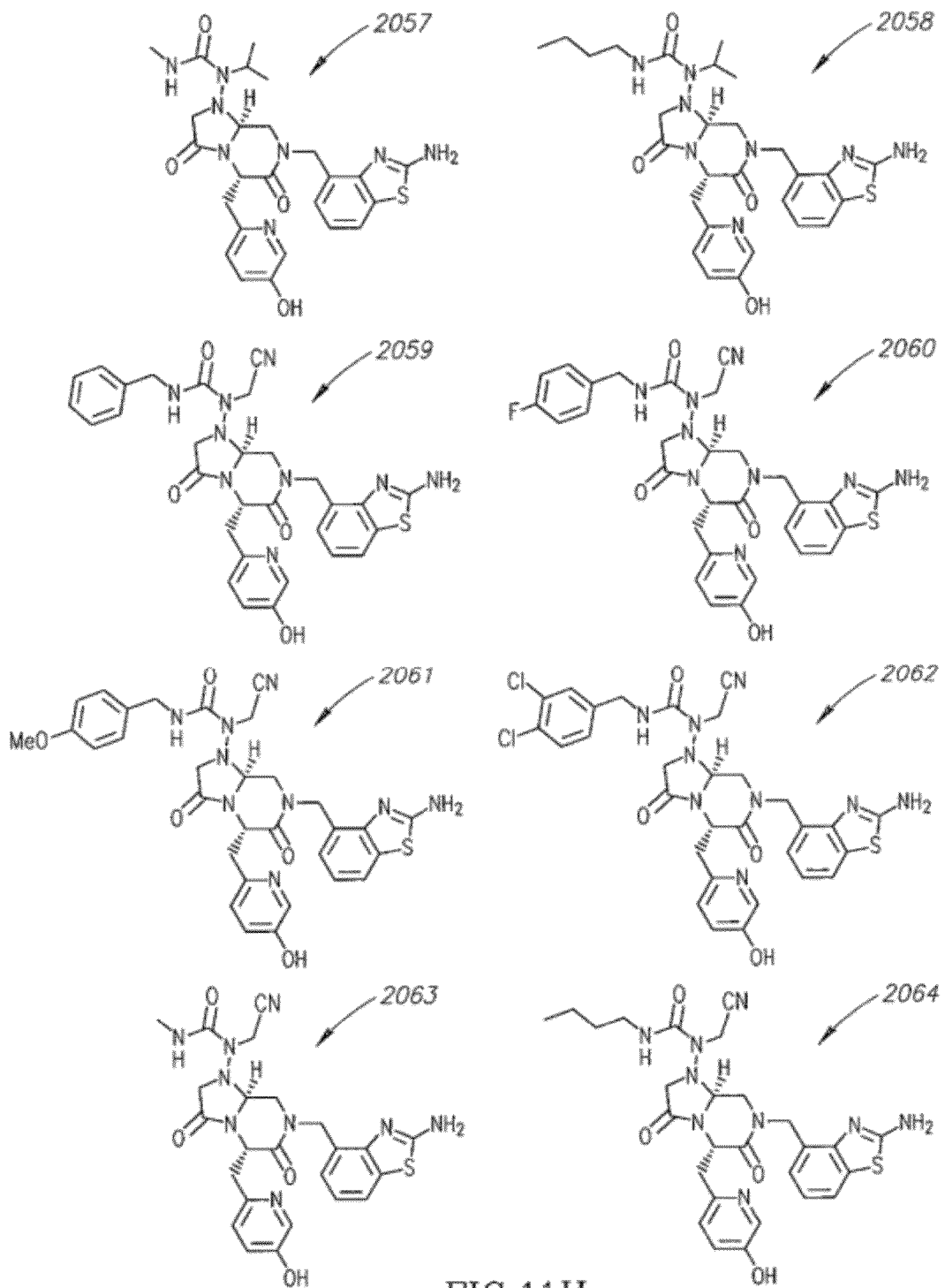
Figure 11I:
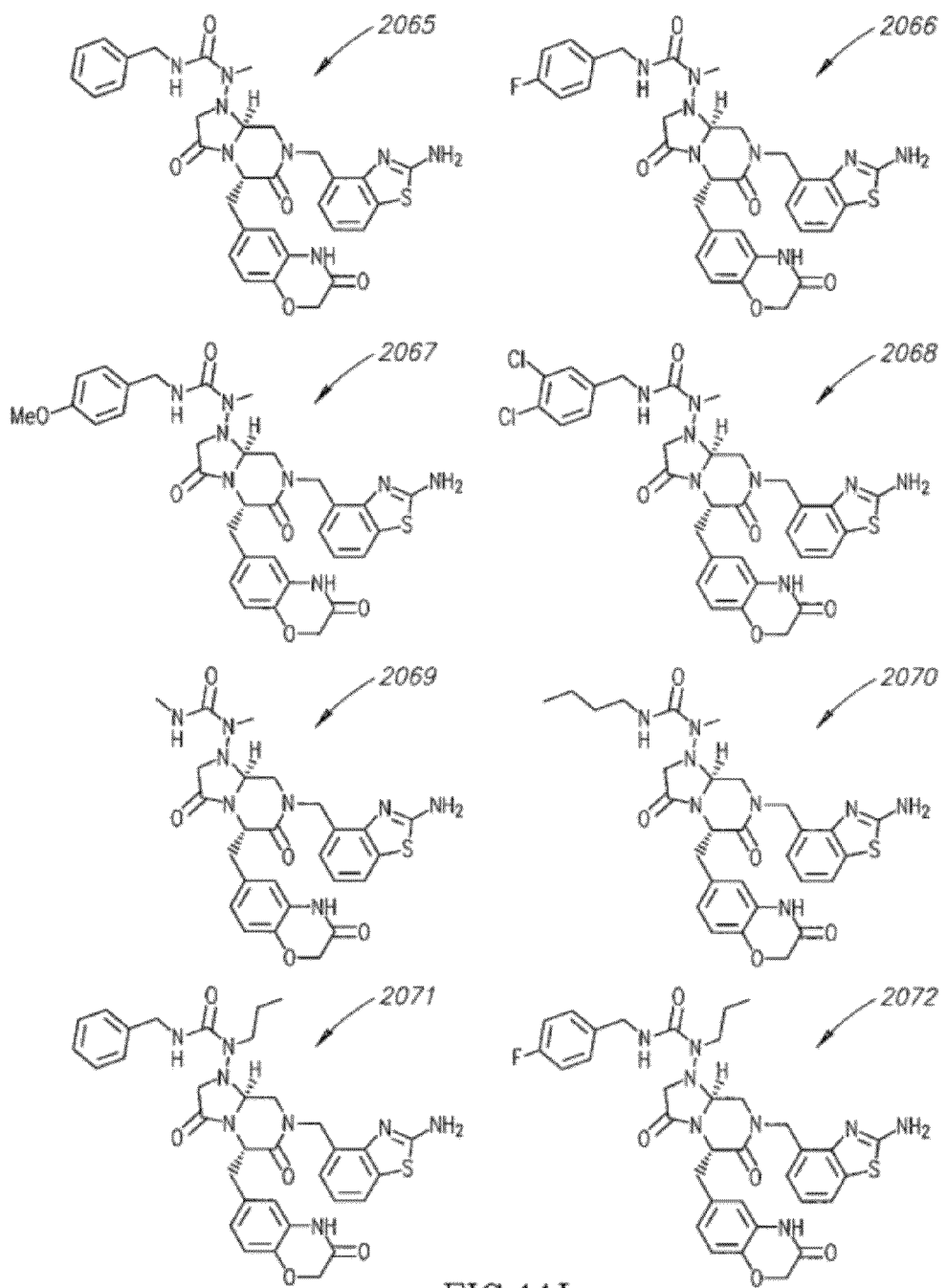
Figure 11J:
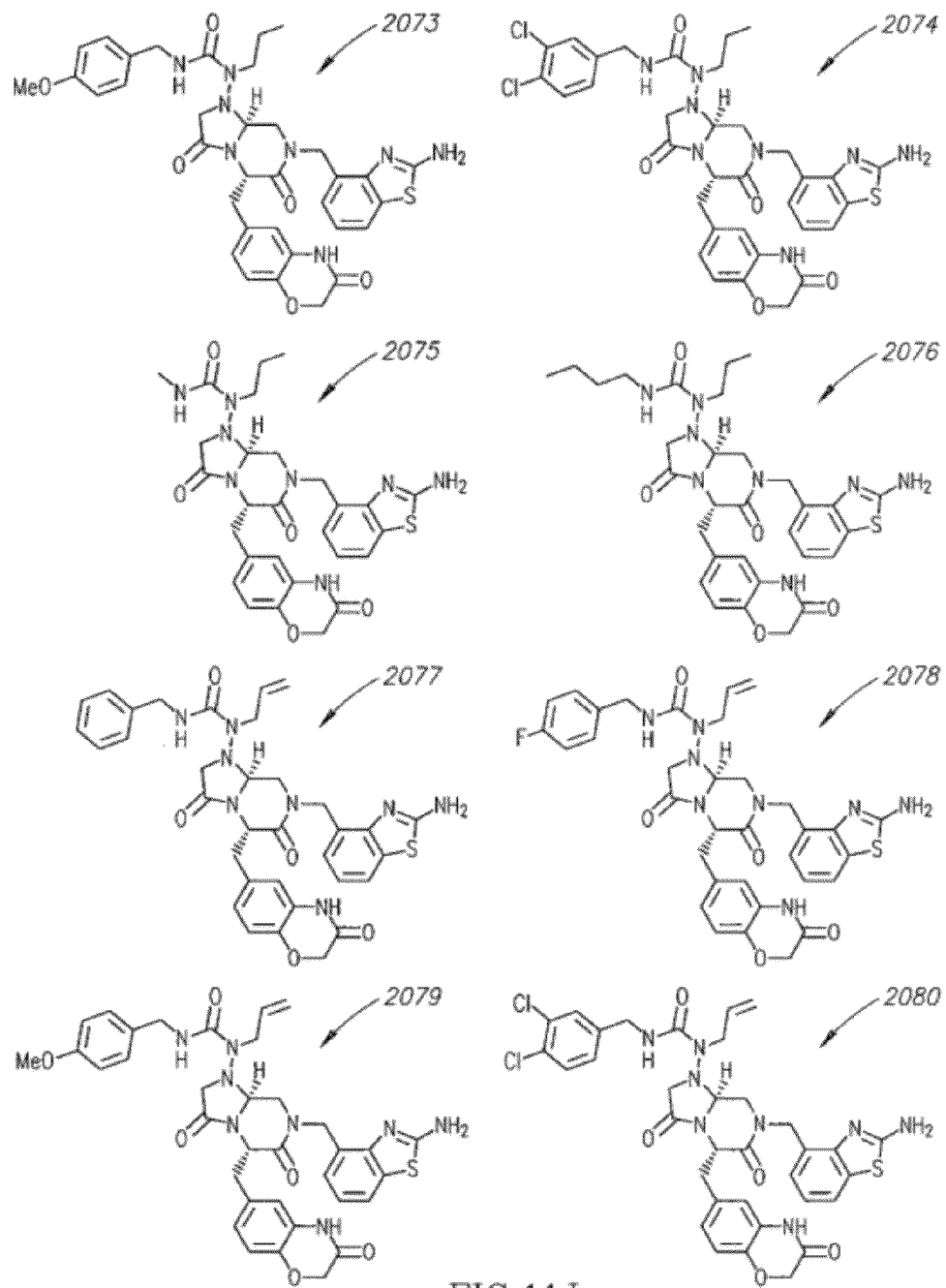
Figure 11K:
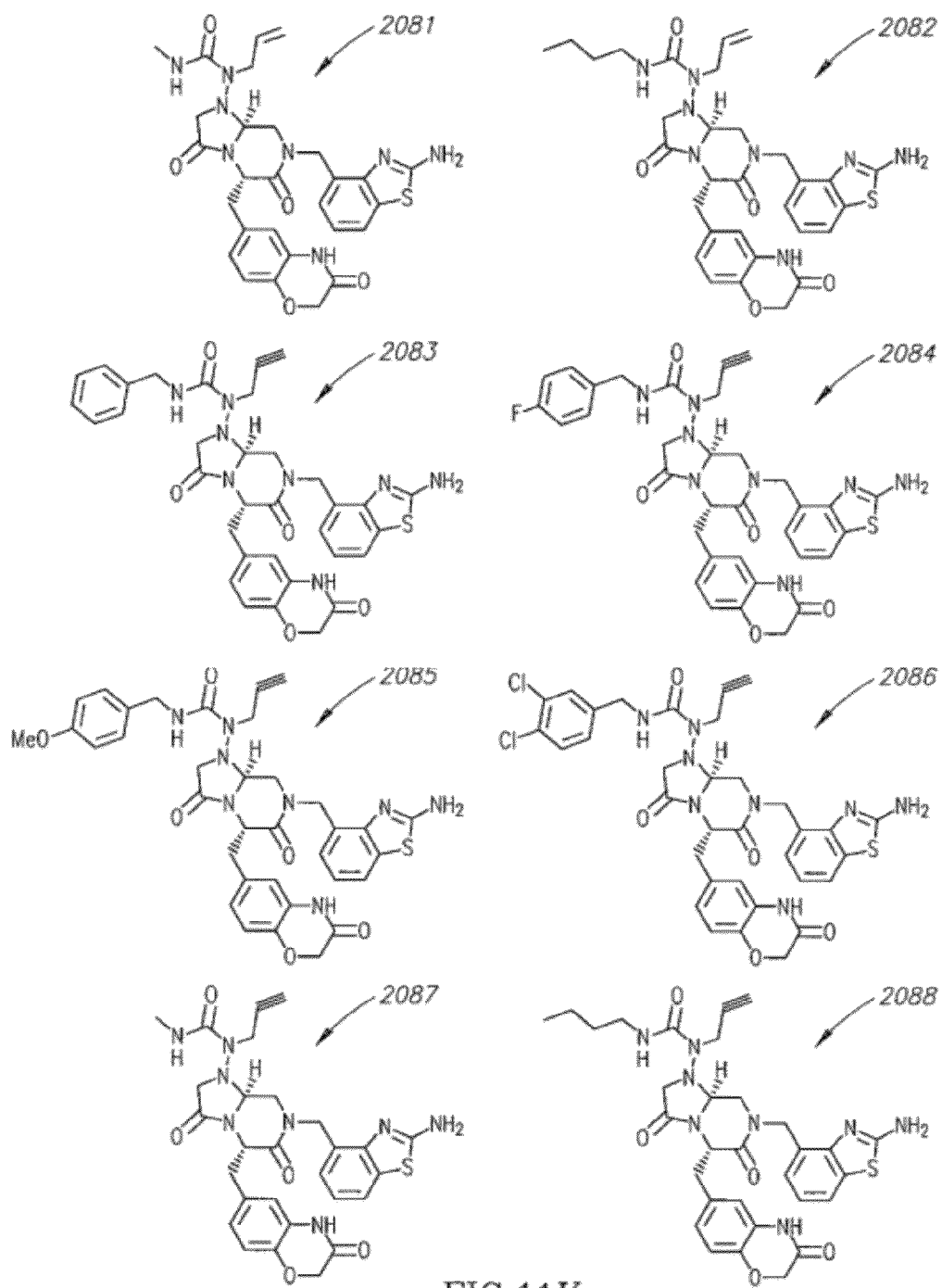
Figure 11L:
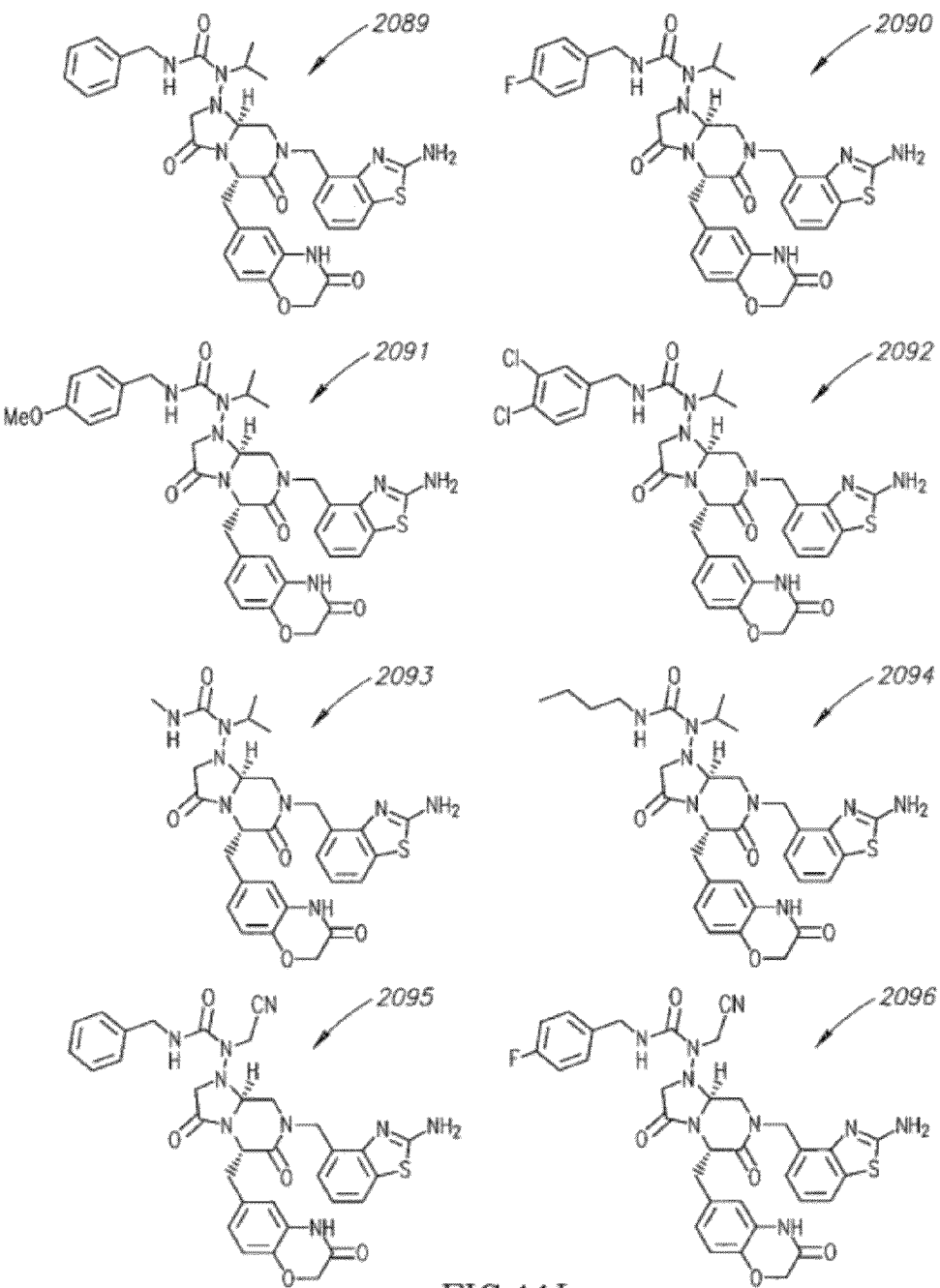
Figure 11M:
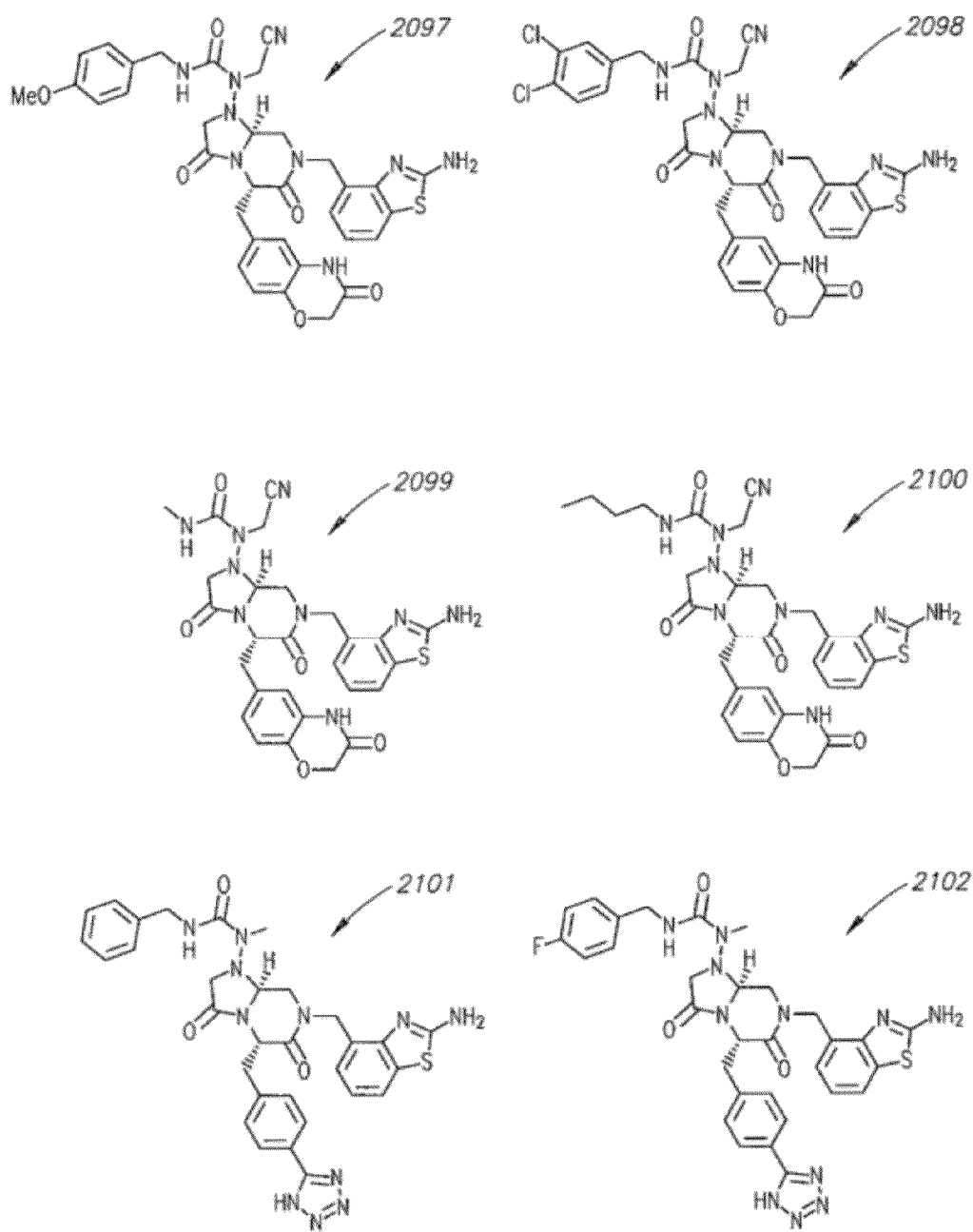
Figure 11N:
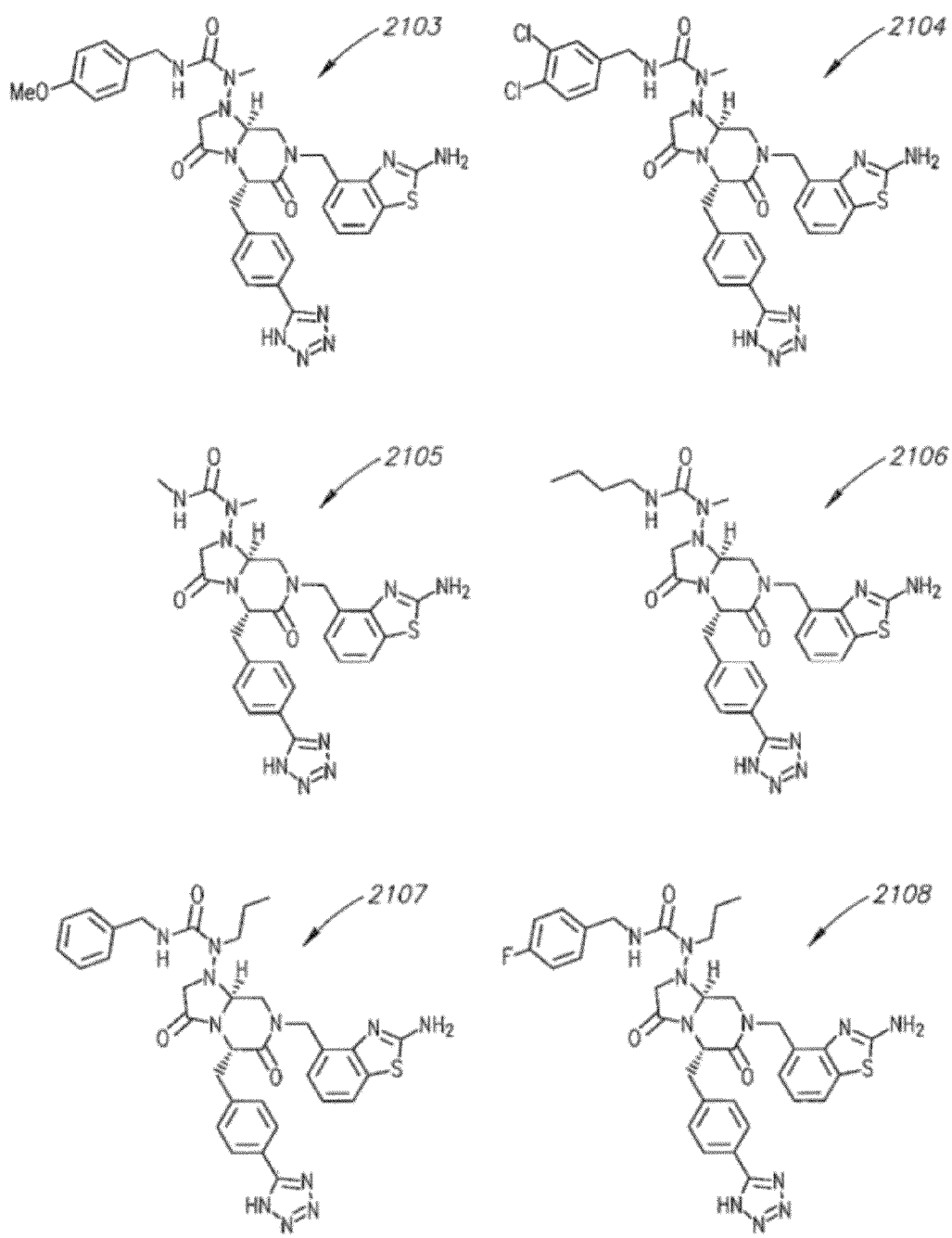
Figure 110:
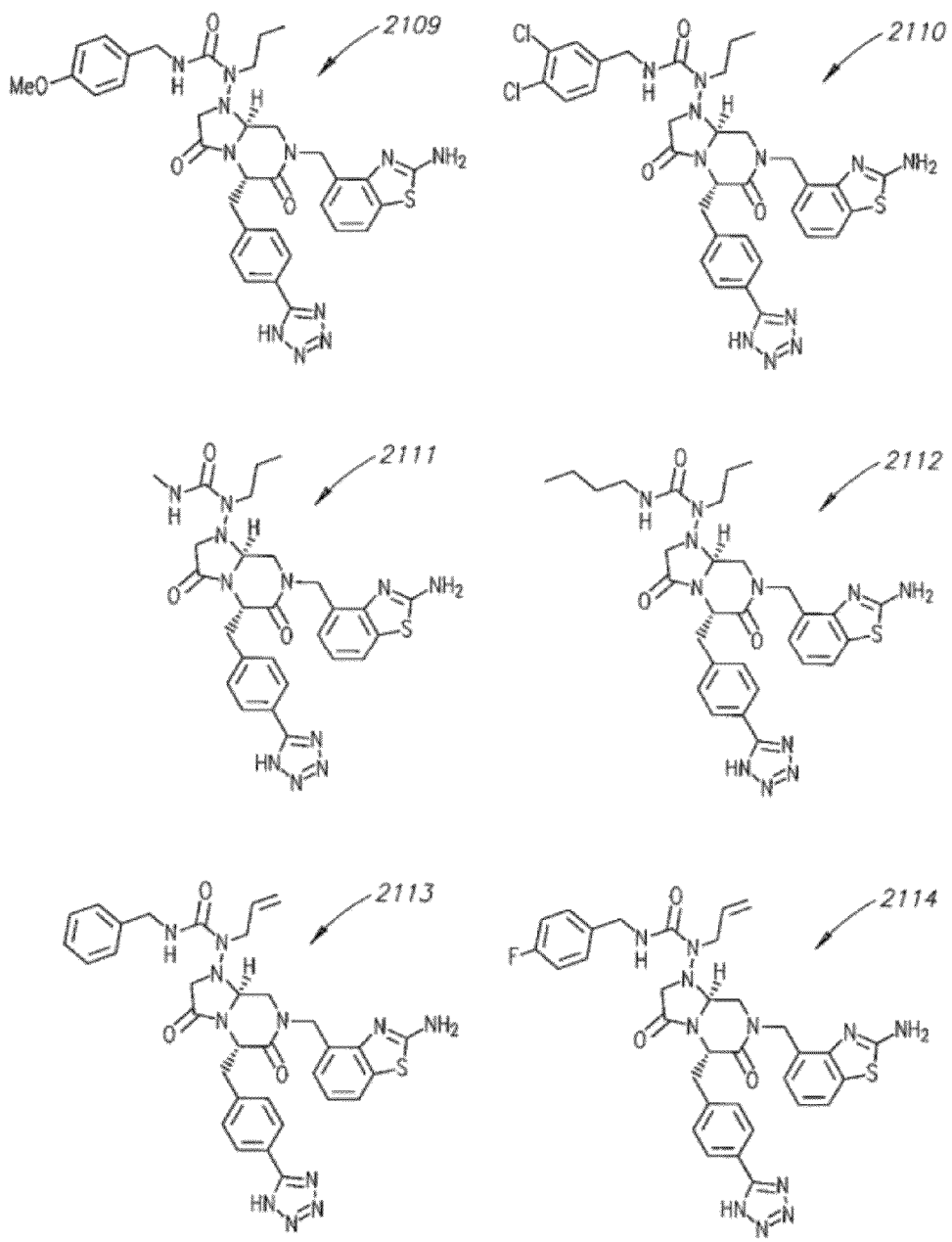
Figure 11P:
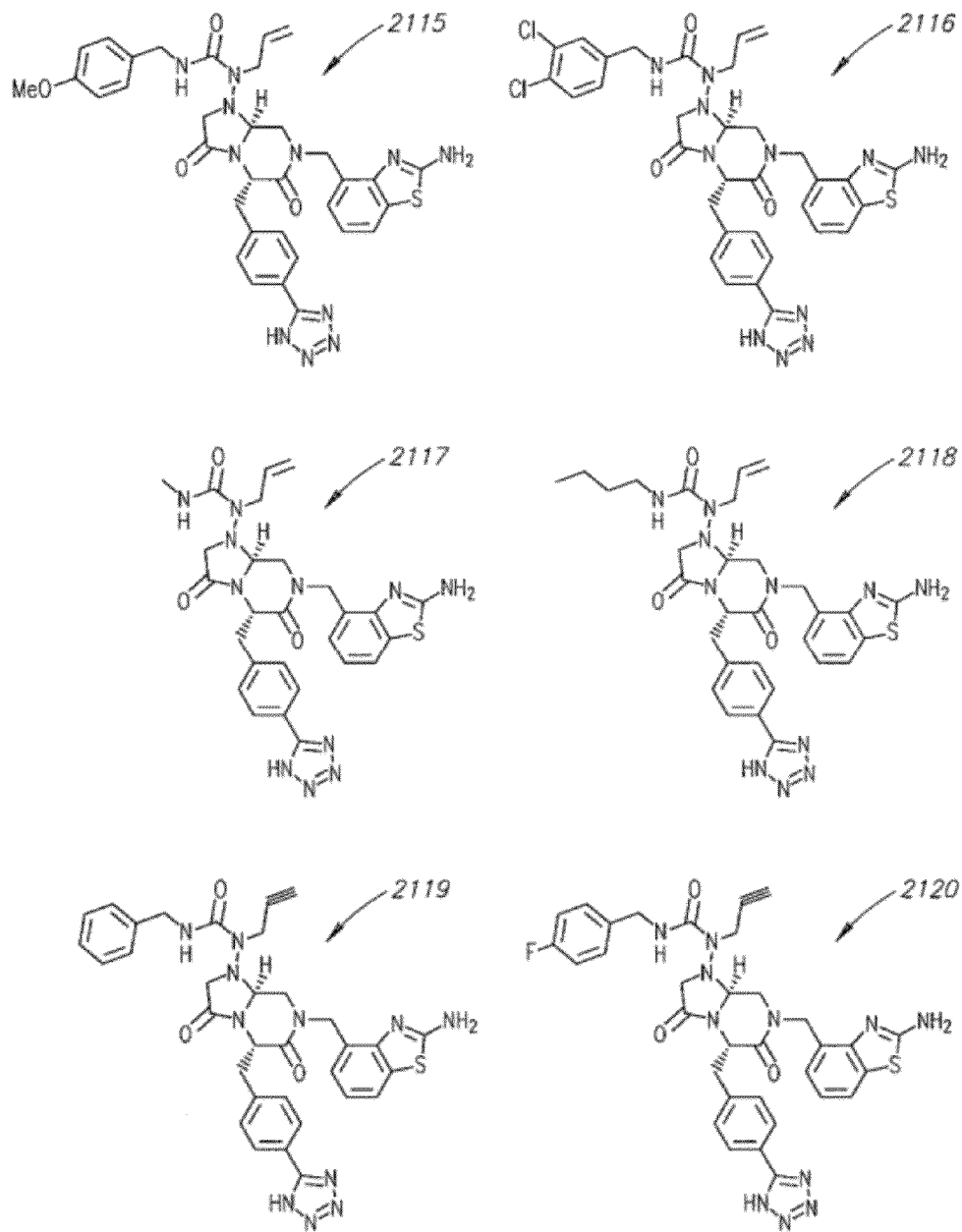
Figure 11Q:
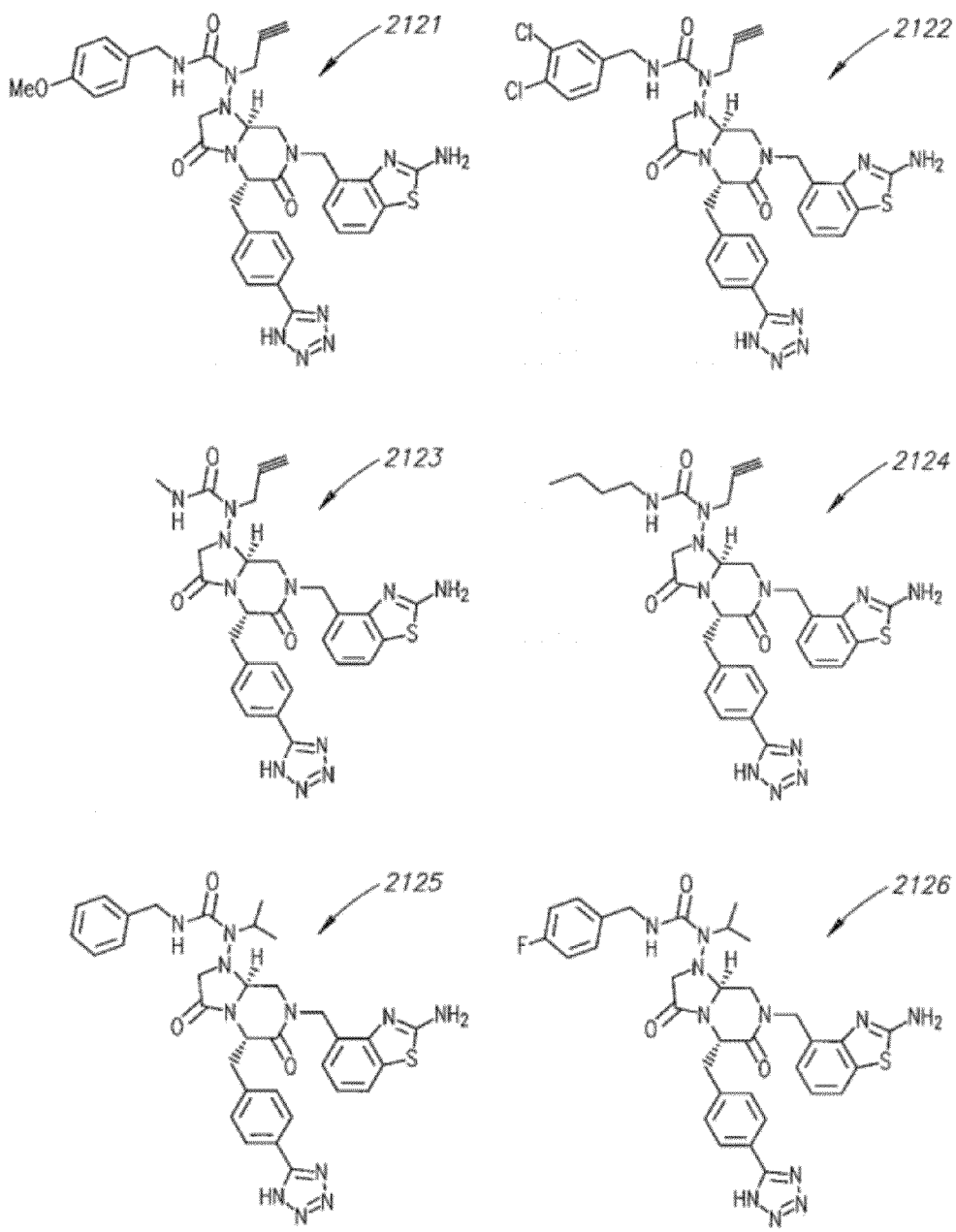
Figure 11R:
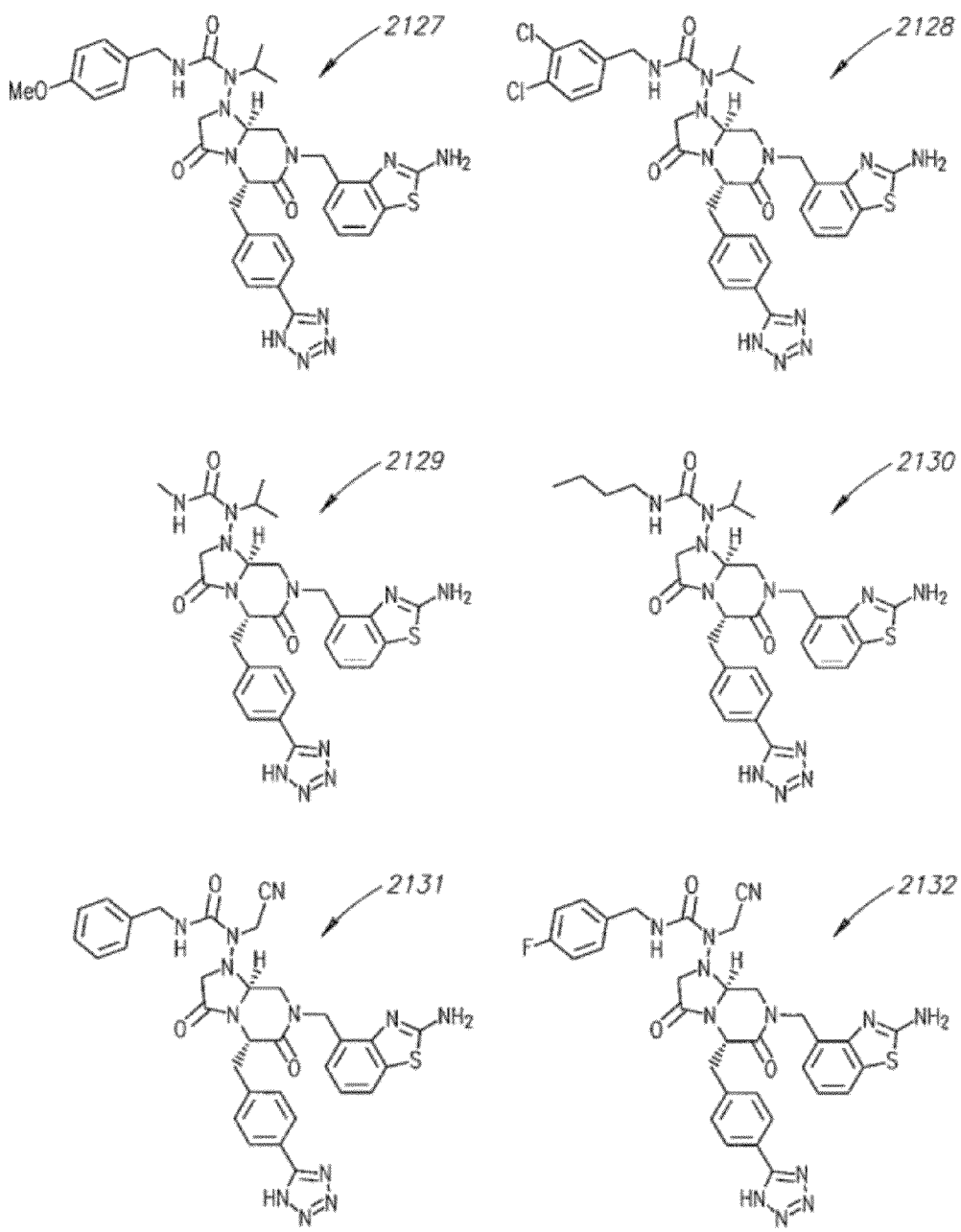
Figure 11S:
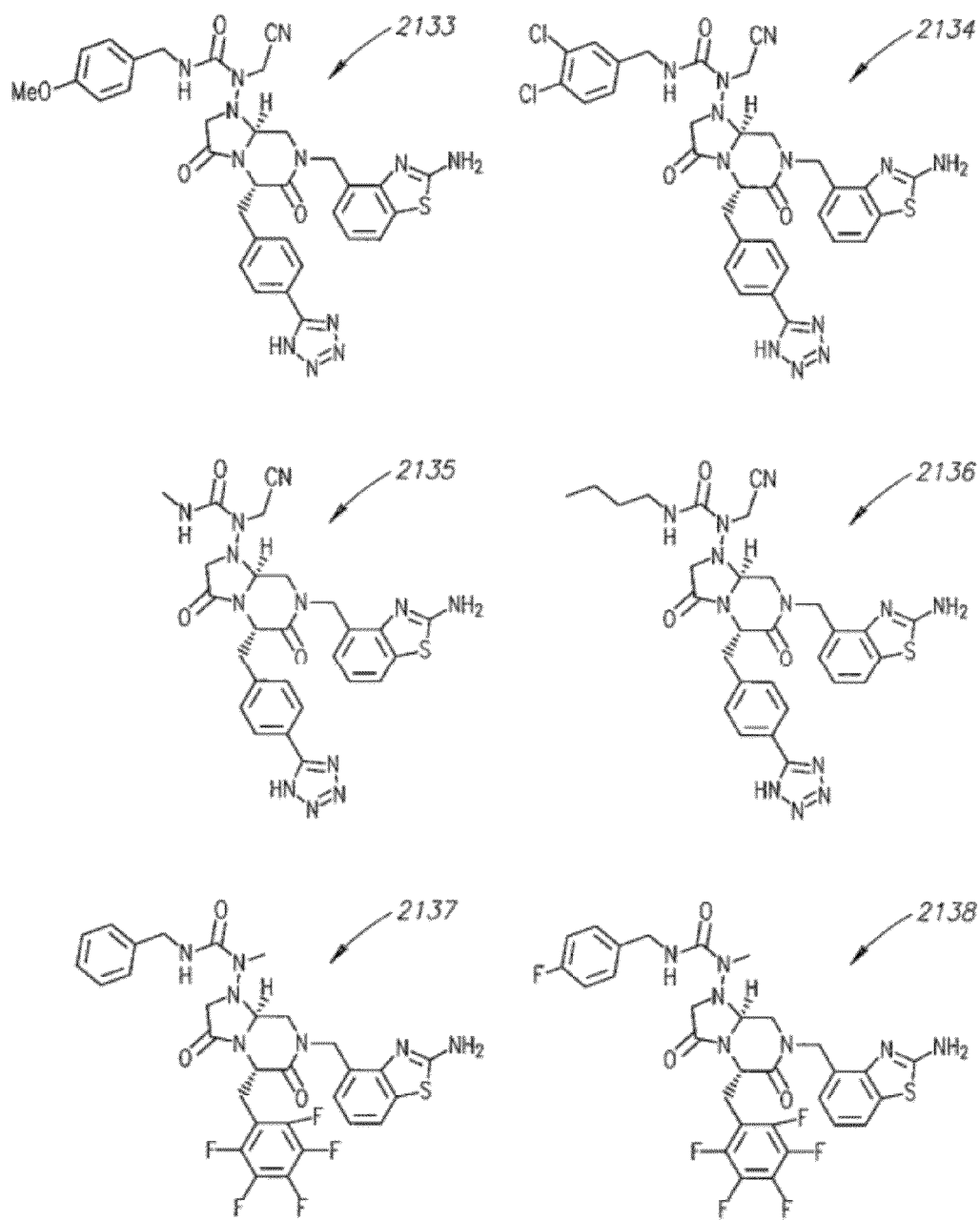
Figure 11T:
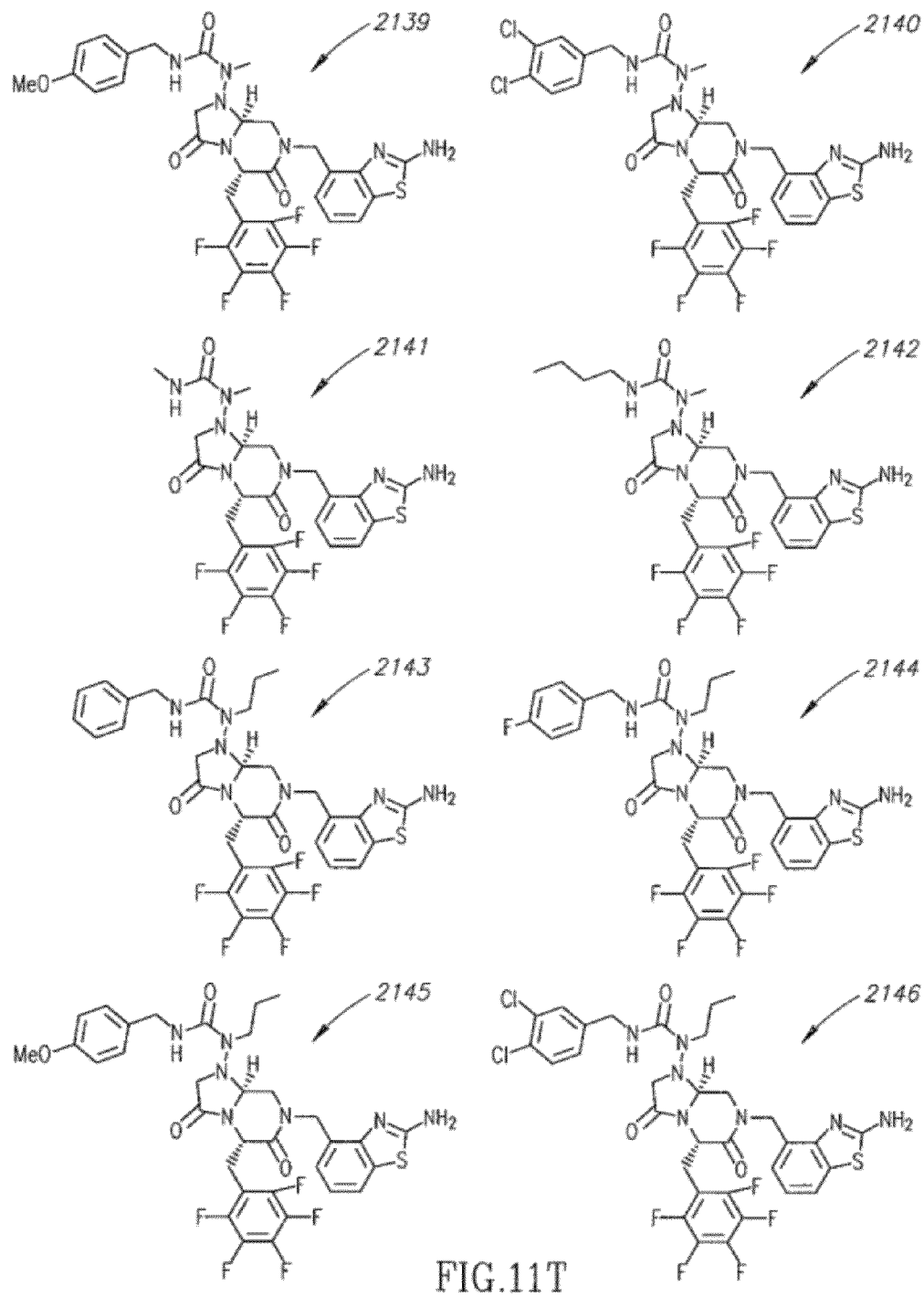
Figure 11U:
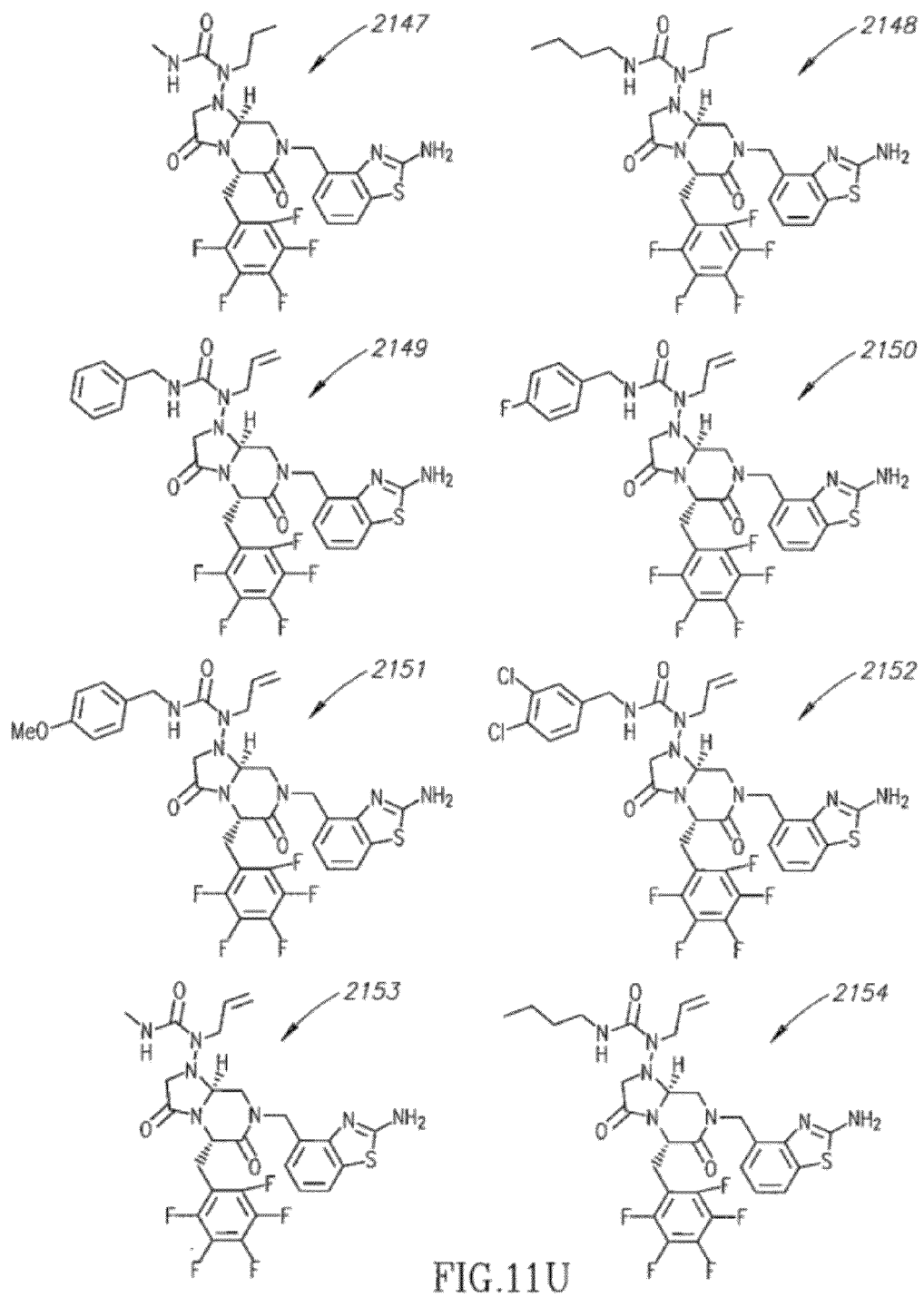
Figure 11V:
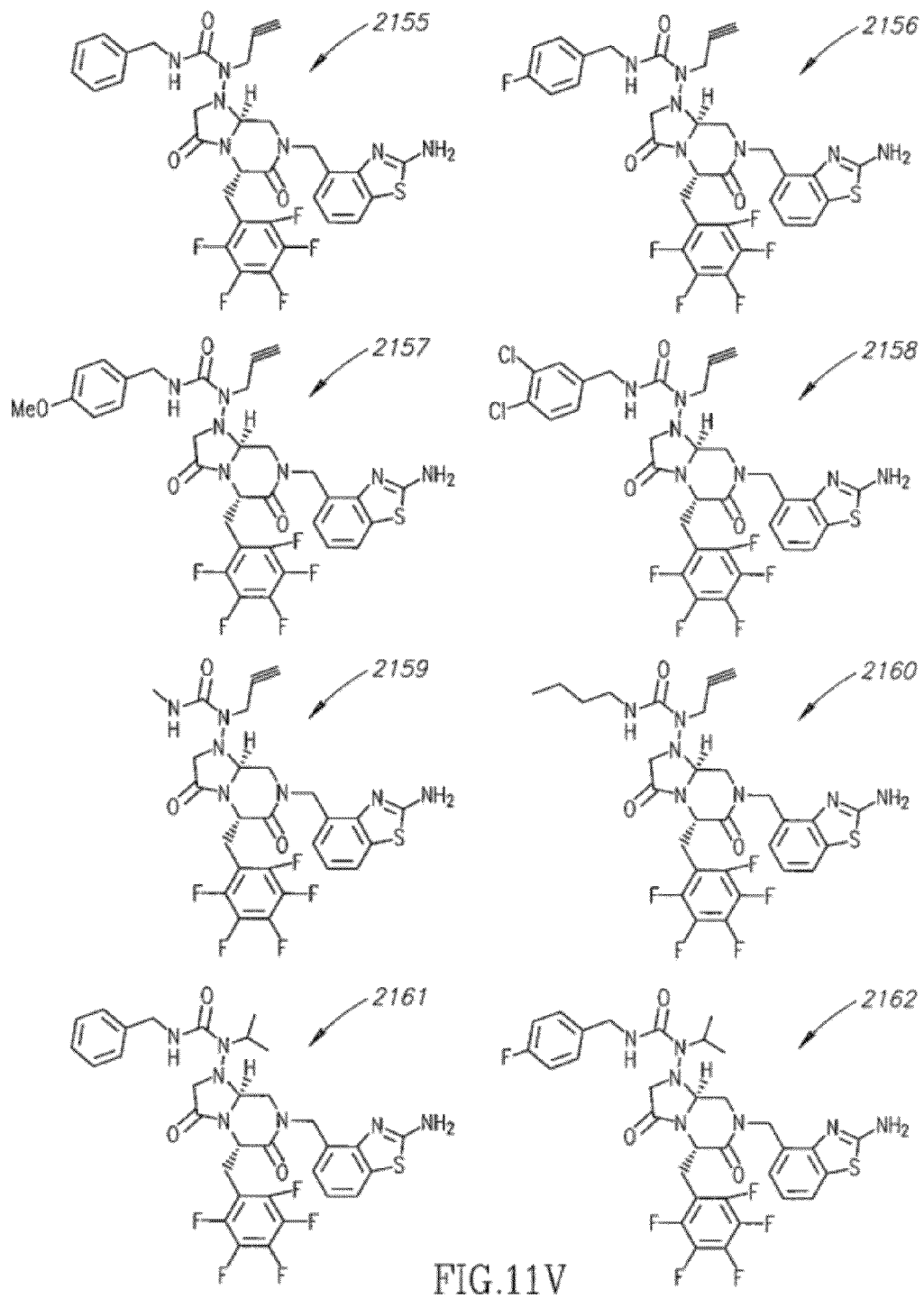
Figure 11W:
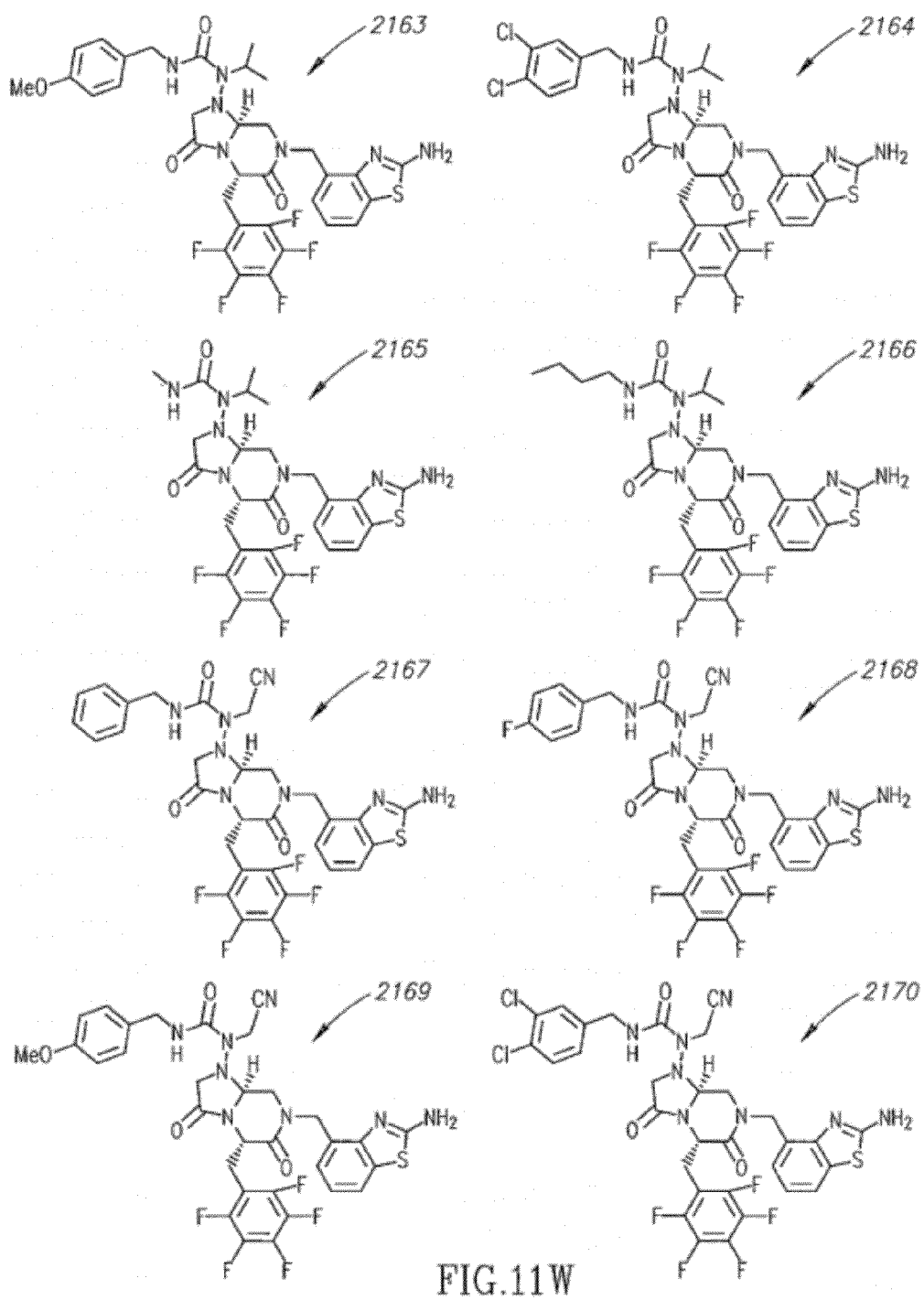
Figure 11X:
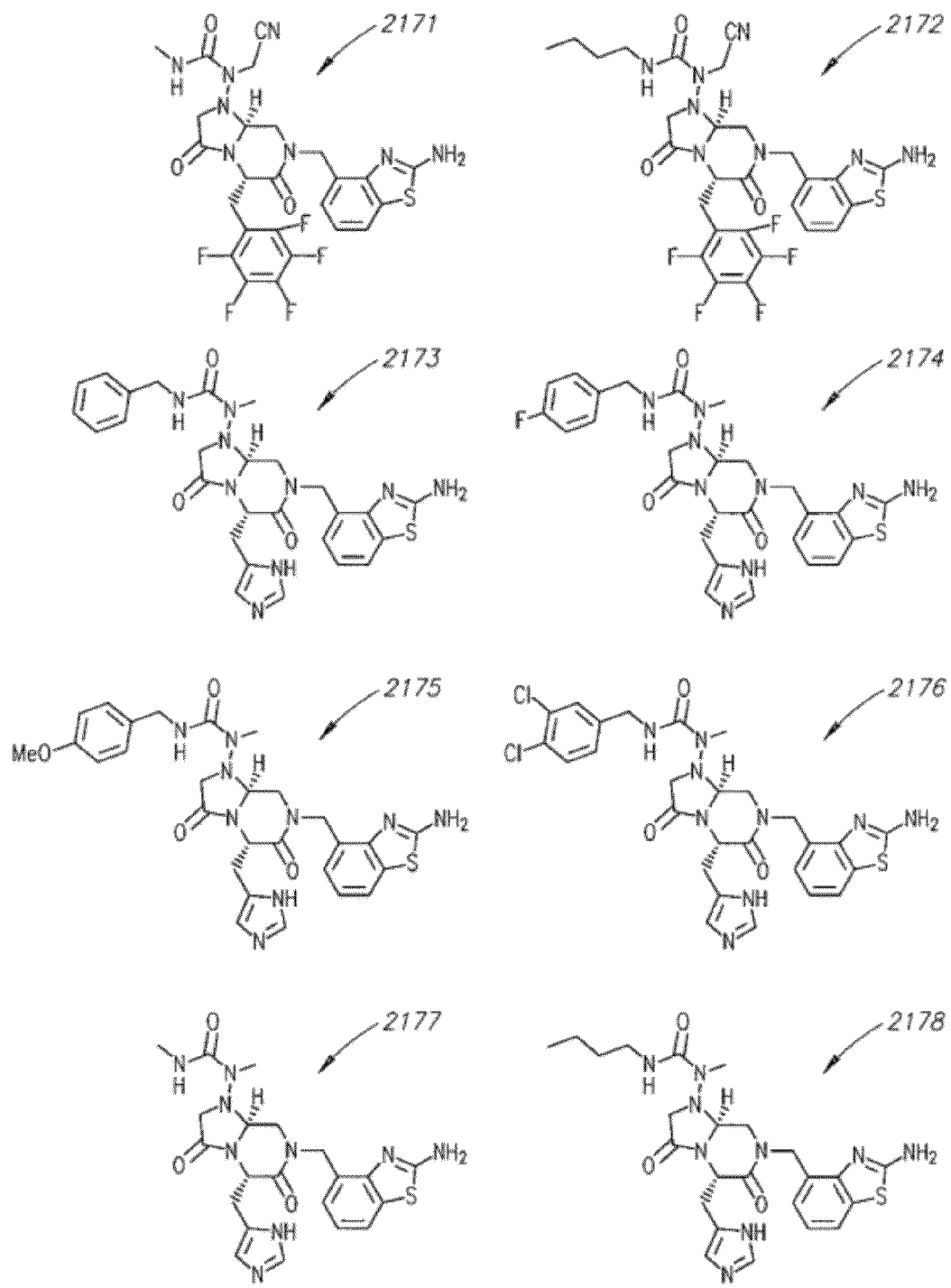
Figure 11Y:
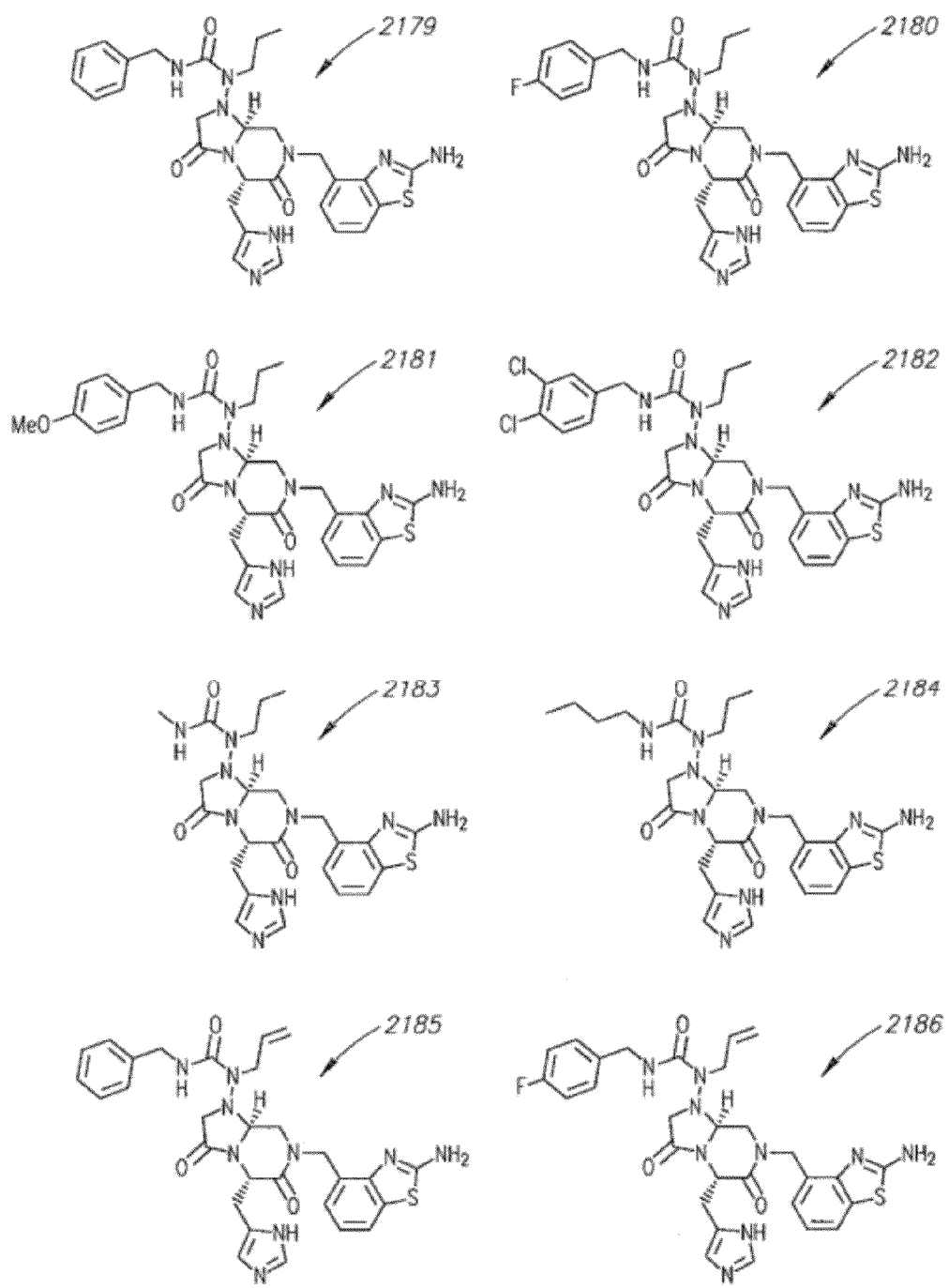
Figure 11Z:
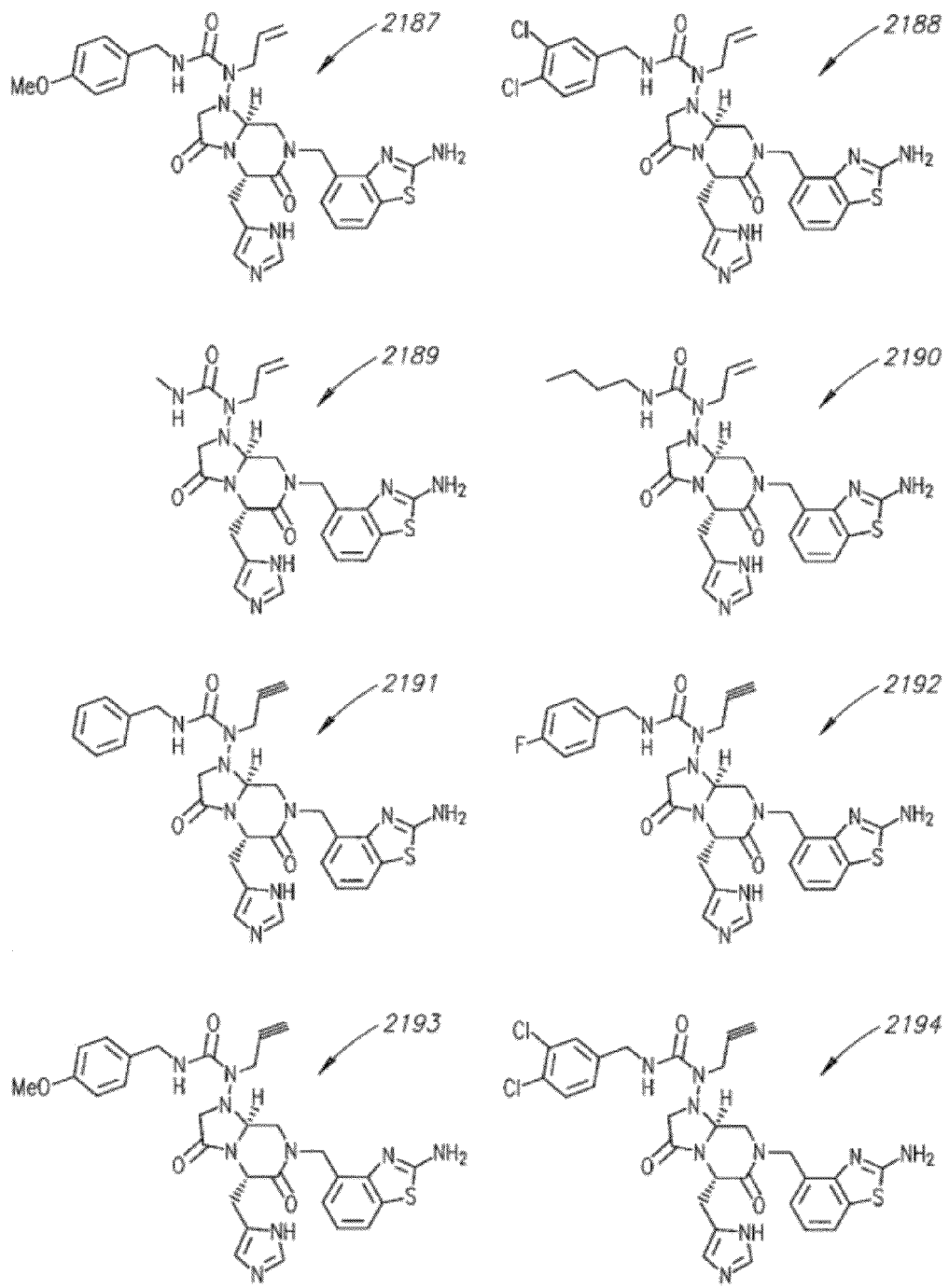

To further investigate the "cancer stem cell" nature of these resistant cell lines, the expression of a number of markers associated with stem cell pluripotency and survival was evaluated. Real time RT-PCR demonstrated an increased expression of Oct4, hTert, Bmi-1 and ABCG-2 in the MES-SA/DX5 and imatinib resistant K562 cells compared to their sensitive counterparts (FIG. 20A). Protein levels for both Oct4 and the stem cell surface marker CD133 were also increased in both resistant cell lines (FIG. 20B).

Figure 21A:
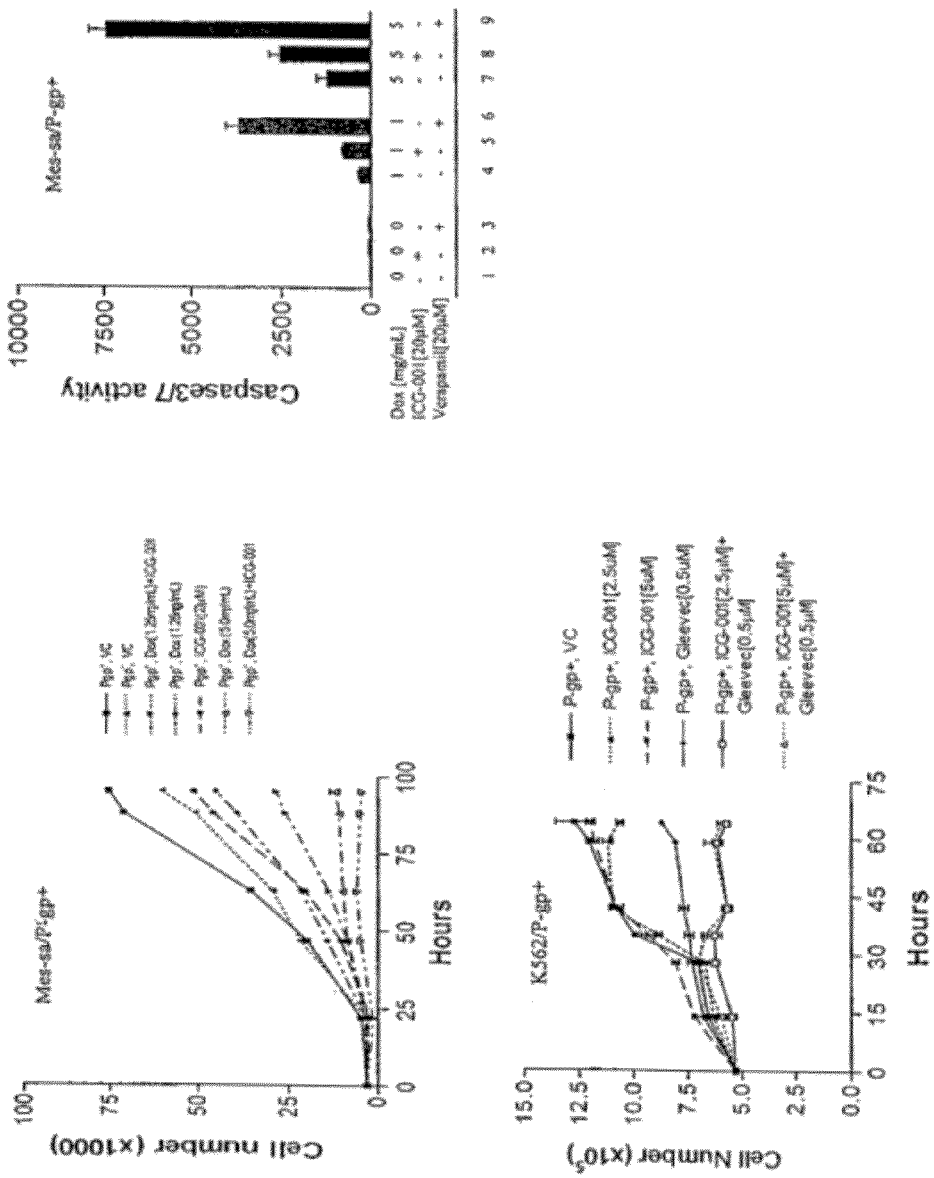
Figure 21B:
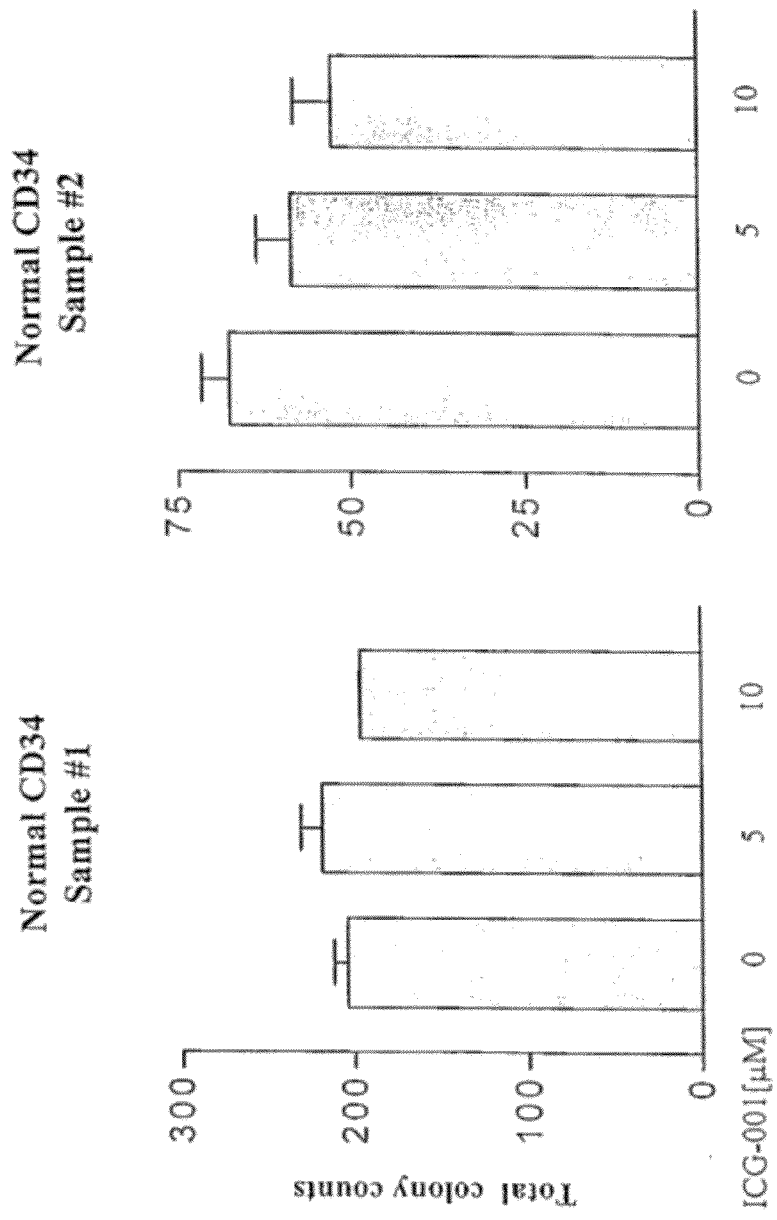

Although modern chemotherapies kill a majority of the cells in a tumor, it is believed that the resistant "cancer stems cells" are significantly associated with disease relapse. MDR transporters are believed to play important roles in protecting cancer stem cells from chemotherapy (Dean et al, Nat. Rev. Cancer 5, 275, 2005). To further study this phenomenon, a series of experiments was performed. Drug resistant MES-SA/Dx5 and K562 imatinib resistant cells were treated with Doxorubicin+/−ICG-001 or Imatinib mesylate+/−001. As can be seen in FIG. 21A, ICG-001 in combination with the respective chemotherapeutic agent was significantly more effective than the chemotherapeutic agent alone or ICG-001 alone in decreasing cell proliferation/viability. The addition of ICG-001 to MES-SA/Dx5 cells treated with either 1 mg/ml or 5 mg/ml of Doxorubicin increased caspase3/7 activation significantly.

EXAMPLE 4

Effect of ICG-001 on Chronic Myelocytic Leukemia (CML)

Despite the significant clinical success achieved in CML patients with imatinib to date, in advanced phase disease, the responses are often short-lived and patients invariably undergo disease progression (Melo J Hematology, 2003). This is the result of the emergence of leukemic drug resistant clones associated with increased nuclear β-catenin levels, a hallmark of increased TCF/β-catenin transcription (Weissman NEJM 2003). The efficacy of ICG-001 either alone or in combination with imatnib mesylate was investigated in both normal CD34+ blast cells (mostly early stem/progenitors) and from bone barrow of CML patients at various stages of progression. CD34+ CML blasts showed significantly higher expression of β-catenin, ABCB1, htert, survivin/variant AEx3 and BMI-1 relative to CD34− cells, indicating constitutive activation of Wnt/catenin signaling and confirming the increased "stem/progenitor-like" features of this CD34+ CML blast cell population (FIG. 21C) (Jamieson et al., 2004).

Figure 21D:
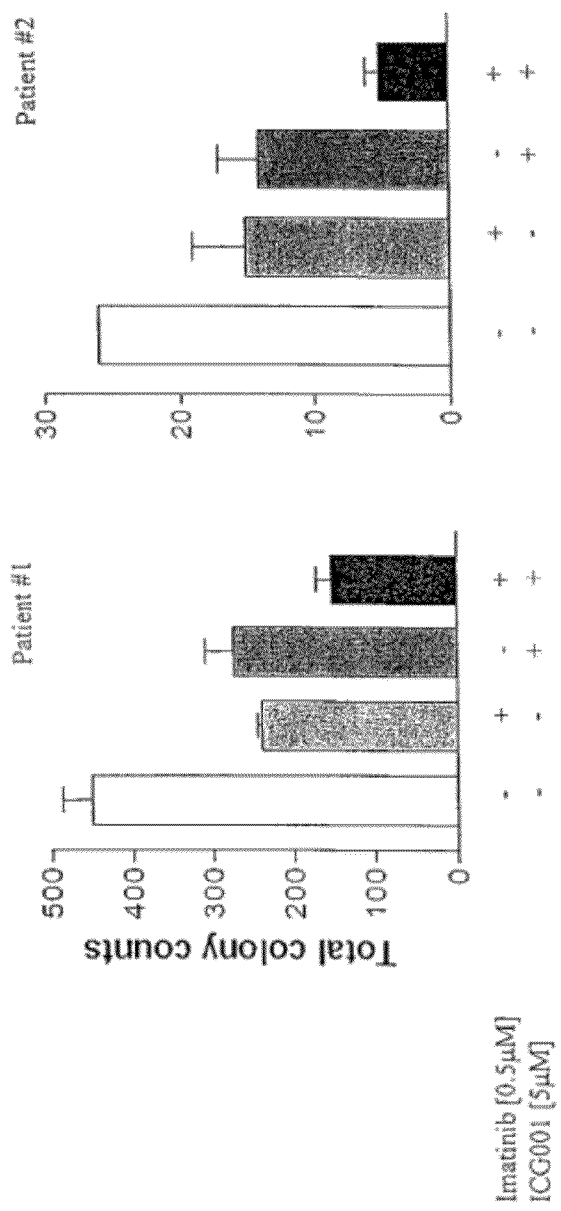
Figure 22:
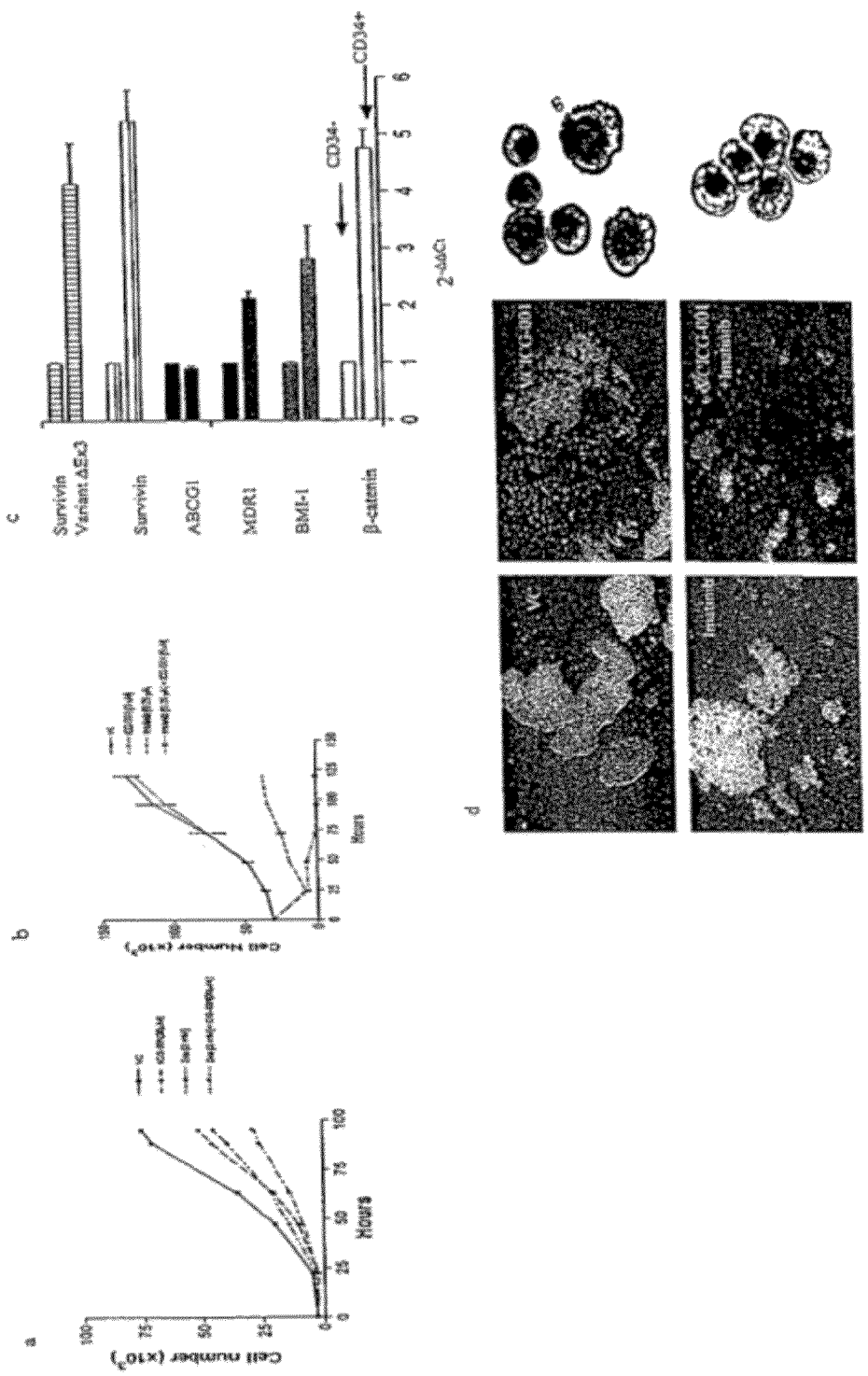
FIGS. 22A-E. The effect of ICG-001 at different doses, with and without imatinib, is shown in FIGS. 22A and 22B.

Combination ICG-001 and imatinib treatment resulted in the most significant reduction in total colony forming units (CFU) as compared to the control of either drug treatment alone in all samples (FIG. 21D). Moreover, the morphological features of the colonies after drug treatment are also altered; the colonies became small and dispersed, and the dispersed colony phenotypes were more profound in the combination treatments, indicating that the treated colonies have an increased state of differentiation. In sharp contrast, the control colonies were large and compact. The H&E staining displayed reduced nuclear/cytoplasmic ratio in the treated cells (FIG. 21E). Importantly, treatment of normal CD34+ cells with ICG-001 had minimal effects on total cellularity, CFU-Es and BFU-Es. ICG-001 did not affect colony formation of normal CD34+ hematopoietic cells.

In summary, whereas imatinib itself had limited effect, imatinib plus IGC-001 had a significant additive effect. ICG-001 up to 20 µM did not have significant adverse effects on normal CD34+ cells and induced differentiation but not capase activation in K562 cells.

EXAMPLE 5

The Effect of ICG-001 and of Cisplatin on Cultured Ovarian Carcinoma and Melanoma Cells Expressing the Stem Cell Markers CD133 or Prominin-1, Respectively This example describes measurements of the sensitivity of ovarian carcinoma cells and to ICG-001.

Colony inhibition assays were performed, in which plated cells from A2780, CP70, IGROV-1 and B16 cells were exposed to doses of ICG-001 within the range of 0.625 to 10 µM. An exemplary experiment is illustrated in Table 3.

TABLE 3

Colony numbers formed by plated cells from the cisplatin-sensitive A2780 exposed in vitro to ICG-001.

| CONCENTRATION OF ICG-001 (µM) | COLONIES (n = 4) M +/− SD | P-VALUE ≦ * |
|---|---|---|
| Control | 160 +/− 21.5 | — |
| 0.625 | 74 +/− 4.7 | 0.003 |
| 1.25 | 28 +/− 13.2 | 0.004 |
| 2.5 | 0.25 +/− 0.5 | 0.001 |
| 5 | 0 | 0.000 |
| *10 | 0 | 0.000 |

Statistical difference, according to t-test, when compared to control.

As shown Table 3, there were statistically significant differences between the control group (medium containing DMSO) and all the experimental groups (medium containing ICG-001 dissolved in DMSO) even at an ICG-001 concentration of 0.625 µM.

Table 4 presents data on the plating efficiencies of cultured cells from A2780, CP70, IGROV-1 and B16 in control wells as well as in wells exposed to ICG-001. The data indicate that the plating efficiency of the various cell lines was high, varying between 21 and 83%, which is commensurate with the fact that most of the plated cells expressed the CD133 marker of CSC.

TABLE 4

Average plating efficiency of 80 cells/well of the ovarian carcinoma lines and the mouse melanoma line treated with ICG-001.

| CONCENTRATION OF ICG-001 (µM) | A2780 % | CP70 % | IGROV-1 % | IGROV-1/CP % | B16 % |
|---|---|---|---|---|---|
| Control | 83 | 23 | 36 | 54 | 21 |
| 0.625 | 25 | 35 | 31 | 59 | 24 |
| 1.25 | 35 | 35 | 24 | 25 | 18 |
| 2.5 | 6 | 13 | 8 | 13 | 3 |
| 5 | 0 | 1 | 1 | 6 | 0 |
| 10 | 0 | 0 | 0 | 0 | 0 |

Figure 23:
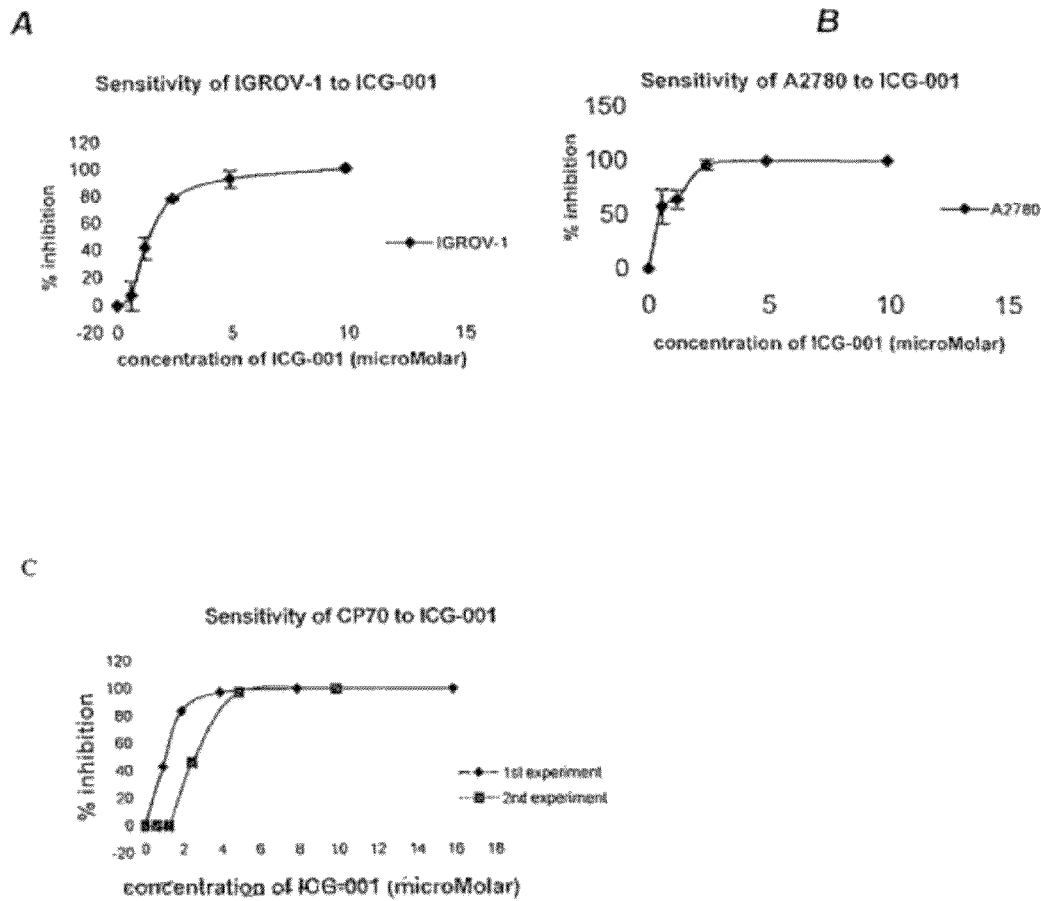
FIG. 23 shows the sensitivity of IGROV-1 (FIG. 23A), A2780 (FIG. 23B) and CP70 (FIG. 23C) to ICG-001, as tested in repeat experiments with different concentrations.
Figure 24:
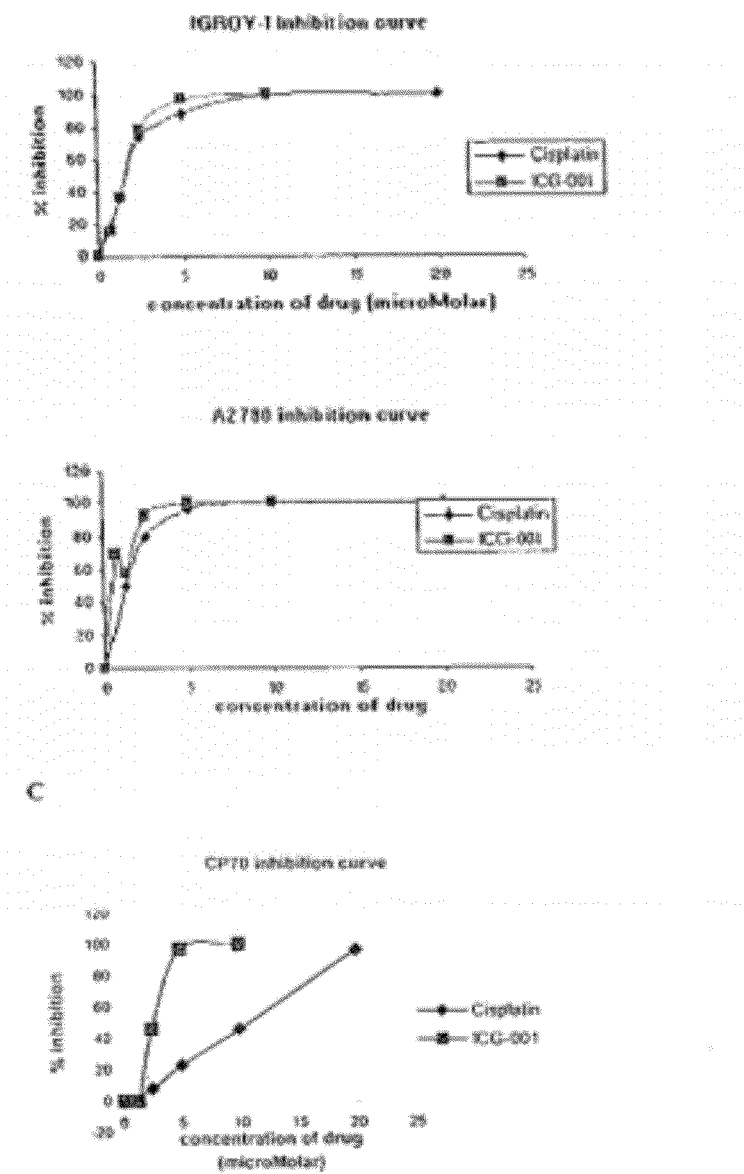
FIG. 24 shows the sensitivity of ovarian cell lines A2780 and CP70 to ICG-001.

The cells were tested at range of concentrations of ICG-001 between 0.625 and 10 µM and at cisplatin concentrations between 1.25 to 20 µM. All three ovarian cancer lines tested (A2780, CP70 and IGROV-1) were more sensitive to ICG-001 than to cisplatin. For the cisplatin-resistant line CP70, >90% inhibition was achieved at 5 µM of ICG-001, as compared to 20 µM of cisplatin (FIG. 23C). The cisplatin-sensitive lines, IGROV-1 and A2780, had similar sensitivity to ICG-001 as to cisplatin (FIGS. 23A and B). FIG. 24 shows experiments in which the sensitivity of ovarian carcinoma lines to ICG-001 and cisplatin were compared.

The cells were tested at range of concentrations of ICG-001 between 0.625 and 10 µM and at cisplatin concentrations between 1.25 to 20 µM. All three ovarian cancer lines tested (A2780, CP70 and IGROV-1) were more sensitive to IC G-001 than to cisplatin. For the cisplatin-resistant line CP70, >90% inhibition was achieved at 5 µM of ICG-001.

EXAMPLE 6

Inhibition of CBP-β-Catenin Interaction in SW480 Cells

The effect of several compounds on CBP-β-catenin binding was tested using the TOPFlash reporter system in SW480 cells.

Figure 25:
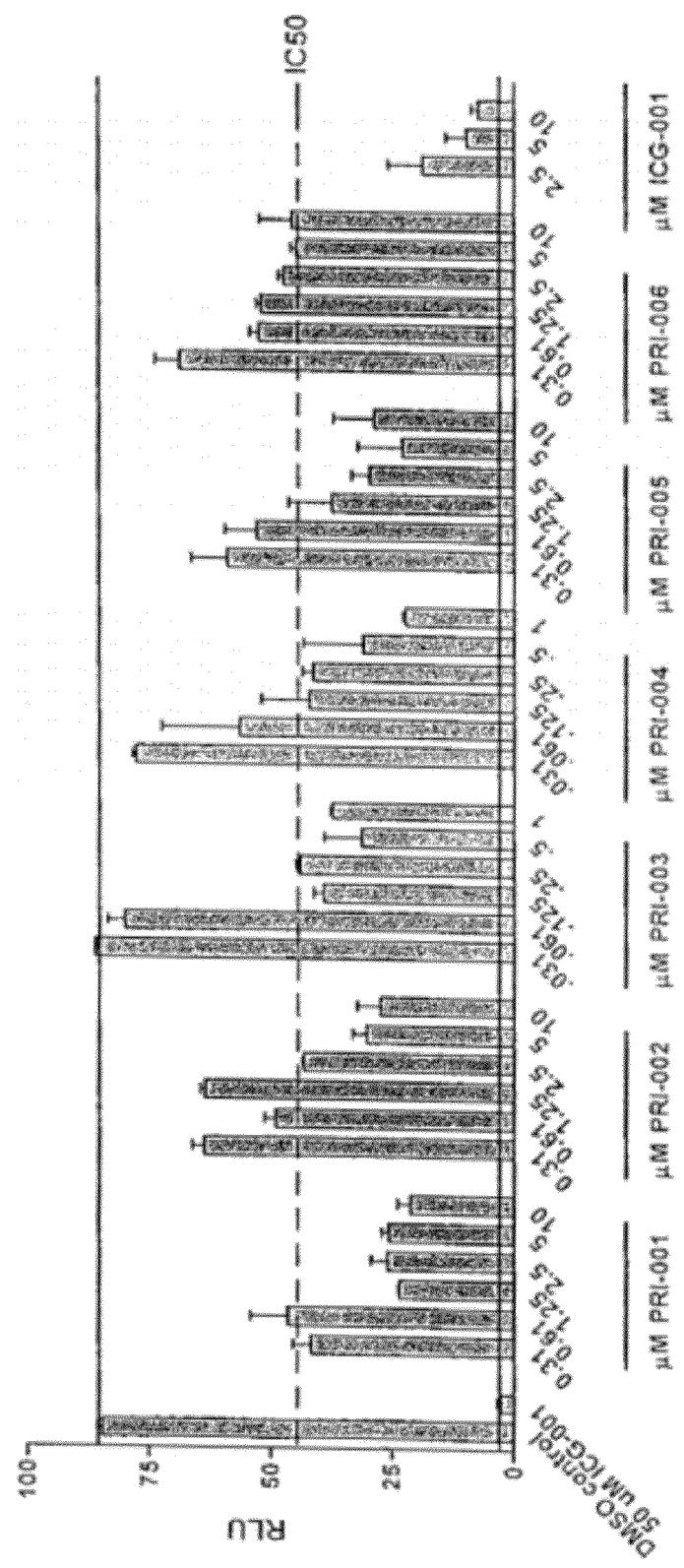
FIG. 25 shows that increasing concentrations of compounds PRI-001, PRI-002, PRI-003, PRI-004, PRI-005, and PRI-006 were effective, as compared with ICG-001, on SW480 cells.
Figure 26:
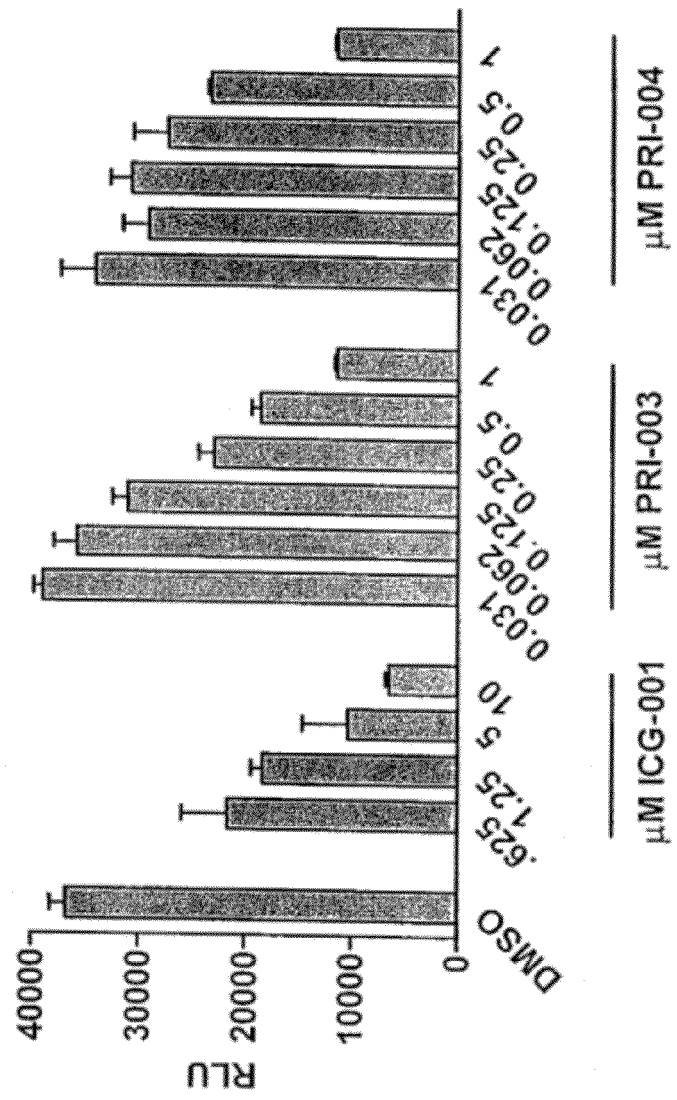
FIG. 26 shows pluc-6270 expression (luciferase) in SW480 cells treated with varying concentrations of ICG-001, PRI-003, and PRI-004.
Figure 27A:
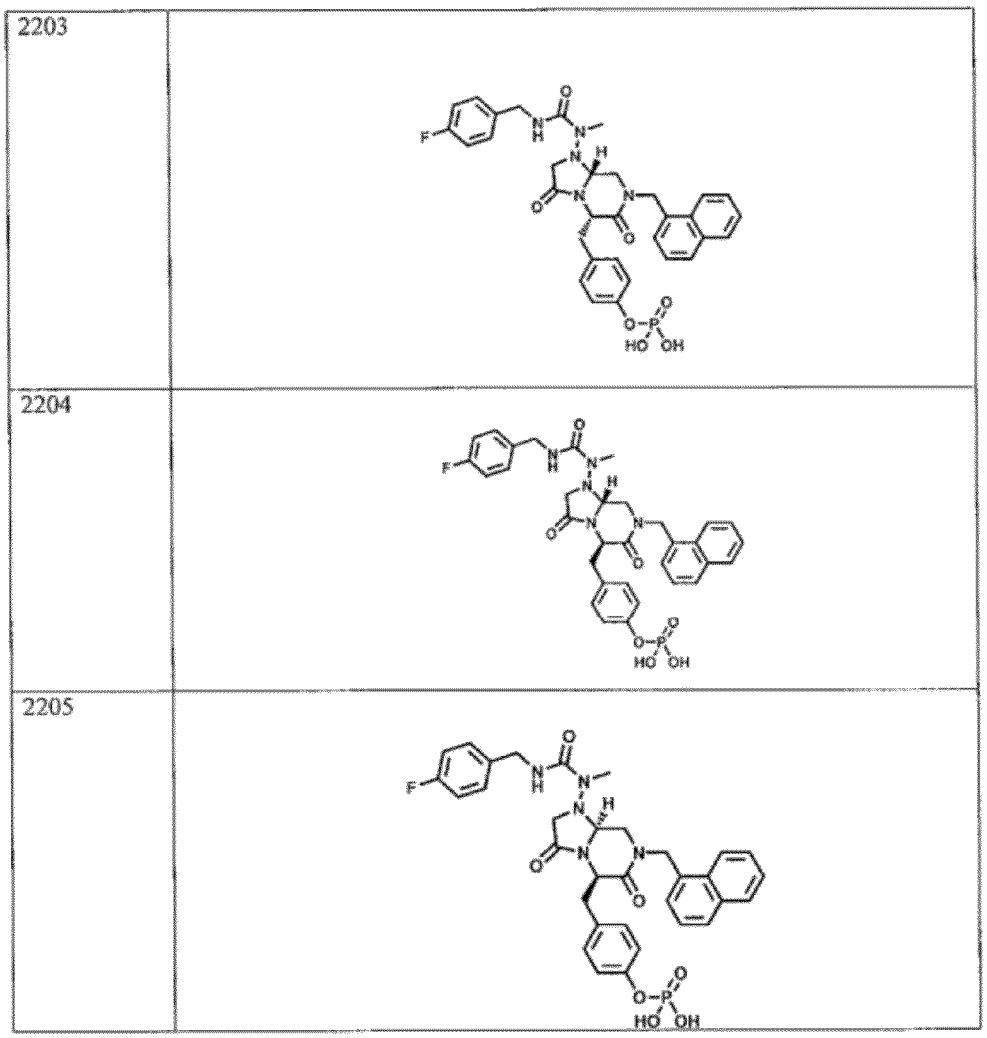
FIG. 27 shows the chemical structures of Compounds 2203-2217.
Figure 27B:
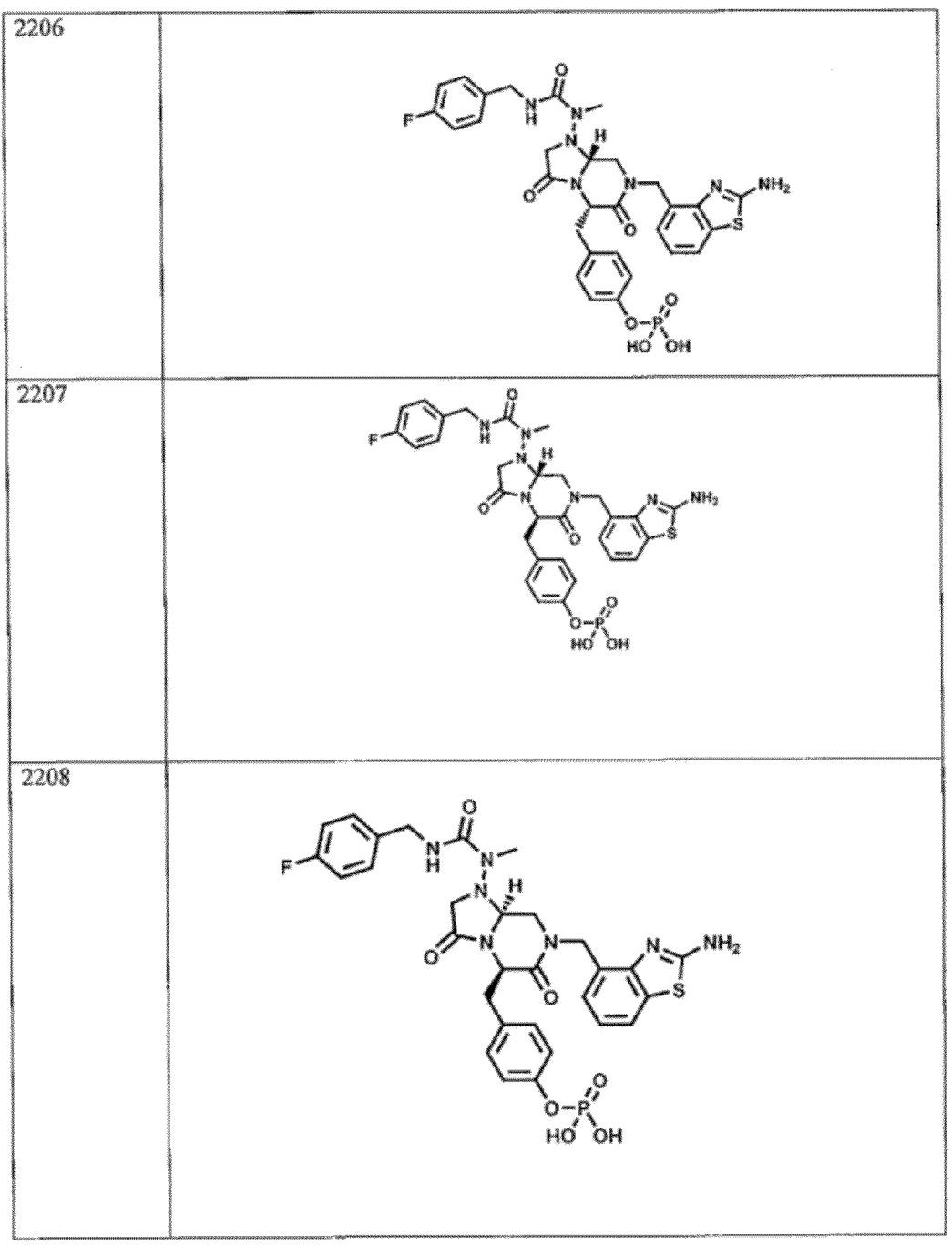
Figure 27C:
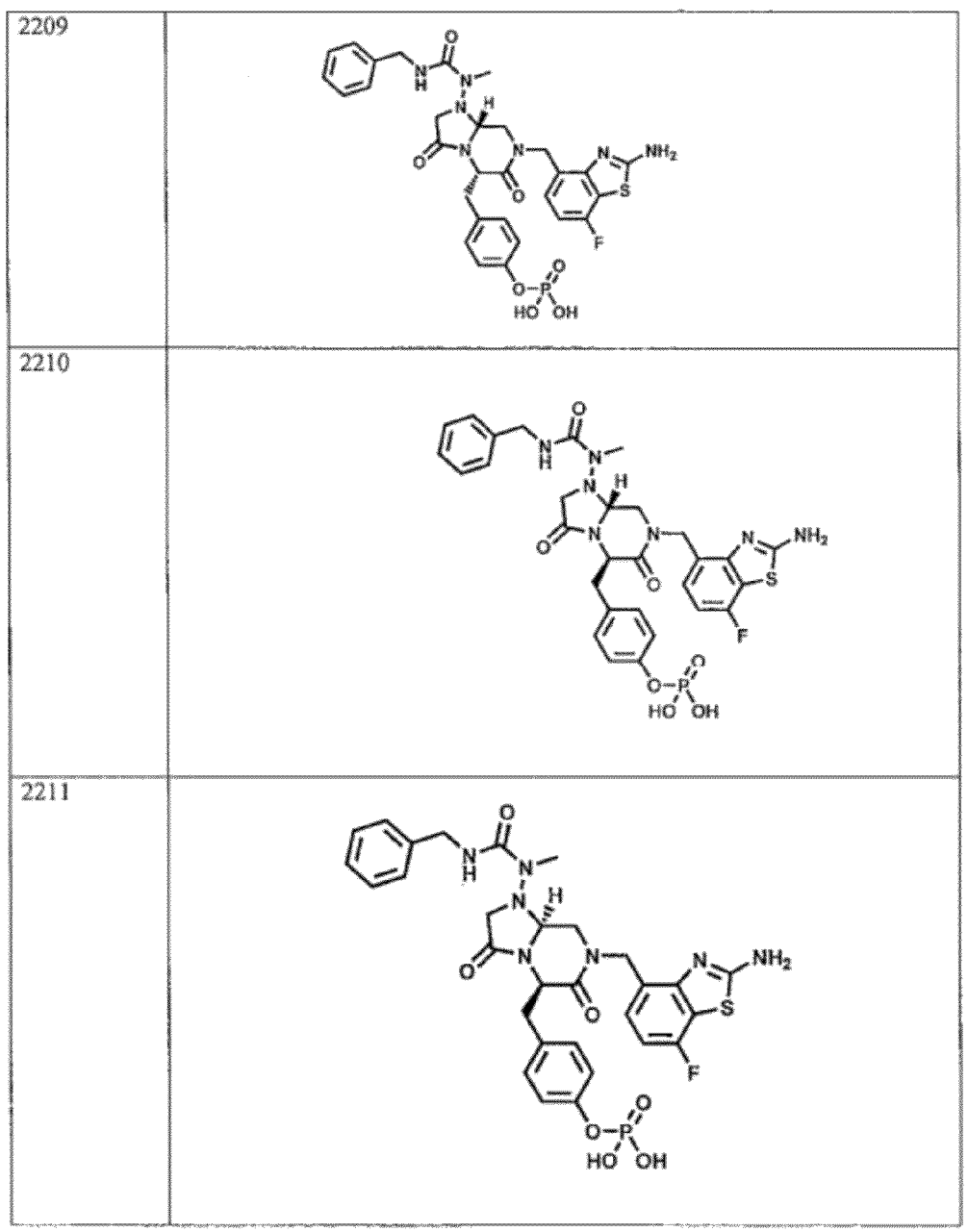
Figure 27D:
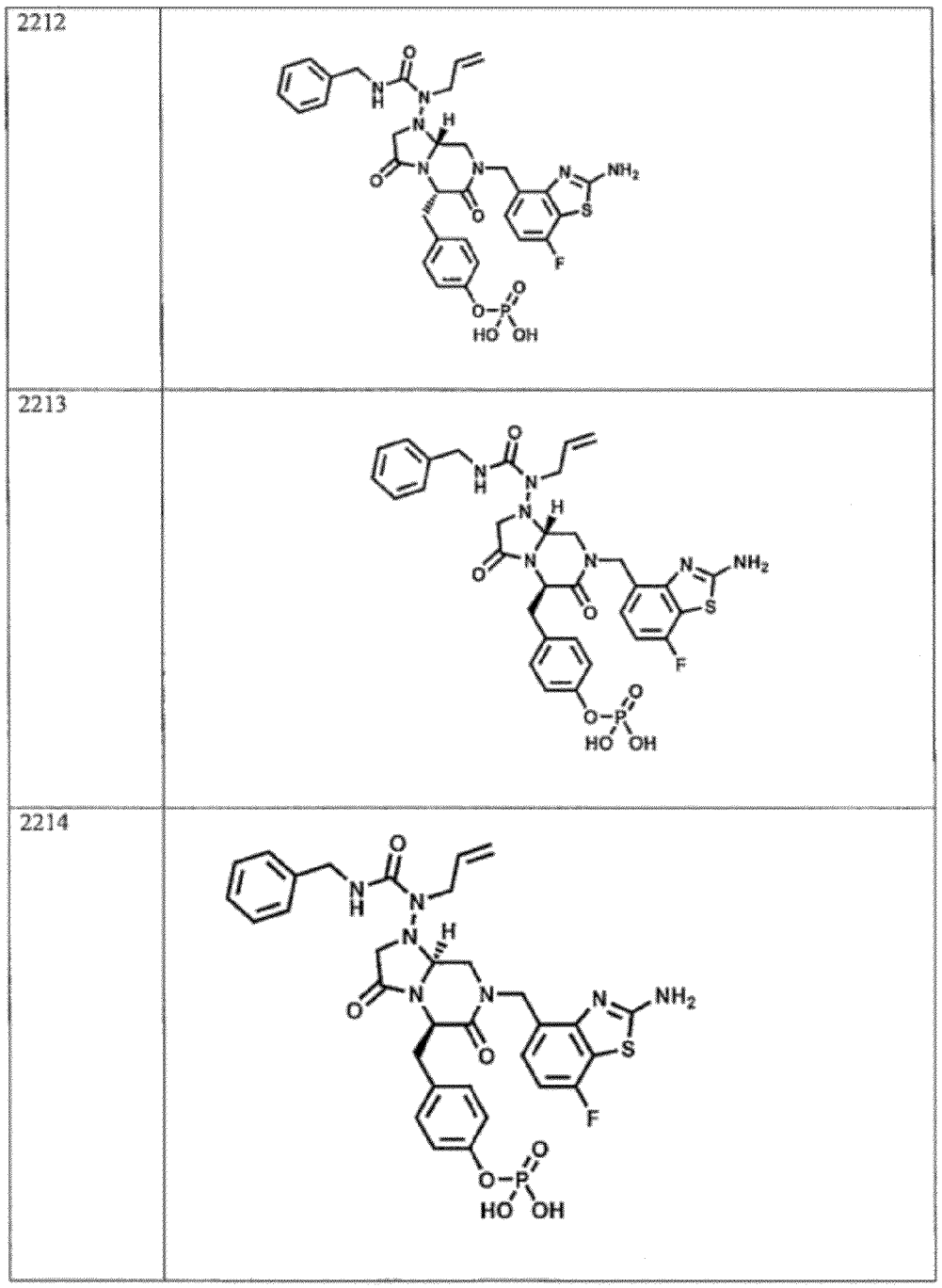
Figure 27E:
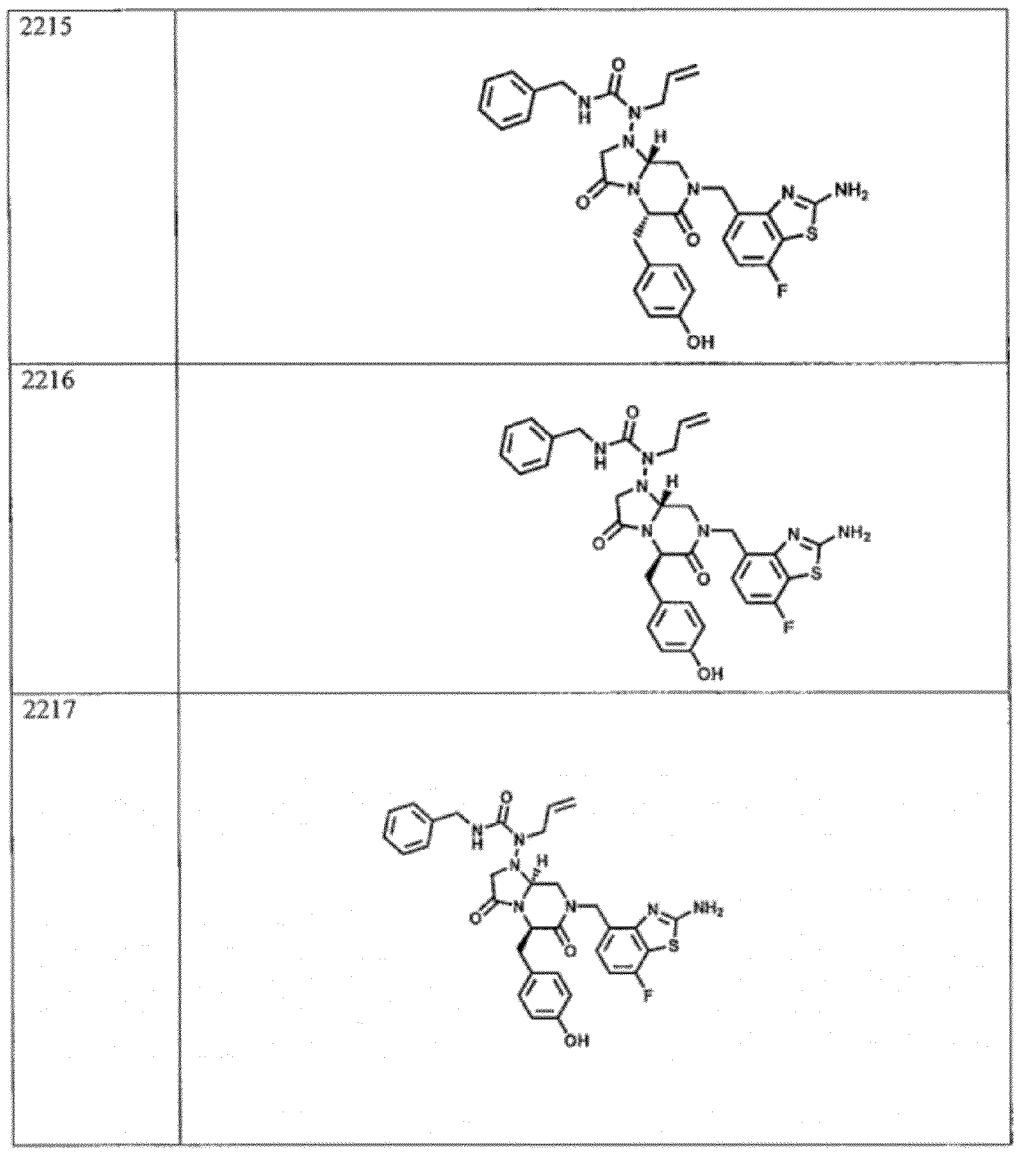

As shown in FIG. 25, increasing concentrations of compounds PRI-001, PRI-002, PRI-003, PRI-004, PRI-005 and PRI-006 were effective, as compared with ICG-001. FIG. 26 shows pluc-6270 expression (luciferase) in SW480 cells treated with varying concentrations of ICG-001, PRI-003, and PRI-004.

All patents, patent applications, provisional applications, and publications referred to or cited herein are incorporated by reference in their entirety, including all figures and tables, to the extent they are not inconsistent with the explicit teachings of this specification.

I claim:

1. A compound selected from the group consisting of Compounds 1-2200 of FIG. 1A, FIG. 1B, FIG. 1C, FIG. 1D, FIG. 1E, FIG. 1F, FIG. 1G, FIG. 1H, FIG. 1I, FIG. 1J, FIG. 1K, FIG. 1L, FIG. 1M, FIG. 1N, FIG. 1O, FIG. 1P, FIG. 1Q, FIG. 1R, FIG. 1S, FIG. 1T, FIG. 1U, FIG. 1V, FIG. 1W, FIG. 1X, FIG. 1Y, FIG. 1Z, FIG. 2A, FIG. 2B, FIG. 2C, FIG. 2D, FIG. 2E, FIG. 2F, FIG. 2G, FIG. 2H, FIG. 2I, FIG. 2J, FIG. 2K, FIG. 2L, FIG. 2M, FIG. 2N, FIG. 2O, FIG. 2P, FIG. 2Q, FIG. 2R, FIG. 2S, FIG. 2T, FIG. 2U, FIG. 2V, FIG. 2W, FIG. 2X, FIG. 2Y, FIG. 2Z, FIG. 3A, FIG. 3B, FIG. 3C, FIG. 3D, FIG. 3E, FIG. 3F, FIG. 3G, FIG. 3H, FIG. 3I, FIG. 3J, FIG. 3K, FIG. 3L, FIG. 3M, FIG. 3N, FIG. 3O, FIG. 3P, FIG. 3Q, FIG. 3R, FIG. 3S, FIG. 3T, FIG. 3U, FIG. 3V, FIG. 3W, FIG. 3X, FIG. 3Y, FIG. 3Z, FIG. 4A, FIG. 4B, FIG. 4C, FIG. 4D, FIG. 4E, FIG. 4F, FIG. 4G, FIG. 4H, FIG. 4I, FIG. 4J, FIG. 4K, FIG. 4L, FIG. 4M, FIG. 4N, FIG. 4O, FIG. 4P, FIG. 4Q, FIG. 4R, FIG. 4S, FIG. 4T, FIG. 4U, FIG. 4V, FIG. 4W, FIG. 4X, FIG. 4Y, FIG. 4Z, FIG. 5A, FIG. 5B, FIG. 5C, FIG. 5D, FIG. 5E, FIG. 5F, FIG. 5G, FIG. 5H, FIG. 5I, FIG. 5J, FIG. 5K, FIG. 5L, FIG. 5M, FIG. 5N, FIG. 5O, FIG. 5P, FIG. 5Q, FIG. 5R, FIG. 5S, FIG. 5T, FIG. 5U, FIG. 5V, FIG. 5W, FIG. 5X, FIG. 5Y, FIG. 5Z, FIG. 6A, FIG. 6B, FIG. 6C, FIG. 6D, FIG. 6E, FIG. 6F, FIG. 6G, FIG. 6H, FIG. 6I, FIG. 6J, FIG. 6K, FIG. 6L, FIG. 6M, FIG. 6N, FIG. 6O, FIG. 6P, FIG. 6Q, FIG. 6R, FIG. 6S, FIG. 6T, FIG. 6U, FIG. 6V, FIG. 6W, FIG. 6X, FIG. 6Y, FIG. 6Z, FIG. 7A, FIG. 7B, FIG. 7C, FIG. 7D, FIG. 7E, FIG. 7F, FIG. 7G, FIG. 7H, FIG. 7I, FIG. 7J, FIG. 7K, FIG. 7L, FIG. 7M, FIG. 7N, FIG. 7O, FIG. 7P, FIG. 7Q, FIG. 7R, FIG. 7S, FIG. 7T, FIG. 7U, FIG. 7V, FIG. 7W, FIG. 7X, FIG. 7Y, FIG. 7Z, FIG. 8A, FIG. 8B, FIG. 8C, FIG. 8D, FIG. 8E, FIG. 8F, FIG. 8G, FIG. 8H, FIG. 8I, FIG. 8J, FIG. 8K, FIG. 8L, FIG. 8M, FIG. 8N, FIG. 8O, FIG. 8P, FIG. 8Q, FIG. 8R, FIG. 8S, FIG. 8T, FIG. 8U, FIG. 8V, FIG. 8W, FIG. 8X, FIG. 8Y, FIG. 8Z, FIG. 9A, FIG. 9B, FIG. 9C, FIG. 9D, FIG. 9E, FIG. 9F, FIG. 9G, FIG. 9H, FIG. 9I, FIG. 9J, FIG. 9K, FIG. 9L, FIG. 9M, FIG. 9N, FIG. 9O, FIG. 9P, FIG. 9Q, FIG. 9R, FIG. 9S, FIG. 9T, FIG. 9U, FIG. 9V, FIG. 9W, FIG. 9X, FIG. 9Y, FIG. 9Z, FIG. 10A, FIG. 10B, FIG. 10C, FIG. 10D, FIG. 10E, FIG. 10F, FIG. 10G, FIG. 10H, FIG. 10I, FIG. 10J, FIG. 10K, FIG. 10L, FIG. 10M, FIG. 10N, FIG. 10O, FIG. 10P, FIG. 10Q, FIG. 10R, FIG. 10S, FIG. 10T, FIG. 10U, FIG. 10V, FIG. 10W, FIG. 10X, FIG. 10Y, FIG. 10Z, FIG. 11A, FIG. 11B, FIG. 11C, FIG. 11D, FIG. 11E, FIG. 11F, FIG. 11G, FIG. 11H, FIG. 11I, FIG. 11J, FIG. 11K, FIG. 11L, FIG. 11M, FIG. 11N, FIG. 11O, FIG. 11P, FIG. 11Q, FIG. 11R, FIG. 11S, FIG. 11T, FIG. 11U, FIG. 11V, FIG. 11W, FIG. 11X, FIG. 11Y, FIG. 11Z, and FIG. 11AA, (Compound 2201)

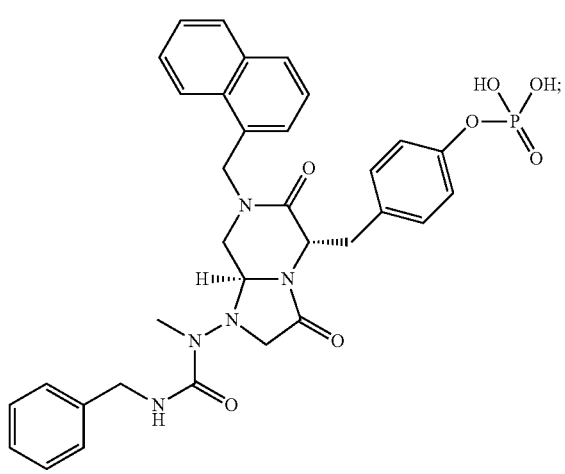

-continued (Compound 2202)

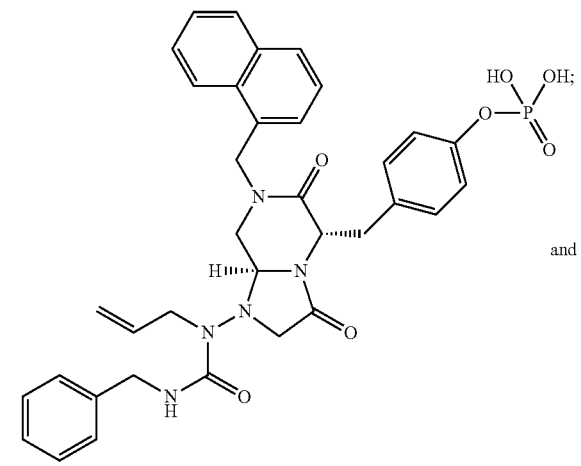

and

Figure 12A:
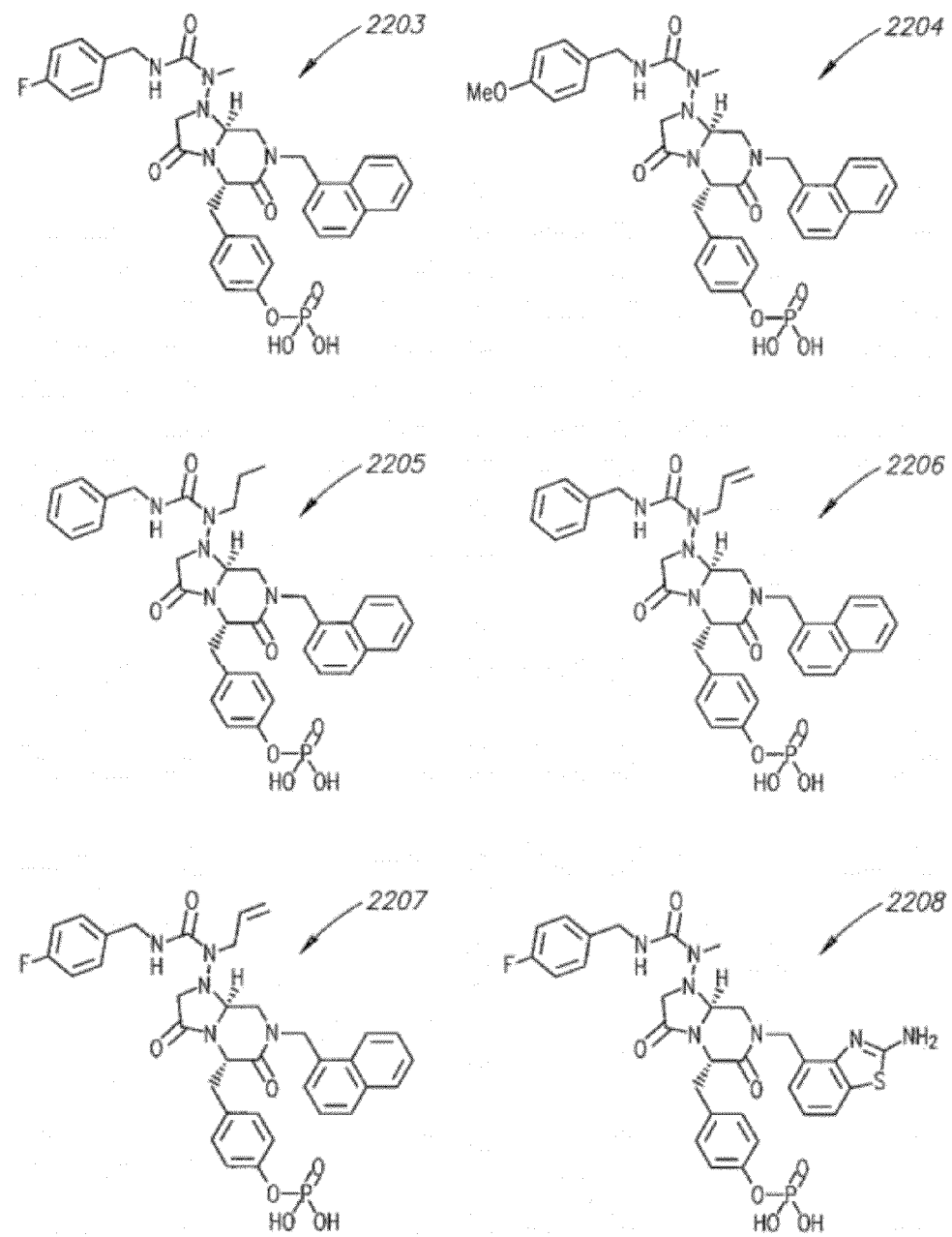
FIGS. 12A-12C shows the chemical structures of diasteric and enantiomeric stereo isomers of Compounds 2203-2217.
Figure 12B:
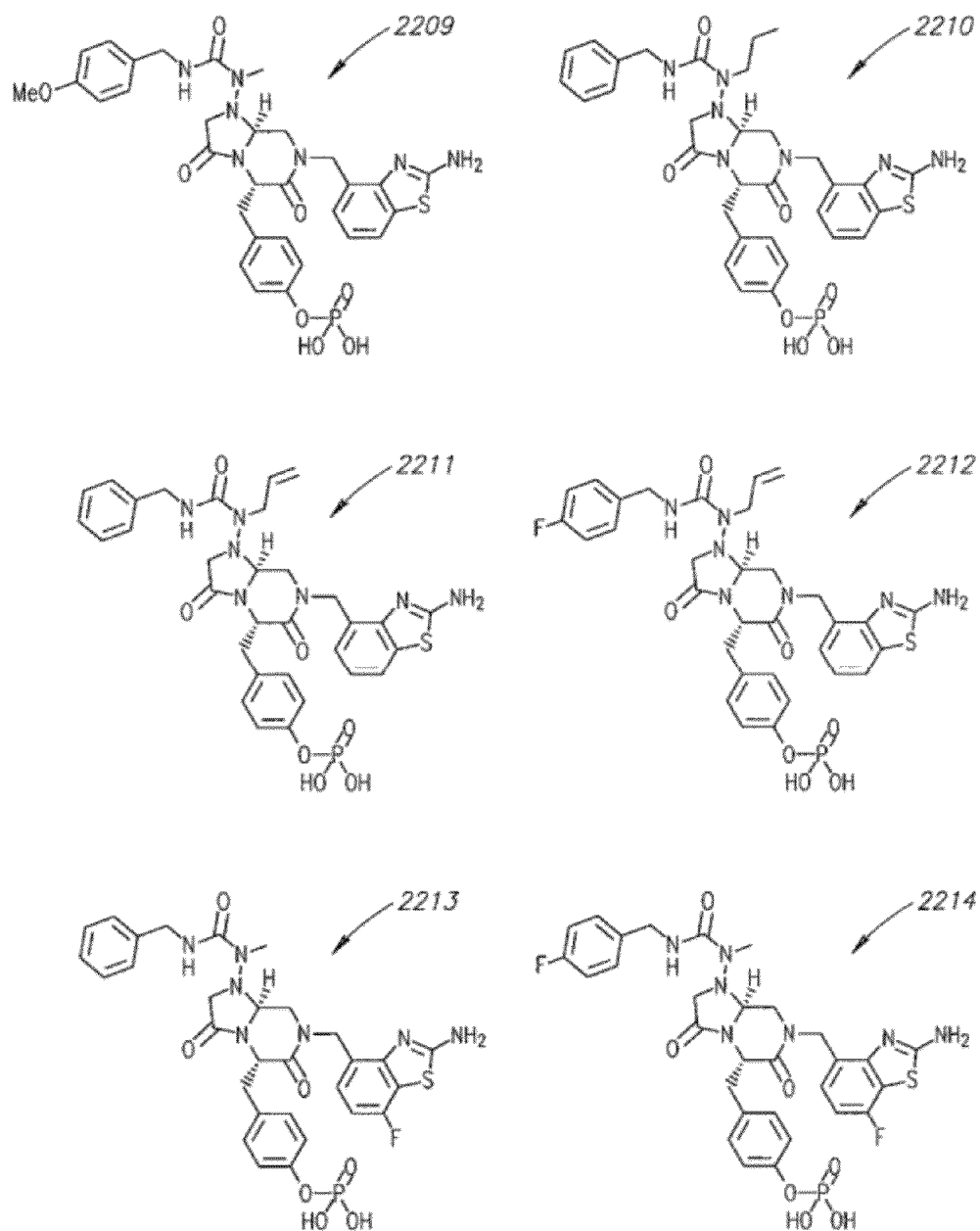
Figure 12C:
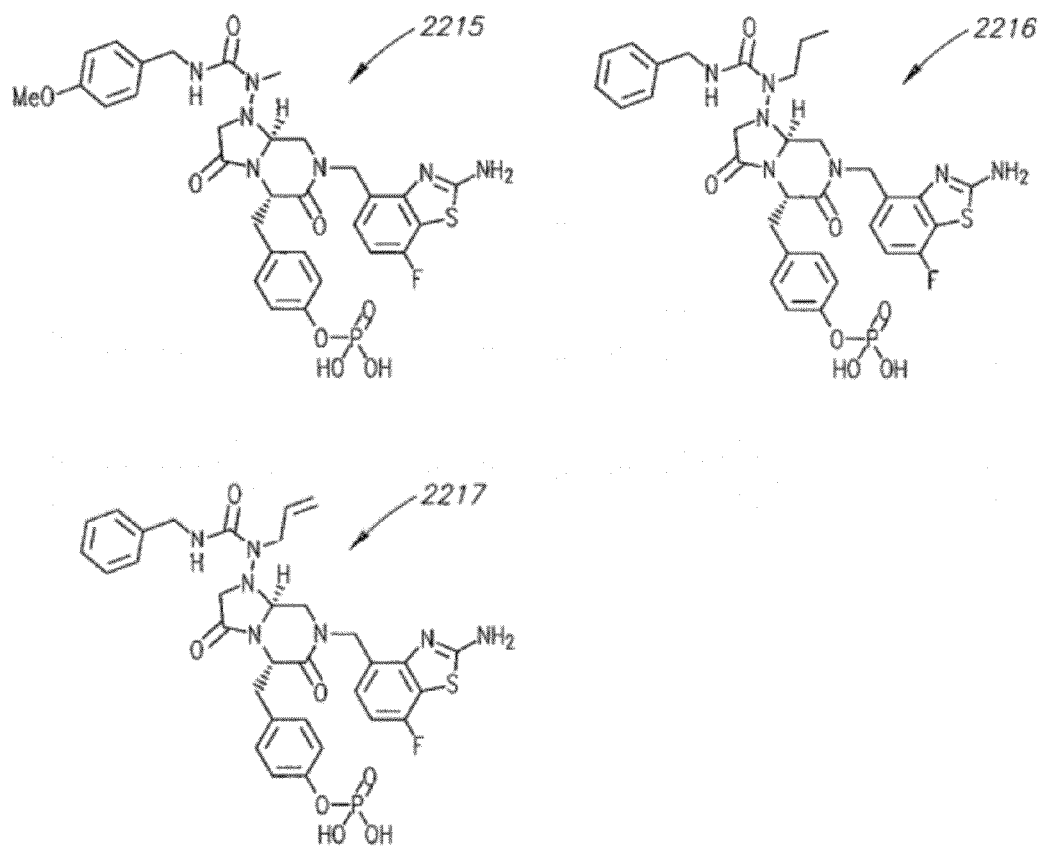

Compounds 2203-2217 shown in FIG. 12A, FIG. 12B, and FIG. 12C, or a pharmaceutically acceptable salt thereof.

2. A pharmaceutical composition comprising at least one compound of claim 1 and a pharmaceutically acceptable carrier.

* * * * *